United States Patent [19]
Ladner et al.

[11] Patent Number: 5,571,698
[45] Date of Patent: *Nov. 5, 1996

[54] DIRECTED EVOLUTION OF NOVEL BINDING PROTEINS

[75] Inventors: Robert C. Ladner, Ijamsville, Md.; Sonia K. Guterman, Belmont, Mass.; Bruce L. Roberts; William Markland, both of Milford, Mass.; Arthur C. Ley, Newton; Rachel B. Kent, Boxborough, both of Mass.

[73] Assignee: Protein Engineering Corporation, Cambridge, Mass.

[*] Notice: The portion of the term of this patent subsequent to Jun. 29, 2010, has been disclaimed.

[21] Appl. No.: 57,667

[22] Filed: Jun. 18, 1993

Related U.S. Application Data

[63] Continuation of Ser. No. 664,989, Mar. 1, 1991, Pat. No. 5,223,409, which is a continuation-in-part of Ser. No. 487,063, Mar. 2, 1990, abandoned, which is a continuation-in-part of Ser. No. 240,160, Sep. 2, 1988, abandoned.

[51] Int. Cl.$^6$ .................................................. C12N 25/62
[52] U.S. Cl. .......................... 435/69.7; 435/6; 435/64.1; 435/172.3; 435/252.3; 435/320.1
[58] Field of Search ............................. 435/6, 64.1, 64.7, 435/172.3, 252.3, 320.1

[56] References Cited

U.S. PATENT DOCUMENTS

| | | | |
|---|---|---|---|
| 4,304,863 | 12/1981 | Collins et al. | 435/69.1 |
| 4,332,897 | 6/1982 | Nakano et al. | 435/69.1 |
| 4,333,397 | 7/1982 | Gilbert et al. | 435/172.3 |
| 4,348,477 | 9/1982 | Nakano et al. | 435/172.3 |
| 4,348,478 | 9/1982 | Nakano et al. | 435/172.3 |
| 4,411,994 | 10/1983 | Gilbert et al. | 435/69.7 |
| 4,503,826 | 4/1985 | Foor et al. | 435/320.1 |
| 4,593,002 | 6/1986 | Dulbecco | 435/172.3 |
| 4,595,658 | 6/1986 | Zinder et al. | 435/69.1 |
| 4,603,112 | 7/1986 | Paulittie et al. | 435/275 |
| 4,642,334 | 2/1987 | Moore et al. | 530/388 |
| 4,683,202 | 7/1987 | Mullis | 435/91 |
| 4,703,004 | 10/1987 | Hopp et al. | 435/69.7 |
| 4,704,692 | 11/1987 | Ladner | 364/496 |
| 4,757,013 | 7/1988 | Inouye et al. | 435/172.3 |
| 4,769,326 | 9/1988 | Rutter | 435/681 |
| 4,769,327 | 9/1988 | Stephens et al. | 435/69.8 |
| 4,774,180 | 9/1988 | Toth et al. | 435/69.7 |
| 4,797,363 | 1/1989 | Teodorescu et al. | 435/235.1 |

FOREIGN PATENT DOCUMENTS

| | | |
|---|---|---|
| 0286239 | 6/1988 | European Pat. Off. |
| 0285123 | 6/1988 | European Pat. Off. |
| WO8801649 | 3/1988 | WIPO |
| WO8806601 | 9/1988 | WIPO |
| WO8806630 | 9/1988 | WIPO |
| 91/18980 | 12/1991 | WIPO |
| 91/19818 | 12/1991 | WIPO |
| WO9206204 | 4/1992 | WIPO |
| WO9206176 | 4/1992 | WIPO |
| WO9211272 | 7/1992 | WIPO |

OTHER PUBLICATIONS

Immumogenicity and Epitope Mapping of Foreign Sequences via Genetically Engineered Filamentous Phage; Vidal F. de la Cruz, Altaf A. Lal and Thomas F. McCutchan; The Journal of Biological Chemistry vol. 263, No. 9, Issue of Mar. 25, pp. 431804322. 1988.

In Vitro Genertic Constructions Devised to Express Given Antigenic Determinants at the Surface of Gram–negative Bacteria, Bernadette Bouges–Bocquet, Jean–Luc Guesdon, Christian Marchal and Maurice Hofnung:Unite de Programmation Moleculaire et Toxicologie Genetique CNRSLA 271, INSERM U.163, Instit Pasteur, 75015 Paris, France.

Probing the topology of a bacterial membrane protein by genetic insertion of a foreign epitope: expression at the cell surface, The EMBO Journal.

Alain Charbit, Jean Claude Boulain, Antoinette Ryter and Maurice Hofnung The EMBO Journal vol. 5, No. 11, pp. 3029–3037, 1986.

Presentation of Two Epitopes of the preS2 Region of Hepatitis B Virus on Live Recombinant Bacteria: Alain Charbit, Eliane Sobczak, Marie–Louise.

Michel, Annie Molla, Pierre Tiollais and Maurice Hofnung; J. Immunology, vo. 139, 1658–1664, No. 5 Sep. 1, 1987.

Filamentous Fusion Phage: Novel Expression Vectors That Display Cloned Antigens on the Virion Surface: Science 228 ('85) 1315017 PEC0406.

Ilichov et al., (1989), Dolle Ahad Nauk SSSR 307: 481–483.

Smith et al., (1986), J. Mol. Biol. 189:227–238.

Subcellular localization of a PhoE–LacZ fusion protein in E. coli by protease accessibility experiments reveals an inner–membrane–spanning form of the ptotein; Jan Tommassen and Toon de Kroon;FEB 05071, vol. 221 No. 2, 226–230, Sep. 1987.

Uses of lac Fusions for the Study of Biological Problems; Thomas J. Silhavy and Jonathan R. Beckwith: Microbiological Reviews, Dec. 1985, pp. 398–418, vol. 49, No. 4—American Society for Microbiology.

(List continued on next page.)

Primary Examiner—John Ulm
Attorney, Agent, or Firm—Iver P. Cooper

[57] ABSTRACT

In order to obtain a novel binding protein against a chosen target, DNA molecules, each encoding a protein comprising one of a family of similar potential binding domains and a structural signal calling for the display of the protein on the outer surface of a chosen bacterial cell, bacterial spore or phage (genetic package) are introduced into a genetic package. The protein is expressed and the potential binding domain is displayed on the outer surface of the package. The cells or viruses bearing the binding domains which recognize the target molecule are isolated and amplified. The successful binding domains are then characterized. One or more of these successful binding domains is used as a model for the design of a new family of potential binding domains, and the process is repeated until a novel binding domain having a desired affinity for the target molecule is obtained. In one embodiment, the first family of potential binding domains is related to bovine pancreatic trypsin inhibitor, the genetic package is M13 phage, and the protein includes the outer surface transport signal of the M13 gene III protein.

83 Claims, 16 Drawing Sheets

OTHER PUBLICATIONS

Sequence Information within the lamB Gene is Required for Proper Routing of the Bacteriophage γ Receptor Protein go the Outer Membrane of Eschichia coli K–12; Michael N. hall, Maxime Schwartz and Thomas J. Silhavy; J. Med. Biol (1982) 156, 93–112.

Selection for Mutants Altered in the Expression or Export of Outer Membrane Porin OmpF; Erica J. Sodergren, Jane Davidson, Ronald K. Taylor and Thomas J. Silhavy; J. of Bacteriology, Jun. 1985, pp. 1047–1053.

Biologe Moleculaire–Une methode genetique pour exposer un epitope chois a la surface de la bacterie Escherichia colo. Perspectives Note of Alain Charbit, Jean–Claude Boulain et Maurice Hofnung; C. R. Acad Sc. Paris, t.302, Serie III, No. 17, 1986.

Affinity–Chromatographic Studies Based on the Binding–Specificity of the Lambda Receptor of Escherichia col I. T. Ferenci; Ann Microbiol. (Inst. Pasteur) 1982, 133 A, 167–169.

Directed Evolution of the Lambda Receptor of Escherichia coli through Affinity Chromatographic Selection: Thomas Ferenci and Kin–Sang Lee J. Bol. Biol. (1982) 160, 431–444.

Isolation by Affinity Chromatography, of Mutant Escherichia coli Cells with Novel Regulation of lamB Expression; Thomas Ferenci and Kin–Sang Lee J. of Bacteriology, May 1983, pp. 984–987, vol. 154, No. 2.

Affinity Engineering of Maltoporin; Variats with Enhanced Affinity for Particular Ligands; Ann clune, Kin–Sang Lee and Thomas Ferenci Biochemical and Biophysical Research Communications, vol. 121, No. 1, 1984 pp. 34–40.

Sequence determinants in the labB gene of Escherichia coli influencing the binding and pore selectivity of maltoporin; Hans–Georg Heine, Joanna Kyngdon and Thomas Ferenci; Gene, 53 (1987)287–292.

Commentaries; Protein Engineering, vol. 1, No. 1, pp. 3–6, 1986.

Cloning of random–sequence oligodeoxynucleotides; Arnold R. Oliphant, Alexander L. Nussbaum and Kevin Struhl; Gene, 44 (1986) 177–183.

The Use of Random–Sequence Oligonuceotides for Determining Consensus Sequences; Arnold R. Oliphant and Kevin Struhl; Methods in Enzymology, vol. 155, pp. 568–582 (1987).

Combinatorial Cassette Mutagenesis as a Probe of the Informational Content of Protein Sequences: John F. Reidhaar–Olson and Robert T. Sauer; Research Articles, *Science,* vol. 241, 1 Jul. 1988, pp. 53–57.

Mutagenesis of the Arc Repressor Using Synthetic Primers with Random Nucleotide Substitutions; Andrew K. Vershon, Karen Blackmer and Robert T. Sauer; Protein Engineering, Applications in Science, Medicine and Industry; 1986, pp. 243–257.

Isolation and Analysis of Arc Repressor Mutants: Evidence for an Unusual Mechanism of DNA Binding; Andrew K. Vershon, James U. Bowie, Theresa M. Karplus and Robert T. Sauer; Proteins: Structure, Function, and Genetics 1:302–311 (1986).

Bacteriophage λ cro mutations: Effects on activity and intracellular degradation: Andrew A. Pakula, Vincent B. Young and Robert T. Sauer; Proc. Natl. Acad. Sci, USA, vol. 83, pp. 8829–8833, Dec. 1986.

Phage Lambda Repressor Revertants—Amino Acid Substitutions that Restore Activity to Mutant Proteins; Michael H. Hecht and Robert T. Sauer; J. Med. Biol. (1985) 186, 53–63.

Lambda Repressor Mutations That Increase the Affinity and Specificity of Operator Binding: Hillary C. M. Nelson and Robert T. Sauer; Cell, vol. 42, 549–558, Sep. 1985.

Intersaction of Mutant λ Repressors with Operator and Non–Operator DNA; Hillary C. M. Nelson and Robert T. Sauer; J. Med. Biol. (1986) 192, 27–38.

Amino Acid Replacements that Compensate for a Large Polypeptide Deletion in an Enzyme; Carvin Ho, Maria Jasin and Paul Schimmel; Science, vol. 229, pp. 389–393; 26 Jul. 1985.

Mutagenesis by random linker insertion into the lamB gene of Escherichia coli K12; Jean Claude Boulain, Alina Charbit and Maurice Hofnung; Med. Gen. Genes (1986) 205: 339–348.

Recruitment of substrate–specificity properties from one enzyme into a related one by protein engineering; James A. Wells, Brian C. Cunningham.

Thomas P. Graycar, and David A. Estell; Proc. Natl. Acad. Sci. USA, vol. 84, pp. 5167–5171, Aug. 1987.

Mutants of Bovine Pancreatic Trypsin Inhibitor Lacking Cysteines 14 and 38 Can Fold Properly; Cara Berman Marks, Hossein Naderi, Phyllis Anne Kosen, Irwin D. Kuntz and Stephen Anderson; Science vol. 235, pp. 1370–1375, Mar. 1987.

Synthesis and Characterization of a Pancreatic Trypsin Inhibitor Homologue and a Model Inhibitor; Nget Hong Tan and E. T. Kaiser; Biochemistry, vol. 16, No. 8, pp. 1531–1541, Apr. 19, 1977.

Transition–state stabilization in the medhanism of tyrosyl–tRNA synthetase revealed by protein engineering; Robin J. Leatherbarrow, Alan R. Fersht and Greg Winter; Proc. Natl. Acad. Sci. USA, Fol 82, pp. 7840–7844, Dec. 1985.

The cloning and expression of an anti–peptide antibody: a system for rapid analysis of the binding properties of engineered antibodies; S. Roberts and A. R. Rees; Protein Engineering, vol. 1, No. 1, pp. 59–65, 1986.

Production in Escherichia coli and one–step purification of bifunctional hybrid proteins which bind maltose: hugues Redouelle and Pascale Duplay; Bur. J. Biochem. 171, 541–549 (1988).

Expression, exportation et purification en une etape de proteines par fusion a la proteine MalE d'E. coli; Hughes Bedouelle, Pascale Duplay and Maruice Hofnung; C. R. Acad. Sci. Paris, t. 305, Serie III, pp. 623–626, 1987.

Linker Mutagenesis in the Gene of an Outer Membrane Protein of Escherichia coli, LamB; B. Bouges–Bocquet, H. Villarroya and M. Hofnung J. Cellular Biochemistry 24: 217–228 (1984).

An Epitope Library; Jamie K. Scott and George P. Smith, Science (Preprint).

Antibody–Selectable Filamentous fd Phage Vectors; Affinity Purification of Target Genes Parmley and Smith; Gene, 73:305–18 (1988).

Valenzuela, Pablo et al, "Antigen Engineering in Yeast: Synthesis and Assembly of Hybrid Hepatitis B Surface Antigen–Herpes Simplex 1 gD Particles," *Bio/Technology,* vol. 3, pp. 323–326, Apr. 1985.

Charbit, et al.; Versatility of a vector for expressing foreign polypeptides at the surface of gram–negative bacteria; Gene (1988); 70(1):181–9.

von Heijne, et al.; Membrane proteins: from sequence to structure; Protein Engineering; (1990) 4(2):109–112.

Fijima et al. 1986 (Mar.) Agric. Biol. Chem 50(3) 589–592.

Fadenci T. 1984 Trends in Biol. Sci. 9: 44–48.

EPINE 1
EPINE 3
EPINE 7

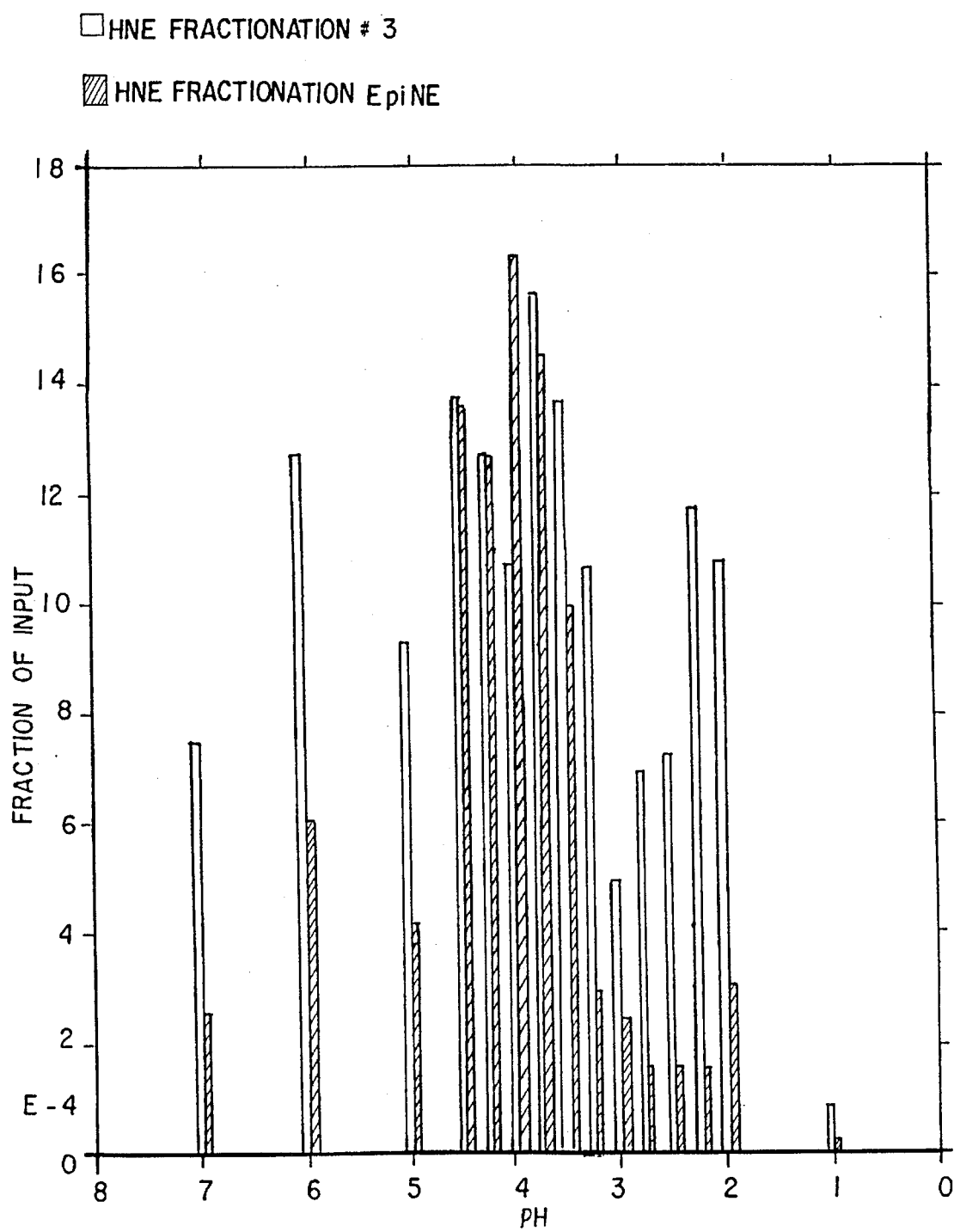

DIRECTED EVOLUTION OF NOVEL BINDING PROTEINS

This is a continuation of application Ser. No. 07/664,989 filed Mar. 1, 1991, now U.S. Pat. No. 5,223,409, which is a continuation-in-part of application Ser. No. 07/487,063 filed Mar. 2, 1990, now abandoned, which is a continuation-in-part of application Ser. No. 07/240,160 filed Sep. 2, 1988, now abandoned, the contents of all of which are hereby incorporated by reference.

CROSS-REFERENCE TO RELATED APPLICATIONS

The following related and commonly-owned applications are also incorporated by reference:

Robert Charles Ladner, Sonia Kosow Guterman, Rachael Baribault Kent, and Arthur Charles Ley are named as joint inventors on U.S. Ser. No. 07/293,980, filed Jan. 8, 1989, and entitled GENERATION AND SELECTION OF NOVEL DNA-BINDING PROTEINS AND POLYPEPTIDES. This application has been assigned to Protein Engineering Corporation.

Robert Charles Ladner, Sonia Kosow Guterman, and Bruce Lindsay Roberts are named as a joint inventors on a U.S. Ser. No. 07/470,651 filed 26 Jan. 1990, entitled "PRODUCTION OF NOVEL SEQUENCE-SPECIFIC DNA-ALTERING ENZYMES", likewise assigned to Protein Engineering Corp.

Ladner, Guterman, Kent, Ley, and Markland, Ser. No. 07/558,011 is also assigned to Protein Engineering Corporation.

BACKGROUND OF THE INVENTION

1. Field of the Invention

This invention relates to development of novel binding proteins (including mini-proteins) by an iterative process of mutagenesis, expression, chromatographic selection, and amplification. In this process, a gene encoding a potential binding domain, said gene being obtained by random mutagenesis of a limited number of predetermined codons, is fused to a genetic element which causes the resulting chimeric expression product to be displayed on the outer surface of a virus (especially a filamentous phage) or a cell. Chromatographic selection is then used to identify viruses or cells whose genome includes such a fused gene which coded for the protein which bound to the chromatographic target.

2. Information Disclosure Statement

A. Protein Structure

The amino acid sequence of a protein determines its three-dimensional (3D) structure, which in turn determines protein function (EPST63, ANFI73). Shortle (SHOR85), Sauer and colleagues (PAKU86, REID88a), and Caruthers and colleagues (EISE85) have shown that some residues on the polypeptide chain are more important than others in determining the 3D structure of a protein. The 3D structure is essentially unaffected by the identity of the amino acids at some loci; at other loci only one or a few types of amino-acid is allowed. In most cases, loci where wide variety is allowed have the amino acid side group directed toward the solvent. Loci where limited variety is allowed frequently have the side group directed toward other parts of the protein. Thus substitutions of amino acids that are exposed to solvent are less likely to affect the 3D structure than are substitutions at internal loci. (See also SCHU79, p169–171 and CREI84, p239–245, 314–315).

The secondary structure (helices, sheets, turns, loops) of a protein is determined mostly by local sequence. Certain amino acids have a propensity to appear in certain "secondary structures," they will be found from time to time in other structures, and studies of pentapeptide sequences found in different proteins have shown that their conformation varies considerably from one occurrence to the next (KABS84, ARGO87). As a result, a priori design of proteins to have a particular 3D structure is difficult.

Several researchers have designed and synthesized proteins de novo (MOSE83, MOSE87, ERIC86). These designed proteins are small and most have been synthesized in vitro as polypeptides rather than genetically. Hecht et al. (HECH90) have produced a designed protein genetically. Moser, et al. state that design of biologically active proteins is currently impossible.

B. Protein Binding Activity

Many proteins bind non-covalently but very tightly and specifically to some other characteristic molecules (SCHU79, CREI84). In each case the binding results from complementarity of the surfaces that come into contact: bumps fit into holes, unlike charges come together, dipoles align, and hydrophobic atoms contact other hydrophobic atoms. Although bulk water is excluded, individual water molecules are frequently found filling space in intermolecular interfaces; these waters usually form hydrogen bonds to one or more atoms of the protein or to other bound water. Thus proteins found in nature have not attained, nor do they require, perfect complementarity to bind tightly and specifically to their substrates. Only in rare cases is there essentially perfect complementarity; then the binding is extremely tight (as for example, avidin binding to biotin).

C. Protein Engineering

"Protein engineering" is the art of manipulating the sequence of a protein in order to alter its binding characteristics. The factors affecting protein binding are known, (CHOT75, CHOT76, SCHU79, p98–107, and CREI84, Ch8), but designing new complementary surfaces has proved difficult. Although some rules have been developed for substituting side groups (SUTC87b), the side groups of proteins are floppy and it is difficult to predict what conformation a new side group will take. Further, the forces that bind proteins to other molecules are all relatively weak and it is difficult to predict the effects of these forces.

Recently, Quiocho and collaborators (QUIO87) elucidated the structures of several periplasmic binding proteins from Gram-negative bacteria. They found that the proteins, despite having low sequence homology and differences in structural detail, have certain important structural similarities. Based on their investigations of these binding proteins, Quiocho et al. suggest it is unlikely that, using current protein engineering methods, proteins can be constructed with binding properties superior to those of proteins that occur naturally.

Nonetheless, there have been some isolated successes. Wilkinson et al. (WILK84) reported that a mutant of the tyrosyl tRNA synthetase of Bacillus stearthermophilus with the mutation $Thr_{51} \rightarrow Pro$ exhibits a 100-fold increase in affinity for ATP. Tan and Kaiser (TANK77) and Tschesche et al. (TSCH87) showed that changing a single amino acid in mini-protein greatly reduces its binding to trypsin, but that some of the mutants retained the parental characteristic of binding to an inhibiting chymotrypsin, while others exhibited new binding to elastase. Caruthers and others (EISE85) have shown that changes of single amino acids on the surface of the lambda Cro repressor greatly reduce its affinity for the natural operator $O_R^3$, but greatly increase the binding of the mutant protein to a mutant operator. Changing three residues in subtilisin from *Bacillus amyloliquefaciens* to be the same as the corresponding residues in subtilisin from *B. licheniformis* produced a protease having nearly the same activity as the latter subtilisin, even though 82 amino acid sequence differences remained (WELL87a). Insertion of DNA encoding 18 amino acids (corresponding to Pro-Glu-Dynorphin-Gly) into the *E. coli* phoA gene so that the additional amino acids appeared within a loop of the alkaline phosphatase protein resulted in a chimeric protein having both phoA and dynorphin activity (FREI90). Thus, changing the surface of a binding protein may alter its specificity without abolishing binding activity.

D. Techniques of Mutagenesis

Early techniques of mutating proteins involved manipulations at the amino acid sequence level. In the semi-synthetic method (TSCH87), the protein was cleaved into two fragments, a residue removed from the new end of one fragment, the substitute residue added on in its place, and the modified fragment joined with the other, original fragment. Alternatively, the mutant protein could be synthesized in its entirety (TANK77).

Erickson et al. suggested that mixed amino acid reagents could be used to produce a family of sequence-related proteins which could then be screened by affinity chromatography (ERIC86). They envision successive rounds of mixed synthesis of variant proteins and purification by specific binding. They do not discuss how residues should be chosen for variation. Because proteins cannot be amplified, the researchers must sequence the recovered protein to learn which substitutions improve binding. The researchers must limit the level of diversity so that each variety of protein will be present in sufficient quantity for the isolated fraction to be sequenced.

With the development of recombinant DNA techniques, it became possible to obtain a mutant protein by mutating the gene encoding the native protein and then expressing the mutated gene. Several mutagenesis strategies are known. One, "protein surgery" (DILL87), involves the introduction of one or more predetermined mutations within the gene of choice. A single polypeptide of completely predetermined sequence is expressed, and its binding characteristics are evaluated.

At the other extreme is random mutagenesis by means of relatively nonspecific mutagens such as radiation and various chemical agents. See Ho et al. (HOCJ85) and Lehtovaara, E.P. Appln. 285,123.

It is possible to randomly vary predetermined nucleotides using a mixture of bases in the appropriate cycles of a nucleic acid synthesis procedure. The proportion of bases in the mixture, for each position of a codon, will determine the frequency at which each amino acid will occur in the polypeptides expressed from the degenerate DNA population. Oliphant et al. (OLIP86) and Oliphant and Struhl (OLIP87) have demonstrated ligation and cloning of highly degenerate oligonucleotides, which were used in the mutation of promoters. They suggested that similar methods could be used in the variation of protein coding regions. They do not say how one should: a) choose protein residues to vary, or b) select or screen mutants with desirable properties. Reidhaar-Olson and Sauer (REID88a) have used synthetic degenerate oligo-nts to vary simultaneously two or three residues through all twenty amino acids. See also Vershon et al. (VERS86a; VERS86b). Reidhaar-Olson and Sauer do not discuss the limits on how many residues could be varied at once nor do they mention the problem of unequal abundance of DNA encoding different amino acids. They looked for proteins that either had wild-type dimerization or that did not dimerize. They did not seek proteins having novel binding properties and did not find any. This approach is likewise limited by the number of colonies that can be examined (ROBE86).

To the extent that this prior work assumes that it is desirable to adjust the level of mutation so that there is one mutation per protein, it should be noted that many desirable protein alterations require multiple amino acid substitutions and thus are not accessible through single base changes or even through all possible amino acid substitutions at any one residue.

D. Affinity Chromatography of Cells

Ferenci and coloborators have published a series of papers on the chromatographic isolation of mutants of the maltose-transport protein LamB of *E. coli* (FERE82a, FERE82b, FERE83, FERE84, CLUN84, HEIN87 and papers cited therein). The mutants were either spontaneous or induced with nonspecific chemical mutagens. Levels of mutagenesis were picked to provide single point mutations or single insertions of two residues. No multiple mutations were sought or found.

While variation was seen in the degree of affinity for the conventional LamB substrates maltose and starch, there was no selection for affinity to a target molecule not bound at all by native LamB, and no multiple mutations were sought or found. FERE84 speculated that the affinity chromatographic selection technique could be adapted to development of similar mutants of other "important bacterial surface-located enzymes", and to selecting for mutations which result in the relocation of an intracellular bacterial protein to the cell surface. Ferenci's mutant surface proteins would not, however, have been chimeras of a bacterial surface protein and an exogenous or heterologous binding domain.

Ferenci also taught that there was no need to clone the structural gene, or to know the protein structure, active site, or sequence. The method of the present invention, however, specifically utilizes a cloned structural gene. It is not possible to construct and express a chimeric, outer surface-directed potential binding protein-encoding gene without cloning.

Ferenci did not limit the mutations to particular loci or particular substitutions. In the present invention, knowledge of the protein structure, active site and/or sequence is used as appropriate to predict which residues are most likely to affect binding activity without unduly destabilizing the protein, and the mutagenesis is focused upon those sites. Ferenci does not suggest that surface residues should be preferentially varied. In consequence, Ferenci's selection system is much less efficient than that disclosed herein.

E. Bacterial and Viral Expression of Chimeric Surface Proteins

A number of researchers have directed unmutated foreign antigenic epitopes to the surface of bacteria or phage, fused to a native bacterial or phage surface protein, and demonstrated that the epitopes were recognized by antibodies. Thus, Charbit, et al. (CHAR86) genetically inserted the C3 epitope of the VP1 coat protein of poliovirus into the LamB outer membrane protein of *E. coli,* and determined immunologically that the C3 epitope was exposed on the bacterial cell surface. Charbit, et al. (CHAR87) likewise produced chimeras of LamB and the A (or B) epitopes of the preS2 region of hepatitis B virus.

A chimeric LacZ/OmpB protein has been expressed in *E. coli* and is, depending on the fusion, directed to either the outer membrane or the periplasm (SILH77). A chimeric LacZ/OmpA surface protein has also been expressed and displayed on the surface of *E. coli* cells (Weinstock et al., WEIN83). Others have expressed and displayed on the surface of a cell chimeras of other bacterial surface proteins, such as *E. coli*, type 1 fimbriae (Hedegaard and Klemm (HEDE89)) and *Bacterioides nodusus* type 1 fimbriae (Jennings et al., JENN89). In none of the recited cases was the inserted genetic material mutagenized.

Dulbecco (DULB86) suggests a procedure for incorporating a foreign antigenic epitope into a viral surface protein so that the expressed chimeric protein is displayed on the surface of the virus in a manner such that the foreign epitope is accessible to antibody. In 1985 Smith (SMIT85) reported inserting a nonfunctional segment of the EcoRI endonuclease gene into gene III of bacteriophage f1, "in phase". The gene III protein is a minor coat protein necessary for infectivity. Smith demonstrated that the recombinant phage were adsorbed by immobilized antibody raised against the EcoRI endonuclease, and could be eluted with acid. De la Cruz et al. (DELA88) have expressed a fragment of the repeat region of the circumsporozoite protein from *Plasmodium falciparum* on the surface of M13 as an insert in the gene III protein. They showed that the recombinant phage were both antigenic and immunogenic in rabbits, and that such recombinant phage could be used for B epitope mapping. The researchers suggest that similar recombinant phage could be used for T epitope mapping and for vaccine development.

None of these researchers suggested mutagenesis of the inserted material, nor is the inserted material a complete binding domain conferring on the chimeric protein the ability to bind specifically to a receptor other than the antigen combining site of an antibody.

McCafferty et al. (MCCA90) expressed a fusion of an Fv fragment of an antibody to the N-terminal of the pIII protein. The Fv fragment was not mutated.

F. Epitope Libraries on Fusion Phage

Parmley and Smith (PARM88) suggested that an epitope library that exhibits all possible hexapeptides could be constructed and used to isolate epitopes that bind to antibodies. In discussing the epitope library, the authors did not suggest that it was desirable to balance the representation of different amino acids. Nor did they teach that the insert should encode a complete domain of the exogenous protein. Epitopes are considered to be unstructured peptides as opposed to structured proteins.

After the filing of the parent application whose benefit is claimed herein under 35 U.S.C. 120, certain groups reported the construction of "epitope libraries." Scott and Smith (SCOT90) and Cwirla et al. (CWIR90) prepared "epitope libraries" in which potential hexapeptide epitopes for a target antibody were randomly mutated by fusing degenerate oligonucleotides, encoding the epitopes, with gene III of fd phage, and expressing the fused gene in phage-infected cells. The cells manufactured fusion phage which displayed the epitopes on their surface; the phage which bound to immobilized antibody were eluted with acid and studied. In both cases, the fused gene featured a segment encoding a spacer region to separate the variable region from the wild type pIII sequence so that the varied amino acids would not be constrained by the nearby pIII sequence. Devlin et al. (DEVL90) similarly screened, using M13 phage, for random 15 residue epitopes recognized by streptavidin. Again, a spacer was used to move the random peptides away from the rest of the chimeric phage protein. These references therefore taught away from constraining the conformational repertoire of the mutated residues.

Another problem with the Scott and Smith, Cwirla et al., and Devlin et al., libraries was that they provided a highly biased sampling of the possible amino acids at each position. Their primary concern in designing the degenerate oligonucleotide encoding their variable region was to ensure that all twenty amino acids were encodible at each position; a secondary consideration was minimizing the frequency of occurrence of stop signals. Consequently, Scott and Smith and Cwirla et al. employed NNK (N=equal mixture of G, A, T, C; K=equal mixture of G and T) while Devlin et al. used NNS (S=equal mixture of G and C). There was no attempt to minimize the frequency ratio of most favored-to-least favored amino acid, or to equalize the rate of occurrence of acidic and basic amino acids.

Devlin et al. characterized several affinity-selected streptavidin-binding peptides, but did not measure the affinity constants for these peptides. Cwirla et al. did determine the affinity constant for his peptides, but were disappointed to find that his best hexapeptides had affinities (350–300 nM), "orders of magnitude" weaker than that of the native Met-enkephalin epitope (7 nM) recognized by the target antibody. Cwirla et al. speculated that phage bearing peptides with higher affinities remained bound under acidic elution, possibly because of multivalent interactions between phage (carrying about 4 copies of pIII) and the divalent target IgG. Scott and Smith were able to find peptides whose affinity for the target antibody (A2) was comparable to that of the reference myohemerythrin epitope (50 nM). However, Scott and Smith likewise expressed concern that some high-affinity peptides were lost, possibly through irreversible binding of fusion phage to target.

G. Non-Commonly Owned Patents and Applications Naming Robert Ladner as an Inventor Ladner, U.S. Pat. No. 4,704,692, "Computer Based System and Method for Determining and Displaying Possible Chemical Structures for Converting Double- or Multiple-Chain Polypeptides to Single-Chain Polypeptides" describes a design method for converting proteins composed of two or more chains into proteins of fewer polypeptide chains, but with essentially the same 3D structure. There is no mention of variegated DNA and no genetic selection. Ladner and Bird, WO88/01649 (Publ. Mar. 10, 1988) disclose the specific application of computerized design of linker peptides to the preparation of single chain antibodies.

Ladner, Glick, and Bird, WO88/06630 (publ. 7 Sep. 1988 and having priority from U.S. application Ser. No. 07/021, 046, assigned to Genex Corp.) (LGB) speculate that diverse single chain antibody domains (SCAD) may be screened for binding to a particular antigen by varying the DNA encoding the combining determining regions of a single chain antibody, subcloning the SCAD gene into the gpV gene of phage lambda so that a SCAD/gpV chimera is displayed on the outer surface of phage lambda, and selecting phage which bind to the antigen through affinity chromatography. The only antigen mentioned is bovine growth hormone. No other binding molecules, targets, carrier organisms, or outer surface proteins are discussed. Nor is there any mention of the method or degree of mutagenesis. Furthermore, there is no teaching as to the exact structure of the fusion nor of how to identify a successful fusion or how to proceed if the SCAD is not displayed.

Ladner and Bird, WO88/06601 (publ. 7 Sep. 1988) suggest that single chain "pseudodimeric" repressors (DNA-binding proteins) may be prepared by mutating a putative linker peptide followed by in vivo selection that mutation and selection may be used to create a dictionary of recognition elements for use in the design of asymmetric repressors. The repressors are not displayed on the outer surface of an organism.

Methods of identifying residues in protein which can be replaced with a cysteine in order to promote the formation of a protein-stabilizing disulfide bond are given in Pantoliano and Ladner, U.S. Pat. No. 4,903,773 (PANT90), Pantoliano and Ladner (PANT87), Pabo and Suchenek (PABO86), MATS89, and SAUE86.

No admission is made that any cited reference is prior art or pertinent prior art, and the dates given are those appearing on the reference and may not be identical to the actual publication date. All references cited in this specification are hereby incorporated by reference.

SUMMARY OF THE INVENTION

The present invention is intended to overcome the deficiencies discussed above. It relates to the construction, expression, and selection of mutated genes that specify novel proteins with desirable binding properties, as well as these proteins themselves. The substances bound by these proteins, hereinafter referred to as "targets", may be, but need not be, proteins. Targets may include other biological or synthetic macromolecules as well as other organic and inorganic substances.

The fundamental principle of the invention is one of forced evolution. In nature, evolution results from the combination of genetic variation, selection for advantageous traits, and reproduction of the selected individuals, thereby enriching the population for the trait. The present invention achieves genetic variation through controlled random mutagenesis ("variegation") of DNA, yielding a mixture of DNA molecules encoding different but related potential binding proteins. It selects for mutated genes that specify novel proteins with desirable binding properties by 1) arranging that the product of each mutated gene be displayed on the outer surface of a replicable genetic package (GP) (a cell, spore or virus) that contains the gene, and 2) using affinity selection—selection for binding to the target material—to enrich the population of packages for those packages containing genes specifying proteins with improved binding to that target material. Finally, enrichment is achieved by allowing only the genetic packages which, by virtue of the displayed protein, bound to the target, to reproduce. The evolution is "forced" in that selection is for the target material provided.

The display strategy is first perfected by modifying a genetic package to display a stable, structured domain (the "initial potential binding domain", IPBD) for which an affinity molecule (which may be an antibody) is obtainable. The success of the modifications is readily measured by, e.g., determining whether the modified genetic package binds to the affinity molecule.

The IPBD is chosen with a view to its tolerance for extensive mutagenesis. Once it is known that the IPBD can be displayed on a surface of a package and subjected to affinity selection, the gene encoding the IPBD is subjected to a special pattern of multiple mutagenesis, here termed "variegation", which after appropriate cloning and amplification steps leads to the production of a population of genetic packages each of which displays a single potential binding domain (a mutant of the IPBD), but which collectively display a multitude of different though structurally related potential binding domains (PBDs). Each genetic package carries the version of the pbd gene that encodes the PBD displayed on the surface of that particular package.

Affinity selection is then used to identify the genetic packages bearing the PBDs with the desired binding characteristics, and these genetic packages may then be amplified. After one or more cycles of enrichment by affinity selection and amplification, the DNA encoding the successful binding domains (SBDs) may then be recovered from selected packages.

If need be, the DNA from the SBD-bearing packages may then be further "variegated", using an SBD of the last round of variegation as the "parental potential binding domain" (PPBD) to the next generation of PBDs, and the process continued until the worker in the art is satisfied with the result. At that point, the SBD may be produced by any conventional means, including chemical synthesis.

When the number of different amino acid sequences obtainable by mutation of the domain is large when compared to the number of different domains which are displayable in detectable amounts, the efficiency of the forced evolution is greatly enhanced by careful choice of which residues are to be varied. First, residues of a known protein which are likely to affect its binding activity (e.g., surface residues) and not likely to unduly degrade its stability are identified. Then all or some of the codons encoding these residues are varied simultaneously to produce a variegated population of DNA. The variegated population of DNA is used to express a variety of potential binding domains, whose ability to bind the target of interest may then be evaluated.

The method of the present invention is thus further distinguished from other methods in the nature of the highly variegated population that is produced and from which novel binding proteins are selected. We force the displayed potential binding domain to sample the nearby "sequence space" of related amino-acid sequences in an efficient, organized manner. Four goals guide the various variegation plans used herein, preferably: 1) a very large number (e.g. $10^7$) of variants is available, 2) a very high percentage of the possible variants actually appears in detectable amounts, 3) the frequency of appearance of the desired variants is relatively uniform, and 4) variation occurs only at a limited number of amino-acid residues, most preferably at residues having side groups directed toward a common region on the surface of the potential binding domain.

This is to be distinguished from the simple use of indiscriminate mutagenic agents such as radiation and hydroxylamine to modify a gene, where there is no (or very oblique) control over the site of mutation. Many of the mutations will affect residues that are not a part of the binding domain. Moreover, since at a reasonable level of mutagenesis, any modified codon is likely to be characterized by a single base change, only a limited and biased range of possibilities will be explored. Equally remote is the use of site-specific mutagenesis techniques employing mutagenic oligonucleotides of nonrandomized sequence, since these techniques do not lend themselves to the production and testing of a large number of variants. While focused random mutagenesis techniques are known, the importance of controlling the distribution of variation has been largely overlooked.

In order to obtain the display of a multitude of different though related potential binding domains, applicants generate a heterogeneous population of replicable genetic packages each of which comprises a hybrid gene including a first DNA sequence which encodes a potential binding domain for the target of interest and a second DNA sequence which encodes a display means, such as an outer surface protein native to the genetic package but not natively associated with the potential binding domain (or the parental binding domain to which it is related) which causes the genetic package to display the corresponding chimeric protein (or a processed form thereof) on its outer surface.

It should be recognized that by expressing a hybrid protein which comprises an outer surface transport signal not natively associated with the binding domain, the utility of the present invention is greatly extended. The binding domain need not be that of a surface protein of the genetic package (or, in the case of a vital package, of its host cell), since the provided outer surface transport signal is responsible for achieving the desired display. Thus, it is possible to display on the surface of a phage, bacterial cell or bacterial spore a binding domain related to the binding domain of a normally cytoplasmic binding protein, or the binding domain of eukaryotic protein which is not found on the surface of prokaryotic cells or viruses.

Another important aspect of the invention is that each potential binding domain remains physically associated with the particular DNA molecule which encodes it. Thus, once successful binding domains are identified, one may readily recover the gene and either express additional quantities of the novel binding protein or further mutate the gene. The form that this association takes is a "replicable genetic package", a virus cell or spore which replicates and expresses the binding domain-encoding gene, and transports the binding domain to its outer surface.

It is also possible chemically or enzymatically to modify the PBDs before selection. The selection then identifies the best modified amino acid sequence. For example, we could treat the variegated population of genetic packages that display a variegated population of binding domains with a protein tyrosine kinase and then select for binding the target. Any tyrosines on the BD surface will be phosphorylated and this could affect the binding properties. Other chemical or enzymatic modifications are possible.

By virtue of the present invention, proteins are obtained which can bind specifically to targets other than the antigen-combining sites of antibodies. A protein is not to be considered a "binding protein" merely because it can be bound by an antibody (see definition of "binding protein" which follows). While almost any amino acid sequence of more than about 6–8 amino acids is likely, when linked to an immunogenic carrier, to elicit an immune response, any given random polypeptide is unlikely to satisfy the stringent definition of "binding protein" with respect to minimum affinity and specificity for its substrate. It is only by testing numerous random polypeptides simultaneously (and, in the usual case, controlling the extent and character of the sequence variation, i.e., limiting it to residues of a potential binding domain having a stable structure, the residues being chosen as more likely to affect binding than stability) that this obstacle is overcome.

In one embodiment, the invention relates to:

a) preparing a variegated population of replicable genetic packages, each package including a nucleic acid construct coding for an outer-surface-displayed potential binding protein other than an antibody, comprising (i) a structural signal directing the display of the protein (or a processed form thereof) on the outer surface of the package and (ii) a potential binding domain for binding said target, where the population collectively displays a multitude of different potential binding domains having a substantially predetermined range of variation in sequence, b) causing the expression of said protein and the display of said protein on the outer surface of such packages, c) contacting the packages with target material, other than an antibody with an exposed antigen-combining site, so that the potential binding domains of the proteins and the target material may interact, and separating packages bearing a potential binding domain that succeeds in binding the target material from packages that do not so bind, d) recovering and replicating at least one package bearing a successful binding domain, e) determining the amino acid sequence of the successful binding domain of a genetic package which bound to the target material, f) preparing a new variegated population of replicable genetic packages according to step (a), the parental potential binding domain for the potential binding domains of said new packages being a successful binding domain whose sequence was determined in step (e), and repeating steps (b)–(e) with said new population, and, when a package bearing a binding domain of desired binding characteristics is obtained, g) abstracting the DNA encoding the desired binding domain from the genetic package and placing it into a suitable expression system. (The binding domain may then be expressed as a unitary protein, or as a domain of a larger protein).

The invention is not, however, limited to proteins with a single BD since the method may be applied to any or all of the BDs of the protein, sequentially or simultaneously. The invention is not, however, limited to biological synthesis of the binding domains; peptides having an amino-acid sequence determined by the isolated DNA can be chemically synthesized.

The invention further relates to a variegated population of genetic packages. Said population may be used by one user to select for binding to a first target, by a second user to select for binding to a second target, and so on, as the present invention does not require that the initial potential binding domain actually bind to the target of interest, and the variegation is at residues likely to affect binding. The invention also relates to the variegated DNA used in preparing such genetic packages.

The invention likewise encompasses the procedure by which the display strategy is verified. The genetic packages are engineered to display a single IPBD sequence. (Variability may be introduced into DNA subsequences adjacent to the ipbd subsequence and within the osp-ipbd gene so that the IPBD will appear on the GP surface.) A molecule, such as an antibody, having high affinity for correctly folded IPBD is used to: a) detect IPBD on the GP surface, b) screen colonies for display of IPBD on the GP surface, or c) select GPs that display IPBD from a population, some members of which might display IPBD on the GP surface. In one preferred embodiment, this verification process (part I) involves:

1) choosing a GP such as a bacterial cell, bacterial spore, or phage, having a suitable outer surface protein (OSP), 2) choosing a stable IPBD, 3) designing an amino acid sequence that: a) includes the IPBD as a subsequence and b) will cause the IPBD to appear on the GP surface, 4) engineering a gene, denoted osp-ipbd, that: a) codes for the designed amino acid sequence, b) provides the necessary genetic regulation, and c) introduces convenient sites for genetic manipulation, 5) cloning the osp-ipbd gene into the GP, and 6) harvesting the transformed GPs and testing them for presence of IPBD on the GP surface; this test is performed with an affinity molecule having high affinity for IPBD, denoted AfM(IPBD).

Once a GP(IPBD) is produced, it can be used many times as the starting point for developing different novel proteins that bind to a variety of different targets. The knowledge of how we engineer the appearance of one IPBD on the surface of a GP can be used to design and produce other GP(IPBD)s that display different IPBDs.

Knowing that a particular genetic package and osp-ipbd fusion are suitable for the practice of the invention, we may variegate the genetic packages and select for binding to a target of interest. Using IPBD as the PPBD to the first cycle of variegation, we prepare a wide variety of osp-pbd genes that encode a wide variety of PBDs. We use an affinity separation to enrich the population of GP(vgPBDs)s for GPs that display PBDs with binding properties relative to the target that are superior to the binding properties of the PPBD. An SBD selected from one variegation Cycle becomes the PPBD to the next variegation cycle. In a preferred embodiment, Part II of the process of the present invention involves:

1) picking a target molecule, and an affinity separation system which selects for proteins having an affinity for that target molecule,
2) picking a GP(IPBD),
3) picking a set of several residues in the PPBD to vary; the principal indicators of which residues to vary include: a) the 3D structure of the IPBD, b) sequences of homologous proteins, and c) computer or theoretical modeling that indicates which residues can tolerate different amino acids without disrupting the underlying structure,
4) picking a subset of the residues picked in Part II.3, to be varied simultaneously; the principal considerations are the number of different variants and which variants are within the detection capabilities of the affinity separation system, and setting the range of variation;
5) implementing the variegation by:
   a) synthesizing the part of the osp-pbd gene that encodes the residues to be varied using a specific mixture of nucleotide substrates for some or all of the bases encoding residues slated for variation, thereby creating a population of DNA molecules, denoted vgDNA,
   b) ligating this vgDNA, by standard methods, into the operative cloning vector (OCV) (e.g. a plasmid or bacteriophage),
   c) using the ligated DNA to transform cells, thereby producing a population of transformed cells,
   d) culturing (i.e. increasing in number) the population of transformed cells and harvesting the population of GP(PBD)s, said population being denoted as GP(vgPBD),
   e) enriching the population for GPs that bind the target by using affinity separation, with the chosen target molecule as affinity molecule,
   f) repeating steps II.5.d and II.5.e until a GP(SBD) having improved binding to the target is isolated, and
   g) testing the isolated SBD or SBDs for affinity and specificity for the chosen target,
6) repeating steps II.3, II.4, and II.5 until the desired degree of binding is obtained.

Part II is repeated for each new target material. Part I need be repeated only if no GP(IPBD) suitable to a chosen target is available.

For each target, there are a large number of SBDs that may be found by the method of the present invention. The process relies on a combination of protein structural considerations, probabilities, and targeted mutations with accumulation of information. To increase the probability that some PBD in the population will bind to the target, we generate as large a population as we can conveniently subject to selection-through-binding in one experiment. Key questions in management of the method are "How many transformants can we produce?", and "How small a component can we find through selection-through-binding?". The optimum level of variegation is determined by the maximum number of transformants and the selection sensitivity, so that for any reasonable sensitivity we may use a progressive process to obtain a series of proteins with higher and higher affinity for the chosen target material.

The appended claims are hereby incorporated by reference into this specification as an enumeration of the preferred embodiments.

BRIEF DESCRIPTION OF THE DRAWINGS

FIG. 16 shows profiles of the elustion of phage that display EpiNE7 and EpiNE7.23 from HNE beads.

DETAILED DESCRIPTION OF THE PREFERRED EMBODIMENTS

Figure 1:
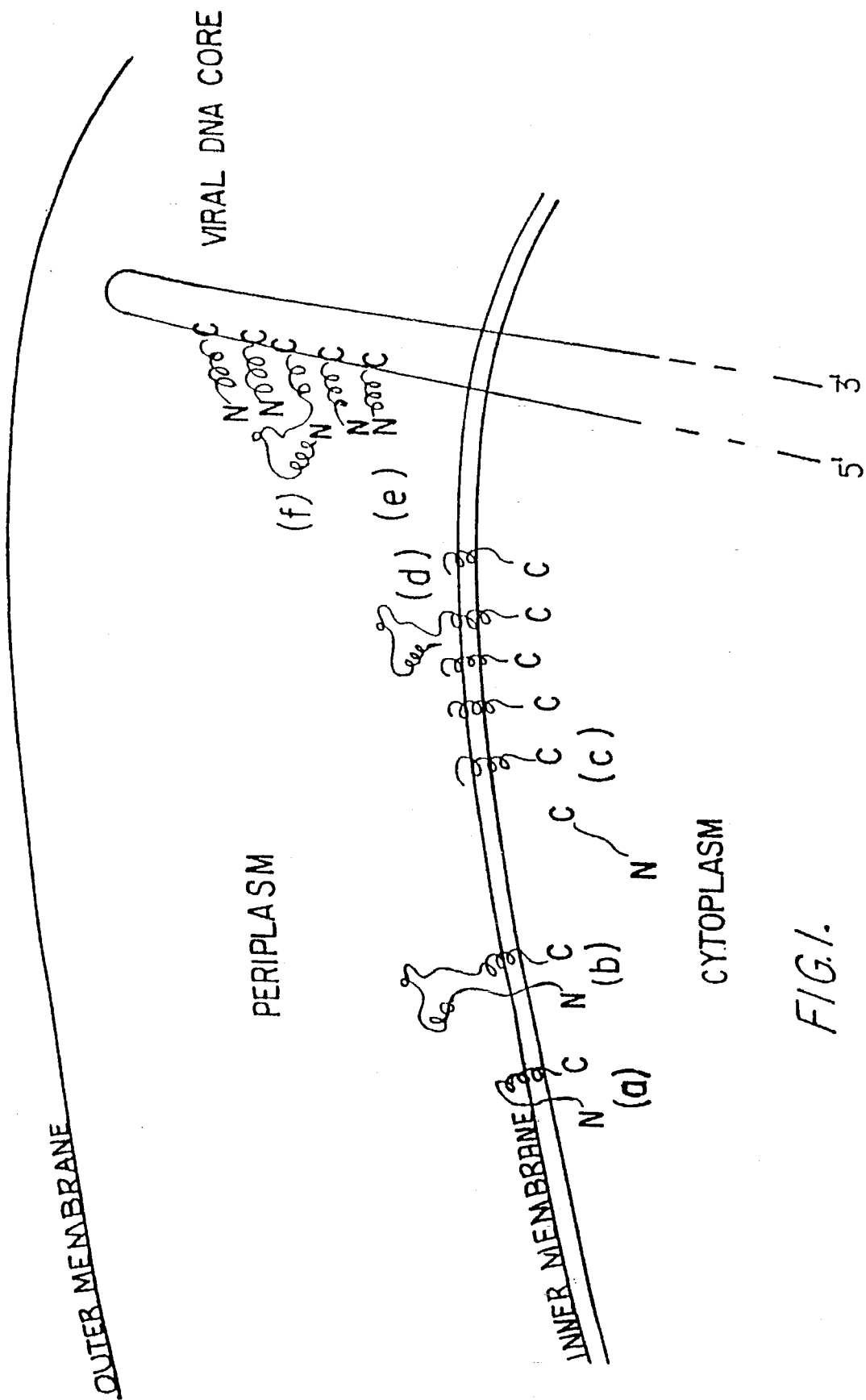
FIG. 1 shows how a phage may be used as a genetic package. At (a) we have a wild-type precoat protein lodged in the lipid bilayer. The signal peptide is in the periplasmic space. At (b), a chimeric precoat protein, with a potential binding domain interposed between the signal peptide and the mature coat protein sequence, is similarly trapped. At (c) and (d), the signal peptide has been cleaved off the wild-type and chimeric proteins, respectively, but certain residues of the coat protein sequence interact with the lipid bilayer to prevent the mature protein from passing entirely into the periplasm. At (e) and (f), mature wild-type and chimeric protein are assembled into the coat of a single stranded DNA phage as it emerges into the periplasmic space. The phage will pass through the outer membrane into the medium where it can be recovered and chromatographically evaluated.
Figure 2:
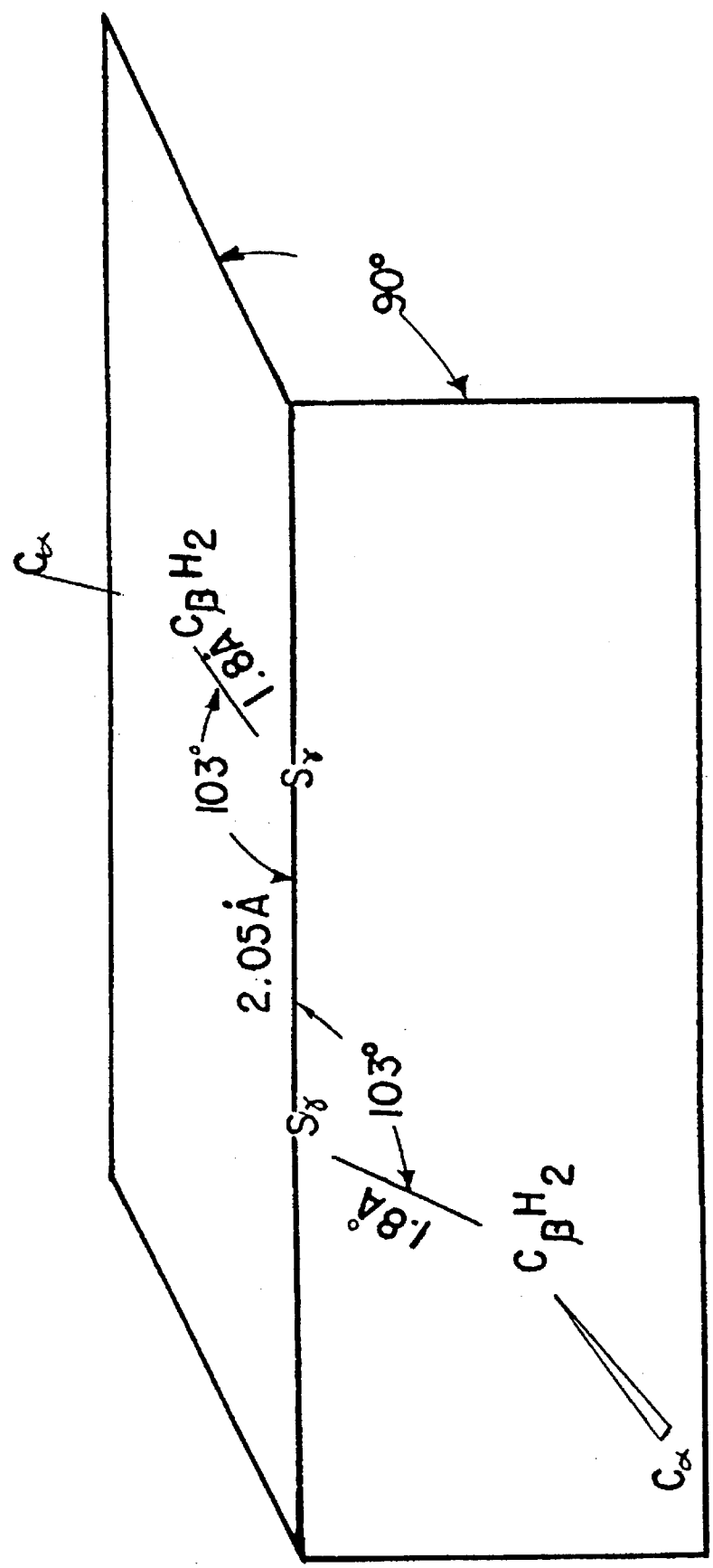
FIG. 2 depicts (a) the optimal stereochemistry of a disulfide bond, based on Creighton, "Disulfide Bonds and Protein Stability" (CREI88) (the two possible torsion angles about the disulfide bond of +90° and −90° are equally likely), and (b) the standard geometric parameters for the disulfide bond, following Katz and Kossiakoff (KATZ86). The average $C\alpha$—$C\alpha$ distance is 5–6 Å, and the typical S—S bond length is ≈2.0 Å. Many left-hand disulfides adopt as a preferred geometry X1=−60°, X2=−60°, X3=−85°, X2'=−60°, X1'=−60°, $C\alpha$—$C\alpha$=5.88 Å; right-hand disulfides are more variable.

OVERVIEW
I. DEFINITIONS AND ABBREVIATIONS
II. THE INITIAL POTENTIAL BINDING DOMAIN

A. Generally

B. Influence of Target Size on Choice of IPBD

C. Influence of Target Charge on Choice of IPBD

D. Other Considerations in the Choice of IPBD

E. Bovine Pancreatic Trypsin Inhibitor (BPTI) as an IPBD

F. Mini-Proteins as IPBDs

G. Modified PBDs

III. VARIEGATION STRATEGY—MUTAGENESIS TO OBTAIN POTENTIAL BINDING DOMAINS WITH DESIRED DIVERSITY

A. Generally

B. Identification of Residues to be Varied

C. Determining the Substitution Set for Each Parental Residue

D. Special Considerations Relating to Variegation of Mini-Proteins with Essential Cysteines E. Planning the Second and Later Rounds of Variegation IV. DISPLAY STRATEGY—DISPLAYING FOREIGN BINDING DOMAINS ON THE SURFACE OF A "GENETIC PACKAGE"

A. General Requirements for Genetic Package

B. Phages for Use as Genetic Packages

C. Bacterial Cells as Genetic Packages

D. Bacterial Spores as Genetic Packages

E. Artificial Outer Surface Protein

F. Designing the osp::ipbd Gene Insert

G. Synthesis of Gene Inserts

H. Operative Cloning Vector

I. Transformation of Cells

J. Verification of Display Strategy

K. Analysis and Correction of Display Problems

V. AFFINITY SELECTION OF TARGET-BINDING MUTANTS

A. Affinity Separation Technology, Generally

B. Affinity Chromatography, Generally

C. Fluorescent-Activated Cell Sorting, Generally

D. Affinity Electrophoresis, Generally

E. Target Materials

F. Immobilization or Labeling of Target Material

G. Elution of Lower Affinity PBD-Bearing Packages

H. Optimization of Affinity Separation

I. Measuring the Sensitivity of Affinity Separation

J. Measuring the Efficiency of Separation

K. Reducing Selection due to Non-Specific Binding

L. Isolation of Genetic Package PBDs with Binding-to-Target Phenotypes

M. Recovery of Packages

N. Amplifying the Enriched Packages

O. Determining Whether Further Enrichment is Needed

P. Characterizing the Putative SBDs

Q. Joint Selections

R. Selection for Non-Binding

S. Selection of Potential Binding Domains for Retention of Structure

T. Engineering of Antagonists

VI. EXPLOITATION OF SUCCESSFUL BINDING DOMAINS AND CORRESPONDING DNAS

A. Generally

B. Production of Novel Binding Proteins

C. Mini-Protein Production

D. Uses of Novel Binding Proteins

VII. EXAMPLES

I. DEFINITIONS AND ABBREVIATIONS

Let $K_d$ (x,y) be a dissociation constant, $$K_d(x, y) = \frac{[x]\,[y]}{[x{:}y]}$$

For the purposes of the appended claims, a protein P is a binding protein if (1) For one molecular, ionic or atomic species A, other than the variable domain of an antibody, the dissociation constant $K_D$ (P,A)$<10^{-6}$ moles/liter (preferably, $<10^{-7}$ moles/liter), and (2) for a different molecular, ionic or atomic species B, $K_D$ (P,B)$>10^{-4}$ moles/liter (preferably, $>10^{-1}$ moles/liter). As a result of these two conditions, the protein P exhibits specificity for A over B, and a minimum degree of affinity (or avidity) for A.

The exclusion of "variable domain of an antibody" in (1) above is intended to make clear that for the purposes herein a protein is not to be considered a "binding protein" merely because it is antigenic. However, an antigen may nonetheless qualify as a binding protein because it specifically binds to a substance other than an antibody, e.g., an enzyme for its substrate, or a hormone for its cellular receptor. Additionally, it should be pointed out that "binding protein" may include a protein which binds specifically to the Fc of an antibody, e.g., staphylococcal protein A.

Normally, the binding protein will not be an antibody or a antigen-binding derivative thereof. An antibody is a crosslinked complex of four polypeptides (two heavy and two light chains). The light chains of IgG have a molecular weight of ≈23,000 daltons and the heavy chains of ≈53,000 daltons. A single binding unit is composed of the variable region of a heavy chain ($V_H$) and the variable region of a light chain ($V_L$), each about 110 amino-acid residues. The $V_H$ and $V_L$ regions are held in proximity by a disulfide bond between the adjoining $C_L$ and $C_{H1}$ regions; altogether, these total 440 residues and correspond to an Fab fragment. Derivatives of antibodies include Fab fragments and the individual variable light and heavy domains. A special case of antibody derivative is a "single chain antibody." A "single-chain antibody" is a single chain polypeptide comprising at least 200 amino acids, said amino acids forming two antigen-binding regions connected by a peptide linker that allows the two regions to fold together to bind the antigen in a manner akin to that of an Fab fragment. Either the two antigen-binding regions must be variable domains of known antibodies, or they must (1) each fold into a β barrel of nine strands that are spatially related in the same way as are the nine strands of known antibody variable light or heavy domains, and (2) fit together in the same way as do the variable domains of said known antibody. Generally speaking, this will require that, with the exception of the amino acids corresponding to the hypervariable region, there is at least 88% homology with the amino acids of the variable domain of a known antibody.

While the present invention may be used to develop novel antibodies through variegation of codons corresponding to the hypervariable region of an antibody's variable domain, its primary utility resides in the development of binding proteins which are not antibodies or even variable domains of antibodies. Novel antibodies can be obtained by immunological techniques; novel enzymes, hormones, etc. cannot.

It will be appreciated that, as a result of evolution, the antigen-obinding domains of antibodies have acquired a structure which tolerates great variability of sequence in the hypervariable regions. The remainder of the variable domain is made up of constant regions forming a distinctive structure, a nine strand β barrel, which hold the hypervariable regions (inter-strand loops) in a fixed relationship with each other. Most other binding proteins lack this molecular design which facilitates diversification of binding characteristics. Consequently, the successful development of novel antibodies by modification of sequences encoding known hypervariable regions—which, in nature, vary from antibody to antibody—does not provide any guidance or assurance of success in the development of novel, non-immunoglobulin binding proteins.

It should further be noted that the affinity of antibodies for their target epitopes is typically on the order of $10^6$ to $10^{10}$ liters/mole; many enzymes exhibit much greater affinities ($10^9$ to $10^{15}$ liters/mole) for their preferred substrates. Thus, if the goal is to develop a binding protein with a very high affinity for a target of interest, e.g., greater than $10^{10}$, the antibody design may in fact be unduly limiting. Furthermore, the complementarity-determining residues of an antibody comprises many residues, 30 to 50. In most cases, it is not known which of these residues participates directly in binding antigen. Thus, picking an antibody as PPBD does not allow us to focus variegation to a small number of residues.

Most larger proteins fold into distinguishable globules called domains (ROSS81). Protein domains have been defined various ways, but all definitions fall into one of three classes: a) those that define a domain in terms of 3D atomic coordinates, b) those that define a domain as an isolable, stable fragment of a larger protein, and c) those that define a domain based on protein sequence homology plus a method from class a) or b). Frequently, different methods of defining domains applied to a single protein yield identical or very similar domain boundaries. The diversity of definitions for domains stems from the many ways that protein domains are perceived to be important, including the concept of domains in predicting the boundaries of stable fragments, and the relationship of domains to protein folding, function, stability, and evolution. The present invention emphasizes the retention of the structured character of a domain even though its surface residues are mutated. Consequently, definitions of "domain" which emphasize stability—retention of the overall structure in the face of perturbing forces such as elevated temperatures or chaotropic agents—are favored, though atomic coordinates and protein sequence homology are not completely ignored.

When a domain of a protein is primarily responsible for the protein's ability to specifically bind a chosen target, it is referred to herein as a "binding domain" (BD). A preliminary operation is to engineer the appearance of a stable protein domain, denoted as an "initial potential binding domain" (IPBD), on the surface of a genetic package.

The term "variegated DNA" (vgDNA) refers to a mixture of DNA molecules of the same or similar length which, when aligned, vary at some codons so as to encode at each such codon a plurality of different amino acids, but which encode only a single amino acid at other codon positions. It is further understood that in variegated DNA, the codons which are variable, and the range and frequency of occurrence of the different amino acids which a given variable codon encodes, are determined in advance by the synthesizer of the DNA, even though the synthetic method does not allow one to know, a priori, the sequence of any individual DNA molecule in the mixture. The number of designated variable codons in the variegated DNA is preferably no more than 20 codons, and more preferably no more than 5–10 codons. The mix of amino acids encoded at each variable codon may differ from codon to codon.

A population of genetic packages into which variegated DNA has been introduced is likewise said to be "variegated".

For the purposes of this invention, the term "potential binding protein" refers to a protein encoded by one species of DNA molecule in a population of variegated DNA wherein the region of variation appears in one or more subsequences encoding one or more segments of the polypeptide having the potential of serving as a binding domain for the target substance.

From time to time, it may be helpful to speak of the "parent sequence" of the variegated DNA. When the novel binding domain sought is an analogue of a known binding domain, the parent sequence is the sequence that encodes the known binding domain. The variegated DNA will be identical with this parent sequence at one or more loci, but will diverge from it at chosen loci. When a potential binding domain is designed from first principles, the parent sequence is a sequence which encodes the amino acid sequence that has been predicted to form the desired binding domain, and the variegated DNA is a population of "daughter DNAs" that are related to that parent by a recognizable sequence similarity.

A "chimeric protein" is a protein composed of a first amino acid sequence substantially corresponding to the sequence of a protein or to a large fragment of a protein (20 or more residues) expressed by the species in which the chimeric protein is expressed and a second amino acid sequence that does not substantially correspond to an amino acid sequence of a protein expressed by the first species but that does substantially correspond to the sequence of a protein expressed by a second and different species of organism. The second sequence is said to be foreign to the first sequence.

One amino acid sequence of the chimeric proteins of the present invention is typically derived from an outer surface protein of a "genetic package" as hereafter defined. The second amino acid sequence is one which, if expressed alone, would have the characteristics of a protein (or a domain thereof) but is incorporated into the chimeric protein as a recognizable domain thereof. It may appear at the amino or carboxy terminal of the first amino acid sequence (with or without an intervening spacer), or it may interrupt the first amino acid sequence. The first amino acid sequence may correspond exactly to a surface protein of the genetic package, or it may be modified, e.g., to facilitate the display of the binding domain.

In the present invention, the words "select" and "selection" are used in the genetic sense; i.e. a biological process whereby a phenotypic characteristic is used to enrich a population for those organisms displaying the desired phenotype.

One affinity separation is called a "separation cycle"; one pass of variegation followed by as many separation cycles as are needed to isolate an SBD, is called a "variegation cycle". The amino acid sequence of one SBD from one round becomes the PPBD to the next variegation cycle. We perform variegation cycles iteratively until the desired affinity and specificity of binding between an SBD and chosen target are achieved.

The following abbreviations will be used throughout the present specification:

| Abbreviation | Meaning |
| --- | --- |
| GP | Genetic Package, e.g. a bacteriophage |
| wtGP | Wild-type GP |
| X | Any protein |
| x | The gene for protein X |
| BD | Binding Domain |
| BPTI | Bovine pancreatic trypsin inhibitor, identical to aprotinin (Merck Index, entry 784, p. 119) |
| IPBD | Initial Potential Binding Domain, e.g. BPTI |
| PBD | Potential Binding Domain, e.g. a derivative of BPTI |
| SBD | Successful Binding Domain, e.g. a derivative of BPTI selected for binding to a target |
| PPBD | Parental Potential Binding Domain, i.e. an IPBD or an SBD from a previous selection |
| OSP | Outer Surface Protein, e.g. coat protein of a phage or LamB from *E. coli* |
| OSP-PBD | Fusion of an OSP and a PBD, order of fusion not specified |
| OSTS | Outer Surface Transport Signal |
| GP(x) | A genetic package containing the x gene |
| GP(X) | A genetic package that displays X on its outer surface |
| GP(osp-pbd) | GP containing an osp-pbd gene |
| GP(OSP-PBD) | A genetic package that displays PBD on its outside as a fusion to OSP |
| GP(pbd) | GP containing a pbd gene, osp implicit |
| GP(PBD) | A genetic package displaying PBD on its outside, OSP unspecified |
| {Q} | An affinity matrix supporting "Q", e.g. {T4 lysozyme} is T4 lysozyme attached to an affinity matrix |
| AfM (W) | A molecule having affinity for "W", e.g. trypsin is an AfM(BPTI) |
| AfM(W)* | AFM(W) carrying a label, e.g. $125_I$ |
| XINDUCE | A chemical that can induce expression of a gene, e.g. IPTG for the lacUV5 promoter |
| OCV | Operative Cloning Vector |
| $K_d$ | A bimolecular dissociation constant, $K_d = [A][B]/[A:B]$ |
| $K_T$ | $K_T = [T][SBD]/[T:SBD]$ (T is a target) |
| $K_N$ | $K_N = [N][SBD]/[N:SBD]$ (N is a non-target) |
| DoAMoM | Density of AFM(W) on affinity matrix |
| mfaa | Most-Favored amino acid |
| lfaa | Least-Favored amino acid |
| Abun (x) | Abundance of DNA molecules encoding amino acid x |
| OMP | Outer membrane protein |
| nt | nucleotide |
| SP-I | Signal-sequence Peptidase I |
| $Y_{DQ}$ | Yield of ssDNA up to Q bases long |
| $M_{DNA}$ | Maximum length of ssDNA that can be synthesized in acceptable yield |
| Ypl | Yield of plasmid DNA per volume of culture |
| $L_{eff}$ | DNA ligation efficiency |
| $M_{ntv}$ | Maximum number of transformants produced from $Y_{D100}$ DNA of Insert |
| $C_{eff}$ | Efficiency of chromatographic enrichment, enrichment per pass |
| $C_{sensi}$ | Sensitivity of chromatographic separation, can find 1 in N, |
| $N_{chrom}$ | Maximum number of enrichment cycles per variegation cycle |
| $S_{err}$ | Error level in synthesizing vgDNA |
| ::  | in-frame genetic fusion or protein produced from in-frame fused gene |

Single-letter codes for amino acids and nucleotides are given in Table 1.

II. THE INITIAL POTENTIAL BINDING DOMAIN (IPBD):

II.A. Generally

The initial potential binding domain may be: 1) a domain of a naturally occurring protein, 2) a non-naturally occurring domain which substantially corresponds in sequence to a naturally occurring domain, but which differs from it in sequence by one or more substitutions, insertions or deletions, 3) a domain substantially corresponding in sequence to a hybrid of subsequences of two or more naturally occurring proteins, or 4) an artificial domain designed entirely on theoretical grounds based on knowledge of amino acid geometries and statistical evidence of secondary structure preferences of amino acids. (However, the limitations of a priori protein design prompted the present invention.) Usually, the domain will be a known binding domain, or at least a homologue thereof, but it may be derived from a protein which, while not possessing a known binding activity, possesses a secondary or higher structure that lends itself to binding activity (clefts, grooves, etc.). The protein to which the IPBD is related need not have any specific affinity for the target material.

In determining whether sequences should be deemed to "substantially correspond", one should consider the following issues: the degree of sequence similarity when the sequences are aligned for best fit according to standard algorithms, the similarity in the connectivity patterns of any crosslinks (e.g., disulfide bonds), the degree to which the proteins have similar three-dimensional structures, as indicated by, e.g., X-ray diffraction analysis or NMR, and the degree to which the sequenced proteins have similar biological activity. In this context, it should be noted that among the serine protease inhibitors, there are families of proteins recognized to be homologous in which there are pairs of members with as little as 30% sequence homology.

A candidate IPBD should meet the following criteria:

1) a domain exists that will remain stable under the conditions of its intended use (the domain may comprise the entire protein that will be inserted, e.g. BPTI, α-conotoxin GI, or CMTI-III), 2) knowledge of the amino acid sequence is obtainable, and 3) a molecule is obtainable having specific and high affinity for the IPBD, AfM(IPBD).

Preferably, in order to guide the variegation strategy, knowledge of the identity of the residues on the domain's outer surface, and their spatial relationships, is obtainable; however, this consideration is less important if the binding domain is small, e.g., under 40 residues.

Preferably, the IPBD is no larger than necessary because small SBDs (for example, less than 30 amino acids) can be chemically synthesized and because it is easier to arrange restriction sites in smaller amino-acid sequences. For PBDs smaller than about 40 residues, an added advantage is that the entire variegated pbd gene can be synthesized in one piece. In that case, we need arrange only suitable restriction sites in the osp gene. A smaller protein minimizes the metabolic strain on the GP or the host of the GP. The IPBD is preferably smaller than about 200 residues. The IPBD must also be large enough to have acceptable binding affinity and specificity. For an IPBD lacking covalent crosslinks, such as disulfide bonds, the IPBD is preferably at least 40 residues; it may be as small as six residues if it contains a crosslink. These small, crosslinked IPBDs, known as "miniproteins", are discussed in more detail later in this section.

Some candidate IPBDs, which meet the conditions set forth above, will be more suitable than others. Information about candidate IPBDs that will be used to judge the suitability of the IPBD includes: 1) a 3D structure (knowledge strongly preferred), 2) one or more sequences homologous to the IPBD (the more homologous sequences known, the better), 3) the pI of the IPBD (knowledge desirable when target is highly charged), 4) the stability and solubility as a function of temperature, pH and ionic strength (preferably known to be stable over a wide range and soluble in conditions of intended use), 5) ability to bind metal ions such as $Ca^{++}$ or $Mg^{++}$ (knowledge preferred; binding per se, no preference), 6) enzymatic activities, if any (knowledge preferred, activity per se has uses but may cause problems), 7) binding properties, if any (knowledge preferred, specific binding also preferred), 8) availability of a molecule having specific and strong affinity ($K_d < 10^{-11}$M) for the IPBD (preferred), 9) availability of a molecule having specific and medium affinity ($10^{-8}$M$<K_d<10^{-6}$M) for the IPBD (preferred), 10) the sequence of a mutant of IPBD that does not bind to the affinity molecule(s) (preferred), and 11) absorption spectrum in visible, UV, NMR, etc. (characteristic absorption preferred).

If only one species of molecule having affinity for IPBD (AfM(IPBD)) is available, it will be used to: a) detect the IPBD on the GP surface, b) optimize expression level and density of the affinity molecule on the matrix, and c) determine the efficiency and sensitivity of the affinity separation. As noted above, however, one would prefer to have available two species of AfM(IPBD), one with high and one with moderate affinity for the IPBD. The species with high affinity would be used in initial detection and in determining efficiency and sensitivity, and the species with moderate affinity would be used in optimization.

If the IPBD is not itself a binding domain of a known binding protein, or if its native target has not been purified, an antibody raised against the IPBD may be used as the affinity molecule. Use of an antibody for this purpose should not be taken to mean that the antibody is the ultimate target.

There are many candidate IPBDs for which all of the above information is available or is reasonably practical to obtain, for example, bovine pancreatic trypsin inhibitor (BPTI, 58 residues), CMTI-III (29 residues), crambin (46 residues), third domain of ovomucoid (56 residues), heat-stable enterotoxin (ST-Ia of *E. coli*) (18 residues), α-conotoxin GI (13 residues), μ-Conotoxin GIII (22 residues), Conus King Kong mini-protein (27 residues), T4 lysozyme (164 residues), and azurin (128 residues). Structural information can be obtained from X-ray or neutron diffraction studies, NMR, chemical cross linking or labeling, modeling from known structures of related proteins, or from theoretical calculations. 3D structural information obtained by X-ray diffraction, neutron diffraction or NMR is preferred because these methods allow localization of almost all of the atoms to within defined limits. Table 50 lists several preferred IPBDs. Works related to determination of 3D structure of small proteins via NMR include: CHAZ85, PEAS90, PEAS88, CLOR86, CLOR87a, HEIT89, LECO87, WAGN79, and PARD89.

In some cases, a protein having some affinity for the target may be a preferred IPBD even though some other criteria are not optimally met. For example, the V1 domain of CD4 is a good choice as IPBD for a protein that binds to gp120 of HIV. It is known that mutations in the region 42 to 55 of V1 greatly affect gp120 binding and that other mutations either have much less effect or completely disrupt the structure of V1. Similarly, tumor necrosis factor (TNF) would be a good initial choice if one wants a TNF-like molecule having higher affinity for the TNF receptor.

Membrane-bound proteins are not preferred IPBPs, though they may serve as a source of outer surface transport signals. One should distinguish between membrane-bound proteins, such as LamB or OmpF, that cross the membrane several times forming a structure that is embedded in the lipid bilayer and in which the exposed regions are the loops that join trans-membrane segments, from non-embedded proteins, such as the soluble domains of CD4, that are simply anchored to the membrane. This is an important distinction because it is quite difficult to create a soluble derivative of a membrane-bound protein. Soluble binding proteins are in general more useful since purification is simpler and they are more tractable and more versatile assay reagents.

Most of the PBDs derived from a PPBD according to the process of the present invention will have been derived by variegation at residues having side groups directed toward the solvent. Reidhaar-Olson and Sauer (REID88a) found that exposed residues can accept a wide range of amino acids, while buried residues are more limited in this regard. Surface mutations typically have only small effects on melting temperature of the PBD, but may reduce the stability of the PBD. Hence the chosen IPBD should have a high melting temperature (50° C. acceptable, the higher the better; BPTI melts at 95° C.) and be stable over a wide pH range (8.0 to 3.0 acceptable; 11.0 to 2.0 preferred), so that the SBDs derived from the chosen IPBD by mutation and selection-through-binding will retain sufficient stability. Preferably, the substitutions in the IPBD yielding the various PBDs do not reduce the melting point of the domain below ≈40° C. Mutations may arise that increase the stability of SBDs relative to the IPBD, but the process of the present invention does not depend upon this occurring. Proteins containing covalent crosslinks, such as multiple disulfides, are usually sufficient stable. A protein having at least two disulfides and having at least 1 disulfide per every twenty residues may be presumed to be sufficiently stable.

Two general characteristics of the target molecule, size and charge, make certain classes of IPBDs more likely than other classes to yield derivatives that will bind specifically to the target. Because these are very general characteristics, one can divide all targets into six classes: a) large positive, b) large neutral, c) large negative, d) small positive, e) small neutral, and f) small negative. A small collection of IPBDs, one or a few corresponding to each class of target, will contain a preferred candidate IPBD for any chosen target.

Alternatively, the user may elect to engineer a GP(IPBD) for a particular target; criteria are given below that relate target size and charge to the choice of IPBD.

II.B. Influence of target size on choice of IPBD:

If the target is a protein or other macromolecule a preferred embodiment of the IPBD is a small protein such as the *Cucurbita maxima* trypsin inhibitor III (29 residues), BPTI from Bos Taurus (58 residues), crambin from rape seed (46 residues), or the third domain of ovomucoid from Coturnix coturnix Japonica (Japanese quail) (56 residues), because targets from this class have clefts and grooves that can accommodate small proteins in highly specific ways. If the target is a macromolecule lacking a compact structure, such as starch, it should be treated as if it were a small molecule. Extended macromolecules with defined 3D structure, such as collagen, should be treated as large molecules.

If the target is a small molecule, such as a steroid, a preferred embodiment of the IPBD is a protein of about 80–200 residues, such as ribonuclease from *Bos taurus* (124 residues), ribonuclease from *Aspergillus oruzae* (104 residues), hen egg white lysozyme from *Gallus gallus* (129 residues), azurin from *Pseudomonas aerugenosa* (128 residues), or T4 lysozyme (164 residues), because such proteins have clefts and grooves into which the small target molecules can fit. The Brookhaven Protein Data Bank contains 3D structures for all of the proteins listed. Genes encoding proteins as large as T4 lysozyme can be manipulated by standard techniques for the purposes of this invention.

If the target is a mineral, insoluble in water, one considers the nature of the molecular surface of the mineral. Minerals that have smooth surfaces, such as crystalline silicon, are best addressed with medium to large proteins, such as ribonuclease, as IPBD in order to have sufficient contact area and specificity. Minerals with rough, grooved surfaces, such as zeolites, could be bound either by small proteins, such as BPTI, or larger proteins, such as T4 lysozyme.

II.C. Influence of target charge on choice of IPBD:

Electrostatic repulsion between molecules of like charge can prevent molecules with highly complementary surfaces from binding. Therefore, it is preferred that, under the conditions of intended use, the IPBD and the target molecule either have opposite charge or that one of them is neutral. In some cases it has been observed that protein molecules bind in such a way that like charged groups are juxtaposed by including oppositely charged counter ions in the molecular interface. Thus, inclusion of counter ions can reduce or eliminate electrostatic repulsion and the user may elect to include ions in the eluants used in the affinity separation step. Polyvalent ions are more effective at reducing repulsion than monovalent ions.

II.D. Other considerations in the choice of IPBD:

If the chosen IPBD is an enzyme, it may be necessary to change one or more residues in the active site to inactivate enzyme function. For example, if the IPBD were T4 lysozyme and the GP were *E. coli* cells or M13, we would need to inactivate the lysozyme because otherwise it would lyse the cells. If, on the other hand, the GP were ΦX174, then inactivation of lysozyme may not be needed because T4 lysozyme can be overproduced inside *E. coli* cells without detrimental effects and ΦX174 forms intracellularly. It is preferred to inactivate enzyme IPBDs that might be harmful to the GP or its host by substituting mutant amino acids at one or more residues of the active site. It is permitted to vary one or more of the residues that were changed to abolish the original enzymatic activity of the IPBD. Those GPs that receive osp-pbd genes encoding an active enzyme may die, but the majority of sequences will not be deleterious.

If the binding protein is intended for therapeutic use in humans or animals, the IPBD may be chosen from proteins native to the designated recipient to minimize the possibility of antigenic reactions.

II.E. Bovine Pancreatic Trypsin Inhibitor (BPTI) as an IPBD:

BPTI is an especially preferred IPBD because it meets or exceeds all the criteria: it is a small, very stable protein with a well known 3D structure. Marks et al. (MARK86) have shown that a fusion of the phoA signal peptide gene fragment and DNA coding for the mature form of BPTI caused native BPTI to appear in the periplasm of *E. coli*, demonstrating that there is nothing in the structure of BPTI to prevent its being secreted.

The structure of BPTI is maintained even when one or another of the disulfides is removed, either by chemical blocking or by genetic alteration of the amino-acid sequence. The stabilizing influence of the disulfides in BPTI is not equally distributed. Goldenberg (GOLD85) reports that blocking CYS14 and CYS38 lowers the Tm of BPTI to ≈75° C. while chemical blocking of either of the other disulfides lowers Tm to below 40° C. Chemically blocking a disulfide may lower Tm more than mutating the cysteines to other amino-acid types because the bulky blocking groups are more destabilizing than removal of the disulfide. Marks et al. (MARK87) replaced both CYS14 and CYS38 with either two alanines or two threonines. The CYS14/CYS38 cystine bridge that Marks et al. removed is the one very close to the scissile bond in BPTI; surprisingly, both mutant molecules functioned as trypsin inhibitors. Schnabel et al. (SCHN86) report preparation of aprotinin (C14A,C38A) by use of Raney nickel. Eigenbrot et al. (EIGE90) report the X-ray structure of BPTI(C30A/C51A) which is stable to at least 50° C. The backbone of this mutant is as similar to BPTI as are the backbones of BPTI molecules that sit in different crystal lattices. This indicates that BPTI is redundantly stable and so is likely to fold into approximately the same structure despite numerous surface mutations. Using the knowledge of homologues, vide infra, we can infer which residues should not be varied if the basic BPTI structure is to be maintained.

The 3D structure of BPTI has been determined at high resolution by X-ray diffraction (HUBE77, MARQ83, WLOD84, WLOD87a, WLOD87b), neutron diffraction (WLOD84), and by NMR (WAGN87). In one of the X-ray structures deposited in the Brookhaven Protein Data Bank, entry 6PTI, there was no electron density for A58, indicating that A58 has no uniquely defined conformation. Thus we know that the carboxy group does not make any essential interaction in the folded structure. The amino terminus of BPTI is very near to the carboxy terminus. Goldenberg and Creighton reported on circularized BPTI and circularly permuted BPTI (GOLD83). Some proteins homologous to BPTI have more or fewer residues at either terminus.

BPTI has been called "the hydrogen atom of protein folding" and has been the subject of numerous experimental and theoretical studies (STAT87, SCHW87, GOLD83, CHAZ83, CREI74, CREI77a, CREI77b, CREI80, SIEK87, SINH90, RUEH73, HUBE74, HUBE75, HUBE77 and others).

BPTI has the added advantage that at least 59 homologous proteins are known. Table 13 shows the sequences of 39 homologues. A tally of ionizable groups in 59 homologues is shown in Table 14 and the composite of amino acid types occurring at each residue is shown in Table 15.

BPTI is freely soluble and is not known to bind metal ions. BPTI has no known enzymatic activity. BPTI is not toxic.

All of the conserved residues are buried; of the six fully conserved residues only G37 has noticeable exposure. The solvent accessibility of each residue in BPTI is given in Table 16 which was calculated from the entry "6PTI" in the Brookhaven Protein Data Bank with a solvent radius of 1.4 Å, the atomic radii given in Table 7, and the method of Lee and Richards (LEEB71). Each of the 52 non-conserved residues can accommodate two or more kinds of amino acids. By independently substituting at each residue only those amino acids already observed at that residue, we could obtain approximately $1.6 \cdot 10^{43}$ different amino acid sequences, most of which will fold into structures very similar to BPTI.

BPTI will be especially useful as a IPBD for macromolecular targets. BPTI and BPTI homologues bind tightly and with high specificity to a number of enzyme macromolecules.

BPTI is strongly positively charged except at very high pH, thus BPTI is useful as IPBD for targets that are not also strongly positive under the conditions of intended use. There exist homologues of BPTI, however, having quite different charges (viz. SCI-III from *Bombyx mori* at −7 and the trypsin inhibitor from bovine colostrum at −1). Once a genetic package is found that displays BPTI on its surface, the sequence of the BPTI domain can be replaced by one of the homologous sequences to produce acidic or neutral IPBDs.

BPTI is quite small; if this should cause a pharmacological problem, two or more BPTI-derived domains may be joined as in humans BPTI homologues, one of which has two domains (BALD85, ALBR83b) and another has three (WUNT88).

Another possible pharmacological problem is immunigenicity. BPTI has been used in humans with very few adverse effects. Siekmann et al. (SIEK89) have studied immunological characteristics of BPTI and some homologues. It is an advantage of the method of the present invention that a variety of SBDs can be obtained so that, if one derivative proves to be antigenic, a different SBD may be used. Furthermore, one can reduce the probability of immune response by starting with a human protein, such as LACI (a BPTI homologue) (WUNT88, GIRA89) or Inter-α-Trypsin Inhibitor (ALBR83a, ALBR83b, DIAR90, ENGH89, TRIB86, GEBH86, GEBH90, KAUM86, ODOM90, SALI90).

Further, a BPTI-derived gene fragment, coding for a novel binding domain, could be fused in-frame to a gene fragment coding for other proteins, such as serum albumin or the constant parts of IgG.

Tschesche et al. (TSCH87) reported on the binding of several BPTI derivatives to various proteases:

| | Dissociation constants for BPTI derivatives, Molar. | | | |
|---|---|---|---|---|
| Residue #15 | Trypsin (bovine pancreas) | Chymo-trypsin (bovine pancreas) | Elastase (porcine pancreas) | Elastase (human leukocytes) |
| lysine | $6.0 \cdot 10^{-14}$ | $9.0 \cdot 10^{-9}$ | − | $3.5 \cdot 10^{-6}$ |
| glycine | − | − | + | $7.0 \cdot 10^{-9}$ |
| alanine | + | − | $2.8 \cdot 10^{-8}$ | $2.5 \cdot 10^{-9}$ |
| valine | − | − | $5.7 \cdot 10^{-8}$ | $1.1 \cdot 10^{-10}$ |
| leucine | − | − | $1.9 \cdot 10^{-8}$ | $2.9 \cdot 10^{-9}$ |

From the report of Tschesche et al. we infer that molecular pairs marked "+" have $K_d s \geq 3.5 \cdot 10^{-6} M$ and that molecular pairs marked "−" have $K_d s >> 3.5 \cdot 10^{-6} M$. Because of the wealth of data about the binding of BPTI and various mutants to trypsin and other proteases (TSCH87), we can proceed in various ways in optimizing the affinity separation conditions. (For other PBDs, we can obtain two different monoclonal antibodies, one with a high affinity having $K_d$ of order $10^{-11} M$, and one with a moderate affinity having $K_d$ on the order of $10^{-6} M$.)

Works concerning BPTI and its homologues include: KIDO88, PONT88, KIDO90, AUER87, AUER90, SCOT87b, AUER88, AUER89, BECK88b, WACH79, WACH80, BECK89a, DUFT85, FIOR88, GIRA89, GOLD84, GOLD88, HOCH84, RITO83, NORR89a, NORR89b, OLTE89, SWAI88, and WAGN79.

II.F. Mini-Proteins as IPBDs:

A polypeptide is a polymer composed of a single chain of the same or different amino acids joined by peptide bonds. Linear peptides can take up a very large number of different conformations through internal rotations about the main chain single bonds of each α carbon. These rotations are hindered to varying degrees by side groups, with glycine interfering the least, and valine, isoleucine and, especially, proline, the most. A polypeptide of 20 residues may have $10^{20}$ different conformations which it may assume by various internal rotations.

Proteins are polypeptides which, as a result of stabilizing interactions between amino acids that are not in adjacent positions in the chain, have folded into a well-defined conformation. This folding is usually essential to their biological activity.

For polypeptides of 40–60 residues or longer, noncovalent forces such as hydrogen bonds, salt bridges, and hydrophobic "interactions" are sufficient to stabilize a particular folding or conformation. The polypeptide's constituent segments are held to more or less that conformation unless it is perturbed by a denaturant such as rising temperature or decreasing pH, whereupon the polypeptide unfolds or "melts". The smaller the peptide, the more likely it is that its conformation will be determined by the environment. If a small unconstrained peptide has biological activity, the peptide ligand will be in essence a random coil until it comes into proximity with its receptor. The receptor accepts the peptide only in one or a few conformations because alternative conformations are disfavored by unfavorable van der Waals and other non-covalent interactions.

Small polypeptides have potential advantages over larger polypeptides when used as therapeutic or diagnostic agents, including (but not limited to):

a) better penetration into tissues,
b) faster elimination from the circulation (important for imaging agents),
c) lower antigenicity, and
d) higher activity per mass.

Moreover, polypeptides of under about 50 residues have the advantage of accessibility via chemical synthesis; polypeptides of under about 30 residues are more easily synthesized than are larger polypeptides. Thus, it would be desirable to be able to employ the combination of variegation and affinity selection to identify small polypeptides which bind a target of choice.

Polypeptides of this size, however, have disadvantages as binding molecules. According to Olivera et al. (OLIV90a): "Peptides in this size range normally equilibrate among many conformations (in order to have a fixed conformation, proteins generally have to be much larger)." Specific binding of a peptide to a target molecule requires the peptide to take up one conformation that is complementary to the binding site. For a decapeptide with three isoenergetic conformations (e.g., β strand, α helix, and reverse turn) at each residue, there are about $6 \cdot 10^4$ possible overall conformations. Assuming these conformations to be equi-probable for the unconstrained decapeptide, if only one of the possible conformations bound to the binding site, then the affinity of the peptide for the target would expected to be about $6 \cdot 10^4$ higher if it could be constrained to that single effective conformation. Thus, the unconstrained decapeptide, relative to a decapeptide constrained to the correct conformation, would be expected to exhibit lower affinity. It would also exhibit lower specificity, since one of the other conformations of the unconstrained decapeptide might be one which bound tightly to a material other than the intended target. By way of corollary, it could have less resistance to degradation by proteases, since it would be more likely to provide a binding site for the protease.

In one embodiment, the present invention overcomes these problems, while retaining the advantages of smaller polypeptides, by fostering the biosynthesis of novel mini-proteins having the desired binding characteristics. Mini-Proteins are small polypeptides (usually less than about 60 residues) which, while too small to have a stable conformation as a result of noncovalent forces alone, are covalently crosslinked (e.g., by disulfide bonds) into a stable conformation and hence have biological activities more typical of larger protein molecules than of unconstrained polypeptides of comparable size.

When mini-proteins are variegated, the residues which are covalently crosslinked in the parental molecule are left unchanged, thereby stabilizing the conformation. For example, in the variegation of a disulfide bonded mini-protein, certain cysteines are invariant so that under the conditions of expression and display, covalent crosslinks (e.g., disulfide bonds between one or more pairs of cysteines) form, and substantially constrain the conformation which may be adopted by the hypervariable linearly intermediate amino acids. In other words, a constraining scaffolding is engineered into polypeptides which are otherwise extensively randomized.

Once a mini-protein of desired binding characteristics is characterized, it may be produced, not only by recombinant DNA techniques, but also by nonbiological synthetic methods.

In vitro, disulfide bridges can form spontaneously in polypeptides as a result of air oxidation. Matters are more complicated in vivo. Very few intracellular proteins have disulfide bridges, probably because a strong reducing environment is maintained by the glutathione system. Disulfide bridges are common in proteins that travel or operate in intracellular spaces, such as snake venoms and other toxins (e.g., conotoxins, charybdotoxin, bacterial enterotoxins), peptide hormones, digestive enzymes, complement proteins, immunoglobulins, lysozymes, protease inhibitors (BPTI and its homologues, CMTI-III (*Cucurbita maxima* trypsin inhibitor III) and its homologues, hirudin, etc.) and milk proteins.

Disulfide bonds that close tight intrachain loops have been found in pepsin, thioredoxin, insulin A-chain, silk fibroin, and lipoamide dehydrogenase. The bridged cysteine residues are separated by one to four residues along the polypeptide chain. Model building, X-ray diffraction analysis, and NMR studies have shown that the α carbon path of such loops is usually flat and rigid.

There are two types of disulfide bridges in immunoglobulins. One is the conserved intrachain bridge, spanning about 60 to 70 amino acid residues and found, repeatedly, in almost every immunoglobulin domain. Buried deep between the opposing β sheets, these bridges are shielded from solvent and ordinarily can be reduced only in the presence of denaturing agents. The remaining disulfide bridges are mainly interchain bonds and are located on the surface of the molecule; they are accessible to solvent and relatively easily reduced (STEI85). The disulfide bridges of the mini-proteins of the present invention are intrachain linkages between cysteines having much smaller chain spacings.

For the purpose of the appended claims, a mini-protein has between about eight and about sixty residues. However, it will be understood that a chimeric surface protein presenting a mini-protein as a domain will normally have more than sixty residues. Polypeptides containing intrachain disulfide bonds may be characterized as cyclic in nature, since a closed circle of covalently bonded atoms is defined by the two cysteines, the intermediate amino acid residues, their peptidyl bonds, and the disulfide bond. The terms "cycle", "span" and "segment" will be used to define certain structural features of the polypeptides. An intrachain disulfide bridge connecting amino acids 3 and 8 of a 16 residue polypeptide will be said herein to have a cycle of 6 and a span of 4. If amino acids 4 and 12 are also disulfide bonded, then they form a second cycle of 9 with a span of 7. Together, the four cysteines divide the polypeptide into four intercysteine segments (1–2, 5–7, 9–11, and 13–16). (Note that there is no segment between Cys3 and Cys4.)

The connectivity pattern of a crosslinked mini-protein is a simple description of the relative location of the termini of the crosslinks. For example, for a mini-protein with two disulfide bonds, the connectivity pattern "1–3, 2–4" means that the first crosslinked cysteine is disulfide bonded to the third crosslinked cysteine (in the primary sequence), and the second to the fourth.

The degree to which the crosslink constrains the conformational freedom of the mini-protein, and the degree to which it stabilizes the mini-protein, may be assessed by a number of means. These include absorption spectroscopy (which can reveal whether an amino acid is buried or exposed), circular dichroism studies (which provides a general picture of the helical content of the protein), nuclear magnetic resonance imaging (which reveals the number of nuclei in a particular chemical environment as well as the mobility of nuclei), and X-ray or neutron diffraction analysis of protein crystals. The stability of the mini-protein may be ascertained by monitoring the changes in absorption at various wavelengths as a function of temperature, pH, etc.; buried residues become exposed as the protein unfolds. Similarly, the unfolding of the mini-protein as a result of denaturing conditions results in changes in NMR line positions and widths. Circular dichroism (CD) spectra are extremely sensitive to conformation.

The variegated disulfide-bonded mini-proteins of the present invention fall into several classes.

Class I mini-proteins are those featuring a single pair of cysteines capable of interacting to form a disulfide bond, said bond having a span of no more than nine residues. This disulfide bridge preferably has a span of at least two residues; this is a function of the geometry of the disulfide bond. When the spacing is two or three residues, one residue is preferably glycine in order to reduce the strain on the bridged residues. The upper limit on spacing is less precise, however, in general, the greater the spacing, the less the constraint on conformation imposed on the linearly intermediate amino acid residues by the disulfide bond.

The main chain of such a peptide has very little freedom, but is not stressed. The free energy released when the disulfide forms exceeds the free energy lost by the main-chain when locked into a conformation that brings the cysteines together. Having lost the free energy of disulfide formation, the proximal ends of the side groups are held in more or less fixed relation to each other. When binding to a target, the domain does not need to expend free energy getting into the correct conformation. The domain can not jump into some other conformation and bind a non-target.

A disulfide bridge with a span of 4 or 5 is especially preferred. If the span is increased to 6, the constraining influence is reduced. In this case, we prefer that at least one of the enclosed residues be an amino acid that imposes restrictions on the main-chain geometry. Proline imposes the most restriction. Valine and isoleucine restrict the main chain to a lesser extent. The preferred position for this constraining non-cysteine residue is adjacent to one of the invariant cysteines, however, it may be one of the other bridged residues. If the span is seven, we prefer to include two amino acids that limit main-chain conformation. These amino acids could be at any of the seven positions, but are preferably two bridged residues that are immediately adjacent to the cysteines. If the span is eight or nine, additional constraining amino acids may be provided.

The disulfide bond of a class I mini-proteins is exposed to solvent. Thus, one should avoid exposing the variegated population of GPs that display class I mini-proteins to reagents that rupture disulfides; Creighton names several such reagents (CREI88).

Class II mini-proteins are those featuring a single disulfide bond having a span of greater than nine amino acids. The bridged amino acids form secondary structures which help to stabilize their conformation. Preferably, these intermediate amino acids form hairpin supersecondary structures such as those schematized below:

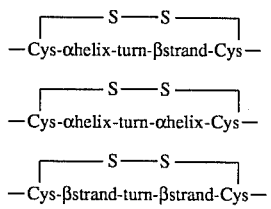

Secondary structures are stabilized by hydrogen bonds between amide nitrogen and carbonyl groups, by interactions between charged side groups and helix dipoles, and by van der Waals contacts. One abundant secondary structure in proteins is the α-helix. The α helix has 3.6 residues per turn, a 1.5 Å rise per residue, and a helical radius of 2.3 Å. All observed α-helices are right-handed. The torsion angles φ (−57°) and ψ (−47°) are favorable for most residues, and the hydrogen bond between the backbone carbonyl oxygen of each residue and the backbone NH of the fourth residue along the chain is 2.86 Å long (nearly the optimal distance) and virtually straight. Since the hydrogen bonds all point in the same direction, the α helix has a considerable dipole moment (carboxy terminus negative).

The β strand may be considered an elongated helix with 2.3 residues per turn, a translation of 3.3 Å per residue, and a helical radius of 1.0 Å. Alone, a β strand forms no main-chain hydrogen bonds. Most commonly, β strands are found in twisted (rather than planar) parallel, antiparallel, or mixed parallel/antiparallel sheets.

A peptide chain can form a sharp reverse turn. A reverse turn may be accomplished with as few as four amino acids. Reverse turns are very abundant, comprising a quarter of all residues in globular proteins. In proteins, reverse turns commonly connect β strands to form β sheets, but may also form other connections. A peptide can also form other turns that are less sharp.

Based on studies of known proteins, one may calculate the propensity of a particular residue, or of a particular dipeptide or tripeptide, to be found in an α helix, β strand or reverse turn. The normalized frequencies of occurrence of the amino acid residues in these secondary structures is given in Table 6-4 of CREI84. For a more detailed treatment on the prediction of secondary structure from the amino acid sequence, see Chapter 6 of SCHU79.

In designing a suitable hairpin structure, one may copy an actual structure from a protein whose three-dimensional conformation is known, design the structure using frequency data, or combine the two approaches. Preferably, one or more actual structures are used as a model, and the frequency data is used to determine which mutations can be made without disrupting the structure.

Preferably, no more than three amino acids lie between the cysteine and the beginning or end of the α helix or β strand.

More complex structures (such as a double hairpin) are also possible.

Class III mini-proteins are those featuring a plurality of disulfide bonds. They optionally may also feature secondary structures such as those discussed above with regard to Class II mini-proteins. Since the number of possible disulfide bond topologies increases rapidly with the number of bonds (two bonds, three topologies; three bonds, 15 topologies; four bonds, 105 topologies) the number of disulfide bonds preferably does not exceed four. With two or more disulfide bonds, the disulfide bridge spans preferably do not exceed 50, and the largest intercysteine chain segment preferably does not exceed 20.

Naturally occurring class III mini-proteins, such as heat-stable enterotoxin ST-Ia frequently have pairs of cysteines that are adjacent in the amino-acid sequence. Adjacent cysteines are very unlikely to form an intramolecular disulfide and cysteines separated by a single amino acids form an intramolecular disulfide with difficulty and only for certain intervening amino acids. Thus, clustering cysteines within the amino-acid sequence reduces the number of realizable disulfide bonding schemes. We utilize such clustering in the class III mini-protein disclosed herein.

Metal Finger Mini-Proteins. The mini-proteins of the present invention are not limited to those crosslinked by disulfide bonds. Another important class of mini-proteins are analogues of finger proteins. Finger proteins are characterized by finger structures in which a metal ion is coordinated by two Cys and two His residues, forming a tetrahedral arrangement around it. The metal ion is most often zinc(II), but may be iron, copper, cobalt, etc. The "finger" has the consensus sequence (Phe or Tyr)-(1 AA)-Cys-(2-4 AAs)-Cys-(3 AAs)-Phe-(5 AAs)-Leu-(2 AAs)-His-(3 AAs)-His- (5 AAs) (BERG88; GIBS88). While finger proteins typically contain many repeats of the finger motif, it is known that a single finger will fold in the presence of zinc ions (FRANS7; PARRS8). There is some dispute as to whether two fingers are necessary for binding to DNA. The present invention encompasses mini-proteins with either one or two fingers. It is to be understood that the target need not be a nucleic acid.

G. Modified PBSs

There exist a number of enzymes and chemical reagents that can selectively modify certain side groups of proteins, including: a) protein-tyrosine kinase, Ellmans reagent, methyl transferases (that methylate GLU side groups), serine kinases, proline hydroxyases, vitamin-K dependent enzymes that convert GLU to GLA, maleic anhydride, and alkylating agents. Treatment of the variegated population of GP(PBD) s with one of these enzymes or reagents will modify the side groups affected by the chosen enzyme or reagent. Enzymes and reagents that do not kill the GP are much preferred. Such modification of side groups can directly affect the binding properties of the displayed PBDs. Using affinity separation methods, we enrich for the modified GPs that bind the predetermined target. Since the active binding domain is not entirely genetically specified, we must repeat the post-morphogenesis modification at each enrichment round. This approach is particularly appropriate with mini-protein IPBDs because we envision chemical synthesis of these SBDs.

III. VARIEGATION STRATEGY—MUTAGENESIS TO OBTAIN POTENTIAL BINDING DOMAINS WITH DESIRED DIVERSITY

III.A. Generally

Using standard genetic engineering techniques, a molecule of variegated DNA can be introduced into a vector so that it constitutes part of a gene (OLIP86, OLIP87, AUSU87, REID88a). When vector containing variegated DNA are used to transform bacteria, each cell makes a version of the original protein. Each colony of bacteria may produce a different version from any other colony. If the variegations of the DNA are concentrated at loci known to be on the surface of the protein or in a loop, a population of proteins will be generated, many members of which will fold into roughly the same 3D structure as the parent protein. The specific binding properties of each member, however, may be different from each other member.

We now consider the manner in which we generate a diverse population of potential binding domains in order to facilitate selection of a PBD-bearing GP which binds with the requisite affinity to the target of choice. The potential binding domains are first designed at the amino acid level. Once we have identified which residues are to be mutagenized, and which mutations to allow at those positions, we may then design the variegated DNA which is to encode the various PBDs so as to assure that there is a reasonable probability that if a PBD has an affinity for the target, it will be detected. Of course, the number of independent transformants obtained and the sensitivity of the affinity separation technology will impose limits on the extent of variegation possible within any single round of variegation.

There are many ways to generate diversity in a protein. (See RICH86, CARU85, and OLIP86.) At one extreme, we vary a few residues of the protein as much as possible (inter alia see CARU85, CA. U87, RICH86, and WHAR86). We will call this approach "Focused Mutagenesis". A typical "Focused Mutagenesis" strategy is to pick a set of five to seven residues and vary each through 13–20 possibilities. An alternative plan of mutagenesis ("Diffuse Mutagenesis") is to vary many more residues through a more limited set of choices (See VERS86a and PAKU86). The variegation pattern adopted may fall between these extremes, e.g., two residues varied through all twenty amino acids, two more through only two possibilities, and a fifth into ten of the twenty amino acids.

There is no fixed limit on the number of codons which can be mutated simultaneously. However, it is desirable to adopt a mutagenesis strategy which results in a reasonable probability that a possible PBD sequence is in fact displayed by at least one genetic package. When the size of the set of amino acids potentially encoded by each variable codon is the same for all variable codons and within the set all amino acids are equiprobable, this probability may be calculated as follows: Let $\Gamma(k,q)$ be the probability that amino acid number k will occur at variegated codon q; these codons need not be contiguous. The probability that a particular vgDNA molecule will encode a PBD containing n variegated amino acids $k_1 \ldots, k_n$ is:

$$p(k_1, \ldots, k_n) = \Gamma(k_1, 1) \cdot \ldots \cdot \Gamma(k_n, n)$$

Consider a library of $N_{it}$ independent transformants prepared with said vgDNA; the probability that the sequence $k_1, \ldots, k_n$ is absent is:

$$P(\text{missing } k_1, \ldots, k_n) = \exp\{-N_{it} \cdot p(k_1, \ldots, k_n)\}.$$

$$P(k_1, \ldots, k_n \text{ in lib}) = 1 - \exp\{-N_{it} \cdot p(k_1, \ldots, k_n)\}.$$

Preferably, the probability that a mutein encoded by the vgDNA and composed of the least favored amino acids at each variegated position will be displayed by at least one independent transformant in the library is at least 0.50, and more preferably at least 0.90. (Muteins composed of more favored amino acids would of course be more likely to occur in the same library.)

Preferably, the variegation is such as will cause a typical transformant population to display $10^6$–$10^7$ different amino acid sequences by means of preferably not more than 10-fold more (more preferably not more than 3-fold) different DNA sequences.

For a mini-protein that lacks $\alpha$ helices and $\beta$ strands, one will, in any given round of mutation, preferably variegate each of 4–6 non-cysteine codons so that they each encode at least eight of the 20 possible amino acids. The variegation at each codon could be customized to that position. Preferably, cysteine is not one of the potential substitutions, though it is not excluded.

When the mini-protein is a metal finger protein, in a typical variegation strategy, the two Cys and two His residues, and optionally also the aforementioned Phe/Tyr, Phe and Leu residues, are held invariant and a plurality (usually 5–10) of the other residues are varied.

When the mini-protein is of the type featuring one or more $\alpha$ helices and $\beta$ strands, the set of potential amino acid modifications at any given position is picked to favor those which are less likely to disrupt the secondary structure at that position. Since the number of possibilities at each variable amino acid is more limited, the total number of variable amino acids may be greater without altering the sampling efficiency of the selection process.

For the last-mentioned class of mini-proteins, as well as domains other than mini-proteins, preferably not more than 20 and more preferably 5–10 codons will be variegated. However, if diffuse mutagenesis is employed, the number of codons which are variegated can be higher.

The decision as to which residues to modify is eased by knowledge of which residues lie on the surface of the domain and which are buried in the interior.

We choose residues in the IPBD to vary through consideration of several factors, including: a) the 3D structure of the IPBD, b) sequences homologous to IPBD, and c) modeling of the IPBD and mutants of the IPBD. When the number of residues that could strongly influence binding is greater than the number that should be varied simultaneously, the user should pick a subset of those residues to vary at one time. The user picks trial levels of variegation and calculate the abundances of various sequences. The list of varied residues and the level of variegation at each varied residue are adjusted until the composite variegation is commensurate with the sensitivity of the affinity separation and the number of independent transformants that can be made.

Preferably, the abundance of PPBD-encoding DNA is 3 to 10 times higher than both $1/M_{ntv}$ and $1/C_{sensi}$ to provide a margin of redundancy. $M_{ntv}$ is the number of transformants that can be made from $Y_{D100}$ DNA. With current technology Mntv is approximately $5 \cdot 10^8$ but the exact value depends on the details of the procedures adapted by the user. Improvements in technology that allow more efficient: a) synthesis of DNA, b) ligation of DNA, or c) transformation of cells will raise the value of $M_{ntv}$. $C_{sensi}$ is the sensitivity of the affinity separation; improvements in affinity separation will raise $C_{sensi}$. If the smaller of $M_{ntv}$ and Csensi is increased, higher levels of variegation may be used. For example, if $C_{sensi}$ is 1 in $10^9$ and $M_{ntv}$ is $10^8$, then improvements in $C_{sensi}$ are less valuable than improvements in $M_{ntv}$.

While variegation normally will involve the substitution of one amino acid for another at a designated variable codon, it may involve the insertion or deletion of amino acids as well.

III.B. Identification of Residues to be Varied

We now consider the principles that guide our choice of residues of the IPBD to vary. A key concept is that only structured proteins exhibit specific binding, i.e. can bind to a particular chemical entity to the exclusion of most others. Thus the residues to be varied are chosen with an eye to preserving the underlying IPBD structure. Substitutions that prevent the PBD from folding will cause GPs carrying those genes to bind indiscriminately so that they can easily be removed from the population.

Sauer and colleagues (PAKU86, REID88), and Caruthers and colleagues (EISE85) have shown that some residues on the polypeptide chain are more important than others in determining the 3D structure of a protein. The 3D structure is essentially unaffected by the identity of the amino acids at some loci; at other loci only one or a few types of amino acid is allowed. In most cases, loci where wide variety is allowed have the amino acid side group directed toward the solvent. Loci where limited variety is allowed frequently have the side group directed toward other parts of the protein. Thus substitutions of amino acids that are exposed to solvent are less likely to affect the 3D structure than are substitutions at internal loci. (See also SCHU79, p169–171 and CREI84, p239–245, 314–315).

The residues that join helices to helices, helices to sheets, and sheets to sheets are called turns and loops and have been classified by Richardson (RICH81), Thornton (THOR88), Sutcliffe et al. (SUTC87a) and others. Insertions and deletions are more readily tolerated in loops than elsewhere. Thornton et al. (THOR88) have summarized many observations indicating that related proteins usually differ most at the loops which join the more regular elements of secondary structure. (These observations are relevant not only to the variegation of potential binding domains but also to the insertion of binding domains into an outer surface protein of a genetic package, as discussed in a later section.)

Burial of hydrophobic surfaces so that bulk water is excluded is one of the strongest forces driving the binding of proteins to other molecules. Bulk water can be excluded from the region between two molecules only if the surfaces are complementary. We should test as many surface variations as possible to find one that is complementary to the target. The selection-through-binding isolates those proteins that are more nearly complementary to some surface on the target.

Proteins do not have distinct, countable faces. Therefore we define an "interaction set" to be a set of residues such that all members of the set can simultaneously touch one molecule of the target material without any atom of the target coming closer than van der Waals distance to any main-chain atom of the IPBD. The concept of a residue "touching" a molecule of the target is discussed below. From a picture of BPTI (such as FIGS. 6–10, p. 225 of CREI84) we can see that residues 3, 7, 8, 10, 13, 39, 41, and 42 can all simultaneously contact a molecule the size and shape of myoglobin. We also see that residue 49 can not touch a single myoglobin molecule simultaneously with any of the first set even though all are on the surface of BPTI. (It is not the intent of the present invention, however, to suggest that use of models is required to determine which part of the target molecule will actually be the site of binding by PBD.)

Variations in the position, orientation and nature of the side chains of the residues of the interaction set will alter the shape of the potential binding surface defined by that set. Any individual combination of such variations may result in a surface shape which is a better or a worse fit for the target surface. The effective diversity of a variegated population is measured by the number of distinct shapes the potentially complementary surfaces of the PBD can adopt, rather than the number of protein sequences. Thus, it is preferable to maximize the former number, when our knowledge of the IPBD permits us to do so.

To maximize the number of surface shapes generated for when N residues are varied, all residues varied in a given round of variegation should be in the same interaction set because variation of several residues in one interaction set generates an exponential number of different shapes of the potential binding surface.

If cassette mutagenesis is to be used to introduce the variegated DNA into the ipbd gene, the protein residues to be varied are, preferably, close enough together in sequence that the variegated DNA (vgDNA) encoding all of them can be made in one piece. The present invention is not limited to a particular length of vgDNA that can be synthesized. With current technology, a stretch of 60 amino acids (180 DNA bases) can be spanned.

Further, when there is reason to mutate residues further than sixty residues apart, one can use other mutational means, such as single-stranded-oligonucleotide-directed mutagenesis (BOTS85) using two or more mutating primers.

Alternatively, to vary residues separated by more than sixty residues, two cassettes may be mutated as follows: 1) vg DNA having a low level of variegation (for example, 20 to 400 fold variegation) is introduced into one cassette in the OCV, 2) cells are transformed and cultured, 3) vg OCV DNA is obtained, 4) a second segment of vgDNA is inserted into a second cassette in the OCV, and 5) cells are transformed and cultured, GPs are harvested and subjected to selection-through-binding.

The composite level of variation preferably does not exceed the prevailing capabilities to a) produce very large numbers of independently transformed cells or b) detect small components in a highly varied population. The limits on the level of variegation are discussed later.

Data about the IPBD and the target that are useful in deciding which residues to vary in the variegation cycle include: 1) 3D structure, or at least a list of residues on the surface of the IPBD, 2) list of sequences homologous to IPBD, and 3) model of the target molecule or a stand-in for the target.

These data and an understanding of the behavior of different amino acids in proteins will be used to answer two questions:

1) which residues of the IPBD are on the outside and close enough together in space to touch the target simultaneously?
2) which residues of the IPBD can be varied with high probability of retaining the underlying IPBD structure?

Although an atomic model of the target material (obtained through X-ray crystallography, NMR, or other means) is preferred in such examination, it is not necessary. For example, if the target were a protein of unknown 3D structure, it would be sufficient to know the molecular weight of the protein and whether it were a soluble globular protein, a fibrous protein, or a membrane protein. Physical measurements, such as low-angle neutron diffraction, can determine the overall molecular shape, viz. the ratios of the principal moments of inertia. One can then choose a protein of known structure of the same class and similar size and shape to use as a molecular stand-in and yardstick. It is not essential to measure the moments of inertia of the target because, at low resolution, all proteins of a given size and class look much the same. The specific volumes are the same, all are more or less spherical and therefore all proteins of the same size and class have about the same radius of curvature. The radii of curvature of the two molecules determine how much of the two molecules can come into contact.

The most appropriate method of picking the residues of the protein chain at which the amino acids should be varied is by viewing, with interactive computer graphics, a model of the IPBD. A stick-figure representation of molecules is preferred. A suitable set of hardware is an Evans & Sutherland PS390 graphics terminal (Evans & Sutherland Corporation, Salt Lake City, Utah) and a MicroVAX II supermicro computer (Digital Equipment Corp., Maynard, Mass.). The computer should, preferably, have at least 150 megabytes of disk storage, so that the Brookhaven Protein Data Bank can be kept on line. A FORTRAN compiler, or some equally good higher-level language processor is preferred for program development. Suitable programs for viewing and manipulating protein models include: a) PS-FRODO, written by T. A. Jones (JONE85) and distributed by the Biochemistry Department of Rice University, Houston, Tex.; and b) PROTEUS, developed by Dayringer, Tramantano, and Fletterick (DAYR86). Important features of PS-FRODO and PROTEUS that are needed to view and manipulate protein models for the purposes of the present invention are the abilities to: 1) display molecular stick figures of proteins and other molecules, 2) zoom and clip images in real time, 3) prepare various abstract representations of the molecules, such as a line joining $C_\alpha$s and side group atoms, 4) compute and display solvent-accessible surfaces reasonably quickly, 5) point to and identify atoms, and 6) measure distance between atoms.

In addition, one could use theoretical calculations, such as dynamic simulations of proteins, to estimate whether a substitution at a particular residue of a particular amino-acid type might produce a protein of approximately the same 3D structure as the parent protein. Such calculations might also indicate whether a particular substitution will greatly affect the flexibility of the protein; calculations of this sort may be useful but are not required.

Residues whose mutagenesis is most likely to affect binding to a target molecule, without destabilizing the protein, are called the "principal set". Using the knowledge of which residues are on the surface of the IPBD (as noted above), we pick residues that are close enough together on the surface of the IPBD to touch a molecule of the target simultaneously without having any IPBD main-chain atom come closer than van der Waals distance (viz. 4.0 to 5.0 Å) from any target atom. For the purposes of the present invention, a residue of the IPBD "touches" the target if: a) a main-chain atom is within van der Waals distance, viz. 4.0 to 5.0 Å of any atom of the target molecule, or b) the $C_\beta$ is within $D_{cutoff}$ of any atom of the target molecule so that a side-group atom could make contact with that atom.

Because side groups differ in size (cf. Table 35), some judgment is required in picking $D_{cutoff}$. In the preferred embodiment, we will use $D_{cutoff}$=8.0 Å, but other values in the range 6.0 Å to 10.0 Å could be used. If IPBD has G at a residue, we construct a pseudo $C_\beta$ with the correct bond distance and angles and judge the ability of the residue to touch the target from this pseudo $C_\beta$.

Alternatively, we choose a set of residues on the surface of the IPBD such that the curvature of the surface defined by the residues in the set is not so great that it would prevent contact between all residues in the set and a molecule of the target. This method is appropriate if the target is a macromolecule, such as a protein, because the PBDs derived from the IPBD will contact only a part of the macromolecular surface. The surfaces of macromolecules are irregular with varying curvatures. If we pick residues that define a surface that is not too convex, then there will be a region on a macromolecular target with a compatible curvature.

In addition to the geometrical criteria, we prefer that there be some indication that the underlying IPBD structure will tolerate substitutions at each residue in the principal set of residues. Indications could come from various sources, including: a) homologous sequences, b) static computer modeling, or c) dynamic computer simulations.

The residues in the principal set need not be contiguous in the protein .sequence and usually are not. The exposed surfaces of the residues to be varied do not need to be connected. We desire only that the amino acids in the residues to be varied all be capable of touching a molecule of the target material simultaneously without having atoms overlap. If the target were, for example, horse heart myoglobin, and if the IPBD were BPTI, any set of residues in one interaction set of BPTI defined in Table 34 could be picked.

The secondary set comprises those residues not in the primary set that touch residues in the primary set. These residues might be excluded from the primary set because: a) the residue is internal, b) the residue is highly conserved, or c) the residue is on the surface, but the curvature of the IPBD surface prevents the residue from being in contact with the target at the same time as one or more residues in the primary set.

Internal residues are frequently conserved and the amino acid type can not be changed to a significantly different type without substantial risk that the protein structure will be disrupted. Nevertheless, some conservative changes of internal residues, such as I to L or F to Y, are tolerated. Such conservative changes subtly affect the placement and dynamics of adjacent protein residues and such "fine tuning" may be useful once an SBD is found.

Surface residues in the secondary set are most often located on the periphery of the principal set. Such peripheral residues can not make direct contact with the target simultaneously with all the other residues of the principal set. The charge on the amino acid in one of these residues could, however, have a strong effect on binding. Once an SBD is found, it is appropriate to vary the charge of some or all of these residues. For example, the variegated codon containing equimolar A and G at base 1, equimolar C and A at base 2, and A at base 3 yields amino acids T, A, K, and E with equal probability.

The assignment of residues to the primary and secondary sets may be based on: a) geometry of the IPBD and the geometrical relationship between the IPBD and the target (or a stand-in for the target) in a hypothetical complex, and b) sequences of proteins homologous to the IPBD. However, it should be noted that the distinction between the principal set and the secondary set is one more of convenience than of substance; we could just as easily have assigned each amino acid residue in the domain a preference score that weighed together the different considerations affecting whether they are suitable for variegation, and then ranked the residues in order, from most preferred to least.

For any given round of variegation, it may be necessary to limit the variegation to a subset of the residues in the primary and secondary sets, based on geometry and on the maximum allowed level of variegation that assures progressivity. The allowed level of variegation determines how many residues can be varied at once; geometry determines which ones.

The user may pick residues to vary in many ways. For example, pairs of residues are picked that are diametrically opposed across the face of the principal set. Two such pairs are used to delimit the surface, up/down and right/left. Alternatively, three residues that form an inscribed triangle, having as large an area as possible, on the surface are picked. One to three other residues are picked in a checkerboard fashion across the interaction surface. Choice of widely spaced residues to vary creates the possibility for high specificity because all the intervening residues must have acceptable complementarity before favorable interactions can occur at widely-separated residues.

The number of residues picked is coupled to the range through which each can be varied by the restrictions discussed below. In the first round, we do not assume any binding between IPBD and the target and so progressivity is not an issue. At the first round, the user may elect to produce a level of variegation such that each molecule of vgDNA is potentially different through, for example, unlimited variegation of 10 codons ($20^{10}$ approx.=$10^{13}$). One run of the DNA synthesizer produces approximately $10^{13}$ molecules of length 100 nts. Inefficiencies in ligation and transformation will reduce the number of proteins actually tested to between $10^7$ and $5 \cdot 10^8$. Multiple replications of the process with such very high levels of variegation will not yield repeatable results; the user decides whether this is important.

III.C. Determining the Substitution Set for Each Parental Residue

Having picked which residues to vary, we now decide the range of amino acids to allow at each variable residue. The total level of variegation is the product of the number of variants at each varied residue. Each varied residue can have a different scheme of variegation, producing 2 to 20 different possibilities. The set of amino acids which are potentially encoded by a given variegated codon are called its "substitution set".

The computer that controls a DNA synthesizer, such as the Milligen 7500, can be programmed to synthesize any base of an oligo-nt with any distribution of nts by taking some nt substrates (e.g. nt phosphoramidites) from each of two or more reservoirs. Alternatively, nt substrates can be mixed in any ratios and placed in one of the extra reservoir for so called "dirty bottle" synthesis. Each codon could be programmed differently. The "mix" of bases at each nucleotide position of the codon determines the relative frequency of occurrence of the different amino acids encoded by that codon.

Simply variegated codons are those in which those nucleotide positions which are degenerate are obtained from a mixture of two or more bases mixed in equimolar proportions. These mixtures are described in this specification by means of the standardized "ambiguous nucleotide" code (Table 1 and 37 CFR §1.822). In this code, for example, in the degenerate codon "SNT", "S" denotes an equimolar mixture of bases G and C, "N", an equimolar mixture of all four bases, and "T", the single invariant base thymidine.

Complexly variegated codons are those in which at least one of the three positions is filled by a base from an other than equimolar mixture of two of more bases.

Either simply or complexly variegated codons may be used to achieve the desired substitution set.

If we have no information indicating that a particular amino acid or class of amino acid is appropriate, we strive to substitute all amino acids with equal probability because representation of one mini-protein above the detectable level is wasteful. Equal amounts of all four nts at each position in a codon (NNN) yields the amino acid distribution in which each amino acid is present in proportion to the number of codons that code for it. This distribution has the disadvantage of giving two basic residues for every acidic residue. In addition, six times as much R, S, and L as W or M occur. If five codons are synthesized with this distribution, each of the 243 sequences encoding some combination of L, R, and S are 7776-times more abundant than each of the 32 sequences encoding some combination of W and M. To have five Ws present at detectable levels, we must have each of the (L,R,S) sequences present in 7776-fold excess.

Preferably, we also consider the interactions between the sites of variegation and the surrounding DNA. If the method of mutagenesis to be used is replacement of a cassette, we consider whether the variegation will generate gratuitous restriction sites and whether they seriously interfere with the intended introduction of diversity. We reduce or eliminate gratuitous restriction sites by appropriate choice of variegation pattern and silent alteration of codons neighboring the sites of variegation.

It is generally accepted that the sequence of amino acids in a protein or polypeptide determine the three-dimensional structure of the molecule, including the possibility of no definite structure. Among polypeptides of definite length and sequence, some have a defined tertiary structure and most do not.

Particular amino acid residues can influence the tertiary structure of a defined polypeptide in several ways, including by:

a) affecting the flexibility of the polypeptide main chain, b) adding hydrophobic groups, c) adding charged groups, d) allowing hydrogen bonds, and e) forming cross-links, such as disulfides, chelation to metal ions, or bonding to prosthetic groups.

Most works on proteins classify the twenty amino acids into categories such as hydrophobic/hydrophilic, positive-negative/neutral, or large/small. These classifications are useful rules of thumb, but one must be careful not to oversimplify. Proteins contain a variety of identifiable secondary structural features, including: a) α helices, b) 3–10 helices, c) antiparallel β sheets, d) parallel β sheets, e) Ω loops, f) reverse turns, and g) various cross links. Many people have analyzed proteins of known structures and assigned each amino-acid to one category or another. Using the frequency at which particular amino acids occur in various types of secondary structures, people have a) tried to predict the secondary structures of proteins for which only the amino-acid sequence is known (CHOU74, CHOU78a, CHOU78b), and b) designed proteins de novo that have a particular set of secondary structural elements (DEGR87, HECH90). Although some amino acids show definite predilection for one secondary form (e.g. VAL for β structure and ALA for α helices), these preferences are not very strong; Creighton has tabulated the preferences (CREI84). In only seven cases does the tendency exceed 2.0:

| Amino acid | distinction | ratio |
|---|---|---|
| MET | α/turn | 3.7 |
| PRO | turn/α | 3.7 |
| VAL | β/turn | 3.2 |
| GLY | turn/α | 2.9 |
| ILE | β/turn | 2.8 |
| PHE | β/turn | 2.3 |
| LEU | α/turn | 2.2 |

Every amino-acid type has been observed in every identified secondary structural motif. ARG is particularly indiscriminate.

PRO is generally taken to be a helix breaker. Nevertheless, proline often occurs at the beginning of helices or even in the middle of a helix, where it introduces a slight bend in the helix. Matthews and coworkers replaced a PRO that occurs near the middle of an α helix in T4 lysozyme. To their surprise, the "improved" protein is less stable than the wild-type. The rest of the structure had been adapted to fit the bent helix.

Lundeen (LUND86) has tabulated the frequencies of amino acids in helices, β strands, turns, and coil in proteins of known 3D structure and has distinguished between CYSs having free thiol groups and half cystines. He reports that free CYS is found most often in helixes while half cystines are found more often in β sheets. Half cystines are, however, regularly found in helices. Pease et al. (PEAS90) constructed a peptide having two cystines; one end of each is in a very stable α helix. Apamin has a similar structure (WEMM83, PEAS88).

Flexibility:

GLY is the smallest amino acid, having two hydrogens attached to the $C_\alpha$. Because GLY has no $C_\beta$, it confers the most flexibility on the main chain. Thus GLY occurs very frequently in reverse turns, particularly in conjunction with PRO, ASP, ASN, SER, and THR.

The amino acids ALA, SER, CYS, ASP, ASN, LEU, MET, PHE, TYR, TRP, ARG, HIS, GLU, GLN, and LYS have unbranched β carbons. Of these, the side groups of SER, ASP, and ASN frequently make hydrogen bonds to the main chain and so can take on main-chain conformations that are energetically unfavorable for the others. VAL, ILE, and THR have branched β carbons which makes the extended main-chain conformation more favorable. Thus VAL and ILE are most often seen in β sheets. Because the side group of THR can easily form hydrogen bonds to the main chain, it has less tendency to exist in a β sheet.

The main chain of proline is particularly constrained by the cyclic side group. The φ angle is always close to −60°. Most prolines are found near the surface of the protein.

Charge:

LYS and ARG carry a single positive charge at any pH below 10.4 or 12.0, respectively. Nevertheless, the methylene groups, four and three respectively, of these amino acids are capable of hydrophobic interactions. The guanidinium group of ARG is capable of donating five hydrogens simultaneously, while the amino group of LYS can donate only three. Furthermore, the geometries of these groups is quite different, so that these groups are often not interchangeable.

ASP and GLU carry a single negative charge at any pH above ≈4.5 and 4.6, respectively. Because ASP has but one methylene group, few hydrophobic interactions are possible. The geometry of ASP lends itself to forming hydrogen bonds to main-chain nitrogens which is consistent with ASP being found very often in reverse turns and at the beginning of helices. GLU is more often found in α helices and particularly in the amino-terminal portion of these helices because the negative charge of the side group has a stabilizing interaction with the helix dipole (NICH88, SALI88).

HIS has an ionization pK in the physiological range, viz. 6.2. This pK can be altered by the proximity of charged groups or of hydrogen donators or acceptors. HIS is capable of forming bonds to metal ions such as zinc, copper, and iron.

Hydrogen bonds:

Aside from the charged amino acids, SER, THR, ASN, GLN, TYR, and TRP can participate in hydrogen bonds.

Cross links:

The most important form of cross link is the disulfide bond formed between two thiols, especially the thiols of CYS residues. In a suitably oxidizing environment, these bonds form spontaneously. These bonds can greatly stabilize a particular conformation of a protein or mini-protein. When a mixture of oxidized and reduced thiol reagents are present, exchange reactions take place that allow the most stable conformation to predominate. Concerning disulfides in proteins and peptides, see also KATZ90, MATS89, PERR84, PEPS86, SAUE86, WELL86, JANA89, HORV89, KISH85, and SCHN86.

Other cross links that form without need of specific enzymes include:

| | |
|---|---|
| 1) $(CYS)_4$:Fe | Rubredoxin (in CREI84, P. 376) |
| 2) $(CYS)_4$:Zn | Aspartate Transcarbamylase (in CREI84, P. 376) and Zn-fingers (HARD90) |
| 3) $(HIS)_2(MET)(CYS)$:Cu | Azurin (in CREI84, P. 376) and Basic "Blue" Cu Cucumber protein (GUSS88) |
| 4) $(HIS)_4$:Cu | CuZn superoxide dismutase |
| 5) $(CYS)_4$:$(Fe_4S_4)$ | Ferredoxin (in CREI84, P. 376) |
| 6) $(CYS)_2(HIS)_2$:Zn | Zinc-fingers (GIBS88) |
| 7) $(CYS)_3(HIS)$:Zn | Zinc-fingers (GAUS87, GIBS88) |

Cross links having $(HIS)_2(MET)(CYS)$:Cu has the potential advantage that HIS and MET can not form other cross links without Cu.

Simply Variegated Codons

The following simply variegated codons are useful because they encode a relatively balanced set of amino acids:

1) SNT which encodes the set [L,P,H,R,V,A,D,G]: a) one acidic (D) and one basic (R), b) both aliphatic (L,V) and aromatic hydrophobics (H), c) large (L,R,H) and small (G,A) side groups, d) ridged (P) and flexible (G) amino acids, e) each amino acid encoded once.
2) RNG which encodes the set [M,T,K,R,V,A,E,G]: a) one acidic and two basic (not optimal, but acceptable), b) hydrophilics and hydrophobics, c) each amino acid encoded once.
3) RMG which encodes the set [T,K,A,E]: a) one acidic, one basic, one neutral hydrophilic, b) three favor $\alpha$ helices, c) each amino acid encoded once.
4) VNT which encodes the set [L,P,H,R,I,T,N,S,V,A,D,G]: a) one acidic, one basic, b) all classes: charged, neutral hydrophilic, hydrophobic, ridged and flexible, etc., c) each amino acid encoded once.
5) RRS which encodes the set [K,S,K,R,D,E,G$^2$]: a) two acidics, two basics, b) two neutral hydrophilics, c) only glycine encoded twice.
6) NNT which encodes the set [F,S,Y,C,L,P,H,R,I,T,N,V,A,D,G]: a) sixteen DNA sequences provide fifteen different amino acids; only serine is repeated, all others are present in equal amounts (This allows very efficient sampling of the library.), b) there are equal numbers of acidic and basic amino acids (D and R, once each), c) all major classes of amino acids are present: acidic, basic, aliphatic hydrophobic, aromatic hydrophobic, and neutral hydrophilic.
7) NNG, which encodes the set [L$^2$,R$^2$,S,W,P,Q,M,T,K,V,A,E,G,stop]: a) fair preponderance of residues that favor formation of $\alpha$-helices [L,M,A,Q,K,E; and, to a lesser extent, S,R,T]; b) encodes 13 different amino acids. (VHG encodes a subset of the set encoded by NNG which encodes 9 amino acids in nine different DNA sequences, with equal acids and bases, and 5/9 being $\alpha$ helix-favoring.)

For the initial variegation, NNT is preferred, in most cases. However, when the codon is encoding an amino acid to be incorporated into an $\alpha$ helix, NNG is preferred.

Below, we analyze several simple variegations as to the efficiency with which the libraries can be sampled.

Libraries of random hexapeptides encoded by-(NNK)$^6$ have been reported (SCOT90, CWIR90). Table 130 shows the expected behavior of such libraries. NNK produces single codons for PHE, TYR, CYS, TRP, HIS, GLN, ILE, MET, ASN, LYS, ASP, and GLU ($\alpha$ set); two codons for each of VAL, ALA, PRO, THR, and GLY ($\Phi$ set); and three codons for each of LEU, ARG, and SER ($\Omega$ set). We have separated the 64,000,000 possible sequences into 28 classes, shown in Table 130A, based on the number of amino acids from each of these sets. The largest class is $\Phi\Omega\alpha\alpha\alpha\alpha$ with $\approx$14.6% of the possible sequences. Aside from any selection, all the sequences in one class have the same probability of being produced. Table 130B shows the probability that a given DNA sequence taken from the (NNK)$^6$ library will encode a hexapeptide belonging to one of the defined classes; note that only $\approx$6.3% of DNA sequences belong to the $\Phi\Omega\alpha\alpha\alpha\alpha$ class.

Table 130C shows the expected numbers of sequences in each class for libraries containing various numbers of independent transformants (viz. 10$^6$, 3·10$^6$, 10$^7$, 3·10$^7$, 10$^8$, 3·10$^8$, 10$^9$, and 3·10$^9$) At 10$^6$ independent transformants (ITs), we expect to see 56% of the $\Omega\Omega\Omega\Omega\Omega\Omega$ class, but only 0.1% of the $\alpha\alpha\alpha\alpha\alpha\alpha$ class. The vast majority of sequences seen come from classes for which less than 10% of the class is sampled. Suppose a peptide from, for example, class $\Phi\Phi\Omega\Omega\alpha\alpha$ is isolated by fractionating the library for binding to a target. Consider how much we know about peptides that are related to the isolated sequence. Because only 4% of the $\Phi\Phi\Omega\Omega\alpha\alpha$ class was sampled, we can not conclude that the amino acids from the $\Omega$ set are in fact the best from the $\Omega$ set. We might have LEU at position 2, but ARG or SER could be better. Even if we isolate a peptide of the $\Omega\Omega\Omega\Omega\Omega\Omega$ class, there is a noticeable chance that better members of the class were not present in the library.

With a library of 10$^7$ ITs, we see that several classes have been completely sampled, but that the $\alpha\alpha\alpha\alpha\alpha\alpha$ class is only 1.1% sampled. At 7.6 10$^7$ ITs, we expect display of 50% of all amino-acid sequences, but the classes containing three or more amino acids of the $\alpha$ set are still poorly sampled. To achieve complete sampling of the (NNK)$^6$ library requires about 3·10$^9$ ITs, 10-fold larger than the largest (NNK)$^6$ library so far reported.

Table 131 shows expectations for a library encoded by (NNT)$^4$(NNG)$^2$. The expectations of abundance are independent of the order of the codons or of interspersed unvaried codons. This library encodes 0.133 times as many amino-acid sequences, but there are only 0.0165 times as many DNA sequences. Thus 5.0·10$^7$ ITs (i.e. 60-fold fewer than required for (NNK)$^6$) gives almost complete sampling of the library. The results would be slightly better for (NNT)$^6$ and slightly, but not much, worse for (NNG)$^6$. The controlling factor is the ratio of DNA sequences to amino-acid sequences.

Table 132 shows the ratio of #DNA sequences/#AA sequences for codons NNK, NNT, and NNG. For NNK and NNG, we have assumed that the PBD is displayed as part of an essential gene, such as gene III in Ff phage, as is indicated by the phrase "assuming stops vanish". It is not in any way required that such an essential gene be used. If a non-essential gene is used, the analysis would be slightly different; sampling of NNK and NNG would be slightly less efficient. Note that (NNT)$^6$ gives 3.6-fold more amino-acid sequences than (NNK)$^5$ but requires 1.7-fold fewer DNA sequences. Note also that (NNT)$^7$ gives twice as many amino-acid sequences as (NNK)$^6$, but 3.3-fold fewer DNA sequences.

Thus, while it is possible to use a simple mixture (NNS, NNK or NNN) to obtain at a particular position all twenty amino acids, these simple mixtures lead to a highly biased set of encoded amino acids. This problem can be overcome by use of complexly variegated codons.

Complexly Variegated Codons

Let Abun(x) be the abundance of DNA sequences coding for amino acid x, defined by the distribution of nts at each base of the nodon. For any distribution, there will be a most-favored amino acid (mfaa) with abundance Abun(mfaa) and a least-favored amino acid (lfaa) with abundance Abun(lfaa). We seek the nt distribution that allows all twenty amino acids and that yields the largest ratio Abun(lfaa)/Abun(mfaa) subject, if desirable to further constraints.

We first will present the mixture calculated to be optimal when the nt distribution is subject to two constraints: equal abundances of acidic and basic amino acids and the least possible number of stop codons. Thus only nt distributions that yield Abun(E)+Abun(D)=Abun(R)+Abun(K) are considered, and the function maximized is:

$$\{(1\text{-}Abun(\text{stop}))\ (Abun(lfaa)/Abun(mfaa))\}.$$

We have simplified the search for an optimal nt distribution by limiting the third base to T or G (C or G is equivalent). All amino acids are possible and the number of accessible stop codons is reduced because TGA and TAA codons are eliminated. The amino acids F, Y, C, H, N, I, and D require T at the third base while W, M, Q, K, and E require G. Thus we use an equimolar mixture of T and G at the third base. However, it should be noted that the present invention embraces use of complexly variegated codons in which the third base is not limited to T or G (or to C or G).

A computer program, written as part of the present invention and named "Find Optimum vgCodon" (See Table 9), varies the composition at bases 1 and 2, in steps of 0.05, and reports the composition that gives the largest value of the quantity {(Abun(lfaa)/Abun(mfaa) (1-Abun(stop)))}. A vg codon is symbolically defined by the nucleotide distribution at each base:

|          | T  | C  | A  | G  |
|----------|----|----|----|----|
| base #1 =| t1 | c1 | a1 | g1 |
| base #2 =| t2 | c2 | a2 | g2 |
| base #3 =| t3 | c3 | a3 | g3 | t1 + c1 + a1 + g1 = 1.0
t2 + c2 + a2 + g2 = 1.0
t3 = g3 = 0.5, c3 = a3 = 0.

The variation of the quantities t1, c1, a1, g1, t2, c2, a2, and g2 is subject to the constraint that:

$Abun(E)+Abun(D)=Abun(K)+Abun(R)$ $Abun(E)+Abun(D)=g1*,a2$ $Abun(K)+Abun(R)=a1*a2/2+c1*g2+a1*g2/2$ $g1*a2=a1,a2/2+c1*g2+a1,g2/2$ Solving for g2, we obtain $g2=(g1*a2-0.5a1*a2)/(c1+0.5*a1)$.

In addition, $t1=1-a1-c1-g1$ $t2=1-a2-c2-g2$.

We vary a1, c1, g1, a2, and c2 and then calculate t1, g2, and t2. Initially, variation is in steps of 5%. Once an approximately optimum distribution of nucleotides is determined, the region is further explored with steps of 1%. The logic of this program is shown in Table 9. The optimum distribution (the "fxS" codon) is shown in Table 10A and yields DNA molecules encoding each type amino acid with the abundances shown.

Note that this chemistry encodes all twenty amino acids, with acidic and basic amino acids being equiprobable, and the most favored amino acid (serine) is encoded only 2.454 times as often as the least favored amino acid (tryptophan). The "fxS" vg codon improves sampling most for peptides containing several of the amino acids [F,Y,C,W,H,Q,I,M,N,K,D,E] for which NNK or NNS provide only one codon. Its sampling advantages are most pronounced when the library is relatively small.

A modification of "Find Optimum vgCodon" varies the composition at bases 1 and 2, in steps of 0.01, and reports the composition that gives the largest value of the quantity {(Abun(lfaa)/Abun(mfaa))} without any restraint on the relative abundance of any amino acids. The results of this optimization is shown in Table 10B. The changes are small, indicating that insisting on equality of acids and bases and minimizing stop codons costs us little. Also note that, without restraining the optimization, the prevalence of acidic and basic amino acids comes out fairly close. On the other hand, relaxing the restriction leaves a distribution in which the least favored amino acid is only 0.412 times as prevalent as SER.

The advantages of an NNT codon are discussed elsewhere in the present application. Unoptimized NNT provides 15 amino acids encoded by only 16 DNA sequences. It is possible to improve on NNT as follows. First note that the SER codons occur in the T and A rows of the genetic-code table and in the C and G columns.

$[SER]=T_1 \times C_2 + A_1 \times G_2$

If we reduce the prevalence of SER by reducing $T_1$, $C_2$, $A_1$, and $G_2$ relative to other bases, then we will also reduce the prevalence of PHE, TYR, CYS, PRO, THR, ALA, ARG, GLY, ILE, and ASN. The prevalence of LEU, HIS, VAL, and ASP will rise. If we assume that $T_1$, $C_2$, $A_1$, and $G_2$ are all lowered to the same extent and that $C_1$, $G_1$, $T_2$, and $A_2$ are increased by the same amount, we can compute a shift that makes the prevalence of SER equal the prevalences of LEU, HIS, VAL, and ASP. The decrease in PHE, TYR, CYS, PRO, THR, ALA, ARG, GLY, ILE, and ASN is not equal; CYS and THR are reduced more than the others.

Let the distribution be

|          | T       | C       | A       | G       |
|----------|---------|---------|---------|---------|
| base #1 =| .25 − q | .25 + q | .25 − q | .25 + q |
| base #2 =| .25 + q | .25 − q | .25 + q | .25 − q |
| base #3 =| 1.00    | 0.0     | 0.0     | 0.0     |

Setting [SER]=[LEU]=[HIS]=[VAL]=[ASP] gives:

$(0.25-q) \cdot (0.25-q) + (0.25-q) \cdot (0.25-q) = (0.25+q) \cdot (0.25+q)$ $2 \cdot (0.25-q)^2 = (0.25+q)$ $q^2 - 1.5 q + 0.0625 = 0$ $q = (3/4) - \sqrt{2}/2 = .0428$ This distribution (shown in Table 10C) gives five amino acids (SER, LEU, HIS, VAL, ASP) in very nearly equal amounts. A further eight amino acids (PHE, TYR, ILE, ASN, PRO, ALA, ARG, GLY) are present at 78% the abundance of SER. THR and CYS remain at half the abundance of SER. When variegating DNA for disulfide-bonded mini-proteins, it is often desirable to reduce the prevalence of CYS. This distribution allows 13 amino acids to be seen at high level and gives no stops; the optimized fxS distribution allows only 11 amino acids at high prevalence.

The NNG codon can also be optimized. Table 10D shows an approximately optimized NNG codon. When equimolar T,C,A,G are used in NNG, one obtains double doses of LEU and ARG. To improve the distribution, we increase $G_1$ by 4δ, decrease $T_1$ and $A_1$ by δ each and $C_1$ by 2δ. We adopt this pattern because $C_1$ affects both LEU and ARG while $T_1$ and $A_1$ each affect either LEU or ARG, but not both. Similarly, we decrease $T_2$ and $G_2$ by τ while we increase $C_2$ and $A_2$ by τ. We adjusted δ and τ until [ALA]≈[ARG]. There are, under this variegation, four equally most favored amino acids: LEU, ARG, ALA, and GLU. Note that there is one acidic and one basic amino acid in this set. There are two equally least favored amino acids: TRP and MET. The ratio of lfaa/mfaa is 0.5258. If this codon is repeated six times, peptides composed entirely of TRP and MET are 2% as common as peptides composed entirely of the most favored amino acids. We refer to this as "the prevalence of (TRP/MET)$^6$ in optimized NNG$^6$ vgDNA".

When synthesizing vgDNA by the "dirty bottle" method, it is sometimes desirable to use only a limited number of mixes. One very useful mixture is called the "optimized NNS mixture" in which we average the first two positions of the fxS mixture: $T_1=0.24$, $C_1=0.17$, $A_1=0.33$, $G_1=0.26$, the second position is identical to the first, $C_3=G_3=0.5$. This distribution provides the amino acids ARG, SER, LEU, GLY, VAL, THR, ASN, and LYS at greater than 5% plus ALA, ASP, GLU, ILE, MET, and TYR at greater than 4%.

An additional complexly variegated codon is of interest. This codon is identical to the optimized NNT codon at the first two positions and has T:G::90:10 at the third position. This codon provides thirteen amino acids (ALA, ILE, ARG, SER, ASP, LEU, VAL, PHE, ASN, GLY, PRO, TYR, and HIS) at more than 5.5%. THR at 4.3% and CYS at 3.9% are more common than the LFAAs of NNK (3.125%). The remaining five amino acids are present at less than 1%. This codon has the feature that all amino acids are present; sequences having more than two of the low-abundance amino acids are rare. When we isolate an SBD using this codon, we can be reasonably sure that the first 13 amino acids were tested at each position. A similar codon, based on optimized NNG, could be used.

Table 10E shows some properties of an unoptimized NNS (or NNK) codon. Mote that there are three equally most-favored amino acids: ARG, LEU, and SER. There are also twelve equally least favored amino acids: PHE, ILE, MET, TYR, HIS, GLN, ASN, LYS, ASP, GLU, CYS, and TRP. Five amino acids (PRO, THR, ALA, VAL, GLY) fall in between. Note that a six-fold repetition of NNS gives sequences composed of the amino acids [PHE, ILE, MET, TYR, HIS, GLN, ASN, LYS, ASP, GLU, CYS, and TRP] at only ≈0.1% of the sequences composed of [ARG, LEU, and SER]. Not only is this ≈20-fold lower that the prevalence of $(TRP/MET)^6$ in optimized $NNG^6$ vgDNA, bit this lower prevalence applies to twelve amino acids.

Diffuse Mutagenesis

Diffuse Mutagenesis can be applied to any part of the protein at any time, but is most appropriate when some binding to the target has been established. Diffuse Mutagenesis can be accomplished by spiking each of the pure nts activated for DNA synthesis (e.g. nt-phosphoramidites) with a small amount of one or more of the other activated nts.

Contrary to general practice, the present invention sets the level of spiking so that only a small percentage (1% to 0.00001%, for example) of the final product will contain the initial DNA sequence. This will insure that many single, double, triple, and higher mutations occur, but that recovery of the basic sequence will be a possible outcome. Let $N_b$ be the number of bases to be varied, and let Q be the fraction of all sequences that should have the parental sequence, then M, the fraction of the mixture that is the majority component, is $$M=\exp\{\log_e(Q)/N_b\}(\log_{10}(Q)N_b.$$

If, for example, thirty base pairs on the DNA chain were to be varied and 1% of the product is to have the parental sequence, then each mixed nt substrate should contain 86% of the parental nt and 14% of other nts. Table 8 shows the fraction (fn) of DNA molecules having n non-parental bases when 30 bases are synthesized with reagents that contain fraction M of the majority component. When M–0.63096, f24 and higher are less than $10^{-8}$. The entry "most" in Table 8 is the number of changes that has the highest probability. Note that substantial probability for multiple substitutions only occurs if the faction of parental sequence (f0) is allowed to drop to around $10^{-6}$. The $N_b$ base pairs of the DNA chain that are synthesized with mixed reagents need not be contiguous. They are picked so that between $N_b/3$ and $N_b$ codons are affected to various degrees. The residues picked for mutation are picked with reference to the 3D structure of the IPBD, if known. For example, one might pick all or most of the residues in the principal and secondary set. We may impose restrictions on the extent of variation at each of these residues based on homologous sequences or other data. The mixture of non-parental nts need not be random, rather mixtures can be biased to give particular amino acid types specific probabilities of appearance at each codon. For example, one residue may contain a hydrophobic amino acid in all known homologous sequences; in such a case, the first and third base of that codon would be varied, but the second would be set to T. Other examples of how this might be done are given in the horse heart myoglobin example. This diffuse structure-directed mutagenesis will reveal the subtle changes possible in protein backbone associated with conservative interior changes, such as V to I, as well as some not so subtle changes that require concomitant changes at two or more residues of the protein.

III.D. Special Considerations Relating to Variegation of Mini-Proteins with Essential Cysteines Several of the preferred simple or complex variegated codons encode a set of amino acids which includes cysteine. This means that some of the encoded binding domains will feature one or more cysteines in addition to the invariant disulfide-bonded cysteines. For example, at each NNT-encoded position, there is a one in sixteen chance of obtaining cysteine. If six codons are so varied, the fraction of domains containing additional cysteines is 0.33. Odd numbers of cysteines can lead to complications, see Perry and Wetzel (PERR84). On the other hand, many disulfide-containing proteins contain cysteines that do not form disulfides, e.g. trypsin. The possibility of unpaired cysteines can be dealt with in several ways:

First, the variegated phage population can be passed over an immobilized reagent that strongly binds free thiols, such as SulfoLink (catalogue number 44895 H from Pierce Chemical Company, Rockford, Ill., 61105). Another product from Pierce is TNB-Thiol Agarose (Catalogue Code 20409 H). BioRad sells Affi-Gel 401 (catalogue 153–4599) for this purpose.

Second, one can use a variegation that excludes cysteines, such as:

NHT that gives [F,S,Y,L,P,H,I,T,N,V,A,D],

VNS that gives
$[L^2,P^2,H,Q,R^3,I,M,T^2,N,K,S,V^2,A^2,E,D,G^2]$,

NNG that gives $[L^2,S,W,P,Q,R^2,M,T,K,R,V,A,E,G,stop]$,

SNT that gives [L,P,H,R,V,A,D,G],

RNG that gives [M,T,K,R,V,A,E,G],

RMG that gives [T,K,A,E],

VNT that gives [L,P,H,R,I,T,N,S,V,A,D,G], or

RRS that gives $[N,S,K,R,D,E,G^2]$.

However, each of these schemes has one or more of the disadvantages, relative to NNT: a) fewer amino acids are allowed, b) amino acids are not evenly provided, c) acidic and basic amino acids are not equally likely), or d) stop codons occur. Nonetheless, NNG, NHT, and VNT are almost as useful as NNT. NNG encodes 13 different amino acids and one stop signal. Only two amino acids appear twice in the 16-fold mix.

Thirdly, one cacan enrich the population for binding to the preselected target, and evaluate selected sequences post hoc for extra cysteines. Those that contain more cysteines than the cysteines provided for conformational constraint may be perfectly usable. It is possible that a disulfide linkage other than the designed one will occur. This does not mean that the binding domain defined by the isolated DNA sequence is in any way unsuitable. The suitability of the isolated domains is best determined by chemical and biochemical evaluation of chemically synthesized peptides.

Lastly, one can block free thiols with reagents, such as Ellman's reagent, iodoacetate, or methyl iodide, that specifically bind free thiols and that do not react with disulfides, and then leave the modified phage in the population. It is to be understood that the blocking agent may alter the binding properties of the mini-protein; thus, one might use a variety of blocking reagent in expectation that different binding domains will be found. The variegated population of thiol-blocked genetic packages are fractionated for binding. If the DNA sequence of the isolated binding mini-protein contains an odd number of cysteines, then synthetic means are used to prepare mini-proteins having each possible linkage and in which the odd thiol is appropriately blocked. Nishiuchi (NISH82, NISH86, and works cited therein) disclose methods of synthesizing peptides that contain a plurality of cysteines so that each thiol is protected with a different type of blocking group. These groups can be selectively removed so that the disulfide pairing can be controlled. We envision using such a scheme with the alteration that one thiol either remains blocked, or is unblocked and then reblocked with a different reagent.

III.E. Planning the Second and Later Rounds of Variegation

The method of the present invention allows efficient accumulation of information concerning the amino-acid sequence of a binding domain having high affinity for a predetermined target. Although one may obtain a highly useful binding domain from a single round of variegation and affinity enrichment, we expect that multiple rounds will be needed to achieve the highest possible affinity and specificity.

If the first round of variegation results in some binding to the target, but the affinity for the target is still too low, further improvement may be achieved by variegation of the SBDs. Preferably, the process is progressive, i.e. each variegation cycle produces a better starting point for the next variegation cycle than the previous cycle produced. Setting the level of variegation such that the ppbd and many sequences related to the ppbd sequence are present in detectable amounts ensures that the process is progressive. If the level of variegation is so high that the ppbd sequence is present at such low levels that there is an appreciable chance that no transformant will display the PPBD, then the best SBD of the next round could be worse than the PPBD. At excessively high level of variegation, each round of mutagenesis is independent of previous rounds and there is no assurance of progressivity. This approach can lead to valuable binding proteins, but repetition of experiments with this level of variegation will not yield progressive results. Excessive variation is not preferred.

Progressivity is not an all-or-nothing property. So long as most of the information obtained from previous variegation cycles is retained and many different surfaces that are related to the PPBD surface are produced, the process is progressive. If the level of variegation is so high that the ppbd gene may not be detected, the assurance of progressivity diminishes. If the probability of recovering PPBD is negligible, then the probability of progressive behavior is also negligible.

A level of variegation that allows recovery of the PPBD has two properties:

1) we can not regress because the PPBD is available,
2) an enormous number of multiple changes related to the PPBD are available for selection and we are able to detect and benefit from these changes.

It is very unlikely that all of the variants will be worse than the PPBD; we desire the presence of PPBD at detectable levels to insure that all the sequences present are indeed related to PPBD.

An opposing force in our design considerations is that PBDs are useful in the population only up to the amount that can be detected; any excess above the detectable amount is wasted. Thus we produce as many surfaces related to PPBD as possible within the constraint that the PPBD be detectable.

If the level of variegation in the previous variegation cycle was correctly chosen, then the amino acids selected to be in the residues just varied are the ones best determined. The environment of other residues has changed, so that it is appropriate to vary them again. Because there are often more residues in the principal and secondary sets than can be varied simultaneously, we start by picking residues that either have never been varied (highest priority) or that have not been varied for one or more cycles. If we find that varying all the residues except those varied in the previous cycle does not allow a high enough level of diversity, then residues varied in the previous cycle might be varied again. For example, if $M_{ntv}$ (the number of independent transformants that can be produced from $Y_{D100}$ of DNA) and $C_{sensi}$ (the sensitivity of the affinity separation) were such that seven residues could be varied, and if the principal and secondary sets contained 13 residues, we would always vary seven residues, even though that implies varying some residue twice in a row. In such cases, we would pick the residues just varied that contain the amino acids of highest abundance in the variegated codons used.

It is the accumulation of information that allows the process to select those protein sequences that produce binding between the SBD and the target. Some interfaces between proteins and other molecules involve twenty or more residues. Complete variation of twenty residues would generate $10^{26}$ different proteins. By dividing the residues that lie close together in space into overlapping groups of five to seven residues, we can vary a large surface but never need to test more than $10^7$ to $10^9$ candidates at once, a savings of $10^{19}$ to $10^{17}$ fold. The power of selection with accumulation of information is well illustrated in Chapter 3 of DAWK86.

Use of NNT or NNG variegated codons leads to very efficient sampling of variegated libraries because the ratio of (different amino-acid sequences)/(different DNA sequences) is much closer to unity than it is for NNK or even the optimized vg codon (fxS). Nevertheless, a few amino acids are omitted in each case. Both NNT and NNG allow members of all important classes of amino acids: hydrophobic, hydrophilic, acidic, basic, neutral hydrophilic, small, and large. After selecting a binding domain, a subsequent variegation and selection may be desirable to achieve a higher affinity or specificity. During this second variegation, amino acid possibilities overlooked by the preceding variegation may be investigated.

In the first round, we assume that the parental protein has no known affinity for the target material. For example, consider the parental mini-protein, similar to that discussed in Example 11, having the structure $X_1$-$C_2$-$X_4$-$X_5$-$X_6$-$C_7$-$X_8$ in which $C_2$ and $C_7$ form a disulfide bond. Introduction of extra cysteines may cause alternative structures to form which might be disadvantageous. Accidental cysteines at positions 4 or 5 are thought to be potentially more troublesome than at the other positions. We adopt the pattern of variegation: $X_1$:NNT, $X_3$:NNT, $X_4$:NNG, $X_5$:NNG, $X_6$:NNT, and $X_8$:NNT, so that cysteine can not occur at positions 4 and 5. (Table 131 shows the number of different amino acids expected in libraries prepared with DNA variegated in this way and comprising different numbers of independent transformants.)

In the second round of variegation, a preferred strategy is to vary each position through a new set of residues which includes the amino acid(s) which were found at that position in the successful binding domains, and which include as many as possible of the residues which were excluded in the first round of variegation.

A few examples may be helpful. Suppose we obtained PRO using NNT. This amino acid is available with either NNT or NNG. We can be reasonably sure that PRO is the best amino acid from the set [PRO, LEU, VAL, THR, ALA, ARG, GLY, PHE, TYR, CYS, HIS, ILE, ASN, ASP, SER]. Thus we need to try a set that includes [PRO, TRP, GLN, MET, LYS, GLU]. The set allowed by NNG is the preferred set.

What if we obtained HIS instead? Histidine is aromatic and fairly hydrophobic and can form hydrogen bonds to and from the imidazole ring. Tryptophan is hydrophobic and aromatic and can donate a hydrogen to a suitable acceptor and was excluded by the NNT codon. Methionine was also excluded and is hydrophobic. Thus, one preferred course is to use the variegated codon HDS that allows [HIS, GLN, ASN, LYS, TYR, CYS, TRP, ARG, SER, GLY, <stop>].

GLN can be encoded by the NNG codon. If GIN is selected, at the next round we might use the vg codon VAS that encodes three of the seven excluded possibilities, viz. HIS, ASN, and ASP. The codon VAS encodes 6 amino acid sequences in six DNA sequences. This leaves PHE, CYS, TYR, and ILE untested, but these are all very hydrophobic. Switching to NNT would be undesirable because that would exclude GLN. One could use NAS that includes TYR and <stop>. Suppose the successful amino acid encoded by an NNG codon was ARG. Here we switch to NNT because this allows ARG plus all the excluded possibilities.

THR is another possibility with the NNT codon. If THR is selected, we switch to NNG because that includes the previously excluded possibilities and includes THR. Suppose the successful amino acid encoded by the NNT codon was ASP. We use RRS at the next variegation because this includes both acidic amino acids plus LYS and ARG. One could also use VRS to allow GLN.

Thus, later rounds of variegation test both amino acid positions not previously mutated, and amino acid substitutions at a previously mutated position which were not within the previous substitution set.

If the first round of variegation is entirely unsuccessful, a different pattern of variegation should be used. For example, if more than one interaction set can be defined within a domain, the residues varied in the next round of variegation should be from a different set than that probed in the initial variegation. If repeated failures are encountered, one may switch to a different IPBD.

IV. DISPLAY STRATEGY, DISPLAYING FOREIGN BINDING DOMAINS ON THE SURFACE OF A "GENETIC PACKAGE"

IV.A. General Requirements for Genetic Packages

It is emphasized that the GP on which selection-through-binding will be practiced must be capable, after the selection, either of growth in some suitable environment or of in vitro amplification and recovery of the encapsulated genetic message. During at least part of the growth, the increase in number is preferably approximately exponential with respect to time. The component of a population that exhibits the desired binding properties may be quite small, for example, one in $10^6$ or less. Once this component of the population is separated from the non-binding components, it must be possible to amplify it. Culturing viable cells is the most powerful amplification of genetic material known and is preferred. Genetic messages can also be amplified in vitro, e.g. by PCR, but this is not the most preferred method.

Preferred GPs are vegetative bacterial cells, bacterial spores and bacterial DNA viruses. Eukaryotic cells could be used as genetic packages but have longer dividing times and more stringent nutritional requirements than do bacteria and it is much more difficult to produce a large number of independent transformants. They are also more fragile than bacterial cells and therefore more difficult to chromatograph without damage. Eukaryotic viruses could be used instead of bacteriophage but must be propagated in eukaryotic cells and therefore suffer from some of the amplification problems mentioned above.

Nonetheless, a strain of any living cell or virus is potentially useful if the strain can be: 1) genetically altered with reasonable facility to encode a potential binding domain, 2) maintained and amplified in culture, 3) manipulated to display the potential binding protein domain where it can interact with the target material during affinity separation, and 4) affinity separated while retaining the genetic information encoding the displayed binding domain in recoverable form. Preferably, the GP remains viable after affinity separation.

When the genetic package is a bacterial cell, or a phage which is assembled periplasmically, the display means has two components. The first component is a secretion signal which directs the initial expression product to the inner membrane of the cell (a host cell when the package is a phage). This secretion signal is cleaved off by a signal peptidase to yield a processed, mature, potential binding protein. The second component is an outer surface transport signal which directs the package to assemble the processed protein into its outer surface. Preferably, this outer surface transport signal is derived from a surface protein native to the genetic package.

For example, in a preferred embodiment, the hybrid gene comprises a DNA encoding a potential binding domain operably linked to a signal sequence (e.g., the signal sequences of the bacterial phoA or bla genes or the signal sequence of M13 phage geneIII) and to DNA encoding a coat protein (e.g., the M13 gene III or gene VIII proteins) of a filamentous phage (e.g., M13). The expression product is transported to the inner membrane (lipid bilayer) of the host cell, whereupon the signal peptide is cleaved off to leave a processed hybrid protein. The C-terminus of the coat protein-like component of this hybrid protein is trapped in the lipid bilayer, so that the hybrid protein does not escape into the periplasmic space. (This is typical of the wild-type coat protein.) As the single-stranded DNA of the nascent phage particle passes into the periplasmic space, it collects both wild-type coat protein and the hybrid protein from the lipid bilayer. The hybrid protein is thus packaged into the surface sheath of the filamentous phage, leaving the potential binding domain exposed on its outer surface. (Thus, the filamentous phage, not the host bacterial cell, is the "replicable genetic package" in this embodiment.)

If a secretion signal is necessary for the display of the potential binding domain, in an especially preferred embodiment the bacterial cell in which the hybrid gene is expressed is of a "secretion-permissive" strain.

When the genetic package is a bacterial spore, or a phage whose coat is assembled intracellularly, a secretion signal directing the expression product to the inner membrane of the host bacterial cell is unnecessary. In these cases, the display means is merely the outer surface transport signal, typically a derivative of a spore or phage coat protein.

There are several methods of arranging that the ipbd gene is expressed in such a manner that the IPBD is displayed on the outer surface of the GP. If one or more fusions of fragments of x genes to fragments of a natural osp gene are known to cause X protein domains to appear on the GP surface, then we pick the DNA sequence in which an ipbd gene fragment replaces the x gene fragment in one of the successful osp-x fusions as a preferred gene to be tested for the display-of-IPBD phenotype. (The gene may be constructed in any manner.) If no fusion data are available, then we fuse an ipbd fragment to various fragments, such as fragments that end at known or predicted domain boundaries, of the osp gene and obtain GPs that display the osp-ipbd fusion on the GP outer surface by screening or selection for the display-of-IPBD pheno-type. The OSP may be modified so as to increase the flexibility and/or length of the linkage between the OSP and the IPBD and thereby reduce interference between the two.

The fusion of ipbd and osp fragments may also include fragments of random or pseudorandom DNA to produce a population, members of which may display IPBD on the GP surface. The members displaying IPBD are isolated by screening or selection for the display-of-binding phenotype.

The replicable genetic entity (phage or plasmid) that carries the osp-pbd genes (derived from the osp-ipbd gene) through the selection-through-binding process, is referred to hereinafter as the operative cloning vector (OCV). When the OCV is a phage, it may also serve as the genetic package. The choice of a GP is dependent in part on the availability of a suitable OCV and suitable OSP.

Preferably, the GP is readily stored, for example, by freezing. If the GP is a cell, it should have a short doubling time, such as 20–40 minutes. If the GP is a virus, it should be prolific, e.g., a burst size of at least 100/infected cell. GPs which are finicky or expensive to culture are disfavored. The GP should be easy to harvest, preferably by centrifugation. The GP is preferably stable for a temperature range of −70° to 42° C. (stable at 4° C. for several days or weeks); resistant to shear forces found in HPLC; insensitive to UV; tolerant of desiccation; and resistant to a pH of 2.0 to 10.0, surface active agents such as SDS or Triton, chaotropes such as 4M urea or 2M guanidinium HCl, common ions such as $K^+$, $Na^+$, and $SO_4^{--}$, common organic solvents such as ether and acetone, and degradative enzymes. Finally, there must be a suitable OCV.

Although knowledge of specific OSPs may not be required for vegetative bacterial cells and endospores, the user of the present invention, preferably, will know: is the sequence of any osp known? (preferably yes, at least one required for phage). How does the OSP arrive at the surface of GP? (knowledge of route necessary, different routes have different uses, no route preferred per se). Is the OSP post-translationally processed? (no processing most preferred, predictable processing preferred over unpredictable processing). What rules are known governing this processing, if there is any processing? (no processing most preferred, predictable processing acceptable). What function does the OSP serve in the outer surface? (preferably not essential). Is the 3D structure of an OSP known? (highly preferred). Are fusions between fragments of osp and a fragment of x known? Does expression of these fusions lead to X appearing on the surface of the GP? (fusion data is as preferred as knowledge of a 3D structure). Is a "2D" structure of an OSP available? (in this context, a "2D" structure indicates which residues are exposed on the cell surface) (2D structure less preferred than 3D structure). Where are the domain boundaries in the OSP? (not as preferred as a 2D structure, but acceptable). Could IPBD go through the same process as OSP and fold correctly? (IPBD might need prosthetic groups) (preferably IPBD will fold after same process). Is the sequence of an osp promoter known? (preferably yes). Is osp gene controlled by regularable promoter available? (preferably yes). What activates this promoter? (preferably a diffusible chemical, such as IPTG). How many different OSPs do we know? (the more the better). How many copies of each OSP are present on each package? (more is better).

The user will want knowledge of the physical attributes of the GP: How large is the GP? (knowledge useful in deciding how to isolate GPs) (preferably easy to separate from soluble proteins such as IgGs). What is the charge on the GP? (neutral preferred). What is the sedimentation rate of the GP? (knowledge preferred, no particular value preferred).

The preferred GP, OCV and OSP are those for which the fewest serious obstacles can be seen, rather than the one that scores highest on any one criterion.

Viruses are preferred over bacterial cells and spores (cp. LUIT85 and references cited therein). The virus is preferably a DNA virus with a genome size of 2 kb to 10 kb base pairs, such as (but not limited to) the filamentous (Ff) phage M13, fd, and f1 (inter alia see RASC86, BOEK80, BOEK82, DAYL88, GRAY81b, KUHN88, LOPE85, WEBS85, MARV75, MARV80, MOSE82, CRIS84, SMIT88a, SMIT88b); the IncN specific phage Ike and If1 (NAKA81, PEET85, PEET87, THOM83, THOM88a); IncP-specific *Pseudomonas aeruginosa* phage Pf1 (THOM83, THOM88a) and Pf3 (LUIT83, LUIT85, LUTI87, THOM88a); and the *Xanthomonas oryzae* phage Xf (THOM83, THOM88a). Filamentous phage are especially preferred.

Preferred OSPs for several GPs are given in Table 2. References to osp-ipbd fusions in this section should be taken to apply, mutatis mutandis, to osp-pbd and osp-sbd fusions as well.

The species chosen as a GP should have a well-characterized genetic system and strains defective in genetic recombination should be available. The chosen strain may need to be manipulated to prevent changes of its physiological state that would alter the number or type of proteins or other molecules on the cell surface during the affinity separation procedure.

IV.B. Phages for Use as GPs:

Unlike bacterial cells and spores choice of a phage depends strongly on knowledge of the 3D structure of an OSP and how it interacts with other proteins in the capsid. This does not mean that we need atomic resolution of the OSP, but that we need to know which segments of the OSP interact to make the viral coat and which segments are not constrained by structural or functional roles. The size of the phage genome and the packaging mechanism are also important because the phage genome itself is the cloning vector. The osp-ipbd gene is inserted into the phage genome; therefore: 1) the genome of the phage must allow introduction of the osp-ipbd gene either by tolerating additional genetic material or by having replaceable genetic material; 2) the virion must be capable of packaging the genome after accepting the insertion or substitution of genetic material, and 3) the display of the OSP-IPBD protein on the phage surface must not disrupt virion structure sufficiently to interfere with phage propagation.

The morphogenetic pathway of the phage determines the environment in which the IPBD will have opportunity to fold. Periplasmically assembled phage are preferred when IPBDs contain essential disulfides, as such IPBDs may not fold within a cell (these proteins may fold after the phage is released from the cell). Intracellularly assembled phage are preferred when the IPBD needs large or insoluble prosthetic groups (such as $Fe_4S_4$ clusters), since the IPBD may not fold if secreted because the prosthetic group is lacking.

When variegation is introduced in Part II, multiple infections could generate hybrid GPs that carry the gene for one PBD but have at least some copies of a different PBD on their surfaces; it is preferable to minimize this possibility by infecting cells with phage under conditions resulting in a low multiple-of-infection (MOI).

Bacteriophages are excellent candidates for GPs because there is little or no enzymatic activity associated with intact mature phage, and because the genes are inactive outside a bacterial host, rendering the mature phage particles metabolically inert.

The filamentous phages (e.g., M13) are of particular interest.

For a given bacteriophage, the preferred OSP is usually one that is present on the phage surface in the largest number of copies, as this allows the greatest flexibility in varying the ratio of OSP-IPBD to wild type OSP and also gives the highest likelihood of obtaining satisfactory affinity separation. Moreover, a protein present in only one or a few copies usually performs an essential function in morphogenesis or infection; mutating such a protein by addition or insertion is likely to result in reduction in viability of the GP. Nevertheless, an OSP such as M13 gIII protein may be an excellent choice as OSP to cause display of the PBD.

It is preferred that the wild-type osp gene be preserved. The ipbd gene fragment may be inserted either into a second copy of the recipient osp gene or into a novel engineered osp gene. It is preferred that the osp-ipbd gene be placed under control of a regulated promoter. Our process forces the evolution of the PBDs derived from IPBD so that some of them develop a novel function, viz. binding to a chosen target. Placing the gene that is subject to evolution on a duplicate gene is an imitation of the widely-accepted scenario for the evolution of protein families. It is now generally accepted that gene duplication is the first step in the evolution of a protein family from an ancestral protein. By having two copies of a gene, the affected physiological process can tolerate mutations in one of the genes. This process is well understood and documented for the globin family (cf. DICK83, p65ff, and CREI84, p117–125).

The user must choose a site in the candidate OSP gene for inserting a ipbd gene fragment. The coats of most bacteriophage are highly ordered. Filamentous phage can be described by a helical lattice; isometric phage, by an icosahedral lattice. Each monomer of each major coat protein sits on a lattice point and makes defined interactions with each of its neighbors. Proteins that fit into the lattice by making some, but not all, of the normal lattice contacts are likely to destabilize the virion by: a) aborting formation of the virion, b) making the virion unstable, or c) leaving gaps in the virion so that the nucleic acid is not protected. Thus in bacteriophage, unlike the cases of bacteria and spores, it is important to retain in engineered OSP-IPBD fusion proteins those residues of the parental OSP that interact with other proteins in the virion. For M13 gVIII, we retain the entire mature protein, while for M13 gIII, it might suffice to retain the last 100 residues (or even fewer). Such a truncated gIII protein would be expressed in parallel with the complete gIII protein, as gIII protein is required for phage infectivity.

Il'ichev et al. (ILIC89) have reported viable phage having alterations in gene VIII. In one case, a point mutation changed one amino acid near the amino terminus of the mature gVIII protein from GLU to ASP. In the other case, five amino acids were inserted at the site of the first mutation. They suggested that similar constructions could be used for vaccines. They did not report on any binding properties of the modified phage, nor did they suggest mutagenizing the inserted material. Furthermore, they did not insert a binding domain, nor did they suggest inserting such a domain.

Further considerations on the design of the ipbd::osp gene is discussed in section IV.F.

Filamentous phage:

Compared to other bacteriophage, filamentous phage in general are attractive and M13 in particular is especially attractive because: 1) the 3D structure of the virion is known; 2) the processing of the coat protein is well understood; 3) the genome is expandable; 4) the genome is small; 5) the sequence of the genome is known; 6) the virion is physically resistant to shear, heat, cold, urea, guanidinium Cl, low pH, and high salt; 7) the phage is a sequencing vector so that sequencing is especially easy; 8) antibiotic-resistance genes have been cloned into the genome with predictable results (HINE80); 9) It is easily cultured and stored (FRIT85), with no unusual or expensive media requirements for the infected cells, 10) it has a high burst size, each infected cell yielding 100 to 1000 M13 progeny after infection; and 11) it is easily harvested and concentrated (SALI64, FRIT85).

The filamentous phage include M13, f1, fd, If1, Ike, Xf, Pf1, and Pf3.

The entire life cycle of the filamentous phage M13, a common cloning and sequencing vector, is well understood. M13 and f1 are so closely related that we consider the properties of each relevant to both (RASC86); any differentiation is for historical accuracy. The genetic structure (the complete sequence (SCHA78), the identity and function of the ten genes, and the order of transcription and location of the promoters) of M13 is well known as is the physical structure of the virion (BANN81, BOEK80, CHAN79, ITOK79, KAPL78, KUHN85b, KUHN87, MAKO80, MARV78, MESS78, OHKA81, RASC86, RUSS81, SCHA78, SMIT85, WEBS78, and ZIMM82); see RASC86 for a recent review of the structure and function of the coat proteins. Because the genome is small (6423 bp), cassette mutagenesis is practical on RF M13 (AUSU87), as is single-stranded oligont directed mutagenesis (FRIT85). M13 is a plasmid and transformation system in itself, and an ideal sequencing vector. M13 can be grown on $Rec^-$ strains of *E. coli*. The M13 genome is expandable (MESS78, FRIT85) and M13 does not lyse cells. Because the M13 genome is extruded through the membrane and coated by a large number of identical protein molecules, it can be used as a cloning vector (WATS87 p278, and MESS77). Thus we can insert extra genes into M13 and they will be carried along in a stable manner.

Marvin and collaborators (MARV78, MAKO80, BANN81) have determined an approximate 3D virion structure of f1 by a combination of genetics, biochemistry, and X-ray diffraction from fibers of the virus. FIG. 4 is drawn after the model of Banner et al. (BANN81) and shows only the C$_\alpha$s of the protein. The apparent holes in the cylindrical sheath are actually filled by protein side groups so that the DNA within is protected. The amino terminus of each protein monomer is to the outside of the cylinder, while the carboxy terminus is at smaller radius, near the DNA. Although other filamentous phages (e.g. Pf1 or Ike) have different helical symmetry, all have coats composed of many short α-helical monomers with the amino terminus of each monomer on the virion surface.

The major coat protein is encoded by gene VIII. The 50 amino acid mature gene VIII coat protein is synthesized as a 73 amino acid precoat (ITOK79). The first 23 amino acids constitute a typical signal-sequence which causes the nascent polypeptide to be inserted into the inner cell membrane. Whether the precoat inserts into the membrane by itself or through the action of host secretion components, such as SecA and SecY, remains controversial, but has no effect on the operation of the present invention.

An *E. coli* signal peptidase (SP-I) recognizes amino acids 18, 21, and 23, and, to a lesser extent, residue 22, and cuts between residues 23 and 24 of the precoat (KUHN85a, KUHN85b, OLIV87). After removal of the signal sequence, the amino terminus of the mature coat is located on the periplasmic side of the inner membrane; the carboxy terminus is on the cytoplasmic side. About 3000 copies of the mature 50 amino acid coat protein associate side-by-side in the inner membrane.

The sequence of gene VIII is known, and the amino acid sequence can be encoded on a synthetic gene, using lacUV5 promoter and used in conjunction with the LacI$^q$ repressor. The lacUV5 promoter is induced by IPTG. Mature gene VIII protein makes up the sheath around the circular ssDNA. The 3D structure of f1 virion is known at medium resolution; the amino terminus of gene VIII protein is on surface of the virion. A few modifications of gene VIII have been made and are discussed below. The 2D structure of M13 coat protein is implicit in the 3D structure. Mature M13 gene VIII protein has only one domain.

When the GP is M13 the gene III and the gene VIII proteins are highly preferred as OSP (see Examples I through IV). The proteins from genes VI, VII, and IX may also be used.

As discussed in the Examples, we have constructed a tripartite gene comprising:

1) DNA encoding a signal sequence directing secretion of parts (2) and (3) through the inner membrane,
2) DNA encoding the mature BPTI sequence, and
3) DNA encoding the mature M13 gVIII protein.

This gene causes BPTI to appear in active form on the surface of M13 phage.

The gene VIII protein is a preferred OSP because it is present in many copies and because its location and orientation in the virion are known (BANN81). Preferably, the PBD is attached to the amino terminus of the mature M13 coat protein. Had direct fusion of PBD to M13 CP failed to cause PBD to be displayed on the surface of M13, we would have varied part of the mini-protein sequence and/or insert short random or nonrandom spacer sequences between miniprotein and M13 CP. The 3D model of f1 indicates strongly that fusing IPBD to the amino terminus of M13 CP is more likely to yield a functional chimeric protein than any other fusion site.

Similar constructions could be made with other filamentous phage. Pf3 is a well known filamentous phage that infects *Pseudomonas aerugenosa* cells that harbor an IncP-1 plasmid. The entire genome has been sequenced (LUIT85) and the genetic signals involved in replication and assembly are known (LUIT87). The major coat protein of PF3 is unusual in having no signal peptide to direct its secretion. The sequence has charged residues ASP$_7$, ARG$_{37}$, LYS$_{40}$, and PHE$_{44}$-COO$^-$ which is consistent with the amino terminus being exposed. Thus, to cause an IPBD to appear on the surface of Pf3, we construct a tripartite gene comprising:

1) a signal sequence known to cause secretion in *P. aerugenosa* (preferably known to cause secretion of IPBD) fused in-frame to,
2) a gene fragment encoding the IPBD sequence, fused in-frame to,
3) DNA encoding the mature Pf3 coat protein.

Optionally, DNA encoding a flexible linker of one to 10 amino acids is introduced between the ipbd gene fragment and the Pf3 coat-protein gene. Optionally, DNA encoding the recognition site for a specific protease, such as tissue plasminogen activator or blood clotting Factor Xa, is introduced between the ipbd gene fragment and the Pf3 coatprotein gene. Amino acids that form the recognition site for a specific protease may also serve the function of a flexible linker. This tripartite gene is introduced into Pf3 so that it does not interfere with expression of any Pf3 genes. To reduce the possibility of genetic recombination, part (3) is designed to have numerous silent mutations relative to the wild-type gene. Once the signal sequence is cleaved off, the IPBD is in the periplasm and the mature coat protein acts as an anchor and phage-assembly signal. It matters not that this fusion protein comes to rest in the lipid bilayer by a route different from the route followed by the wild-type coat protein.

The amino-acid sequence of M13 pre-coat (SCHA78), called AA_seq1, is

```
                         AA_seq1
                   1    1    2  ||2    3    3    4    4    5
         5         0    5    0  ↓5    0    5    0    5    0
         MKKSLVLKASVAVATLVPMLSFAAEGDDPAKAAFNSLQASATEYIGYAWA 5    6    6    7    7
         5    0    5    0    3
         MVVVIVGATIGIKLFKKFTSKAS
```

The single-letter codes for amino acids and the codes for ambiguous DNA are given in Table 1. The best site for inserting a novel protein domain into M13 CP is after A23 because SP-I cleaves the precoat protein after A23, as indicated by the arrow. Proteins that can be secreted will appear connected to mature M13 CP at its amino terminus. Because the amino terminus of mature M13 CP is located on the outer surface of the virion, the introduced domain will be displayed on the outside of the virion. The uncertainty of the mechanism by which M13CP appears in the lipid bilayer raises the possibility that direct insertion of bpti into gene VIII may not yield a functional fusion protein. It may be necessary to change the signal sequence of the fusion to, for example, the phoA signal sequence (MKQSTIALALLPLL-FTPVTKA . . . ). Marks et al. (MARK86) showed that the phoA signal peptide could direct mature BPTI to the *E. coli* periplasm.

Another vehicle for displaying the IPBD is by expressing it as a domain of a chimeric gene containing part or all of gene III. This gene encodes one of the minor coat proteins of M13. Genes VI, VII, and IX also encode minor coat proteins. Each of these minor proteins is present in about 5 copies per virion and is related to morphogenesis or infection. In contrast, the major coat protein is present in more than 2500 copies per virion. The gene VI, VII, and IX proteins are present at the ends of the virion; these three proteins are not post-translationally processed (RASC86).

The single-stranded circular phage DNA associates with about five copies of the gene III protein and is then extruded through the patch of membrane-associated coat protein in such a way that the DNA is encased in a helical sheath of protein (WEBS78). The DNA does not base pair (that would impose severe restrictions on the virus genome); rather the bases intercalate with each other independent of sequence.

Smith (SMIT85) and de la Cruz et al. (DELA88) have shown that insertions into gene III cause novel protein domains to appear on the virion outer surface. The miniprotein's gene may be fused to gene III at the site used by Smith and by de la Cruz et al., at a codon corresponding to another domain boundary or to a surface loop of the protein, or to the amino terminus of the mature protein.

All published works use a vector containing a single modified gene III of fd. Thus, all five copies of gIII are identically modified. Gene III is quite large (1272 b.p. or about 20% of the phage genome) and it is uncertain whether a duplicate of the whole gene can be stably inserted into the phage. Furthermore, all five copies of gIII protein are at one end of the virion. When bivalent target molecules (such as antibodies) bind a pentavalent phage, the resulting complex may be irreversible. Irreversible binding of the GP to the target greatly interferes with affinity enrichment of the GPs that carry the genetic sequences encoding the novel polypeptide having the highest affinity for the target.

To reduce the likelihood of formation of irreversible complexes, we may use a second, synthetic gene that encodes carboxy-terminal parts of III. We might, for example, engineer a gene that consists of (from 5' to 3'):

1) a promoter (preferably regulated),
2) a ribosome-binding site,
3) an initiation codon,
4) a functional signal peptide directing secretion of parts (5) and (6) through the inner membrane,
5) DNA encoding an IPBD,
6) DNA encoding residues 275 through 424 of M13 gIII protein,
7) a translation stop codon, and
8) (optionally) a transcription stop signal.

We leave the wild-type gene III so that some unaltered gene III protein will be present. Alternatively, we may use gene VIII protein as the OSP and regulate the osp::ipbd fusion so that only one or a few copies of the fusion protein appear on the phage.

M13 gene VI, VII, and IX proteins are not processed after translation. The route by which these proteins are assembled into the phage have not been reported. These proteins are necessary for normal morphogenesis and infectivity of the phage. Whether these molecules (gene VI protein, gene VII protein, and gene IX protein) attach themselves to the phage: a) from the cytoplasm, b) from the periplasm, or c) from within the lipid bilayer, is not known. One could use any of these proteins to introduce an IPBD onto the phage surface by one of the constructions:

1) ipbd::pmcp,
2) pmcp::ipbd,
3) signal::ipbd::pmcp, and
4) signal::pmcp::ipbd.

where ipbd represents DNA coding on expression for the initial potential binding domain; pmcp represents DNA coding for one of the phage minor coat proteins, VI, VII, and IX; signal represents a functional secretion signal peptide, such as the phoA signal (MKQSTIALALLPLLFTPVTKA); and "::" represents in-frame genetic fusion. The indicated fusions are placed downstream of a known promoter, preferably a regulated promoter such as lacUV5, tac, or trp. Fusions (1) and (2) are appropriate when the minor coat protein attaches to the phage from the cytoplasm or by autonomous insertion into the lipid bilayer. Fusion (1) is appropriate if the amino terminus of the minor coat protein is free and (2) is appropriate if the carboxy terminus is free. Fusions (3) and (4) are appropriate if the minor coat protein attaches to the phage from the periplasm or from within the lipid bilayer. Fusion (3) is appropriate if the amino terminus of the minor coat protein is free and (4) is appropriate if the carboxy terminus is free.

Bacteriophage ΦX174:

The bacteriophage ΦX174 is a very small icosahedral virus which has been thoroughly studied by genetics, biochemistry, and electron microscopy (See *The Single-Stranded DNA Phages* (DENH78)). To date, no proteins from ΦX174 have been studied by X-ray diffraction. ΦX174 is not used as a cloning vector because ΦX174 can accept very little additional DNA; the virus is so tightly constrained that several of its genes overlap. Chambers et al. (CHAM82) showed that mutants in gene G are rescued by the wild-type G gene carried on a plasmid so that the host supplies this protein.

Three gene products of ΦX174 are present on the outside of the mature virion: F (capsid), G (major spike protein, 60 copies per virion), and H (minor spike protein, 12 copies per virion). The G protein comprises 175 amino acids, while H comprises 328 amino acids. The F protein interacts with the single-stranded DNA of the virus. The proteins F, G, and H are translated from a single mRNA in the viral infected cells. If the G protein is supplied from a plasmid in the host, then the viral g gene is no longer essential. We introduce one or more stop codons into g so that no G is produced from the viral gene. We fuse a pbd gene fragment to h, either at the 3' or 5' terminus. We eliminate an amount of the viral g gene equal to the size of pbd so that the size of the genome is unchanged.

Large DNA Phages

Phage such as λ or T4 have much larger genomes than do M13 or ΦX174. Large genomes are less conveniently manipulated than small genomes. Phage λ has such a large genome that cassette mutagenesis is not practicable. One can not use annealing of a mutagenic oligonucleotide either, because there is no ready supply of single-stranded λ DNA. (λ DNA is packaged as double-stranded DNA.) Phage such as λ and T4 have more complicated 3D capsid structures than M13 or ΦX174, with more OSPs to choose from. Intracellular morphogenesis of phage λ could cause protein domains that contain disulfide bonds in their folded forms not to fold.

Phage λ virions and phage T4 virions form intracellularly, so that IPBDs requiring large or insoluble prosthetic groups might fold on the surfaces of these phage.

RNA Phages

RNA phage are not preferred because manipulation of RNA is much less convenient than is the manipulation of DNA. If the RNA phage MS2 were modified to make room for an osp-ipbd gene and if a message containing the A protein binding site and the gene for a chimera of coat protein and a PBD were produced in a cell that also contained A protein and wild-type coat protein (both produced from regulated genes on a plasmid), then the RNA coding for the chimeric protein would get packaged. A package comprising RNA encapsulated by proteins encoded by that RNA satisfies the major criterion that the genetic message inside the package specifies something on the outside. The particles by themselves are not viable unless the modified A protein is functional. After isolating the packages that carry an SBD, we would need to: 1) separate the RNA from the protein capsid; 2) reverse transcribe the RNA into DNA, using AMV or MMTV reverse transcriptase, and 3) use *Thermus aquaticus* DNA polymerase for 25 or more cycles of Polymerase Chain Reaction$^{(TM)}$ to amplify the osp-sbd DNA until there is enough to subclone the recovered genetic message into a plasmid for sequencing and further work.

Alternatively, helper phage could be used to rescue the isolated phage. In one of these ways we can recover a sequence that codes for an SBD having desirable binding properties.

IV.C. Bacterial Cells as Genetic Packages:

One may choose any well-characterized bacterial strain which (1) may be grown in culture (2) may be engineered to display PBDs on its surface, and (3) is compatible with affinity selection.

Among bacterial cells, the preferred genetic packages are *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis,* and especially *Escherichia coli.* The potential binding mini-protein may be expressed as an insert in a chimeric bacterial outer surface protein (OSP). All bacteria exhibit proteins on their outer surfaces. Works on the localization of OSPs and the methods of determining their structure include: CALA90, HEIJ90, EHRM90, BENZ88a, BENZ88b, MANO88, BAKE87, RAND87, HANC87, HENR87, NAKA86b, MANO86, SILH85, TOMM85, NIKA84, LUGT83, and BECK83.

In *E. coli,* LamB is a preferred OSP. As discussed below, there are a number of very good alternatives in *E. coli* and there are very good alternatives in other bacterial species. There are also methods for determining the topology of OSPs so that it is possible to systematically determine where to insert an ipbd into an osp gene to obtain display of an IPBD on the surface of any bacterial species.

In view of the extensive knowledge of *E. coli,* a strain of *E. coli,* defective in recombination, is the strongest candidate as a bacterial GP.

Oliver has reviewed mechanisms of protein secretion in bacteria (OLIV85a and OLIV87). Nikaido and Vaara (NIKA87), Benz (BENZ88b), and Baker et al. (BAKE87) have reviewed mechanisms by which proteins become localized to the outer membrane of gram-negative bacteria. While most bacterial proteins remain in the cytoplasm, others are transported to the periplasmic space (which lies between the plasma membrane and the cell wall of gram-negative bacteria), or are conveyed and anchored to the outer surface of the cell. Still others are exported (secreted) into the medium surrounding the-cell. Those characteristics of a protein that are recognized by a cell and that cause it to be transported out of the cytoplasm and displayed on the cell surface will be termed "outer-surface transport signals".

Gram-negative bacteria have outer-membrane proteins (OMP), that form a subset of OSPs. Many OMPs span the membrane one or more times. The signals that cause OMPs to localize in the outer membrane are encoded in the amino acid sequence of the mature protein. Outer membrane proteins of bacteria are initially expressed in a precursor form including a so-called signal peptide. The precursor protein is transported to the inner membrane, and the signal peptide moiety is extruded into the periplasmic space. There, it is cleaved off by a "signal peptidase", and the remaining "mature" protein can now enter the periplasm. Once there, other cellular mechanisms recognize structures in the mature protein which indicate that its proper place is on the outer membrane, and transport it to that location.

It is well known that the DNA coding for the leader or signal peptide from one protein may be attached to the DNA sequence coding for another protein, protein X, to form a chimeric gene whose expression causes protein X to appear free in the periplasm (BECK83, INOU86 Ch10, LEEC86, MARK86, and BOQU87). That is, the leader causes the chimeric protein to be secreted through the lipid bilayer; once in the periplasm, it is cleaved off by the signal peptidase SP-I.

The use of export-permissive bacterial strains (LISS85, STAD89) increases the probability that a signal-sequence-fusion will direct the desired protein to the cell surface. Liss et al. (LISS85) showed that the mutation prlA4 makes *E. coli* more permissive with respect to signal sequences; Similarly, Stader et al. (STAD89) found a strain that bears a prlG mutation and that permits export of a protein that is blocked from export in wild-type cells. Such export-permissive strains are preferred.

OSP-IPBD fusion proteins need not fill a structural role in the outer membranes of Gram-negative bacteria because parts of the outer membranes are not highly ordered. For large OSPs there is likely to be one or more sites at which osp can be truncated and fused to ipbd such that cells expressing the fusion will display IPBDs on the cell surface. Fusions of fragments of omp genes with fragments of an x gene have led to X appearing on the outer membrane (CHAR88b, BENS84, CLEM81). When such fusions have been made, we can design an osp-ipbd gene by substituting ipbd for x in the DNA sequence. Otherwise, a successful OMP-IPBD fusion is preferably sought by fusing fragments of the best omp to an ipbd, expressing the fused gene, and testing the resultant GPs for display-of-IPBD phenotype. We use the available data about the OMP to pick the point or points of fusion between omp and ipbd to maximize the likelihood that IPBD will be displayed. (Spacer DNA encoding flexible linkers, made, e.g., of GLY, SER, and ASN, may be placed between the osp- and ipbd-derived fragments to facilitate display.) Alternatively, we truncate osp at several sites or in a manner that produces osp fragments of variable length and fuse the osp fragments to ipbd; cells expressing the fusion are screened or selected which display IPBDs on the cell surface. Freudl et al. (FREU89) have shown that fragments of OSPs (such as OmpA) above a certain size are incorporated into the outer membrane. An additional alternative is to include short segments of random DNA in the fusion of omp fragments to ipbd and then screen or select the resulting variegated population for members exhibiting the display-of-IPBD phenotype.

In *E. coli,* the LamB protein is a well understood OSP and can be used (BENS84, CHAR90, RONC90, VAND90, CHAP90, MOLL90, CHAR88b, CHAR88c, CLEM81, DARG88, FERE82a, FERE82b, FERE83, FERE84, FERE86a, FERE86b, FERE89a, FERE89b, GEHR87, HALL82, NAKA86a, STAD86, HEIN88, BENS87b, BENS87c, BOUG84, BOUL86a, CHAR84). The *E. coli* LamB has been expressed in functional form in *S. typhimurium* (DEVR84, BARB85, HARK87), *V. cholerae* (HARK86), and *K. pneumonia* (DEVR84, WEHM89), so that one could display a population of PBDs in any of these species as a fusion to *E. coli* LamB. *K. pneumonia* expresses a maltoporin similar to LamB (WEHM89) which could also be used. In *P. aeruginosa*, the D1 protein (a homologue of LamB) can be used (TRIA88).

LamB of *E. coli* is a porin for maltose and malto-dextrin transport, and serves as the receptor for adsorption of bacteriophages λ and K10. LamB is transported to the outer membrane if a functional N-terminal sequence is present; further, the first 49 amino acids of the mature sequence are required for successful transport (BENS84). As with other OSPs, LamB of *E. coli* is synthesized with a typical signal-sequence which is subsequently removed. Homology between parts of Lamb protein and other outer membrane proteins OmpC, OmpF, and PhoE has been detected (NIKA84), including homology between Lamb amino acids 39–49 and sequences of the other proteins. These subsequences may label the proteins for transport to the outer membrane.

The amino acid sequence of Lamb is known (CLEM81), and a model has been developed of how it anchors itself to the outer membrane (Reviewed by, among others, BENZ88b). The location of its maltose and phage binding domains are also known (HEIN88). Using this information, one may identify several strategies by which a PBD insert may be incorporated into LamB to provide a chimeric OSP which displays the PBD on the bacterial outer membrane.

When the PBDs are to be displayed by a chimeric transmembrane protein like LamB, the PBD could be inserted into a loop normally found on the surface of the cell (cp. BECK83, MANO86). Alternatively, we may fuse a 5' segment of the osp gene to the ipbd gene fragment; the point of fusion is picked to correspond to a surface-exposed loop of the OSP and the carboxy terminal portions of the OSP are omitted. In LamB, it has been found that up to 60 amino acids may be inserted (CHAR88b) with display of the foreign epitope resulting; the structural features of OmpC, OmpA, OmpF, and PhoE are so similar that one expects similar behavior from these proteins.

It should be noted that while LamB may be characterized as a binding protein, it is used in the present invention to provide an OSTS; its binding domains are not variegated.

Other bacterial outer surface proteins, such as OmpA, OmpC, OmpF, PhoE, and pilin, may be used in place of LamB and its homologues. OmpA is of particular interest because it is very abundant and because homologues are known in a wide variety of gram-negative bacterial species. Baker et al. (BAKE87) review assembly of proteins into the outer membrane of *E. coli* and cite a topological model of OmpA (VOGE86) that predicts that residues 19–32, 62–73, 105–118, and 147–158 are exposed on the cell surface. Insertion of a ipbd encoding fragment at about codon 111 or at about codon 152 is likely to cause the IPBD to be displayed on the cell surface. Concerning OmpA, see also MACI88 and MANO88. Porin Protein F of *Pseudomonas aeruginosa* has been cloned and has sequence homology to OmpA of *E. coli* (DUCH88). Although this homology is not sufficient to allow prediction of surface-exposed residues on Porin Protein F, the methods used to determine the topological model of OmpA may be applied to Porin Protein F. Works related to use of OmpA as an OSP include BECK80 and MACI88.

Misra and Benson (MISR88a, MISR88b) disclose a topological model of *E. coli* OmpC that predicts that, among others, residues $GLY_{164}$ and $LEU_{250}$ are exposed on the cell surface. Thus insertion of an ipbd gene fragment at about codon 164 or at about codon 250 of the *E. coli* ompC gene or at corresponding codons of the *S. typhimurium* ompC gene is likely to cause IPBD to appear on the cell surface. The ompC genes of other bacterial species may be used. Other works related to OmpC include CATR87 and CLIC88.

OmpF of *E. coli* is a very abundant OSP, $\geqq 10^4$ copies/cell. Pages et al. (PAGE90) have published a model of OmpF indicating seven surface-exposed segments. Fusion of an ipbd gene fragment, either as an insert or to replace the 3' part of ompF, in one of the indicated regions is likely to produce a functional ompF::ipbd gene the expression of which leads to display of IPBD on the cell surface. In particular, fusion at about codon 111, 177, 217, or 245 should lead to a functional ompF::ipbd gene. Concerning OmpF, see also REID88b, PAGE88, BENS88, TOMM82, and SODE85.

Pilus proteins are of particular interest because piliated cells express many copies of these proteins and because several species (*N. gonorrhoeae, P. aeruginosa, Moraxella bovis, Bacteroides nodosus,* and *E. coli*) express related pilins. Getzoff and coworkers (GETZ88, PARG87, SOME85) have constructed a model of the gonococcal pilus that predicts that the protein forms a four-helix bundle having structural similarities to tobacco mosaic virus protein and myohemerythrin. On this model, both the amino and carboxy termini of the protein are exposed. The amino terminus is methylated. Elleman (ELLE88) has reviewed pilins of *Bacteroides nodosus* and other species and serotype differences can be related to differences in the pilin protein and that most variation occurs in the C-terminal region. The amino-terminal portions of the pilin protein are highly conserved. Jennings et al. (JENN89) have grafted a fragment of foot-and-mouth disease virus (residues 144–159) into the *B. nodosus* type 4 fimbrial protein which is highly homologous to gonococcal pilin. They found that expression of the 3'-terminal fusion in *P. aeruginosa* led to a viable strain that makes detectable amounts of the fusion protein. Jennings et al. did not vary the foreign epitope nor did they suggest any variation. They inserted a GLY-GLY linker between the last pilin residue and the first residue of the foreign epitope to provide a "flexible linker". Thus a preferred place to attach an IPBD is the carboxy terminus. The exposed loops of the bundle could also be used, although the particular internal fusions tested by Jennings et al. (JENN89) appeared to be lethal in *P. aeruginosa.* Concerning pilin, see also MCKE85 and ORND85.

Judd (JUDD86, JUDD85) has investigated Protein IA of *N. gonorrhoeae* and found that the amino terminus is exposed; thus, one could attach an IPBD at or near the amino terminus of the mature P.IA as a means to display the IPBD on the *N. gonorrhoeae* surface.

A model of the topology of PhoE of *E. coli* has been disclosed by van der Ley et al. (VAND86). This model predicts eight loops that are exposed; insertion of an IPBD into one of these loops is likely to lead to display of the IPBD on the surface of the cell. Residues 158, 201, 238, and 275 are preferred locations for insertion of and IPBD.

Other OSPs that could be used include *E. coli* BtuB, FepA, FhuA, IutA, FecA, and FhuE (GUDM89) which are receptors for nutrients usually found in low abundance. The genes of all these proteins have been sequenced, but topological models are not yet available. Gudmunsdottir et al. (GUDM89) have begun the construction of such a model for BtuB and FepA by showing that certain residues of BtuB face the periplasm and by determining the functionality of various BtuB::FepA fusions. Carmel et al. (CARM90) have reported work of a similar nature for FhuA. All Neisseria species express outer surface proteins for iron transport that have been identified and, in many cases, cloned. See also MORS87 and MORS88.

Many gram-negative bacteria express one or more phospholipases. E. coli phospholipase A, product of the pldA gene, has been cloned and sequenced by de Geus et al. (DEGE84). They found that the protein appears at the cell surface without any posttranslational processing. A ipbd gene fragment can be attached at either terminus or inserted at positions predicted to encode loops in the protein. That phospholipase A arrives on the outer surface without removal of a signal sequence does not prove that a PldA::IPBD fusion protein will also follow this route. Thus we might cause a PldA::IPBD or IPBD:PldA fusion to be secreted into the periplasm by addition of an appropriate signal sequence. Thus, in addition to simple binary fusion of an ipbd fragment to one terminus of pldA, the constructions:

1) ss::iDbd::pldA 2) ss::pldA::ipbd should be tested. Once the PldA::IPBD protein is free in the periplasm it does not remember how it got there and the structural features of PldA that cause it to localize on the outer surface will direct the fusion to the same destination.

IV.D. Bacterial Spores as Genetic Packages:

Bacterial spores have desirable properties as GP candidates. Spores are much more resistant than vegetative bacterial cells or phage to chemical and physical agents, and hence permit the use of a great variety of affinity selection conditions. Also, Bacillus spores neither actively metabolize nor alter the proteins on their surface. Spores have the disadvantage that the molecular mechanisms that trigger sporulation are less well worked out than is the formation of M13 or the export of protein to the outer membrane of *E. coli.*

Bacteria of the genus Bacillus form endospores that are extremely resistant to damage by heat, radiation, desiccation, and toxic chemicals (reviewed by Losick et al. (LOSI86)). This phenomenon is attributed to extensive intermolecular crosslinking of the coat proteins. Endospores from the genus Bacillus are more stable than are exospores from Streptomyces. *Bacillus subtilis* forms spores in 4 to 6 hours, but Streptomyces species may require days or weeks to sporulate. In addition, genetic knowledge and manipulation is much more developed for *B. subtilis* than for other spore-forming bacteria. Thus Bacillus spores are preferred over Streptomyces spores. Bacteria of the genus Clostridium also form very durable endospores, but clostridia, being strict anaerobes, are not convenient to culture.

Viable spores that differ only slightly from wild-type are produced in *B. subtilis* even if any one of four coat proteins is missing (DONO87). Moreover, plasmid DNA is commonly included in spores, and plasmid encoded proteins have been observed on the surface of Bacillus spores (DEBR86). For these reasons, we expect that it will be possible to express during sporulation a gene encoding a chimeric coat protein, without interfering materially with spore formation.

Donovan et al. have identified several polypeptide components of *B. subtilis* spore coat (DONO87); the sequences of two complete coat proteins and amino-terminal fragments of two others have been determined. Some, but not all, of the coat proteins are synthesized as precursors and are then processed by specific proteases before deposition in the spore coat (DONO87). The 12 kd coat protein, CotD, contains 5 cysteines. CotD also contains an unusually high number of histidines (16) and prolines (7). The 11 kd coat protein, CotC, contains only one cysteine and one methionine. CotC has a very unusual amino-acid sequence with 19 lysines (K) appearing as 9 K-K dipeptides and one isolated K. There are also 20 tyrosines (Y) of which 10 appear as 5 Y—Y dipeptides. Peptides rich in Y and K are known to become crosslinked in oxidizing environments (DEVO78, WAIT83, WAIT85, WAIT86). CotC contains 16 D and E amino acids that nearly equals the 19 Ks. There are no A, F, R, I, L, N, P, Q, S, or W amino acids in CotC. Neither CotC nor CotD is post-translationally cleaved, but the proteins CotA and CotB are.

Since, in *B. subtilis,* some of the spore coat proteins are post-translationally processed by specific proteases, it is valuable to know the sequences of precursors and mature coat proteins so that we can avoid incorporating the recognition sequence of the specific protease into our construction of an OSP-IPBD fusion. The sequence of a mature spore coat protein contains information that causes the protein to be deposited in the spore coat; thus gene fusions that include some or all of a mature coat protein sequence are preferred for screening or selection for the display-of-IPBD phenotype.

Fusions of ipbd fragments to cotC or cotD fragments are likely to cause IPBD to appear on the spore surface. The genes cotC and cotD are preferred osp genes because CotC and CotD are not post-translationally cleaved. Subsequences from cotA or cotB could also be used to cause an IPBD to appear on the surface of *B. subtilis* spores, but we must take the post-translational cleavage of these proteins into account. DNA encoding IPBD could be fused to a fragment of cotA or cotB at either end of the coding region or at sites interior to the coding region. Spores could then be screened or selected for the display-of-IPBD phenotype.

The promoter of a spore coat protein is most active: a) when spore coat protein is being synthesized and deposited onto the spore and b) in the specific place that spore coat proteins are being made. The sequences of several sporulation promoters are known; coding sequences operatively linked to such promoters are expressed only during sporulation. Ray et al. (RAYC87) have shown that the G4 promoter of *B. subtilis* is directly controlled by RNA polymerase bound to $\sigma^E$. To date, no Bacillus sporulation promoter has been shown to be inducible by an exogenous chemical inducer as the lac promoter of *E. coli.* Nevertheless, the quantity of protein produced from a sporulation promoter can be controlled by other factors, such as the DNA sequence around the Shine-Dalgarno sequence or codon usage. Chemically inducible sporulation promoters can be developed if necessary.

IV.E. Artificial OSPs

It is generally preferable to use as the genetic package a cell, spore or virus for which an outer surface protein which can be engineered to display a IPBD has already been identified. However, the present invention is not limited to such genetic packages.

It is believed that the conditions for an outer surface transport signal in a bacterial cell or spore are not particularly stringent, i.e., a random polypeptide of appropriate length (preferably 30–100 amino acids) has a reasonable chance of providing such a signal. Thus, by constructing a chimeric gene comprising a segment encoding the IPBD linked to a segment of random or pseudorandom DNA (the potential OSTS), and placing this gene under control of a suitable promoter, there is a possibility that the chimeric protein so encoded will function as an OSP-IPBD.

This possibility is greatly enhanced by constructing numerous such genes, each having a different potential OSTS, cloning them into a suitable host, and selecting for transformants bearing the IPBD (or other marker) on their outer surface. Use of secretion-permissive mutants, such as prlA4 (LISS85) or prlG (STAD89), can increase the probability of obtaining a working OSP-IPBD.

When seeking to display a IPBD on the surface of a bacterial cell, as an alternative to choosing a natural OSP and an insertion site in the OSP, we can construct a gene (the "display probe") comprising: a) a regulatable promoter (e.g. lacUV5), b) a Shine-Dalgarno sequence, c) a periplasmic transport signal sequence, d) a fusion of the ipbd gene with a segment of random DNA (as in Kaiser et al. (KAIS87)), e) a stop codon, and f) a transcriptional terminator.

When the genetic package is a spore, we can use the approach described above for attaching a IPBD to an $E.\ coli$ cell, except that: a) a sporulation promoter is used, and b) no periplasmic signal sequence should be present.

For phage, because the OSP-IPBD fulfills a structural role in the phage coat, it is unlikely that any particular random DNA sequence coupled to the ipbd gene will produce a fusion protein that fits into the coat in a functional way. Nevertheless, random DNA inserted between large fragments of a coat protein gene and the pbd gene will produce a population that is likely to contain one or more members that display the IPBD on the outside of a viable phage.

As previously stated, the purpose of the random DNA is to encode an OSTS, like that embodied in known OSPs. The fusion of ipbd and the random DNA could be in either order, but ipbd upstream is slightly preferred. Isolates from the population generated in this way can be screened for display of the IPBD. Preferably, a version of selection-through-binding is used to select GPs that display IPBD on the GP surface. Alternatively, clonal isolates of GPs may be screened for the display-of-IPBD phenotype.

The preference for ipbd upstream of the random DNA arises from consideration of the manner in which the successful GP(IPBD) will be used. The present invention contemplates introducing numerous mutations into the pbd region of the osp-pbd gene, which, depending on the variegation scheme, might include gratuitous stop codons. If pbd precedes the random DNA, then gratuitous stop codons in pbd lead to no OSP-PBD protein appearing on the cell surface. If pbd follows the random DNA, then gratuitous stop codons in pbd might lead to incomplete OSP-PBD proteins appearing on the cell surface. Incomplete proteins often are non-specifically sticky so that GPs displaying incomplete PBDs are easily removed from the population.

The random DNA may be obtained in a variety of ways. Degenerate synthetic DNA is one possibility. Alternatively, pseudorandom DNA can be generated from any DNA having high sequence diversity, e.g., the genome of the organism, by partially digesting with an enzyme that cuts very often, e.g., Sau3AI. Alternatively, one could shear DNA having high sequence diversity, blunt the sheared DNA with the large fragment of *E. coli* DNA polymerase I (hereinafter referred to as Klenow fragment), and clone the sheared and blunted DNA into blunt sites of the vector (MANI82, p295, AUSU87).

If random DNA and phenotypic selection or screening are used to obtain a GP(IPBD), then we clone random DNA into one of the restriction sites that was designed into the display probe. A plasmid-carrying .the display probe is digested with the appropriate restriction enzyme and the fragmented, random DNA is annealed and ligated by standard methods. The ligated plasmids are used to transform cells that are grown and selected for expression of the antibiotic-resistance gene. Plasmid-bearing GPs are then selected for the display-of-IPBD phenotype by the affinity selection methods described hereafter, using AfM(IPBD) as if it were the target.

As an alternative to selecting GP(IPBD)s through binding to an affinity column, we can isolate colonies or plaques and screen for successful artificial OSPs through use of one of the methods listed below for verification of the display strategy.

IV.F Designing the osp-ipbd gene insert:

Genetic Construction and Expression Considerations

The (i)pbd-osp gene may be: a) completely synthetic, b) a composite of natural and synthetic DNA, or c) a composite of natural DNA fragments. The important point is that the pbd segment be easily variegated so as to encode a multitudinous and diverse family of PBDs as previously described. A synthetic ipbd segment is preferred because it allows greatest control over placement of restriction sites. Primers complementary to regions abutting the osp-ipbd gene on its 3' flank and to parts of the osp-ipbd gene that are not to be varied are needed for sequencing.

The sequences of regulatory parts of the gene are taken from the sequences of natural regulatory elements: a) promoters, b) Shine-Dalgarno sequences, and c) transcriptional terminators. Regulatory elements could also be designed from knowledge of consensus sequences of natural regulatory regions. The sequences of these regulatory elements are connected to the coding regions; restriction sites are also inserted in or adjacent to the regulatory regions to allow convenient manipulation.

The essential function of the affinity separation is to separate GPs that bear PBDs (derived from IPBD) having high affinity for the target from GPs bearing PBDs having low affinity for the target. If the elution volume of a GP depends on the number of PBDs on the GP surface, then a GP bearing many PBDs with low affinity, GP($PBD_w$), might co-elute with a GP bearing fewer PBDs with high affinity, GP($PBD_s$). Regulation of the osp-pbd gene preferably is such that most packages display sufficient PBD to effect a good separation according to affinity. Use of a regulatable promoter to control the level of expression of the osp-pbd allows fine adjustment of the chromatographic behavior of the variegated population.

Induction of synthesis of engineered genes in vegetative bacterial cells has been exercised through the use of regulated promoters such as lacUV5, trpP, or tac (MANI82). The factors that regulate the quantity of protein synthesized include: a) promoter strength (cf. HOOP87), b) rate of initiation of translation (cf. GOLD87), c) codon usage, d) secondary structure of mRNA, including attenuators (cf. LAND87) and terminators (cf. YAGE87), e) interaction of proteins with mRNA (cf. MCPH86, MILL87b, WINT87), f) degradation rates of mRNA (cf. BRAW87, KING86), g) proteolysis (cf. GOTT87). These factors are sufficiently well understood that a wide variety of heterologous proteins can now be produced in *E. coli, B. subtilis* and other host cells in at least moderate quantities (SKER88, BETT88). Preferably, the promoter for the osp-ipbd gene is subject to regulation by a small chemical inducer. For example, the lac promoter and the hybrid trp-lac (tac) promoter are regulatable with isopropyl thiogalactoside (IPTG). Hereinafter, we use "XINDUCE" as a generic term for a chemical that induces expression of a gene. The promoter for the constructed gene need not come from a natural OSP gene; any regulatable bacterial promoter can be used.

Transcriptional regulation of gene expression is best understood and most effective, so we focus our attention on the promoter. If transcription of the osp-ipbd gene is controlled by the chemical XINDUCE, then the number of OSP-IPBDs per GP increases for increasing concentrations of XINDUCE until a fall-off in the number of viable packages is observed or until sufficient IPBD is observed on the surface of harvested GP(IPBD)s. The attributes that affect the maximum number of OSP-IPBDs per GP are primarily structural in nature. There may be steric hindrance or other unwanted interactions between IPBDs if OSP-IPBD is substituted for every wild-type OSP. Excessive levels of OSP-IPBD may also adversely affect the solubility or morphogenesis of the GP. For cellular and viral GPs, as few as five copies of a protein having affinity for another immobilized molecule have resulted in successful affinity separations (FERE82a, FERE82b, and SMIT85).

A non-leaky promoter is preferred. Non-leakiness is useful: a) to show that affinity of GP(osp-ipbd)s for AfM(IPBD) is due to the osp-ipbd gene, and b) to allow growth of GP(osp-ipbd) in the absence of XINDUCE if the expression of osp-ipbd is disadvantageous. The lacUV5 promoter in conjunction with the $LacI^q$ repressor is a preferred example.

An exemplary osp-ipbd gene has the DNA sequence shown in Table 25 and there annotated to explain the useful restriction sites and biologically important features, viz. the lacUV5 promoter, the lacO operator, the Shine-Dalgarno sequence, the amino acid sequence, the stop codons, and the trp attenuator transcriptional terminator.

The present invention is not limited to a single method of gene design. The osp-ipbd gene need not be synthesized in toto; parts of the gene may be obtained from nature. One may use any genetic engineering method to produce the correct gene fusion, so long as one can easily and accurately direct mutations to specific sites in the pbd DNA subsequence. In all of the methods of mutagenesis considered in the present invention, however, it is necessary that the coding sequence for the osp-ipbd gene be different from any other DNA in the OCV. The degree and nature of difference needed is determined by the method of mutagenesis to be used. If the method of mutagenesis is to be replacement of subsequences coding for the PBD with vgDNA, then the subsequences to be mutagenized are preferably bounded by restriction sites that are unique with respect to the rest of the OCV. Use of non-unique sites involves partial digestion which is less efficient than complete digestion of a unique site and is not preferred. If single-stranded-oligonucleotide-directed mutagenesis is to be used, then the DNA sequence of the subsequence coding for the IPBD must be unique with respect to the rest of the OCV.

The coding portions of genes to be synthesized are designed at the protein level and then encoded in DNA. The amino acid sequences are chosen to achieve various goals, including: a) display of a IPBD on the surface of a GP, b) change of charge on a IPBD, and c) generation of a population of PBDs from which to select an SBD. These issues are discuss in more detail below. The ambiguity in the genetic code is exploited to allow optimal placement of restriction sites and to create various distributions of amino acids at variegated codons.

While the invention does not require any particular number or placement of restriction sites, it is generally preferable to engineer restriction sites into the gene to facilitate subsequent manipulations. Preferably, the gene provides a series of fairly uniformly spaced unique restriction sites with no more than a preset maximum number of bases, for example 100, between sites. Preferably, the gene is designed so that its insertion into the OCV does not destroy the uniqueness of unique restriction sites of the OCV. Preferred recognition sites are those for restriction enzymes which a) generate cohesive ends, b) have unambiguous recognition, or c) have higher specific activity.

The ambiguity of the DNA between the restriction sites is resolved from the following considerations. If the given amino acid sequence occurs in the recipient organism, and if the DNA sequence of the gene in the organism is known, then, preferably, we maximize the differences between the engineered and natural genes to minimize the potential for recombination. In addition, the following codons are poorly translated in *E. coli* and, therefore, are avoided if possible: cta(L), cga (R), cgg (R), and egg (R). For other host species, different coden restrictions would be appropriate. Finally, long repeats of any one base are prone to mutation and thus are avoided. Balancing these considerations, we can design a DNA sequence.

Structural Considerations

The design of the amino-acid sequence for the ipbd-osp gene to encode involves a number of structural considerations. The design is somewhat different for each type of GP. In bacteria, OSPs are not essential, so there is no requirement that the OSP domain of a fusion have any of its parental functions beyond lodging in the outer membrane.

Relationship between PBD and OSP

It is not required that the PBD and OSP domains have any particular spatial relationship; hence the process of this invention does not require use of the method of U.S. Pat. '692.

It is, in fact, desirable that the OSP not constrain the orientation of the PBD domain; this is not to be confused with lack of constraint within the PBD. Cwirla et al. (CWIR90), Scott and Smith (SCOT90), and Devlin et al. (DEVL90), have taught that variable residues in phage-displayed random peptides should be free of influence from the phage OSP. We teach that binding domains having a moderate to high degree of conformational constraint will exhibit higher specificity and that higher affinity is also possible. Thus, we prescribe picking codons for variegation that specify amino acids that will appear in a well-defined framework. The nature of the side groups is varied through a very wide range due to the combinatorial replacement of multiple amino acids. The main chain conformations of most PBDs of a given class is very similar. The movement of the PBD relative to the OSP should not, however, be restricted. Thus it is often appropriate to include a flexible linker between the PBD and the OSP. Such flexible linkers can be taken from naturally occurring proteins known to have flexible regions. For example, the gIII protein of M13 contains glycine-rich regions thought to allow the amino-terminal domains a high degree of freedom. Such flexible linkers may also be designed. Segments of polypeptides that are rich in the amino acids GLY, ASN, SER, and ASP are likely to give rise to flexibility. Multiple glycines are particularly preferred.

Constraints imposed by OSP

When we choose to insert the PBD into a surface loop of an OSP such as LamB, OmpA, or M13 gIII protein, there are a few considerations that do not arise when PBD is joined to the end of an OSP. In these cases, the OSP exerts some constraining influence on the PBD; the ends of the PBD are held in more or less fixed positions. We could insert a highly varied DNA sequence into the osp gene at codons that encode a surface-exposed loop and select for cells that have a specific-binding phenotype. When the identified amino-acid sequence is synthesized (by any means), the constraint of the OSP is lost and the peptide is likely to have a much lower affinity for the target and a much lower specificity. Tan and Kaiser (TANN77) found that a synthetic model of BPTI containing all the amino acids of BPTI that contact trypsin has a $K_d$ for trypsin $\approx 10^7$ higher than BPTI. Thus, it is strongly preferred that the varied amino acids be part of a PBD in which the structural constrains are supplied by the PBD.

It is known that the amino acids adjoining foreign epitopes inserted into LamB influence the immunological properties of these epitopes (VAND90). We expect that PBDs inserted into loops of LamB, OmpA, or similar OSPs will be influenced by the amino acids of the loop and bit the OSP in general. To obtain appropriate display of the PBD, it may be necessary to add one or more linker amino acids between the OSP and the PBD. Such linkers may be taken from natural proteins or designed on the basis of our knowledge of the structural behavior of amino acids. Sequences rich in GLY, SER, ASN, ASP, ARG, and THR are appropriate. One to five amino acids at either junction are likely to impart the desired degree of flexibility between the OSP and the PBD.

Phage OSP

A preferred site for insertion of the ipbd gene into the phage osp gene is one in which: a) the IPBD folds into its original shape, b) the OSP domains fold into their original shapes, and c) there is no interference between the two domains.

If there is a model of the phage that indicates that either the amino or carboxy terminus of an OSP is exposed to solvent, then the exposed terminus of that mature OSP becomes the prime candidate for insertion of the ipbd gene. A low resolution 3D model suffices.

In the absence of a 3D structure, the amino and carboxy termini of the mature OSP are the best candidates for insertion of the ipbd gene. A functional fusion may require additional residues between the IPBD and OSP domains to avoid unwanted interactions between the domains. Random-sequence DNA or DNA coding for a specific sequence of a protein homologous to the IPBD or OSP, can be inserted between the osp fragment and the ipbd fragment if needed.

Fusion at a domain boundary within the OSP is also a good approach for obtaining a functional fusion. Smith exploited such a boundary when subcloning heterologous DNA into gene III of f1 (SMIT85).

The criteria for identifying OSP domains suitable for causing display of an IPBD are somewhat different from those used to identify and IPBD. When identifying an OSP, minimal size is not so important because the OSP domain will not appear in the final binding molecule nor will we need to synthesize the gene repeatedly in each variegation round. The major design concerns are that: a) the OSP::IPBD fusion causes display of IPBD, b) the initial genetic construction be reasonably convenient, and c) the osp::ipbd gene be genetically stable and easily manipulated. There are several methods of identifying domains. Methods that rely on atomic coordinates have been reviewed by Janin and Chothia (JANI85). These methods use matrices of distances between $\alpha$ carbons ($C_\alpha$), dividing planes (cf. ROSE85), or buried surface (RASH84). Chothia and collaborators have correlated the behavior of many natural proteins with domain structure (according to their definition). Rashin correctly predicted the stability of a domain comprising residues 206–316 of thermolysin (VITA84, RASH84).

Many researchers have used partial proteolysis and protein sequence analysis to isolate and identify stable domains. (See, for example, VITA84, POTE83, SCOT87a, and PABO79.) Pabo et al. used calorimetry as an indicator that the cI repressor from the coliphage $\lambda$ contains two domains; they then used partial proteolysis to determine the location of the domain boundary.

If the only structural information available is the amino acid sequence of the candidate OSP, we can use the sequence to predict turns and loops. There is a high probability that some of the loops and turns will be correctly predicted (cf. Chou and Fasman, (CHOU74)); these locations are also candidates for insertion of the ipbd gene fragment.

Bacterial OSPs

In bacterial OSPs, the major considerations are: a) that the PBD is displayed, and b) that the chimeric protein not toxic.

From topological models of OSPs, we can determine whether the amino or carboxy termini of the OSP is exposed. If so, then these are excellent choices for fusion of the osp fragment to the ipbd fragment.

The lamB gene has been sequenced and is available on a variety of plasmids (CLEM81, CHAR88). Numerous fusions of fragments of lamb with a variety of other genes have been used to study export of proteins in *E. coli*. From various studies, Charbit et al. (CHAR88) have proposed a model that specifies which residues of LamB are: a) embedded in the membrane, b) facing the periplasm, and c) facing the cell surface; we adopt the numbering of this model for amino acids in the mature protein. According to this model, several loops on the outer surface are defined, including: 1) residues 88 through 111, 2) residues 145 through 165, and 3) 236 through 251.

Consider a mini-protein embedded in LamB. For example, insertion of DNA encoding $G_1NXCX_5XXXCX_{10}SG_{12}$ between codons 153 and 154 of lamb is likely to lead to a wide variety of LamB derivatives being expressed on the surface of *E. coli* cells. $G_1$, $N_2$, $S_{11}$, and $G_{12}$ are supplied to allow the mini-protein sufficient orientational freedom that is can interact optimally with the target. Using affinity enrichment (involving, for example, FACS via a fluorescently labeled target, perhaps through several rounds of enrichment), we might obtain a strain (named, for example, BEST) that expresses a particular LamB derivative that shows high affinity for the predetermined target. An octapeptide having the sequence of the inserted residues 3 through 10 from BEST is likely to have an affinity and specificity similar to that observed in BEST because the octapeptide has an internal structure that keeps the amino acids in a conformation that is quite similar in the LamB derivative and in the isolated mini-protein.

Consideration of the Signal Peptide

Fusing one or more new domains to a protein may make the ability of the new protein to be exported from the cell different from the ability of the parental protein. The signal peptide of the wild-type coat protein may function for authentic polypeptide but be unable to direct export of a fusion. To utilize the Sec-dependent pathway, one may need a different signal peptide. Thus, to express and display a chimeric BPTI/M13 gene VIII protein, we found it necessary to utilize a heterologous signal peptide (that of phoA).

Provision of a Means to Remove PBD from the GP

GPs that display peptides having high affinity for the target may be quite difficult to elute from the target, particularly a multivalent target. (Bacteria that are bound very tightly can simply multiply in situ.) For phage, one can introduce a cleavage site for a specific protease, such as blood-clotting Factor Xa, into the fusion OSP protein so that the binding domain can be cleaved from the genetic package. Such cleavage has the advantage that all resulting phage have identical OSPs and therefore are equally infective, even if polypeptide-displaying phage can be eluted from the affinity matrix without cleavage. This step allows recovery of valuable genes which might otherwise be lost. To our knowledge, no one has disclosed or suggested using a specific protease as a means to recover an information-containing genetic package or of converting a population of phage that vary in infectivity into phage having identical infectivity.

IV.G. Synthesis of Gene Inserts

The present invention is not limited as to how a designed DNA sequence is divided for easy synthesis. An established method is to synthesize both strands of the entire gene in overlapping segments of 20 to 50 nucleotides (nts) (THER88). An alternative method that is more suitable for synthesis of vgDNA is an adaptation of methods published by Oliphant et al. (OLIP86 and OLIP87) and Ausubel et al. (AUSU87). It differs from previous methods in that it: a) uses two synthetic strands, and b) does not cut the extended DNA in the middle. Our goals are: a) to produce longer pieces of dsDNA than can be synthesized as ssDNA on commercial DNA synthesizers, and b) to produce strands complementary to single-stranded vgDNA. By using two synthetic strands, we remove the requirement for a palindromic sequence at the 3' end.

DNA synthesizers can currently produce oligo-nts of lengths up to 200 nts in reasonable yield, $M_{DNA}=200$. The parameters $N_w$ (the length of overlap needed to obtain efficient annealing) and $N_s$ (the number of spacer bases needed so that a restriction enzyme can cut near the end of blunt-ended dsDNA) are determined by DNA and enzyme chemistry. $N_w=10$ and $N_s=5$ are reasonable values. Larger values of $N_w$ and $N_s$ are allowed but add to the length of ssDNA that is to be synthesized and reduce the net length of dsDNA that can be produced.

Let $A_L$ be the actual length of dsDNA to be synthesized, including any spacers. $A_L$ must be no greater than $(2 M_{DNA}-N_w)$. Let $Q_w$ be the number of nts that the overlap window can deviate from center, $$Q_w = (2 M_{DNA} - N_w - A_L)/2.$$

$Q_w$ is never negative. It is preferred that the two fragments be approximately the same length so that the amounts synthesized will be approximately equal. This preference may be overridden by other considerations. The overall yield of dsDNA is usually dominated by the synthetic yield of the longer oligo-nt.

We use the following procedure to generate dsDNA of lengths up to $(2 M_{DNA}-N_w)$ nts through the use of Klenow fragment to extend synthetic ss DNA fragments that are not more than $M_{DNA}$ nts long. When a pair of long oligo-nts, complementary for $N_w$ nts at their 3' ends, are annealed there will be a free 3' hydroxyl and a long ssDNA chain continuing in the 5' direction on either side. We will refer to this situation as a 5' superoverhang. The procedure comprises:

1) picking a non-palindromic subsequence of $N_w$ to $N_w+4$ nts near the center of the dsDNA to be synthesized; this region is called the overlap (typically, $N_w$ is 10), 2) synthesizing ass DNA molecule that comprises that part of the anti-sense strand from its 5' end up to and including the overlap, 3) synthesizing ass DNA molecule that comprises that part of the sense strand from its 5' end up to and including the overlap, 4) annealing the two synthetic strands that are complementary throughout the overlap region, and 5) extending both superoverhangs with Klenow fragment and all four deoxynucleotide triphosphates.

Because $M_{DNA}$ is not rigidly fixed at 200, the current limits of 390 $(=2 M_{DNA}-N_w)$ nts overall and 200 in each fragment are not rigid, but can be exceeded by 5 or 10 nts. Going beyond the limits of 390 and 200 will lead to lower yields, but these may be acceptable in certain cases.

Restriction enzymes do not cut well at sites closer than about five base pairs from the end of blunt ds DNA fragments (OLIP87 and p.132 New England BioLabs 1990–1991 Catalogue). Therefore $N_s$ nts (with $N_s$ typically set to 5) of spacer are added to ends that we intend to cut with a restriction enzyme. If the plasmid is to be cut with a blunt-cutting enzyme, then we do not add any spacer to the corresponding end of the ds DNA fragment.

To choose the optimum site of overlap for the oligont fragments, first consider the anti-sense strand of the DNA to be synthesized, including any spacers at the ends, written (in upper case) from 5' to 3' and left-to-right. N.B.: The $N_w$ nt long overlap window can never include bases that are to be variegated. N.B.: The $N_w$ nt long overlap should not be palindromic lest single DNA molecules prime themselves. Place a $N_w$ nt long window as close to the center of the anti-sense sequence as possible. Check to see whether one or more codons within the window can be changed to increase the GC content without: a) destroying a needed restriction site, b) changing amino acid sequence, or c) making the overlap region palindromic. If possible, change some AT base pairs to GC pairs. If the GC content of the window is less than 50%, slide the window right or left as much as $Q_w$ nts to maximize the number of C's and G's inside the window, but without including any variegated bases. For each trial setting of the overlap window, maximize the GC content by silent codon changes, but do not destroy wanted restriction sites or make the overlap palindromic. If the best setting still has less than 50% GC, enlarge the window to $N_w+2$ nts and place it within five nts of the center to obtain the maximum GC content. If enlarging the window one of two nts will increase the GC content, dc so, but do not include variegated bases.

Underscore the anti-sense strand from the 5' end up to the right edge of the window. Write the complementary sense sequence 3'-to-5' and left-to-right and in lower case letters, under the anti-sense strand starting at the left edge of the window and continuing all the way to the right end of the anti-sense strand.

We will synthesize the underscored anti-sense strand and the part of the sense strand that we wrote. These two fragments, complementary over the length of the window of high GC content, are mixed in equimolar quantities and annealed. These fragments are extended with Klenow fragment and all four deoxynucleotide triphosphates to produce ds blunt-ended DNA. This DNA can be cut with appropriate restriction enzymes to produce the cohesive ends needed to ligate the fragment to other DNA.

The present invention is not limited to any particular method of DNA synthesis or construction. Conventional DNA synthesizers may be used, with appropriate reagent modifications for production of variegated DNA (similar to that now used for production of mixed probes). For example, the Milligen 7500 DNA synthesizer has seven vials from which phosphoramidites may be taken. Normally, the first four contain A, C, T, and G. The other three vials may contain unusual bases such as inosine or mixtures of bases, the so-called "dirty bottle". The standard software allows programmed mixing of two, three, or four bases in equimolar quantities.

The synthesized DNA may be purified by any art recognized technique, e.g., by high-pressure liquid chromatography (HPLC) or PAGE.

The osp-pbd genes may be created by inserting vgDNA into an existing parental gene, such as the osp-ipbd shown to be displayable by a suitably transformed GP. The present invention is not limited to any particular method of introducing the vgDNA, however, two techniques are discussed below.

In the case of cassette mutagenesis, the restriction sites that were introduced when the gene for the inserted domain was synthesized are used to introduce the synthetic vgDNA into a plasmid or other OCV. Restriction digestions and ligations are performed by standard methods (AUSU87).

In the case of single-stranded-oligonucleotide-directed mutagenesis, synthetic vgDNA is used to create diversity in the vector (BOTS85).

The modes of creating diversity in the population of GPs discussed herein are not the only modes possible. Any method of mutagenesis that preserves at least a large fraction of the information obtained from one selection and then introduces other mutations in the same domain will work. The limiting factors are the number of independent transformants that can be produced and the amount of enrichment one can achieve through affinity separation. Therefore the preferred embodiment uses a method of mutagenesis that focuses mutations into those residues that are most likely to affect the binding properties of the PBD and are least likely to destroy the underlying structure of the IPBD.

Other modes of mutagenesis might allow other GPs to be considered. For example, the bacteriophage λ is not a useful cloning vehicle for cassette mutagenesis because of the plethora of restriction sites. One can, however, use single-stranded-oligo-nt-directed mutagenesis on λ without the need for unique restriction sites. No one has used single-stranded-oligo-nt-directed mutagenesis to introduce the high level of diversity called for in the present invention, but if it is possible, such a method would allow use of phage with large genomes.

IV.H. Operative Cloning Vector

The operative cloning vector (OCV) is a replicable nucleic acid used to introduce the chimeric ipbd-osp or ipbd-osp gene into the genetic package. When the genetic package is a virus, it may serve as its own OCV. For cells and spores, the OCV may be a plasmid, a virus, a phagemid, or a chromosome.

The OCV is preferably small (less than 10 KB), stable (even after insertion of at least 1 kb DNA), present in multiple copies within the host cell, and selectable with appropriate media. It is desirable that cassette mutagenesis be practical in the OCV; preferably, at least 25 restriction enzymes are available that do not cut the OCV. It is likewise desirable that single-stranded mutagenesis be practical. If a suitable OCV does not already exist, it may be engineered by manipulation of available vectors.

When the GP is a bacterial cell or spore, the OCV is preferably a plasmid because genes on plasmids are much more easily constructed and mutated than are genes in the bacterial chromosome. When bacteriophage are to be used, the osp-ipbd gene is inserted into the phage genome. The synthetic osp-ipbd genes can be constructed in small vectors and transferred to the GP genome when complete.

Phage such as M13 do not confer antibiotic resistance on the host so that one can not select for cells infected with M13. An antibiotic resistance gene can be engineered into the M13 genome (HINE80). More virulent phage, such as ΦX174, make discernable plaques that can be picked, in which case a resistance gene is not essential; furthermore, there is no room in the ΦX174 virion to add any new genetic material. Inability to include an antibiotic resistance gene is a disadvantage because it limits the number of GPs that can be screened.

It is preferred that GP(IPBD) carry a selectable marker not carried by wtGP. It is also preferred that wtGP carry a selectable marker not carried by GP(IPBD).

A derivative of M13 is the most preferred OCV when the phage also serves as the GP. Wild-type M13 does not confer any resistances on infected cells; M13 is a pure parasite. A "phagemid" is a hybrid between a phage and a plasmid, and is used in this invention. Double-stranded plasmid DNA isolated from phagemid-bearing cells is denoted by the standard convention, e.g. pXY24. Phage prepared from these cells would be designated XY24. Phagemids such as Bluescript K/S (sold by Stratagene) are not preferred for our purposes because Bluescript does not contain the full genome of M13 and must be rescued by coinfection with competent wild-type M13. Such coinfections could lead to genetic recombination yielding heterogeneous phage unsuitable for the purposes of the present invention. Phagemids may be entirely suitable for developing a gene that causes an IPBD to appear on the surface of phage-like genetic packages.

It is also well known that plasmids containing the ColE1 origin of replication can be greatly amplified if protein synthesis is halted in a log-phase culture. Protein synthesis can be halted by addition of chloramphenicol or other agents (MANI82).

The bacteriophage M13 bla 61 (ATCC 37039) is derived from wild-type M13 through the insertion of the β lactamase gene (HINE80). This phage contains 8.13 kb of DNA. M13 bla cat 1 (ATCC 37040) is derived from M13 bla 61 through the additional insertion of the chloramphenicol resistance gene (HINE80); M13 bla cat 1 contains 9.88 kb of DNA. Although neither of these variants of M13 contains the ColE1 origin of replication, either could be used as a starting point to construct a cloning vector with this feature.

IV.I. Transformation of cells:

When the GP is a cell, the population of GPs is created by transforming the cells with suitable OCVs. When the GP is a phage, the phage are genetically engineered and then transfected into host cells suitable for amplification. When the GP is a spore, cells capable of sporulation are transformed with the OCV while in a normal metabolic state, and then sporulation is induced so as to cause the OSP-PBDs to be displayed. The present invention is not limited to any one method of transforming cells with DNA. The procedure given in the examples is a modification of that of Maniatis (p250, MANI82). One preferably obtains at least $10^7$ and more preferably at least $10^8$ transformants/μg of CCC DNA.

The transformed cells are grown first under non-selective conditions that allow expression of plasmid genes and then selected to kill untransformed cells. Transformed cells are then induced to express the osp-pbd gene at the appropriate level of induction. The GPs carrying the IPBD or PBDs are then harvested by methods appropriate to the GP at hand, generally, centrifugation to pelletize GPs and resuspension of the pellets in sterile medium (cells) or buffer (spores or phage). They are then ready for verification that the display strategy was successful (where the GPs all display a "test" IPBD) or for affinity selection (where the GPs display a variety of different PBDs).

IV.J. Verification of Display Strategy:

The harvested packages are tested to determine whether the IPBD is present on the surface. In any tests of GPs for the presence of IPBD on the GP surface, any ions or cofactors known to be essential for the stability of IPBD or AfM(IPBD) are included at appropriate levels. The tests can be done: a) by affinity labeling, b) enzymatically, c) spectrophotometrically, d) by affinity separation, or e) by affinity precipitation. The AfM(IPBD) in this step is one picked to have strong affinity (preferably, $K_d < 10^{-11}$M) for the IPBD molecule and little or no affinity for the wtGP. For example, if BPTI were the IPBD, trypsin, anhydrotrypsin, or antibodies to BPTI could be used as the AfM(BPTI) to test for the presence of BPTI. Anhydrotrypsin, a trypsin derivative with serine 195 converted to dehydroalanine, has no proteolytic activity but retains its affinity for BPTI (AKOH72 and HUBE77).

Preferably, the presence of the IPBD on the surface of the GP is demonstrated through the use of a soluble, labeled derivative of a AfM(IPBD) with high affinity for IPBD. The label could be: a) a radioactive atom such as $^{125}$I, b) a chemical entity such as biotin, or 3) a fluorescent entity such as rhodamine or fluorescein. The labeled derivative of AfM(IPBD) is denoted as AfM(IPBD)*. The preferred procedure is:

1) mix AfM(IPBD), with GPs that are to be tested for the presence of IPBD; conditions of mixing should favor binding of IPBD to AfM(IPBD)*,
2) separate GPs from unbound AfM(IPBD)* by use of:
   a) a molecular sizing filter that will pass AfM(IPBD)* but not GPs,
   b) centrifugation, or
   c) a molecular sizing column (such as Sepharose or Sephadex) that retains free AfM(IPBD)* but not GPs,
3) quantitate the AfM(IPBD)* bound by GPs.

Alternatively, if the IPBD has a known biochemical activity (enzymatic or inhibitory), its presence on the GP can be verified through this activity. For example, if the IPBD were BPTI, then one could use the stoichiometric inactivation of trypsin not only to demonstrate the presence of BPTI, but also to quantitate the amount.

If the IPBD has strong, characteristic absorption bands in the visible or UV that are distinct from absorption by the wtGP, then another alternative for measuring the IPBD displayed on the GP is a spectrophotometric measurement. For example, if IPBD were azurin, the visible absorption could be used to identify GPs that display azurin.

Another alternative is to label the GPs and measure the amount of label retained by immobilized AfM(IPBD). For example, the GPs could be grown with a radioactive precursor, such as $^{32}$P or $^3$H-thymidine, and the radioactivity retained by immobilized AfM(IPBD) measured.

Another alternative is to use affinity chromatography; the ability of a GP bearing the IPBD to bind a matrix that supports a AfM(IPBD) is measured by reference to the wtGP.

Another alternative for detecting the presence of IPBD on the GP surface is affinity precipitation.

If random DNA has been used, then affinity selection procedures are used to obtain a clonal isolate that has the display-of-IPBD phenotype. Alternatively, clonal isolates may be screened for the display-of-IPBD phenotype. The tests of this step are applied to one or more of these clonal isolates.

If no isolates that bind to the affinity molecule are obtained we take corrective action as disclosed below.

If one or more of the tests above indicates that the IPBD is displayed on the GP surface, we verify that the binding of molecules having known affinity for IPBD is due to the chimeric osp-ipbd gene through the use of standard genetic and biochemical techniques, such as:

1) transferring the osp-ipbd gene into the parent GP to verify that osp-ipbd confers binding,
2) deleting the osp-ipbd gene from the isolated GP to verify that loss of osp-ipbd causes loss of binding,
3) showing that binding of GPs to AfM(IPBD) correlates with [XINDUCE] (in those cases that expression of osp-ipbd is controlled by [XINDUCE]), and
4) showing that binding of GPs to AfM(IPBD) is specific to the immobilized AfM(IPBD) and not to the support matrix.

Variation of: a) binding of GPs by soluble AfM(IPBDb)*, b) absorption caused by IPBD, and c) biochemical reactions of IPBD are linear in the amount of IPBD displayed. Presence of IPBD on the GP surface is indicated by a strong correlation between [XINDUCE] and the reactions that are linear in the amount of IPBD. Leakiness of the promoter is not likely to present problems of high background with assays that are linear in the amount of IPBD. These experiments may be quicker and easier than the genetic tests. Interpreting the effect of [XINDUCE] on binding to a {AfM(IPBD)} column, however, may be problematic unless the regulated promoter is completely repressed in the absence of [XINDUCE]. The affinity retention of GP(IPBD) s is not linear in the number of IPBDs/GP and there may be, for example, little phenotypic difference between GPs bearing 5 IPBDs and GPs bearing 50 IPBDs. The demonstration that binding is to AfM(IPBD) and the genetic tests are essential; the tests with XINDUCE are optional.

We sequence the relevant ipbd gene fragment from each of several clonal isolates to determine the construction. We also establish the maximum salt concentration and pH range for which the GP(IPBD) binds the chosen AfM(IPBD). This is preferably done by measuring, as a function of salt concentration and pH, the retention of AfM(IPBD)* on molecular sizing filters that pass AfM(IPBD)* but not GP. This information will be used in refining the affinity selection scheme.

IV.K. Analysis and Correction of Display Problems

If the IPBD is displayed on the outside of the GP, and if that display is clearly caused by the introduced osp-ipbd gene, we proceed with variegation, otherwise we analyze the result and adopt appropriate corrective measures. If we have unsuccessfully attempted to fuse an ipbd fragment to a natural osp fragment, our options are: 1) pick a different fusion to the same osp by a) using opposite end of OSP, b) keeping more or fewer residues from osp in the fusion; for example, in increments of 3 or 4 residues, c) trying a known or predicted domain boundary, d) trying a predicted loop or turn position, 2) pick a different osp, or 3) switch to random DNA method. If we have just tried the random DNA method unsuccessfully, our options are: 1) choose a different relationship between ipbd fragment and random DNA (ipbd first, random DNA second or vice versa), 2) try a different degree of partial digestion, a different enzyme for partial digestion, a different degree of shearing or a different source of natural DNA, or 3) switch to the natural OSP method. If all reasonable OSPs of the current GP have been tried and the random DNA method has been tried, both without success, we pick a new GP.

We may illustrate the ways in which problems may be attacked by using the example of BPTI as the IPBD, the M13 phage as the GP, and the major coat (gene VIII) protein as the OSP. The following amino-acid sequence, called AA_seq2, illustrates how the sequence for mature BPTI (shown underscored) may be inserted immediately after the signal sequence of M13 precoat protein (indicated by the arrow) and before the sequence for the M13 CP.

```
                        AA_seq2
        1      1      2 ⇓ 2      3      3      4      4      5
   5    0      5      0 ⇓ 5      0      5      0      5      0
   MKKSLVLKASVAVATLVPMLSFARPDFCLEPPYTGPCKARIIRYFYNAKA 5      6      6      7      7      8      8      9      9     10
   5    0      5      0      5      0      5      0      5      0
   GLCQTFVYGGCRAKRNNFKSAEDCMRTCGGAAEGDDPAKAAFNSLQASAT 10     11     11     12     12     13
   5    0      5      0      5      0
   EYIGYAWAMVVVIVGATIGIKLFKKFTSKAS
```

We adopt the convention that sequence numbers of fusion proteins refer to the fusion, as coded, unless otherwise noted. Thus the alenine that begins M13 CP is referred to as "number 82", "number 1 of M13 CP", or "number 59 of the mature BPTI-M13 CP fusion".

It is desirable to determine where, exactly, the BPTI binding domain is being transported: is it remaining in the cytoplasm? Is it free within the periplasm? Is it attached to the inner membrane? Proteins in the periplasm can be freed through spheroplast formation using lysozyme and EDTA in a concentrated sucrose solution (BIRD67, MALA64). If BPTI were free in the periplasm, it would be found in the supernatant. Trypsin labeled with $^{125}$I would be mixed with supernatant and passed over a non-denaturing molecular sizing column and the radioactive fractions collected. The radioactive fractions would then be analyzed by SDS-PAGE and examined for BPTI-sized bands by silver staining.

Spheroplast formation exposes proteins anchored in the inner membrane. Spheroplasts would be mixed with AHTrp* and then either filtered or centrifuged to separate them from unbound AHTrp*. After washing with hypertonic buffer, the spheroplasts would be analyzed for extent of AHTrp* binding.

If BPTI were found free in the periplasm, then we would expect that the chimeric protein was being cleaved both between BPTI and the M13 mature coat sequence and between BPTI and the signal sequence. In that case, we should alter the BPTI/M13 CP junction by inserting vgDNA at codons for residues 78–82 of AA_seq2.

If BPTI were found attached to the inner membrane, then two hypotheses can be formed. The first is that the chimeric protein is being cut after the signal sequence, but is not being incorporated into LG7 virion; the treatment would also be to insert vgDNA between residues 78 and 82 of AA_seq2. The alternative hypothesis is that BPTI could fold and react with trypsin even if signal sequence is not cleaved. N-terminal amino acid sequencing of trypsin-binding material isolated from cell homogenate determines what processing is occurring. If signal sequence were being cleaved, we would use the procedure above to vary residues between C78 and A82; subsequent passes would add residues after residue 81. If signal sequence were not being cleaved, we would vary residues between 23 and 27 of AA_seq2. Subsequent passes through that process would add residues after 23.

If BPTI were found neither in the periplasm nor on the inner membrane, then we would expect that the fault was in the signal sequence or the signal-sequence-to-BPTI junction. The treatment in this case would be to vary residues between 23 and 27.

Analytical experiments to determine what has gone wrong take time and effort and, for the foreseen outcomes, indicate variations in only two regions. Therefore, we believe it prudent to try the synthetic experiments described below without doing the analysis. For example, these six experiments that introduce variegation into the bpti-gene VIII fusion could be tried:

1) 3 variegated codons between residues 78 and 82 using olig#12 and olig#13,
2) 3 variegated codons between residues 23 and 27 using olig#14 and olig#15,
3) 5 variegated codons between residues 78 and 82 using olig#13 and olig#12a,
4) 5 variegated codons between residues 23 and 27 using olig#15 and olig#14a,
5) 7 variegated codons between residues 78 and 82 using olig#13 and olig#12b, and
6) 7 variegated codons between residues 23 and 27 using olig#15 and olig#14b.

To alter the BPTI-M13 CP junction, we introduce DNA variegated at codons for residues between 78 and 82 into the sphI and SfiI sites of pLG7. The residues after the last cysteine are highly variable in amino acid sequences homologous to BPTI, both in composition and length; in Table 25 these residues are denoted as G79, G80, and A81. The first part of the M13 CP is denoted as A82, E83, and G84. One of the oligo-nts olig#12, olig#12a, or olig#12b and the primer olig#13 are synthesized by standard methods. The oligo-nts are:

```
residue    75  76  77  78  79  80  81  82  83
5' gc gag CGC ATG CGT ACC TGC qfk qfk qfk GCT GAA -

84  85  86  87  88  89  90  91
          GGT GAT GAT CCG GCC AAA GCG GCC gcg cc 3' olig#12 residue    75  76  77  78  79  80  81 81a 81b
5' gc gag cGC ATG CGT ACC TGC qfk qfk qfk qfk qfk -

82  83  84  85  86  87
          GCT GAA GGT GAT GAT CCG -

88  89  90  91
                          GCC AAA GCG GCC gcg cc 3' olig#12a residue    75  76  77  78  79  80  81 81a 81b
5' gc gag cGC ATG CGT ACC TGC qfk qfk qfk qfk qfk -

81c 81d 82  83  84  85  86  87
          qfk qfk GCT GAA GGT GAT GAT CCG -

88  89  90  91
                          GCC AAA GCG GCC gcg cc 3' olig#12b residue    91  90  89  88  87  86
5' g cgc GGC CGC TTT GGC CGG ATC 3' olig#13
``` where q is a mixture of (0.26 T, 0.18C, 0.26 A, and 0.30 G), f is a mixture of (0.22 T, 0.16 C, 0.40 A, and 0.22 G), and k is a mixture of equal parts of T and G. The bases shown in lower case at either end are spacers and are not incorporated into the cloned gene. The primer is complementary to the 3' end of each of the longer oligonts. One of the variegated oligo-nts and the primer olig#13 are combined in equimolar amounts and annealed. The dsDNA is completed with all four (nt)TPs and Klenow fragment. The resulting dsDNA and RF pLG7 are cut with both SfiI and SphI, purified, mixed, and ligated. We then select a transformed clone that, when induced with IPTG, binds AHTrp.

To vary the junction between M13 signal sequence and BPTI, we introduce DNA variegated at codons for residues between 23 and 27 into the KpnI and XhoI sites of pLG7. The first three residues are highly variable in amino acid sequences homologous to BPTI. Homologous sequences also vary in length at the amino terminus. One of the oligonts olig#14, olig#14a, or olig#14b and the primer olig#15 are synthesized by standard methods. The oligo-nts are:

```
residue      17 18 19  20  21  22  23  24  25
5' g|gcc|gcG|GTA|CCG|ATG|CTG|TCT|TTT|GCT|fxk|fxk|-

26  27  28  29  30
             |fxk|TTC|TGT|CTC|GAG|cgc|ccg|cga|3' olig#14 residue      17 18 19  20  21  22  23  24  25  26
5'g|gcc|gcG|GTA|CCG|ATG|CTG|TCT|TTT|GCT|fxk|fxk|fxk|-

26a 26b 27  28  29  30
          |fxk|fxk|TTC|TGT|CTC|GAG|cgc|ccg|cga|3' olig#14a, residue      17 18 19  20  21  22  23  25  26
5'g|gcc|gcG|GTA|CCG|ATG|CTG|TCT|TTT|GCT|fxk|fxk|-

26a 26b 26c 26d 27  28  29  30
          |fxk|fxk|fxk|fxk|TTC|TGT|CTC|GAG|cgc|ccg|cga|3'olig#14b 5'|tcg|cgg|gcg|CTC|GAG|ACA|GAA|3' olig#15
``` where f is a mixture of (0.26 T, 0.18 C, 0.26 A, and 0.30 G), x is a mixture of (0.22 T, 0.16 C, 0.40 A, and 0.22 G), and k is a mixture of equal parts of T and G. The bases shown in lower case at either end are spacers and are not incorporated into the cloned gene. One of the variegated-oligo-nts and the primer are combined in equimolar amounts and annealed. The ds DNA is completed with all four (nt)TPs and Klenow fragment. The resulting dsDNA and RF pLG7 are cut with both KpnI and XhoI, purified, mixed, and ligated. We select a transformed clone that, when induced with IPTG, binds AHTrp or trp.

Other numbers of variegated codons could be used.

If none of these approaches produces a working chimeric protein, we may try a different signal sequence. If that doesn't work, we may try a different OSP.

V. AFFINITY SELECTION OF TARGET-BINDING MUTANTS

V.A. Affinity Separation Technology, Generally

Affinity separation is used initially in the present invention to verify that the display system is working, i.e., that a chimeric outer surface protein has been expressed and transported to the surface of the genetic package and is oriented so that the inserted binding domain is accessible to target material. When used for this purpose, the binding domain is a known binding domain for a particular target and that target is the affinity molecule used in the affinity separation process. For example, a display system may be validated by using inserting DNA encoding BPTI into a gene encoding an outer surface protein of the genetic package of interest, and testing for binding to anhydrotrypsin, which is normally bound by BPTI.

If the genetic packages bind to the target, then we have confirmation that the corresponding binding domain is indeed displayed by the genetic package. Packages which display the binding domain (and thereby bind the target) are separated from those which do not.

Once the display system is validated, it is possible to use a variegated population of genetic packages which display a variety of different potential binding domains, and use affinity separation technology to determine how well they bind to one or more targets. This target need not be one bound by a known binding domain which is parental to the displayed binding domains, i.e., one may select for binding to a new target.

For example, one may variegate a BPTI binding domain and test for binding, not to trypsin, but to another serine protease, such as human neutrophil elastase or cathepsin G, or even to a wholly unrelated target, such as horse heart myoglobin.

The term "affinity separation means" includes, but is not limited to: a) affinity column chromatography, b) batch elution from an affinity matrix material, c) batch elution from an affinity material attached to a plate, d) fluorescence activated cell sorting, and e) electrophoresis in the presence of target material. "Affinity material" is used to mean a material with affinity for the material to be purified, called the "analyte". In most cases, the association of the affinity material and the analyte is reversible so that the analyte can be freed from the affinity material once the impurities are washed away.

The procedures described in sections V.H, V.I and V.J are not required for practicing the present invention, but may facilitate the development of novel binding proteins thereby.

V.B. Affinity Chromatography, Generally

Affinity column chromatography, batch elution from an affinity matrix material held in some container, and batch elution from a plate are very similar and hereinafter will be treated under "affinity chromatography."

If affinity chromatography is to be used, then:

1) the molecules of the target material must be of sufficient size and chemical reactivity to be applied to a solid support suitable for affinity separation, 2) after application to a matrix, the target material preferably does not react with water, 3) after application to a matrix, the target material preferably does not bind or degrade proteins in a non-specific way, and 4) the molecules of the target material must be sufficiently large that attaching the material to a matrix allows enough unaltered surface area (generally at least 500 $Å^2$, excluding the atom that is connected to the linker) for protein binding.

Affinity chromatography is the preferred separation means, but FACS, electrophoresis, or other means may also be used.

V.C. Fluorescent-Activated Cell Sorting, Generally

Fluorescent-activated cell sorting involves use of an affinity material that is fluorescent per se or is labeled with a fluorescent molecule. Current commercially available cell sorters require 800 to 1000 molecules of fluorescent dye, such as Texas red, bound to each cell. FACS can sort $10^3$ cells or viruses/sec.

FACS (e.g. FACStar from Beckton-Dickinson, Mountain View, Calif.) is most appropriate for bacterial cells and spores because the sensitivity of the machines requires approximately 1000 molecules of fluorescent label bound to each GP to accomplish a separation. OSPs such as OmpA, OmpF, OmpC are present at $\geq 10^4$/cell, often as much as $10^5$/cell. Thus use of FACS with PBDs displayed on one of the OSPs of a bacterial cell is attractive. This is particularly true if the target is quite small so that attachment to a matrix has a much greater effect than would attachment to a dye. To optimize FACS separation of GPs, we use a derivative of Afm(IPBD) that is labeled with a fluorescent molecule, denoted Afm(IPBD)*. The variables to be optimized include: a) amount of IPBD/GP, b) concentration of Afm(IPBD)*, c) ionic strength, d) concentration of GPs, and e) parameters pertaining to operation of the FACS machine. Because Afm(IPBD)* and GPs interact in solution, the binding will be linear in both [Afm(IPBD)*] and [displayed IPBD]. Preferably, these two parameters are varied together. The other parameters can be optimized independently.

If FACS is to be used as the affinity separation means, then:

1) the molecules of the target material must be of sufficient size and chemical reactivity to be conjugated to a suitable fluorescent dye or the target must itself be fluorescent, 2) after any necessary fluorescent labeling, the target preferably does not react with water, 3) after any necessary fluorescent labeling, the target material preferably does not bind or degrade proteins in a non-specific way, and 4) the molecules of the target material must be sufficiently large that attaching the material to a suitable dye allows enough unaltered surface area (generally at least 500 $Å^2$, excluding the atom that is connected to the linker) for protein binding.

V.D. Affinity Electrophoresis, Generally

Electrophoretic affinity separation involves electrophoresis of viruses or cells in the presence of target material, wherein the binding of said target material changes the net charge of the virus particles or cells. It has been used to separate bacteriophages on the basis of charge. (SERW87).

Electrophoresis is most appropriate to bacteriophage because of their small size (SERW87). Electrophoresis is a preferred separation means if the target is so small that chemically attaching it to a column or to a fluorescent label would essentially change the entire target. For example, chloroacetate ions contain only seven atoms and would be essentially altered by any linkage. GPs that bind chloroacetate would become more negatively charged than GPs that do not bind the ion and so these classes of GPs could be separated.

If affinity electrophoresis is to be used, then:

1) the target must either be charged or of such a nature that its binding to a protein will change the charge of the protein, 2) the target material preferably does not react with water, 3) the target material preferably does not bind or degrade proteins in a non-specific way, and 4) the target must be compatible with a suitable gel material.

The present invention makes use of affinity separation of bacterial cells, or bacterial viruses (or other genetic packages) to enrich a population for those cells or viruses carrying genes that code for proteins with desirable binding properties.

V.E. Target Materials

The present invention may be used to select for binding domains which bind to one or more target materials, and/or fail to bind to one or more target materials. Specificity, of course, is the ability of a binding molecule to bind strongly to a limited set of target materials, while binding more weakly or not at all to another set of target materials from which the first set must be distinguished.

The target materials may be organic macromolecules, such as polypeptides, lipids, polynucleic acids, and polysaccharides, but are not so limited. Almost any molecule that is stable in aqueous solvent may be used as a target. The following list of possible targets is given as illustration and not as limitation. The categories are not strictly mutually exclusive. The omission of any category is not to be construed to imply that said category is unsuitable as a target.

A. Peptides
  1) human β endorphin (Merck Index 3528)
  2) dynorphin (MI 3458)
  3) Substance P (MI 8834)
  4) Porcine somatostatin (MI 8671)
  5) human atrial natriuretic factor (MI 887)
  6) human calcitonin
  7) glucagon B. Proteins
I. Soluble Proteins
  a. Hormones
    1) human TNF (MI 9411)
    2) Interleukin-1 (MI 4895)
    3) Interferon-γ (MI 4894)
    4) Thyrotropin (MI 9709)
    5) Interferon-α (MI 4892)
    6) Insulin (MI 4887, p.789)
  b. Enzymes
    1) human neutrophil elastase
    2) Human thrombin
    3) human Cathepsin G
    4) human tryptase
    5) human chymase
    6) human blood clotting Factor Xa
    7) any retro-viral Pol protease
    8) any retro-viral Gag protease
    9) dihydrofolate reductase
    10) *Pseudomonas putida* cytochrome P450$_{CAM}$
    11) human pyruvate kinase
    12) *E. coli* pyruvate kinase
    13) jack bean urease
    14) aspartate transcarbamylase (*E. coli*)
    15) ras protein
    16) any protein-tyrosine kinase
  c. Inhibitors
    1) aprotinin (MI 784)
    2) human α1-anti-trypsin
    3) phage λ cI (inhibits DNA transcription)
  d. Receptors
    1) TNF receptor
    2) IgE receptor
    3) LamB
    4) CD4
    5) IL-1 receptor
  e. Toxins
    1) ricin (also an enzyme)
    2) α Conotoxin GI
    3) mellitin 4) *Bordetella pertussis* adenylate cyclase (also an enzyme)
5) *Pseudomonas aeruginosa* hemolysin
f. Other proteins
1) horse heart myoglobin
2) human sickle-cell haemoglobin
3) human deoxy haemoglobin
4) human CO haemoglobin
5) human low-density lipoprotein (a lipoprotein)
6) human IgG (combining site removed or blocked) (a glycoprotein)
7) influenza haemagglutinin
8) phage λ capsid
9) fibrinogen
10) HIV-1 gp120
11) *Neisseria gonorrhoeae* pilin
12) fibril or flagellar protein from spirochaete bacterial species such as those that cause syphilis, Lyme disease, or relapsing fever
13) pro-enzymes such as prothrombin and trypsinogen II. Insoluble Proteins
1) silk
2) human elastin
3) keratin
4) collagen
5) fibrin C. Nucleic acids
a. DNA 1) ds DNA: 5'-ACTAGTCTC-3'
3'-TGATCAGAG-5'

2) ds DNA: 5'-CCGTCGAATCCGC-3'
3'-GGCAGTTTAGGCG-5'
(Note mismatch)

3) ss DNA: 5'-CGTAACCTCGTCATTA-3'
(No hair pin)

4) ss DNA: 5'-CCGTAGGT⏋
3'-GGCATCCA⏌
(Note hair pin)

5) dsDNA with cohesive ends:
5'-CACGGCTATTACGGT-3'
3'-   CCGATAATGCCA-5' b. RNA
1) yeast Phe tRNA
2) ribosomal RNA
3) segment of mRNA

D. Organic molecules (not peptide, protein, or nucleic acid)
I. Small and monomeric
1) cholesterol
2) aspartame
3) bilirubin
4) morphine
5) codeine
6) heroine
7) dichlorodiphenyltrichlorethane (DDT)
8) prostaglandin PGE2
9) actinomycin
10) 2,2,3 trimethyldecane
11) Buckminsterfullerene
12) cortavazol (MI 2536, p.397)

II. Polymers
1) cellulose
2) chitin

III. Others
1) O-antigen of *Salmonella enteritidis* (a lipopolysaccharide)

E. Inorganic compounds
1) asbestos
2) zeolites
3) hydroxylapatite
4) 111 face of crystalline silicon
5) paulingite
6) U(IV) (uranium ions)
7) Au(III) (gold ions)

F. Organometallic compounds
1) iron(III) haem
2) cobalt haem
3) cobalamine
4) (isopropylamino)$_6$Cr(III)

Serine proteases are an especially interesting class of potential target materials. Serine proteases are ubiquitous in living organisms and play vital roles in processes such as: digestion, blood clotting, fibrinolysis, immune response, fertilization, and post-translational processing of peptide hormones. Although the role these enzymes play is vital, uncontrolled or inappropriate proteolytic activity can be very damaging. Several serine proteases are directly involved in serious disease states. Uncontrolled neutrophil elastase (NE) (also known as leukocyte elastase) is thought to be the major cause of emphysema (BEIT86, HUBB86, HUBB89, HUTC87, SOMM90, WEWE87) whether caused by congenital lack of α-1-antitrypsin or by smoking. NE is also implicated as an essential ingredient in the pernicious cycle of:

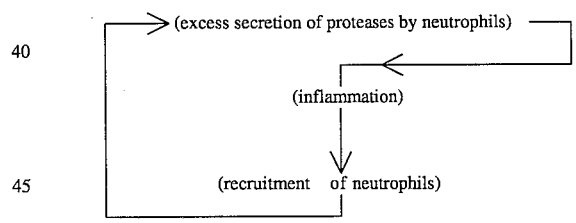

observed in cystic fibrosis (CF) (NADE90). Inappropriate NE activity is very harmful and to stop the progression of emphysema or to alleviate the symptoms of CF, an inhibitor of very high affinity is needed. The inhibitor must be very specific to NE lest it inhibit other vital serine proteases or esterases. Nadel (NADE90) has suggested that onset of excess secretion is initiated by $10^{-10}$M NE; thus, the inhibitor must reduce the concentration of free NE to well below this level. Thus human neutrophil elastase is a preferred target and a highly stable protein is a preferred IPBD. In particular, BPTI, ITI-D1, or another BPTI homologue is a preferred IPBD for development of an inhibitor to HNE. Other preferred IPBDs for making an inhibitor to HNE include CMTI-III, SLPI, Eglin, α-conotoxin GI, and Ω Conotoxins.

HNE is not the only serine protease for which an inhibitor would be valuable. Works concerning uses of protease inhibitors and diseases thought to result from inappropriate protease activity include: NADE87, REST88, SOMM90, and SOMM89. Tryptase and chymase may be involved in asthma, see FRAN89 and VAND89. There are reports that suggest that Proteinase 3 (also known as p29) is as important or even more important than HNE; see NILE89, ARNA90, KAOR88, CAMP90, and GUPT90. Cathepsin G is another protease that may cause disease when present in excess; see FERR90, PETE89, SALV87, and SOMM90. These works indicate that a problem exists and that blocking one or another protease might well alleviate a disease state. Some of the cited works report inhibitors having measurable affinity for a target protease, but none report truly excellent inhibitors that have $K_d$ in the range of $10^{-12}M$ as may be obtained by the method of the present invention. The same IPBDs used for HNE can be used for any serine protease.

The present invention is not, however, limited to any of the above-identified target materials. The only limitation is that the target material be suitable for affinity separation.

A supply of several milligrams of pure target material is desired. With HNE (as discussed in Examples II and III), 400 µg of enzyme is used to prepare 200 µl of ReactiGel beads. This amount of beads is sufficient for as many as 40 fractionations. Impure target material could be used, but one might obtain a protein that binds to a contaminant instead of to the target.

The following information about the target material is highly desirable: 1) stability as a function of temperature, pH, and ionic strength, 2) stability with respect to chaotropes such as urea or guanidinium Cl, 3) pI, 4) molecular weight, 5) requirements for prosthetic groups or ions, such as haem or $Ca^{+2}$, and 6) proteolytic activity, if any. It is also potentially useful to know: 1) the target's sequence, if the target is a macromolecule, 2) the 3D structure of the target, 3) enzymatic activity, if any, and 4) toxicity, if any.

The user of the present invention specifies certain parameters of the intended use of the binding protein: 1) the acceptable temperature range, 2) the acceptable pH range, 3) the acceptable concentrations of ions and neutral solutes, and 4) the maximum acceptable dissociation constant for the target and the SBD:

$K_T=[Target][SBD]/[Target:SBD]$.

In some cases, the user may require discrimination between T, the target, and N, some non-target. Let $K_T=[T][SBD]/[T:SBD]$, and $K_N=[N][SBD]/[N:SBD]$, then $K_T/K_N=([T][N:SBD])/([N][T:SBD])$.

The user then specifies a maximum acceptable value for the ratio $K_T/K_N$.

The target material preferably is stable under the specified conditions of pH, temperature, and solution conditions.

If the target material is a protease, one considers the following points:

1) a highly specific protease can be treated like any other target,
2) a general protease, such as subtilisin, may degrade the OSPs of the GP including OSP-PBDs; there are several alternative ways of dealing with general proteases, including: a) use a protease inhibitor as PPBD so that the SBD is an inhibitor of the protease, b) a chemical inhibitor may be used to prevent proteolysis (e.g. phenylmethylfluorosulfate (PMFS) that inhibits serine proteases), c) one or more active-site residues may be mutated to create an inactive protein (e.g. a serine protease in which the active serine is mutated to alanine), or d) one or more active-site amino-acids of the protein may be chemically modified to destroy the catalytic activity (e.g. a serine protease in which the active serine is converted to anhydroserine),
3) SBDs selected for binding to a protease need not be inhibitors; SBDs that happen to inhibit the protease target are a fairly small subset of SBDs that bind to the protease target,
4) the more we modify the target protease, the less like we are to obtain an SBD that inhibits the target protease, and
5) if the user requires that the SBD inhibit the target protease, then the active site of the target protease must not be modified any more than necessary; inactivation by mutation or chemical modification are preferred methods of inactivation and a protein protease inhibitor becomes a prime candidate for IPBD. For example, BPTI has been mutated, by the methods of the present invention, to bind to proteases other than trypsin.

Example III–VI disclose that uninhibited serine proteases may be used as targets quite successfully and that protein protease inhibitors derived from BPTI and selected for binding to these immobilized proteases are excellent inhibitors.

V.F. Immobilization or Labeling of Target Material

For chromatography, FACS, or electrophoresis there may be a need to covalently link the target material to a second chemical entity. For chromatography the second entity is a matrix, for FACS the second entity is a fluorescent dye, and for electrophoresis the second entity is a strongly charged molecule. In many cases, no coupling is required because the target material already has the desired property of: a) immobility, b) fluorescence, or c) charge. In other cases, chemical or physical coupling is required.

Various means may be used to immobilize or label the target materials. The means of immobilization or labeling is, in part, determined by the nature of the target. In particular, the physical and chemical nature of the target and its functional groups of the target material determine which types of immobilization reagents may be most easily used.

For the purpose of selecting an immobilization method, it may be more helpful to classify target materials as follows: (a) solid, whether crystalline or amorphous, and insoluble in an aqueous solvent (e.g., many minerals, and fibrous organics such as cellulose and silk); (b) solid, whether crystalline or amorphous, and soluble in an aqueous solvent; (c) liquid, but insoluble in aqueous phase (e.g., 2,3,3-trimethyldecane); or (d) liquid, and soluble in aqueous media.

It is not necessary that the actual target material be used in preparing the immobilized or labeled analogue that is to be used in affinity separation; rather, suitable reactive analogues of the target material may be more convenient. If 2,3,3-trimethyldecane were the target material, for example, then 2,3,3-trimethyl-10-aminodecane would be far easier to immobilize than the parental compound. Because the latter compound is modified at one end of the chain, it retains almost all of the shape and charge attributes that differentiate the former compound from other alkanes.

Target materials that do not have reactive functional groups may be immobilized by first creating a reactive functional group through the use of some powerful reagent, such as a halogen. For example, an alkane can be immobilized for affinity by first halogenating it and then reacting the halogenated derivative with an immobilized or immobilizable amine.

In some cases, the reactive groups of the actual target material may occupy a part on the target molecule that is to be left undisturbed. In that case, additional functional groups may be introduced by synthetic chemistry. For example, the most reactive groups in cholesterol are on the steroid ring system, viz, —OH and >C=C. We may wish to leave this ring system as it is so that it binds to the novel binding protein. In this case, we prepare an analogue having a reactive group attached to the aliphatic chain (such as 26-aminocholesterol) and immobilize this derivative in a manner appropriate to the reactive group so attached.

Two very general methods of immobilization are widely used. The first is to biotinylate the compound of interest and then bind the biotinylated derivative to immobilized avidin. The second method is to generate antibodies to the target material, immobilize the antibodies by any of numerous methods, and then bind the target material to the immobilized antibodies. Use of antibodies is more appropriate for larger target materials; small targets (those comprising, for example, ten or fewer non-hydrogen atoms) may be so completely engulfed by an antibody that very little of the target is exposed in the target-antibody complex.

Non-covalent immobilization of hydrophobic molecules without resort to antibodies may also be used. A compound, such as 2,3,3-trimethyldecane is blended with a matrix precursor, such as sodium alginate, and the mixture is extruded into a hardening solution. The resulting beads will have 2,3,3-trimethyldecane dispersed throughout and exposed on the surface.

Other immobilization methods depend on the presence of particular chemical functionalities. A polypeptide will present —$NH_2$ (N-terminal; Lysines), —COOH (C-terminal; Aspartic Acids; Glutamic Acids), —OH (Serines; Threonines; Tyrosines), and —SH (Cysteines). A polysaccharide has free —OH groups, as does DNA, which has a sugar backbone.

The following table is a nonexhaustive review of reactive functional groups and potential immobilization reagents:

| Group | Reagent |
| --- | --- |
| R-$NH_2$ | Derivatives of 2,4,6-trinitro benzene sulfonates (TNBS), (CREI84, p. 11) |
| R-$NH_2$ | Carboxylic acid anhydrides, e.g. derivatives of succinic anhydride, maleic anhydride, citraconic anhydride (CREI84, |
| R-$NH_2$ | Aldehydes that form reducible Schiff bases (CREI84, p. 12) |
| guanido | cyclohexanedione derivatives (CREI84, p. 14) |
| R-$CO_2H$ | Diazo cmpds (CREI84, p. 10) |
| R-$CO_2$— | Epoxides (CREI84, p. 10) |
| R-OH | Carboxylic acid anhydrides |
| Aryl-OH | Carboxylic acid anhydrides |
| Indole ring | Benzyl halide and sulfenyl halides (CREI84, p. 19) |
| R-SH | N-alkylmaleimides (CREI84, p. 21) |
| R-SH | ethyleneimine derivatives (CREI84, p. 21) |
| R-SH | Aryl mercury compounds, (CREI84, P.21) |
| R-SH | Disulfide reagents, (CREI84, p. 23) |
| Thiol ethers | Alkyl iodides, (CREI84, p. 20) |
| Ketones | Make Schiff's base and reduce with $NaBH_4$. (CREI84, p. 12–13) |
| Aldehydes | Oxidize to COOH, vide supra. |
| R-$SO_3H$ | Convert to R-$SO_2Cl$ and react with immobilizes alcohol or amine. |
| R-$PO_3H$ | Convert to R-$PO_2Cl$ and react with immobilized alcohol or amine. |
| CC double bonds | Add HBr and then make amine or thiol. |

The next table identifies the reactive groups of a number of potential targets.

| Compound (Item#, page)* | Reactive groups or [derivatives] |
| --- | --- |
| prostaglandin E2 (2893, 1251) | —OH, keto, —COOH, C=C |
| aspartame (861, 132) | —$NH_2$, –COOH, –$COOCH_3$ |
| haem (4558, 732) | vinyl, —COOH, Fe |
| bilirubin (1235, 189) | vinyl, —COOH, keto, —NH— |
| morphine (6186, 988) | —OH, —C=C—, reactive phenyl ring |
| codeine (2459, 384) | —OH, —C=C—, reactive phenyl ring |
| dichlorodiphenyltri-chlorethane (2832, 446) | aromatic chlorine, aliphatic chlorine |
| benzo(a)pyrene (1113, 172) | [Chlorinate->amine, or make sulfonate-> Aryl-$SO_2Cl$] |
| actinomycin D (2804, 441) | aryl-$NH_2$, —OH |
| cellulose | self immobilized |
| hydroxylapatite | self immobilized |
| cholesterol (2204, 341) | —OH, >C=C— |

*Note: Item# and page refer to The Merck Index, 11th Edition.

The extensive literature on affinity chromatography and related techniques will provide further examples.

Matrices suitable for use as support materials include polystyrene, glass, agarose and other chromatographic supports, and may be fabricated into beads, sheets, columns, wells, and other forms as desired. Suppliers of support material for affinity chromatography include: Applied Protein Technologies Cambridge, Mass.; BioRad Laboratories, Rockville Center, N.Y.; Pierce Chemical Company, Rockford, Ill. Target materials are attached to the matrix in accord with the directions of the manufacturer of each matrix preparation with consideration of good presentation of the target.

Early in the selection process, relatively high concentrations of target materials may be applied to the matrix to facilitate binding; target concentrations may subsequently be reduced to select for higher affinity SBDs.

V.G. Elution of Lower Affinity PBD-Bearing Genetic Packages

The population of GPs is applied to an affinity matrix under conditions compatible with the intended use of the binding protein and the population is fractionated by passage of a gradient of some solute over the column. The process enriches for PBDs having affinity for the target and for which the affinity for the target is least affected by the eluants used. The enriched fractions are those containing viable GPs that elute from the column at greater concentration of the eluant.

The eluants preferably are capable of weakening noncovalent interactions between the displayed PBDs and the immobilized target material. Preferably, the eluants do not kill the genetic package; the genetic message corresponding to successful mini-proteins is most conveniently amplified by reproducing the genetic package rather than by in vitro procedures such as PCR. The list of potential eluants includes salts (including Na+, $NH_4$+, Rb+, $SO_4$—, $H_2PO_4-$, citrate, $K+$, $Li+$, $Cs+$, $HSO_4-$, $CO_3--$, $Ca++$, $Sr++$, $Cl--$, $PO_4--$, $HCO_3-$, $Mg++$, $Ba++$, $Br-$, $HPO_4--$ and acetate), acid, heat, compounds known to bind the target, and soluble target material (or analogues thereof).

Because bacteria continue to metabolize during affinity separation, the choice of buffer components is more restricted for bacteria than for bacteriophage or spores. Neutral solutes, such as ethanol, acetone, ether, or urea, are frequently used in protein purification and are known to weaken non-covalent interactions between proteins and other molecules. Many of these species are, however, very harmful to bacteria and bacteriophage. Urea is known not to harm M13 up to 8M. Bacterial spores, on the other hand, are impervious to most neutral solutes. Several affinity separation passes may be made within a single round of variegation. Different solutes may be used in different analyses, salt in one, pH in the next, etc.

Any ions or cofactors needed for stability of PBDs (derived from IPBD) or target are included in initial and elution buffers at appropriate levels. We first remove GP(PBD)s that do not bind the target by washing the matrix with the initial buffer. We determine that this phase of washing is complete by plating aliquots of the washes or by measuring the optical density (at 260 nm or 280 nm). The matrix is then eluted with a gradient of increasing: a) salt, b) [H+] (decreasing pH), c) neutral solutes, d) temperature (increasing or decreasing), or e) some combination of these factors. The solutes in each of the first three gradients have been found generally to weaken non-covalent interactions between proteins and bound molecules. Salt is a preferred solute for gradient formation in most cases. Decreasing pH is also a highly preferred eluant. In some cases, the preferred matrix is not stable to low pH so that salt and urea are the most preferred reagents. Other solutes that generally weaken non-covalent interaction between proteins and the target material of interest may also be used.

The uneluted genetic packages contain DNA encoding binding domains which have a sufficiently high affinity for the target material to resist the elution conditions. The DNA encoding such successful binding domains may be recovered in a variety of ways. Preferably, the bound genetic packages are simply eluted by means of a change in the elution conditions. Alternatively, one may culture the genetic package in situ, or extract the target-containing matrix with phenol (or other suitable solvent) and amplify the DNA by PCR or by recombinant DNA techniques. Additionally, if a site for a specific protease has been engineered into the display vector, the specific protease is used to cleave the binding domain from the GP.

V.H. Optimization of Affinity Chromatography Separation:

For linear gradients, elution volume and eluant concentration are directly related. Changes in eluant concentration cause GPs to elute from the column. Elution volume, however, is more easily measured and specified. It is to be understood that the eluant concentration is the agent causing GP release and that an eluant concentration can be calculated from an elution volume and the specified gradient.

Using a specified elution regime, we compare the elution volumes of GP(IPBD)s with the elution volumes of wtGP on affinity columns supporting AfM(IPBD). Comparisons are made at various: a) amounts of IPBD/GP, b) densities of AfM(IPBD)/(volume of matrix) (DoAMoM), c) initial ionic strengths, d) elution rates, e) amounts of GP/(volume of support), f) pHs, and g) temperatures, because these are the parameters most likely to affect the sensitivity and efficiency of the separation. We then pick those conditions giving the best separation.

We do not optimize pH or temperature; rather we record optimal values for the other parameters for one or more values of pH and temperature. The pH used must be within the range of pH for which GP(IPBD) binds the AfM(IPBD) that is being used in this step. The conditions of intended use specified by the user may include a specification of pH or temperature. If pH is specified, then pH will not be varied in eluting the column. Decreasing pH may, however, be used to liberate bound GPs from the matrix. Similarly, if the intended use specifies a temperature, we will held the affinity column at the specified temperature during elution, but we might vary the temperature during recovery. If the intended use specifies the pH or temperature, then we prefer that the affinity separation be optimized for all other parameters at the specified pH and temperature.

In the optimization devised in this step, we preferably use a molecule known to have moderate affinity for the IPBD ($K_d$ in the range $10^{-6}$M to $10^{-8}$M), for the following reason. When populations of GP(vgPBD)s are fractionated, there will be roughly three subpopulations: a) those with no binding, b) those that have some binding but can be washed off with high salt or low pH, and c) those that bind very tightly and are most easily rescued in situ. We optimize the parameters to separate (a) from (b) rather than (b) from (c). Let $PBD_w$ be a PBD having weak binding to the target and $PBD_s$ be a PBD having strong binding. Higher DoAMoM might, for example, favor retention of GP($PBD_w$) but also make it very difficult to elute viable GP($PBD_s$). We will optimize the affinity separation to retain GP($PBD_w$) rather than to allow release of GP($PBD_s$) because a tightly bound GP(PBDs) can be rescued by in situ growth. If we find that DoAMoM strongly affects the elution volume, then in part III we may reduce the amount of target on the affinity column when an SBD has been found with moderately strong affinity ($K_d$ on the order of $10^{-7}$M) for the target.

In case the promoter of the osp-ipbd gene is not regulated by a chemical inducer, we optimize DoAMoM, the elution rate, and the amount of GP/volume of matrix. If the optimized affinity separation is acceptable, we proceed. If not, we develop a means to alter the amount of IPBD per GP. Among GPs considered in the present invention, this case could arise only for spores because regulatable promoters are available for all other systems.

If the amount of IPBD/spore is too high, we could engineer an operator site into the osp-ipbd gene. We choose the operator sequence such that a repressor sensitive to a small diffusible inducer recognizes the operator. Alternatively, we could alter the Shine-Dalgarno sequence to produce a lower homology with consensus Shine-Dalgarno sequences. If the amount of IPBD/spore is too low, we can introduce variability into the promoter or Shine-Dalgarno sequences and screen colonies for higher amounts of IPBD/spore.

In this step, we measure elution volumes of genetically pure GPs that elute from the affinity matrix as sharp bands that can be detected .by UV absorption. Alternatively, samples from effluent fractions can be plated on suitable medium (cells or spores) or on sensitive cells (phage) and colonies or plaques counted.

Several values of IPBD/GP, DoAMoM, elution rates, initial ionic strengths, and loadings should be examined. The following is only one of many ways in which the affinity separation could be optimized. We anticipate that optimal values of IPBD/GP and DoAMoM will be correlated and therefore should be optimized together. The effects of initial ionic strength, elution rate, and amount of GP/(matrix volume) are unlikely to be strongly correlated, and so they can be optimized independently.

For each set of parameters to be tested, the column is eluted in a specified manner. For example, we may use a regime called Elution Regime 1: a KCl gradient runs from 10 mM to maximum allowed for the GP(IPBD) viability in 100 fractions of 0.05 $V_V$, followed by 20 fractions of 0.05 $V_V$ at maximum allowed KCl; pH of the buffer is maintained at the specified value with a convenient buffer such as phosphate, Tris, or MOPS. Other elution regimes can be used; what is important is that the conditions of this optimization be similar to the conditions that are used in Part III for selection for binding to target and recovery of GPs from the chromatographic system.

When the osp-ipbd gene is regulated by [XINDUCE], IPBD/GP can be controlled by varying [XINDUCE]. Appropriate values of [XINDUCE] depend on the identity of [XINDUCE] and the promoter; if, for example, XINDUCE is isopropylthiogalactoside (IPTG) and the promoter is lacUV5, then [IPTG]=0, 0.1 uM, 1.0 uM, 10.0 uM, 100.0 uM, and 1.0 mM would be appropriate levels to test. The range of variation of [XINDUCE] is extended until an optimum is found or an acceptable level of expression is obtained.

DoAMoM is varied from the maximum that the matrix material can bind to 1% or 0.1% of this level in appropriate steps. We anticipate that the efficiency of separation will be a smooth function of DoAMoM so that it is appropriate to cover a wide range of values for DoAMoM with a coarse grid and then explore the neighborhood of the approximate optimum with a finer grid.

Several values of initial ionic strength are tested, such as 1.0 mM, 5.0 mM, 10.0 mM and 20.0 mM. Low ionic strength favors binding between oppositely charged groups, but could also cause GP to precipitate.

The elution rate is varied, by successive factors of ½, from the maximum attainable rate to 1/16 of this value. If the lowest elution rate tested gives the best separation, we test lower elution rates until we find an optimum or adequate separation.

The goal of the optimization is to obtain a sharp transition between bound and unbound GPs, triggered by increasing salt or decreasing pH or a combination of both. This optimization need be performed only: a) for each temperature to be used, b) for each pH to be used, and c) when a new GP(IPBD) is created.

V.I. Measuring the sensitivity of affinity separation:

Once the values of IPBD/GP, DoAMoM, initial ionic strength, elution rate, and amount of GP/(volume of affinity support) have been optimized, we determine the sensitivity of the affinity separation ($C_{sensi}$) by the following procedure that measures the minimum quantity of GP(IPBD) that can be detected in the presence of a large excess of wtGP. The user chooses a number of separation cycles, denoted $N_{chrom}$, that will be performed before an enrichment is abandoned; preferably, $N_{chrom}$ is in the range 6 to 10 and $N_{chrom}$ must be greater than 4. Enrichment can be terminated by isolation of a desired GP(SBD) before $N_{chrom}$ passes.

The measurement of sensitivity is significantly expedited if GP(IPBD) and wtGP carry different selectable markers because such markers allow easy identification of colonies obtained by plating fractions obtained from the chromatography column. For example, if wtGP carries kanamycin resistance and GP(IPBD) carries ampicillin resistance, we can plate fractions from a column on non-selective media suitable for the GP. Transfer of colonies onto ampicillin- or kanamycin-containing media will determine the identity of each colony.

Mixtures of GP(IPBD) and wtGP are prepared in the ratios of 1:$V_{lim}$, where $V_{lim}$ ranges by an appropriate factor (e.g. 1/10) over an appropriate range, typically $10^{11}$ through $10^4$. Large values of $V_{lim}$ are tested first; once a positive result is obtained for one value of $V_{lim}$, no smaller values of $V_{lim}$ need be tested. Each mixture is applied to a column supporting, at the optimal DoAMoM, an AfM(IPBD) having high affinity for IPBD and the column is eluted by the specified elution regime, such as Elution Regime 1. The last fraction that contains viable GPs and an inoculum of the column matrix material are cultured. If GP(IPBD) and wtGP have different selectable markers, then transfer onto selection plates identifies each colony. If GP(IPBD) and wtGP have no selectable markers or the same selectable markers, then a number (e.g. 32) of GP clonal isolates are tested for presence of IPBD. If IPBD is not detected on the surface of any of the isolated GPs, then GPs are pooled from: a) the last few (e.g. 3 to 5) fractions that contain viable GPs, and b) an inoculum taken from the column matrix. The pooled GPs are cultured and passed over the same column and enriched for GP(IPBD) in the manner described. This process is repeated until $N_{chrom}$ passes have been performed, or until the IPBD has been detected on the GPs. If GP(IPBD) is not detected after $N_{chrom}$ passes, $V_{lim}$ is decreased and the process is repeated.

Once a value for $V_{lim}$ is found that allows recovery of GP(IPBD)s, the factor by which $V_{lim}$ is varied is reduced and additional values are tested until $V_{lim}$ is known to within a factor of two.

$C_{sensi}$ equals the highest value of $V_{lim}$ for which the user can recover GP(IPBD) within $N_{chrom}$ passes. The number of chromatographic cycles ($K_{cyc}$) that were needed to isolate GP(IPBD) gives a rough estimate of $C_{eff}$; $C_{eff}$ is approximately the $K_{cyc}$th root of Vlim:

$$C_{eff} \approx \exp\{\log_e(V_{lim})/K_{cyc}\}$$

For example, if $V_{lim}$ were $4.0\times10^8$ and three separation cycles were needed to isolate GP(IPBD), then $C_{eff} \approx 736$.

V.J. Measuring the efficiency of separation:

To determine $c_{eff}$ more accurately, we determine the ratio of GP(IPBD)/wtGP loaded onto an AfM(IPBD) column that yields approximately equal amounts of GP(IPBD) and wtGP after elution. We prepare mixtures of GP(IPBD) and wtGP in ratios GP(IPBD):wtGP::1:Q; we start Q at twenty times the approximate $C_{eff}$ found above. A 1:Q mixture of GP(IPBD) and WtGP is applied to a AfM(IPBD) column and eluted by the specified elution regime, such as Elution Regime 1. A sample of the last fraction that contains viable GPs is plated at a dilution that gives well separated colonies or plaques. The presence of IPBD or the osp-ipbd gene in each colony or plaque can be determined by a number of standard methods, including: a) use of different selectable markers, b) nitrocellulose filter lift of GPs and detection with AfM(IPBD)* (AUSU87), or c) nitrocellulose filter lift of GPs and detection with radiolabeled DNA that is complementary to the osp-ipbd gene (AUSU87). Let F be the fraction of GP(IPBD) colonies found in the last fraction containing viable GPs. When a Q is found such that $0.20<F<0.80$, then $$C_{eff}=Q*F.$$

If $F<0.2$, then we reduce Q by an appropriate factor (e.g. 1/10) and repeat the procedure. If $F>0.8$, then we increase Q by an appropriate factor (e.g. 2) and repeat the procedure.

V.K. Reducing selection due to non-specific binding:

When affinity chromatography is used for separating bound and unbound GPs, we may reduce non-specific binding of GP(PBD)s to the matrix that bears the target in the following ways:

1) we treat the column with blocking agents such as genetically defective GPs or a solution of protein before the population of GP(vgPBD)s is chromatographed, and 2) we pass the population of GP(vgPBD)s over a matrix containing no target or a different target from the same class as the actual target prior to affinity chromatography.

Step (1) above saturates any non-specific binding that the affinity matrix might show toward wild-type GPs or proteins in general; step (2) removes components of our population that exhibit non-specific binding to the matrix or to molecules of the same class as the target. If the target were horse heart myoglobin, for example, a column supporting bovine serum albumin could be used to trap GPs exhibiting PBDs with strong non-specific binding to proteins. If cholesterol were the target, then a hydrophobic compound, such as p-tertiarybutylbenzyl alcohol, could be used to remove GPs displaying PBDs having strong non-specific binding to hydrophobic compounds. It is anticipated that PBDs that fail to fold or that are prematurely terminated will be non-specifically sticky. These sequences could outnumber the PBDs having desirable binding properties. Thus, the capacity of the initial column that removes indiscriminately adhesive PBDs should be greater (e.g. 5 fold greater) than the column that supports the target molecule.

Variation in the support material (polystyrene, glass, agarose, cellulose, etc.) in analysis of clones carrying SBDs is used to eliminate enrichment for packages that bind to the support material rather than the target.

FACs may be used to separate GPs that bind fluorescent labeled target. We discriminate against artifactual binding to the fluorescent label by using two or more different dyes, chosen to be structurally different. GPs isolated using target labeled with a first dye are cultured. These GPs are then tested with target labeled with a second dye.

Electrophoretic affinity separation uses unaltered target so that only other ions in the buffer can give rise to artifactual binding. Artifactual binding to the gel material gives rise to retardation independent of field direction and so is easily eliminated.

A variegated population of GPs will have a variety of charges. The following 2D electrophoretic procedure accommodates this variation in the population. First the variegated population of GPs is electrophoresed in a gel that contains no target material. The electrophoresis continues until the GPs are distributed along the length of the lane. The gels described by Sewer for phage are very low in agarose and lack mechanical stability. The target-free lane in which the initial electrophoresis is conducted is separate from a square of gel that contains target material by a removable baffle. After the first pass, the baffle is removed and a second electrophoresis is conducted at right angles to the first. GPs that do not bind target migrate with unaltered mobility while GPs that do bind target will separate from the majority that do not bind target. A diagonal line of non-binding GPs will form. This line is excised and discarded. Other parts of the gel are dissolved and the GPs cultured.

V.L. Isolation of GP(PBD)s with binding-to-target phenotypes:

The harvested packages are now enriched for the binding-to-target phenotype by use of affinity separation involving the target material immobilized on an affinity matrix. Packages that fail to bind to the target material are washed away. If the packages are bacteriophage or endospores, it may be desirable to include a bacteriocidal agent, such as azide, in the buffer to prevent bacterial growth. The buffers used in chromatography include: a) any ions or other solutes needed to stabilize the target, and b) any ions or other solutes needed to stabilize the PBDs derived from the IPBD.

V.M. Recovery of packages:

Recovery of packages that display binding to an affinity column may be achieved in several ways, including:

1) collect fractions eluted from the column with a gradient as described above; fractions eluting later in the gradient contain GPs more enriched for genes encoding PBDs with high affinity for the column, 2) elute the column with the target material in soluble form, 3) flood the matrix with a nutritive medium and grow the desired packages in situ, 4) remove parts of the matrix and use them to inoculate growth medium, 5) chemically or enzymatically degrade the linkage holding the target to the matrix so that GPs still bound to target are eluted, or 6) degrade the packages and recover DNA with phenol or other suitable solvent; the recovered DNA is used to transform cells that regenerate GPs.

It is possible to utilize combinations of these methods. It should be remembered that what we want to recover from the affinity matrix is not the GPs per se, but the information in them. Recovery of viable GPs is very strongly preferred, but recovery of genetic material is essential. If cells, spores, or virions bind irreversibly to the matrix but are not killed, we can recover the information through in situ cell division, germination, or infection respectively. Proteolytic degradation of the packages and recovery of DNA is not preferred.

Although degradation of the bound GPs and recovery of genetic material is a possible mode of operation, inadvertent inactivation of the GPs is very deleterious. It is preferred that maximum limits for solutes that do not inactivate the GPs or denature the target or the column are determined. If the affinity matrices are expendable, one may use conditions that denature the column to elute GPs; before the target is denatured, a portion of the affinity matrix should be removed for possible use as an inoculum. As the GPs are held together by protein-protein interactions and other non-covalent molecular interactions, there will be cases in which the molecular package will bind so tightly to the target molecules on the affinity matrix that the GPs can not be washed off in viable form. This will only occur when very tight binding has been obtained. In these cases, methods (3) through (5) above can be used to obtain the bound packages or the genetic messages from the affinity matrix.

It is possible, by manipulation of the elution conditions, to isolate SBDs that bind to the target at one pH ($pH_b$) but not at another pH ($pH_o$). The population is applied at $pH_b$ and the column is washed thoroughly at $pH_b$. The column is then eluted with buffer at $pH_o$ and GPs that come off at the new pH are collected and cultured. Similar procedures may be used for other solution parameters, such as temperature. For example, GP(vgPBD)s could be applied to a column supporting insulin. After eluting with salt to remove GPs with little or no binding to insulin, we elute with salt and glucose to liberate GPs that display PBDs that bind insulin or glucose in a competitive manner.

V.N. Amplifying the Enriched Packages

Viable GPs having the selected binding trait are amplified by culture in a suitable medium, or, in the case of phage, infection into a host so cultivated. If the GPs have been inactivated by the chromatography, the OCV carrying the osp-pbd gene are recovered from the GP, and introduced into a new, viable host.

V.O. Determining whether further enrichment is needed:

The probability of isolating a GP with improved binding increases by $C_{eff}$ with each separation cycle. Let N be the number of distinct amino-acid sequences produced by the variegation. We want to perform K separation cycles before attempting to isolate an SBD, where K is such that the probability of isolating a single SBD is 0.10 or higher.

$K$=the smallest integer$>=\log_{10}(0.10N)/\log_{10}(C_{eff})$

For example, if N were $1.0 \cdot 10^7$ and $C_{eff}=6.31 \cdot 10^2$, then $\log_{10}(1.0 \cdot 10^6)/\log_{10}(6.31 \cdot 10^2)=6.0000/2.8000=2.14$. Therefore we would attempt to isolate SBDs after the third separation cycle. After only two separation cycles, the probability of finding an SBD is $(6.31 \times 10^2)^2/(1.0 \times 10^7)=0.04$ and attempting to isolate SBDs might be profitable.

Clonal isolates from the last fraction eluted which contained any viable GPs, as well as clonal isolates obtained by culturing an inoculum taken from the affinity matrix, are cultured in a growth step that is similar to that described previously. Other fractions may be cultured too. If K separation cycles have been completed, samples from a number, e.g. 32, of these clonal isolates are tested for elution properties on the {target} column. If none of the isolated, genetically pure GPs show improved binding to target, or if K cycles have not yet been completed, then we pool and culture, in a manner similar to the manner set forth previously, the GPs from the last few fractions eluted that contained viable GPs and from the GPs obtained by culturing an inoculum taken from the column matrix. We then repeat the enrichment procedure described above. This cyclic enrichment may continue $N_{chrom}$ passes or until an SBD is isolated.

If one or more of the isolated GPs has improved retention on the {target} column, we determine whether the retention of the candidate SBDs is due to affinity for the target material as follows. A second column is prepared using a different support matrix with the target material bound at the optimal density. The elution volumes, under the same elution conditions as used previously, of candidate GP(SBD)s are compared to each other and to GP(PPBD of this round). If one or more candidate GP(SBD)s has a larger elution volume than GP(PPBD of this round), then we pick the GP(SBD) having the highest elution volume and proceed to characterize the population. If none of the candidate GP(SBD)s has higher elution volume than GP(PPBD of this round), then we pool and culture, in a manner similar to the manner used previously, the GPs from the last few fractions that contained viable GPs and the GPs obtained by culturing an inoculum taken from the column matrix. We then repeat the enrichment procedure.

If all of the SBDs show binding that is superior to PPBD of this round, we pool and culture the GPs from the last fraction that contains viable GPs and from the inoculum taken from the column. This population is rechromatographed at least one pass to fractionate further the GPs based on $K_d$.

If an RNA phage were used as GP, the RNA would either be cultured with the assistance of a helper phage or be reverse transcribed and the DNA amplified. The amplified DNA could then be sequenced or subcloned into suitable plasmids.

V.P. Characterizing the Putative SBDs:

We characterize members of the population showing desired binding properties by genetic and biochemical methods. We obtain clonal isolates and test these strains by genetic and affinity methods to determine genotype and phenotype with respect to binding to target. For several genetically pure isolates that show binding, we demonstrate that the binding is caused by the artificial chimeric gene by excising the osp-sbd gene and crossing it into the parental GP. We also ligate the deleted backbone of each GP from which the osp-sbd is removed and demonstrate that each backbone alone cannot confer binding to the target on the GP. We sequence the Osp-sbd gene from several clonal isolates. Primers for sequencing are chosen from the DNA flanking the osp-ppbd gene or from parts of the osp-ppbd gene that are not variegated.

The present invention is not limited to a single method of determining protein sequences, and reference in the appended claims to determining the amino acid sequence of a domain is intended to include any practical method or combination of methods, whether direct or indirect. The preferred method, in most cases, is to determine the sequence of the DNA that encodes the protein and then to infer the amino acid sequence. In some cases, standard methods of protein-sequence determination may be needed to detect post-translational processing.

The present invention is not limited to a single method of determining the sequence of nucleotides (nts) in DNA subsequences. In the preferred embodiment, plasmids are isolated and denatured in the presence of a sequencing primer, about 20 nts long, that anneals to a region adjacent, on the 5' side, to the region of interest. This plasmid is then used as the template in the four sequencing reactions with one dideoxy substrate in each. Sequencing reactions, agarose gel electrophoresis, and polyacrylamide gel electrophoresis (PAGE) are performed by standard procedures (AUSU87).

For one or more clonal isolates, we may subclone the sbd gene fragment, without the osp fragment, into an expression vector such that each SBD can be produced as a free protein. Because numerous unique restriction sites were built into the inserted domain, it is easy to subclone the gene at any time. Each SBD protein is purified by normal means, including affinity chromatography. Physical measurements of the strength of binding are then made on each free SBD protein by one of the following methods: 1) alteration of the Stokes radius as a function of binding of the target material, measured by characteristics of elution from a molecular sizing column such as agarose, 2) retention of radiolabeled binding protein on a spun affinity column to which has been affixed the target material, or 3) retention of radiolabeled target material on a spun affinity column to which has been affixed the binding protein. The measurements of binding for each free SBD are compared to the corresponding measurements of binding for the PPBD.

In each assay, we measure the extent of binding as a function of concentration of each protein, and other relevant physical and chemical parameters such as salt concentration, temperature, pH, and prosthetic group concentrations (if any).

In addition, the SBD with highest affinity for the target from each round is compared to the best SBD of the previous round (IPBD for the first round) and to the IPBD (second and later rounds) with respect to affinity for the target material. Successive rounds of mutagenesis and selection-through-binding yield increasing affinity until desired levels are achieved.

If we find that the binding is not yet sufficient, we decide which residues to vary next. If the binding is sufficient, then we now have a expression vector bearing a gene encoding the desired novel binding protein.

V.Q. Joint selections:

One may modify the affinity separation of the method described to select a molecule that binds to material A but not to material B. One needs to prepare two selection columns, one with material A and the other with material B. The population of genetic packages is prepared in the manner described, but before applying the population to A, one passes the population over the B column so as to remove those members of the population that have high affinity for B ("reverse affinity chromatography"). In the preceding specification, the initial column supported some other molecule simply to remove GP(PBD)s that displayed PBDs having indiscriminate affinity for surfaces.

It may be necessary to amplify the population that does not bind to B before passing it over A. Amplification would most likely be needed if A and B were in some ways similar and the PPBD has been selected for having affinity for A. The optimum order of interactions might be determined empirically. For example, to obtain an SBD that binds A but not B, three columns could be connected in series: a) a column supporting some compound, neither A nor B, or only the matrix material, b) a column supporting B, and c) a column supporting A. A population of GP(vgPBD)s is applied to the series of columns and the columns are washed with the buffer of constant ionic strength that is used in the application. The columns are uncoupled, and the third column is eluted with a gradient to isolate GP(PBD)s that bind A but not B.

One can also generate molecules that bind to both A and B. In this case we can use a 3D model and mutate one face of the molecule in question to get binding to A. One can then mutate a different face to produce binding to B. When an SBD binds at least somewhat to both A and B, one can mutate the chain by Diffuse Mutagenesis to refine the binding and use a sequential joint selection for binding to both A and B.

The materials A and B could be proteins that differ at only one or a few residues. For example, A could be a natural protein for which the gene has been cloned and B could be a mutant of A that retains the overall 3D structure of A. SBDs selected to bind A but not B probably bind to A near the residues that are mutated in B. If the mutations were picked to be in the active site of A (assuming A has an active site), then an SBD that binds A but not B will bind to the active site of A and is likely to be an inhibitor of A.

To obtain a protein that will bind to both A and B, we can, alternatively, first obtain an SBD that binds A and a different SBD that binds B. We can then combine the genes encoding these domains so that a two-domain single-polypeptide protein is produced. The fusion protein will have affinity for both A and B because one of its domains binds A and the other binds B.

One can also generate binding proteins with affinity for both A and B, such that these materials will compete for the same site on the binding protein. We guarantee competition by overlapping the sites for A and B. Using the procedures of the present invention, we first create a molecule that binds to target material A. We then vary a set of residues defined as: a) those residues that were varied to obtain binding to A, plus b) those residues close in 3D space to the residues of set (a) but that are internal and so are unlikely to bind directly to either A or B. Residues in set (b) are likely to make small changes in the positioning of the residues in set (a) such that the affinities for A and B will be changed by small amounts. Members of these populations are selected for affinity to both A and B.

V.R. Selection for non-binding:

The method of the present invention can be used to select proteins that do not bind to selected targets. Consider a protein of pharmacological importance, such as streptokinase, that is antigenic to an undesirable extent. We can take the pharmacologically important protein as IPBD and antibodies against it as target. Residues on the surface of the pharmacologically important protein would be variegated and GP(PBD)s that do not bind to an antibody column would be collected and cultured. Surface residues may be identified in several ways, including: a) from a 3D structure, b) from hydrophobicity considerations, or c) chemical labeling. The 3D structure of the pharmacologically important protein remains the preferred guide to picking residues to vary, except now we pick residues that are widely spaced so that we leave as little as possible of the original surface unaltered.

Destroying binding frequently requires only that a single amino acid in the binding interface be changed. If polyclonal antibodies are used, we face the problem that all or most of the strong epitopes must be altered in a single molecule. Preferably, one would have a set of monoclonal antibodies, or a narrow range of antibody species. If we had a series of monoclonal antibody columns, we could obtain one or more mutations that abolish binding to each monoclonal antibody. We could then combine some or all of these mutations in one molecule to produce a pharmacologically important protein recognized by none of the monoclonal antibodies. Such mutants are tested to verify that the pharmacologically interesting properties have not be altered to an unacceptable degree by the mutations.

Typically, polyclonal antibodies display a range of binding constants for antigen. Even if we have only polyclonal antibodies that bind to the pharmacologically important protein, we may proceed as follows. We engineer the pharmacologically important protein to appear on the surface of a replicable GP. We introduce mutations into residues that are on the surface of the pharmacologically important protein or into residues thought to be on the surface of the pharmacologically important protein so that a population of GPs is obtained. Polyclonal antibodies are attached to a column and the population of GPs is applied to the column at low salt. The column is eluted with a salt gradient. The GPs that elute at the lowest concentration of salt are those which bear pharmacologically important proteins that have been mutated in a way that eliminates binding to the antibodies having maximum affinity for the pharmacologically important protein. The GPs eluting at the lowest salt are isolated and cultured. The isolated SBD becomes the PPBD to further rounds of variegation so that the antigenic determinants are successively eliminated.

V.S. Selection of PBDs for retention of structure:

Let us take an SBD with known affinity for a target as PPBD to a variegation of a region of the PBD that is far from the residues that were varied to create the SBD. We can use the target as an affinity molecule to select the PBDs that retain binding for the target, and that presumably retain the underlying structure of the IPBD. The variegations in this case could include insertions and deletions that are likely to disrupt the IPBD structure. We could also use the IPBD and AfM(IPBD) in the same way.

For example, if IPBD were BPTI and AfM(BPTI) were trypsin, we could introduce four or five additional residue after residue 26 and select GPs that display PBDs having specific affinity for AfM(BPTI). Residue 26 is chosen because it is in a turn and because it is about 25 A from K15, a key amino acid in binding to trypsin.

The underlying structure is most likely to be retained if insertions or deletions are made at loops or turns.

V.T. Engineering of Antagonists

It may be desirable to provide an antagonist to an enzyme or receptor. This may be achieved by making a molecule that prevents the natural substrate or agonist from reaching the active site. Molecules that bind directly to the active site may be either agonists or antagonists. Thus we adopt the following strategy. We consider enzymes and receptors together under the designation TER (Target Enzyme or Receptor).

For most TERs, there exist chemical inhibitors that block the active site. Usually, these chemicals are useful only as research tools due to highly toxicity. We make two affinity matrices: one with active TER and one with blocked TER. We make a variegated population of GP(PBD)s and select for SBPs that bind to both forms of the enzyme, thereby obtaining SDPs that do not bind to the active site. We expect that SBDs will be found that bind different places on the enzyme surface. Pairs of the sbd genes are fused with an intervening peptide segment. For example, if SBD-1 and SBD-2 are binding domains that show high affinity for the target enzyme and for which the binding is non-competitive, then the gene sbd-1::linker::sbd-2 encodes a two-domain protein that will show high affinity for the target. We make several fusions having a variety of SBDs and various linkers. Such compounds have a reasonable probability of being an antagonist to the target enzyme.

VI. EXPLOITATION OF SUCCESSFUL BINDING DOMAINS AND CORRESPONDING DNAS

VI.A. Generally

Using the method of the present invention, we can obtain a replicable genetic package that displays a novel protein domain having high affinity and specificity for a target material of interest. Such a package carries both amino-acid embodiments of the binding protein domain and a DNA embodiment of the gene encoding the novel binding domain. The presence of the DNA facilitates expression of a protein comprising the novel binding protein domain within a high-level expression system, which need not be the same system used during the developmental process.

VI.B. Production of Novel Binding Proteins

We can proceed to production of the novel binding protein in several ways, including: a) altering of the gene encoding the binding domain so that the binding domain is expressed as a soluble protein, not attached to a genetic package (either by deleting codons 5' of those encoding the binding domain or by inserting stop codons 3' of those encoding the binding domain), b) moving the DNA encoding the binding domain into a known expression system, and c) utilizing the genetic package as a purification system. (If the domain is small enough, it may be feasible to prepare it by conventional peptide synthesis methods.)

Option (c) may be illustrated as follows. Assume that a novel BPTI derivative has been obtained by selection of M13 derivatives in which a population of BPTI-derived domains are displayed as fusions to mature coat protein. Assume that a specific protease cleavage site (e.g. that of activated clotting factor X) is engineered into the amino-acid sequence between the carboxy terminus of the BPTI-derived domain and the mature coat domain. Furthermore, we alter the display system to maximize the number of fusion proteins displayed on each phage. The desired phage can be produced and purified, for example by centrifugation, so that no bacterial products remain. Treatment of the purified phage with a catalytic amount of factor X cleaves the binding domains from the phage particles. A second centrifugation step separates the cleaved protein from the phage, leaving a very pure protein preparation.

VI.C. Mini-protein Production

As previously mentioned, an advantage inhering from the use of a mini-protein as an IPBD is that it is likely that the derived SBD will also behave like a mini-protein and will be obtainable by means of chemical synthesis. (The term "chemical synthesis", as used herein, includes the use of enzymatic agents in a cell-free environment.)

It is also to be understood that mini-proteins obtained by the method of the present invention may be taken as lead compounds for a series of homologues that contain non-naturally occurring amino acids and groups other than amino acids. For example, one could synthesize a series of homologues in which each member of the series has one amino acid replaced by its D enantiomer. One could also make homologues containing constituents such as β alanine, aminobutyric acid, 3-hydroxyproline, 2-Aminoadipic acid, N-ethylasperagine, norvaline, etc.; these would be tested for binding and other properties of interest, such as stability and toxicity.

Peptides may be chemically synthesized either in solution or on supports. Various combinations of stepwise synthesis and fragment condensation may be employed.

During synthesis, the amino acid side chains are protected to prevent branching. Several different protective groups are useful for the protection of the thiol groups of cysteines:

1) 4-methoxybenzyl (MBzl; Mob)(NISH82; ZAFA88), removable with HF;

2) acetamidomethyl (Acm)(NISH82; NISH86; BECK89c), removable with iodine; mercury ions (e.g., mercuric acetate); silver nitrate; and 3) S-para-methoxybenzyl (HOUG84).

Other thiol protective groups may be found in standard reference works such as Greene, PROTECTIVE GROUPS IN ORGANIC SYNTHESIS (1981).

Once the polypeptide chain has been synthesized, disulfide bonds must be formed. Possible oxidizing agents include air (HOUG84; NISH86), ferricyanide (NISH82; HOUG84), iodine (NISH82), and performic acid (HOUG84). Temperature, pH, solvent, and chaotropic chemicals may affect the course of the oxidation. biologically active form: conotoxin G1 (13AA, 4 Cys)(NISH82); heat-stable enterotoxin ST (18AA, 6 Cys) (HOUG84); analogues of ST (BHAT86); Ω-conotoxin GVIA (27AA, 6Cys) (NISH86; RIVI87b); Ω-conotoxin MVIIA (27 AA, 6 Cys) (OLIV87b); α-conotoxin SI (13 AA, 4 Cys) (ZAFA88); μ-conotoxin IIIa (22AA, 6 Cys) (BECK89c, CRUZ89, HATA90). Sometimes, the polypeptide naturally folds so that the correct disulfide bonds are formed. Other times, it must be helped along by use of a differently removable protective group for each pair of cysteines.

VI.D. Uses of Novel Binding Proteins

The successful binding domains of the present invention may, alone or as part of a larger protein, be used for any purpose for which binding proteins are suited, including isolation or detection of target materials. In furtherance of this purpose, the novel binding proteins may be coupled directly or indirectly, covalently or noncovalently, to a label, carrier or support.

When used as a pharmaceutical, the novel binding proteins may be contained with suitable carriers or adjuvanants.

All references cited anywhere in this specification are incorporated by reference to the extent which they may be pertinent.

EXAMPLE I

Display of BPTI as a Fusion to M13 Gene VIII Protein

Example I involves display of BPTI on M13 as a fusion to the mature gene VIII coat protein. Each of the DNA constructions was confirmed by restriction digestion analysis and DNA sequencing.

1. Construction of the viii-signal-sequence::bpti::mature-viii-coat-protein Display Vector.

A. Operative cloning vectors (OCV).

The operative cloning vectors are M13 and phagemids derived from M13 or f1. The initial construction was in the f1-based phagemid pGEM-3Zf(−)$^{(TM)}$ (Promega Corp., Madison, Wis.).

A gene comprising, in order,: i) a modified lacUV5 promoter, ii) a Shine-Dalgarno sequence, iii) DNA encoding the M13 gene VIII signal sequence, iv) a sequence encoding mature BPTI, v) a sequence encoding the mature-M13-gene-VIII coat-protein, vi) multiple stop codons, and vii) a transcription terminator, was constructed. This gene is illustrated in Tables 101–105; each table shows the same DNA sequence with different features annotated. There are a number of differences between this gene and the one proposed in the hypothetical example in the generic specification of the parent application. Because the actual construction was made in pGEM-3Zf(−), the ends of the synthetic DNA were made compatible with SalI and BamHI. The lacO operator of lacUV5 was changed to the symmetrical lacO with the intention of achieving tighter repression in the absence of IPTG. Several silent codon changes were made so that the longest segment that is identical to wild-type gene VIII is minimized so that genetic recombination with the co-existing gene VIII is unlikely.

i) OCV based upon pGEM-3Zf.

pGEM-3Zf$^{(TM)}$ (Promega Corp., Madison, Wis.) is a plasmid-based vector containing the amp gene, bacterial origin of replication, bacteriophage f1 origin of replication, a lacZ operon containing a multiple cloning site sequence, and the T7 and SP6 polymerase binding sequences.

Two restriction enzyme recognition sites were introduced, by site-directed oligonucleotide mutagenesis, at the boundaries of the lacZ operon. This allowed for the removal of the lacZ operon and its replacement with the synthetic gene. A BamHI recognition site (GGATCC) was introduced at the 5' end of the lacZ operon by the mutation of bases $C_{331}$ and $T_{332}$ to G and A respectively (numbering of Promega). A SalI recognition site (GTCGAC) was introduced at the 3' end of the operon by the mutation of bases $C_{3021}$ and $T_{3023}$ to G and C respectively. A construct combining these variants of pGEM-3Zf was designated pGEM-MB3/4.

ii) OCV based upon M13mp18.

M13mp18 (YANI85) is an M13 bacteriophage-based vector (available from, inter alia, New England Biolabs, Beverly, Mass.) consisting of the whole of the phage genome into which has been inserted a lacZ operon containing a multiple cloning site sequence (MESS77). Two restriction enzyme sites were introduced into M13mp18 using standard methods. A BamHI recognition site (GGATCC) was introduced at the 5' end of the lacZ operon by the mutation of bases $C_{6003}$ and $G_{6004}$ to A and T respectively (numbering of Messing). This mutation also destroyed a unique NarI site. A SalI recognition site (GTCGAC) was introduced at the 3' end of the operon by the mutation of bases $A_{6430}$ and $C_{6432}$ to C and A respectively. A construct combining these variants of M13mp18 was designated M13-MB1/2.

B) Synthetic Gene.

A synthetic gene (VIII-signal-sequence::mature-bpti::mature-VIII-coat-protein) was constructed from 16 synthetic oligonucleotides (Table 105), custom synthesized by Genetic Designs Inc. of Houston, Tex., using methods detailed in KIMH89 and ASHM89. Table 101 shows the DNA sequence; Table 102 contains an annotated version of this sequence. Table 103 shows the overlaps of the synthetic oligonucleotides in relationship to the restriction sites and coding sequence. Table 104 shows the synthetic DNA in double-stranded form. Table 105 shows each of the 16 synthetic oligonucleotides from 5'-to-3'. The oligonucleotides were phosphorylated, with the exception of the 5' most molecules, using standard methods, annealed and ligated in stages such that a final synthetic duplex was generated. The overhanging ends of this duplex was filled in with T4 DNA polymerase and it was cloned into the HincII site of pGEM-3Zf(−); the initial construct is called pCEM-MB1 (Table 101a). Double-stranded DNA of pGEM-MB1 was cut with PstI, filled in with T4 DNA polymerase and ligated to a SalI linker (New England BioLabs) so that the synthetic gene is bounded by BamHI and SalI sites (Table 101b and Table 102b). The synthetic gene was obtained on a BamHI-SalI cassette and cloned into pGEM-MB3/4 and M13-MB1/2 utilizing the BamHI and SalI sites previously introduced, to generate the constructs designated pGEM-MB16 and M13-MB15, respectively. The full length of the synthetic insert was sequenced and found to be unambiguously correct except for: 1) a missing G in the Shine-Dalgarno sequence; and 2) a few silent errors in the third bases of some codons (shown as upper case in Table 101). Table 102 shows the Ribosome-binding site $A_{104}$GGAGG but the actual sequence is A104GAGG. Efforts to express protein from this construction, in vivo and in vitro, were unavailing.

C) Alterations to the synthetic gene.

i) Ribosome binding site (RBS).

Starting with the construct pGEM-MB16, a fragment of DNA bounded by the restriction enzyme sites SacI and NheI (containing the original RBS). was replaced with a synthetic oligonucleotide duplex (with compatible SaCI and NheI overhangs) containing the sequence for a new RBS that is very similar to the RBS of E. coli phoA and that has been shown to be functional.

Original putative RBS (5'-to-3')

```
GAGCTCagaggCTTACTATGAAGAAATCTCTGGTTCTTAAGGCTAGC
 | SacI |                                | Nhe I   |
 +------+                                +---------+
```

New RBS (5'-to-3')

```
GAGCTCTggaggaAATAAAATGAAGAAATCTCTGGTTCTTAAGGCTAGC
 | SacI |                                  | Nhe I   |
 +------+                                  +---------+
```

The putative RBSs above are lower case and the initiating methionine codon is underscored and bold. The resulting construct was designated pGEM-MB20. In vitro expression of the gene carried by pGEM-MB20 produced a novel protein species of the expected size, about 14.5 kd.

ii) tac promoter

In order to obtain higher expression levels of the fusion protein, the lacUV5 promoter was changed to a tac promoter. Starting with the construct pGEM-MB16, which contains the lacUV5 promoter, a fragment of DNA bounded by the restriction enzyme sites BamHI and HpaII was excised and replaced with a compatible synthetic oligonucleotide duplex containing the −35 sequence of the trp promoter, Cf RUSS82. This converted the lacUV5 promoter to a tac promoter in a construct designated pGEM-MB22, Table 112.

MB16

5'- GATCC t ct agagt cggc TTTACA ct t t at gct t c (cg-gct cg. . -3'
3'-       G agat ct cagccg a a a t g t  gaaat acgaag  gc(cgagc. . -5'

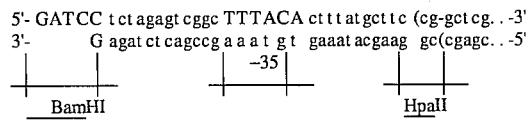

MB22 insert

5'- GATCC act ccccat cccccct g TTGACA at t aat cat   -3'
3'-       G t gaggggt agggggac AACTGT t aat t agt agc-5'

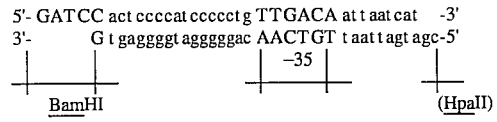

Promoter and RBS variants of the fusion protein gene were constructed by basic DNA manipulation techniques to generate the following:

| | Promoter | RBS | Encoded Protein. |
|---|---|---|---|
| pGEM-MB16 | lac | old | VIII s.p.-BPTI-mature VIII |
| pGEM-MB20 | lac | new | " |
| PGIM-MB22 | tac | old | " |
| pGEM-MB26 | tac | new | " |

The synthetic gene from variants pGEM-MB20 and pGEM-MB26 were recloned into the altered phage vector M13-MB1/2 to generate the phage constructs designated M13-MB27 and M13-MB28 respectively.

iii. Signal Peptide Sequence.

In vitro expression of the synthetic gene regulated by tac and the "new" RBS produced a novel protein of the expected size for the unprocessed protein (about 16 kd). In vivo expression also produced novel protein of full size; no processed protein could be seen on phage or in cell extracts by silver staining or by Western analysis with anti-BPTI antibody.

Thus we analyzed the signal sequence of the fusion. Table 106 shows a number of typical signal sequences. Charged residues are generally thought to be of great importance and are shown bold and underscored. Each signal sequence contains a long stretch of uncharged residues that are mostly hydrophobic; these are shown in lower case. At the right, in parentheses, is the length of the stretch of uncharged residues. We note that the fusions of gene VIII signal to BPTI and gene III signal to BPTI have rather short uncharged segments. These short uncharged segments may reduce or prevent processing of the fusion peptides. We know that the gene III signal sequence is capable of directing: a) insertion of the peptide comprising (mature-BPTI)::(mature-gene-III-protein) into the lipid bilayer, and b) translocation of BPTI and most of the mature gene III protein across the lipid bilayer (vide infra). That the gene III remains anchored in the lipid bilayer until the phage is assembled is directed by the uncharged anchor region near the carboxy terminus of the mature gene III protein (see Table 116) add not by the secretion signal sequence. The phoA signal sequence can direct secretion of mature BPTI into the periplasm of E. coli (MARK86). Furthermore, there is controversy over the mechanism by which mature authentic gene VIII protein comes to be in the lipid bilayer prior to phage assembly.

Thus we decided to replace the DNA coding on expression for the gene-VIII-putative-signal-sequence by each of:
1) DNA coding on expression for the phoA signal sequence,
2) DNA coding on expression for the bla signal sequence, or
3) DNA coding on expression for the M13 gene III signal.
Each of these replacements produces a tripartite gene encoding a fusion protein that comprises, in order: (a) a signal peptide that directs secretion into the periplasm of parts (b) and (c), derived from a first gene; (b) an initial potential binding domain (BPTI in this case), derived from a second gene (in this case, the second gene is an animal gene); and (c) a structural packaging signal (the mature gene VIII coat protein), derived from a third gene.

The process by which the IPBD::packaging-signal fusion arrives on the phage surface is illustrated in FIG. 1. In FIG. 1a, we see that authentic gene VIII protein appears (by whatever process) in the lipid bilayer so that both the amino and carboxy termini are in the cytoplasm. Signal peptidase-I cleaves the gene VIII protein liberating the signal peptide (that is absorbed by the cell) and mature gene VIII coat protein that spans the lipid bilayer. Many copies of mature gene VIII coat protein accumulate in the lipid bilayer awaiting phage assembly (FIG. 1c). Some signal sequences are able to direct the translocation of quite large proteins across the lipid bilayer. If additional codons are inserted after the codons that encode the cleavage site of the signal peptidase-I of such a potent signal sequence, the encoded amino acids will be translocated across the lipid bilayer as shown in FIG. 1b. After cleavage by signal peptidase-I, the amino acids encoded by the added codons will be in the periplasm but anchored to the lipid bilayer by the mature gene VIII coat protein, FIG. 1d. The circular single-stranded phage DNA is extruded through a part of the lipid bilayer containing a high concentration of mature gene VIII coat protein; the carboxy terminus of each coat protein molecule packs near the DNA while the amino terminus packs on the outside. Because the fusion protein is identical to mature gene VIII coat protein within the trans-bilayer domain, the fusion protein will co-assemble with authentic mature gene VIII coat protein as shown in FIG. 1e.

In each case, the mature VIII coat protein moiety is intended to co-assemble with authentic mature VIII coat protein to produce phage particle having BPTI domains displayed on the surface. The source and character of the secretion signal sequence is not important because the signal sequence is cut away and degraded. The structural packaging signal, however, is quite important because it must co-assemble with the authentic coat protein to make a working virus sheath.

a) Bacterial Alkaline Phosphatase (phoA) Signal Peptide.

Construct pGEM-MB26 contains a fragment of DNA bounded by restriction enzyme sites SacI and AccIII which contains the new RBS and sequences encoding the initiating methionine and the signal peptide of M13 gene VIII protein. This fragment was replaced with a synthetic duplex (constructed from four annealed oligonucleotides) containing the RBS and DNA coding for the initiating methionine and signal peptide of PhoA (INOU82). The resulting construct was designated pGEM-MB42; the sequence of the fusion gene is shown in Table 113. M13MB48 is a derivative of GemMB42. A BamHI-SalI DNA fragment from GenMB42, containing the gene construct, was ligated into a similarly cleaved vector M13MB1/2 giving rise to M13MB48.

M13-MB51. Because M13-MB51 contains no gene III, the phage can not form plaques. M13-MB51 can, however, render cells $Km^R$. Infectious phage particles can be obtained by use of helper phage. As explained below, the gene III signal sequence is capable of directing (BPTI)::(mature-gene-III-protein) to the surface of phage. In M13-MB51, we have inserted DNA encoding gene VIII coat protein (50 amino acids) and three stop codons 5' to the DNA encoding the mature gene III protein.

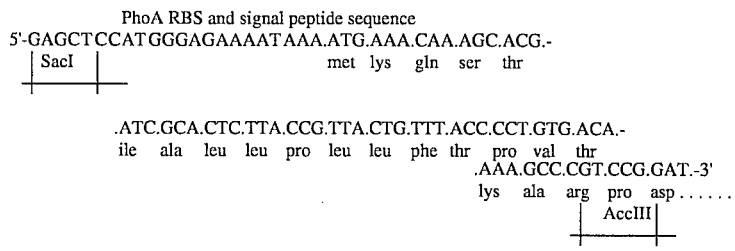

PhoA RBS and signal peptide sequence
5'-GAGCT CCAT GGG AGA AAA T AAA.ATG.AAA.CAA.AGC.ACG.-
    SacI                         met lys gln ser thr .ATC.GCA.CTC.TTA.CCG.TTA.CTG.TTT.ACC.CCT.GTG.ACA.-
ile  ala  leu  leu  pro  leu  leu  phe  thr  pro  val  thr
                                  .AAA.GCC.CGT.CCG.GAT.-3'
                                   lys  ala  arg  pro  asp ......
                                                    AccIII b) Beta-lactamase signal peptide.

To enable the introduction of the beta-lactamase (amp) promoter and DNA coding for the signal peptide into the gene encoding (mature-BPTI)::(mature-VIII-coat-protein) an initial manipulation of the amp gene (encoding beta-lactamase) was required. Starting with pGEM-3Zf an AccIII recognition site (TCCGGA) was introduced into the amp gene adjacent to the DNA sequence encoding the amino acids at the beta-lactamase signal peptide cleavage site. Using standard methods of in vitro site-directed oligonucleotide mutagenesis bases $C_{2504}$ and $A_{2501}$ were converted to T and G respectively to generate the construct designated pGEM-MB40. Further manipulation of pGEM-MB40 entailed the insertion of a synthetic oligonucleotide linker (CGGATCCG) containing the BamHI recognition sequence (GGATCC) into the AatII site (GACGTC starting at nucleotide number 2260) to generate the construct designated pGEM-MB45. The DNA bounded by the restriction enzyme sites of BamHI and AccIII contains the amp promoter, amp RBS, initiating methionine and beta-lactamase signal peptide. This fragment was used to replace the corresponding fragment from pGEM-MB26 to generate construct pGEM-MB46.

Summary of signal peptide fusion protein variants.

| | Promoter | RBS | Signal sequence | Fusion protein |
|---|---|---|---|---|
| pGEM-MB26 | tac | new | VIII | BPTI/VIII-coat |
| pGEM-MB42 | tac | new | phoA | BPTI/VIII-coat |
| pGEM-MB46 | amp | amp | amp | BPTI/VIII-coat |
| pGEM-MB51 | III | III | III | BPTI/VIII-coat |
| M13 MB48 | tac | new | phoA | BPTI/VIII-coat |

2. Analysis of the Protein Products Encoded by the Synthetic (signal-peptide::mature-bpti::viii-coat-protein) Genes i) In vitro analysis amp gene promoter and signal peptide sequences

5'-GGAT CCGGT GGCACT TTT CGGGGAAAT GT GCGCGGAACCCCT ATTT GTT —

T AT T T TT CT AAAT ACAT T CAAAT AT GT AT CCGCT CAT GAGACA AT AACC —

CT GAT AAAT GCT T CAAT AAT ATT GAAAAAGGAAGAGT —

ATG.AGT.ATT.CAA.CAT.TTC.CGT.GTC.GCC.CTT.ATT.—
met  ser  ile  gln  his  phe  arg  val  ala  leu  ile CCC.TTT.TTT.GCG.GCA.TTT.TGC.CTT.CCT.GTT.TTT.—
pro  phe  phe  ala  ala  phe  cys  leu  pro  val  phe GCT.CAT.CCG.-3'
ala  his  pro ...

c) M13-gene-III-signal::bpti::mature-VIII-coat-protein

Figure 5:
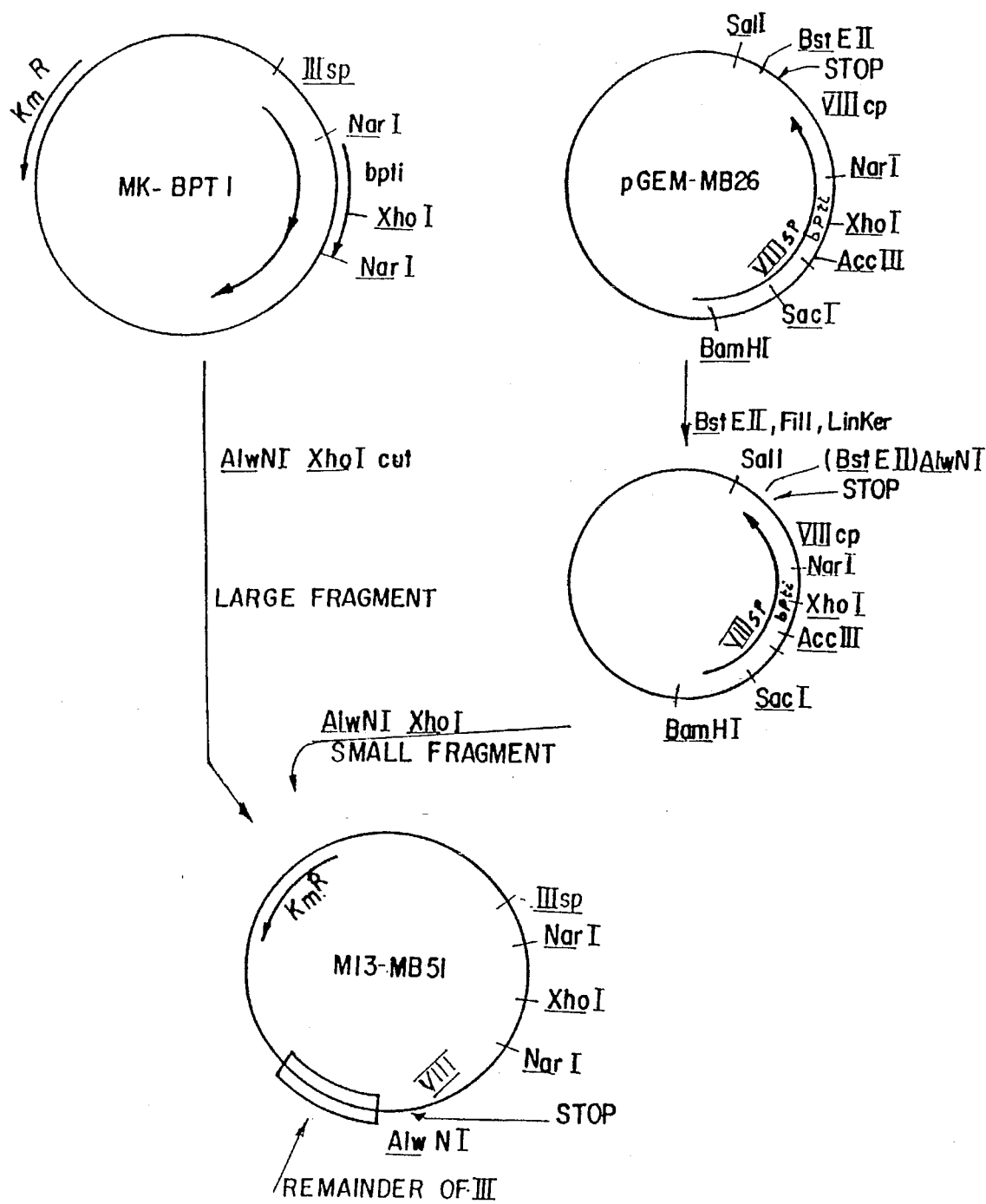
FIG. 5 shows the construction of M13-MB51.

We may also construct, as depicted in FIG. 5, M13-MB51 which would carry a gene encoding a fusion of M13-gene-III-signal-peptide to the previously described BPTI::mature VIII coat protein. First the BstEII site that follows the stop codons of the synthetic gene VIII is changed to an AlwNI site as follows. DNA of pGEM-MB26 is cut with BstEII and the ends filled in by use of Klenow enzyme; a blunt AlWNI linker is ligated to this DNA. This construction is called pGEM-MB26Alw. The XhoI to AlwNI fragment (approximately 300 bp) of pGEM-MB26Alw is purified. RF DNA from phage MK-BPTI (vide infra) is cut with AlwNI and XhOI and the large fragment purified. These two fragments are ligated together; the resulting construction is named A coupled transcription/translation prokaryotic system (Amersham Corp., Arlington Heights, Ill.) was utilized for the in vitro analysis of the protein products encoded by the BPTI/VIII synthetic gene and the variants derived from this.

Table 107 lists the protein products encoded by the listed vectors which are visualized by the standard method of fluorography following in vitro synthesis in the presence of $^{35}$S-methionine and separation of the products using SDS polyacrylamide gel electrophoresis. In each sample a pre-beta-lactamase product (approximately 31 kd) can be seen. This is derived from the amp gene which is the common selection gene for each of the vectors. In addition, a (pre-BPTI/VIII) product encoded by the synthetic gene and variants can be seen as indicated. The migration of these species (approximately 14.5 kd) is consistent with the expected size of the encoded proteins.

ii) In vivo analysis.

The vectors detailed in sections (B) and (C) were freshly transfected into the E. coli strain XL1-blue$^{(TM)}$ (Stratagene, La Jolla, Calif.) and in strain SEF'. E. coli strain SE6004 (LISS85) carries the prlA4 mutation and is more permissive in secretion than strains that carry the wild-type prlA allele. SE6004 is F$^-$ and is deleted for lacI; thus the cells can not be infected by M13 and lacUV5 and tac promoters can not be regulated with IPTG. Strain SEF' is derived from strain SE6004 (LISS85) by crossing with XL1-Blue$^{(TM)}$; the F' in XL1-Blue$^{(TM)}$ carries Tc$^R$ and lacI$^q$. SE6004 is streptomycin$^R$, Tc$^S$ while XL1-Blue$^{(TM)}$ is streptomycin$^S$, Tc$^R$ so that both parental strains can be killed with the combination of Tc and streptomycin. SEF' retains the secretion-permissive phenotype of the parental strain, SE6004(prlA4).

The fresh transfectants were grown in NZYCM medium (SAMB89) for 1 hour after which IPTG was added over the range of concentrations 1.0 μM to 0.5 μM (to derepress the lacUV5 and tac promoters) and grown for an additional 1.5 hours.

Aliquots of the bacterial cells expressing the synthetic insert encoded proteins together with the appropriate controls (no vector, vector with no insert and zero IPTG) were lysed in SDS gel loading buffer and electrophoresed in 20% polyacrylamide gels containing SDS and urea. Duplicate gels were either silver stained (Daiichi, Tokyo, Japan) or electrotransferred to a nylon matrix (Immobilon from Millipore, Bedford, Mass.) for western analysis by standard means using rabbit anti-BPTI polyclonal antibodies.

Table 108 lists the interesting proteins visualized on a silver stained gel and by western analysis of an identical gel. We can see clearly in the western analysis that protein species containing BPTI epitopes are present in the test strains which are absent from the control strains and which are also IPTG inducible. In XL1-Blue$^{(TM)}$, the migration of this species is predominantly that of the unprocessed form of the pro-protein although a small proportion of the encoded proteins appear to migrate at a size consistent with that of a fully processed form. In SEF', the processed form predominates, there being only a faint band corresponding to the unprocessed species.

Thus in strain SEF', we have produced a tripartite fusion protein that is specifically cleaved after the secretion signal sequence. We believe that the mature protein comprises BPTI followed by the gene VIII coat protein and that the coat protein moiety spans the membrane. We believe that it is highly likely that one or more copies, perhaps hundreds of copies, of this protein will co-assemble into M13 derived phage or M13-like phagemids. This construction will allow us to a) mutagenize the BPTI domain, b) display each of the variants on the coat of one or more phage (one type per phage), and c) recover those phage that display variants having novel binding properties with respect to target materials of our choice.

Rasched and Oberer (RASC86) report that phage produced in cells that express two alleles of gene VIII, that have differences within the first 11 residues of the mature coat protein, contain some of each protein. Thus, because we have achieved in vivo processing of the phoA(signal)::bpti::matureVIII fusion gene, it is highly likely that co-expression of this gene with wild-type VIII will lead to production of phage bearing BPTI domains on their surface. Mutagenesis of the bpti domain of these genes will provide a population of phage, each phage carrying a gene that codes for the variant of BPTI displayed on the phage surface.

VIII Display Phage: Production, Preparation and Analysis.

i. Phage Production

The OCV can be grown in XL1-Blue$^{(TM)}$ in the absence of the inducing agent, IPTG. Typically, a plaque plug is taken from a plate and grown in 2 ml of medium, containing freshly diluted bacterial cells, for 6 to 8 hours. Following centrifugation of this culture the supernatant is taken and the phage titer determined. This is kept as a phage stock for further infection, phage production and display of the gene product of interest.

A 100 fold dilution of a fresh overnight culture of SEF' bacterial cells in 500 ml of NZCYM medium is allowed to grow to a cell density of 0.4 (Ab 600 nm) in a shaker incubator at 37° C. To this culture is added a sufficient amount of the phage stock to give a MOI of 10 together with IPTG to give a final concentration of 0.5 mM. The culture is allowed to grow for a further 2 hrs.

ii. Phage Preparation and Purification.

The phage producing bacterial culture is centrifuged to separate the phage in the supernatant from the bacterial pellet. To the supernatant is added one quarter by volume of phage precipitation solution (20% PEG, 3.75M ammonium acetate) and PMSF to a final concentration of 1 mM. It is left on ice for 2 hours after which the precipitated phage is retrieved by centrifugation. The phage pellet is redissolved in TrisEDTA containing 0.1% Sarkosyl and left at 4° C. for 1 hour after which any bacteria and bacterial debris is removed by centrifugation. The phage in the supernatant is reprecipitated with PEG overnight at 4° C. The phage pellet is resuspended in LB medium and reprecipitated another two times to remove the detergent. The phage is stored in LB medium at 4° C., titered and used for analysis and binding studies.

A more stringent phage purification scheme involves centrifugation in a CsCl gradient 3.86 g of CsCl is dissolved in NET buffer (0.1M NaCl, 1 mM EDTA, 0.1M Tris pH 7.7) upto a volume of 10 ml. $10^{12}$ to $10^{13}$ phage in TE Sarkosyl buffer are mixed with 5 ml of CsCl NET buffer and transferred to a sealable ultracentrifuge tube. Centrifugation is performed overnight at 34K rpm in a Sorvall OTD-65B Ultracentrifuge. The tubes are opened and 400 μl aliqouts are carefully removed. 5 μl aliqouts are removed from the fractions and analysed by agarose gel electrophoresis after heating at 65° C. for 15 minutes together with the gel loading buffer containing 0.1% SDS. Fractions containing phage are pooled, the phage reprecipitated and finally redissolved in LB medium to a concentration of $10^{12}$ to $10^{13}$ phage per ml.

iii. Phage Analysis

The display phage, together with appropriate controls are analyzed using standard methods of polyacrylamide gel electrophoresis and either silver staining of the gel or electrotransfer to a nylon matrix followed by analysis with anti-BPTI antiserum (Western analysis). Quantitation of the display of heterologous proteins is achieved by running a serial dilution of the starting protein, for example BPTI, together with the display phage samples in the electrophoresis and Western analyses described above. An alternative method involves running a 2 fold serial dilution of a phage in which both the major coat protein and the fusion protein are visualized by silver staining. A comparison of the relative ratios of the two protein species allows one to estimate the number of fusion proteins per phage since the number of VIII gene encoded proteins per phage (approximately 3000) is known.

Incorporation of fusion protein into bacteriophage.

In vivo expression of the processed BPTI:VIII fusion protein, encoded by vectors GemMB42 (above and Table 113) and M13MB48 (above), impliea that the processed fusion product was likely to be correctly located within the bacterial cell membrane. This localization made it possible that it could be incorporated into the phage and that the BPTI moiety would be displayed at the bacteriophage surface.

SEF' cells were infected with either M13MB48 (consisting of the starting phage vector M13mp18, altered as described above, containing the synthetic gene consisting of a tac promoter, functional ribosome binding site, phoA signal peptide, mature BPTI and mature major coat protein) or M13mp18, as a control. Phage infections, preparation and purification was performed as described in Example VIII.

The resulting phage were electrophoresed (approximately $10^{11}$ phage per lane) in a 20% polyacrylamide gel containing urea followed by electrotransfer to a nylon matrix and western analysis using anti-BPTI rabbit serum. A single species of protein was observed in phage derived from infection with the M13MB48 stock phage which was not observed in the control infection. This protein had a migration of about 12 kd, consistent with that of the fully processed fusion protein.

Western analysis of SEF' bacterial lysate with or without phage infection demonstrated another species of protein of about 20 kd. This species was also present, to a lesser degree, in phage preparations which were simply PEG precipitated without further purification (for example, using nonionic detergent or by CsCl gradient centrifugation). A comparison of M13MB48 phage progoff eparations made in the presence or absence of detergent aldemonstrated that sarkosyl treatment and CsCl gradient purification did remove the bacterial contaminant while having no effect on the presence of the BPTI:VIII fusion protein. This indicates that the fusion protein has been incorporated and is a constituent of the phage body.

The time course of phage production and BPTI:VIII incorporation was followed post-infection and after IPTG induction. Phage production and fusion protein incorporation appeared to be maximal after two hours. This time course was utilized in further phage productions and analyses.

Polyacrylamide electrophoresis of the phage preparations, followed by silver staining, demonstrated that the preparations were essentially free of contaminating protein species and that an extra protein band was present in M13MB48 derived phage which was not present in the control phage. The size of the new protein was consistent with that seen by western analysis. A similar analysis of a serially diluted BPTI:VIII incorporated phage demonstrated that the ratio of fusion protein to major coat protein was typically in the range of 1:150. Since the phage is known to contain in the order of 3000 copies of the gene VIII product, this means that the phage population contains, on average, 10's of copies of the fusion protein per phage.

Altering the Initiating Methionine of the Natural Gene VIII.

The OCV M13MB48 contains the synthetic gene encoding the BPTI:VIII fusion protein in the intergenic region of the modified M13mp18 phage vector. The remainder of the vector consists of the M13 genome which contains the genes necessary for various bacteriophage functions, such as DNA replication and phage formation etc. In an attempt to increase the phage incorporation of the fusion protein, we decided to try to diminish the production of the natural gene VIII product, the major coat protein, by altering the codon for the initiating methionine of this gene to one encoding leucine. In such cases, methionine is actually incorporated, but the rate of initiation is reduced. The change was achieved by standard methods of site-specific oligonucleotide mutagenesis as follows.

```
                    M   K   K   S   -rest of VIII
            ACT.TCC.TC.ATG.AAA.AAG.TCT.
rest of XI -  T    S    S   stop
```

Site-specific mutagenesis.

```
                   (L)  K   K   S   -rest of VIII
            ACT.TCC.AG.CTG.AAA.AAG.TCT.
rest of XI - T    S    S   stop
```

Note that the 3' end of the XI gene overlaps with the 5' end of the VIII gene. Changes in DNA sequence were designed such that the desired change in the VIII gene product could be achieved without alterations to the predicted amino acid sequence of the gene XI product. A diagnostic PvuII recognition site was introduced at this site.

It was anticipated that initiation of the natural gene VIII product would be hindered, enabling a higher proportion of the fusion protein to be incorporated into the resulting phage.

Analyses of the phage derived from this modified vector indicated that there was a significant increase in the ratio of fusion protein to major coat protein. Quantitative estimates indicated that within a phage population as much as 100 copies of the BPTI:VIII fusion were incorporated per phage. Incorporation of interdomain extension fusion proteins into phage.

A phage pool containing a variegated pentapeptide extension at the BPTI:coat protein interface (see Example VII) was used to infect SEF' cells. IPTG induction, phage production and preparation were as described in Example VIII. Using the criteria detailed in the previous section, it was determined that extended fusion proteins were incorporated into phage. Gel electrophoresis of the generated phage, followed by either silver staining or western analysis with anti-BPTI rabbit serum, demonstrated fusion proteins that migrated similarly to but discernably slower that of the starting fusion protein.

With regard to the 'EGGGS linker' extensions of the domain interface, individual phage stocks predicted to contain one or more 5-amino-acid unit extensions were analyzed in a similar fashion. The migration of the extended fusion proteins were readily distinguishable from the parent fusion protein when viewed by western analysis or silver staining. Those clones analyzed in more detail included M13.3X4 (which contains a single inverted EGGGS linker with a predicted amino acid sequence of GGGSL), M13.3X7 (which contains a correctly orientated linker with a predicted amino acid sequence of EGGGS), M13.3X11 (which contains 3 linkers with an inversion and a predicted amino acid sequence for the extension of EGGGSGSSSLGSSSL) and M13.3Xd which contains an extension consisting of at least 5 linkers or 25 amino acids.

The extended fusion proteins were all incorporated into phage at high levels (on average 10's of copies per phage were present and when analyzed by gel electrophoresis migrated rates consistent with the predicted size of the extension. Clones M13.3X4 and M13.3X7 migrated at a position very similar to but discernably different from the parent fusion protein, while M13.3X11 and M13.3Xd were markedly larger.

Display of BPTI:VIII fusion protein by bacteriophage.

The BPTI:VIII fusion protein had been shown to be incorporated into the body of the phage. This phage was analyzed further to demonstrate that the BPTI moiety was accessible to specific antibodies and hence displayed at the phage surface.

The assay is detailed in section EE, but principally involves the addition of purified anti-BPTI IgG (from the serum of BPTI injected rabbits) to a known titer of phage. Following incubation, protein A-agarose beads are added to bind the IgG and left to incubate overnight. The IgG-protein A beads and any bound phage are removed by centrifugation followed by a retitering of the supernatant to determine any loss of phage. The phage bound to the beads can be acid eluted and titered also. Appropriate controls are included in the assay, such as a wild type phage stock (M13mp18) and IgG purified from normal rabbit pre-immune serum.

Table 140 shows that while the titer of the wild type phage is unaltered by the presence of anti-BPTI IgG, BPT-IIIMK (the positive control for the assay), demonstrated a significant drop in titer with or without the extra addition of protein A beads. (Note that since the BPTI moiety is part of the III gene product which is involved in the binding of phage to bacterial pili, such a phenomenon is entirely expected.) Two batches of M13MB48 phage (containing the BPTI:VIII fusion protein) demonstrated a significant reduction in titer, as judged by plaque forming units, when anti-BPTI antibodies and protein A beads were added to the phage. The initial drop in titer with the antibody alone, differs somewhat between the two batches of phage. This may be a result of experimental or batch variation. Retrieval of the immunoprecipitated phage, while not quantitative, was significant when compared to the wild type phage control.

Further control experiments relating to this section are shown in Table 141 and Table 142. The data demonstrated that the loss in titer observed for the BPTI:VIII containing phage is a result of the display of BPTI epitopes by these phage and the specific interaction with anti-BPTI antibodies. No significant interaction with either protein A agarose beads or IgG purified from normal rabbit serum could be demonstrated. The larger drop in titer for M13MB48 batch five reflects the higher level incorporation of the fusion protein in this preparation. Functionality of the BPTI moiety in the BPTI-VIII display phage.

The previous two sections demonstrated that the BPTI:VIII fusion protein has been incorporated into the phage body and that the BPTI moiety is displayed at the phage surface. To demonstrate that the displayed molecule is functional, binding experiments were performed in a manner almost identical to that described in the previous section except that proteases were used in place of antibodies. The display phage, together with appropriate controls, are allowed to interact with immobilized proteases or immobilized inactivated proteases. Binding can be assessed by monitoring the loss in titer of the display phage or by determining the number of phage bound to the respective beads.

Table 143 shows the results of an experiment in which BPTI.VIII display phage, M13MB48, were allowed to bind to anhydrotrypsin-agarose beads. There was a significant drop in titer when compared to wild type phage, which do not display BPTI. A pool of phage (5AA Pool), each contain a variegated 5 amino acid extension at the BPTI:major coat protein interface, demonstrated a similar decline in titer. In a control experiment (table 143) very little non-specific binding of the above display phage was observed with agarose beads to which an unrelated protein (streptavidin) is attached.

Actual binding of the display phage is demonstrated by the data shown for two experiments in Table 144. The negative control is wild type M13mp18 and the positive control is BPTI-IIIMK, a phage in which the BPTI moiety, attached to the gene III protein, has been shown to be displayed and functional. M13MB48 and M13MB56 both bind to anhydrotrypsin beads in a manner comparable to that of the positive control, being 40 to 60 times better than the negative control (non-display phage). Hence functionality of the BPTI moiety, in the major coat fusion protein, was established.

To take this analysis one step further, a comparison of phage binding to active and inactivated trypsin is shown in Table 145. The control phage, M13mp18 and BPTI-III MK, demonstrated binding similar to that detailed in Example III. Note that the relative binding is enhanced with trypsin due to the apparent marked reduction in the non-specific binding of the wild type phage to the active protease. M13.3X7 and M13.3X11, which both contain 'EGGGS' linker extensions at the domain interface, bound to anhydrotrypsin and trypsin in a manner similar to BPTI-IIIMK phage. The binding, relative to non-display phage, was approximately 100 fold higher in the anhydrotrypsin binding assay and at least 1000 fold higher in the trypsin binding assay. The binding of another 'EGGGS' linker variant (M13.3Xd) was similar to that of M13.3X7.

To demonstrate the specificity of binding the assays were repeated with human neutrophil elastase (HNE) beads and compared to that seen with trypsin beads Table 146. BPTI has a very high affinity for trypsin and a low affinity for HNE, hence the BPTI display phage should reflect these affinities when used in binding assays with these beads. The negative and positive controls for trypsin binding were as already described above while an additional positive control for the HNE beads, BPTI(K15L,MGNG)-III MA (see Example III) was included. The results, shown in Table 146, confirmed this prediction. M13MB48, M13.3X7 and M13.3X11 phage demonstrated good binding to trypsin, relative to wild type phage and the HNE control (BPTI(K15L,MGNG)-III MA), being comparable to BPTI-IIIMK phage. Conversely poor binding occurred when HNE beads were used, with the exception of the HNE positive control phage.

Taken together the accumulated data demonstrated that when BPTI is part of a fusion protein with the major coat protein of M13 phage, the molecule is both displayed at the surface of the phage and a significant proportion of it is functional in a specific protease binding manner.

EXAMPLE II

Construction of BPTI/GENE-III Display Vector

DNA manipulations were conducted according to standard procedures as described in Maniatis et al. (MANI82). First the unwanted lacZ gene of M13-MB1/2 was removed. M13-MB1/2 RF was cut with BamHI and SalI and the large fragment was isolated by agarose gel electrophoresis. The recovered 6819 bp fragment was filled in with Klenow fragment of *E. coli* DNA polymerase and ligated to a synthetic HindIII 8mer linker (CAAGCTTG). The ligation sample was used to transfect competent XL1-Blue$^{(TM)}$ (Stratagene, La Jolla, Calif.) cells which were subsequently plated for plaque formation. RF DNA was prepared from chosen plaques and a clone, M13-MB1/2-delta, containing regenerated BamHI and SalI sites as well as a new HindIII site, all 500 bp upstream of the BglII site (6935) was picked.

A unique NarI site was introduced into codons 17 and 18 of gene III (changing the amino acids from H-S to G-A, Cf. Table 110). $10^6$ phage produced from bacterial cells harboring the M13-MB1/2-delta RF DNA were used to infect a culture of CJ236 cells (relevant genotype: F', dut1, ung1, Cm$^R$) (OD595=0.35). Following overnight incubation at 37° C., phage were recovered and uracil-containing ss DNA was extracted from phage in accord with the instructions for the MUTA-GENE(R) M13 in vitro Mutagenesis Kit (Catalogue Number 170-3571, Bio-Rad, Richmond, Calif.). Two hundred nanograms of the purified single stranded DNA was annealed to 3 picomoles of a phosphorylated 25mer mutagenic oligonucleotide, 5'-gtttcagcggCgCCagaatagaaag-3', where upper case indicates the changes). Following filling in with T4 DNA polymerase and ligation with T4 DNA ligase, the reaction sample was used to transfect competent XL1-Blue(TM) cells which were subsequently plated to permit the formation of plaques.

RF DNA, isolated from phage-infected cells which had been allowed to propagate in liquid culture for 8 hours, was denatured, spotted on a Nytran membrane, baked and hybridized to the 25mer mutagenic oligonucleotide which had previously been phosphorylated with $^{32}$P-ATP. Clones exhibiting strong hybridization signals at 70° C. (6° C. less than the theoretical Tm of the mutagenic oligonucleotide) were chosen for large scale RF preparation. The presence of a unique NarI site at nucleotide 1630 was confirmed by restriction enzyme analysis. The resultant RF DNA, M13-MB1/2-delta-NarI was cut with BamHI, dephosphorylated with calf intestinal phosphatase, and ligated to a 1.3 Kb BamHI fragment, encoding the kanamycin-resistance gene (kan), derived from plasmid pUC4K (Pharmacia, Piscataway, N.J.). The ligation sample was used to transfect competent XL1-Blue(TM) cells which were subsequently plated onto LB plates containing kanamycin (Km). RF DNA prepared from Km$^R$ colonies was prepared and subjected to restriction enzyme analysis to confirm the insertion of kan into M13-MB1/2-delta-NarI DNA thereby creating the phage MK. Phage MK grows as well as wild-type M13, indicating that the changes at the cleavage site of gene III protein are not detectably deleterious to the phage.

Insertion of Synthetic BPTI Gene

Figure 6:
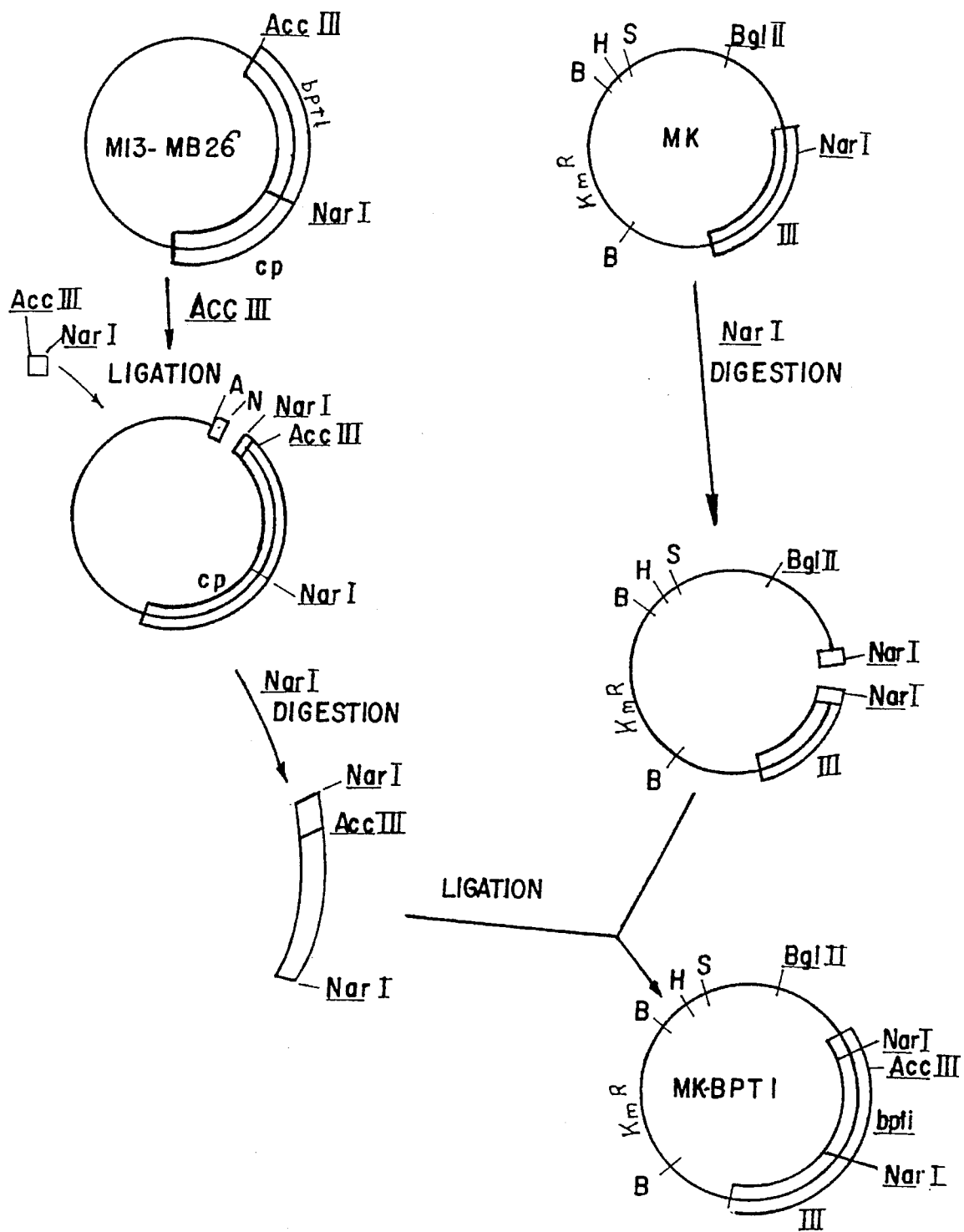
FIG. 6 shows construction of MK-BPTI, also known as BPTI-III MK.

The construction of the BPTI-III expression vector is shown in FIG. 6. The synthetic bpti-VIII fusion contains a NarI site that comprises the last two codons of the BPTI-encoding region. A second NarI site was introduced upstream of the BPTI-encoding region as follows. RF DNA of phage M13-MB26 was cut with AccIII and ligated to the dsDNA adaptor:

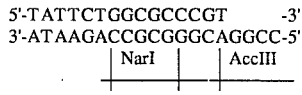

The ligation sample was subsequently restricted with NarI and a 180 bp DNA fragment encoding BPTI was isolated by agarose gel electrophoresis. RF DNA of phage MK was digested with NarI, dephosphorylated with calf intestinal phosphatase and ligated to the 180 bp fragment. Ligation samples were used to transfect competent XL1-Blue(TM) cells which were plated to enable the formation of plaques. DNA, isolated from phage derived from plaques, was denatured, applied to a Nytran membrane, baked and hybridized to a $^{32}$P-phosphorylated double stranded DNA probe corresponding to the BPTI gene. Large scale RF preparations were made for clones exhibiting a strong hybridization signal. Restriction enzyme digestion analysis confirmed the insertion of a single copy of the synthetic BPTI gene into gene III of MK to generate phage MK-BPTI. Subsequent DNA sequencing confirmed that the sequence of the bpti-III fusion gene is correct and that the correct reading frame is maintained (Table 111). Table 116 shows the entire coding region, the translation into protein sequence, and the functional parts of the polypeptide chain.

Expression of the BPTI-III Fuson Gene in vitro

MK-BPTI RF DNA was added to a coupled prokaryotic transcription-translation extract (Amersham). Newly synthesized radiolabelled proteins were produced and subsequently separated by electrophoresis on a 15% SDS-polyacrylamide gel subjected to fluorography. The MK-BPTI DNA directs the synthesis of an unprocessed gene III fusion protein which is 7 Kd larger than the gene III product encoded by MK. This is consistent with the insertion of 58 amino acids of BPTI into the gene III protein. Immunoprecipitation of radiolabelled proteins generated by the cell-free prokaryotic extract was conducted. Neither rabbit anti(M13-gene-VIII-protein) IgG nor normal rabbit IgG were able to immunoprecipitate the gene III protein encoded by either MK or MK-BPTI. However, rabbit anti-BPTI IgG is able to immunoprecipitate the gene III protein encoded by MK-BPTI but not by MK. This confirms that the increase in size of the III protein encoded by MK-BPTI is attributable to the insertion of the BPTI protein.

Western Analysis

Phage were recovered from bacterial cultures by PEG precipitation. To remove residual bacterial cells, recovered phage were resuspended in a high salt buffer and subjected to centrifugation, in accord with the instructions for the MUTA-GENE(R) M13 in vitro Mutagenesis Kit (Catalogue Number 170-3571, Bio-Rad, Richmond, Calif.). Aliquots of phage (containing up to 40 µg of protein) were subjected to electrophoresis on a 12.5% SDS-urea-polyacrylamide gel and proteins were transferred to a sheet of Immobilon by electro-transfer. Western blots were developed using rabbit anti-BPTI serum, which had previously been incubated with an E. coli extract, followed by goat ant-rabbit antibody conjugated to alkaline phosphatase. An immunoreactive protein of 67 Kd is detected in preparations of the MK-BPTI but not the MK phage. The size of the immunoreactive protein is consistent with the predicted size of a processed BPTI-III fusion protein (6.4 Kd plus 60 Kd). These data indicate that BPTI-specific epitopes are presented on the surface of the MK-BPTI phage but not the MK phage.

Neutralization of Phage Titer with Agarose-Immobilized Anhydro-Trypsin

Anhydro-trypsin is a derivative of trypsin in which the active site serine has been converted to dehydroalanine. Anhydro-trypsin retains the specific binding of trypsin but not the protease activity. Unlike polyclonal-antibodies, anhydro-trypsin is not expected to bind unfolded BPTI or incomplete fragments.

Phage MK-BPTI and MK were diluted to a concentration 1.4·10$^{12}$ particles per ml. in TBS buffer (PARM88) containing 1.0 mg/ml BSA. Thirty microliters of diluted phage were added to 2, 5, or 10 microliters of a 50% slurry of agarose-immobilized anhydro-trypsin (Pierce Chemical Co., Rockford, Ill.) in TBS/BSA buffer. Following incubation at 25° C., aliquots were removed, diluted in ice cold LB broth and titered for plaque-forming units on a lawn of XL1-Blue(TM) cells. Table 114 illustrates that incubation of the MK-BPTI phage with immobilized anhydro-trypsin results in a very significant loss in titer over a four hour period while no such effect is observed with the MK (control) phage. The reduction in phage titer is also proportional to the amount of immobilized anhydro-trypsin added to the MK-BPTI phage. Incubation with five microliters of a 50% slurry of agarose-immobilized streptavidin (Sigma, St. Louis, Mo.) in TBS/BSA buffer does not reduce the titer of either the MK-BPTI or MK phage. These data are consistent with the presentation of a correctly-folded, functional BPTI protein on the surface of the MK-BPTI phage but not on the MK phage. Unfolded or incomplete BPTI domains are not expected to bind anhydro-trypsin. Furthermore, unfolded BPTI domains are expected to be non-specifically sticky.

Neutralization of Phage Titer with Anti-BPTI Antibody

MK-BPTI and MK phage were diluted to a concentration of $4 \cdot 10^8$ plaque-forming units per ml in LB broth. Fifteen microliters of diluted phage were added to an equivalent volume of either rabbit anti-BPTI serum or normal rabbit serum (both diluted 10 fold in LB broth). Following incubation at 37° C., aliquots were removed, diluted by $10^4$ in ice-cold LB broth and titered for plaque-forming units on a lawn of XL1-Blue$^{(TM)}$ cells. Incubation of the MK-BPTI phage with anti-BPTI serum results in a steady loss in titer over a two hour period while no such effect is observed with the MK phage. As expected, normal rabbit serum does not reduce the titer of either the MK-BPTI or the MK phage. Prior incubation of the anti-BPTI serum with authentic BPTI protein but not with an equivalent amount of E. coli protein, blocks the ability of the serum to reduce the titer of the MK-BPTI phage. This data is consistent with the presentation of BPTI-specific epitopes on the surface of the MK-BPTI phage but not the MK phage. More specifically, the data indicates that these BPTI epitopes are associated with the gene III protein and their association of this fusion protein with an anti-BPTI antibody blocks its ability to mediate the infection of bacterial cells.

Neutralization of Phage Titer with Trypsin

MK-BPTI and M1 phage were diluted to a concentration of $4 \cdot 10^8$ plaque-forming units per ml in LB broth. Diluted phage were added to an equivalent volume of trypsin diluted to various concentrations in LB broth. Following incubation at 37° C., aliquots were removed, diluted by $10^4$ in ice cold LB broth and titered for plaque-forming units on a lawn of XL1-Blue$^{(TM)}$ cells. Incubation of the MK-BPTI phage with 0.15 µg of trypsin results in a 70% loss in titer after a two hour period while only a 15% loss in titer is observed for the MK phage. A reduction in the amount of trypsin added to phage results in a reduction in the loss of titer. However, at all trypsin concentrations investigated, the MK-BPTI phage are more sensitive to incubation with trypsin than the MK phage. An interpretation of this data is that association of the BPTI-III fusion protein displayed on the surface of the MK-BPTI phage with trypsin blocks its ability to mediate the infection of bacterial cells.

The reduction in titer of phage MK by trypsin is an example of a phenomenon that is likely to be general: proteases, if present in sufficient quantity, will degrade proteins on the phage and reduce infectivity. The present application lists several means that can be used to overcome this problem.

Affinity Selection System

Affinity Selection with Immobilized Anhydro-Trypsin

MK-BPTI and MK phage were diluted to a concentration of $1.4 \cdot 10^{12}$ particles per ml in TBS buffer (PARM88) containing 1.0 mg/ml BSA. We added $4.0 \cdot 10^{10}$ phage to 5 microliters of either a 50% slurry of agarose-immobilized anhydro-trypsin beads (Pierce Chemical Co.) or agarose-immobilized streptavidin beads (Sigma) in TBS/BSA. Following a 3 hour incubation at room temperature, the beads were pelleted by centrifugation for 30 seconds at 5000 rpm in a microfuge and the supernatant fraction was collected. The beads were washed 5 times with TBS/Tween buffer (PARM88) and after each wash the beads were pelleted by centrifugation and the supernatant was removed. Finally, beads were resuspended in elution buffer (0.1N HCl containing 1.0 mg/ml BSA adjusted to pH 2.2 with glycine) and following a 5 minute incubation at room temperature, the beads were pelleted by centrifugation. The supernatant was removed and neutralized by the addition of 1.0M Tris-HCl buffer, pH 8.0.

Aliquots of phage samples were applied to a Nytran membrane using a Schleicher and Schuell (Keene, N.H.) filtration minifold and phage DNA was immobilized onto the Nytran by baking at 80° C. for 2 hours. The baked filter was incubated at 42° C. for 1 hour in pre-wash solution (MANI82) and pre-hybridization solution (5Prime-3Prime, West Chester, Pa.). The 1.0 Kb NarI (base 1630)/XmnI (base 2646) DNA fragment from MK RF was radioactively labelled with $^{32}$P-dCTP using an oligolabelling kit (Pharmacia, Piscataway, N.J.). The radioactive probe was added to the Nytran filter in hybridization solution (5Prime-3Prime) and, following overnight incubation at 42° C., the filter was washed and subjected to autoradiography.

The efficiency of this affinity selection system can be semi-quantitatively determined using the dot-blot procedure described elsewhere in the present application. Exposure of MK-BPTI-phage-treated anhydro-trypsin beads to elution buffer releases bound MK-BPTI phage. Streptavidin beads do not retain phage MK-BPTI. Anhydro-trypsin beads do not retain phage MK. In the experiment depicted in Table 115, we estimate that 20% of the total MK-BPTI phage were bound to 5 microliters of the immobilized anhydro-trypsin and were subsequently recovered by washing the beads with elution buffer (pH 2.2 HCl/glycine). Under the same conditions, no detectable MK-BPTI phage were bound and subsequently recovered from the streptavidin beads. The amount of MK-BPTI phage recovered in the elution fraction is proportional to the amount of immobilized anhydro-trypsin added to the phage. No detectable MK phage were bound to either the immobilized anhydro-trypsin or streptavidin beads and no phage were recovered with elution buffer. These data indicate that the affinity selection system described above can be utilized to select for phage displaying a specific folded protein (in this case, BPTI). Unfolded or incomplete BPTI domains are not expected to bind anhydro-trypsin.

Affinity Selection with Anti-BPTI antibodies

MK-BPTI and MK phage were diluted to a concentration of $1 \cdot 10^{10}$ particles per ml in Tris buffered saline solution (PARM88) containing 1.0 mg/ml BSA. Two·$10^8$ phage were added to 2.5 µg of either biotinylated rabbit anti-BPTI IgG in TBS/BSA or biotinylated rabbit anti-mouse antibody IgG (Sigma) in TBS/BSA, and incubated overnight at 4° C. A 50% slurry of streptavidin-agarose (Sigma), washed three times with TBS buffer prior to incubation with 30 mg/ml BSA in TBS buffer for 60 minutes at room temperature, was washed three times with TBS/Tween buffer (PARM88) and resuspended to a final concentration of 50% in this buffer. Samples containing phage and biotinylated IgG were diluted with TBS/Tween prior to the addition of streptavidin-agarose in TBS/Tween buffer. Following a 60 minute incubation at room temperature, streptavidin-agarose beads were pelleted by centrifugation for 30 seconds and the supernatant fraction was collected. The beads were washed 5 times with TBS/Tween buffer and after each wash, the beads were pelleted by centrifugation and the supernatant was removed. Finally, the streptavidin-agarose beads were resuspended in elution buffer (0.1N HCl containing 1.0 mg/ml BSA adjusted to pH 2.2 with glycine), incubated 5 minute at room temperature, and pelleted by centrifugation. The supernatant was removed and neutralized by the addition of 1.0M Tris-HCl buffer, pH 8.0.

Aliquots of phage samples were applied to a Nytran membrane using a Schleicker and Schuell minifold apparatus. Phage DNA was immobilized onto the Nytran by baking at 80° C. for 2 hours. Filters were washed for 60 minutes in pre-wash solution (MANI82) at 42° C. then incubated at 42° C. for 60 minutes in Southern pre-hybridization solution (5Prime-3Prime). The 1.0 Kb NarI (1630bp)/XmnI (2646 bp) DNA fragment from MK RF was radioactively labelled with $^{32}$P-$\alpha$dCTP using an oligolabelling kit (Pharmacia, Piscataway, N.J.). Nytran membranes were transferred from pre-hybridization solution to Southern hybridization solution (5Prime-3Prime) at 42° C. The radioactive probe was added to the hybridization solution and following overnight incubation at 42° C., the filter was washed 3 times with 2× SSC, 0.1% SDS at room temperature and once at 65° C. in 2× SSC, 0.1% SDS. Nytran membranes were subjected to autoradiography. The efficiency of the affinity selection system can be semi-quantitatively determined using the above dot blot procedure. Comparison of dots A1 and B1 or C1 and D1 indicates that the majority of phage did not stick to the streptavidin-agarose beads. Washing with TBS/Tween buffer removes the majority of phage which are non-specifically associated with streptavidin beads. Exposure of the streptavidin beads to elution buffer releases bound phage only in the case of MK-BPTI phage which have previously been incubated with biotinylated rabbit anti-BPTI IgG. This data indicates that the affinity selection system described above can be utilized to select for phage displaying a specific antigen (in this case BPTI). We estimate an enrichment factor of at least 40 fold based on the calculation $$\text{Enrichment Factor} = \frac{\text{Percent MK-BPTI phage recovered}}{\text{Percent MK phage recovered}}$$

EXAMPLE III

Characterization and Fractionation of Clonally Pure Populations of Phage, Each Displaying a Single Chimeric Aprotinin Homologue/M13 Gene III Protein This Example demonstrates that chimeric phage proteins displaying a target-binding domain can be eluted from immobilized target by decreasing pH, and the pH at which the protein is eluted is dependent on the binding affinity of the domain for the target.

Standard Procedures:

Unless otherwise noted, all manipulations were carried out at room temperature. Unless otherwise noted, all cells are XL1-Blue$^{(TM)}$ (Stratagene, La Jolla, Calif.).

1) Demonstration of the Binding of BPTI-III MK Phage to Active Trypsin Beads

Previous experiments designed to verify that BPTI displayed by fusion phage is functional relied on the use of immobilized anhydro-trypsin, a catalytically inactive form of trypsin. Although anhydro-trypsin is essentially identical to trypsin structurally (HUBE75, YOKO77) and in binding properties (VINC74, AKOH72), we demonstrated that BPTI-III fusion phage also bind immobilized active trypsin. Demonstration of the binding of fusion phage to immobilized active protease and subsequent recovery of infectious phage facilitates subsequent experiments where the preparation of inactive forms of serine proteases by protein modification is laborious or not feasible.

Fifty μl of BPTI-III MK phage (identified as MK-BPTI in U.S. Ser. No. 07/487,063) (3.7·10$^{11}$ pfu/ml) in either 50 mM Tris, pH 7.5, 150 mM NaCl, 1.0 mg/ml BSA (TBS/BSA) buffer or 50 mM sodium citrate, pH 6.5, 150 mM NaCl, 1.0 mg/ml BSA (CBS/BSA) buffer were added to 10 μl of a 25% slurry of immobilized trypsin (Pierce Chemical Co., Rockford, Ill.) also in TBS/BSA or CBS/BSA. As a control, 50 μl MK phage (9.3·10$^{12}$ pfu/ml) were added to 10 μl of a 25% slurry of immobilized trypsin in either TBS/BSA or CBS/BSA buffer. The infectivity of BPTI-III MK phage is 25-fold lower than that of MK phage; thus the conditions chosen above ensure that an approximately equivalent number of phage particles are added to the trypsin beads. After 3 hours of mixing on a Labquake shaker (Labindustries Inc., Berkeley, Calif.) 0.5 ml of either TBS/BSA or CBS/BSA was added where appropriate to the samples. Beads were washed for 5 min and recovered by centrifugation for 30 sec. The supernatant was removed and 0.5 ml of TBS/0.1% Tween-20 was added. The beads were mixed for 5 minutes on the shaker and recovered by centrifugation as above. The supernatant was removed and the beads were washed an additional five times with TBS/0.1% Tween-20 as described above. Finally, the beads were resuspended in 0.5 ml of elution buffer (0.1M HCl containing 1.0 mg/ml BSA adjusted to pH 2.2 with glycine), mixed for 5 minutes and recovered by centrifugation. The supernatant fraction was removed and neutralized by the addition of 130 μl of 1M Tris, pH 8.0. Aliquots of the neutralized elution sample were diluted in LB broth and titered for plaque-forming units on a lawn of cells.

Table 201 illustrates that a significant percentage of the input BPTI-III MK phage bound to immobilized trypsin and was recovered by washing with elution buffer. The amount of fusion phage which bound to the beads was greater in TBS buffer (pH 7.5) than in CBS buffer (pH 6.5). This is consistent with the observation that the affinity of BPTI for trypsin is greater at pH 7.5 than at pH 6.5 (VINC72, VINC74). A much lower percentage of the MK control phage (which do not display BPTI) bound to immobilized trypsin and this binding was independent of the pH conditions. At pH 6.5, 1675 times more of the BPTI-III MK phage than of the MK phage bound to trypsin beads while at pH 7.5, a 2103-fold difference was observed. Hence fusion phage displaying BPTI adhere not only to anhydro-trypsin beads but also to active trypsin beads and can be recovered as infectious phage. These data, in conjunction with earlier findings, strongly suggest that BPTI displayed on the surface of fusion phage is appropriately folded and functional.

2) Generation of P1 Mutants of BPTI

To demonstrate the specificity of interaction of BPTI-III fusion phage with immobilized serine proteases, single amino acid substitutions were introduced at-the P1 position (residue 15 of mature BPTI) of the BPTI-III fusion protein by site-directed mutagenesis. A 25mer mutagenic oligonucleotide (P1) was designed to substitute a LEU codon for the $LYS_{15}$ codon. This alteration is desired because BPTI(K15L) is a moderately good inhibitor of human neutrophil elastase (HNE)($K_i$=2.9·10$^{-9}$M) (BECK88b) and a poor inhibitor of trypsin. A fusion phage displaying BPTI(K15L) should bind to immobilized HNE but not to immobilized trypsin. BPTI-III MK fusion phage would be expected to display the opposite phenotype (bind to trypsin, fail to bind to HNE). These observations would illustrate the binding specificity of BPTI-III fusion phage for immobilized serine proteases.

Mutagenesis of the P1 region of the BPTI-VIII gene contained within the intergenic region of recombinant phage MB46 was carried out using the Muta-Gene M13 In Vitro Mutagenesis Kit (Bio-Rad, Richmond, Calif.). MB46 phage (7.5·10$^6$ pfu) were used to infect a 50 ml culture of CJ236 cells (O.D.600=0.5). Following overnight incubation at 37° C., phage were recovered and uracil-containing single-stranded DNA was extracted from the phage. The single-stranded DNA was further purified by NACS chromatography as recommended by the manufacturer (B.R.L., Gaithersburg, Md.).

Two hundred nanograms of the purified single-stranded DNA were annealed to 3 picomoles of the phosphorylated 25mer mutagenic oligonucleotide (P1). Following filling in with T4 DNA polymerase and ligation with T4 DNA ligase, the sample was used to transfect competent cells which were subsequently plated on LB plates to permit the formation of plaques. Phage derived from picked plaques were applied to a Nytran membrane using a Schleicher and Schuell (Keene, N.H.) minifold I apparatus (Dot Blot Procedure). Phage DNA was immobilized onto the filter by baking at 80° C. for 2 hours. The filter was bathed in 1× Southern pre-hybridization buffer (5Prime-3Prime, West Chester, Pa.) for 2 hours. Subsequently, the filter was incubated in 1× Southern hybridization solution (5Prime-3Prime) containing a 21mer probing oligonucleotide (LEU1) which had been radioactively labelled with gamma-$^{32}$P-ATP (N.E.N./DuPont, Boston, Mass.) by T4 polynucleotide kinase (New England BioLabs (NEB), Beverly, Mass.). Following overnight hybridization, the filter was washed 3 times with 6× SSC at room temperature and once at 60° C. in 6× SSC prior to autoradiography. Clones exhibiting strong hybridization signals were chosen for large scale Rf preparation using the PZ523 spin column protocol (5Prime-3Prime). Restriction enzyme analysis confirmed that the structure of the Rf was correct and DNA sequencing confirmed the substitution of a LEU codon (TTG) for the $LYS_{15}$ codon (AAA). This Rf DNA was designated MB46(K15L).

3) Generation of the BPTI-III MA Vector

The original gene III fusion phage MK can be detected on the basis of its ability to transduce cells to kanamycin resistance ($Km^R$). It was deemed advantageous to generate a second gene III fusion vector which can confer resistance to a different antibiotic, namely ampicillin (Ap). One could then mix a fusion phage conferring $Ap^R$ while displaying engineered protease inhibitor A (EPI-A) with a second fusion phage conferring $Km^R$ while displaying EPI-B. The mixture could be added to an immobilized serine protease and, following elution of bound fusion phage, one could evaluate the relative affinity of the two EPIs for the immobilized protease from the relative abundance of phage that transduce cells to $Km^R$ or $Ap^R$.

The $ap^R$ gene is contained in the vector pGem3Zf (Promega Corp., Madison, Wis.) which can be packaged as single stranded DNA contained in bacteriophage when helper phage are added to bacteria containing this vector. The recognition sites for restriction enzymes smaI and SnaBI were engineered into the 3' non-coding region of the $Ap^R$ (β-lactamase) gene using the technique of synthetic oligonucleotide directed site specific mutagenesis. The single stranded DNA was used as the template for in vitro mutagenesis leading to the following DNA sequence alterations (numbering as supplied by Promega): a) to create a SmaI (or XmaI) site, bases $T_{1115} \rightarrow C$ and $A_{1116} \rightarrow C$, and b) to create a SnaBI site, $G_{1125} \rightarrow T$, $C_{1129} \rightarrow T$, and $T_{1130} \rightarrow A$. The alterations were confirmed by radiolabelled probe analysis with the mutating oligonucleotide and restriction enzyme analysis; this plasmid is named pSGK3.

Plasmid SGK3 was cut with AatII and SmaI and treated with T4 DNA polymerase (NEB) to remove overhanging 3' ends (MANI82, SAMB89). Phosphorylated HindIII linkers (NEB) were ligated to the blunt ends of the DNA and following HindIII digestion, the 1.1 kb fragment was isolated by agarose gel electrophoresis followed by purification on an Ultrafree-MC filter unit as recommended by the manufacturer (Millipore, Bedford, Mass.). M13-MB1/2-delta Rf DNA was cut with HindIII and the linearized Rf was purified and ligated to the 1.1 kb fragment derived from pSGK3. Ligation samples were used to transfect competent cells which were plated on LB plates containing Ap. Colonies were picked and grown in LB broth containing Ap overnight at 37° C. Aliquots of the culture supernatants were assayed for the presence of infectious phage. Rf DNA was prepared from cultures which were both $Ap^R$ and contained infectious phage. Restriction enzyme analysis confirmed that the Rf contained a single copy of the $Ap^R$ gene inserted into the intergenic region of the M13 genome in the same transcriptional orientation as the phage genes. This Rf DNA was designated MA.

The 5.9 kb BglII/BsmI fragment from MA Rf DNA and the 2.2 kb BglII/BsmI fragment from BPTI-III MK Rf DNA were ligated together and a portion of the ligation mixture was used to transfect competent cells which were subsequently plated to permit plaque formation on a lawn of cells. Large and small size plaques were observed on the plates. Small size plaques were picked for further analysis since BPTI-III fusion phage give rise to small plaques due to impairment of gene III protein function. Small plaques were added to LB broth containing Ap and cultures were incubated overnight at 37° C. An $Ap^R$ culture which contained phage which gave rise to small plaques when plated on a lawn of cells was used as a source of Rf DNA. Restriction enzyme analysis confirmed that the BPTI-III fusion gene had been inserted into the MA vector. This Rf was designated BPTI-III MA.

4) Construction of BPTI(K15L)-III MA

MB46(K15L) Rf DNA was digested with XhoI and EagI and the 125 bp DNA fragment was isolated by electrophoresis on a 2% agarose gel followed by extraction from an agarose slice by centrifugation through an Ultrafree-MC filter unit. The 8.0 kb XhoI/EagI fragment derived from BPTI-III MA Rf was also prepared. The above two fragments were ligated and the ligation sample was used to transfect competent cells which were plated on LB plates containing Ap. Colonies were picked and used to inoculate LB broth containing Ap. Cultures were incubated overnight at 37° C. and phage within the culture supernatants was probed using the Dot Blot Procedure. Filters were hybridized to a radioactively labelled oligonucleotide (LEU1). Positive clones were identified by autoradiography after washing filters under high stringency conditions. Rf DNA was prepared from $Ap^R$ cultures which contained phage carrying the K15L mutation. Restriction enzyme analysis and DNA sequencing confirmed that the K15L mutation had been introduced into the BPTI-III MA Rf. This Rf was designated BPTI(K15L)-III MA. Interestingly, BPTI(K15L)-III MA phage gave rise to extremely small plaques on a lawn of cells and the infectivity of the phage is 4 to 5 fold less than that of BPTI-III MK phage. This suggests that the substitution of LEU for LYS15 impairs the ability of the BPTI:gene III fusion protein to mediate phage infection of bacterial cells.

5) Preparation of Immobilized Human Neutrophil Elastase

One ml of Reacti-Gel 6× CDI activated agarose (Pierce Chemical Co.) in acetone (200 µl packed beads) was introduced into an empty Select-D spin column (5Prime-3Prime). The acetone was drained out and the beads were washed twice rapidly with 1.0 ml of ice cold water and 1.0 ml of ice cold 100 mM boric acid, pH 8.5, 0.9% NaCl. Two hundred µl of 2.0 mg/ml human neutrophil elastase (HNE) (CalBiochem, San Diego, Calif.) in borate buffer were added to the beads. The column was sealed and mixed end over end on a Labquake Shaker at 4° C. for 36 hours. The HNE solution was drained off and the beads were washed with ice cold 2.0M Tris, pH 8.0 over a 2 hour period at 4° C. to block remaining reactive groups. A 50% slurry of the beads in TBS/BSA was prepared. To this was added an equal volume of sterile 100% glycerol and the beads were stored as a 25% slurry at −20° C. Prior to use, the beads were washed 3 times with TBS/BSA and a 50% slurry in TBS/BSA was prepared.

6Characterization of the Affinity of BPTI-III MK and BPTI(K15L)-III MA Phage for Immobilized Trypsin and Human Neutrophil Elastase Thirty µl of BPTI-III MK phage in TBS/BSA ($1.7 \cdot 10^{11}$ pfu/ml) was added to 5 µl of a 50% slurry of either immobilized human neutrophil elastase or immobilized trypsin (Pierce Chemical Co.) also in TBS/BSA. Similarly 30 µl of BPTI(K15L)-III MA phage in TBS/BSA ($3.2 \cdot 10^{10}$ pfu/ml) was added to either immobilized HNE or trypsin. Samples were mixed on a Labquake shaker for 3 hours. The beads were washed with 0.5 ml of TBS/BSA for 5 minutes and recovered by centrifugation. The supernatant was removed and the beads were washed 5 times with 0.5 ml of TBS/0.1% Tween-20. Finally, the beads were resuspended in 0.5 ml of elution buffer (0.1M HCl containing 1.0 mg/ml BSA adjusted to pH 2.2 with glycine), mixed for 5 minutes and recovered by centrifugation. The supernatant fraction was removed, neutralized with 130 µl of 1M Tris, pH 8.0, diluted in LB broth, and titered for plaque-forming units on a lawn of cells.

Table 202 illustrates that 82 times more of the BPTI-III MK input phage bound to the trypsin beads than to the PINE beads. By contrast, the BPTI(K15L)-III MA phage bound preferentially to HNE beads by a factor of 36. These results are consistent with the known affinities of wild type and the K15L variant of BPTI for trypsin and HNE. Hence BPTI-III fusion phage bind selectively to immobilized proteases and the nature of the BPTI variant displayed on the surface of the fusion phage dictates which particular protease is the optimum receptor for the fusion phage.

7) Effect of pH on the Dissociation of Bound BPTI-III MK and BPTI(K15L)-III MA Phage from Immobilized Neutrophil Elastase The affinity of a given fusion phage for an immobilized serine protease can be characterized on the basis of the amount of bound fusion phage which elutes from the beads by washing with a pH 2.2 buffer. This represents rather extreme conditions for the dissociation of fusion phage from beads. Since the affinity of the BPTI variants described above for HNE is not high ($K_d > 1 \cdot 10^{-9}$M) it was anticipated that fusion phage displaying these variants might dissociate from HNE beads under less severe pH conditions. Furthermore fusion phage might dissociate from HNE beads under specific pH conditions characteristic of the particular BPTI variant displayed by the phage. Low pH buffers providing stringent wash conditions might be required to dissociate fusion phage displaying a BPTI variant with a high affinity for HNE whereas neutral pH conditions might be sufficient to dislodge a fusion phage displaying a BPTI variant with a weak affinity for HNE.

Thirty µl of BPTI(K15L)-III MA phage ($1.7 \cdot 10^{10}$ pfu/ml in TBS/BSA) were added to 5 µl of a 50% slurry of immobilized HNE also in TBS/BSA. Similarly, 30 µl of BPTI-III MA phage ($8.6 \cdot 10^{10}$ pfu/ml in TBS/BSA) were added to 5 µl of immobilized HNE. The above conditions were chosen to ensure that an approximately equivalent number of phage particles were added to the beads. The samples were incubated for 3 hours on a Labquake shaker. The beads were washed with 0.5 ml of TBS/BSA for 5 min on the shaker, recovered by centrifugation and the supernatant was removed. The beads were washed with 0.5 ml of TBS/0.1% Tween-20 for 5 minutes and recovered by centrifugation. Four additional washes with TBS/0.1% Tween-20 were performed as described above. The beads were washed as above with 0.5 ml of 100 mM sodium citrate, pH 7.0 containing 1.0 mg/ml BSA. The beads were recovered by centrifugation and the supernatant was removed. Subsequently, the HNE beads were washed sequentially with a series of 100 mM sodium citrate, 1.0 mg/ml BSA buffers of pH 6.0, 5.0, 4.0 and 3.0 and finally with the 2.2 elution buffer described above. The pH washes were neutralized by the addition of 1M Tris, pH 8.0, diluted in LB broth and titered for plaque-forming units on a lawn of cells.

Table 203 illustrates that a low percentage of the input BPTI-III MK fusion phage adhered to the HNE beads and was recovered in the pH 7.0 and 6.0 washes predominantly. By contrast, a significantly higher percentage of the BPTI(K15L)-III MA phage bound to the HNE beads and was recovered predominantly in the pH 5.0 and 4.0 washes. Hence lower pH conditions (i.e. more stringent) are required to dissociate BPTI(K15L)-III MA than BPTI-MK phage from immobilized HNE. The affinity of BPTI(K15L) is over 1000 times greater than that of BPTI for HNE (based on reported $K_d$ values (BECK88b)). Hence this suggests that lower pH conditions are indeed required to dissociate fusion phage displaying a BPTI variant with a higher affinity for HNE.

8) Construction of BPTI(MGNG)-III MA Phage

The light chain of bovine inter-α-trypsin inhibitor contains 2 domains highly homologous to BPTI. The amino terminal proximal domain (called BI-Se) has been generated by proteolysis and shown to be a potent inhibitor of HNE ($K_d = 4.4 \cdot 10^{-11}$M) (ALBR83). By contrast a BPTI variant with the single substitution of LEU for $LYS_{15}$ exhibits a moderate affinity for HNE ($K_d = 2.9 \cdot 10^{-9}$M) (BECK88b). It has been proposed that the P1 residue is the primary determinant of the specificity and potency of BPTI-like molecules (BECK88b, LASK80 and works cited therein). Although both BI-Se and BPTI(K15L) feature LEU at their respective P1 positions, there is a 66 fold difference in the affinities of these molecules for HNE. Structural features, other than the P1 residue, must contribute to the affinity of BPTI-like molecules for HNE.

A comparison of the structures of BI-Se and BPTI(K15L) reveals the presence of three positively charged residues at positions 39, 41, and 42 of BPTI which are absent in BI-Se.

These hydrophilic and highly charged residues of BPTI are displayed on a loop which underlies the loop containing the P1 residue and is connected to it via a disulfide bridge. Residues within the underlying loop (in particular residue 39) participate in the interaction of BPTI with the surface of trypsin near the catalytic pocket (BLOW72) and may contribute significantly to the tenacious binding of BPTI to trypsin. However, these hydrophilic residues might hamper the docking of BPTI variants with HNE. In support of this hypothesis, BI-8e displays a high affinity for HNE and contains no charged residues in the region spanning residues 39–42. Hence residues 39 through 42 of wild type BPTI were replaced with the corresponding residues of the human homologue of BI-8e. We anticipated that a BPTI derivative containing the MET-GLY-ASN-GLY (MGNG) sequence would exhibit a higher affinity for HNE than corresponding derivatives which retain the sequence of wild type BPTI at residues 39–42.

A double stranded oligonucleotide with AccI and EagI compatible ends was designed to introduce the desired alteration of residues 39 to 42 via cassette mutagenesis. Codon 45 was altered to create a new XmnI site, unique in the structure of the BPTI gene, which could be used to screen for mutants. This alteration at codon 45 does not alter the encoded amino-acid sequence. BPTI-III MA Rf DNA was digested with AccI. Two oligonucleotides (CYSB and CYST) corresponding to the bottom and top strands of the mutagenic DNA were annealed and ligated to the AccI digested BPTI-III MA Rf DNA. The sample was digested with BglII and the 2.1 kb BglII/EagI fragment was purified. BPTI-III MA Rf was also digested with BglII and EagI and the 6.0 kb fragment was isolated and ligated to the 2.1 kb BglII/EagI fragment described above. Ligation samples were used to transfect competent cells which were plated to permit the formation of plaques on a lawn of cells. Phage derived from plaques were probed with a radioactively labelled oligonucleotide (CYSB) using the Dot Blot Procedure. Positive clones were identified by autoradiography of the Nytran membrane after washing at high stringency conditions. Rf DNA was prepared from $Ap^R$ cultures containing fusion phage which hybridized to the CYSB probe. Restriction enzyme analysis and DNA sequencing confirmed that codons 39–42 of BPTI had been altered. The Rf DNA was designated BPTI(MGNG)-III MA.

9) Construction of BPTI(K15L,MGNG)-III MA

BPTI(MGNG)-III MA Rf DNA was digested with AccI and the 5.6 kb fragment was purified. BPTI(K15L)-III MA was digested with ACcI and the 2.5 kb DNA fragment was purified. The two fragments above were ligated together and ligation samples were used to transfect competent cells which were plated for plaque production. Large and small plaques were observed on the plate. Representative plaques of each type were picked and phage were probed with the LEU1 oligonucleotide via the Dot Blot Procedure. After the Nytran filter had been washed under high stringency conditions, positive clones were identified by autoradiography. Only the phage which hybridized to the LEU1 oligonucleotide gave rise to the small plaques confirming an earlier observation that substitution of LEU for $LYS_{15}$ substantially reduces phage infectivity. Appropriate cultures containing phage which hybridized to the LEU1 oligonucleotide were used to prepare Rf DNA. Restriction enzyme analysis and DNA sequencing confirmed that the K15L mutation had been introduced into BPTI(MGNG)-III MA. This Rf DNA was designated BPTI(K15L,MGNG)-III MA.

10) Effect of Mutation of Residues 39–42 of BPTI(K15L) on its Affinity for Immobilized HNE Thirty μl of BPTI(K15L,MGNG)-III MA phage ($9.2 \cdot 10^9$ pfu/ml in TBS/BSA) were added to 5 μl of a 50% slurry of immobilized HNE also in TBS/BSA. Similarly 30 μl of BPTI(K15L)-III MA phage ($1.2 \cdot 10^{10}$ pfu/ml in TBS/BSA) were added to immobilized HNE. The samples were incubated for 3 hours on a Labquake shaker. The beads were washed for 5 min with 0.5 ml of TBS/BSA and recovered by centrifugation. The beads were washed 5 times with 0.5 ml of TBS/0.1% Tween-20 as described above. Finally, the beads were washed sequentially with a series of 100 mM sodium citrate buffers of pH 7.0, 6.0, 5.5, 5.0, 4.75, 4.5, 4.25, 4.0 and 3.5 as described above. pH washes were neutralized, diluted in LB broth and titered for plaque-forming units on a lawn of cells.

Table 204 illustrates that almost twice as much of the BPTI(K15L,MGNG)-III MA as BPTI(K15L)-III MA phage bound to HNE beads. In both cases the pH 4.75 fraction contained the largest proportion of the recovered phage. This confirms that replacement of residues 39–42 of wild type BPTI with the corresponding residues of BI-8e enhances the binding of the BPTI(K15L) variant to HNE.

11) Fractionation of a Mixture of BPTI-III MK and BPTI(K15L,MGNG)-III MA Fusion Phage The observations described above indicate that BPTI(K15L,MGNG)-III MA and BPTI-III MK phage exhibit different pH elution profiles from immobilized HNE. It seemed plausible that this property could be exploited to fractionate a mixture of different fusion phage.

Fifteen μl of BPTI-III MK phage ($3.92 \cdot 10^{10}$ pfu/ml in TBS/BSA), equivalent to $8.91 \cdot 10^7$ $Km^R$ transducing units, were added to 15 μl of BPTI(K15L,MGNG)-III MA phage ($9.85 \cdot 10^9$ pfu/ml in TBS/BSA), equivalent to $4.44 \cdot 10^7$ $Ap^R$ transducing units. Five μl of a 50% slurry of immobilized HNE in TBS/BSA was added to the phage and the sample was incubated for 3 hours on a Labquake mixer. The beads were washed for 5 minutes with 0.5 ml of TBS/BSA prior to being washed 5 times with 0.5 ml of TBS/2.0% Tween-20 as described above. Beads were washed for 5 minutes with 0.5 ml of 100 mM sodium citrate, pH 7.0 containing 1.0 mg/ml BSA. The beads were recovered by centrifugation and the supernatant was removed. Subsequently, the HNE beads were washed sequentially with a series of 100 mM citrate buffers of pH 6.0, 5.0 and 4.0. The pH washes were neutralized by the addition of 130 μl of 1M Tris, pH 8.0.

The relative proportion of BPTI-III MK and BPTI(K15L,MGNG)-III MA phage in each pH fraction was evaluated by determining the number of phage able to transduce cells to $Km^R$ as opposed to $Ap^R$. Fusion phage diluted in 1× Minimal A salts were added to 100 μl of cells (O.D. 600=0.8 concentrated to 1/20 original culture volume) also in Minimal salts in a final volume of 200 μl. The sample was incubated for 15 min at 37° C. prior to the addition of 200 μl of 2× LB broth. After an additional 15 min incubation at 37° C., duplicate aliquots of cells were plated on LB plates containing either Ap or Km to permit the formation of colonies. Bacterial colonies on each type of plate were counted and the data was used to calculate the number of $Ap^R$ and $Km^R$ transducing units in each pH fraction. The number of $Ap^R$ transducing units is indicative of the amount of BPTI(K15L, MGNG)-III MA phage in each pH fraction while the total number of $Km^R$ transducing units is indicative of the amount of BPTI-III MKphage.

Table 205 illustrates that a low percentage of the BPTI-III MK input phage (as judged by $Km^R$ transducing units) adhered to the HNE beads and was recovered predominantly in the pH 7.0 fraction. By contrast, a significantly higher percentage of the BPTI(K15L,MGNG)-III MA phage (as judged by $Ap^R$ transducing units) adhered to the HNE beads and was recovered predominantly in the pH 4.0 fraction. A comparison of the total number of $Ap^R$ and $Km^R$ transducing units in the pH 4.0 fraction shows that a 984-fold enrichment of BPTI(K15L,MGNG)-III MA phage over BPTI-III MKphage was achieved. Hence, the above procedure can be utilized to fractionate mixtures of fusion phage on the basis of their relative affinities for immobilized HNE.

12) Construction of BPTI(K15V,R17L)-III MA

A BPTI variant containing the alterations K15V and R17L demonstrates the highest affinity for HNE of any BPTI variant described to date ($K_d=6.10^{-11}$M) (AUER89). As a means of testing the selection system described herein, a fusion phage displaying this variant of BPTI was generated and used as a "reference" phage to characterize the affinity for immobilized HNE of fusion phage displaying a BPTI variant with a known affinity for free HNE. A 76 bp mutagenic oligonucleotide (VAL1) was designed to convert the $LYS_{15}$ codon (AAA) to a VAL codon (GTT) and the $ARG_{17}$ codon (CGA) to a LEU codon (CTG). At the same time codons 11, 12 and 13 were altered to destroy the ApaI site resident in the wild type BPTI gene while creating a new RsrII site, which could be used to screen for correct clones.

The single stranded VAL1 oligonucleotide was converted to the double stranded form following the procedure described in Current Protocols in Molecular Biology (AUSU87). One µg of the VAL1 oligonucleotide was annealed to one µg of a 20 bp primer (MBS). The sample was heated to 80° C., cooled to 62° C. and incubated at this temperature for 30 minutes before being allowed to cool to 37° C. Two µl of a 2.5 mM mixture of dNTPs and 10 units of Sequenase (U.S.B., Cleveland, Ohio) were added to the sample and second strand synthesis was allowed to proceed for 45 minutes at 37° C. One hundred units of XhoI was added to the sample and digestion was allowed to proceed for 2 hours at 37° C. in 100 µl of 1 X XhOI digestion buffer. The digested DNA was subjected to electrophoreses on a 4% GTG NuSieve agarose (FMC Bioproducts, Rockland, Me.) gel and the 65 bp fragment was excised and purified from melted agarose by phenol extraction and ethanol precipitation. A portion of the recovered 65 bp fragment was subjected to electrophoresis on a 4% GTG NuSieve agarose gel for quantitation. One hundred nanograms of the recovered fragment was dephosphorylated with 1.9 µl of $HK^{(TM)}$ phosphatase (Epicentre Technologies, Madison, Wis.) at 37° C. for 60 minutes. The reaction was stopped by heating at 65° C. for 15 minutes. BPTI-MA Rf DNA was digested with XhoI and StuI and the 8.0 kb fragment was isolated. One µl of the dephosphorylation reaction (5 ng of double-stranded VAL1 oligonucleotide) was ligated to 50 ng of the 8.0 kb XhoI/StUI fragment derived from BPTI-III MA Rf. Ligation samples were subjected to phenol extraction and DNA was recovered by ethanol precipitation. Portions of the recovered ligation DNA were added to 40 µl of electrocompetent cells which were shocked using a Bio-Rad Gene Pulser device set at 1.7 kv, 25 µF and 800 Ω. One ml of SOC media was immediately added to the cells which were allowed to recover at 37° C. for one hour. Aliquots of the electroporated cells were plated onto LB plates containing Ap to permit the formation of colonies.

Phage contained within cultures derived from picked $Ap^R$ colonies were probed with two radiolabelled oligonucleotides (PRP1 and ESP1) via the Dot Blot Procedure. Rf DNA was prepared from cultures containing phage which exhibited a strong hybridization signal with the ESP1 oligonucleotide but not with the PRP1 oligonucleotide. Restriction enzyme analysis verified loss of the ApaI site and acquisition of a new RsrII site diagnostic for the changes in the P1 region. Fusion phage were also probed with a radiolabelled oligonucleotide (VLP1) via the Dot Blot Procedure. Autoradiography confirmed that fusion phage which previously failed to hybridize to the PRP1 probe, hybridized to the VLP1 probe. DNA sequencing confirmed that the $LYS_{15}$ and $ARG_{17}$ codons had been converted to VAL and LEU codons respectively. The Rf DNA was designated BPTI(K15V,R17L)-III MA.

13) Affinity of BPTI(K15V,R17L)-III MA Phage for Immobilized HNE

Forty µl of BPTI (K15, R17L) -III MA phage ($9.8 \cdot 10^{10}$ pfu/ml) in TBS/BSA were added to 10 µl of a 50% slurry of immobilized HNE also in TBS/BSA. Similarly, 40 µl of BPTI(K15L,MGNG)-III MA phage ($5.13 \cdot 10^9$ pfu/ml) in TBS/BSA were added to immobilized HNE. The samples were mixed for 1.5 hours on a Labquake shaker. Beads were washed once for 5 min with 0.5 ml of TBS/BSA and then 5 times with 0.5 ml of TBS/1.0% Tween-20 as described previously. Subsequently the beads were washed sequentially with a series of 50 mM sodium citrate buffers containing 150 mM NaCl, 1.0 mg/ml BSA of pH 7.0, 6.0, 5.0, 4.5, 4.0, 3.75, 3.5 and 3.0. In the case of the BPTI(K15L, MGNG)-III MA phage, the pH 3.75 and 3.0 washes were omitted. Two washes were performed at each pH and the supernatants were pooled, neutralized with 1M Tris pH 8.0, diluted in LB broth and titered for plaque-forming units on a lawn of cells.

Table 206 illustrates that the pH 4.5 and 4.0 fractions contained the largest proportion of the recovered BPTI(K15V,R17L)-III MA phage. By contrast, the BPTI(K15L,MGNG)-III MA phage, like BPTI(K15L)-III MA phage, were recovered predominantly in the pH 5.0 and 4.5 fractions, as shown above. The affinity of BPTI(K15V, R17L) is 48 times greater than that of BPTI(K15L) for HNE (based on reported $K_d$ values, AUER89 for BPTI(K15V, R17L) and BECK88b for BPTI(K15L)). That the pH elution profile for BPTI(K15V,R17L)-III MA phage exhibits a peak at pH 4.0 while the profile for BPTI(K15L)-III MA phage displays a peak at pH 4.5 supports the contention that lower pH conditions are required to dissociate, from immobilized HNE, fusion phage displaying a BPTI variant with a higher affinity for free HNE.

EXAMPLE IV

Construction of a Variegated Population of Phage Displaying BPTI Derivatives and Fractionation for Members that Display Binding Domains Having High Affinity for Human Neutrophil Elastase We here describe generation of a library of 1000 different potential engineered protease inhibitors (PEPIs) and the fractionation with immobilized HNE to obtain an engineered protease inhibitor (Epi) having high affinity for HNE. Successful Epis that bind HNE are designated EpiNEs.

1) Design of a Mutagenic Oligonucleotide to Create a Library of Fusion Phase

A 76 bp variegated oligonucleotide (MYMUT) was designed to construct a library of fusion phage displaying 1000 different PEPIs derived from BPTI. The oligonucleotide contains 1728 different DNA sequences but due to the degeneracy of the genetic code, it encodes 1000 different protein sequences. The oligonucleotide was designed so as to destroy an ApaI site (shown in Table 113) encompassing codons 12 and 13. ApaI digestion could be used to select against the parental Rf DNA used to construct the library.

The MYMUT oligonucleotide permits the substitution of 5 hydrophobic residues (PHE, LEU, ILE, VAL, and MET via a DTS codon (D=approximately equimolar A, T, and G; S=approximately equimolar C and G)) for $LYS_{15}$. Replacement of $LYS_{15}$ in BPTI with aliphatic hydrophobic residues via semi-synthesis has provided proteins having higher affinity for HNE than BPTI (TANN77, JERI74a,b, WENZ80, TSCH86, BECK88b). At position 16, either GLY or ALA are permitted (GST codon). This is in keeping with the predominance of these two residues at the corresponding positions in a variety of BPTI homologues (CREI87). The variegation scheme at position 17 is identical to that at 15. Limited data is available on the relative contribution of this residue to the interaction of BPTI homologues with HNE. A variety of hydrophobic residues at position 17 was included with the anticipation that they would enhance the docking of a BPTI variant with HNE. Finally at positions 18 and 19, 4 (PHE, SER, THR, and ILE via a WYC codon (W=approximately equimolar A and T; Y=approximately equimolar T and C)) and 5 (SER, PRO, THR, LYS, GLN, and stop via an HMA codon (H=approximately equimolar A, C, and T; M=approximately equimolar A and C)) different amino acids respectively are encoded. These different amino acid residues are found in the corresponding positions of BPTI homologues that are known to bind to HNE (CREI87). Although the amino acids included in the PEPI library were chosen because there was some indication that they might facilitate binding to PINE, it was not and is not possible to predict which combination of these amino acids will lead to high affinity for HNE. The mutagenic oligonucleotide MYMUT was synthesized by Genetic Design Inc. (Houston, Tex.).

2) Construction of Library of Fusion Phage Displaying Potential Engineered Protease Inhibitors The single-stranded mutagenic MYMUT DNA was converted to the double stranded form with compatible XhoI and StuI ends and dephosphorylated with HK$^{(TM)}$ phosphatase as described above for the VAL1 oligonucleotide. BPTI(MGNG)-III MA Rf DNA was digested with XhoI and StuI for 3 hours at 37° C. to ensure complete digestion. The 8.0 kb DNA fragment was purified by agarose gel electrophoresis and Ultrafree-MC unit filtration. One μl of the dephosphorylated MYMUT DNA (5 ng) was ligated to 50 ng of the 8.0 kb fragment derived from BPTI(MGNG)-III MA Rf DNA. Under these conditions, the 10:1 molar ratio of insert to vector was found to be optimal for the generation of transformants. Ligation samples were extracted with phenol, phenol/chloroform/IAA (25:24:1, v:v:v) and chloroform/IAA (24:1, v:v) and DNA was-ethanol precipitated prior to electroporation. One μl of the recovered ligation DNA was added to 40 μl of electro-competent cells. Cells were shocked using a Bio-Rad Gene Pulser device as described above. Immediately following electroshock, 1.0 ml of SOC media was added to the cells which were allowed to recover at 37° C. for 60 minutes with shaking. The electroporated cells were plated onto LB plates containing Ap to permit the formation of colonies.

To assess the efficiency of the cassette mutagenesis procedure, 39 transformants were picked at random and phage present in culture supernatants were applied to a Nytran membrane and probed using the Dot Blot Procedure. Two Nytran membranes were prepared in this manner. The first filter was allowed to hybridize to the CYSB oligonucleotide which had previously been radiolabelled. The second membrane was allowed to hybridize to the PRP1 oligonucleotide which had also been radiolabelled. Filters were subjected to autoradiography following washing under high stringency conditions. Of the 39 phage samples applied to the membrane, all 39 hybridized to the CYSB probe. This indicated that there was fusion phage in the culture supernatants and that at least the DNA encoding residues 35–47 appeared to be present in the phage genomes. Only 11 of the 39 samples hybridized to the PRP1 oligonucleotide indicating that 28% of the transformants were probably the parental phage BPTI(MGNG)-III MA used to generate the library. The remaining 28 clones failed to hybridize to the PRP1 probe indicating that substantial alterations were introduced into the P1 region by cassette mutagenesis using the MYMUT oligonucleotide. Of these 28 samples, all were found to contain infectious phage indicating that mutagenesis did not result in frame shift mutations which would lead to the generation of defective gene III products and non-infectious phage. (These 28 PEPI-displaying phage constitute a mini-library, the fractionation of which is discussed below.) Hence the overall efficiency of mutagenesis was estimated to be 72% in those cases where ligation DNA was not subjected to ApaI digestion prior to electroporation.

Bacterial colonies were harvested by overlaying chilled LB plates containing Ap with 5 ml of ice cold LB broth and scraping off cells using a sterile glass rod. A total of 4899 transformants were harvested in this manner of which 3299 were obtained by electroporation of ligation samples which were not digested with ApaI. Hence we estimate that 72% of these transformants (i.e. 2375) represent mutants of the parental BPTI(MGNG)-III MA phage derived by cassette mutagenesis of the P1 position. An additional 1600 transformants were obtained by electroporation of ligation samples which had been digested with ApaI. If we assume that all of these clones contain new sequences at the P1 position then the total number of mutants in the pool of 4899 transformants is estimated to be 2375+1600=3975. The total number of potentially different DNA sequences in the MYMUT library is 1728. We calculate that the library should display about 90% of the potential engineered protease inhibitor sequences as follows:

$$N_{displayed} = N_{possible} \cdot (1 - \exp\{-Libsize/N(DNA)\})$$
$$= 1000 \cdot (1 - \exp\{-3975/1728\}) = 900$$
$$\% \text{ of possible sequences displayed} = 100 \cdot (900 \div 1000)$$
$$= 90\%$$

3) Fractionation of a Mini-Library of Fusion Phage

We studied the fractionation of the mini library of 28 PEPIs to establish the appropriate parameters for fractionation of the entire MYMUT PEPI library. We anticipated that fractionation could be easier when the library of fusion phage was much less diverse than the entire MYMUT library. Fewer cycles of fractionation might be required to affinity purify a fusion phage exhibiting a high affinity for HNE. Secondly, since the sequences of all the fusion phage in the mini-library can be determined, one can determine the probability of selecting a given fusion phage from the initial population.

Two ml of the culture supernatants of the 28 PEPIs described above were pooled. Fusion phage were recovered, resuspended in 300 mM NaCl, 100 mM Tris, pH 8.0, 1 mM EDTA and stored on ice for 15 minutes. Insoluble material was removed by centrifugation for 3 minutes in a microfuge at 4° C. The supernatant fraction was collected and PEPI phage were precipitated with PEG-8000. The final phage pellet was resuspended in TBS/BSA. Aliquots of the recovered phage were titered for plaque-forming units on a lawn of cells. The final stock solution consisted of 200 μl of fusion phage at a concentration of $5.6 \cdot 10^{12}$ pfu/ml.

a) First Enrichment Cycle

Forty μl of the above phage stock was added to 10 μl of a 50% slurry of PINE beads in TBS/BSA. The sample was allowed to mix on a Labquake shaker for 1.5 hours. Five hundred μl of TBS/BSA was added to the sample and after an additional 5 minutes of mixing, the HNE beads were collected by centrifugation. The supernatant fraction was removed and the beads were resuspended in 0.5 ml of TBS/0.5% Tween-20. Beads were washed for 5 minutes on the shaker and recovered by centrifugation as above. The supernatant fraction was removed and the beads were subjected to 4 additional washes with TBS/Tween-20 as described above to reduce non-specific binding of fusion phage to HNE beads. Beads were washed twice as above with 0.5 ml of 50 mM sodium citrate pH 7.0, 150 mM NaCl containing 1.0 mg/ml BSA. The supernatants from the two washes were pooled. Subsequently, the HNE beads were washed sequentially with a series of 50 mM sodium citrate, 150 mM NaCl, 1.0 mg/ml BSA buffers of pH 6.0, 5.0, 4.5, 4.0, 3.5, 3.0, 2.5 and 2.0. Two washes were performed at each pH and the supernatants were pooled and neutralized by the addition of 260 μl of 1M Tris, pH 8.0. Aliquots of each pH fraction were diluted in LB broth and titered for plaque-forming units on a lawn of cells. The total amount of fusion phage (as judged by pfu) appearing in each pH wash fraction was determined.

Figure 7:
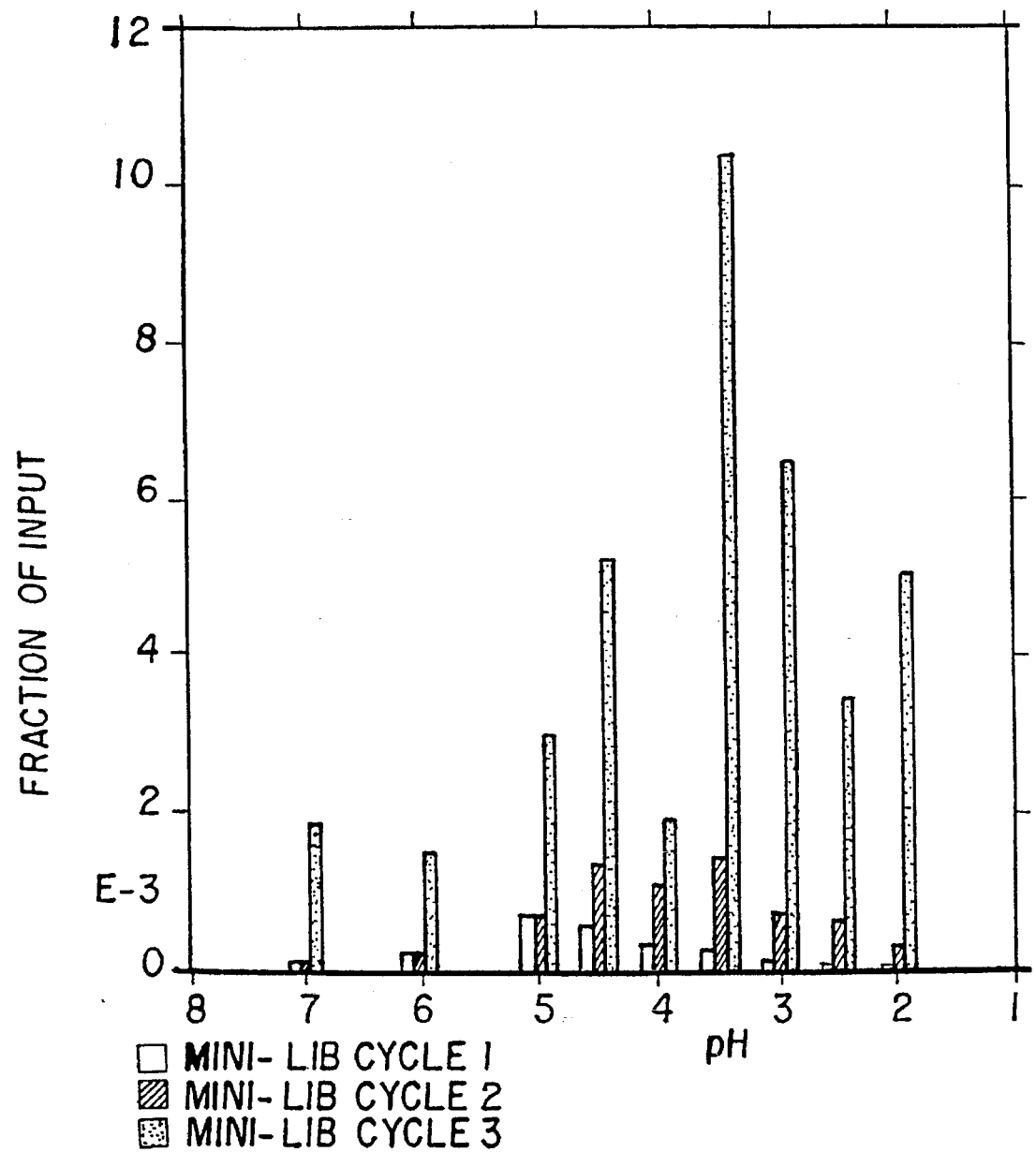
FIG. 7 illustrates fractionation of the Mini PEPI library on HNE beads. The abscissae shows pH of buffer. The ordinants show amount of phage (as fraction of input phage) obtained at given pH. Ordinants scaled by $10^3$.

FIG. 7 illustrates that the largest percentage of input phage which bound to the HNE beads was recovered in the pH 5.0 fraction. The elution peak exhibits a trailing edge on the low pH side suggesting that a small proportion of the total bound fusion phage might elute from the HNE beads at a pH<5. BFTI(K15L)-III phage display a BPTI variant with a moderate affinity for HNE ($K_d$=2.9·10$^{-9}$M) (BECK88b). Since BPTI(K15L)-III phage elute from HNE beads as a peak centered on pH 4.75 and the highest peak in the first passage of the mini-library over HNE beads is centered on pH 5.0, we infer that many members of the MYMUT PEPI mini-library display PEPIs having moderate to high affinity for HNE.

To enrich for fusion phage displaying the highest affinity for HNE, phage contained in the lowest pH fraction (pH 2.0) from the first enrichment cycle were amplified and subjected to a second round of fractionation. Amplification involved the Transduction Procedure described above. Fusion phage (2000 pfu) were incubated with 100 μl of cells for 15 minutes at 37° C. in 200 μl of 1× Minimal A salts. Two hundred μl of 2× LB broth was added to the sample and cells were allowed to recover for 15 minutes at 37° C. with shaking. One hundred μl portions of the above sample were plated onto LB plates containing Ap. Five such transduction reactions were performed yielding a total of 20 plates, each containing approximately 350 colonies (7000 transformants in total). Bacterial cells were harvested as described for the preparation of the MYMUT library and fusion phage were collected as described for the preparation of the mini-library. A total of 200 μl of fusion phage (4.3·10$^{12}$ pfu/ml in TBS/BSA) derived from the pH 2.0 fraction from the first passage of the mini-library was obtained in this manner.

b) Second Enrichment Cycle

Forty μl of the above phage stock was added to 10 μl of a 50% slurry of HNE beads in TBS/BSA. The sample was allowed to mix for 1.5 hours and the HNE beads were washed with TBS/BSA, TBS/0.5% Tween and sodium citrate buffers as described above. Aliqouts of neutralized pH fractions were diluted and titered as described above.

The elution profile for the second passage of the mini-library over HNE beads is shown in FIG. 7. The largest percentage of the input phage which bound to the HNE beads was recovered in the pH 3.5 wash. A smaller peak centered on pH 4.5 may represent residual fusion phage from the first passage of the mini-library which eluted at pH 5.0. The percentage of total input phage which eluted at pH 3.5 in the second cycle exceeds the percentage of input phage which eluted at pH 5.0 in the first cycle. This is indicative of more avid binding of fusion phage to the HNE matrix. Taken together, the significant shift in the pH elution profile suggests that selection for fusion phage displaying BPTI variants with higher affinity for HNE occurred.

c) Third Cycle

Phage obtained in the pH 2.0 fraction from the second passage of the mini-library were amplified as above and subjected to a third round of fractionation. The pH elution profile is shown in FIG. 7. The largest percentage of input phage was recovered in the pH 3.5 wash as is the case with the second passage of the mini-library. However, the minor peak centered on pH 4.5 is diminished in the third passage relative to the second passage. Furthermore, the percentage of input phage which eluted at pH 3.5 is greater in the third passage than in the second passage. In comparison, the BPTI(K15V,R17L)-III fusion phage elute from HNE beads as a peak centered on pH 4.25. Taken together, the data suggests that a significant selection for fusion phage displaying PEPIs with high affinity for HNE occurred. Furthermore, since more extreme pH conditions are required to elute fusion phage in the third passage of the MYMUT library relative to those conditions needed to elute BPTI(K15V,R17L)-III MA phage, this suggests that those fusion phage which appear in the pH 3.5 fraction may display a PEPI with a higher affinity for HNE than the BPTI(K15V,R17L) variant (i.e. $K_d$<6·10$^{-11}$M).

d) Characterization of Selected Fusion Phage

The pH 2.0 fraction from the third passage of the mini-library was titered and plaques were obtained on a lawn of cells. Twenty plaques were picked at random and phage derived from plaques were probed with the CYSB oligonucleotide via the Dot Blot Procedure. Autoradiography of the filter revealed that all 20 samples gave a positive hybridization signal indicating that fusion phage were present and the DNA encoding residues 35 to 47 of BPTI(MGNG) is contained within the recombinant M13 genomes. Rf DNA was prepared for the 20 clones and initial dideoxy sequencing revealed that 12 clones were identical. This sequence was designated EpiNEα (Table 207). No DNA sequence changes were observed apart from the planned variegation. Hence the cassette mutagenesis procedure preserved the context of the planned variegation of the pepi gene. The Dot Blot Procedure was employed to probe all 20 selected clones from the pH 2.0 fraction from the third passage of the mini-library with an oligonucleotide homologous to the sequence of EpiNEα. Following high stringency washing, autoradiography revealed that all 20 selected clones were identical in the P1 region. Furthermore dot blot analysis revealed that of the 28 different phage samples pooled to create the mini-library, only one contained the EpiNEα sequence. Hence in just three passes of the mini-library over HNE beads, 1 out of 28 input fusion phage was selected for and appears as a pure population in the lowest pH fraction from the third passage of the library. That the EpiNEα phage elute at pH 3.5 while BPTI(K15V,R17L)-III MA phage elute at a higher pH strongly suggests that the EpiNEα protein has a significantly higher affinity than BPTI(K15V,R17L) for HNE.

4) Fractionation of the MYMUT Library a) Three cycles of enrichment

Figure 8:
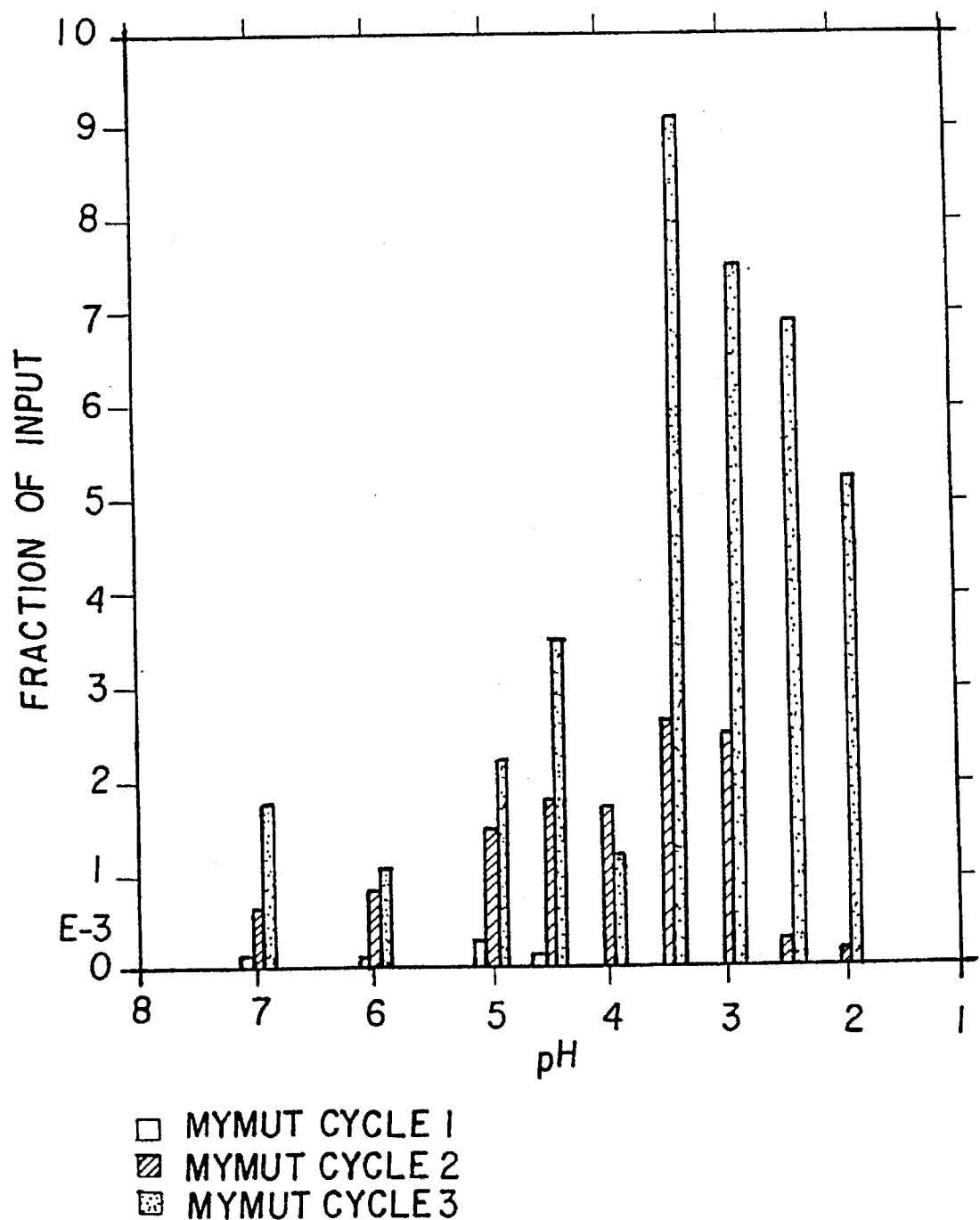
FIG. 8 illustrates fractionation of the MYMUT PEPI library on HNE beads. The abscissae shows pH of buffer. The ordinants show amount of phage (as fraction of input phage) obtained at given pH. Ordinants scaled by $10^3$.

The same procedure used above to fractionation the mini-library was used to fractionate the entire MYMUT PEPI library consisting of fusion phage displaying 1000 different proteins. The phage inputs for the first, second and third rounds of fractionation were $4.0 \cdot 10^{11}$, $5.8 \cdot 10^{10}$, and $1.1 \cdot 10^{11}$ pfu respectively. FIG. 8 illustrates that the largest percentage of input phage which bound to the HNE matrix was recovered in the pH 5.0 wash in the first enrichment cycle. The pH elution profile is very similar to that seen for the first passage of the mini-library over HNE beads. A trailing edge is also observed on the low pH side of the pH 5.0 peak however this is not as prominent as that observed for the mini-library. The percentage of input phage which eluted in the pH 7.0 wash was greater than that eluted in the pH 6.0 wash. This is in contrast to the result obtained for the first passage of the mini library and may reflect the presence of ≈20% parental BPTI(MGNG)-III MA phage in the MYMUT library pool. These phage adhere to the HNE beads weakly (if at all) and elute in the pH 7.0 fraction. That no parent phage were present in the mini-library is consistent with the absence of a peak at pH 7.0 in the first passage of the mini-library.

Phage present in the pH 2.0 fraction from the first passage of the MYMUT library were amplified as described previously and subjected to a second round of fractionation. The largest percentage of input phage which bound to the HNE beads was recovered in the pH 3.5 wash (FIG. 8). A minor peak centered on pH 4.5 was also evident. The fact that more extreme pH conditions were required to elute the majority of bound fusion phage suggested that selection of fusion phage displaying PEPIs with higher affinity for HNE had occurred. This was also indicated by the fact that the total percentage of input phage which appeared in the pH 3.5 wash in the second enrichment cycle was 10 times greater than the percentage of input which appeared in the pH 5.0 wash in the first cycle.

Fusion phage from the pH 2.0 fraction of the second pass of the MYMUT library were amplified and subjected to a third passage over HNE beads. The proportion of fusion phage appearing in the pH 3.5 fraction relative to that in the 4.5 fraction was greater in the third passage than in the second passage (FIG. 8). Also the amount of fusion phage appearing in the pH 3.5 fraction was higher in the third passage than in the second passage. The fact that wash conditions less than pH 4.25 were required to elute bound fusion phage derived from the MYMUT library suggests that the EpiNEs displayed by these phage possess a higher affinity for HNE than the BPTI(K15V,R17L) variant.

b) Characterization of Selected Clones

Figure 9:
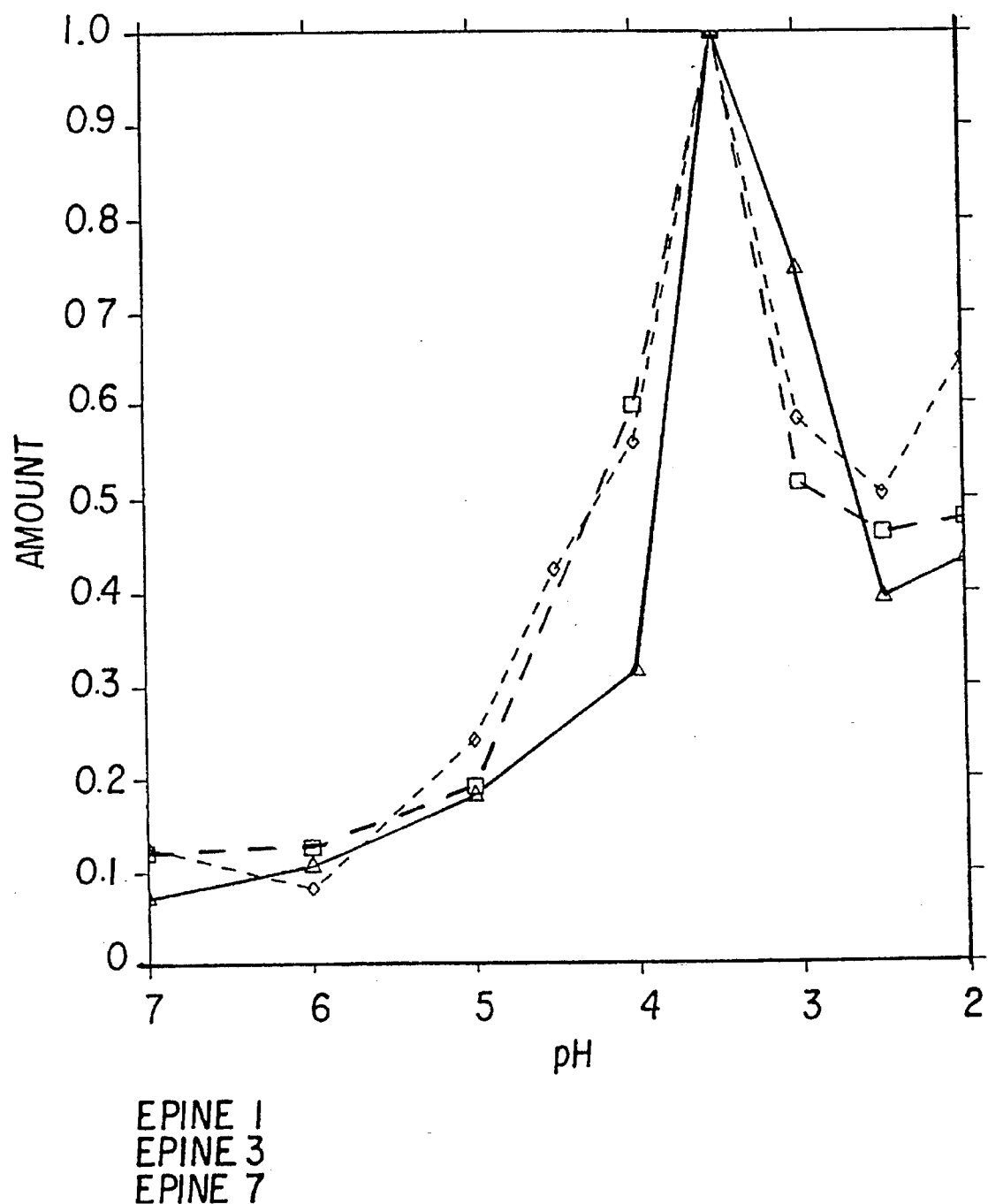
FIG. 9 shows the elution profiles for EpiNE clones 1, 3, and 7. Each profile is scaled so that the peak is 1.0 to emphasize the shape of the curve.

The pH 2.0 fraction from the third enrichment cycle of the MYMUT library was titered on a lawn of cells. Twenty plaques were picked at random. Rf DNA was prepared for each of the clones and fusion phage were collected by PEG precipitation. Clonally pure populations of fusion phage in TBS/BSA were prepared and characterized with respect to their affinity for immobilized HNE. pH elution profiles were obtained to determine the stringency of the conditions required to elute bound fusion phage from the HNE matrix. FIG. 9 illustrates the pH profiles obtained for EpiNE clones 1, 3, and 7. The pH profiles for all 3 clones exhibit a peak centered on pH 3.5. Unlike the pH profile obtained for the third passage of the MYMUT library, no minor peak centered on pH 4.5 is evident. This is consistent with the clonal purity of the selected EpiNE phage utilized to generate the profiles. The elution peaks are not symmetrical and a prominent trailing edge on the low pH side. In all probability, the 10 minute elution period employed is inadequate to remove bound fusion phage at the low pH conditions. EpiNE clones 1 through 8 have the following characteristics: five clones (identified as EpiNE1, EpiNE3, EpiNE5, EpiNE6, and EpiNE7) display very similar pH profiles centered on pH 3.5. The remaining 3 clones elute in the pH 3.5 to 4.0 range. There remains some diversity amongst the 20 randomly chosen clones obtained from the pH 2.0 fraction of the third passage of the MYMUT library and these clones might exhibit different affinities for HNE.

c) Sequences of the EpiNE Clones

The DNA sequences encoding the P1 regions of the different EpiNE clones were determined by dideoxy sequencing of Rf DNA. The sequences are shown in Table 208. Essentially, only the codons targeted for mutagenesis (i.e. 15 to 19) were altered as a consequence of cassette mutagenesis using the MYMUT oligonucleotide. Only 1 codon outside the target region was found to contain an unexpected alteration. In this case, codon 21 of EpiNE8 was altered from a tyrosine codon (TAT) to a SER codon (TCT) by a single nucleotide substitution. This error could have been introduced into the MYMUT oligonucleotide during its synthesis. Alternatively, an error could have been introduced when the single-stranded MYMUT oligonucleotide was converted to the double-stranded form by Sequenase. Regardless of the reason, the error rate is extremely low considering only 1 unexpected alteration was observed after sequencing 20 codons in 19 different clones. Furthermore, the value of such a mutation is not diminished by its accidental nature.

Some of the EpiNE clones are identical. The sequences of EpiNE1, EpiNE3, and EpiNE7 appear a total of 4, 6 and 5 times respectively. Assuming the 1745 potentially different DNA sequences encoded by the MYMUT oligonucleotide were present at equal frequency in the fusion phage library, the frequent appearance of the sequences for clones EpiNE1, EpiNE3, and EpiNE7 may have important implications. EpiNE1, EpiNE3, and EpiNE7 fusion phage may display BPTI variants with the highest affinity for HNE of all the 1000 potentially different BPTI variants in the MYMUT library.

An examination of the sequences of the EpiNE clones is illuminating. A strong preference for either VAL or ILE at the P1 position (residue 15) is indicated with VAL being favored over ILE by 14 to 6. In the MYMUT library, VAL at position 15 is approximately twice as prevalent as ILE. No examples of LEU, PHE, or MET at the P1 position were observed although the MYMUT oligonucleotide has the potential to encode these residues at P1. This is consistent with the observation that BPTI variants with single amino acid substitutions of LEU, PHE, or MET for $LYS_{15}$ exhibit a significantly lower affinity for HNE than their counterparts containing either VAL or ILE (BECK88b).

PHE is strongly favored at position 17, appearing in 12 of 20 codons. MET is the second most prominent residue at this position but it only appears when VAL is present at position 15. At position 18 PHE was observed in all 20 clones sequenced even though the MYMUT oligonucleotide is capable of encoding other residues at this position. This result is quite surprising and could not be predicted from previous mutational analysis of BPTI, model building, or on any theoretical grounds. We infer that the presence of PHE at position 18 significantly enhances the ability each of the EpiNEs to bind to HNE. Finally at position 19, PRO appears in 10 of 20 codons while SER, the second most prominent residue, appears at 6 of 20 codons. Of the residues targeted for mutagenesis in the present study, residue 19 is the nearest to the edge of the interaction surface of a PEPI with HNE. Nevertheless, a preponderance of PRO is observed and may indicate that PRO at 19, like PHE at 18, enhances the binding of these proteins to HNE. Interestingly, EpiNE5 appears only once and differs from EpiNE1 only at position 19; similarly, EpiNE6 differs from EpiNE3 only at position 19. These alterations may have only a minor effect on the ability of these proteins to interact with HNE. This is supported by the fact that the pH elution profiles for EpiNE5 and EpiNE6 are very similar to those of EpiNE1 and EpiNE3 respectively.

Only EpiNE2 and EpiNE8 exhibit pH profiles which differ from those of the other selected clones. Both clones contain LYS at position 19 which may restrict the interaction of BPTI with PINE. However, we can not exclude the possibility that other alterations within EpiNE2 and EpiNE8 (R15L and Y21S respectively) influence their affinity for HNE.

EpiNE7 was expressed as a soluble protein and analyzed for HNE inhibition activity by the fluorometric assay of Castillo et al. (CAST79); the data were analyzed by the method of Green and Work (GREE53). Preliminary results indicate that $K_d(HNE,EpiNE7) \leq 8. \cdot 10^{-12}M$, i.e. at least 7.5-fold lower than the lowest $K_d$ reported for a BPTI derivative with restect to HNE.

C. Summary

Taken together, these data show that the alterations which appear in the P1 region of the EPI mutants confer the ability to bind to HNE and hence be selected through the fractionation process. That the Sequences of EpiNE1, EpiNE3, and EpiNE7 appear frequently in the population of selected clones suggests that these clones display BPTI variants with the highest affinity for PINE of any of the 1000 potentially different variants in the MYMUT library. Furthermore, that pH conditions less than 4.0 are required to elute these fusion phage from immobilized HNE suggests that they display BPTI variants having a higher affinity for HNE than BPTI(K15V,R17L). EpiNE7 exhibits a lower $K_d$ toward HNE than does BPTI(K15V,R17L); EpiNE1 and EpiNE3 should are also expected to exhibit lower $K_d$s for HNE than BPTI(K15V,R17L). It is possible that all of the listed EpiNEs have lower $K_d$s than BPRI(K15V,R17L).

Position 18 has not previously been identified as a key position in determining specificity or affinity of aprotinin homologues or derivatives for particular serine proteases. None have reported or suggested that phenylalanine at position 18 will confer specificity and high affinity for HNE. One of the powerful advantages of the present invention is that many diverse amino-acid sequences may be tested simultaneously.

EXAMPLE V

Screening of the Mymut Library for Binding to Cathepsin G Beads

We fractionated the MYMUT library over immobilized human Cathepsin G to find an engineered protease inhibitor having high affinity for Cathepsin G, hereafter designated as an EpiC. The details of phage binding, elution of bound phage with buffers of decreasing pH (pH profile), titering of the phage contained in these fractions, composition of the MYMUT library, and the preparation of cathepsin G (Cat G) beads are essentially the same as detailed in Example IV.

Figure 10:
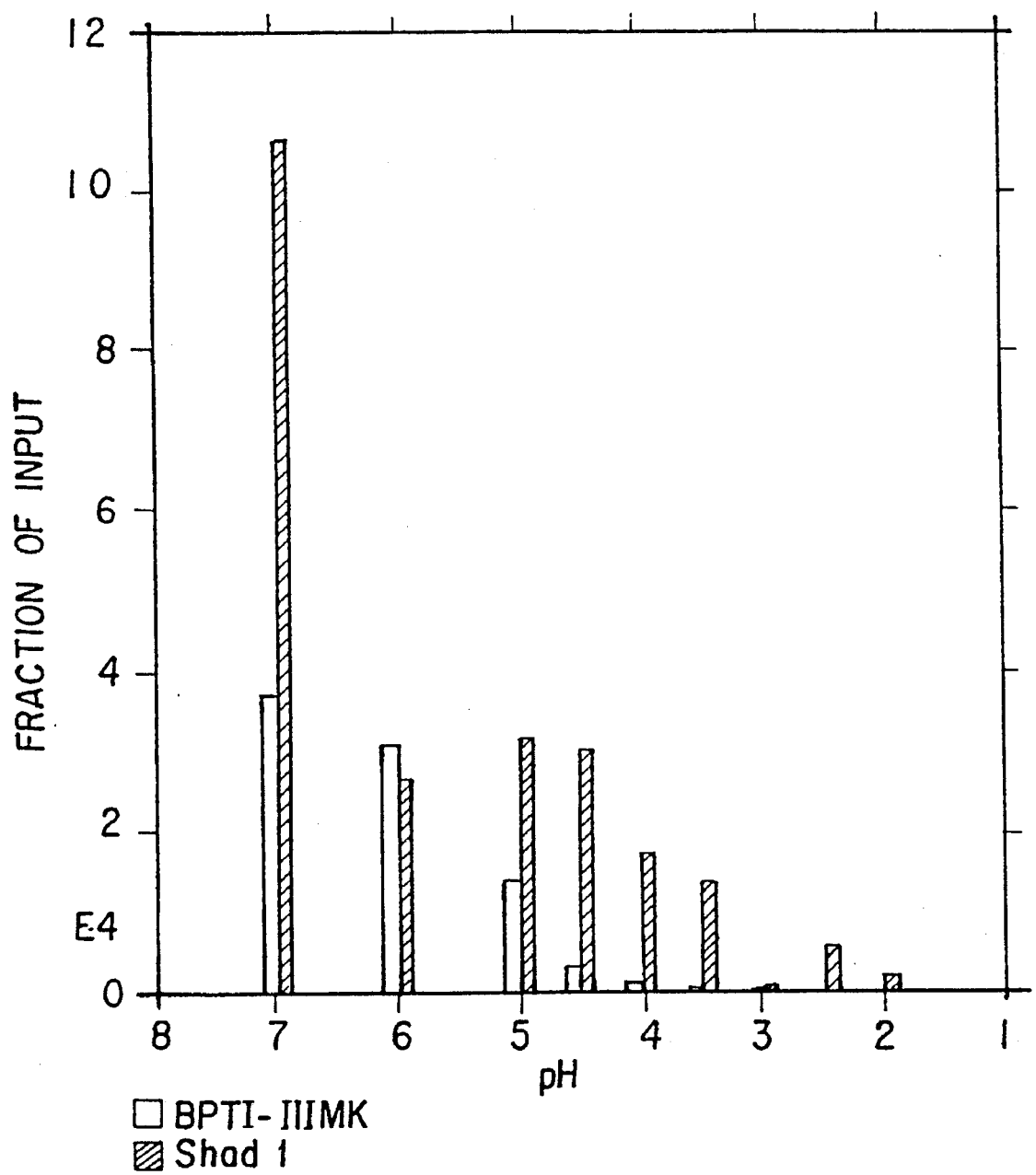
FIG. 10 shows pH profile for the binding of BPTI-III MK and EpiNE1 on cathepsin G beads. The abscissae shows pH of buffer. The ordinants show amount of phage (as fraction of input phage) obtained at given pH. Ordinants scaled by $10^3$.

A pH profile for the binding of two starting controls, BPTI-III MK and EpiNE1, are shown in FIG. 10. BPTI-III MK phage, which contains wild type BPTI fused to the III gene product, shows no apparent binding to Cat G beads in this assay. EpiNE1 phage was obtained by enrichment with HNE beads (Example IV and Table 208). EpiNEi-III MK demonstrated little binding to Cat G beads in the assay, although a small peak or shoulder is visible in the pH 5 eluted fraction.

Figure 11:
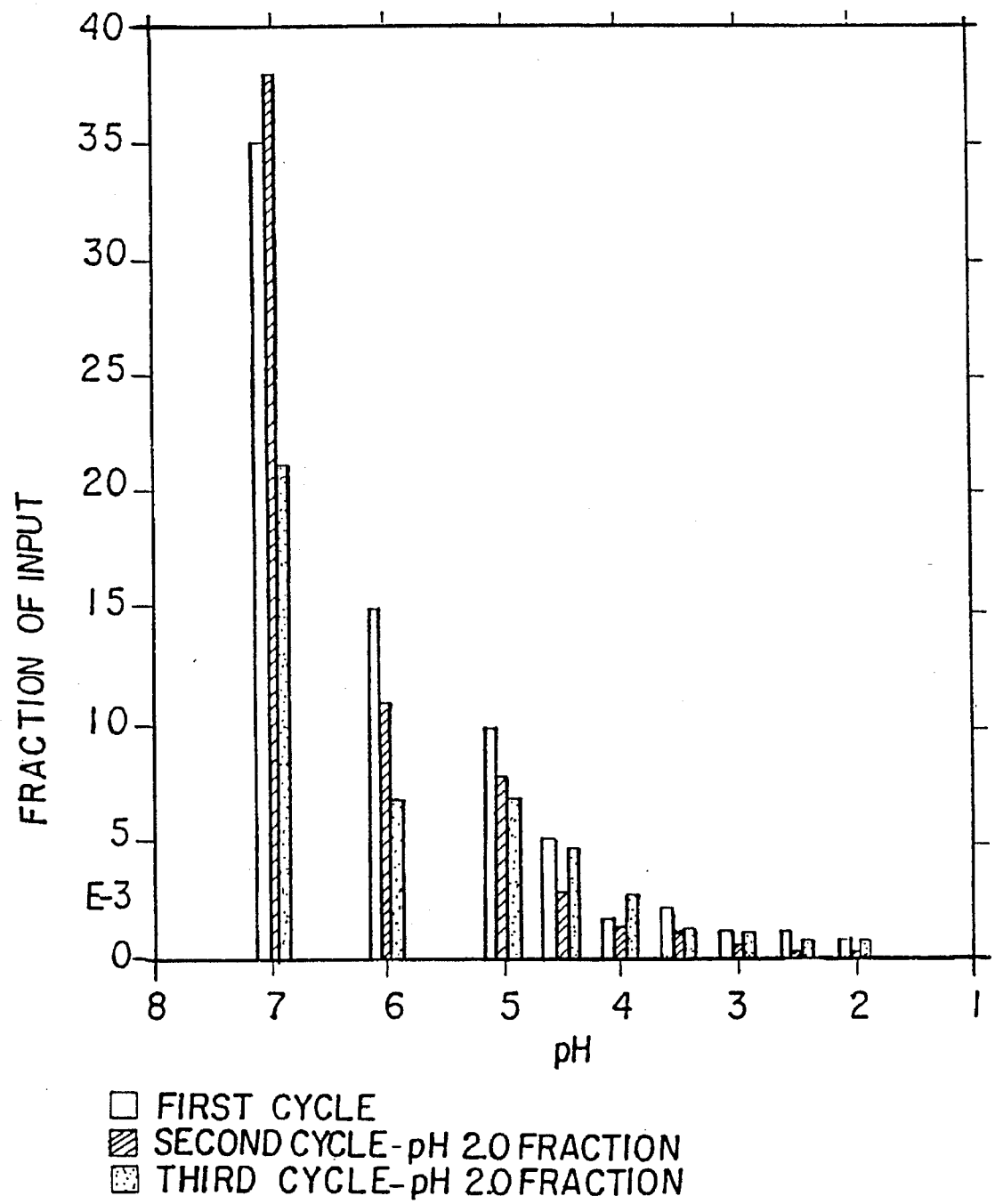
FIG. 11 shows pH profile for the fraxctionation of the MYMUT Library on cathepsin G beads. The abscissae shows pH of buffer. The ordinants show amount of phage (as fraction of input phage) obtained at given pH. Ordinants scaled by $10^3$.

FIG. 11 shows the pH profiles of the MYMUT library phage when bound to Cat G beads. Library-Cat G interaction was monitored using three cycles of binding, pH elution, transduction of the pH 2 eluted phage, growth of the transduced phage and rebinding of any selected phage to Cat G beads, in an exact copy of that used to find variants of BPTI which bound to HNE. In contrast to the pH profiles elicited with HNE beads, little enhancement of binding was observed for the same phage library when cycled with Cat G beads (with the exception of a possible 'shoulder' developing in the pH 5 elutions).

Figure 12:
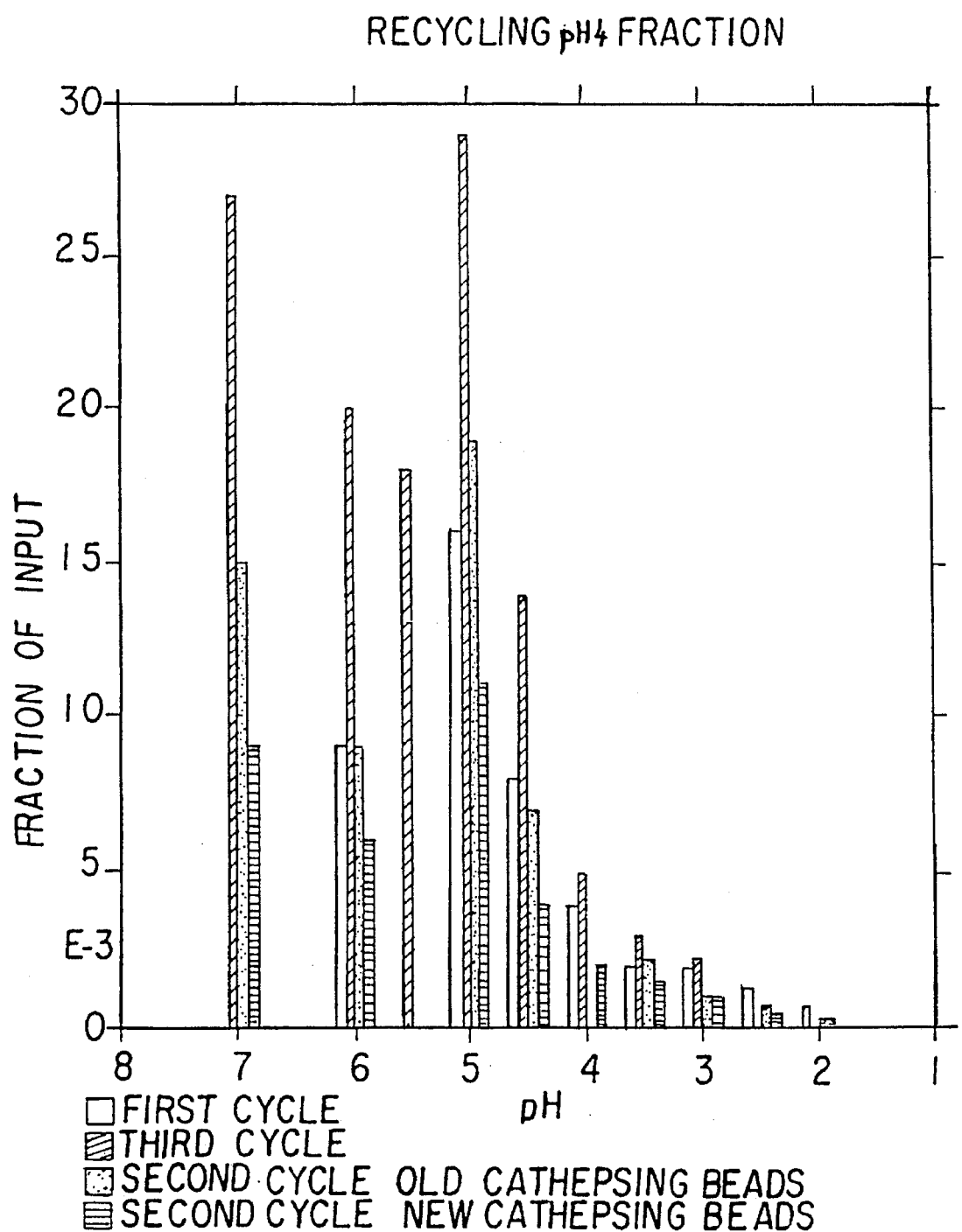
FIG. 12 shows a second fractionation of MYMUT library over cathepsin G.

To investigate the elution profile around the pH 5 point in more detail, the binding of phage taken from the pH 4 eluted fraction (bound to Cat G beads) rather than the previously used pH 2 fraction was examined. FIG. 12 demonstrates a marked enhancement of phage binding to the Cat G beads with an apparent elution peak of pH 5. The binding, as a fraction of the input phage population, increased with subsequent binding and elution cycles.

Figure 13:
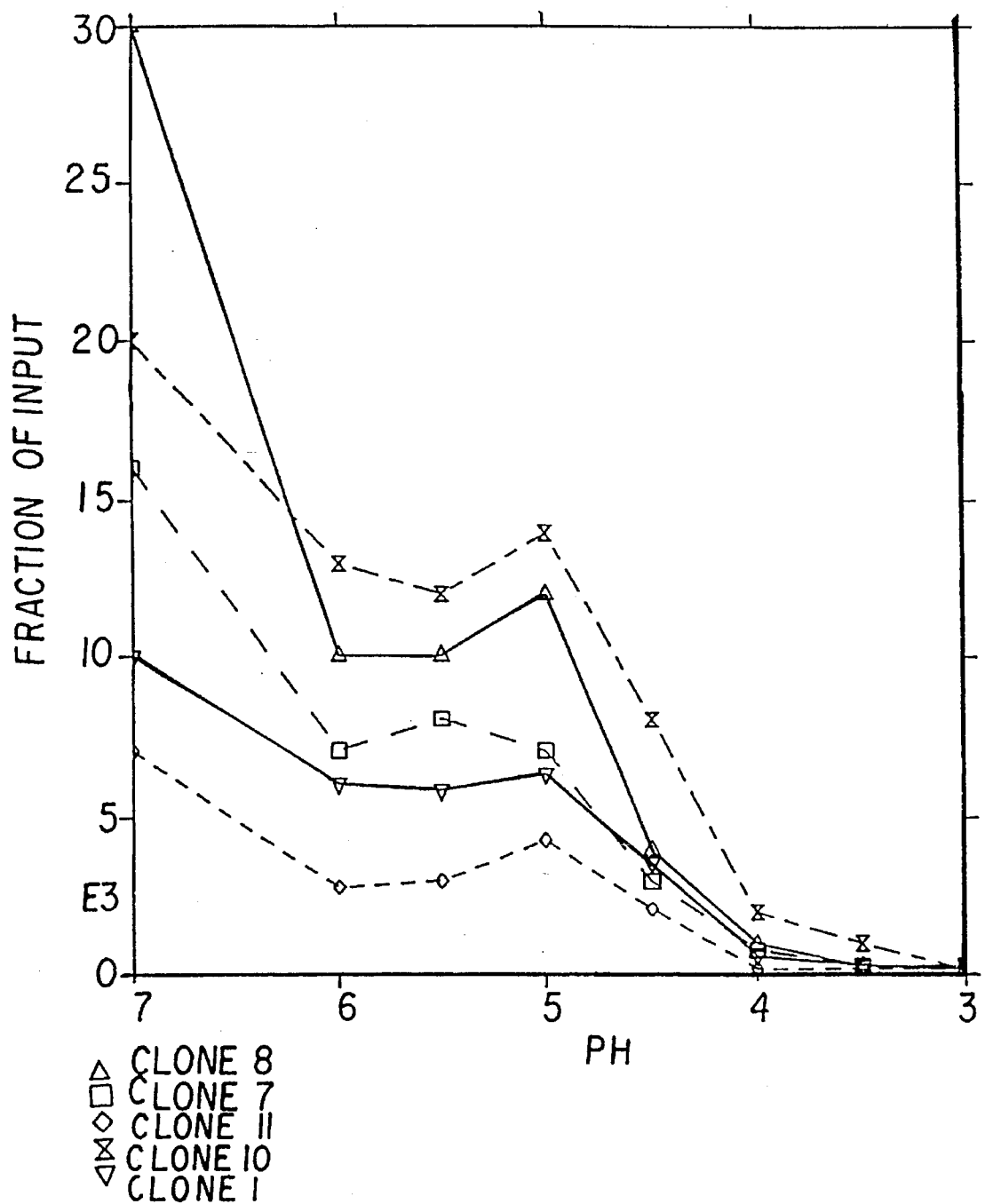
FIG. 13 shows elution profiles on immobilized cathepsin G for phage selected for binding to cathepsin G.

Individual phage clones were picked, grown and analyzed for binding to Cat G beads. FIG. 13 shows the binding and pH profiles for the individual Cat G binding clones (designated Epic variants). All clones exhibited minor peaks, superimposed upon a gradual fall in bound phage, at pH elutions of 5 (clones 1, 8, 10 and 11) or pH 4.5 (clone 7).

DNA sequencing of the Epic clones, shown in Table 209, demonstrated that the clones selected for binding to Cat G beads represented a distinct subset of the available sequences in the MYMUT library and a cluster of sequences different from that obtained when enriched with HNE beads. The P1 residue in the Epic mutants is predominantly MET, with one example of PHE, while in BPTI it is LYS and in the EpiNE variants it is either VAL or LEU. In the Epic mutants residue 16 is predominantly ALA with one example of GLY and residue 17 is PHE, ILE or LEU. Interestingly residues 16 and 17 appear to pair off by complementary size, at least in this small sample. The small GLY residue pairs with the bulky PHE while the relatively larger ALA residue pairs with the less bulky LEU and ILE. The majority of the available residues in the MYMUT library for positions 18 and 19 are represented in the Epic variants.

Hence, a distinct subset of related sequences from the MYMUT library have been selected for and demonstrated to bind to Cat G. A comparison of the pH profiles elicited for the Epic variants with Cat G and the EpiNE variants for HNE indicates that the EpiNE variants have a high affinity for HNE while the Epic variants have a moderate affinity for Cat G. Nonetheless, the starting molecule, BPTI, has virtually no detectable affinity for Cat G and the selection of clones with a moderate affinity is a significant finding.

EXAMPLE VI

Second Round of Variegation of EpiNE7 to Enhance Binding to HNE

A. Mutagenesis of EpiNE7 Protein in the Loop Comprising Residues 34–41

In Example IV, we described engineered protease inhibitors EpiNE1 through EpiNE8 that were obtained by affinity selection. Modeling of the structure of the BPTI-Trypsin complex (Brookhaven Protein Data Bank entry 1TPA) indicates that the EpiNE protein surface that interacts with HNE is formed not only by residues 15–19 but also by residues 34–40 that are brought close to this primary loop when the protein folds (HUBE74, HUBE75, OAST88). Acting upon this assumption, we changed amino acid residues in a second loop of the EpiNE7 protein to find EpiNE7 derivatives having higher affinity for HNE.

In the complex of BPTI and trypsin found in Brookhaven Protein Data Bank entry 1TPA ("1TPA complex"), $VAL_{34}$ contacts $TYR_{151}$ and $GLN_{192}$. (Residues in trypsin or HNE are underscored to distinguish them from the inhibitor.) In HNE, the corresponding residues are $ILE_{151}$ and $PHE_{192}$. ILE is smaller and more hydrophobic than TYR. PHE is larger and more hydrophobic than GLN. Neither of the HNE side groups have the possibility to form hydrogen bonds. When side groups larger than that of VAL are substituted at position 34, interactions with residues other than 151 and 192 may be possible. In particular, an acidic residue at 34 might interact with $ARG_{147}$ of HNE that corresponds to $SER_{147}$ of trypsin in 1TPA. Table 15 shows that, in 59 homologues of BPTI, 13 different amino acids have been seen at position 34. Thus we allow all twenty amino acids at 34.

Position 36 is not highly varied; only GLY, SER, and ARG have been observed with GLY by far the most prevalent. In the 1TPA complex, $GLY_{36}$ contacts $HIS_{57}$ and $GLN_{192}$. $HIS_{57}$ is conserved and $GLN_{192}$ corresponds to $PHE_{192}$ of HNE. Adding a methyl group to $GLY_{36}$ could increase hydrophobic interactions with $PHE_{92}$ of HNE. $GLY_{36}$ is in a conformation that most amino acids can achieve: $\phi=-79°$ and $\psi=-9°$ (Deisenhoffer cited in CREI84, p.222.).

In the 1TPA complex, $ARG_{39}$ contacts $SER_{96}$, $ASN_{97}$, $THR_{98}$, $LEU_{99}$, $GLN_{175}$, and $TRP_{215}$. In HNE, all of the corresponding residues are different! $SER_{96}$ is deleted; $ASN_{97}$ corresponds to $ASP_{97}$ (bearing a negative charge); $THR_{98}$ corresponds to $PRO_{98}$; $LEU_{99}$ corresponds to the residues $VAL_{99}$, $ASN_{99a}$, and $LEU_{99b}$; $GLN_{175}$ is deleted; and $TRP_{215}$ corresponds to $PHE_{215}$. Position 39 shows a moderately high degree of variability with 7 different amino acids observed, viz. ARG, GLY, LYS, GLN, ASP, PRO, and MET. Having seen PRO (the most rigid amino acid), GLY (the most flexible amino acid), LYS and ASP (basic and acidic amino acids), we assume that all amino acids are structurally compatible with the aprotinin backbone. Because the context of residue 39 has changed so much, we allow all 20 amino acids.

Position 40 is not highly variable; only GLY and ALA have been observed (with similar frequency, 24:16). Position 41 is moderately varied, showing ASN, LYS, ASP, GLN, HIS, GLU, and TYR. The side groups of residues 40 and 41 are not thought to contact trypsin in the 1TPA complex. Nevertheless, these residues can exert electrostatic effects and can influence the dynamic properties of residues 39, 38, and others. The choice of residues 34, 36, 39, 40, and 41 to be varied simultaneously illustrates the rule that the varied residues should be able to touch one molecule of the target material at one time or be able to influence residues that touch the target. These residues are not contiguous in sequence, nor are they contiguous on the surface of EpiNE7. They can, nonetheless, all influence the contacts between the EpiNE and HNE.

Amino acid residues $VAL_{34}$, $GLY_{36}$, $MET_{39}$, $GLY_{40}$, and $ASN_{41}$ were variegated as follows: any of 20 genetically encodable amino acids at positions 34 and 39 (NNS codons in which N is approximately equimolar A,C,T,G and S is approximately equimolar C and G), GLY or ALA at position 36 and 40 (GST codon), and [ASP, GLU, HIS, LYS, ASN, GLN, TYR, or stop] at position 41 (NAS codon). Because the PEPIs are displayed fused to gIII protein, DNA containing stop codons will not give rise to infectuous phage in non-suppressor hosts.

For cassette mutagenesis, a 61 base long oligonucleotide DNA population was synthesized that contained 32,768 different DNA sequences coding on expression for a total of 11,200 amino acid sequences. This oligonucleotide extends from the third base of codon 51 in Table 113 (the middle of the StuI site) to base 2 of codon 70 (the EagI site (identified as XmaIII in Table 113)).

We used a mutagenesis method similar to that described by Cwirla et al. (CWIR90) and other standard DNA manipulations described in Maniatis et al. (MANI82) and Sambrook et al. (SAMB89). EpiNE7 RF DNA was restricted with EagI and StuI, agarose gel purified, and dephosphorylated using $HK^{(TM)}$ phosphatase (Epicentre Technologies). We prepared insert by annealing two small, 16 base and 17 base, phosphorylated synthetic DNA primers to the phosphorylated 61 base long oligonucleotide population described above. The resulting insert DNA population had the following features: double stranded DNA ends capable of regenerating upon ligation the EagI (5' overhang) and StuI (blunt) restricted sites of the EpiNE7 RF DNA, and single stranded DNA in the central mutagenic region. Insert and EpiNE7 vector DNA were ligated. Ligation samples were used to transfect competent XL1-Blue$^{(TM)}$ cells which were subsequently plated for formation of ampicillin resistant ($Ap^R$) colonies. The resulting phage-producing, $Ap^R$ colonies were harvested and recombinant phage was isolated. By following these procedures, a phage library of $1.2 \cdot 10^5$ independent transformants was assembled. We estimated that 97.4% of the approximately $3.3 \cdot 10^4$ possible DNA sequences were represented:

$$0.974 = (1 - \exp\{-1.2 \cdot 10^5 / 32768\})$$

The probability of observing the parental sequence is higher than 0.974 because VAL occurs twice in the NNS codon:

| Probability of seeing $(V_{34}, G_{36}, M_{39}, G_{40}, N_{41})$ | = | $(1 - \exp\{-(1.2 \cdot 10^5 \times 2/32768)\})$ |
|---|---|---|
| | = | $(1 - \exp\{-7.32\})$ |
| | = | $(1 - 6.5 \cdot 10^{-4})$ |
| | = | 0.99934 |

Furthermore, we expect that a small amount (for example, 1 part in 1000) of uncut or once-cut and religated parental vector would come through the procedures used. Thus the parental sequence is almost certainly present in the library. This library is designated the KLMUT library.

B. Affinity Selection with Immobilized Human Neutrophil Elastase

1) First Fractionation

We added $1.1 \cdot 10^8$ plaque forming units of the KLMUT library to 10 µl of a 50% slurry of agarose-immobilized human neutrophil elastase beads (HNE from Calbiochem cross-linked to Reacti-Gel$^{(TM)}$ agarose beads from Pierce Chemical Co. following manufacturer's directions) in TBS/BSA. Following 3 hours incubation at room temperature, the beads were washed and phage was eluted as done in the selection of EpiNE phage isolates (Example IV). The progression in lowering pH during the elution was: pH 7.0, 6.0, 5.0, 4.5, 4.0, 3.5, 3.0, 2.5, and 2.0. Beads carrying phage remaining after pH 2.0 elution were used to infect XL1-Blue$^{(TM)}$ cells that were plated to allow plaque formation. The 348 resulting plaques were pooled to form a phage population for further affinity selection. A population of phage particles containing $6.0 \cdot 10^8$ plaque forming units was added to 10 μl of a 50% slurry of agarose-immobilized HNE beads in TBS/BSA and the above selection procedure was repeated.

Following this second round of affinity selection, a portion of the beads was mixed with XL1-Blue$^{(TM)}$ cells and plated to allow plaque formation. Of the resulting plaques, 480 were pooled to form a phage population for a third affinity selection. We repeated the selection procedure described above using a population of phage particles containing $3.0 \cdot 10^9$ plaque forming units. Portions of the pH 2.0 eluate and of the beads were plated with XL1-Blue$^{(TM)}$ cells to allow formation of plaques. Individual plaques were picked for preparation of RF DNA. From DNA sequencing, we determined the amino acid sequence in the mutated secondary loop of 15 EpiNE7-homolog clones. The sequences are given in Table 210 as EpiNE7.1 through EpiNE7.20. Three sequences were observed twice: EpiNE7.4 and EpiNE7.14; EpiNE7.8 and EpiNE7.9; and EpiNE7.10 and EpiNE7.20. EpiNE7.4 was eluted at pH 2 while EpiNE7.14 was obtained by culturing HNE beads that had been washed with pH 2 buffer. Similarly, EpiNE7.10 came from pH 2 elution but EpiNE7.20 came from beads. EpiNE7.8 and EpiNE7.9 both came from pH 2 elution. Interestingly, EpiNE7.8 is found in both the first and second fractionations (EpiNE7.31 (vide infra)).

2) Second Fractionation

The purpose of affinity fractionation is to reduce diversity on the basis of affinity for the target. The first enrichment step of the first fractionation reduced the population from $3 \cdot 10^4$ possible DNA sequences to no more than 348. This might be too severe and some of the loss of diversity might not be related to affinity. Thus we carried out a second fractionation of the entire KLMUT library seeking to reduce the diversity more gradually.

We added $2.0 \cdot 10^{11}$ plaque forming units of the KLMUT library to 10 μl of a 50% slurry of agarose-immobilized HNE beads in TBS/BSA. Following 3 hours incubation at room temperature, phage were eluted as described above. We then transduced XL1-Blue$^{(TM)}$ cells with portions of the pH 2.0 eluate and plated for Ap$^R$ colonies.

The resulting phage-producing colonies were harvested to obtain amplified phage for further affinity selection. A population of these phage particles containing $2.0 \cdot 10^{10}$ plaque forming units was added to 10 μl of a 50% slurry of agarose-immobilized HNE beads in TBS/BSA and incubated for 90 minutes at room temperature. Phage were eluted as described above and portions of the pH 2.0 eluate were used to transduce XL1-Blue$^{(TM)}$ cells. We plated the transductants for Ap$^R$ colonies and obtained amplified phage from the harvested colonies.

In a third round of affinity selection, a population of phage particles containing $3.0 \cdot 10^{10}$ plaque forming units was added to 20 μl of 50% slurry of agarose-immobilized HNE beads and incubated for 2 hours at room temperature. We eluted the phage with the following pH washes: pH 7.0, 6.0, 5.0, 4.5, 4.0, 3.5, 3.25, 3.0, 2.75, 2.5, 2.25, and 2.0. After plating a portion of the pH 2.0 eluate fraction for plaque formation, we picked individual plaques for preparation of RF DNA. DNA sequencing yielded the amino acid sequence in the mutated secondary loop for 20 EpiNE7 homolog clones. These sequences, together with EpiNE7, are given in Table 210 as EpiNE7.21 through EpiNE7.40. The plaques observed when EpiNEs are plated display a variety of sizes. EpiNE7.21 through EpiNE7.30 were picked with attention to plaque size: 7.21, 7.22, and 7.23 from small plaques, 7.24 through 7.30 from plaques of increasing size, with 7.30 coming from a large plaque. TRP occurs at position 39 in EpiNE7.21, 7.22, 7.23, 7.25, and 7.30. Thus plaque size does not correlate with the appearance of TRP at 39. One sequence, EpiNE7.31, from this fractionation is identical to sequences EpiNE7.8 and EpiNE7.9 obtained in the first fractionation. EpiNE7.30, EpiNE7.34, and EpiNE7.35 are identical, indicating that the diversity of the library has been greatly reduced. It is believed that these sequences have an affinity for HNE that is at least comparable to that of EpiNE7 and probably higher. Because the parental EpiNE7 sequence did not recur, it is quite likely that some or all of the EpiNE7.nn derivatives have higher affinity for HNE than does EpiNE7.

3) Conclusions

One can draw some conclusions. First, because some sequences have been isolated repeatedly, the fractionation is nearly complete. The diversity has been reduced from $\geq 10^4$ to a few tens of sequences.

Second, the parental sequence has not recurred. At 39, MET did not occur! At position 34 VAL occurred only once in 35 sequences. At 41, ASN occurred only 4 of 35 times. At 40, GLY occurred 17 of 35 times. At position 36, GLY occurred 34 of 35 times, indicating that ALA is undesirable here. EpiNE7.24 and EpiNE7.36 are most like EpiNE7, having three of the varied residues identical to EpiNE7.

Third, the results of the first and second fractionation are similar. In the second fractionation, the prevalence of TRP at position 39 is more marked (5/15 in fractionation #1, 14/20 in #2). It is possible that the first fractionation lost some high-affinity EPIs through under-sampling. Nevertheless, the first fractionation was clearly quite successful.

Fourth, there are strong preferences at positions 39 and 36 and lesser but significant preferences at positions 34 and 41 with little preference at 40.

Heretofore, no homologues of aprotinin have been reported having ALA at 36. In the selected EpiNE7.nn sequences, the preference for GLY over ALA at position 36 is 34:1. This preference is probably not due to differences in protein stability. The process of the present invention, as applied in the present example, does not select against proteins on the basis of stability so long as the protein does fold and function at the temperature used in the procedure. ALA is probably tolerated at position 36 well enough to allow those proteins having ALA$_{36}$ to fold and function; one example was found having ALA$_{36}$. It may be relevant that the sole sequence having ALA$_{36}$ also has GLY$_{34}$. The flexibility of GLY at 34 may allow the methyl of ALA at 36 to fit into HNE in a way that is not possible when other amino acids occupy position 34.

At position 39, all 20 amino acids were allowed, but only seven were seen. TRP is strongly preferred with 19 occurrences, HIS second with six occurences, and LEU third with 5 occurrences. No homologues of aprotinin have been reported having either TRP or HIS at position 39 as are now disclosed. Although LEU is represented in the NNS codon thrice, TRP and HIS have but one codon each and their prevalence is surprising. We constructed a model having HNE (Brookhaven Protein Data Bank entry 1HNE) and EpiNE7.9 spatially related as in the 1TPA complex. (The α carbons of HNE of conserved internal residues were superimposed on the corresponding α carbons of trypsin, rms deviation ≈0.5 Å) Inspection of this model indicates that TRP$_{39}$ could interact with the loop of HNE that comprises VAL$_{99}$, ASN$_{99a}$, and LEU$_{99b}$. HIS is observed in six cases; HIS is hydrophobic, aromatic, and in some ways similar to TRP. LEU$_{39}$ in EpiNE7.5 could also interact with these residues if the loop moves a short distance. GLU occurred twice while LYS, ARG, and GLN occurred once each. In BPTI, the $C_\alpha$ of residue 39 is ≈10 Å from the $C_\alpha$ of residue 15 so that $TRP_{39}$ interacts with different features of HNE than do the amino acids substituted at position 15. Residue 34 is well separated from each of the residues 15, 18, and 39; thus it contacts different features on the HNE surface from these residues. Although serine proteases are highly similar near the catalytic site, the similarity diminishes rapidly outside this conserved region. The specificity of serine proteases is in fact determined by more interactions than the P1 residue. To make an inhibitor that is highly specific to HNE, we must go beyond matching the requirement at P1. Thus, the substitutions at 18 (determined in Example IV), 39, 34, and other non-P1 positions are invaluable in customizing the EpiNE to HNE. When making an inhibitor customized to a different serine protease, it is likely that many, if not all, of these positions will be changed to obtain high affinity and specificity. It is a major advantage of the present method that many such derivatives may be tested rapidly.

At position 34, all 20 amino acids were allowed. Fourteen have been seen. LYS appeared seven times, GLU five times, THR four times, LEU three times, GLY, ASP, GLN, MET, ASN, and HIS twice each, and ARG, PRO, VAL, and TYR once each. There were no instances of ALA, CYS, PHE, ILE, SER, or TRP. No homologue of aprotinin with GLU, GLY, or MET at 34 has been reported heretofore. Here, as at position 39, the library contains an excess of LEU over LYS and GLU. Thus, we infer that the prevalence of LYS, GLU, THR, and LEU is related to tighter binding of EpiNEs having these amino acids at position 34. The prevalence of LYS is surprising, as there are no acidic groups on HNE in the neighborhood. The $N_{zeta}$ of $LYS_{34}$ could interact with a main-chain carbonyl oxygen while the methylene groups interact with $ILE_{151}$ and/or $PHE_{192}$. $LEU_{34}$ could interact with $ILE_{151}$ and/or PHE192 while $GLU_{34}$ could interact with $ARG_{147}$.

There has been little if any enrichment at positions 40 and 41. Alanine is somewhat preferred at 40; ALA:GLY::19:16. Both ALA and GLY have been reported in aprotinin homologues.

Position 41 shows a preponderance of LYS (12 occurrences) and GLU (7), but all eight possibilities have been seen. The overall distribution is $LYS^{12}$, $GLU^7$, $ASP^4$, $ASN^4$, $GLN^3$, $HIS^3$, and $TYR^2$. Heretofore no homologues of aprotinin having GLU, GLN, HIS, or TYR at position 41 have been reported.

One sequence, EpiNE7.25 contains an unexpected change at position 47, SER to LEU. Heretofore, all homologues of aprotinin reported have had either SER or THR at position 47. The side groups of SER and THR can form hydrogen bonds to main-chain atoms at the beginning of the short α helix.

The consensus sequence, $LYS_{34}$, $GLY_{36}$, $TRP_{39}$, $ALA_{40}$, $LYS_{41}$ was not observed. EpiNE7.23 is quite close, differing only at position 40 where the preference for ALA is very, very weak.

We tested EpiNE7.23 (the sequence closest to consensus) against EpiNE7 on HNE beads. FIG. 16 shows the fractionation of strains of phage that display these two EpiNEs. Phage that display EpiNE7 are eluted at higher pH than are phage that display EpiNE7.23. Furthermore, more of the EpiNE7.23 phage are retained than of the EpiNE7 phage. Note the peak at pH 2.25 in the EpiNE7.23 elution. This suggests that EpiNE7.23 has a higher affinity for HNE than does EpiNE7. In a similar way, we tested EpiNE7.4 and found that it is not retained on HNE so well as EpiNE7. This is consistent with the fractionation not being complete.

Further fractionation, characterization of clonally pure EpiNE7.nn strains, and biochemical characterization of soluble EpiNE7.nn derivatives will reveal which sequences in this collection have the highest affinity for HNE.

Fractionation of the library involves a number of factors. Differential binding allows phage that display PBDs having the desired binding properties to be enriched. Differences in infectivity, plaque size, and phage yield are related to differences in the sequence of the PBDs, but are not directly correlated to affinity for the target. These factors may reduce the effectiveness of the desired fractionation. An additional factor that may be present is differential abundance Of PBD sequences in the initial library. One step we employ to reduce the effect of differential infectivity is to transduce cells with isolated phage rather than to infect them. In the first fractionation, we did not obtain sufficient material for transduction and so infected cells; this fractionation was successful. Because the parental sequence, EpiNE7, was selected for a sequence at residues 15 through 19 that confer high affinity for HNE, we believe that many, if not most, members of the KLMUT population have significant affinity for HNE. Thus the present fractionations must separate variants having very high affinity for HNE from those merely having high affinity for HNE. It is perhaps relevant that BPTI-III MK phage are only partially eluted from immobilized trypsin at pH 2.2.; Kd(trypsin,BPTI)=$6.0 \cdot 10^{-14}$M. Elution of EpiNE7-III MA phage from immobilized HNE gives a peak at about pH 3.5 with some phage appearing at lower pH; Kd(HNE,EpiNE7)≧$1 \cdot 10^{-11}$M. We recycled phage that either were eluted at pH 1.0 or that were retained after elution with pH 2.0 buffer. A large percentage of EpiNE7-III MA phage would have been washed away with the fractions at pHs less acid than 2.0. This, together with the marked preferences at positons 39, 36, and 34, strongly sugestes that we have successfully fractionated the KLMUT library on the basis of affinity for HNE and that the EpiNE7.nn proteins have higher affinity for HNE than does EpiNE7 or any other reported aprotinin derivative.

Fractionation in a few stringent steps emphasizes the affinity of the PBD and allows isolation of variants that confer a small-plaque phenotype on cells (through low infectivity or by slowing cell growth). More gradual fractionation allows observation of a wider variety of variants that show high affinity and favors sequences that start at low abundance. Gradual fractionation also favors selection of variants that do not confer a small-plaque phenotype; such variants may be easier to work with and are preferred for some purposes. In either case, it is preferred to fractionate until there is a manageable number of distinct isolates and to characterize these isolates as pure clones. Thus, it is desirable, in most cases, to fractionate a library in more than one way.

None have identified positions 39 and 34 as key in determining the affinity and specificity of aprotinin homologues and derivatives for particular serine proteases. None have suggested the tryptophan at 39 or charged amino acids (LYS or GLU) at 34 will enhance binding of an aprotinin homologue to HNE. Different substitutions at these positions is likely to confer different specificity on those derivatives. One of the major advantages of the present invention is that many substitutions at several locations may be tested with an amount of effort not much greater than is required to test a single derivative by previously used methods.

There exist a number of proteases produced by lymphocytes. Neutrophil elastase is not the only lymphocytic protease that degrades elastin. The protease p29 is related to HNE. Screening the MYMUT and KLMUT libraries against immobilized p29 is likely to allow isolation of an aprotinin derivative having high affinity for p29.

EXAMPLE VII

BPTI:VIII Boundary Expressions

The aim of this work was to introduce peptide extensions between the C-terminus of the BPTI domain and the N-terminus of the M13 major coat protein within the fusion protein. The reasons for this were two fold; firstly to alter potential protease cleavage sites at the interdomain boundary (as evidenced by an apparent instability of the fusion protein) and secondly to increase interdomain flexibility.
1) Insertion of a variegated pentapeptide at the BPTI:VIII interface.

The gene shown in Table 113 was modified by insertion of five RVT codons between codon 81 and 82. Two synthetic oligonucleotides were designed and custom synthesized. The first consisted of, from 5' to 3': a) from base 2 of codon 77 to the end of codon 81, b) five copies of RVT, and c) from codon 82 to the second base of codon 94. The second comprised of 20 bases complementary to the 3' end of the first oligonucleotide. Each RVT codon allows one of the amino acids [T, N, S, A, D, and G] to be encoded. This variegation codon was picked because: a) each amino acid occurs once, and b) all these amino acids are thought to foster a flexible linker. When annealed, the primed variegated oligonucleotide was converted to double-stranded DNA using standard methods.

The duplex was digested with restriction enzymes SfiI and NarI and the resulting 45 base-pair fragment was ligated into a similarly cleaved OCV, M13MB48 (Example I.1.iii.a). The ligated material was transfected into competent *E. coli* cells (strain XL1-Blue$^{(TM)}$) and plated onto a lawn of the same cells on normal bacterial growth plates to form plaques. The bacteriophage contained within the plaques were analyzed using standard methods of nitrocellulose lifts and probing using a $^{32}$P-labeled oligonucleotide complementary to the DNA sequence encoding the fusion protein interface. Approximately 80% of the plaques probed poorly with this oligonucleotide and hence contained new sequences at this position.

A pool of phages, containing the novel interface pentapeptide extensions, was collected by combining the phage extracted from the plated plaques.
2. Adding multiple unit extensions to the fusion protein interface.

The M13 gene III product contains 'stalk-like' regions as implied by electron micrographic visualization of the bacteriophage (LOPE85). The predicted amino acid sequence of this protein contains repeating motifs, which include:

glu.gly.gly.gly.ser (EGGGS) seven times gly.gly.gly.ser (GGGS) three times glu.gly.gly.gly.thr (EGGGT) once.

The aim of this section was to insert, at the domain interface, multiple unit extensions which would mirror the repeating motifs observed in the III gene product.

Two synthetic oligonucleotides were designed and custom synthesized. GLY is encoded by four codons (GGN); when translated in the opposite direction, these codons give rise to THR, PRO, ALA, and SER. The third base of these codons was picked so that translation of the oligonucleotide in the opposite direction would encode SER. When annealed the synthetic oligonucleotides give the following unit duplex sequence (an EGGGS linker):

```
      E   G   G   G   S
5' C.GAG.GGA.GGA.GGA.TC   3'
3'    TC.CCT.CCT.CCT.AGG.C 5'
     (L) (S) (S) (S) (G)
```

The duplex has a common two base pair 5' overhang (GC) at either end of the linker which allows for both the ligation of multiple units and the ability to clone into the unique NarI recognition sequence present in OCV's M13MB48 and Gem MB42. This site is positioned within 1 codon of the DNA encoding the interface. The cloning of an EGGGS linker (or multiple linker) into the vector NarI site destroys this recognition sequence. Insertion of the EGGGS linker in reverse orientation leads to insertion of GSSSL into the fusion protein.

Addition of a single EGGGS linker at the NarI site of the gene shown in Table 113 leads to the following gene:

```
79  80  80a 80b 80c 80d 80e 81  82  83  84
 G   G   E   G   G   G   S   A   A   E   G
 ---------------------
GGT.GGC.GAG.GGA.GGA.GGA.TCC.GCC.GCT.GAA.GGT
 ---------------------
```

Note that there is no preselection for the orientation of the linker(s) inserted into the OCV and that multiple linkers of either orientation (with the predicted EGGGS or GSSSL amino acid sequence) or a mixture of orientations (inverted repeats of DNA) could occur.

A ladder of increasingly large multiple linkers was established by annealing and ligating the two starting oligonucleotides containing different proportions of 5' phosphorylated and non-phosphorylated ends. The logic behind this is that ligation proceeds from the 3' unphosphorylated end of an oligonucleotide to the 5' phosphorylated end of another. The use of a mixture of phosphorylated and non-phosphorylated oligonucleotides allows for an element of control over the extent of multiple linker formation. A ladder showing a range of insert sizes was readily detected by agarose gel electrophoresis spanning 15 bp (1 unit duplex-5 amino acids) to greater than 600 base pairs (40 ligated linkers-200 amino acids).

Large inverted repeats can lead to genetic instability. Thus we chose to remove them, prior to ligation into the OCV, by digesting the population of multiple linkers with the restriction enzymes AccIII or XhoI, since the linkers, when ligated 'head-to-head' or 'tail-to-tail', generate these recognition sequences. Such a digestion significantly reduces the range in sizes of the multiple linkers to between 1 and 8 linker units (i.e. between 5 and 40 amino acids in steps of 5), as assessed by agarose gel electrophoresis.

The linkers were ligated (as a pool of different insert sizes or as gel-purified discrete fragments) into NarI cleaved OCVs M13MB48 or GemMB42 using standard methods. Following ligation the restriction enzyme NarI was added to remove the self-ligating starting OCV (since linker insertion destroys the NarI recognition sequence). This mixture was used to transform competent XL-1 blue cells and appropriately plated for plaques (OCV M13-MB48) or ampicillin resistant colonies (OCV GemMB42).

The transformants were screened using dot blot DNA analysis with one of two $^{32}$P labeled oligonucleotide probes. One probe consisted of a sequence complementary to the DNA encoding the P1 loop of BPTI while the second had a sequence complementary to the DNA encoding the domain interface region. Suitable linker candidates would probe positively with the first probe and negatively or poorly with the second. Plaque purified clones were used to generate phage stocks for binding analyses and BPTI display while the Rf DNA derived from phage infected bacterial cells was used for restriction enzyme analysis and sequencing. Representative insert sequences of selected clones analyzed are as follows:

```
M13.3X4    (GG)C.GGA.TCC.TCC.TCC.CT(C.GCC)
              gly ser ser ser leu M13.3X7    (G C.GAG.GGA.GGA.GGA.TC(C.GCC)
              glu gly gly gly ser M13.3X11   (GG)C.GAG.GGA.GGA.GGA.TCC.GGA.TCC.TCC.
              glu gly gly gly ser gly ser ser TCC.CTC.GGA.TCC.TCC.TCC.CT(C.GCCC)
           ser leu gly ser ser ser leu
```

These highly flexible oligomeric linkers are believed to be useful in joining a binding domain to the major coat (gene VIII) protein of filamentous phage to facilitate the display of the binding domain on the phage surface. They may also be useful in the construction of chimeric OSPs for other genetic packages as well.

EXAMPLE VIII

Bacterial Expression Vectors

The expression vectors were designed for the bacterial production of BPTI analogues resulting from the mutagenesis and screening for variants with specific binding properties. The expression vectors used are derivatives of the OCV's M13MB48 and GemMB42. The conversion was achieved by replacing the first codon of the mature VIII gene (codon 82 as shown in Table 113) with a translational stop codon by site specific mutagenesis.

The salient points of the expression vector composition are identical to that of the parent OCV's, namely a lacUV5 promoter (hence IPTG induction), ribosome binding site, initiating methionine, pho A signal peptide and transcriptional termination signal (see Table 113). The placement of the stop codon allows for the expression of only the first half the fusion protein. The Gem-based expression system, containing the genes encoding BPTI analogues, is stored as plasmid DNA, being freshly transfected into cells for expression of the analogue protein. The M13-based expression system is stored as both RF DNA and as phage stocks. The phage stocks are used to infect fresh bacterial cells for expression of the protein of interest.

Bacterial Expression of BPTI and Analogues i. Gem-based Expression Vector and Protocol.

The gem-based expression vector is a derivative of the OCV GemMB42 (Eample I and Table 113). This vector, at least when it contains the BPTI or analogue genes, has demonstrated a degree of insert instability on prolonged growth in liquid culture. To reduce the risk of this the following protocol is used.

Expression vector DNA (containing the BPTI or analogue gene) is transfected into the E. coli strain, XL1-Blue(TM), which is plated on bacterial plates containing ampicillin and allowed to incubate overnight at 37° C. to give a dense population of colonies. The colonies are scraped from the plate with a glass spreader in 1 ml of NZCYM medium and combined with the scraped cells from other duplicate plates. This stock of cells is diluted approximately one hundred fold into NZCYM liquid medium containing ampicillin (100 μg per ml) and allowed to grow in a shaking incubator to a cell density of approximately half log (absorbance of 0.3 at 600 nm). IPTG is added to a final concentration of 0.5 mM and the induced culture allowed to grow for a further two hours when it is processed as described below.

ii. M13-based expression vector and protocol.

The M13-based expression vector is derived from OCV M13MB48 (Example I). The BPTI gene (or analogue) is contained within the intergenic region and its transcription is under the control of a lacUV5 promoter, hence IPTG inducible. The expression vector, containing the gene of interest, is maintained and utilized as a phage stock. This method enables a potentially lethal or deleterious gene to be supplied to a bacterial culture and gene induction to occur only when the bacterial culture has achieved sufficient mass. Poor growth and insert instability can be circumvented to a large extent, giving this system an advantage over the Gem-based vector described above.

An overnight bacterial culture of XL1-Blue(TM) or SEF' is grown in LB medium containing tetracycline (50 μg per ml) to ensure the presence of pili as sites for bacteriophage binding and infection. This culture is diluted 100-fold into NZCYM medium containing tetracycline and bacterial growth allowed to proceed in an incubator shaker until a cell density of 1.0 (Ab 600 nm) has been achieved. Phage, containing the expression vector and gene of interest, are added to the bacterial culture at a multiplicity of infection (MOI) of 10 and allowed to infect the cells for 30 minutes. Gene expression is then induced by the addition of IPTG to a final concentration of 0.5 mM and the culture allowed to grow overnight. Media collection and cell fractionation is as described elsewhere.

Bacterial Cell Fractionation

After heterologous gene expression the bacterial cell culture can be separated into the following fractions: conditioned medium, periplasmic fraction and post-periplasmic cell lysate. This is achieved using the following procedures.

The culture is centrifuged to pellet the bacteria, allowing the supernatant to be stored as conditioned medium. This fraction contains any exported proteins. The pellet is taken up in 20% sucrose, 30 mM Tris pH 8 and 1 mM EDTA (80 ml of buffer per gram of fresh weight pellet) and allowed to sit at room temperature for 10 minutes. The cells are repelleted and taken up in the same volume of ice cold 5 mM MgSO$_4$ and left on ice for 10 minutes. Following centrifugation, to pellet the cells, the supernatant (periplasmic fraction) is stored. A second round of osmotic shock fractionation can be undertaken if desired.

The post-periplasmic pellet can be further lysed as follows. The pellet is resuspended in 1.5 ml of 20% sucrose, 40 mM Tris pH 8, 50 mM EDTA and 2.5 mg of lysozyme (per gram fresh weight of starting pellet). After 15 minutes at room temperature 1.15 ml of 0.1% Triton X is added together with 30 μl of 5M NaCl and incubated for a further 15 minutes. 2.5 ml of 0.2M triethanolamine (pH 7.8), 150 μl of 1M CaCl$_2$, 100 μl of 1M MgCl$_2$ and 5 μg of DNA'se are added and allowed to incubate/with end-over-end mixing, for 20 minutes to reduce viscosity. This is followed by centrifugation with the supernatant being retained as the post-periplasmic lysate.

The present invention is not, of course, limited to any particular expression system, whether bacterial or not.

EXAMPLE IX

Construction of an ITI-Domain I/Gene III Display Vector

1. ITI domain I as an IPBD

Inter-α-trypsin inhibitor (ITI) is a large ($M_r$ ca 240,000) circulating protease inhibitor found in the plasma of many mammalian species (for recent reviews see ODOM90, SALI90, GEBH90, GEBH86). The intact inhibitor is a glycoprotein and is currently believed to consist of three glycosylated subunits that interact through a strong glycosaminoglycan linkage (ODOM90, SALI90, ENGH89, SELL87). The anti-trypsin activity of ITI is located on the smallest subunit (ITI light chain, unglycosylated $M_r$ ca 15,000) which is identical in amino acid sequence to an acid stable inhibitor found in urine (UTI) and serum (STI) (GEBH86, GEBH90). The mature light chain consists of a 21 residue N-terminal sequence, glycosylated at $SER_{10}$, followed by two tandem Kunitz-type domains the first of which is glycosylated at $ASN_{45}$ (ODOM90). In the human protein, the second Kunitz-type domain has been shown to inhibit trypsin, chymotrypsin, and plasmin (ALBR83a, ALBR83b, SELL87, SWAI88). The first domain lacks these activities but has been reported to inhibit leukocyte elastase ($10^{-6} > K_i > 10^{-9}$) (ALBR83a,b, ODOM90). cDNA encoding the ITI light chain also codes for α-1-microgulobulin (TRAB86, KAUM86, DIAR90);-the proteins are separated post-translationally by proteolysis.

The N-terminal Kunitz-type of the ITI light chain (ITI-D1, comprising residues 22 to 76 of the UTI sequence shown in FIG. 1 of GEBH86) possesses a number of characteristics that make it useful as an IPBD. The domain is highly homologous to both BPTI and the EpiNE series of proteins described elsewhere in the present application. Although an x-ray structure of the isolated domain is not available, crystallographic studies of the related Kunitz-type domain isolated from the Alzheimer's amyloid β-protein (AAβP) precursor show that this polypeptide assumes a crystal structure almost identical to that of BPTI (HYNE90). Thus, it is likely that the solution structure of the isolated ITI-D1 polypeptide will be highly similar to the structures of BPTI and AAβP. In this case, the advantages described previously for use of BPTI as an IPBD apply to ITI-D1. ITI-D1 provides additional advantages as an IDBP for the development of specific anti-elastase inhibitory activity. First, this domain has been reported to inhibit both leukocyte elastase (ALBR83a,b, ODOM90) and Cathepsin-G (SWAI88, ODOM90); activities which BPTI lacks. Second, ITI-D1 lacks affinity for the related serine proteases trypsin, chymotrypsin, and plasmin (ALBR83a,b, SWAI88), an advantage for the development of specificity in inhibition. Finally, ITI-D1 is a human-derived polypeptide so derivatives are anticipated to show minimal antigenicity in clinical applications.

2. Construction of the display vector.

For purposes of this discussion, numbering of the nucleic acid sequence for the ITI light chain gene is that of TRAB86 and of the amino acid sequence is that shown for UTI in FIG. 1 of GEBH86. DNA manipulations were conducted according to standard methods as described in SAMB89 and AUSU87.

The protein sequence of human ITI-D1 consists of 56 amino acid residues extending from $LYS_{22}$ to $ARG_{77}$ of the complete ITI light chain sequence. This sequence is encoded by the 168 bases between positions 750 and 917 in the cDNA sequence presented in TRAB86. The majority of the domain is contained between a BglI site spanning bases 663 to 773 and a PstI site spanning bases 903 to 908. The insertion of the ITI-D1 sequence into M13 gene III was conducted in two steps. First a linker containing the appropriate ITI sequences outside the central BglI to PstI region was ligated into the NarI site of phage MA RF DNA. In the second step, the remainder of the ITI-D1 sequence was incorporated into the linker-bearing phage RF DNA.

The linker DNA consisted of two synthetic oligonucleotides (top and bottom strands) which, when annealed, produced a 54 bp double-stranded fragment with the following structure (5' to 3'):

NARI OVERHANG/ITI-5'/BGLI/STUFFER/pSTI/ITI-3'/NARI OVERHANG

The NarI OVERHANG sequences provide compatible ends for ligation into a cut NarI site. The ITI-5' sequence consists of ds DNA corresponding to the thirteen positions from A750 to T662 immediately 5' adjacent to the BglI site in the ITI-D1 sequence. Two changes, both silent, are introduced in this sequence: T to C at position 658 (changes codon for $ASP_{24}$ from GAT to GAC) and G to T at position 661 (changes codon for SER25 from TCG to TCT). The sequences BGLI and pSTI are identical to the BglI and pstI sites, respectively, in the ITI-D1 sequence. The ITI-3' sequence consists of dsDNA corresponding to the nine positions from A909 to T917 immediately 3' adjacent to the PstI site in the ITI-D1 sequence. The one base change included in this sequence, A to T at position 917, is silent and changes the codon for ARG77 from CGA to CGT. The STUFFER sequence consists of dsDNA encoding three residues (5' to 3'): LEU (TTA), TRP(TGG), and SER(TCA). The reverse complement of the STUFFER sequence encodes two translation termination codons (TGA and TAA). Phage expressing gene III containing the linker in opposite orientation to that shown above will not produce a functional gene III product.

Phage MA RF DNA was digested with NarI and the linear ca. 8.2 kb fragment was gel purified and subsequently dephosphorylated using HK phosphatase (Epicentre). The linker oligonucleotides were annealed to form the linker fragment described above, which was then kinased using T4 Polynucleotide Kinase. The kinased linker was ligated to the NarI-digested MA RF DNA in a 10:1 (linker:RF) molar ratio. After 18 hrs at 16° C., the ligation was stopped by incubation at 65° C. for 10 min and the ligation products were ethanol precipitated in the presence of 10 μg of yeast tRNA. The dried precipitate was dissolved in 5 μl of water and used to transform D1210 cells by electroporation. After 60 min of growth in SOC at 37° C., transformed cells were plated onto LB plates supplemented with ampicillin (Ap, 200 μg/ml). RF DNA prepared from $AP^r$ isolates was subjected to restriction enzyme analysis. The DNA sequences of the linker insert and the immediately surrounding regions were confirmed by DNA sequencing. Phage strains containing the ITI Linker sequence inserted into the NarI site in gene III are called MA-IL.

Phage MA-IL RF DNA was partially digested with BglI and the ca. 8.2 kb linear fragment was gel purified. This fragment was digested with PstI and the large linear fragment was gel purified. The BglI to PstI fragment of ITI-D1 was isolated from pMG1A (a plasmid carrying the sequence shown in TRAB86). pMG1A was digested to completion with BglI and the ca. 1.6 kb fragment was isolated by agarose gel electrophoresis and subsequent Geneclean (Bio101, La Jolla, Calif.) purification. The purified BglI fragment was digested to completion with PstI and EcoRI and the resulting mixture of fragments was used in a ligation with the BgII and PstI cut MA-IL RF DNA described above. Ligation, transformation, and plating were as described above. After 18 hr. of growth on LB Ap plates at 37° C., Ap$^r$ colonies were harvested with LB broth supplemented with Ap (200 μg/ml) and the resulting cell suspension was grown for two hours at 37° C. Cells were pelleted by centrifugation (10 min at 5000×g, 4° C.). The supernatant fluid was transferred to sterile centrifugation tubes and recentrifuged as above. The supernatant fluid from the second centrifugation step was retained as the phage stock POP1.

PCR was used to demonstrate the presence of phage containing the complete ITI-DI-III fusion gene. Upstream PCR primers, 1UP and 2UP, are located spanning nucleotides 1470 to 1494 and 1593 to 1618 of the phage M13 DNA sequence, respectively. A downstream PCR primer 3DN spans nucleotides 1779 to 1804. Two ITI-Dl-specific primers, IAI-1 and IAI-2, are located spanning positions 789 to 810 and 894 to 914, respectively, in the ITI light chain sequence of TRAB86. IAI-1 and IAI-2 are used as downstream primers in PCR reactions with 1UP or 2UP. IAI-1 is entirely contained within the BgII to PstI region of the ITI-D1 sequence, while IAI-2 spans the PstI site in the ITI-D1 sequence. When aliquots of POP1 phage were used as substrates for PCR, template-specific products of characteristic size were produced in reactions containing 1UP or 2UP plus IAI-1 or IAI-2 primer pairs. No such products are obtained using MA-IL phage as template. No PCR products with sizes corresponding to complete ITI-D1-gene III templates were obtained using POP1 phage and the 1UP or 2UP plus 3DN primer pairs. This last result reflects the low abundance (<1%) of phage containing the complete ITI-D1 sequence in POP1.

Preparative PCR was used to generate substrate amounts of the 330 bp PCR product of a reaction using the 1UP and IAI-2 primer pair to amplify the POP1 template. The 330 bp PCR product was gel purified and then cut to completion with BgII and PstI. The 138 bp BgII to PstI fragment from ITI-D1 was isolated by agarose gel electrophoresis followed by Qiaex extraction (Qiagen, Studio City, Calif.). MA-IL phage RF DNA was digested to completion with PstI. The ca. 8.2 kb linear fragment was gel purified and subsequently digested to completion with BgII. The BgII digest was extracted once with phenol:chloroform (1:1), the aqueous phase was ethanol precipitated, and the pellet was dissolved in TE (pH 8.0). An aliquot of this solution was used in a ligation reaction with the 138 bp BgII to PstI fragment as described above. The ethanol precipitated ligation products were used to transform XL1-Blue$^{(TM)}$ cells by electroporation and after 1 hr growth in SOC at 37° C., cells were plated on LB Ap plates. A phage population, POP2, was prepared from Ap$^r$ colonies as described previously.

Phage stocks obtained from individual plaques produced on titration of POP2 were tested by PCR for the presence of the complete ITI-D1-III gene fusion. PCR results indicate the entire fusion gene was present in seven of nine isolates tested. RF DNA from the seven isolates testing positive was subjected to restriction enzyme analysis. The complete sequence of the ITI-D1 insertion into gene III was confirmed in four of the seven isolates by DNA sequence analysis. Phage isolates containing the ITI-Di-III fusion gene are called MA-ITI.

3. Expression and display of ITI-DI.

Expression of the ITI domain I-Gene III fusion protein and its display on the surface of phage were demonstrated by Western analysis and phage titer neutralization experiments.

For Western analysis, aliquots of PEG-purified phage preparations containing up to $4 \cdot 10^{10}$ infective particles were subjected to electrophoresis on a 12.5% SDS-ureapolyacrylamide gel. Proteins were transferred to a sheet of Immobilon-P transfer membrane (Millipore, Bedford, Mass.) by electrotransfer. Western blots were developed using a rabbit anti-ITI serum (SALI87) which had previously been incubated with an *E. coli* extract, followed by goat anti-rabbit IgG conjugated to horse radish peroxidase (#401315, Calbiochem, La Jolla, Calif.). An immunoreactive protein with an apparent size of ca. 65–69 kD is detected in preparations of MA-ITI phage but not with preparations of the parental MA phage. The size of the immunoreactive protein is consistent with the expected size of the processed ITI-Di-III fusion protein (ca. 67 kD, as previously observed for the BPTI-III fusion protein).

Rabbit anti-BPTI serum has been 'shown to block the ability of MK-BPTI phage to infect *E. coli* cells (Example II). To test for a similar effect of rabbit anti-ITI serum on the infectivity of MA-ITI phage, 10 μl aliquots of MA or MA-ITI phage were incubated in 100 μl reactions containing 10μl aliquots of PBS, normal rabbit serum (NRS), or anti-ITI serum. After a three hour incubation at 37° C., phage suspensions were titered to determine residual plaque-forming activity. These data are summarized in Table 211. Incubation of MA-ITI phage with rabbit anti-ITI serum reduces titers 10- to 100-fold, depending on initial phage titer. A much smaller decrease in phage titer (10 to 40%) is observed when MA-ITI phage are incubated with NRS. In contrast, the titer of the parental MA phage is unaffected by either NRS or anti-ITI serum.

Taken together, the results of the Western analysis and the phage-titer neutralization experiments are consistent with the expression of an ITI-DI-III fusion protein in MA-ITI phage, but not in the parental MA phage, such that ITI-specific epitopes are present on the phage surface. The ITI-specific epitopes are located with respect to III such that antibody binding to these epitopes prevents phage from infecting *E. coli* cells.

4. Fractionation of MA-ITI phage bound to agarose-immobilized protease beads.

To test if phage displaying the ITI-DI-III fusion protein interact strongly with the proteases human neutrophil elastase (HNE) or cathepsin-G, aliquots of display phage were incubated with agarose-immobilized HNE or cathepsin-G beads (HNE beads or Cat-G beads, respectively). The beads were washed and bound phage eluted by pH fractionation as described in Examples II and III. The procession in lowering pH during the elution was: pH 7.0, 6.0, 5.5, 5.0, 4.5, 4.0, 3.5, 3.0, 2.5, and 2.0. Following elution and neutralization, the various input, wash, and pH elution fractions were titered.

The results of several fractionations are summarized in Table 212 (EpiNE-7 or MA-ITI phage bound to HNE beads) and Table 213 (EpiC-10 or MA-ITI phage bound to Cat-G beads). For the two types of beads (HNE or Cat-G), the pH elution profiles obtained using the control display phage (EpiNE-7 or EpiC-10, respectively) were similar to those seen previously (Examples II and III). About 0.3% of the EpiNE-7 display phage applied to the HNE beads were eluted during the fractionation procedure and the elution profile had a maximum for elution at about pH 4.0. A smaller fraction, 0.02%, of the EpiC-10 phage applied to the Cat-G beads were eluted and the elution profile displayed a maximum near pH 5.5.

The MA-ITI phage show no evidence of great affinity for either HNE or cathepsin-G immobilized on agarose beads. The pH elution profiles for MA-ITI phage bound to HNE or Cat-G beads show essentially monotonic decreases in phage recovered with decreasing pH. Further, the total fractions of the phage applied to the beads that were recovered during the fractionation procedures were quite low: 0.002% from PINE beads and 0.003% from Cat-G beads.

Published values of $K_i$ for inhibition neutrophil elastase by the intact, large ($M_r$=240,000) ITI protein range between 60 and 150 nM and values between 20 and 6000 nM have been reported for the inhibition of Cathepsin G by ITI (SWAI88, ODOM90). Our own measurements of pH fraction of display phage bound to HNE beads show that phage displaying proteins with low affinity (>μM) for HNE are not bound by the beads while phage displaying proteins with greater affinity (nM) bind to the beads and are eluted at about pH 5. If the first Kunitz-type domain ot the ITI light chain is entirely responsible for the inhibitory activity of ITI against HNE, and if this domain is correctly displayed on the MA-ITI phage, then it appears that the minimum affinity of an inhibitor for HNE that allows binding and fractionation of display phage on HNE beads is 50 to 100 nM.

5. Alteration of the P1 region of ITI-DI.

If ITI-DI and EpiNE-7 assume the same configuration in solution as BPTI, then these two polypeptides have identical amino acid sequences in both the primary and secondary binding loops with the exception of four residues about the P1 position. For ITI-DI the sequence for positions 15 to 20 is (position 15 in ITI-DI corresponds to position 36 in the UTI sequence of GEBH86): MET15, GLY16, MET17, THR18, SER19, ARG20. In EpiNE-7 the equivalent sequence is: VAL15, ALA16, MET17, PHE18, PRO19, ARG20. These two proteins appear to differ greatly in their affinities for HNE. To improve the affinity of ITI-DI for HNE, the EpiNE-7 sequence shown above was incorporated into the ITI-DI sequence at positions 15 through 20.

The EpiNE-7 sequence was incorporated into the ITI-DI sequence in MA-ITI by cassette mutagenesis. The mutagenic cassette consisted of two synthetic 51 base oligonucleotides (top and bottom stands) which were annealed to make double stranded DNA containing an Eag I overhang at the 5' end and a sty I overhang at the 3' end. The DNA sequence between the Eag I and Sty I overhangs is identical to the ITI-DI sequence between these sites except at four codons: the codon for position 15, AT (MET), was changed to GTC (VAL), the codon for position 16, GGA (GLY), was changed to GCT (ALA), the codon for position 18, ACC (THR) was changed to TTC (PHE), and the codon for position 19, AGC (SER), was changed to CCA (PRO). MA-ITI RF DNA was digested with Eag I and Sty I. The large, linear fragment was gel purified and used in a ligation with the mutagenic cassette described above. Ligation products were used to transform XL1-Blue$^{tm}$ cells as described previously. Phage stocks obtained from overnight cultures of Ap$^r$ transductants were screened by. PCR for incorporation of the altered sequence and the changes in the codons for positions 15, 16, 18, and 19 were confirmed by DNA sequencing. Phage isolates containing the ITI-DI-III fusion gene with the EpiNE,7 changes around the P1 position are called MA-ITI-E7.

6. Fractionation of MA-ITI-E7 phage.

To test if the changes at positions 15, 16, 18, and 19 of the ITI-DI-III fusion protein influence binding of display phage to HNE beads, abbreviated pH elution profiles were measured. Aliquots of EpiNE-7, MA-ITI, and MA-ITI-E7 display phage were incubated with HNE beads for three hours at room temperature. The beads were washed and phage were eluted as described (Example III), except that only three pH elutions were performed: pH 7.0, 3.5, and 2.0. The results of these elutions are shown in Table 214.

Binding and elution of the EpiNE-7 and MA-ITI display phage were found to be as previously described. The total fraction of input phages was high (0.4%) for EpiNE-7 phage and low (0.001%) for MA-ITI phage. Further, the EpiNE-7 phage showed maximum phage elution in the pH 3.5 fraction while the MA-ITI phage showed only a monotonic decrease in phage yields with decreasing pH, as seen above.

The two strains of MA-ITI-E7 phage show increased levels of binding to HNE beads relative to MA-ITI phage. The total fraction of the input phage eluted from the beads is 10-fold greater for both MA-ITI-E7 phage strains than for MA-ITI phage (although still 40-fold lower that EpiNE-7 phage). Further, the pH elution profiles of the MA-ITI-E7 phage strains show maximum elutions in the pH 3.5 fractions, similar to EpiNE-7 phage.

To further define the binding properties of MA-ITI-E7 phage, the extended pH fractionation procedure described previously was performed using phage bound to HNE beads. These data are summarized in Table 215. The pH elution profile of EpiNE-7 display phage is as previously described. In this more resolved, pH elution profile, MA-ITI-E7 phage show a broad elution maximum centered around pH 5. Once again, the total fraction of MA-ITI-E7 phage obtained on pH elution from HNE beads was about 40-fold less than that obtained using EpiNE-7 display phage.

The pH elution behavior of MA-ITI-E7 phage bound to HNE beads is qualitatively similar to that seen using BPTI [K15L]-III-MA phage. BPTI with the K15L mutation has an affinity for HNE of $\approx 3 \cdot 10^{-9}$M. Assuming all else remains the same, the pH elution profile for MA-ITI-E7 suggests that the affinity of the free ITI-DI-E7 domain for HNE might be in the nM range. If this is the case, the substitution of the EpiNE-7 sequence in place of the ITI-DI sequence around the P1 region has produced a 20- to 50-fold increase in affinity for HNE (assuming $K_i$=60 to 150 nM for the unaltered ITI-DI).

If EpiNE-7 and ITI-DI-E7 have the same solution structure, these proteins present the identical amino acid sequences to HNE over the interaction surface. Despite this similarity, EpiNE-7 exhibits a roughly 1000-fold greater affinity for HNE than does ITI-DI-E7. Again assuming similar structure, this observation highlights the importance of non-contacting secondary residues in modulating interaction strengths.

Native ITI light chain is glycosylated at two positions, SER10 and ASN45 (GEBH86). Removal of the glycosaminoglycan chains has been shown to decrease the affinity of the inhibitor for HNE about 5-fold (SELL87). Another potentially important difference between EpiNE-7 and ITI-DI-E7 is that of net charge. The changes in BPTI that produce EpiNE-7 reduce the total charge on the molecule from +6 to +1. Sequence differences between EpiNE-7 and ITI-DI-E7 further reduce the charge on the latter to −1. Furthermore, the change in net charge between these two molecules arises from sequence differences occurring in the central portions of the molecules. Position 26 is LYS in EpiNE-7 and is THR in ITI-DI-E7, while at position 31 these residues are GLN and GLU, respectively. These changes in sequence not only alter the net charge on the molecules but also position negatively charged residue close to the interaction surface in ITI-DI-E7. It may be that the occurrence of a negative charge at position 31 (which is not found in any other of the HNE inhibitors described here) destabilized the inhibitor-protease interaction.

EXAMPLE X

Generation of a Variegated ITI-DI Population

The following is a hypothetical example demonstating how to obtain a derivative of ITI having high affinity for HNE.

The results of Example IX demonstrate that the nature of the protein sequence around the P1 position in ITI-DI can significantly influence the strength of the interaction between ITI-DI and HNE. While incorporation of the EpiNE-7 sequence increases the affinity of ITI-DI for HNE, it is unlikely that this particular sequence is optimal for binding.

We generate a large population of potential binding proteins having differing sequences in the P1 region of ITI-DI using the oligonucleotide ITIMUT. ITIMUT is designed to incorporate variegation in ITI-DI at the six positions about and including the P1 residue: 13, 15, 16, 17, 18, and 19. ITIMUT is synthesized as one long (top strand) 73 base oligonucleotide and one shorter (24 base) bottom strand oligonucleotide. The top strand sequence extends from position 770 (G) to position 842 (G) in the sequence of TREB86. This sequence includes the codons for the positions of variegation as well as the recognition sequences for the flanking restriction enzymes Eag I (778 to 783) and Sty I (829 to 834). The bottom strand oligonucleotide comprises the complement of the sequence from positions 819 to 842.

To generate the. mutagenic cassette, the top and bottom strand oligonucleotide are annealed and the resulting duplex is completed in an extension reaction using DNA polymerase. Following digestion of the 73 bp dsDNA with Eag I and Sty I, the purified 51 bp mutagenic cassette is ligated with the large linear fragment obtained from a similar digestion of MA-ITI RF DNA. Ligation products are Used to transform competent cells by electroporation and phage stocks produced from $Ap^r$ transductants are analyzed for the presence and nature of novel sequences as described previously.

The variegation in the ITIMUT cassette is confined to the codons for the six positions in ITI-DI (13, 15, 16, 17, 18, and 19), and employs three different nucleotide mixes: N, R, and S. For this mutagenesis, the composition of the N-mix is 36%A, 17%C, 23%G, and 24%T, and corresponds to the N-mix composition in the optimized NNS codon described elsewhere. The R-mix composition is 50%A, 50%G, and the S-mix composition is 50%C, 50%G.

The codon for ITI-DI position 13 (CCC, PRO) is changed to SNG in ITIMUT. This codon encodes the eight residues PRO, VAL, GLU, ALA, GLY, LEU, GLN, and ARG. The encoded group includes the parental residue (PRO) as well as the more commonly observed variants at the position, ARG and LEU (see Table 15), and also provides for the occurrence of acidic (GLU), large polar (GLN) and nonpolar (VAL), and small (ALA, GLY) residues.

The codons for positions 15 and 17 (ATG, MET) are changed to the optimized NNS codon. All 20 natural amino acid residues and a translation termination are allowed.

The codon for position 16 (CGA, GLY) is changed to RNS in ITIMUT. This codon encodes the twelve amino acids GLY, ALA, ASP, GLU, VAL, MET, ILE, THR, SER, ARG, ASN, and LYS. The encoded group includes the most commonly observed residues at this position, ALA and GLY, and provides for the occurrence of both positively (ARG, LYS) and negatively (GLU, ASP) charged amino acids. Large nonpolar residues are also included (ILE, MET, VAL).

Finally, at positions 18 and 19, the ITI-DI sequence is changed from ACC-AGC (THR-SER) to NNT-NNT. The NNT codon encodes the fifteen amino acid residues PHE, SER, TYR, CYS, LEU, PRO, HIS, ARG, ILE, THR, ASN, VAL, ALA, ASP, and GLY. This group includes the parental residues and the further advantages of the NNT codon have been discussed elsewhere.

The ITIMUT DNA sequence encodes a total of:

$$8*20*12*20*15*15=8,640,000$$

different protein sequences in a total of:

$$2^{25}=33,554,422$$

different DNA sequences. The total number of protein sequences encoded by ITIMUT is only 7.4-fold fewer than the total possible number of natural sequences obtained from variation at six positions ($=20^6=6.4 \cdot 10^7$). However, this degree of variation in protein sequence is obtained from a minimum of $1.07 \times 10^9$ ($NNS^6=2^{30}$) DNA sequences, a 32-fold greater number than that comprising ITIMUT. Thus, ITIMUT is an efficient vehicle for the generation of a large and diverse population of potential binding proteins.

EXAMPLE XI

Development and Selection of BPTI Mutants for Binding to Horse Heart Myoglobin (HHMB)

The following example is hypothetical and illustrates alternative embodiments of the invention not given in other examples.

HHMb is chosen as a typical protein target; any other protein could be used. HHMb satisfies all of the criteria for a target: 1) it is large enough to be applied to an affinity matrix, 2) after attachment it is not reactive, and 3) after attachment there is sufficient unaltered surface to allow specific binding by PBDs.

The essential information for HHMb is known: 1) HHMb is stable at least up to 70° C., between pH 4.4 and 9.3, 2) HHMb is stable up to 1.6 M Guanidinium Cl, 3) the pI of tHMb is 7.0, 4) for HHMb, $M_r=16,000$, 5) HHMb requires haem, 6) HHMb has no proteolytic activity.

In addition, the following information about HHMb and other myoglobins is available: 1) the sequence of HHMb is known, 2) the 3D structure of sperm whale myoglobin is known; HHMb has 19 amino acid differences and it is generally assumed that the 3D structures are almost identical, 3) HMMb has no enzymatic activity, 4) HHMb is not toxic.

We set the specifications of an SBD as: 1) T=25° C.; 2) pH=8.0; 3) Acceptable solutes ((A) for binding: i) phosphate, as buffer, 0 to 20 mM, and ii) KCl, 10 mM; (B) for column elution: i) phosphate, as buffer, 0 to 30 mM, ii) KCl, up to 5 M, and iii) Guanidinium Cl, up to 0.8M.); 4) Acceptable $K_d<1.0 \cdot 10^{-8}M$.

As stated in Sec. III.B, the residues to be varied are picked, in part, through the use of interactive computer graphics to visualize the structures. In this example, all residue numbers refer to BPTI. We pick a set of residues that forms a surface such that all residues can contact one target molecule. Information that we refer to during the process of choosing residues to vary includes: 1) the 3D structure of BPTI, 2) solvent accessibility of each residue as computed by the method of Lee and Richards (LEEB71), 3) a compilation of sequences of other proteins homologous to BPTI, and 4) knowledge of the structural nature of different amino acid types.

Tables 16 and 34 indicate which residues of BPTI: a) have substantial surface exposure, and b) are known to tolerate other amino acids in other closely related proteins. We use interactive computer graphics to pick sets of eight to twenty residues that are exposed and variable and such that all members of one set can touch a molecule of the target material at one time. If BPTI has a small amino acid at a given residue, that amino acid may not be able to contact the target simultaneously with all the other residues in the interaction set, but a larger amino acid might well make contact. A charged amino acid might affect binding without making direct contact. In such cases, the residue should be included in the interaction set, with a notation that larger residues might be useful. In a similar way, large amino acids near the geometric center of the interaction set may prevent residues on either side of the large central residue from making simultaneous contact. If a small amino acid, however, were substituted for the large amino acid, then the surface would become flatter and residues on either side could make simultaneous contact. Such a residue should be included in the interaction set with a notation that small amino acids may be useful.

Table 35 was prepared from standard model parts and shows the maximum span between $C_\beta$ and the tip of each type of side group. $C_\beta$ is used because it is rigidly attached to the protein main-chain; rotation about the $C_\alpha$–$C_\beta$ bond is the most important degree of freedom for determining the location of the side group.

Table 34 indicates five surfaces that meet the given criteria. The first surface comprises the set of residues that actually contacts trypsin in the complex of trypsin with BPTI as reported in the Brookhaven Protein Data Bank entry "1TPA". This set is indicated by the number "1". The exposed surface of the residues in this set (taken from Table 16) totals 1148 Å$^2$. Although this is not strictly the area of contact between BPTI and trypsin, it is approximately the same.

Other surfaces, numbered 2 to 5, were picked by first picking one exposed, variable residue and then picking neighboring residues until a surface was defined. The choice of sets of residues shown in Table 34 is in no way exhaustive or unique; other sets of variable, surface residues can be picked. Set #2 is shown in stereo view, FIG. 14, including the α carbons of BPTI, the disulfide linkages, and the side groups of the set. We take the orientation of BPTI in FIG. 14 as a standard orientation and hereinafter refer to K15 as being at the top of the molecule, while the carboxy and amino termini are at the bottom.

Solvent accessibilities are useful, easily tabulated indicators of a residue's exposure. Solvent accessibilities must be used with some caution; small amino acids are under-represented and large amino acids over-represented. The user must consider what the solvent accessibility of a different amino acid would be when substituted into the structure of BPTI.

To create specific binding between a derivative of BPTI and HHMb, we will vary the residues in set #2. This set includes the twelve principal residues 17(R), 19(I), 21(Y), 27 (A), 28(G), 29(L), 31(Q), 32(T), 34(V), 48(A), 49(E), and 52(M) (Sec. III.B). None of the residues in set #2 is completely conserved in the sample of sequences reported in Table 34; thus we can vary them with a high probability of retaining the underlying structure. Independent substitution at each of these twelve residues of the amino acid types observed at that residue would produce approximately 4.4·10$^9$ amino acid sequences and the same number of surfaces.

BPTI is a very basic protein. This property has been used in isolating and purifying BPTI and its homologues so that the high frequency of arginine and lysine residues may reflect bias in isolation and is not necessarily required by the structure. Indeed, SCI-III from *Bombyx mori* contains seven more acidic than basic groups (SASA84).

Residue 17 is highly variable and fully exposed and can contain R, K, A, Y, H, F, L, M, T, G, Y, P, or S. All types of amino acids are seen: large, small, charged, neutral, and hydrophobic. That no acidic groups are observed may be due to bias in the sample.

Residue 19 is also variable and fully exposed, containing P, R, I, S, K, Q, and L.

Residue 21 is not very variable, containing F or Y in 31 of 33 cases and I and W in the remaining cases. The side group of Y21 fills the space between T32 and the main chain of residues 47 and 48. The OH at the tip of the Y side group projects into the solvent. Clearly one can vary the surface by substituting Y or F so that the surface is either hydrophobic or hydrophilic in that region. It is also possible that the other aromatic amino acid (viz. H) or the other hydrophobics (L, M, or V) might be tolerated.

Residue 27 most often contains A, but S, K, L, and T are also observed. On structural grounds, this residue will probably tolerate any hydrophilic amino acid and perhaps any amino acid.

Residue 28 is G in BPTI. This residue is in a turn, but is not in a conformation peculiar to glycine. Six other types of amino acids have been observed at this residue: K, N, Q, R, H, and N. Small side groups at this residue might not contact HHMb simultaneously with residues 17 and 34. Large side groups could interact with HHMb at the same time as residues 17 and 34. Charged side groups at this residue could affect binding of HHMb on the surface defined by the other residues of the principal set. Any amino acid, except perhaps P, should be tolerated.

Residue 29 is highly variable, most often containing L. This fully exposed position will probably tolerate almost any amino acid except, perhaps, P.

Residues 31, 32, and 34 are highly variable, exposed, and in extended conformations; any amino acid should be tolerated.

Residues 48 and 49 are also highly variable and fully exposed, any amino acid should be tolerated.

Residue 52 is in an α helix. Any amino acid, except perhaps P, might be tolerated.

Now we consider possible variation of the secondary set (Sec. 13.1.2) of residues that are in the neighborhood of the principal set. Neighboring residues that might be varied at later stages include 9(P), 11(T), 15(K), 16(A), 18(I), 20(R), 22(F), 24(N), 26(K), 35(Y), 47(S), 50(D), and 53(R).

Residue 9 is highly variable, extended, and exposed. Residue 9 and residues 48 and 49 are separated by a bulge caused by the ascending chain from residue 31 to 34. For residue 9 and residues 48 and 49 to contribute simultaneously to binding, either the target must have a groove into which the chain from 31 to 34 can fit, or all three residues (9, 48, and 49) must have large amino acids that effectively reduce the radius of curvature of the BPTI derivative.

Residue 11 is highly variable, extended, and exposed. Residue 11, like residue 9, is slightly far from the surface defined by the principal residues and will contribute to binding in the same circumstances.

Residue 15 is highly varied. The side group of residue 15 points away form the face defined by set #2. Changes of charge at residue 15 could affect binding on the surface defined by residue set #2.

Residue 16 is varied but points away from the surface defined by the principal set. Changes in charge at this residue could affect binding on the face defined by set #2.

Residue 18 is. I in BPTI. This residue is in an extended conformation and is exposed. Five other amino acids have been observed at this residue: M, F, L, V, and T. Only T is hydrophilic. The side group points directly away from the surface defined by residue set #2. Substitution of charged amino acids at this residue could affect binding at surface defined by residue set #2.

Residue 20 is R in BPTI. This residue is in an extended conformation and is exposed. Four other amino acids have been observed at this residue: A, S, L, and Q. The side group points directly away from the surface defined by residue set #2. Alteration of the charge at this residue could affect binding at surface defined by residue set #2.

Residue 22 is only slightly varied, being Y, F, or H in 30 of 33 cases. Nevertheless, A, N, and S have been observed at this residue. Amino acids such as L, M, I, or Q could be tried here. Alterations at residue 22 may affect the mobility of residue 21; changes in charge at residue 22 could affect binding at the surface defined by residue set #2.

Residue 24 shows some variation, but probably can not interact with one molecule of the target simultaneously with all the residues in the principal set. Variation in charge at this residue might have an effect on binding at the surface defined by the principal set.

Residue 26 is highly varied and exposed. Changes in charge may affect binding at the surface defined by residue set #2; substitutions may affect the mobility of residue 27 that is in the principal set.

Residue 35 is most often Y, W has been observed. The side group of 35 is buried, but substitution of F or W could affect the mobility of residue 34.

Residue 47 is always T or S in the sequence sample used. The $O_{gamma}$ probably accepts a hydrogen bond from the NH of residue 50 in the alpha helix. Nevertheless, there is no overwhelming steric reason to preclude other amino acid types at this residue. In particular, other amino acids the side groups of which can accept hydrogen bonds, viz. N, D, Q, and E, may be acceptable here.

Residue 50 is often an acidic amino acid, but other amino acids are possible.

Residue 53 is often R, but other amino acids have been observed at this residue. Changes of charge may affect binding to the amino acids in interaction set #2.

Figure 14:
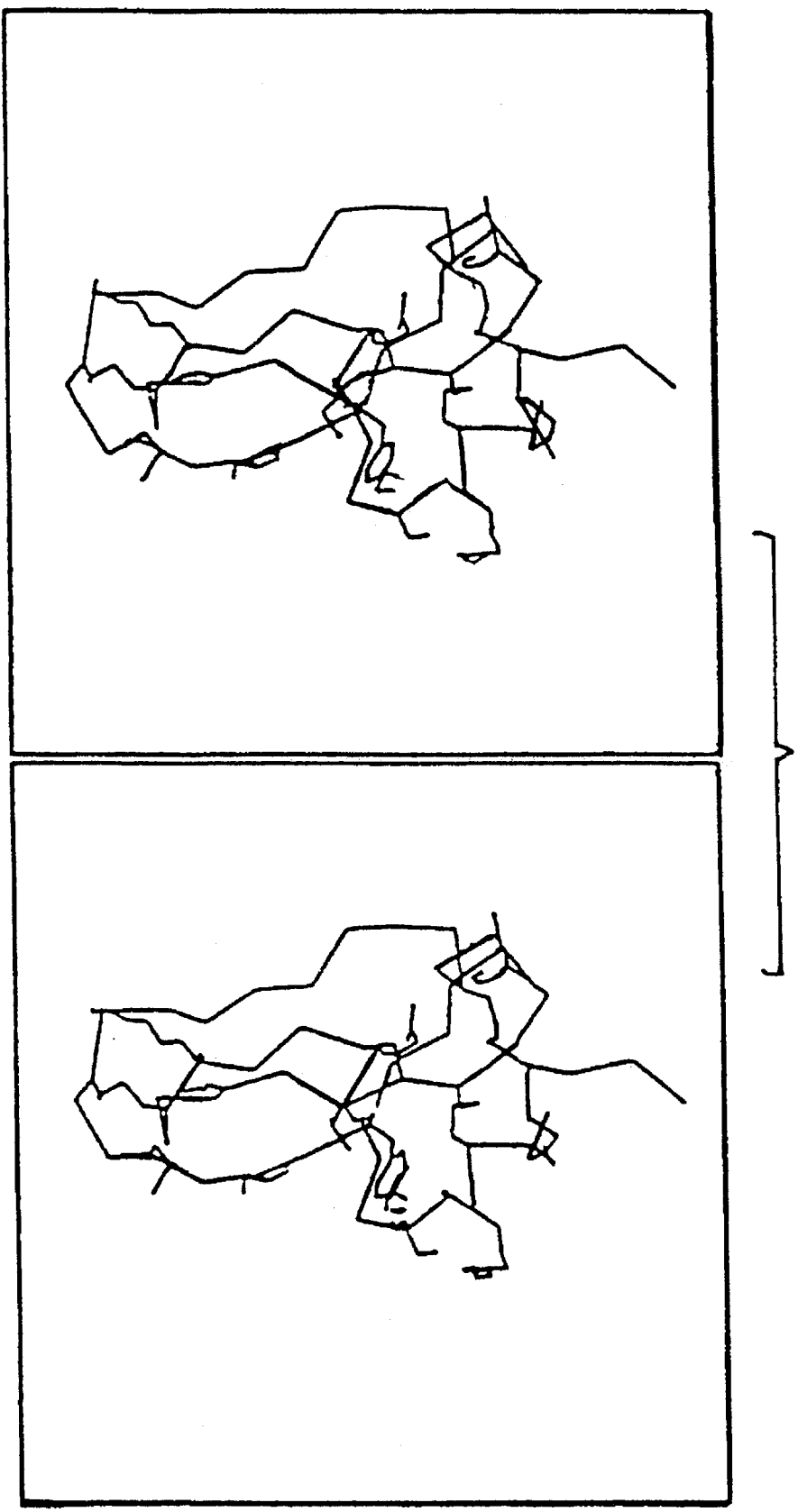
FIG. 14 shows the $C_\alpha$s of BPTI and interaction set #2.
Figure 15:
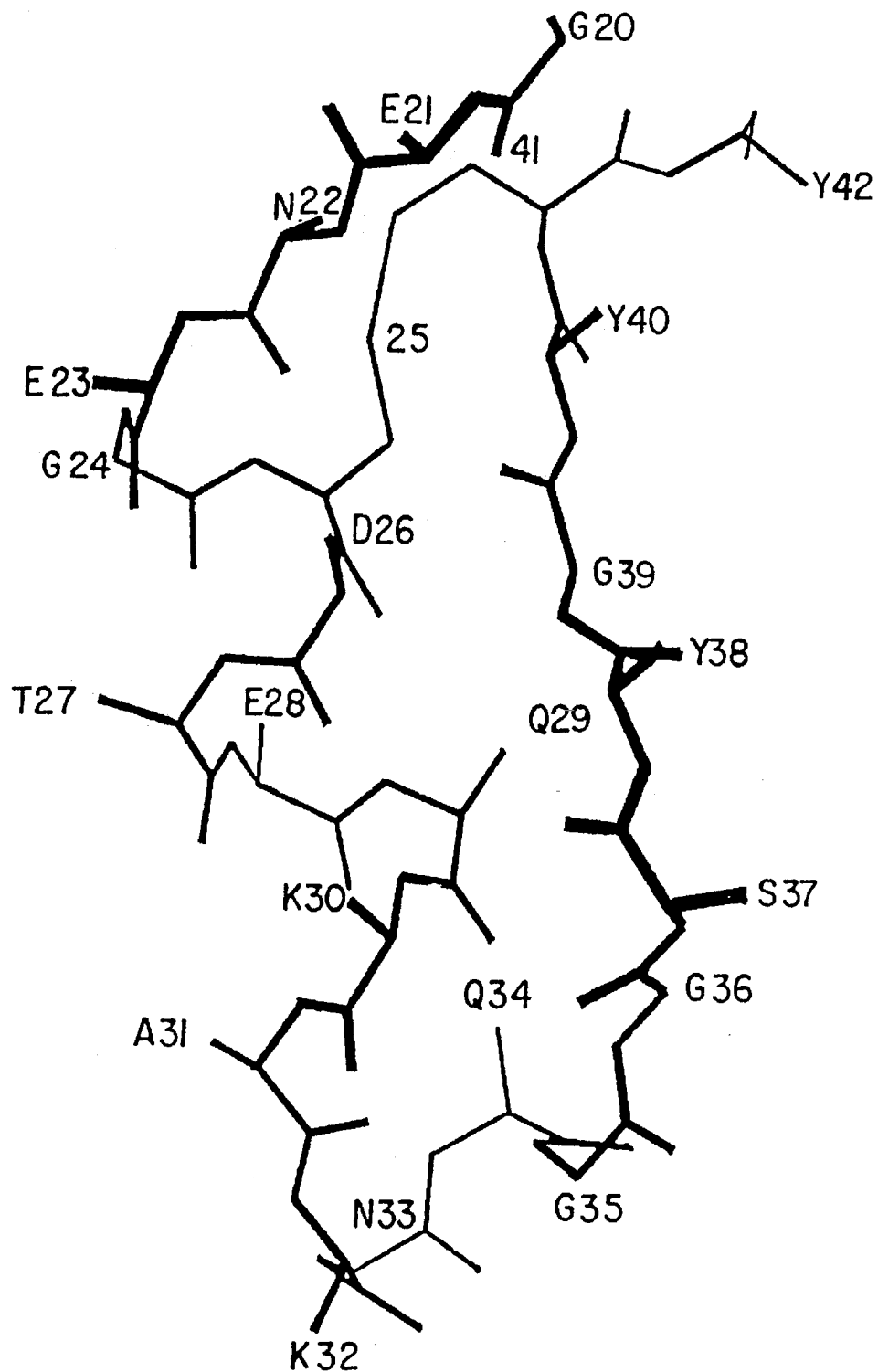
FIG. 15 shows the main chain of scorpion toxin (Brookhaven Protein Data Bank entry 1SN3) residues 20 through 42. $CYS_{25}$ and $CYS_{41}$ are shown forming a disulfide. In the native protein these groups form disulfides to other cysteines, but no main-chain motion is required to bring the gamma sulphurs into acceptable geometry. Residues, other than GLY, are labeled at the β carbon with the one-letter code.

Stereo FIG. 14 shows the residues in set #2, plus R39. From FIG. 14, One can see that R39 is on the opposite side of BPTI form the surface defined by the residues in set #2. Therefore, variation at residue 39 at the same time as variation of some residues in set #2 is much less likely to improve binding that occurs along surface #2 than is variation of the other residues in set #2.

In addition to the twelve principal residues and 13 secondary residues, there are two other residues, 30(C) and 33(F), involved in surface #2 that we will probably not vary, at least not until late in the procedure. These residues have their side groups buried inside BPTI and are conserved. Changing these residues does not change the surface nearly so much as does changing residues in the principal set. These buried, conserved residues do, however, contribute to the surface area of surface #2. The surface of residue set #2 is comparable to the area of the trypsin-binding surface. Principal residues 17, 19, 21, 27, 28, 29, 31, 32, 34, 48, 49, and 52 have a combined solvent-accessible area of 946.9 $A^2$. Secondary residues 9, 11, 15, 16, 18, 20, 22, 24, 26, 35, 47, 50, and 53 have combined surface of 1041.7 $A^2$. Residues 30 and 33 have exposed surface totaling 38.2 $A^2$. Thus the three groups' combined surface is 2026.8 $A^2$.

Residue 30 is C in BPTI and is conserved in all homologous sequences. It should be noted, however, that C14/C38 is conserved in all natural sequences, yet Marks et al. (MARK87) showed that changing both C14 and C38 to A,A or T,T yields a functional trypsin inhibitor. Thus it is possible that BPTI-like molecules will fold if C30 is replaced.

Residue 33 is F in BPTI and in all homologous sequences. Visual inspection of the BPTI structure suggests that substitution of Y, M, H, or L might be tolerated.

Having identified twenty residues that define a possible binding surface, we must choose some to vary first. Assuming a hypothetical affinity separation sensitivity, $C_{sensi}$, of 1 in $4 \cdot 10^8$ we decide to vary six residues (leaving some margin for error in the actual base composition of variegated bases). To obtain maximal recognition, we choose residues from the principal set that are as far apart as possible. Table 36 shows the distances between the β carbons of residues in the principal and peripheral set. R17 and V34 are at one end of the principal surface. Residues A27, G28, L29, A48, E49, and M52 are at the other end, about twenty Angstroms away; of these, we will vary residues 17, 27, 29, 34, and 48. Residues 28, 49, and 52 will be varied at later rounds.

Of the remaining principal residues, 21 is left to later variations. Among residues 19, 31, and 32, we arbitrarily pick 19 to vary.

Unlimited variation of six residues produces $6.4 \cdot 10^7$ amino acid sequences. By hypothesis, $C_{sensi}$ is 1 in $4 \cdot 10^8$. Table 37 shows the programmed variegation at the chosen residues. The parental sequence is present as 1 part in $5.5 \cdot 10^7$ but the least favored sequences are present at only 1 part in $4.2 \cdot 10^9$. Among single-amino-acid substitutions from the PPBD, the least favored is F17-I19-A27-L29-V34-A48 and has a calculated abundance of 1 part in $1.6 \cdot 10^8$. Using the optimal qfk codon, we can recover the parental sequence and all one-amino-acid substitutions to the PPBD if actual nt compositions come within 5% of programmed compositions. The number of transformants is $M_{ntv}=1.0 \cdot 10^9$ (also by hypothesis), thus we will produce most of the programmed sequences.

The residue numbers of the preceding section are referred to mature BPTI (R1-P2- . . . -A58). Table 25 has residue numbers referring to the pre-M13CP-BPTI protein; all mature BPTI sequence numbers have been increased by the length of the signal sequence, i.e. 23. Thus in terms of the pre-OSP-PBD residue numbers, we wish to vary residues 40, 42, 50, 52, 57, and 71. A DNA subsequence containing all these codons is found between the (ApaI/DraII/psSI) sites at base 191 and the Sph I site at base 309 of the osp-pbd gene. Among ApaI, DraI, and PssI, ApaI is preferred because it recognizes six bases without any ambiguity. DraII and PssI, on the other hand, recognize six bases with two-fold ambiguity at two of the bases. The vgDNA will contain more DraII and PssI recognition sites at the varied locations than it will contain ApaI recognition sites. The unwanted extraneous cutting of the vgDNA by ApaI and SphI will eliminate a few sequences from our population. This is a minor problem, but by using the more specific enzyme (ApaI), we minimize the unwanted effects. The sequence shown in Table 37 illustrates an additional way in which gratuitous restriction sites can be avoided in some cases. The osp-ipbd gene had the codon GGC for g51; because we are varying both residue 50 and 52, it is possible to obtain an ApaI site. If we change the glycine codon to GGT, the ApaI site can no longer arise. ADaI recognizes the DNA sequence (GGGCC/C).

Each piece of dsDNA to be synthesized needs six to eight bases added at either end to allow cutting with restriction enzymes and is shown in Table 37. The first synthetic base (before cutting with ApaI and SphI) is 184 and the last is 322. There are 142 bases to be synthesized. The center of the piece to the synthesized lies between Q54 and V57. The overlap can not include varied bases, so we choose bases 245 to 256 as the overlap that is 12 bases long. Note that the codon for F56 has been changed to TTC to increase the GC content of the overlap. The amino acids that are being varied are marked as X with a plus over them. Codons 57 and 71 are synthesized on the sense (bottom) strand. The design calls for "qfk" in the antisense strand, so that the sense strand contains (from 5' to 3') a) equal part C and A (i.e. the complement of k), b) (0.40 T, 0.22 A, 0.22 C, and 0.16 G) (i.e. the complement of f), and c) (0.26 T, 0.26 A, 0.30 C, and 0.18 G).

Each residue that is encoded by "qfk" has 21 possible outcomes, each of the amino acids plus stop. Table 12 gives the distribution of amino acids encoded by "qfk", assuming 5% errors. The abundance of the parental sequence is the product of the abundances of R×I×A×L×V×A. The abundance of the least-favored sequence is 1 in $4.2 \cdot 10^9$.

Olig#27 and olig#28 are annealed and extended with Klenow fragment and all four (nt)TPs. Both the ds synthetic DNA and RF pLG7 DNA are cut with both ApaI and SphI. The cut DNA is purified and the appropriate pieces ligated (See Sec. 14.1) and used to transform competent PE383. (Sec. 14.2). In order to generate a sufficient number of transformants, $V_c$ is set to 5000 ml.

1) culture *E. coli* in 5.0 l of LB broth at 37° C. until cell density reaches $5 \cdot 10^7$ to $7 \cdot 10^7$ cells/ml,
2) chill on ice for 65 minutes, centrifuge the cell suspension at 4000 g for 5 minutes at 4° C.,
3) discard supernatant; resuspend the cells in 1667 ml of an ice-cold, sterile solution of 60 mM $CaCl_2$,
4) chill on ice for 15 minutes, and then centrifuge at 4000 g for 5 minutes at 4° C.,
5) discard supernatant; resuspend cells in 2×400 ml of ice-cold, sterile 60 mM $CaCl_2$; store cells at 4° C. for 24 hours,
6) add DNA in ligation or TE buffer; mix and store on ice for 30 minutes; 20 ml of solution containing 5 μg/ml of DNA is used,
7) heat shock cells at 42° C. for 90 seconds,
8) add 200 ml LB broth and incubate at 37° C. for 1 hour,
9) add the culture to 2.0 l of LB broth containing ampicillin at 35–100 μg/ml and culture for 2 hours at 37° C.,
10) centrifuge at 8000 g for 20 minutes at 4° C.,
11) discard supernatant, resuspend cells in 50 ml of LB broth plus ampicillin and incubate 1 hour at 37° C.,
12) plate cells on LB agar containing ampicillin,
13) harvest virions by method of Salivar et al. (SALI64).

The heat shock of step (7) can be done by dividing the 200 ml into 100 200 μl aliquots in 1.5 ml plastic Eppendorf tubes. It is possible to optimize the heat shock for other volumes and kinds of container. It is important to: a) use all or nearly all the vgDNA synthesized in ligation, this will require large amounts of pLG7 backbone, b) use all or nearly all the ligation mixture to transform cells, and c) culture all or nearly all the transformants at high density. These measures are directed at maintaining diversity.

IPTG is added to the growth medium at 2.0 mM (the optimal level) and virions are harvested in the usual way. It is important to collect virions in a way that samples all or nearly all the transformants. Because F⁻ cells are used in the transformation, multiple infections do not pose a problem.

HHMb has a pI of 7.0 and we carry out chromatography at pH 8.0 so that HHMb is slightly negative while BPTI and most of its mutants are positive. HHMb is fixed (Sec. V.F) to a 2.0 ml column on Affi-Gel 10$^{(TM)}$ or Affi-Gel 15$^{(TM)}$ at 4.0 mg/ml support matrix, the same density that is optimal for a column supporting trp.

We note that charge repulsion between BPTI and HHMb should not be a serious problem and does not impose any constraints on ions or solutes allowed as eluants. Neither BPTI nor HHMb have special requirements that constrain choice of eluants. The eluant of choice is KCl in varying concentrations.

To remove variants of BPTI with strong, indiscriminate binding for any protein or for the support matrix, we pass the variegated population of virions over a column that supports bovine serum albumin (BSA) before loading the population onto the {HHMb} column. Affi-Gel 10$^{(TM)}$ or Affi-Gel 15$^{(TM)}$ is used to immobilize BSA at the highest level the matrix will support. A 10.0 ml column is loaded with 5.0 ml of Affi-Gel-linked-BSA; this column, called {BSA}, has $V_V$=5.0 ml. The variegated population of virions containing $10^{12}$ pfu in 1 ml (0.2×$V_V$) of 10 mM KCl, 1 mM phosphate, pH 8.0 buffer is applied to {BSA}. We wash {BSA} with 4.5 ml (0.9×$V_V$) of 50 mM KCl, mM phosphate, pH 8.0 buffer. The wash with 50 mM salt will elute virions that adhere slightly to BSA but not virions with strong binding. The pooled effluent of the {BSA} column is 5.5 ml of approximately 13 mM KCl.

The column {HHMb} is first blocked by treatment with $10^{11}$ virions of M13(am429) in 100 ul of 10 mM KCl buffered to pH 8.0 with phosphate; the column is washed with the same buffer until OD260 returns to base line or 2×$V_V$ have passed through the column, whichever comes first. The pooled effluent from {BSA} is added to {HHMb} in 5.5 ml of 13 mM KCl, 1 mM phosphate, pH 8.0 buffer. The column is eluted in the following way:

1) 10 mM KCl buffered to pH 8.0 with phosphate, until optical density at 280 nm falls to base line or 2× $V_V$, whichever is first, (effluent discarded),
2) a gradient of 10 mM to 2M KCl in 3×$V_V$, pH held at 8.0 with phosphate, (30·100μl fractions),
3) a gradient of 2M to 5M KCl in 3×$V_V$, phosphate buffer to pH 8.0 (30·100μl fractions),
4) constant 5M KCl plus 0 to 0.8M guanidinium Cl in 2×$V_V$, with phosphate buffer to pH 8.0, (20·100 μl fractions), and
5) constant 5M KCl plus 0.8M guanidinium Cl in 1×$V_V$, with phosphate buffer to pH 8.0, (10·100 μl fractions).

In addition to the elution fractions, a sample is removed from the column and used as an inoculum for phage-sensitive Sup⁻ cells (Sec. V). A sample of 4 μl from each fraction is plated on phage-sensitive Sup⁻ cells. Fractions that yield too many colonies to count are replated at lower dilution. An approximate titre of each fraction is calculated. Starting with the last fraction and working toward the first fraction that was titered, we pool fractions until approximately $10^9$ phage are in the pool, i.e. about 1 part in 1000 of the phage applied to the column. This population is infected into $3 \cdot 10^{11}$ phage-sensitive PE384 in 300 ml of LB broth. The very low multiplicity of infection (moi) is chosen to reduce the possibility of multiple infection. After thirty minutes, viable phage have entered recipient cells but have not yet begun to produce new phage. Phage-born genes are expressed at this phase, and we can add ampicillin that will kill uninfected cells. These cells still carry F-pili and will absorb phage helping to prevent multiple infections.

If multiple infection should pose a problem that cannot be solved by growth at low multiple-of-infection on F⁺ cells, the following procedure can be employed to obviate the problem. Virions obtained from the affinity separation are infected into F⁺ *E. coli* and cultured to amplify the genetic messages (Sec. V). CCC DNA is obtained either by harvesting RF DNA or by in vitro extension of primers annealed to ss phage DNA. The CCC DNA is used to transform F⁻ cells at a high ratio of cells to DNA. Individual virions obtained in this way should bear only proteins encoded by the DNA within.

The phagemid population is grown and chromatographed three times and then examined for SBDs (Sec. V). in each separation cycle, phage from the last three fractions that contain viable phage are pooled with phage obtained by removing some of the support matrix as an inoculum. At each cycle, about $10^{12}$ phage are loaded onto the column and about $10^9$ phage are cultured for the next separation cycle. After the third separation cycle, SBD colonies are picked from the last fraction that contained viable phage.

Each of the SBDs is cultured and tested for retention on a Pep-Tie column supporting HHMb. The phage showing the greatest retention on the Pep-Tie {HHMb} column. This SBD! becomes the parental amino-acid sequence to the second variegation cycle.

Assume for the sake of argument that, in SBD!, R40 changed to D, I42 changed to Q, A50 changed to E, L52 remained L, and A71 changed to W (see Table 38). If so, a rational plan for the second round of variegation would be that which is set forth in Table 39. The residues to be varied are chosen by: a) choosing some of the residues in the principal set that were not varied in the first round (viz. residues 42, 44, 51, 54, 55, 72, or 75 of the fusion), and b) choosing some residues in the secondary set. Residues 51, 54, 55, and 72 are varied through all twenty amino acids and, unavoidably, stop. Residue 44 is only varied between Y and F. Some residues in the secondary set are varied through a restricted range; primarily to allow different charges (+, 0, −) to appear. Residue 38 is varied through K, R, E, or G. Residue 41 is varied through I, V, K, or E. Residue 43 is varied through R, S, G, N, K, D, E, T, or A.

Now assume that in the most successful SBD of the second round of variegation (SBD-2!), residue 38 (K15 of BPTI) changed to E, 41 becomes V, 43 goes to N, 44 goes to F, 51 goes to F, 54 goes to S, 55 goes to A, and 72 goes to Q (see Table 40)° A third round of variation is illustrated in Table 41; eight amino acids are varied. Those in the principal set, residues 40, 55, and 57, are varied through all twenty amino acids. Residue 32 is varied through P, Q, T, K, A, or E. Residue 34 is varied through T, P, Q, K, A, or E. Residue 44 is varied through F, L, Y, C, W, or stop. Residue 50 is varied through E, K, or Q. Residue 52 is varied through L, F, I, M, or V. The result of this variation is shown in Table 42.

This example is hypothetical. It is anticipated that more variegation cycles will be needed to achieve dissociation constants of $10^{-8}$M. It is also possible that more than three separation cycles will be needed in some variegation cycles. Real DNA chemistry and DNA synthesizers may have larger errors than our hypothetical 5%. If $S_{err} > 0.05$, then we may not be able to vary six residues at once. Variation of 5 residues at once is certainly possible.

EXAMPLE XII

Design and Mutagenesis of a Class 1 Mini-Protein

To obtain a library of binding domains that are conformationally constrained by a single disulfide, we insert DNA coding for the following family of mini-proteins into the gene coding for a suitable OSP.

Figure 3:
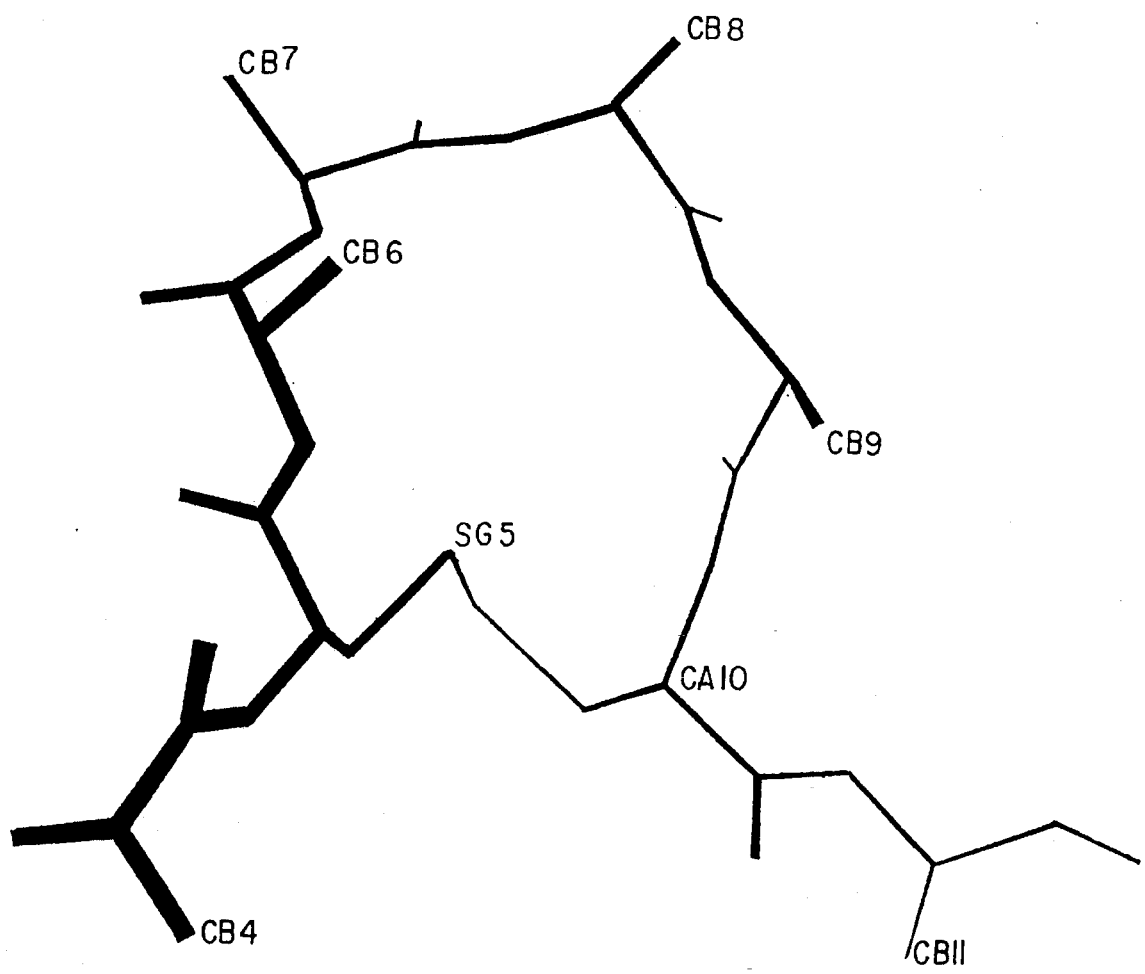
FIG. 3 shows a mini-protein comprising eight residues, numbered 4 through 11 and in which residues 5 and 10 are joined by a disulfide. The β carbons are labeled for residues 4, 6, 7, 8, 9, and 11; these residues are preferred sites of variegation.
Figure 4:
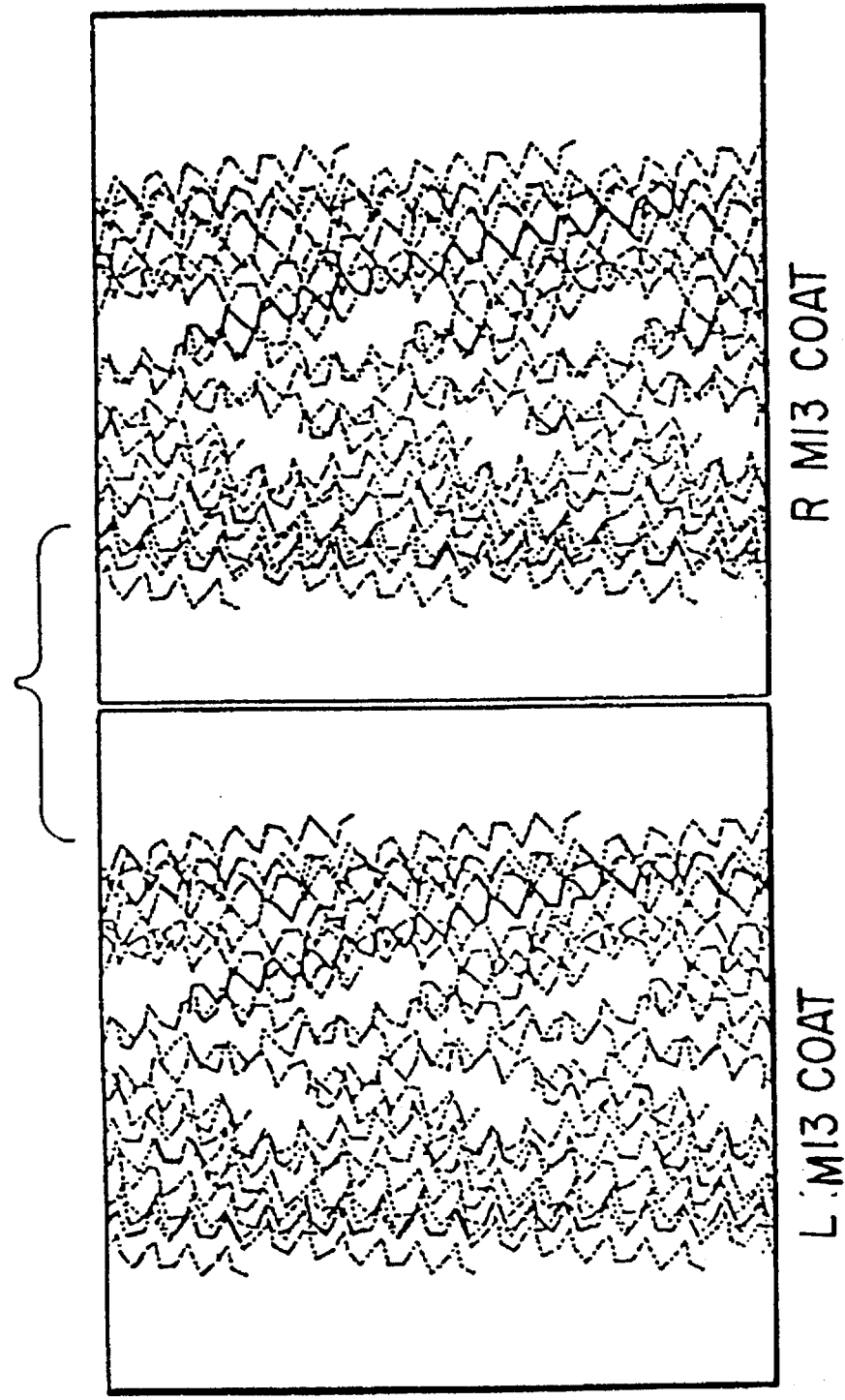
FIG. 4 shows the $C_\alpha$ of the coat protein of phage f1.

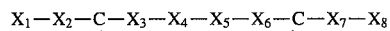

Where ⌊__⌋ indicates disulfide bonding; this mini-protein is depicted in FIG. 3. Disulfides normally do not form between cysteines that are consecutive on the polypeptide chain. One or more of the residues indicated above as $X_n$ will be varied extensively to obtain novel binding. There may be one or more amino acids that precede $X_1$ or follow X8, however, these additional residues will not be significantly constrained by the diagrammed disulfide bridge, and it is less advantageous to vary these remote, unbridged residues. The last X residue is connected to the OSP of the genetic package.

$X_1$, $X_2$, $X_3$, $X_4$, $X_5$, $X_6$, $X_7$, and $X_8$ can be varied independently; i.e. a different scheme of variegation could be used at each position. $X_1$ and $X_8$ are the least constrained residues and may be varied less than other positions.

$X_1$ and $X_8$ can be, for example, one of the amino acids [E, K, T, and A]; this set of amino acids is preferred because: a) the possibility of positively charged, negatively charged, and neutral amino acids is provided, b) these amino acids can be provided in 1:1:1:1 ratio via the codon RMG (R=equimolar A and G, M=equimolar A and C), and c) these amino acids allow proper processing by signal peptidases.

One option for variegation of $X_2$, $X_3$, $X_4$, $X_5$, $X_6$, and $X_7$ is to vary all of these in the same way. For example, each of $X_2$, $X_3$, $X_4$, $X_5$, $X_6$, and $X_7$ can be chosen from the set [F, S, Y, C, L, P, H, R, I, T, N, V, A, D, and G] which is encoded by the mixed codon NNT. Tables 10 and 130 compares libraries in which six codons have been varied either by NNT or NNK codons. NNT encodes 15 different amino acids and only 16 DNA sequences. Thus, there are $1.139 \cdot 10^7$ amino-acid sequences, no stops, and only $1.678 \cdot 10^7$ DNA sequences. A library of $10^8$ independent transformants will contain 99% of all possible sequences. The NNK library contains $6.4 \cdot 10^7$ sequences, but complete sampling requires a much larger number of independent transformants.

EXAMPLE XIII

A CYS::HELIX::TURN::STRAND::CYS Unit

The parental Class 2 mini-proteins may be a naturally-occurring Class 2 mini-protein. It may also be a domain of a larger protein whose structure satisfies or may be modified so as to satisfy the criteria of a class 2 mini-protein. The modification may be a simple one, such as the introduction of a cysteine (or a pair of cysteines) into the base of a hairpin structure so that the hairpin may be closed off with a disulfide bond, or a more elaborate one, so as the modification of intermediate residues so as to achieve the hairpin structure. The parental class 2 mini-protein may also be a composite of structures from two or more naturally-occurring proteins, e.g., an α helix of one protein and a β strand of a second protein.

One mini-protein motif of potential use comprises a disulfide loop enclosing a helix, a turn, and a return strand. Such a structure could be designed or it could be obtained from a protein of known 3D structure. Scorpion neurotoxin, variant 3, (ALMA83a, ALMA83b) (hereafter ScorpTx) contains a structure diagrammed in FIG the allowed sequences. Other variegations are also appropriate. Concerning α conotoxins, see, inter alia, ALMQ89, CRUZ85, GRAY83, GRAY84, and PARD89.

The parental mini-protein may instead be one of the proteins designated "Hybrid-I" and "Hybrid-II" by Pease et al. (PEAS90); cf. FIG. 4 of PEAS90. One preferred set of residues to vary for either protein consists of:

| Parental Amino acid | Variegated Codon | Allowed Amino acids | AA seqs/ DNA seqs |
|---|---|---|---|
| A5 | RVT | ADGTNS | 6/6 |
| P6 | VYT | PTALIV | 6/6 |
| E7 | RRS | EDNKSRGI | 7/8 |
| T8 | VHG | TPALMVQKE | 9/9 |
| A9 | VHG | ATPLMVQKE | 9/9 |
| A10 | RMG | AEKT | 4/4 |
| K12 | VHG | KQETPALMV | 9/9 |
| Q16 | NNG | $L^2R^2$S.WPOMTKVAEG | 13/15 |

This provides $9.55 \cdot 10^6$ amino-acid sequences encoded by $1.26 \cdot 10^7$ DNA sequences. A library comprising $5.0 \cdot 10^7$ transformants allows expression of 98.2% of all possible sequences. At each position, the parental amino acid is allowed.

At position 5 we provide amino acids that are compatible with a turn. At position 6 we allow ILE and VAL because they have branched β carbons and make the chain ridged. At position 7 we allow ASP, ASN, and SER that often appear at the amino termini of helices. At positions 8 and 9 we allow several helix-favoring amino acids (ALA, LEU, MET, GLN, GLU, and LYS) that have differing charges and hydrophobicities because these are part of the helix proper. Position 10 is further around the edge of the helix, so we allow a smaller set (ALA, THR, LYS, and GLU). This set not only includes 3 helix-favoring amino acids plus THR that is well tolerated but also allows positive, negative, and neutral hydrophilic. The side groups of 12 and 16 project into the same region as the residues already recited. At these positions we allow a wide variety of amino acids with a bias toward helix-favoring amino acids.

The parental mini-protein may instead be a polypeptide composed of residues 9–24 and 31–40 of aprotinin and possessing two disulfides (Cys9–Cys22 and Cys14–Cys38). Such a polypeptide would have the same disulfide bond topology as α-conotoxin, and its two bridges would have spans of 12 and 17, respectively.

Residues 23, 24 and 31 are variegated to encode the amino acid residue set [G,S,R,D,N,H,P,T,A] so that a sequence that favors a turn of the necessary geometry is found. We use trypsin or anhydrotrypsin as the affinity molucule to enrich for GPs that display a mini-protein that folds into a stable structure similar to BPTI in the P1 region.

Three Disulfide Bond Parental Mini-Proteins

The cone snails (Conus) produce venoms (conotoxins) which are 10–30 amino acids in length and exceptionally rich in disulfide bonds. They are therefore archetypal mini-proteins. Novel mini-proteins with three disulfide bonds may be modelled after the μ-(GIIIA, GIIIB, GIIIC) or Ω-(GVIA, GVIB, GVIC, GVIIA, GVIIB, MVIIA, MVIIB, etc.) conotoxins. The μ-conotoxins have the following conserved structure:

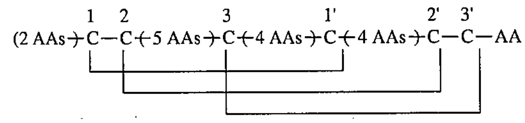

No 3D structure of a μ-conotoxin has been published. Hidaka et al. (HIDA90) have established the connectivity of the disulfides. The following diagram depicts geographutoxin I (also known as μ-conotoxin GIIIA).

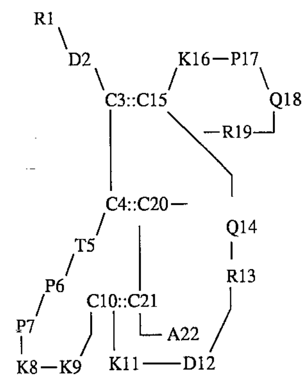

The connection from R19 to C20 could go over or under the strand from Q14 to C15. One preferred form of variegation is to vary the residues in one loop. Because the longest loop contains only five amino acids, it is appropriate to also vary the residues connected to the cysteines that form the loop. For example, we might vary residues 5 through 9 plus 2, 11, 19, and 22. Another useful variegation would be to vary residues 11–14 and 16–19, each through eight amino acids. Concerning μ conotoxins, see BECK89b, BECK89c, CRUZ89, and HIDA90.

The Ω-conotoxins may be represented as follows:

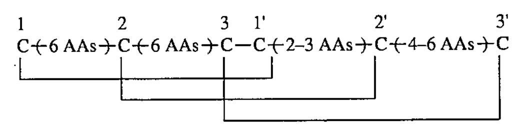

The King Kong peptide has the same disulfide arrangement as the Ω-conotoxins but a different biological activity. Woodward et al. (WOOD90) report the sequences of three homologuous proteins from *C. textile.* Within the mature toxin domain, only the cysteines are conserved. The spacing of the cysteines is exactly conserved, but no other position has the same amino acid in all three sequences and only a few positions show even pair-wise matches. Thus we conclude that all positions (except the cysteines) may be substituted freely with a high probability that a stable disulfide structure will form. Concerning Ω conotoxins, see HILL89 and SUNX87.

Another mini-protein which may be used as a parental binding domain is the *Cucurbita maxima* trypsin inhibitor I (CMTI-I); CMTI-III is also appropriate. They are members of the squash family of serine protease inhibitors, which also includes inhibitors from summer squash, zucchini, and cucumbers (WIEC85). McWherter et al. (MCWH89) describe synthetic sequence-variants of the squash-seed protease inhibitors that have affinity for human leukocyte elastase and cathepsin G. Of course, any member of this family might be used.

CMTI-I is one of the smallest proteins known, comprising only 29 amino acids held in a fixed comformation by three disulfide bonds. The structure has been studied by Bode and colleagues using both X-ray diffraction (BODE89) and NMR (HOLA89a,b). CMTI-I is of ellipsoidal shape; it lacks helices or β-Sheets, but consists of turns and connecting short polypeptide stretches. The disulfide pairing is Cys3–Cys20, Cys10–Cys22 and Cys16–Cys28. In the CMTI-I:trypsin complex studied by Bode et al., 13 of the 29 inhibitor residues are in direct contact with trypsin; most of them are in the primary binding segment Val2(P4)-Glu9 (P4') which contains the reactive site bond Arg5(P1)-Ile6 and is in a conformation observed also for other serine proteinase inhibitors.

CMTI-I has a $K_i$ for trypsin of $\approx 1.5 \cdot 10^{-12}$M. McWherter et al. suggested substitution of "moderately bulky hydrophobic groups" at P1 to confer HLE specificity. They found that a wider set of residues (VAL, ILE, LEU, ALA, PHE, MET, and GLY) gave detectable binding to HLE. For cathepsin G, they expected bulky (especially aromatic) side groups to be strongly preferred. They found that PHE, LEU, MET, and ALA were functional by their criteria; they did not test TRP, TYR, or HIS. (Note that ALA has the second smallest side group available.)

A preferred initial variegation strategy would be to vary some or all of the residues $ARG_1$, $VAL_2$, $PRO_4$, $ARG_5$, $ILE_6$, $LEU_7$, $MET_8$, $GLU_9$, $LYS_{11}$, $HIS_{25}$, $GLY_{26}$, $TYR_{27}$, and $GLY_{29}$. If the target were HNE, for example, one could synthesize DNA embodying the following possibilities:

| Parental | vg Codon | Allowed amino acids | #AA seqs/ #DNA seqs |
|---|---|---|---|
| $ARG_1$ | VNT | RSLPHITNVADG | 12/12 |
| $VAL_2$ | NWT | VILFYHND | 8/8 |
| $PRO_4$ | VYT | PLTIAV | 6/6 |
| $ARG_5$ | VNT | RSLPHITNVADG | 12/12 |
| $ILE_6$ | NNK | all 20 | 20/31 |
| $LEU_7$ | VWG | LQMKVE | 6/6 |
| $TYR_{27}$ | NAS | YHONKDE. | 7/8 |

This allows about $5.81 \cdot 10^6$ amino-acid sequences encoded by about $1.03 \cdot 10^7$ DNA sequences. A library comprising $5.0 \cdot 10^7$ independent transformants would give ≈99% of the possible sequences. Other variegation schemes could also be used.

Other inhibitors of this family include:

- Trypsin inhibitor I from *Citrullus vulgaris* (OTLE87),
- Trypsin inhibitor II from *Bryonia dioica* (OTLE87),
- Trypsin inhibitor I from *Cucurbita maxima* (in OTLE87),
- trypsin inhibitor III from *Cucurbita maxima* (in OTLE87),
- trypsin inhibitor IV from *Cucurbita maxima* (in OTLE87),
- trypsin inhibitor II from *Cucurbita pepo* (in OTLE87),
- trypsin inhibitor III from *Cucurbita pepo* (in OTLE87),
- trypsin inhibitor IIb from *Cucumis sativus* (in OTLE87),
- trypsin inhibitor IV from *Cucumis sativus* (in OTLE87),
- trypsin inhibitor II from *Ecballium elaterium* (FAVE89),
- and inhibitor CM-1 from *Momordica repens* (in OTLE87).

Another mini-protein that may be used as an initial potential binding domain is the heat-stable enterotoxins derived from some enterotoxogenic *E. coli, Citrobacter freundii,* and other bacteria (GUAR89). These mini-proteins are known to be secreted from *E. coli* and are extremely stable. Works related to synthesis, cloning, expression and properties of these proteins include: BHAT86, SEKI85, SHIM87, TAKA85, TAKE90, THOM85a,b, YOSH85, DALL90, DWAR89, GARI87, GUZM89, GUZM90, HOUG84, KUBO89, KUPE90, OKAM87, OKAM88, and OKAM90.

Another preferred IPBD is crambin or one of its homologues, the phoratoxins and ligatoxins (LECO87). These proteins are secreted in plants. The 3D structure of crambin has been determined. NMR data on homologues indicate that the 3D structure is conserved. Residues thought to be on the surface of crambin, phoratoxin, or ligatoxin are preferred residues to vary.

EXAMPLE XV

A Mini-Protein Having a Cross-Link Consisting of CU(II), One Cysteine, Two Histidines, and One Methionine Sequences such as HIS-ASN-GLY-MET-Xaa-Xaa-Xaa-Xaa-Xaa-Xaa-HIS-ASN-GLY-CYS and CYS-ASN-GLY-MET-Xaa-Xaa-Xaa-Xaa-Xaa-Xaa-HIS-ASN-GLY-HIS are likely to combine with Cu(II) to form structures as shown in the diagram:

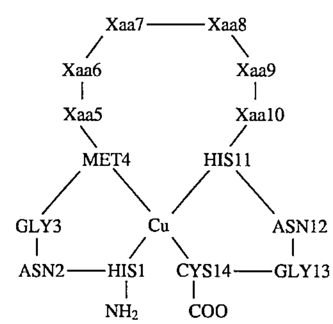

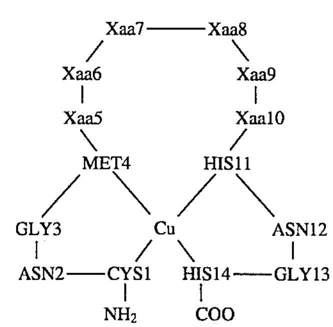

Other arrangements of HIS, MET, HIS, and CYS along the chain are also likely to form similar structures. The amino acids ASN-GLY at positions 2 and 3 and at positions 12 and 13 give the amino acids that carry the metal-binding ligands enough flexibility for them to come together and bind the metal. Other connecting sequences may be used, e.g. GLY-ASN, SER-GLY, GLY-PRO, GLY-PRO-GLY, or PRO-GLY-ASN could be used. It is also possible to vary one or more residues in the loops that join the first and second or the third and fourth metal-binding residues. For example,

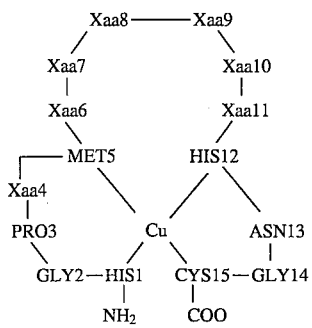

is likely to form the diagrammed structure for a wide variety of amino acids at Xaa4. It is expected that the side groups of Xaa4 and Xaa6 will be close together and on the surface of the mini-protein.

The variable amino acids are held so that they have limited flexibility. This cross-linkage has some differences from the disulfide linkage. The separation between $C_{\alpha 4}$ and $C_{\alpha 11}$ is greater than the separation of the $C_{\alpha}s$ of a cystine. In addition, the interaction of residues 1 through 4 and 11 through 14 with the metal ion are expected to limit the motion of residues 5 through 10 more than a disulfide between rsidues 4 and 11. A single disulfide bond exerts strong distance constrains on the α carbons of the joined residues, but very little directional constraint on, for example, the vector from N to C in the main-chain.

For the desired sequence, the side groups of residues 5 through 10 can form specific interactions with the target. Other numbers of variable amino acids, for example, 4, 5, 7, or 3, are appropriate. Larger spans may be used when the enclosed sequence contains segments having a high potential to form α helices or other secondary structure that limits the conformational freedom of the polypeptide main chain. Whereas a mini-protein having four CYSs could form three distinct pairings, a mini-protein having two HISs, one MET, and one CYS can form only two distinct complexes with Cu. These two structures are related by mirror symmetry through the Cu. Because the two HISs are distinguishable, the structures are different.

When such metal-containing mini-proteins are displayed on filamentous phage, the cells that produce the phage can be grown in the presence of the appropriate metal ion, or the phage can be exposed to the metal only after they are separated from the cells.

EXAMPLE XVI

A Mini-Protein Having a Cross-Link Consisting of ZN(II) and Four Cysteines

A cross link similar to the one shown in Example XV is exemplified by the Zinc-finger proteins (GIBS88, GAUS87, PARR88, FRAN87, CHOW87, HARD90). One family of Zinc-fingers has two CYS and two HIS residues in conserved positions that bind Zn++(PARR88, FRAN87, CHOW87, EVAN88, BERG88, CHAV88). Gibson et al. (GIBS88) review a number of sequences thought to form zinc-fingers and propose a three-dimensional model for these compounds. Most of these sequences have two CYS and two HIS residues in conserved positions, but some have three CYS and one HIS residue. Gauss et al. (GAUSS7) also report a zinc-finger protein having three CYS and one HIS residues that bind zinc. Hard et al. (HARD90) report the 3D structure of a protein that comprises two zinc-fingers, each of which has four CYS residues. All of these zinc-binding proteins are stable in the reducing intracellular environment.

One preferred example of a CYS::zinc cross linked miniprotein comprises residues 440 to 461 of the sequence shown in FIG. 1 of HARD90. The resiudes 444 through 456 may be variegated. One such variegation is as follows:

| Parental | Allowed | #AA/#DNA |
|---|---|---|
| SER444 | SER, ALA | 2/2 |
| ASP445 | ASP, ASN, GLU, LYS | 4/4 |
| GLU446 | GLU, LYS, GLN | 3/3 |
| ALA447 | ALA, THR, GLY, SER | 4/4 |
| SER448 | SER, ALA | 2/2 |
| GLY449 | GLY, SER, ASN, ASP | 4/4 |
| CYS450 | CYS, PHE, ARG, LEU | 4/4 |
| HIS451 | HIS, GLN, ASN, LYS, ASP, GLU | 6/6 |
| TYR452 | TYR, PHE, HIS, LEU | 4/4 |
| GLY453 | GLY, SER, ASN, ASP | 4/4 |
| VAL454 | VAL, ALA, ASP, GLY, SER, ASN, THR, ILE | 8/8 |
| LEU455 | LEU, HIS, ASP, VAL | 4/4 |
| THR456 | THR, ILE, ASN, SER | 4/4 |

This leads to $3.77 \cdot 10^7$ DNA sequences that encode the same number of amino-acid sequences. A library having $1.0 \cdot 10^8$ indepentent transformants will display 93% of the allowed sequences; $2.0 \cdot 10^8$ independent transformants will display 99.5% of allowed sequences.

TABLE 1

Single-letter codes.

Single-letter code is used for proteins:

| | | | | |
|---|---|---|---|---|
| a = ALA | c = CYS | d = ASP | e = GLU | f = PHE |
| g = GLY | h = HIS | i = ILE | k = LYS | l = LEU |
| m = MET | n = ASN | p = PRO | q = GLN | r = ARG |
| s = SER | t = THR | v = VAL | w = TRP | y = TYR |
| . = STOP | * = any amino acid | | | |
| b = n or d | | | | |
| z = e or q | | | | |
| x = any amino acid | | | | |

Single-letter IUB codes for DNA:

T, C, A, G stand for themselves
M for A or C
R for puRines A or G
W for A or T
S for C or G
Y for pYrimidines T or C

TABLE 1-continued

Single-letter codes.

K for G or T
V for A, C, or G (not T)
H for A, C, or T (not G)
D for A, G, or T (not C)
B for C, G, or T (not A)
N for any base.

TABLE 2

Preferred Outer-Surface Proteins

| Genetic Package | Preferred Outer-Surface Protein | Reason for preference |
|---|---|---|
| M13 | coat protein (gPVIII) | a) exposed amino terminus, b) predictable post-translational processing, c) numerous copies in virion. d) fusion data available |
|  | gp III | a) fusion data available. b) amino terminus exposed. c) working example available. |
| PhiX174 | G protein | a) known to be on virion exterior, b) small enough that the G-ipbd gene can replace H gene. |
| E. coli | LamB | a) fusion data available, b) non-essential. |
|  | OmpC | a) topological model b) non-essential; abundant |
|  | OmpA | a) topological model b) non-essential; abundant c) homologues in other genera |
|  | OmpF | a) topological model b) non-essential; abundant |
|  | PhoE | a) topological model b) non-essential; abundant c) inducible |
| B. subtilis spores | CotC | a) no post-translational processing, b) distinctive sequence that causes protein to localize in spore coat, c) non-essential. |
|  | CotD | Same as for CotC. |

TABLE 3

Ambiguous DNA for AA_seq2

| m 1 A.T.G | k 2 A.A.r | k 3 A.A.r | s 4 T.C.n A.G.y | l 5 T.T.r C.T.n | v 6 G.T.n | l 7 T.T.r C.T.n | k 8 A.A.r |
|---|---|---|---|---|---|---|---|
| a 9 G.C.n | s 10 T.C.n A.G.y | v 11 G.T.n | a 12 G.C.n | v 13 G.T.n | a 14 G.C.n | t 15 A.C.n | l 16 T.T.r C.T.n |
| v 17 G.T.n | p 18 C.C.n | m 19 A.T.G | l 20 T.T.r C.T.n | s 21 T.C.n A.G.y | f 22 T.T.y | a 23 G.C.n | r 24 C.G.n A.G.r |

TABLE 3-continued

Ambiguous DNA for AA_seq2

| p 25 C.C.n | d 26 G.A.y | f 27 T.T.y | c 28 T.G.y | l 29 T.T.r C.T.n | e 30 G.A.r | p 31 C.C.n | p 32 C.C.n |
|---|---|---|---|---|---|---|---|
| y 33 T.A.y | t 34 A.C.n | g 35 G.G.n | p 36 C.C.n | c 37 T.G.y | k 38 A.A.r | a 39 G.C.n | r 40 C.G.n A.G.r |
| i 41 A.T.h | i 42 A.T.h | r 43 C.G.n | y 44 T.A.y | f 45 T.T.y | y 46 T.A.y | n 47 A.A.y | a 48 G.C.n |
| k 49 A.A.r | a 50 G.C.n | g 51 G.G.n | l 52 T.T.r C.T.n | c 53 T.G.y | q 54 C.A.r | t 55 A.C.n | f 56 T.T.y |
| v 57 G.T.n | y 58 T.A.y | g 59 G.G.n | g 60 G.G.n | c 61 T.G.y | r 62 C.G.n A.G.r | a 63 G.C.n | k 64 A.A.r |
| r 65 C.G.n A.G.r | n 66 A.A.y | n 67 A.A.y | f 68 T.T.y | k 69 A.A.r | s 70 T.C.n A.G.y | e 71 G.C.n | e 72 G.A.r |
| d 73 G.A.y | c 74 T.G.y | m 75 A.T.G | r 76 C.G.n | t 77 A.C.n | c 78 T.G.y | g 79 G.G.n | g 80 G.G.n |
| a 81 G.C.n | a 82 G.C.n | e 83 G.A.r | g 84 G.G.n | d 85 G.A.y | d 86 G.A.y | p 87 C.C.n | a 88 G.C.n |
| k 89 A.A.r | a 90 G.C.n | a 91 G.C.n | f 92 T.T.y | N 93 A.A.y | s 94 T.C.n A.G.y | l 95 T.T.r C.T.n | q 96 C.A.r |
| a 97 G.C.n | s 98 T.C.n A.G.y | a 99 G.C.n | t 100 A.C.n | e 101 G.C.n | y 102 T.A.y | i 103 A.T.h | g 104 G.G.n |
| y 105 T.A.y | a 106 G.C.n | w 107 T.G.G | a 108 G.C.n | m 109 A.T.G | v 110 G.T.n | v 111 G.T.n | v 112 G.T.n |
| i 113 A.T.h | v 114 G.T.n | g 115 G.G.n | a 116 G.C.n | t 117 A.C.n | i 118 A.T.h | g 119 G.G.n | i 120 A.T.h |
| k 121 A.A.r | l 122 T.T.r C.T.n | f 123 T.T.y | k 124 A.A.r | k 125 A.A.r | f 126 T.T.y | t 127 A.C.n | s 128 T.C.n A.G.y |

TABLE 3-continued

Ambiguous DNA for AA_seq2

| k<br>129<br>A.A.r | a<br>130<br>G.C.n | s<br>131<br>T.C.n<br>A.G.y | .<br>132<br>T.A.r<br>T.G.A | .<br>133<br>T.A.r<br>T.G.A | .<br>134<br>T.A.r<br>T.G.A |
|---|---|---|---|---|---|

TABLE 4

Table of Restriction Enzyme Suppliers

Suppliers: Sigma Chemical Co.
P.O. Box 14508
St. Louis, Mo. 63178
Bethesda Research Laboratories
P.O. Box 6009
Gaithersburg, Maryland, 20877
Boehringer Mannheim Biochemicals
7941 Castleway Drive
Indianapolis, Indiana, 46250
International Biochemicals, Inc.
P.O.Box 9558
New Haven, Connecticutt, 06535
New England BioLabs
32 Tozer Road
Beverly, Massachusetts, 01915
Promega
2800 S. Fish Hatchery Road
Madison, Wisconsin, 53711
Stratagene Cloning Systems
11099 North Torrey Pines Road
La Jolla, California, 92037

TABLE 5

Potential sites in ipbd gene.

Summary of cuts.

Enz = %Acc I has 3 elective sites: 96 169 281
Enz = Afl II has 1 elective sites: 19
Enz = Apa I has 2 elective sites: 102 103
Enz = Asu II has 1 elective sites: 381
Enz = Ava III has 1 elective sites: 314
Enz = BspM II has 1 elective sites: 72
Enz = BssH II has 2 elective sites: 67 115
Enz = %BstX I has 1 elective sites: 323
Enz = +Dra II has 3 elective sites: 102 103 226
Enz = +EcoN I has 2 elective sites: 62 94
Enz = +Esp I has 2 elective sites: 57 187
Enz = Hind III has 6 elective sites: 9 23 60 287 361 386
Enz = Kpn I has 1 elective sites: 48
Enz=n Mlu I has 1 elective sites: 314
Enz = Nar I has 2 elective sites: 238 343
Enz = Nco I has 1 elective sites: 323
Enz = Nhe I has 3 elective sites: 25 289 388
Enz = Nru I has 2 elective sites: 38 65
Enz = +PflM I has 1 elective sites: 94
Enz = PmaC I has 1 elective sites: 228
Enz = +PpuM I has 2 elective sites: 102 226
Enz = +Rsr II has 1 elective sites: 102
Enz = +Sfi I has 2 elective sites: 24 261
Enz = Spe I has 3 elective sites: 12 45 379
Enz = Sph I has 1 elective sites: 221
Enz = Stu I has 5 elective sites: 23 70 150 287 386
Enz = %Sty I has 6 elective sites: 11 44 143 263 323 383
Enz = Xba I has 1 elective sites: 84
Enz = Xho I has 1 elective sites: 85
Enz = Xma III has 3 elective sites: 70 209 242

Enzymes not cutting ipbd.

| Avr II | BamH I | Bcl I | BstE II |
|---|---|---|---|
| EcoR I | EcoR V | Hpa I | Not I |

TABLE 5-continued

Potential sites in ipbd gene.

| Sac I | Sal I | Sau I | Sma I |
|---|---|---|---|
| Xma I | | | |

TABLE 6

Exposure of amino acid types in T4 lzm & HEWL.

HEADER HYDROLASE 18-AUG-86 2LZM
(O-GLYCOSYL)
COMPND LYSOZYME (E.C.3.2.1.17)
AUTHOR L. K. WEAVER,
B. W. MATTHEWS
Coordinates from Brookhaven Protein Data Bank: 1LYM.
Only Molecule A was considered.
HEADER HYDROLASE 29-JUL-82 1LYM
(O-GLYCOSYL)
COMPND LYSOZYME (E.C.3.2.1.17)
AUTHOR J. HOGLE, S. T. RAO,
M. SUNDARALINGAM
Solvent radius = 1.40 Atomic radii in Table 7.
Surface area measured in Å$^2$.

| Type | N | <area> | sigma | max | min | Max exposed(fraction) |
|---|---|---|---|---|---|---|
| ALA | 27 | 211.0 | 1.47 | 214.3 | 207.1 | 85.1(0.40) |
| CYS | 10 | 239.8 | 3.56 | 245.5 | 234.4 | 38.3(0.16) |
| ASP | 17 | 271.1 | 5.36 | 281.4 | 262.5 | 127.1(0.47) |
| GLU | 10 | 297.2 | 5.78 | 304.9 | 285.4 | 100.7(0.34) |
| PHE | 8 | 316.6 | 5.92 | 325.4 | 307.5 | 99.8(0.32) |
| GLY | 23 | 185.5 | 1.31 | 188.3 | 183.3 | 91.9(0.50) |
| HIS | 2 | 297.7 | 3.23 | 301.0 | 294.5 | 32.9(0.11) |
| ILE | 16 | 278.1 | 3.61 | 285.6 | 269.6 | 57.5(0.21) |
| LYS | 19 | 309.2 | 5.38 | 321.9 | 300.1 | 147.1(0.48) |
| LEU | 24 | 282.6 | 6.75 | 304.0 | 269.8 | 109.9(0.39) |
| MET | 7 | 293.0 | 5.70 | 299.5 | 283.1 | 88.2(0.30) |
| ASN | 26 | 273.0 | 5.75 | 285.1 | 262.6 | 143.4(0.53) |
| PRO | 5 | 239.9 | 2.75 | 242.1 | 234.6 | 128.7(0.54) |
| GLN | 8 | 299.5 | 4.75 | 305.8 | 291.5 | 145.9(0.49) |
| ARG | 24 | 344.7 | 8.66 | 355.8 | 326.7 | 240.7(0.70) |
| SER | 16 | 228.6 | 3.59 | 236.6 | 223.3 | 98.2(0.43) |
| THR | 18 | 250.3 | 3.89 | 257.2 | 244.2 | 139.9(0.56) |
| VAL | 15 | 254.3 | 4.05 | 261.8 | 245.7 | 111.1(0.44) |
| TRP | 9 | 359.4 | 3.38 | 366.4 | 355.1 | 102.0(0.28) |
| TYR | 9 | 335.8 | 4.97 | 342.0 | 325.0 | 72.6(0.22) |

TABLE 7

Atomic radii

| | Å |
|---|---|
| $C_\alpha$ | 1.70 |
| $O_{carbonyl}$ | 1.52 |
| $N_{amide}$ | 1.55 |
| Other atoms | 1.80 |

TABLE 8

Fraction of DNA molecules having
n non-parental bases when
reagents that have fraction
M of parental nucleotode.

| M | .9965 | .97716 | .92612 | .8577 | .79433 | .63096 |
|---|---|---|---|---|---|---|
| f0 | .9000 | .5000 | .1000 | .0100 | .0010 | .000001 |
| f1 | .09499 | .35061 | .2393 | .04977 | .00777 | .0000175 |
| f2 | .00485 | .1188 | .2768 | .1197 | .0292 | .000149 |

TABLE 8-continued

Fraction of DNA molecules having n non-parental bases when reagents that have fraction M of parental nucleotode.

| M | .9965 | .97716 | .92612 | .8577 | .79433 | .63096 |
|---|---|---|---|---|---|---|
| f3 | .00016 | .0259 | .2061 | .1854 | .0705 | .000812 |
| f4 | .000004 | .00409 | .1110 | .2077 | .1232 | .003207 |
| f8 | 0. | $2 \cdot 10^{-7}$ | .00096 | .0336 | .1182 | .080165 |
| f16 | 0. | 0. | 0. | $5 \cdot 10^{-7}$ | .00006 | .027281 |
| f23 | 0. | 0. | 0. | 0. | 0. | .0000089 |
| most | 0 | 0 | 2 | 5 | 7 | 12 |

"most" is the value of n having the highest probability.

TABLE 9 best vgCodon

```
Program "Find Optimum vgCodon."
INITIALIZE-MEMORY-OF-ABUNDANCES
DO ( t1 = 0.21 to 0.31 in steps of 0.01 )
. DO ( c1 = 0.13 to 0.23 in steps of 0.01 )
. . DO ( a1 = 0.23 to 0.33 in steps of 0.01 )
Comment    calculate g1 from other concentrations
. . . g1 = 1.0 - t1 - c1 - a1
. . . IF( g1 .ge. 0.15 )
. . . . DO ( a2 = 0.37 to 0.50 in steps of 0.01 )
. . . . . DO ( c2 = 0.12 to 0.20 in steps of 0.01 )
Comment    Force D+E = R + K
. . . . . . g2 = ( g1*a2 - .5*a1*a2)/(c1+0.5*a1)
Comment    Calc t2 from other concentrations.
. . . . . . t2 = 1. - a2 - c2 - g2
. . . . . . IF(g2.gt. 0.1.and. t2.gt.0.1)
. . . . . . . CALCULATE-ABUNDANCES
. . . . . . . COMPARE-ABUNDANCES-TO-PREVIOUS-ONES
. . . . . . .end_IF_block
. . . . . .end_DO_loop ? c2
. . . . .end_DO_loop ? a2
. . . ..end_IF_block ? if g1 big enough
. . ..end_DO_loop ? a1
. ..end_DO_loop ? c1
..end_DO_loop ? t1
WRITE the best distribution and the abundances.
```

TABLE 10

Abundances obtained from various vgCodons

A. Optimized fxS Codon, Restrained by [D] + [E] = [K] + [R]

| | T | C | A | G | |
|---|---|---|---|---|---|
| 1 | .26 | .18 | .26 | .30 | f |
| 2 | 22 | .16 | .40 | .22 | x |
| 3 | .5 | .0 | .0 | .5 | s |

| Amino acid | Abundance | Amino acid | Abundance |
|---|---|---|---|
| A | 4.80% | C | 2.86% |
| D | 6.00% | E | 6.00% |
| F | 2.86% | G | 6.60% |
| H | 3.60% | I | 2.86% |
| K | 5.20% | L | 6.82% |
| M | 2.86% | N | 5.20% |
| P | 2.88% | Q | 3.60% |
| R | 6.82% | S | 7.02% mfaa |
| T | 4.16% | V | 6.60% |
| W | 2.86% lfaa | Y | 5.20% |
| stop | 5.20% | | |

[D] + [E] ≡ [K] + [R] = .12

TABLE 10-continued

Abundances obtained from various vgCodons ratio = Abun(W)/Abun(S) = 0.4074

| j | (1/ratio)$^j$ | (ratio)$^j$ | stop-free |
|---|---|---|---|
| 1 | 2.454 | .4074 | .9480 |
| 2 | 6.025 | .1660 | .8987 |
| 3 | 14.788 | .0676 | .8520 |
| 4 | 36.298 | .0275 | .8077 |
| 5 | 89.095 | .0112 | .7657 |
| 6 | 218.7 | $4.57 \cdot 10^{-3}$ | .7258 |
| 7 | 536.8 | $1.86 \cdot 10^{-3}$ | .6881 |

TABLE 10-continued

Abundances obtained from various vgCodons

B. Unrestrained, optimized

| | T | C | A | G |
|---|---|---|---|---|
| 1 | .27 | .19 | .27 | .27 |
| 2 | .21 | .15 | .43 | .21 |
| 3 | .5 | .0 | .0 | .5 |

| Amino acid | Abundance | Amino acid | Abundance |
|---|---|---|---|
| A | 4.05% | C | 2.84% |
| D | 5.81% | E | 5.81% |
| P | 2.844 | G | 5.67% |
| H | 4.08% | I | 2.84% |
| K | 5.81% | L | 6.83% |
| M | 27.84% | N | 5.81% |
| P | 2.85% | Q | 4.08% |
| R | 6.83% | S | 6.89% mfaa |
| T | 4.05% | V | 5.67% |
| W | 2.84% lfaa | Y | 5.81% |
| stop | 5.81% | | |

[D] + [E] = 0.1162 [K] + [R] = 0.1264
ratio = Abun(W)/Abun(S) = 0.41176

TABLE 10-continued

Abundances obtained from various vgCodons

| j | (1/ratio)$^j$ | (ratio)$^j$ | stop-free |
|---|---|---|---|
| 1 | 2.4286 | .41176 | .9419 |
| 2 | 5.8981 | .16955 | .8872 |
| 3 | 14.3241 | .06981 | .8356 |
| 4 | 34.7875 | .02875 | .7871 |
| 5 | 84.4849 | .011836 | .74135 |
| 6 | 205.180 | .004874 | .69828 |
| 7 | 498.3 | $2.007 \cdot 10^{-3}$ | .6577 |

C. optimized NNT

|   | T | C | A | G |
|---|---|---|---|---|
| 1 | .2071 | .2929 | .2071 | .2929 |
| 2 | .2929 | .2071 | .2929 | .2071 |
| 3 | 1. | .0 | .0 | .0 |

| Amino acid | Abundance | Amino acid | Abundance |
|---|---|---|---|
| A | 6.06% | C | 4.29% lfaa |
| D | 8.58% | E | none |
| F | 6.06% | G | 6.06% |
| H | 8.58% | I | 6.06% |
| K | none | L | 8.58% |
| M | none | N | 6.06% |
| P | 6.06% | Q | none |
| R | 6.06% | S | 8.58% mfaa |
| T | 4.29% lfaa | V | 8.58% |
| W | none | Y | 6.06% |
| stop | none | | |

| j | (1/ratio)$^j$ | (ratio)$^j$ | stop-free |
|---|---|---|---|
| 1 | 2.0 | .5 | 1. |
| 2 | 4.0 | .25 | 1. |
| 3 | 8.0 | .125 | 1. |
| 4 | 6.0 | .0625 | 1. |
| 5 | 2.0 | .03125 | 1. |
| 6 | 4.0 | .015625 | 1. |
| 7 | 128.0 | .0078125 | 1. |

D. Optimized NNG

|   | T | C | A | G |
|---|---|---|---|---|
| 1 | .23 | .21 | .23 | .33 |
| 2 | .215 | .285 | .285 | .215 |
| 3 | 0 | .0 | .0 | 1.0 |

| Amino acid | Abundance | Amino acid | Abundance |
|---|---|---|---|
| A | 9.40% | C | none |
| D | none | E | 9.40% |
| F | none | G | 7.10% |
| H | none | I | none |
| K | 6.60% | L | 9.50% mfaa |
| M | 4.90% | N | none |
| P | 6.00% | Q | 6.00% |
| R | 9.50% | S | 6.60% |
| T | 6.6% | V | 7.10% |
| W | 4.90% lfaa | Y | none |
| stop | 6.60% | | |

| j | (1/ratio)$^j$ | (ratio)$^j$ | stop-free |
|---|---|---|---|
| 1 | 1.9388 | .51579 | 0.934 |
| 2 | 3.7588 | .26604 | 0.8723 |
| 3 | 7.2876 | .13722 | 0.8148 |
| 4 | 14.1289 | .07078 | 0.7610 |
| 5 | 27.3929 | $3.65 \cdot 10^2$ | 0.7108 |
| 6 | 53.109 | $1.88 \cdot 10^2$ | 0.6639 |
| 7 | 102.96 | $9.72 \cdot 10^3$ | 0.6200 |

E. Unoptimized NNS (NNK gives identical distribution)

|   | T | C | A | G |
|---|---|---|---|---|
| 1 | .25 | .25 | .25 | .25 |
| 2 | .25 | .25 | .25 | .25 |
| 3 | .0 | .5 | .0 | 0.5 |

| Amino acid | Abundance | Amino acid | Abundance |
|---|---|---|---|
| A | 6.25% | C | 3.125% |
| D | 3.125% | E | 3.125% |
| F | 3.125% | G | 6.25% |
| H | 3.125% | I | 3.125% |
| K | 3.125% | L | 9.375% |
| M | 3.125% | N | 3.125% |
| P | 6.25% | Q | 3.125% |
| R | 9.375% | S | 9.375% |
| T | 6.25% | V | 6.25% |
| W | 3.125% | Y | 3.125% |
| stop | 3.125% | | |

| j | (1/ratio)$^j$ | (ratio)$^j$ | stop-free |
|---|---|---|---|
| 1 | 3.0 | .33333 | .96875 |
| 2 | 9.0 | .11111 | .9385 |
| 3 | 27.0 | .03704 | .90915 |
| 4 | 81.0 | .01234567 | .8807 |
| 5 | 243.0 | .0041152 | .8532 |
| 6 | 729.0 | $1.37 \cdot 10^{-3}$ | .82655 |
| 7 | 2187.0 | $4.57 \cdot 10^{-4}$ | .8007 |

TABLE 11

Calculate worst codon.

```
Program   "Find worst vgCodon within Serr of given
          distribution."
    INITIALIZE-MEMORY-OF-ABUNDANCES
Comment Serr is % error level.
    READ Serr
Comment T1i,C1i,A1i,G1i, T2i,C2i,A2i,G2i, T3i,G3i
Comment are the intended nt-distribution.
    READ T1i, C1i, A1i, G1i
    READ T2i, C2i, A2i, G2i
    READ T3i, G3i
    Fdwn = 1.-Serr
    Fup = 1.+Serr
    DO ( t1 = T1i*Fdwn to T1i*Fup in 7 steps)
    . DO ( c1 = C1i*Fdwn to C1i*Fup in 7 steps)
    .. DO ( a1 = A1i*Fdwn to A1i*Fup in 7 steps)
    ... g1 = 1. - t1 - c1 - a1
    ... IF( (g1-G1i)/G1i .lt. -Serr)
Comment g1 too far below G1i, push it back
```

TABLE 11-continued

Calculate worst codon.

```
.... g1 = G1i*Fdwn
.... factor = (1.-g1)/(t1 + c1 + a1)
.... t1 = t1*factor
.... c1 = c1*factor
.... a1 = a1*factor
.....end_IF_block
... IF( (g1-G1i)/G1i .gt. Serr)
```
Comment  g1 too far above G1i, push it back
```
.... g1 = G1i*Fup
.... factor = (1.-g1)/(t1 + c1 + a1)
.... t1 = t1*factor
.... c1 = c1*factor
.... a1 = a1*factor
.....end_IF_block
... DO ( a2 = A2i*Fdwn to A2i*Fup in 7 steps)
.... DO ( c2 = C2i*Fdwn to C2i*Fup in 7 steps)
..... DO ( g2 = G2i*Fdwn to G2i*Fup in 7 steps)
```
Comment  Calc t2 from other concentrations.
```
...... t2 = 1. - a2 - c2 - g2
...... IF( (t2-T2i)/T2i .lt. -Serr)
```
Comment  t2 too far below T2i, push it back
```
....... t2 = T2i*Fdwn
....... factor = (1.-t2)/(a2 + c2 + g2)
....... a2 = a2*factor
....... C2 = c2*factor
....... g2 = g2*factor
.......end_IF_block
....... IF( (t2-T2i)/T2i .gt. Serr)
```
Comment  t2 too far above T2i, push it back
```
....... t2 = T2i*Fup
....... factor = (1.-t2)/(a2 + c2 + g2)
....... a2 = a2*factor
....... C2 = c2*factor
....... g2 = g2*factor
.......end_IF_block
....... IF(g2.gt. 0.0 and. t2.gt.0.0)
....... t3 = 0.5*(1.-Serr)
....... g3 = 1. - t3
....... CALCULATE-ABUNDANCES
....... COMPARE-ABUNDANCES-TO-PREVIOUS-ONES
....... t3 = 0.5
....... g3 = 1. - t3
....... CALCULATE-ABUNDANCES
....... COMPARE-ABUNDANCES-TO-PREVIOUS-ONES
....... t3 = 0.5*(1.+Serr)
....... g3 = 1. - t3
....... CALCULATE-ABUNDANCES
....... COMPARE-ABUNDANCES-TO-PREVIOUS-ONES
.......end_IF_block
......end_DO_loop ! g2
.....end_DO_loop ! c2
....end_DO_loop ! a2
...end_DO_loop ! a1
..end_DO_loop ! c1
..end_DO_loop ! t1
```
WRITE the WORST distribution and the abundances.

TABLE 12

Abundances obtained using optimum vgCodon assuming 5% errors

| Amino acid | Abundance | Amino acid | Abundance |
|---|---|---|---|
| A | 4.59% | C | 2.76% |
| D | 5.45% | E | 6.02% |
| F | 2.49% lfaa | G | 6.63% |
| H | 3.59% | I | 2.71% |
| K | 5.73% | L | 6.714 |
| M | 3.00% | N | 5.19% |
| P | 3.02% | Q | 3.97% |
| R | 7.68% mfaa | S | 7.01% |
| T | 4.37% | V | 6.00% |
| W | 3.05% | Y | 4.77% |
| stop | 5.27% | | | ratio = Abun(F)/Abun(R) = 0.3248

| j | $(1/\text{ratio})^j$ | $(\text{ratio})^j$ | stop-free |
|---|---|---|---|
| 1 | 3.079 | .3248 | .9473 |
| 2 | 9.481 | .1055 | .8973 |
| 3 | 29.193 | .03425 | .8500 |
| 4 | 89.888 | .01112 | .8052 |
| 5 | 276.78 | $3.61 \cdot 10^{-3}$ | .7627 |

TABLE 12-continued

| | Abundances obtained using optimum vgCodon assuming 5% errors | | | 5 |
|---|---|---|---|---|
| 6 | 852.22 | $1.17 \cdot 10^{-3}$ | .7225 | |
| 7 | 2624.1 | $3.81 \cdot 10^{-4}$ | .6844 | |

TABLE 13

BPTI Homologues

| R # | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| −3 | — | — | — | F | — | — | — | — | — | — | — | — | — | — | — | — | Z | — | — |
| −2 | — | — | — | Q | T | — | — | — | — | — | — | Q | — | — | — | H | G | Z | — |
| −1 | — | — | — | T | E | — | — | — | — | — | — | P | — | — | — | D | D | G | — |
| 1 | R | R | R | P | R | R | R | R | R | R | R | L | A | R | R | R | K | R | A |
| 2 | P | P | P | P | P | P | P | P | P | P | P | R | A | P | P | P | R | P | A |
| 3 | D | D | D | D | D | D | D | D | D | D | D | K | K | D | R | T | D | S | K |
| 4 | F | F | F | L | F | F | F | F | F | F | F | L | Y | F | F | F | I | F | Y |
| 5 | C | C | C | C | C | C | C | C | C | C | C | C | C | C | C | C | C | C | C |
| 6 | L | L | L | Q | L | L | L | L | L | L | L | I | K | E | E | N | R | N | K |
| 7 | E | E | E | L | E | E | E | E | E | E | E | L | L | L | L | L | L | L | L |
| 8 | P | P | P | P | P | P | P | P | P | P | P | H | P | P | P | P | P | P | P |
| 9 | P | P | P | Q | P | P | P | P | P | P | P | R | L | A | A | P | P | A | V |
| 10 | Y | Y | Y | A | Y | Y | Y | Y | Y | Y | Y | N | R | E | E | E | E | E | R |
| 11 | T | T | T | R | T | T | T | T | T | T | T | P | I | T | T | S | Q | T | Y |
| 12 | G | G | G | G | G | G | G | G | G | G | G | G | G | G | G | G | G | G | G |
| 13 | P | P | P | P | P | P | P | P | P | P | P | R | P | L | L | R | P | P | P |
| 14 | C | T | A | C | C | C | C | C | C | C | C | C | C | C | C | C | C | C | C |
| 15 | K | K | K | K | K | V | G | A | L | I | K | Y | K | K | K | R | K | K | K |
| 16 | A | A | A | A | A | A | A | A | A | A | A | Q | R | A | A | G | G | A | K |
| 17 | R | R | R | A | A | R | R | R | R | R | R | K | K | Y | R | H | R | S | K |
| 18 | I | I | I | L | M | I | I | I | I | I | I | I | I | I | I | L | I | F |
| 19 | I | I | I | L | I | I | I | I | I | I | I | P | P | R | R | R | P | R | P |
| 20 | R | R | R | R | R | R | R | R | R | R | A | S | S | S | R | R | Q | S |
| 21 | Y | Y | Y | Y | Y | Y | Y | Y | Y | Y | Y | F | F | F | F | I | Y | Y | F |
| 22 | F | F | F | F | F | F | F | F | F | F | F | Y | Y | H | H | Y | F | Y | Y |
| 23 | Y | Y | Y | Y | Y | Y | Y | Y | Y | Y | Y | Y | Y | Y | Y | Y | Y | Y | Y |
| 24 | N | N | N | N | N | N | N | N | N | N | N | K | N | N | N | N | N | N | N |
| 25 | A | A | A | S | A | A | A | A | A | A | A | Q | W | L | R | L | P | S | W |
| 26 | K | K | K | T | K | K | K | K | K | K | K | K | K | A | A | E | A | K | K |
| 27 | A | A | A | S | A | A | A | A | A | A | A | K | A | A | A | S | S | S | A |
| 28 | G | G | G | N | G | G | G | G | G | G | G | K | K | Q | Q | N | R | G | K |
| 29 | L | L | L | A | F | L | L | L | L | L | L | Q | Q | Q | Q | K | M | G | Q |
| 30 | C | C | C | C | C | C | C | C | C | C | C | C | C | C | C | C | C | C | C |
| 31 | Q | Q | Q | E | E | Q | Q | Q | Q | Q | Q | E | L | L | L | K | E | Q | L |
| 32 | T | T | T | P | T | T | T | T | T | T | T | G | P | Q | E | V | S | Q | P |
| 33 | F | F | F | F | F | F | F | F | F | F | F | F | F | F | F | F | F | F | F |
| 34 | V | V | V | T | V | V | V | V | V | V | V | T | D | I | I | F | I | I | N |
| 35 | Y | Y | Y | Y | Y | Y | Y | Y | Y | Y | Y | W | Y | Y | Y | Y | Y | Y | Y |
| 36 | G | G | G | G | G | G | G | G | G | G | G | S | S | G | G | G | G | G | S |
| 37 | G | G | G | G | G | G | G | G | G | G | G | G | G | G | G | G | G | G | G |
| 38 | C | T | A | C | C | C | C | C | C | C | C | C | C | C | C | C | C | C | C |
| 39 | R | R | R | Q | R | R | R | R | R | R | R | G | G | G | G | G | K | R | G |
| 40 | A | A | A | G | A | A | A | A | A | A | A | G | G | G | G | G | G | G | G |
| 41 | K | K | K | N | K | K | K | K | K | K | K | N | N | N | N | N | N | N | N |
| 42 | R | R | R | N | S | R | R | R | R | R | R | S | A | A | A | A | K | Q | A |
| 43 | N | N | N | N | N | N | N | N | N | N | N | N | N | N | N | N | N | N | N |
| 44 | N | N | N | N | N | N | N | N | N | N | N | R | R | R | R | N | N | R | R |
| 45 | F | F | F | F | F | F | F | F | F | F | F | F | F | F | F | F | F | F | F |
| 46 | K | K | K | E | K | K | K | K | K | K | K | K | K | K | E | K | D | K |
| 47 | S | S | S | T | S | S | S | S | S | S | S | T | T | T | T | T | T | T |
| 48 | A | A | A | T | A | A | A | A | A | A | I | I | I | I | R | K | T | I |
| 49 | E | E | E | E | E | E | E | E | E | E | E | E | D | D | D | A | Q | E |

TABLE 13-continued

BPTI Homologues

| | | | | | | | | | | | | | | | | | | | |
|---|---|---|---|---|---|---|---|---|---|---|---|---|---|---|---|---|---|---|---|
| 50 | D | D | D | M | D | D | D | D | D | D | D | E | E | E | E | E | E | Q | E |
| 51 | C | C | C | C | C | C | C | C | C | C | C | C | C | C | C | C | C | C | C |
| 52 | M | M | M | L | M | M | M | M | M | M | E | R | R | R | H | R | V | Q | R |
| 53 | R | R | R | R | R | R | R | R | R | R | R | R | R | R | R | E | R | G | R |
| 54 | T | T | T | I | T | T | T | T | T | T | T | T | T | T | T | T | A | V | T |
| 55 | C | C | C | C | C | C | C | C | C | C | C | C | C | C | C | C | C | C | C |
| 56 | G | G | G | E | G | G | G | G | G | G | I | V | V | V | G | R | V | V |  |
| 57 | G | G | G | P | G | G | G | G | G | G | R | G | G | G | G | P | — | G |  |
| 58 | A | A | A | P | A | A | A | A | A | A | K | — | — | — | K | P | — | — |  |
| 59 | — | — | — | Q | — | — | — | — | — | — | — | — | — | — | — | E | — | — |  |
| 60 | — | — | — | Q | — | — | — | — | — | — | — | — | — | — | — | R | — | — |  |
| 61 | — | — | — | T | — | — | — | — | — | — | — | — | — | — | — | P | — | — |  |
| 62 | — | — | — | D | — | — | — | — | — | — | — | — | — | — | — | — | — | — |  |
| 63 | — | — | — | K | — | — | — | — | — | — | — | — | — | — | — | — | — | — |  |
| 64 | — | — | — | S | — | — | — | — | — | — | — | — | — | — | — | — | — | — |  |

1 BPTI
2 Engineered BPTI From MARK87
3 Engineered BPTI From MARK87
4 Bovine Colostrum (DUFT85)
5 Bovine Serum (DUFT85)
6 Semisynthetic BPTI, TSCH87
7 Semisynthetic BPTI, TSCH87
8 Semisynthetic BPTI, TSCH87
9 Semisynthetic BPTI, TSCH87
10 Semisynthetic BPTI, TSCH87
11 Engineered BPTI, AUER87
12 *Dendroaspis polylepis polylepis* (Black mamba) venom I (DUFT85)
13 *Dendroaspis polylepis polylepis* (Black Mamba) venom K (DUFT85)
14 *Hemachatus hemachates* (Ringhals Cobra) HHV II (DUFT85)
15 *Naja nivea* (Cape cobra) NNV II (DUFT85)
16 *Vipera russelli* (Russel's viper) RVV II (TAKA74)
17 Red sea turtle egg white (DUFT85)
18 Snail mucus (*Helix pomania*) (WAGN78)
19 *Dendroaspis angusticeps* (Eastern green mamba) C13 S1 C3 toxin (DUFT85)

| R # | 20 | 21 | 22 | 23 | 24 | 25 | 26 | 27 | 28 | 29 | 30 | 31 | 32 | 33 | 34 | 35 |
|---|---|---|---|---|---|---|---|---|---|---|---|---|---|---|---|---|
| −5 | — | — | — | — | — | — | — | — | — | — | — | — | — | D | — | — |
| −4 | — | — | — | — | — | — | — | — | — | — | — | — | — | E | — | — |
| −3 | — | — | — | — | — | — | — | — | — | — | — | — | T | P | — | — |
| −2 | Z | — | L | Z | R | K | — | — | — | R | R | — | E | T | — | — |
| −1 | P | — | Q | D | D | N | — | — | — | Q | K | — | R | T | — | — |
| 1 | R | R | H | H | R | R | I | K | T | R | R | R | G | D | K | T |
| 2 | R | P | R | P | P | P | N | E | V | H | H | P | F | L | A | V |
| 3 | K | Y | T | K | K | T | G | D | A | R | P | D | L | P | D | E |
| 4 | L | A | F | F | F | F | D | S | A | D | D | F | D | I | S | A |
| 5 | C | C | C | C | C | C | C | C | C | C | C | C | C | C | C | C |
| 6 | I | E | K | Y | Y | N | E | Q | N | D | D | L | T | E | Q | N |
| 7 | L | L | L | L | L | L | L | L | L | K | K | E | S | Q | L | L |
| 8 | H | I | P | P | P | L | P | G | P | P | P | P | P | A | D | P |
| 9 | R | V | A | A | A | P | K | Y | V | P | P | P | P | FG | Y | I |
| 10 | N | A | E | D | D | E | V | S | I | D | D | Y | V | D | S | V |
| 11 | P | A | P | P | P | T | V | A | R | K | T | T | T | A | Q | Q |
| 12 | G | G | G | G | G | G | G | G | G | G | K | G | G | G | G | G |
| 13 | R | P | P | R | R | R | P | P | P | N | I | P | P | L | P | P |
| 14 | C | C | C | C | C | C | C | C | C | C | C | C | C | C | C | C |
| 15 | Y | M | K | K | L | N | R | M | R | — | — | K | R | F | L | R |
| 16 | D | F | A | A | A | A | A | G | A | G | Q | A | A | G | G | A |
| 17 | K | F | S | H | Y | L | R | M | F | P | T | K | G | Y | L | F |
| 18 | I | I | I | I | N | I | F | T | I | V | V | M | F | M | F | I |
| 19 | P | S | P | P | P | P | P | S | Q | R | R | R | I | K | K | Q |
| 20 | A | A | A | R | R | A | R | L | A | A | R | R | L | R | L |  |
| 21 | F | F | F | F | F | F | Y | Y | W | F | F | Y | Y | Y | Y | W |
| 22 | Y | Y | Y | Y | Y | Y | Y | F | A | Y | Y | F | N | S | F | A |
| 23 | Y | Y | Y | Y | Y | Y | Y | Y | F | Y | Y | Y | Y | Y | Y | F |
| 24 | N | S | N | D | N | N | N | N | D | D | K | N | N | N | N | D |
| 25 | Q | K | W | S | P | S | S | G | A | T | P | A | T | Q | G | A |
| 26 | K | G | A | A | A | H | S | T | V | R | S | K | R | E | T | V |
| 27 | K | A | A | S | S | L | S | S | K | L | A | R | A | T | S | K |
| 28 | K | N | K | N | N | H | K | M | G | K | K | G | K | K | M | G |

TABLE 13-continued

BPTI Homologues

| | | | | | | | | | | | | | | | |
|---|---|---|---|---|---|---|---|---|---|---|---|---|---|---|---|
| 29 | Q | K | K | K | K | K | R | A | K | T | R | F | Q | N | A | K |
| 30 | C | C | C | C | C | C | C | C | C | C | C | C | C | C | C | C |
| 31 | E | Y | Q | N | E | Q | E | E | V | K | V | E | E | E | E | V |
| 32 | R | P | L | K | K | K | K | T | L | A | Q | T | P | E | T | R |
| 33 | F | F | F | F | F | F | F | F | F | F | F | F | F | F | F | F |
| 34 | D | T | H | I | I | N | I | Q | P | Q | R | V | K | I | L | S |
| 35 | W | Y | Y | Y | Y | Y | Y | Y | Y | Y | Y | Y | Y | Y | Y | Y |
| 36 | S | S | G | G | G | G | G | G | G | R | G | G | G | G | G | G |
| 37 | G | G | G | G | G | G | G | G | G | G | G | G | G | G | G | G |
| 38 | C | C | C | C | C | C | C | C | C | C | C | C | C | C | C | C |
| 39 | G | R | K | P | R | G | G | M | Q | D | D | K | K | Q | M | K |
| 40 | G | G | G | G | G | G | G | G | G | G | G | A | G | G | G | G |
| 41 | N | N | N | N | N | N | N | N | N | D | D | K | N | N | N | N |
| 42 | S | A | A | A | A | A | A | G | G | H | H | S | G | D | L | G |
| 43 | N | N | N | N | N | N | N | N | N | G | G | N | N | N | N | N |
| 44 | R | R | R | N | N | N | N | N | K | N | N | N | R | R | N | K |
| 45 | F | F | F | F | F | F | F | F | F | F | F | F | Y | F | F | F |
| 46 | K | K | S | K | K | K | H | V | Y | K | K | R | K | S | L | Y |
| 47 | T | T | T | T | T | T | T | T | S | T | S | S | S | T | S | S |
| 48 | I | I | I | W | W | I | L | E | E | E | D | A | E | L | Q | Q |
| 49 | E | E | E | D | D | D | E | K | K | T | H | E | Q | A | K | K |
| 50 | E | E | K | E | E | E | E | E | E | L | L | D | D | E | E | E |
| 51 | C | C | C | C | C | C | C | C | C | C | C | C | C | C | C | C |
| 52 | R | R | R | R | R | Q | E | L | R | R | R | M | L | E | L | K |
| 53 | R | R | H | Q | H | R | K | Q | E | C | C | R | D | Q | Q | E |
| 54 | T | T | A | T | T | T | V | T | Y | E | E | T | A | K | T | Y |
| 55 | C | C | C | C | C | C | C | C | C | C | C | C | C | C | C | C |
| 56 | I | V | V | G | V | A | G | R | G | L | E | G | S | I | R | G |
| 57 | G | V | G | A | A | A | V | V | V | L | G | G | N | — | I | — |
| 58 | — | — | — | S | S | K | R | — | P | Y | Y | A | F | — | — | P |
| 59 | — | — | — | A | G | Y | S | — | G | P | R | — | — | — | — | G |
| 60 | — | — | — | — | I | G | — | — | D | — | — | — | — | — | — | E |
| 61 | — | — | — | — | — | — | — | — | E | — | — | — | — | — | — | A |

20 *Dendroaspis angusticeps* (Eastern Green Mamba) C13 S2 C3 toxin (DUFT85)
21 *Dendroaspis polylepis polylepes* (Black mamba) B toxin (DUFT85)
22 *Dendroaspis polylepis polylepes* (Black Mamba) E toxin (DUFT85)
23 *Vipera ammodytes* TI toxin (DUFT85)
24 *Vipera ammodytes* CTI toxin (DUFT85)
25 *Bungarus fasciatus* VIII B toxin (DUFT85)
26 *Anemonia sulcata* (sea anemone) 5 II (DUFT85)
27 *Homo sapiens* HI-14 "inactive" domain (DUFT85)
28 *Homo sapiens* HI-8 "active" domain (DUFT85)
29 beta bungarotoxin B1 (DUFT85)
30 beta bungarotoxin B2 (DUFT85)
31 Bovine spleen TI II (FIOR85)
32 *Tachypleus tridentatus* (Horseshoe crab) hemocyte inhibitor (NAKA87)
33 *Bombyx mori* (silkworm) SCI-III (SASA84)
34 *Bos taurus* (inactive) BI-14
35 *Bos taurus* (active) BI-8

| R # | 36 | 37 | 38 | 39 | 40 |
|---|---|---|---|---|---|
| −5 | — | — | — | — | — |
| −4 | — | — | — | — | — |
| −3 | — | — | — | — | — |
| −2 | — | — | — | — | — |
| −1 | — | Z | — | — | — |
| 1 | R | R | R | R | R |
| 2 | P | P | P | P | P |
| 3 | D | D | D | D | D |
| 4 | F | P | F | F | F |
| 5 | C | C | C | C | C |
| 6 | L | L | L | L | L |
| 7 | E | E | E | E | E |
| 8 | P | P | P | P | P |
| 9 | P | P | P | P | P |

TABLE 13-continued

BPTI Homologues

| | | | | | |
|---|---|---|---|---|---|
| 10 | Y | Y | Y | Y | Y |
| 11 | T | T | T | T | T |
| 12 | G | G | G | G | G |
| 13 | P | P | P | P | P |
| 14 | C | C | C | C | C |
| 15 | R | K | K | K | K |
| 16 | A | A | A | A | A |
| 17 | R | R | R | R | K |
| 18 | I | M | I | M | M |
| 19 | I | I | I | I | I |
| 20 | R | R | R | R | R |
| 21 | Y | Y | Y | Y | Y |
| 22 | F | F | F | F | F |
| 23 | Y | Y | Y | Y | Y |
| 24 | N | N | N | N | N |
| 25 | A | A | A | A | A |
| 26 | K | K | K | K | K |
| 27 | A | A | A | A | A |
| 28 | G | G | G | G | G |
| 29 | L | L | L | L | F |
| 30 | C | C | C | C | C |
| 31 | Q | Q | Q | Q | E |
| 32 | T | P | P | P | T |
| 33 | F | F | F | F | F |
| 34 | V | V | V | V | V |
| 35 | Y | Y | Y | Y | Y |
| 36 | G | G | G | G | G |
| 37 | G | G | G | G | G |
| 38 | C | C | C | C | C |
| 39 | R | R | R | R | K |
| 40 | A | A | A | A | A |
| 41 | K | K | K | K | K |
| 42 | R | S | R | R | S |
| 43 | N | N | N | N | N |
| 44 | N | N | N | N | N |
| 45 | F | F | F | F | F |
| 46 | K | K | K | K | R |
| 47 | S | S | S | S | S |
| 48 | A | A | S | A | A |
| 49 | E | E | E | E | E |
| 50 | D | D | D | D | D |
| 51 | C | C | C | C | C |
| 52 | E | K | M | M | M |
| 53 | R | R | R | R | R |
| 54 | T | T | T | T | T |
| 55 | C | C | C | C | C |
| 56 | G | G | G | G | G |
| 57 | G | G | G | G | G |
| 58 | A | A | A | A | A |
| 59 | — | — | — | — | — |
| 60 | — | — | — | — | — |
| 61 | — | — | — | — | — |

36: Engineered BPTI (KR15, ME52): Auerswald '88, Biol Chem Hoppe-Seyler, 369 Supplement, pp 27–35.
37: Isoaprotinin G-1: Siekmann, Wenzel, Schroder, and Tschesche '88, Biol Chem Hoppe-Seyler, 369:157–163.
38: Isoaprotinin 2: Siekmann, Wenzel, Schroder, and Tschesche '88, Biol Chem Hoppe-Seyler, 369:157–163.
39: Isoaprotinin G-2: Siekmann, Wenzel, Schroder, and Tschesche '88, Biol Chem Hoppe-Seyler, 369:157–163.

TABLE 13-continued

BPTI Homologues

40: Isoaprotinin 1: Siekmann, Wenzel, Schroder, and
  Tschesche '88, Biol Chem Hoppe-Seyler, 369:157–163.

Notes:
a) both beta bungarotoxins have residue 15 deleted.
b) *B. mori* has an extra residue between C5 and C14; we have assigned F and G to residue 9.
c) all natural proteins have C at 5, 14, 30, 38, 50, & 55.
d) all homologues have F33 and G37.
e) extra C's in bungarotoxins form interchain cystine bridges

Identification codes for Tables 14 and 15

1. BPTI
2. synthetic BPTI, Tan & Kaiser, biochem. 16(8)1531–41
3. Semisynthetic BPTI, TSCH87
4. Semisynthetic BPTI, TSCH87
5. Semisynthetic BPTI, TSCH87
6. Semisynthetic BPTI, TSCH87
7. Semisynthetic BPTI, TSCH87
8. Engineered BPTI, AUER87
9. BPTI Auerswald &al GB 2 208 511A
10. BPTI Auerswald &al GB 2 208 511A
11. Engineered BPTI From MARK87
12. Engineered BPTI From MARK87
13. BPTI(KR15, ME512): Auerswald '88, Biol Chem Hoppe-Seyler, 360 Suppl, pp 27–35.
14. BPTI CA30/CA51 Eigenbrot &al, Protein Engineering 3(7)591–598 (190)
15. Isoaprotinin 2 Siekmann et al '88, Biol Chem Hoppe-Seyler, 369:157–163.
16. Isoaprot.inin G-2: Siekmann et al '88, Biol Chem Hoppe-Seyler, 369:157–163.
17. BPTI Engineered, Auerswald &al GB 2208 511A
18. BPTI Engineered, Auerswald &al GB 2208 511A
19. BPTI Engineered, Auerswald &al GB 2208 511A
20. Isoaprotinin G-1 Siekmann &al '88, Biol Chem Hoppe-Seyler, 369:157–163.
21. BPTI Engineered, Auerswald &al GB 2208 511A
22. BPTI Engineered, Auerswald &al GB 2208 511A
23. Bovine Serum (in Dufton 185)
24. Bovine spleen TI II (FIOR85)
25. Snail mucus (Helix pomatia) (WAGN78)
26. Hemachatus hemachates (Ringhals Cobra) HHV II (in Dufton '85)
27. Red sea turtle egg white (in Dufton 185)
28. Bovine Colostrum (in Dufton 185)
29. Naja nivea (Cape cobra) NNV II (in Dufton 185)
30. Bungarus fasciatus VIII B toxin (in Dufton 185)
31. Vipera ammodytes TI toxin (in Dufton 185)
32. Porcine ITI domain 1, (in CREI87)
33. Human Alzheimer's beta APP protease inhibitor, (SHIN90)
34. Equine ITI domain 1, in Creighton & Charles
35. Bos taurus (inactive) BI-8e (ITI domain 1)
36. Anemonia sulcata (sea anemone) 5 II (in Dufton '85)
37. Dendroaspis polylepis polylepes (Black Mamba) E toxin (in Dufton '85)
38. Vipera russelli (Russel's viper) RVV II (TAKA74)
39. Tachypleus tridentatus (Horseshoe crab) hemocyte inhibitor (NAKA87)
40. LACI 2 (Factor Xa) (WUNT88)
41. Vipera ammodytes CTI toxin (in Dufton '85)
42. Dendroaspis polylepis polylepis (Black Mamba) venom K (in Dufton '85)
43. Homo sapiens HI-8e "inactive" domain (in Dufton '85)
44. Green Mamba toxin K, (in CREI87)
45. Dendroaspis angusticeps (Eastern green mamba) C13 S1 C3 toxin (in Dufton '85)
46. LACI 3
47. Equine ITI domain 2, (CREI87)
48. LACI 1 (VIIA)
49. Dendroaspis polylepis polylepes (Black mamba) B toxin (in Dufton '85)
50. Porcine ITI domain 2, Creighton and Charles
51. Homo sapiens HI-8t "active" domain (in Dufton '85)
52. Bos taurus (active) BI-8t
53. Trypstatin Kito &al ('88) J Biol Chem 263(34)18104-07-
54. Dendroaspis angusticeps (Eastern Green Mamba) C13 S2 C3 toxin (in Dufton '85)
55. Green Mamba I venom Creighton & Charles 187 CSHSQB 52:511–519.
56. beta bungarotoxin B2 (in Dufton '85)
57. Dendroaspis polylepis polylepis (Black mamba) venom I (in Dufton '85)
58. beta bungarotoxin B1 (in Dufton '85)
59. Bombyx mori (silkworm) SCI-III (SASA84)

TABLE 14

Tally of Ionizable groups

| Identifier | D | E | X | R | Y | H | NH | $CO_2$ | + | ions |
|---|---|---|---|---|---|---|---|---|---|---|
| 1 | 2 | 2 | 4 | 6 | 4 | 0 | 1 | 1 | 6 | 16 |
| 2 | 2 | 2 | 4 | 6 | 4 | 0 | 1 | 1 | 6 | 16 |
| 3 | 2 | 2 | 3 | 6 | 4 | 0 | 1 | 1 | 5 | 15 |
| 4 | 2 | 2 | 3 | 6 | 4 | 0 | 1 | 1 | 5 | 15 |
| 5 | 2 | 2 | 3 | 6 | 4 | 0 | 1 | 1 | 5 | 15 |
| 6 | 2 | 2 | 3 | 6 | 4 | 0 | 1 | 1 | 5 | 15 |
| 7 | 2 | 2 | 3 | 6 | 4 | 0 | 1 | 1 | 5 | 15 |
| 8 | 2 | 3 | 4 | 6 | 4 | 0 | 1 | 1 | 5 | 17 |
| 9 | 2 | 2 | 3 | 5 | 4 | 0 | 1 | 1 | 4 | 14 |
| 10 | 2 | 3 | 3 | 6 | 4 | 0 | 1 | 1 | 4 | 16 |
| 11 | 2 | 2 | 4 | 6 | 4 | 0 | 1 | 1 | 6 | 16 |
| 12 | 2 | 2 | 4 | 6 | 4 | 0 | 1 | 1 | 6 | 16 |
| 13 | 2 | 3 | 3 | 7 | 4 | 0 | 1 | 1 | 5 | 17 |
| 14 | 2 | 2 | 4 | 6 | 4 | 0 | 1 | 1 | 6 | 16 |
| 15 | 2 | 2 | 4 | 6 | 4 | 0 | 1 | 1 | 6 | 16 |
| 16 | 2 | 2 | 4 | 6 | 4 | 0 | 1 | 1 | 6 | 16 |
| 17 | 2 | 2 | 3 | 5 | 4 | 0 | 1 | 1 | 4 | 14 |
| 18 | 2 | 3 | 3 | 5 | 4 | 0 | 1 | 1 | 3 | 15 |
| 19 | 2 | 3 | 3 | 5 | 4 | 0 | 1 | 1 | 3 | 15 |
| 20 | 2 | 2 | 4 | 5 | 4 | 0 | 1 | 1 | 5 | 15 |
| 21 | 2 | 3 | 3 | 4 | 4 | 0 | 1 | 1 | 2 | 14 |
| 22 | 2 | 4 | 3 | 4 | 4 | 0 | 1 | 1 | 1 | 15 |
| 23 | 2 | 4 | 4 | 4 | 4 | 0 | 1 | 1 | 2 | 16 |
| 24 | 2 | 3 | 5 | 4 | 4 | 0 | 1 | 1 | 4 | 16 |
| 25 | 1 | 1 | 2 | 4 | 4 | 0 | 1 | 1 | 4 | 10 |
| 26 | 2 | 3 | 2 | 5 | 3 | 1 | 1 | 1 | 2 | 14 |
| 27 | 2 | 4 | 6 | 8 | 3 | 0 | 1 | 1 | 8 | 22 |
| 28 | 2 | 4 | 2 | 3 | 3 | 0 | 1 | 1 | −1 | 13 |
| 29 | 1 | 4 | 2 | 7 | 2 | 2 | 1 | 1 | 4 | 16 |
| 30 | 1 | 2 | 5 | 3 | 4 | 2 | 1 | 1 | 5 | 13 |
| 31 | 4 | 1 | 5 | 3 | 4 | 2 | 1 | 1 | 3 | 15 |
| 32 | 1 | 4 | 3 | 2 | 4 | 1 | 1 | 1 | 0 | 12 |
| 33 | 2 | 6 | 1 | 5 | 3 | 0 | 1 | 1 | −2 | 16 |
| 34 | 2 | 4 | 2 | 2 | 3 | 1 | 1 | 1 | −2 | 12 |
| 35 | 2 | 2 | 3 | 2 | 4 | 0 | 1 | 1 | 1 | 11 |
| 36 | 1 | 5 | 4 | 5 | 4 | 1 | 1 | 1 | 3 | 17 |
| 37 | 0 | 2 | 6 | 3 | 3 | 3 | 1 | 1 | 7 | 13 |
| 38 | 2 | 5 | 3 | 7 | 3 | 2 | 1 | 1 | 3 | 19 |
| 39 | 3 | 3 | 5 | 5 | 4 | 0 | 1 | 1 | 4 | 18 |
| 40 | 3 | 7 | 4 | 3 | 4 | 0 | 1 | 1 | −3 | 19 |
| 41 | 3 | 2 | 4 | 6 | 5 | 1 | 1 | 1 | 5 | 17 |
| 42 | 1 | 2 | 8 | 5 | 4 | 0 | 1 | 1 | 10 | 18 |
| 43 | 1 | 4 | 2 | 2 | 4 | 0 | 1 | 1 | −1 | 11 |

TABLE 14-continued

Tally of Ionizable groups

| Identifier | D | E | X | R | Y | H | NH | CO2 | + | ions |
|---|---|---|---|---|---|---|---|---|---|---|
| 44 | 1 | 2 | 9 | 4 | 5 | 0 | 1 | 1 | 10 | 18 |
| 45 | 0 | 2 | 8 | 4 | 5 | 0 | 1 | 1 | 10 | 16 |
| 46 | 1 | 3 | 5 | 5 | 3 | 0 | 1 | 1 | 6 | 16 |
| 47 | 3 | 4 | 4 | 3 | 3 | 0 | 1 | 1 | 0 | 16 |
| 48 | 3 | 6 | 5 | 4 | 1 | 1 | 1 | 1 | 0 | 20 |
| 49 | 0 | 3 | 3 | 5 | 5 | 0 | 1 | 1 | 5 | 13 |
| 50 | 2 | 6 | 4 | 2 | 3 | 0 | 1 | 1 | -2 | 16 |
| 51 | 2 | 4 | 4 | 3 | 3 | 0 | 1 | 1 | 1 | 15 |
| 52 | 1 | 4 | 6 | 2 | 3 | 0 | 1 | 1 | 3 | 15 |
| 53 | 2 | 2 | 5 | 1 | 4 | 0 | 1 | 1 | 2 | 12 |
| 54 | 2 | 3 | 6 | 8 | 3 | 1 | 1 | 1 | 9 | 21 |
| 55 | 1 | 3 | 6 | 7 | 3 | 1 | 1 | 1 | 9 | 19 |
| 56 | 6 | 2 | 6 | 7 | 4 | 3 | 1 | 1 | 5 | 23 |
| 57 | 0 | 3 | 7 | 7 | 3 | 1 | 1 | 1 | 11 | 19 |
| 58 | 6 | 2 | 5 | 7 | 4 | 2 | 1 | 1 | 4 | 22 |
| 59 | 4 | 7 | 3 | 1 | 4 | 0 | 1 | 1 | -7 | 17 |

TABLE 15

Frequency of Amino Acids at Each Position in BPTI and 58 Homologues

| Res. Id. | Different AAs | Contents | First |
|---|---|---|---|
| -5 | 2 | -58 D | — |
| -4 | 2 | -58 E | — |
| -3 | 5 | -55 P T Z F | — |
| -2 | 10 | -43 R3 Z3 Q3 T2 E G H K L | — |
| -1 | 11 | -41 D4 P3 R2 T2 Q2 G K N Z E | — |
| 1 | 13 | R35 K6 T4 A3 H2 G2 L M N P I D — | R |
| 2 | 10 | P35 R6 A4 V4 H3 E3 N F I L | P |
| 3 | 11 | D32 K8 S4 A3 T3 R2 E2 P2 G L Y | D |
| 4 | 9 | F34 A6 D4 L4 S4 Y3 I2 W V | F |
| 5 | 1 | C59 | C |
| 6 | 13 | L25 N7 E6 K4 Q4 I3 D2 S2 Y2 R F T A | L |
| 7 | 7 | L28 E25 K2 F Q S T | E |
| 8 | 10 | P46 H3 D2 G2 E I K L A Q | P |
| 9 | 12 | P30 A9 I4 V4 R3 Y3 L F Q H E K | P |
| 9a | 3 | -58 G | — |
| 10 | 9 | Y24 E8 D8 V6 R3 S3 A3 N3 I | Y |
| 11 | 11 | T31 Q8 P7 R3 A3 Y2 K S D V I | T |
| 12 | 2 | G58 K | G |
| 13 | 5 | P45 R7 L4 I2 N | P |
| 14 | 3 | C57 A T | C |
| 15 | 12 | K22 R12 L7 V6 Y3 M2 -2 N I A F G | K |
| 16 | 7 | A41 G9 F2 D2 K2 Q2 R | A |
| 17 | 14 | R19 L8 K7 F5 M4 Y4 H2 A2 S2 G2 I N T P | R |
| 18 | 8 | I41 M7 F4 L2 V2 E T A | I |
| 19 | 10 | I24 P12 R8 K5 S4 Q2 L N E T | I |
| 20 | 5 | R39 A8 L6 S5 Q | R |
| 21 | 5 | Y35 F17 W5 I L | Y |
| 22 | 6 | F32 Y18 A5 H2 S N | F |
| 23 | 2 | Y52 F7 | Y |
| 24 | 4 | N47 D8 K3 S | N |
| 25 | 13 | A29 S6 Q4 G4 W4 P3 T2 L2 R N K V I | A |
| 26 | 11 | K31 A9 T5 S3 V3 R2 E2 G H F Q | K |
| 27 | 8 | A32 S11 K5 T4 Q3 L2 I E | A |
| 28 | 7 | G32 K13 N5 M4 Q2 R2 H | G |
| 29 | 10 | L22 K13 Q11 A5 F2 R2 N G M T | L |
| 30 | 2 | C58 A | C |
| 31 | 10 | Q25 E17 L5 V5 K2 N A R I Y | Q |
| 32 | 11 | T25 P11 K4 Q4 L4 R3 E3 G2 S A V | T |
| 33 | 1 | F59 | F |
| 34 | 13 | V24 I10 T5 N3 Q3 D3 K3 F2 H2 R S P L | V |
| 35 | 2 | Y56 W3 | Y |
| 36 | 3 | G50 S8 R | G |
| 37 | 1 | G59 | G |
| 38 | 3 | C57 A T | C |
| 39 | 9 | R25 G13 K6 Q4 E3 M3 L2 D2 P | R |
| 40 | 2 | G35 A24 | A |
| 41 | 3 | N33 K24 D2 | K |
| 42 | 12 | R22 A12 G8 S6 Q2 H2 N2 M D E K L | R |
| 43 | 2 | N57 G2 | N |
| 44 | 3 | N40 R14 K5 | N |
| 45 | 2 | F58 Y | F |
| 46 | 11 | K39 Y5 E4 S2 V2 D2 R H T A L | K |
| 47 | 2 | S36 T23 | S |
| 48 | 11 | A23 I11 E6 Q6 L4 K2 T2 W2 S D R | A |
| 49 | 8 | E37 K8 D6 Q3 A2 P H T | E |
| 50 | 7 | E27 D25 K2 L2 M Q Y | D |
| 51 | 2 | C58 A | C |
| 52 | 9 | M17 R15 E8 L7 K6 Q2 T2 H V | M |
| 53 | 11 | R37 E6 Q5 K2 C2 H2 A N G D W | R |
| 54 | 8 | T41 Y5 A4 V3 I2 E2 M K | T |
| 55 | 8 | C59 | C |
| 56 | 10 | G33 V9 R5 I4 E3 L A S T K | G |
| 57 | 12 | G34 V6 -5 A3 R2 I2 P2 D K S L N | G |
| 58 | 10 | A25 -15 P7 K3 S2 Y2 G2 F D R | A |

TABLE 16

Exposure in BPTI
Coordinates taken from Brookhaven Protein Data Bank entry 6PTI.
HEADER   PROTEINASE INHIBITOR (TRYPSIN) 13-MAY-87 6PTI
COMPND   BOVINE PANCREATIC TRYPSIN INHIBITOR
COMPND   2(/BPTI$, CRYSTAL FORM /III$)
AUTHOR   A. WLODAWER
Solvent radius = 1.40
Atomic radii given in Table 7
Areas in Å².

| Residue | Total area | Not Covered by M/C | fraction | Not covered at all | fraction |
|---|---|---|---|---|---|
| ARG 1 | 342.45 | 205.09 | 0.5989 | 152.49 | 0.4453 |
| PRO 2 | 239.12 | 92.65 | 0.3875 | 47.56 | 0.1989 |
| ASP 3 | 272.39 | 158.77 | 0.5829 | 143.23 | 0.5258 |
| PHE 4 | 311.33 | 137.82 | 0.4427 | 43.21 | 0.1388 |
| CYS 5 | 241.06 | 48.36 | 0.2006 | 0.23 | 0.0010 |
| LEU 6 | 280.98 | 151.45 | 0.5390 | 115.87 | 0.4124 |
| GLU 7 | 291.39 | 128.91 | 0.4424 | 90.39 | 0.3102 |
| PRO 8 | 236.12 | 128.71 | 0.5451 | 99.98 | 0.4234 |
| PRO 9 | 236.09 | 109.82 | 0.4652 | 45.80 | 0.1940 |
| TYR 10 | 330.97 | 153.63 | 0.4642 | 79.49 | 0.2402 |
| THR 11 | 249.20 | 80.10 | 0.3214 | 64.99 | 0.2608 |
| GLY 12 | 184.21 | 56.75 | 0.3081 | 23.05 | 0.1252 |
| PRO 13 | 240.07 | 130.25 | 0.5426 | 75.27 | 0.3136 |
| CYS 14 | 237.10 | 75.55 | 0.3186 | 53.52 | 0.2257 |
| LYS 15 | 310.77 | 200.25 | 0.6444 | 192.00 | 0.6178 |
| ALA 16 | 209.41 | 66.63 | 0.3182 | 45.59 | 0.2177 |
| ARG 17 | 351.09 | 243.67 | 0.6940 | 201.48 | 0.5739 |
| ILE 18 | 277.10 | 100.51 | 0.3627 | 58.95 | 0.2127 |
| ILE 19 | 278.03 | 146.00 | 0.5254 | 96.05 | 0.3455 |
| ARG 20 | 339.11 | 144.65 | 0.4266 | 43.81 | 0.1292 |
| TYR 21 | 333.60 | 102.24 | 0.3065 | 69.67 | 0.2089 |
| PHE 22 | 306.08 | 70.64 | 0.2308 | 23.01 | 0.0752 |
| TYR 23 | 338.65 | 77.05 | 0.2275 | 17.34 | 0.0512 |
| ASN 24 | 264.88 | 99.03 | 0.3739 | 38.69 | 0.1461 |
| ALA 25 | 211.15 | 85.13 | 0.4032 | 48.20 | 0.2283 |
| LYS 26 | 313.29 | 216.14 | 0.6899 | 202.84 | 0.6474 |
| ALA 27 | 210.66 | 96.05 | 0.4560 | 54.78 | 0.2601 |
| GLY 28 | 186.83 | 71.52 | 0.3828 | 32.09 | 0.1718 |
| LEU 29 | 280.70 | 132.42 | 0.4718 | 93.61 | 0.3335 |
| CYS 30 | 238.15 | 57.27 | 0.2405 | 19.33 | 0.0812 |
| GLN 31 | 301.15 | 141.80 | 0.4709 | 82.64 | 0.2744 |
| THR 32 | 251.26 | 138.17 | 0.5499 | 76.47 | 0.3043 |
| PHE 33 | 304.27 | 59.79 | 0.1965 | 18.91 | 0.0622 |
| VAL 34 | 251.56 | 109.78 | 0.4364 | 42.36 | 0.1684 |
| TYR 35 | 332.64 | 80.52 | 0.2421 | 15.05 | 0.0452 |

TABLE 16-continued

Exposure in BPTI
Coordinates taken from Brookhaven Protein Data Bank
entry 6PTI.
HEADER    PROTEINASE INHIBITOR
(TRYPSIN) 13-MAY-87 6PTI
COMPND    BOVINE PANCREATIC TRYPSIN
INHIBITOR
COMPND    2(/BPTIS, CRYSTAL FORM /III$)
AUTHOR    A. WLODAWER
Solvent radius = 1.40
Atomic radii given in Table 7
Areas in Å².

| Residue | Total area | Not Covered by M/C | fraction | Not covered at all | fraction |
|---|---|---|---|---|---|
| GLY 36 | 187.06 | 11.90 | 0.0636 | 1.97 | 0.0105 |
| GLY 37 | 185.28 | 84.26 | 0.4548 | 39.17 | 0.2114 |
| CYS 38 | 234.56 | 73.64 | 0.3139 | 26.40 | 0.1125 |
| ARG 39 | 417.13 | 304.62 | 0.7303 | 250.73 | 0.6011 |
| ALA 40 | 209.53 | 94.01 | 0.4487 | 52.95 | 0.2527 |
| LYS 41 | 314.60 | 166.23 | 0.5284 | 108.77 | 0.3457 |
| ARG 42 | 349.06 | 232.83 | 0.6670 | 179.59 | 0.5145 |
| ASN 43 | 266.47 | 38.53 | 0.1446 | 5.32 | 0.0200 |
| ASN 44 | 269.65 | 91.08 | 0.3378 | 23.39 | 0.0867 |
| PHE 45 | 313.22 | 69.73 | 0.2226 | 14.79 | 0.0472 |
| LYS 46 | 309.83 | 217.18 | 0.7010 | 155.73 | 0.5026 |
| SER 47 | 224.78 | 69.11 | 0.3075 | 24.80 | 0.1103 |
| ALA 48 | 211.01 | 82.06 | 0.3889 | 31.07 | 0.1473 |
| GLU 49 | 286.62 | 161.00 | 0.5617 | 100.01 | 0.3489 |
| ASP 50 | 299.53 | 156.42 | 0.5222 | 95.96 | 0.3204 |
| CYS 51 | 238.68 | 24.51 | 0.1027 | 0.00 | 0.0000 |
| MET 52 | 293.05 | 89.48 | 0.3054 | 66.70 | 0.2276 |
| ARG 53 | 356.20 | 224.61 | 0.6306 | 189.75 | 0.5327 |
| THR 54 | 251.53 | 116.43 | 0.4629 | 51.64 | 0.2053 |
| CYS 55 | 240.40 | 69.95 | 0.2910 | 0.00 | 0.0000 |
| GLY 56 | 184.66 | 60.79 | 0.3292 | 32.78 | 0.1775 |
| GLY 57 | 106.58 | 49.71 | 0.4664 | 38.28 | 0.3592 |
| ALA 58 | no position given in Protein Data Bank | | | | |

"Total area" is the area measured by a rolling sphere of radius 1.4 Å, where only the atoms within the residue are considered. This takes account of conformation.
"Not covered by M/C" is the area measured by a rolling sphere of radius 1.4 Å where all main-chain atoms are considered, fraction is the exposed area divided by the total area. Surface buried by main-chain atoms is more definitely covered than is surface covered by side group atoms.
"Not covered at all" is the area measured by a rolling sphere of radius 1.4 Å where all atoms of the protein are considered.

TABLE 17

Plasmids used in Detailed Example I

| Phage | Contents |
|---|---|
| LG1 | M13mp18 with Ava II/Aat II/Acc I/Rsr II/Sau I adaptor |
| pLG2 | LG1 with amp$^R$ and ColE1 of pBR322 cloned into Aat II/Acc I sites |
| pLG3 | pLG2 with Acc I site removed |
| pLG4 | pLG3 with first part of osp-pbd gene cloned into Rsr II/Sau I sites, Avr II/Asu II sites created |
| pLG5 | pLG4 with second part of osp-pbd gene cloned into Avr II/Asu II sites, BssH I site created |
| pLG6 | pLG5 with third part of osp-pbd gene cloned into Asu II/BssH I sites, Bbe I site created |
| pLG7 | pLG6 with last part of osp-pbd gene cloned into Bbe I/Asu II sites |
| pLG8 | pLG7 with disabled osp-pbd gene, same length DNA. |
| pLG9 | pLG7 mutated to display BPTI(V15$_{BPTI}$) |
| pLG10 | pLG8 + tet$^R$ gene − amp$^R$ gene |
| pLG11 | pLG9 + tet$^R$ gene − amp$^R$ gene |

TABLE 18

Enzyme sites eliminated when
M13mp18 is cut by AvaII and Bsu36I

| AhaII | NarI | GdiII | PvuI |
| FspI | BglI | HgiEII | Bsu36I |
| EcoRI | SacI | KpnI | XmaI |
| SmaI | BamHI | XbaI | SalI |
| HindIII | AccI | PstI | SphI |
| HindII | | | |

TABLE 19

Enzymes not cutting M13mp18

| AatII | AflI | ApaI | AvrII |
| BbvII | BclI | BspMI | BssHI |
| BstBI | BstEII | BstXI | EagI |
| Eco57I | EcoNI | Eco0109I | EcoRV |
| EspI | HpaI | MluI | NcoI |
| NheI | NotI | NruI | NsiI |
| PflMI | PmaCI | PpaI | PpuMI |
| RsrI | SacI | ScaI | SfiI |
| SpeI | StuI | StyI | Tth111I |
| XcaI | XhoI | | |

TABLE 20

Enzymes cutting AmpR gene and ori

| AatII | BbvII | Eco57I | PpaI |
| ScaI | Tth111I | AhaII | GdiII |
| PvuI | FspI | BglI | HgiEII |
| HindII | PstI | XbaI | AflIII |
| NdeI | | | |

TABLE 21

Enzymes tested on Ambig DNA

| Enzyme | Recognition | Symm cuts | Supply |
|---|---|---|---|
| %AccI | GTMKAC | P 2 & 4 | <B,M,I,N,P,T |
| AflII | CTTAAG | P 1 & 5 | <N |
| ApaI | GGGCCC | P 5 & 1 | <M,I,N,P,T |
| AsuII | TTCGAA | P 2 & 4 | <P,N(BstBI) |
| AvaIII | ATGCAT | P 5 & 1 | <T; NsiI:M,N,P,T; EcoT22I:T |
| AvrII | CCTAGG | P 1 & 5 | <N |
| BamHI | GGATCC | P 1 & 5 | <S,B,M,I,N,P,T |
| BclI | TGATCA | P 1 & 5 | <S,B,M,I,N,T |
| BspMII | TCCGGA | P 1 & 5 | <N |
| BssHII | GCGCGC | P 1 & 5 | <N,T |
| +BstEII | GGTNACC | P 1 & 6 | <S,B,M,N,T |
| %BstXI | CCANNNNN | P 8 & 4 | <N,P,T |
| +DraII | RGGNCCY | P 2 & 5 | <M,T; Eco0109I:N |
| +EcoNI | CCTNNNNN | P 5 & 6 | <N(soon) |
| EcoRI | GAATTC | P 1 & 5 | <S,B,M,I,N,P,T |
| EcoRV | GATATC | P 3 & 3 | <S,B,M,I,N,P,T |
| +EspI | GCTNAGC | P 2 & 5 | <T |
| HindIII | AAGCTT | P 1 & 5 | <S,B,M,I,N,P,T |
| HpaI | GTTAAC | P 3 & 3 | <S,B,M,I,N,P,T |
| KpnI | GGTACC | P 5 & 1 | <S,B,M,I,N,P,T; Asp718:M |
| MluI | ACGCGT | P 1 & 5 | <M,N,P,T |

| | | | | | | |
|---|---|---|---|---|---|---|
| NarI | GGCGCC | P 2 & 4 <B,N,T | | +SfiI· | GGCCNNNNNGGCC | P 8 & 5 <N,P,T |
| NcoI | CCATGG | P 1 & 5 <B,M,N,P,T | | SmaI | CCCGGG | P 3 & 3 <B,M,I,N,P,T |
| NheI | GCTAGC | P 1 & 5 <M,N,P,T | | SpeI | ACTAGT | P 1 & 5 <M,N,T |
| NotI | GCGGCCGC | P 2 & 6 <M,N,P,T | | SphI | GCATGC | P 5 & 1 <B,M,I,N,P,T |
| NruI | TCGCGA | P 3 & 3 <B,M,N,T | | StuI | AGGCCT | P 3 & 3 <M,N,I(AatI),P,T |
| +PflMI | CCANNNN | P 7 & 4 <N | | %StyI | CCWWGG | P 1 & 5 <N,P,T |
| PmaCI | CACGTG | P 3 & 3 <none | | XcaI | GTATAC | P 3 & 3 <N(soon) |
| +PpuMI | RGGWCCY | P 2 & 5 <N | | XhoI | CTCGAG | P 1 & 5 <B,M,I,P,T; CcrI:T; PaeR7I:N |
| +RsrII | CGGWCCG | P 2 & 5 <N,T | | | | |
| SacI | GAGCTC | P 5 & 1 <B(SstI),M,I,N,P,T | | XmaI | CCCGGG | P 1 & 5 <I,N,P,T |
| | | | | XmaIII | CGGCCG | P 1 & 5 <B; EagI:N; Eco52I:T |
| SalI | GTCGAC | P 1 & 5 <B,M,I,N,P,T | | | | |
| +SauI | CCTNAGG | P 2 & 5 <M; CvnI:B; MstII:T; Bsu36I:N; AocI:T | | N_restrct = 43 | | |

TABLE 22 ipbd gene pbd mod10 29III88:
    lacUV5 RsrII/AvrII/gene/TrpA attenuator/MstII;

| | |
|---|---|
| 5'-   CGGaCCG TaT | ! RsrII site |
| CCAGGC tttaca CTTTATGCTTCCGGCTCG tataat GTG | ! lacUV5 |
| TGG aATTGTGAGCGGATAACAATT | ! lacO operator |
| CCT AGGAgg CtcaCT | ! Shine-Dalgarno seg. |
| atg aag aaa tct ctg gtt ctt aag gct agc | ! 10, M13 leader |
| gtt gct gtc gcg acc ctg gta ccg atg ctg | ! 20 |
| tct ttt gct cgt ccg gat ttc tgt ctc gag | ! 30 |
| ccg cca tat act ggg ccc tgc aaa gcg cgc | ! 40 |
| atc atc cgt tat ttc tac aac gct aaa gca | ! 50 |
| ggc ctg tgc cag acc ttt gta tac ggt ggt | ! 60 |
| tgc cgt gct aag cgt aac aac ttt aaa tcg | ! 70 |
| gcc gaa gat tgc atg cgt acc tgc ggt ggc | ! 80 |
| gcc gct gaa ggt gat gat ccg gcc aaa gcg | ! 90 |
| gcc ttt aac tct ctg caa gct tct gct acc | ! 100 |
| gaa tat atc ggt tac gcg tgg gcc atg gtg | ! 110 |
| gtg gtt atc gtt ggt gct acc atc ggt atc | ! 120 |
| aaa ctg ttt aag aaa ttt act tcg aaa gcg | ! 130 |
| tct taa tag tga ggttacc | ! BstEII |
| agtcta agcccgc ctaatga gcggget tttttttt | ! terminator |
| CCTgAGG     -3' | ! MstII |

TABLE 23 ipbd DNA sequence
DNA Sequence file = UV5_M13PTIM13.DNA;17
DNA Sequence title = pbd mod10 29III88: lac-UV5 RsrII/AvrII/gene/TrpA attenuator/MstII; !

```
  1 C I GGA I CCG I TAT I CCA I GGC I TTT I ACA I CTT I TAT I GCT I TCC I GGC I TCG I
 41 TAT I AAT I GTG I TGG I AAT I TGT I GAG I CGG I ATA I ACA I ATT I CCT I AGG I AGG I
 83 CTC I ACT I ATG I AAG I AAA I TCT I CTG I GTT I CTT I AAG I GCT I AGC I GTT I GCT I
125 GTC I GCG I ACC I CTG I GTA I CCG I ATG I CTG I TCT I TTT I GCT I CGT I CCG I GAT I
167 TTC I TGT I CTC I GAG I CCG I CCA I TAT I ACT I GGG I CCC I TGC I AAA I GCG I CGC I
209 ATC I ATC I CGT I TAT I TTC I TAC I AAC I GCT I AAA I GCA I GGC I CTG I TGC I CAG I
251 ACC I TTT I GTA I TAC I GGT I GGT I TGC I CGT I GCT I AAG I CGT I AAC I AAC I TTT I
293 AAA I TCG I GCC I GAA I GAT I TGC I ATG I CGT I ACC I TGC I GGT I GGC I GCC I GCT I
335 GAA I GGT I GAT I GAT I CCG I GCC I AAA I GCG I GCC I TTT I AAC I TCT I CTG I CAA I
377 GCT I TCT I GCT I ACC I GAA I TAT I ATC I GGT I TAC I GCG I TGG I GCC I ATG I GTG I
419 GTG I GTT I ATC I GTT I GGT I GCT I ACC I ATC I GGT I ATC I AAA I CTG I TTT I AAG I
461 AAA I TTT I ACT I TCG I AAA I GCG I TCT I TAA I TAG I TGA I GGT I TAC I CAG I TCT I
503 AAG I CCC I GCC I TAA I TGA I GCG I GGC I TTT I TTT I TTT I CCT I GAG I G
Total = 539 bases
```

TABLE 24

Summary of Restriction Cuts

Enz = %Acc I has 1 observed sites: 259
Enz = Acc III has 1 observed sites: 162
Enz = Acy I has 1 observed sites: 328
Enz = Afl II has 1 observed sites : 109
Enz = %Afl III has 1 observed sites: 404
Enz = Aha III has 1 observed sites: 292
Enz = Apa I has 1 observed sites: 193
Enz = Asp718 has 1 observed sites: 138
Enz = Asu II has 1 observed sites: 471
Enz = %Ava I has 1 observed sites: 175
Enz = Avr II has 1 observed sites: 76
Enz = %Ban I has 3 observed sites: 138 328 540
Enz = Bbe I has 1 observed sites: 328
Enz = +Bgl I has 1 observed sites: 352
Enz = +Bin I has 1 observed sites: 346
Enz = %BspM I has 1 observed sites: 319
Enz = BssH II has 1 observed sites: 205
Enz = +BstE II has 1 observed sites: 493
Enz = %BstX I has 1 observed sites: 413
Enz = Cfr I has 2 observed sites: 299 350
Enz = +Dra II has 1 observed sites: 193
Enz = +Esp I has 1 observed sites: 277
Enz = %Fok I has 1 observed sites: 213
Enz = Gdi II has 2 observed sites: 299 350
Enz = Hae I has 1 observed sites: 240
Enz = Hae II has 1 observed sites: 328
Enz = +Hga I has 1 observed sites: 478
Enz = %HgiC I has 3 observed sites: 138 328 540
Enz = %HgiJ II has 1 observed sites: 193
Enz = Hind III has 1 observed sites: 377
Enz = +Hph I has 1 observed sites: 340
Enz = Kpn I has 1 observed sites: 138

TABLE 24-continued

Enz = +Mbo II has 2 observed sites: 93 304
Enz = Mlu I has 1 observed sites: 404
Enz = Nar I has 1 observed sites: 328
Enz = Nco I has 1 observed sites: 413
Enz = Nhe I has 1 observed sites: 115
Enz = Nru I has 1 observed sites: 128
Enz = Nsp (7524) I has 1 observed sites: 311
Enz = NspB II has 1 observed sites: 332
Enz = +PflM I has 1 observed sites: 184
Enz = +Pss I has 1 observed sites: 193
Enz = +Rsr II has 1 observed sites: 3
Enz = +Sau I has 1 observed sites: 535
Enz = %SfaN I has 2 observed sites: 144 209
Enz = +Sfi I has 1 observed sites: 351
Enz = Sph I has 1 observed sites: 311
Enz = Stu I has 1 observed sites: 240
Enz = %Sty I has 2 observed sites: 76 413
Enz = Xca I has 1 observed sites: 259
Enz = Xho I has 1 observed sites: 175
Enz = Xma III has 1 observed sites: 299

Enzymes that do not cut

| | | | | |
|---|---|---|---|---|
| Aat II | AlwN I | ApaL I | Asc I | Ava III |
| Bal I | BamH I | Bbv I | Bbv II | Bcl I |
| Bgl II | Bsm I | BspH I | Cla I | Dra III |
| Eco47 III | EcoN I | EcoR I | EcoR V | HgiA I |
| Hinc II | Hpa I | Mst I | Nae I | Nde I |
| Not I | Ple I | PmaC I | PpuM I | Pst I |
| Pvu I | Pvu II | Sac I | Sac II | Sal I |
| Sca I | Sma I | SnaB I | Spe I | Ssp I |
| Taq II | Tth111 I | Tth111 II | Xho II | Xma I |
| Xmn I | | | | |

TABLE 25

Annotated Sequence of ipbd gene

```
5'- C|GGA|CCG|TAT|CCA|GGC|TTT|ACA|CTT|TAT|    28
    | Rsr II  |              -35

|GCT|TCC|GGC|TCG|TAT|AAT|GTG|TGG|              52
                    -10

|AAT|TGT|GAG|CGG|ATA|ACA|ATT|               73
       lac operator

|CCT|AGG|AGG|CTC|ACT                     88
         |Avr II|
              | S.  D.  |

| m | k | k | s | l | v | l | k | a | s |
  | 1 | 2 | 3 | 4 | 5 | 6 | 7 | 8 | 9 | 10|
  |ATG|AAG|AAA|TCT|CTG|GTT|CTT|AAG|GCT|AGC|      118
                          Afl II  Nhe I

| v | a | v | a | t | l | v | p | m | l |
  |11 |12 |13 |14 |15 |16 |17 |18 |19 |20 |
  |GTT|GCT|GTC|GCG|ACC|CTG|GTA|CCG|ATG|CTG|      148
              | Nru I |       | Kpn I |

| s | f | r | r | p | d | f | c | l | e |
  |21 |22 |23 |24 |25 |26 |27 |28 |29 |30 |
  |TCT|TTT|GCT|CGT|CCG|GAT|TTC|TGT|CTC|GAG|      178
                  | AccIII |         Ava I
                                     Xho I
```

TABLE 25-continued

Annotated Sequence of ipbd gene

| p 31 | p 32 | y 33 | t 34 | g 35 | p 36 | c 37 | k 38 | a 39 | r 40 | |
|---|---|---|---|---|---|---|---|---|---|---|
| CCG | CCA | TAT | ACT | GGG | CCC | TGC | AAA | GCG | CGC | 208 |
| | pflM I | | | Apa I | | | | BssH II | | |
| | | | | Dra II | | | | | | |
| | | | | Pss I | | | | | | |

| i 41 | i 42 | r 43 | y 44 | f 45 | y 46 | n 47 | a 48 | k 49 | |
|---|---|---|---|---|---|---|---|---|---|
| ATC | ATC | CGT | TAT | TTC | TAC | AAC | GCT | AAA | 235 |

| a 50 | g 51 | l 52 | c 53 | q 54 | t 55 | f 56 | v 57 | y 58 | g 59 | g 60 | |
|---|---|---|---|---|---|---|---|---|---|---|---|
| GCA | GGC | CTG | TGC | CAG | ACC | TTT | TTC | TAC | GGT | GGT | 268 |
| | Stu I | | | | | | Acc I | | | | |
| | | | | | | | Xca I | | | | |

| c 61 | r 62 | a 63 | k 64 | r 65 | n 66 | n 67 | f 68 | k 69 | |
|---|---|---|---|---|---|---|---|---|---|
| TGC | CGT | GCT | AAG | CGT | AAC | AAC | TTT | AAA | 295 |
| | | Esp I | | | | | | | |

| s 70 | a 71 | e 72 | d 73 | c 74 | m 75 | r 76 | t 77 | c 78 | g 79 | |
|---|---|---|---|---|---|---|---|---|---|---|
| TCG | GCC | GAA | GAT | TGC | ATG | CGT | ACC | TGC | GGT | 325 |
| XmaIII | | | | Sph I | | | | | | |

| g 80 | a 81 | a 82 | e 83 | g 84 | d 85 | d 86 | |
|---|---|---|---|---|---|---|---|
| GGC | GCC | GCT | GAA | GGT | GAt | GAT | 346 |
| Bbe I | | | | | | | |
| Nar I | | | | | | | |

| p 87 | a 88 | k 89 | a 90 | a 91 | |
|---|---|---|---|---|---|
| CCG | GCC | AAA | GCG | GCC | 361 |
| | Sfi I | | | | |

| f 92 | n 93 | s 94 | l 95 | q 96 | a 97 | s 98 | a 99 | t 100 | |
|---|---|---|---|---|---|---|---|---|---|
| TTT | AAC | TCT | CTG | CAA | GCT | TCT | GCT | ACC | 388 |
| | | | | Hind 3 | | | | | |

| e 101 | y 102 | i 103 | g 104 | y 105 | a 106 | w 107 | |
|---|---|---|---|---|---|---|---|
| GAA | TAT | ATC | GGT | TAC | GCG | TGG | 409 |
| | | | | Mlu I | | | |

| a 108 | m 109 | v 110 | v 111 | v 112 | |
|---|---|---|---|---|---|
| GCC | ATG | GTG | GTG | GTT | 424 |
| BstX I | | | | | |
| Nco I | | | | | |

| i 113 | v 114 | g 115 | a 116 | t 117 | i 118 | g 119 | i 120 | |
|---|---|---|---|---|---|---|---|---|
| ATC | GTT | GGT | GCT | GCC | ATC | GGT | ATC | 448 |

| k 121 | l 122 | f 123 | k 124 | k 125 | f 126 | t 127 | s 128 | k 129 | a 130 | |
|---|---|---|---|---|---|---|---|---|---|---|
| AAA | CTG | TTT | AAG | AAA | TTT | ACT | TCG | AAA | GCG | 478 |
| | | | | | | | Asu II | | | |

| s 131 | . 132 | . 133 | . 134 | | | | |
|---|---|---|---|---|---|---|---|
| TCT | TAA | TAG | TGA | GGT | TAC | CAG | TCT | 502 |
| | | | | BstE II | | | |

| AAG | CCC | GCC | TAA | TGA | GCG | GGC | TTT | TTT | TTT | 532 |
|---|---|---|---|---|---|---|---|---|---|---|
| Trp terminator | | | | | | | | | | |

TABLE 25-continued

Annotated Sequence of ipbd gene

```
|CCT|GAG|G-3'                                                       539
| Sau  I  |
```

Note the following enzyme equivalences,

Xma III = Eaq I
Acc III = BspM II
Dra II = EcoO109 I
Asu II = BstB I
Sau I = Bsu36 I

TABLE 26

DNA_seq1

```
5' | ccg | tcc | gtC | GGA | CCG | TAT | CCA | GGC | TTT | ACA | CTT | TAT |
       spacer         Rsr II                          -35

| GCT | TCC | GGC | TCG | TAT | AAT | GTG | TGG |
                             -10

| AAT | TGT | GAG | CGG | ATA | ACA | ATT |
            lac operator

| CCT | AGG |
               Avr II s     k     a
                                             128   129   130
                     | gcc | gct | ccT | TCG | AAA | GCG |
                         spacer            Asu II s     .     .     .
   131   132   133   134
   | TCT | TAA | TAG | TGA | GGT | TAC | CAG | TCT |
                                   BstE II

| AAG | CCC | GCC | TAA | TGA | GCG | GGC | TTT | TTT | TTT |
             Trp terminator

| CCT | GAG | Gca | ggt | gag | cg -3'
      Sau I              spacer
```

TABLE 27

DNA_synth1

```
5' | CCG | TCC | GTC | GGA | CCG | TAT | CCA | GGC | TTT | ACA | CTT | TAT |

| GCT | TCC | GGC | TCG | TAT | AAT | GTG | TGG |

| AAT | TGT | GAG | CGG | ATA | ACA | ATT |
                      olig#4 = 3'-       gt    taa

| CCT | AGG |
                gga    tcc
```

TABLE 27-continued

DNA_synth1

```
                                              / 3' = olig#3
                      | GCC | GCT | CCT | TCG | AAA | GCG |
                        cgg   cga   gga   agc   ttt   cgc

| TCT | TAA | TAG | TGA | GGT | TAC | CAG | TCT |
  aga   att   atc   act   cca   atg   gtc   aga

| AAG | CCC | GCC | TAA | TGA | GCG | GGC | TTT | TTT | TTT |
  ttc   ggg   cgg   att   act   cgc   ccg   aaa   aaa   aaa

| CCT | GAG | GCA | GGT | GAG | CG
  gga   ctc   cgt   cca   ctc   gc - 5'
```

"Top" strand      99

"Bottom" strand    100

Overlap           23 (14 c/g and 9 a/t)

Net length       158

TABLE 28

DNA_seq2

```
                   5'- | gca | cca | acg |
                             spacer

| CCT | AGG | AGG | CTC | ACT |
          Avr II
               | S. D. |

| m  | k  | k  | s  | l  | v  | l  | k  | a  | s  |
| 1  | 2  | 3  | 4  | 5  | 6  | 7  | 8  | 9  | 10 |
|ATG |AAG |AAA |TCT |CTG |GTT |CTT |AAG |GCT |AGC |
                              Afl II       Nhe I

| v  | a  | v  | a  | t  | l  | v  | p  | m  | l  |
| 11 | 12 | 13 | 14 | 15 | 16 | 17 | 18 | 19 | 20 |
|GTT |GCT |GTC |GCG |ACC |CTG |GTA |CCG |ATG |CTG |
               Nru I           Kpn I

| s  | f  | a  | r  | p  | d  | f  | c  | l  | e  |
| 21 | 22 | 23 | 24 | 25 | 26 | 27 | 28 | 29 | 30 |
|TCT |TTT |GCT |CGT |CCG |GAT |TTC |TGT |CTC |GAG |
               AccIII                    Ava I
                                          Xho I

| p  | p  | y  | t  | g  | p  | c  | k  | a  | r  |
| 31 | 32 | 33 | 34 | 35 | 36 | 37 | 38 | 39 | 40 |
|CCG |CCA |TAT |ACT |GGG |CCC |TGC |AAA |GCG |CGC |
         PflM I                          BssH II
                         Apa I
                         Dra II
                         Pss I

| i  | i  | r  |
| 41 | 42 | 43 |
|atc |atc |cgt |
```

TABLE 28-continued

DNA_seq2

```
                          |  t  |  s  |  k  |
                          | 127 | 128 | 129 |
                          | ACT | TCG | AAa | gcg | gct | gcg | -3'
                          |   Asu II        |       spacer      |
```

TABLE 29

DNA_synth2

```
5'-  | GCA | CCA | ACG |

| CCT | AGG | AGG | CTC | ACT |

| ATG | AAG | AAA | TCT | CTG | GTT | CTT | AAG | GCT | AGC |

| GTT | GCT | GTC | GCG | ACC | CTG | GTA | CCG | ATG | CTG |
                              olig#6 = 3'-   ggc   tac   gac
                          / 3' = olig#5
| TCT | TTT | GCT | CGT | CCG | GAT | TTC | TGT | CTC | GAG |
  aga   aaa   cga   gca   ggc   cta   aag   aca   gag   ctc

| CCG | CCA | TAT | ACT | GGG | CCC | TGC | AAA | GCG | CGC |
  ggc   ggt   ata   tga   ccc   ggg   acg   ttt   cgc   gcg

| ATC | ATC | CGT |
  tag   tag   gca
                              | ACT | TCG | AAA | GCG | GCT | GCG |
                                tga   agc   ttt   cgc   cga   cgc  - 5'
```

| | |
|---|---|
| "Top" strand | 99 |
| "Bottom" strand | 99 |
| Overlap | 24 (14 c/g and 10 a/t) |
| Net length | 155 |

TABLE 30

DNA_seq3

```
                                              |  a  |  r  |
                                              | 39  | 40  |
                          5'- | ccc | tgc | aca | GCG | CGC |
                              |      spacer    |   BssH II   |

|  i  |  i  |  r  |  y  |  f  |  y  |  n  |  a  |  k  |
| 41  | 42  | 43  | 44  | 45  | 46  | 47  | 48  | 49  |
| ATC | ATC | CGT | TAT | TTC | TAC | AAC | GCT | AAA |

|  a  |  g  |  l  |  c  |  q  |  t  |  f  |  v  |  y  |  g  |  g  |
| 50  | 51  | 52  | 53  | 54  | 55  | 56  | 57  | 58  | 59  | 60  |
| GCA | GGC | CTG | TGC | CAG | ACC | TTT | GTA | TAC | GGT | GGT |
  |    Stu I    |                               |    Acc I    |
                                                |    Xca I    |

|  c  |  r  |  a  |  k  |  r  |  n  |  n  |  f  |  k  |
| 61  | 62  | 63  | 64  | 65  | 66  | 67  | 68  | 69  |
| TGC | CGT | GCT | AAG | CGT | AAC | AAC | TTT | AAA |
  |      Esp I      |
```

TABLE 30-continued

DNA_seq3

| | s<br>70<br>TCG | a<br>71<br>GCC | e<br>72<br>GAA | d<br>73<br>GAT | c<br>74<br>TGC | m<br>75<br>ATG | r<br>76<br>CGT | t<br>77<br>ACC | c<br>78<br>TGC | g<br>79<br>GGT |
|---|---|---|---|---|---|---|---|---|---|---|
| | | XmaIII | | | Sph I | | | | | |

| | g<br>80<br>GGC | a<br>81<br>GCC | gct | gaa |
|---|---|---|---|---|
| | Bbe I | | spacer | |
| | Nar I | | | |

| | ttt | t<br>127<br>acT | s<br>128<br>TCG | k<br>129<br>AAa | gcg | tcg | ccg | - 3' |
|---|---|---|---|---|---|---|---|---|
| | | | Asu II | | | | | |

TABLE 31

DNA_synth3

5'-| CCC | TGC | ACA | GCG | CGC |

| ATC | ATC | CGT | TAT | TTC | TAC | AAC | GCT | AAA |

| GCA | GGC | CTG | TGC | CAG | ACC | TTT | GTA | TAC | GGT | GGT |
                                                                     olig#8 = 3'-  g    cca    cca / 3' = olig#7

| TGC | CGT | GCT | AAG | CGT | AAC | AAC | TTT | AAA |
  acg    gca    cga    ttc    gca    ttg    ttg    aaa    ttt

| TCG | GCC | GAA | GAT | TGC | ATG | CGT | ACC | TGC | GGT |
  agc    cgg    ctt    cta    acg    tac    gca    tgg    acg    cca

| GGC | GCC | GCT | GAA |
  ccg    cgg    cgt    ctt

| TTT | ACT | TCG | AAA | GCG | TCG | CCG |
                   aaa    tga    agc    ttt    cgc    agc    ggc  -5'

"Top" strand     93
"Bottom" strand  97
Overlap           25 (15 g/c & 10 a/t)
Net length       146

TABLE 32

DNA_seq4

| 5' | cct | cgc | cct | g<br>80<br>GGC | a<br>81<br>GCC | a<br>82<br>GCT | e<br>83<br>GAA | g<br>84<br>GGT | d<br>85<br>GAT | d<br>86<br>GAT |
|---|---|---|---|---|---|---|---|---|---|---|
| | | spacer | | Bbe I | | | | | | |
| | | | | Nar I | | | | | | |

| | p<br>87<br>CCG | a<br>88<br>GCC | k<br>89<br>AAA | a<br>90<br>GCG | a<br>91<br>GCC |
|---|---|---|---|---|---|
| | | Sfi I | | | |

TABLE 32-continued

DNA_seq4

| f 92 TTT | n 93 AAC | s 94 TCT | l 95 CTG | q 96 CAA | a 97 GCT | s 98 TCT | a 99 GCT | t 100 ACC |
|---|---|---|---|---|---|---|---|---|

Hind 3

| e 101 GAA | y 102 TAT | i 103 ATC | g 104 GGT | y 105 TAC | a 106 GCG | w 107 TGG |
|---|---|---|---|---|---|---|

Mlu I

| a 108 GCC | m 109 ATG | v 110 GTG | v 111 GTG | v 112 GTT |
|---|---|---|---|---|

BstX I
  Nco I

| i 113 ATC | v 114 GTT | g 115 GGT | a 116 GCT | t 117 ACC | i 118 ATC | g 119 GGT | i 120 ATC |
|---|---|---|---|---|---|---|---|

| k 121 AAA | l 122 CTG | f 123 TTT | k 124 AAG | k 125 AAA | f 126 TTT | t 127 ACT | s 128 TCG | k 129 AAa | gcg | tcg | ggc | -3' |
|---|---|---|---|---|---|---|---|---|---|---|---|---|

Asu II      spacer

TABLE 33

DNA_synth4

```
5' | GCT | CGC | CCT | GGC | GCC | GCT | GAA | GGT | GAT | GAT |

| CCG | GCC | AAA | GCG | GCC |

| TTT | AAC | TCT | CTG | CAA | GCT | TCT | GCT | ACC |

| GAA | TAT | ATC | GGT | TAC | GCG | TGG |
    olig#10 = 3'-   ata   tag   cca   atg   cgc   acc / 3' = olig#9
  | GCC | ATG | GTG | GTG | GTT |
    cgg   tac   cac   cac   caa

| ATC | GTT | GGT | GCT | ACC | ATC | GGT | ATC |
    tag   caa   cca   cga   tgg   tag   cca   tag

| AAA | CTG | TTT | AAG | AAA | TTT | ACT | TCG | AAA | GCG | TCT | TGA |
    ttt   gac   aaa   ttc   ttt   aaa   tga   agc   ttt   cgc   aga   act   -5'
```

"Top" strand    100
"Bottom" strand  93
Overlap         25 (14 c/g and 11 a/t)
Net length     149

TABLE 34

Some interaction sets in BPTI

| Res. # | Number Diff. AAs | Contents | BPTI | 1 | 2 | 3 | 4 | 5 |
|---|---|---|---|---|---|---|---|---|
| −5 | 2 | D −32 | — | | | | | |
| −4 | 2 | E −32 | — | | | | | |
| −3 | 5 | T P F Z −29 | — | | | | | |
| −2 | 10 | Z3 R3 Q2 T2 H G L K E −18 | — | | | | | |
| −1 | 10 | D4 T2 P2 Q2 E G N K R −18 | — | | | | | |
| 1 | 10 | R21 A2 K2 H2 P L I T G D | R | | | | | 5 |
| 2 | 9 | P20 R4 A2 H2 N E V F L | P | | | s | | 5 |
| 3 | 10 | D15 K6 T3 R2 P2 S Y G A L | D | | | | 4 | s |

TABLE 34-continued

Some interaction sets in BPTI

| Res. # | Number Diff. AAs | Contents | BPTI | 1 | 2 | 3 | 4 | 5 |
|---|---|---|---|---|---|---|---|---|
| 4 | 7 | F19 D4 L3 Y2 I2 A2 S | F | | | | s | 5 |
| 5 | 1 | C33 | C | | | | x | x |
| 6 | 10 | L11 E5 N4 K3 Q2 I2 Y2 D2 T R | L | | | | 4 | |
| 7 | 5 | L18 E11 K2 S Q | E | | | s | 4 | |
| 8 | 7 | P26 H2 A2 I L G F | P | | | 3 | 4 | |
| 9 | 9 | P17 A6 V3 R2 Q L K Y F | P | | s | 3 | 4 | |
| 10 | 10 | Y11 E7 D4 A2 N2 R2 V2 S I D | Y | s | | s | 4 | |
| 11 | 10 | T17 P5 A3 R2 I S Q Y V K | T | 1 | s | 3 | 4 | |
| 12 | 2 | G32 K | G | x | | x | x | |
| 13 | 5 | P22 R6 L3 N I | P | 1 | | s | 4 | s |
| 14 | 3 | C31 T A | C | 1 | | s | s | 5 |
| 15 | 12 | K15 R4 Y2 M2 L2 −2 V G A I N F | K | 1 | s | 3 | 4 | s |
| 16 | 7 | A22 G5 Q2 R K D F | A | 1 | s | s | s | 5 |
| 17 | 12 | R12 K5 A2 Y3 H2 S2 F2 L M T G P | R | 1 | 2 | 3 | | s |
| 18 | 6 | I21 M4 F3 L2 V2 T | I | 1 | s | s | | 5 |
| 19 | 7 | I11 P10 R6 S2 K2 L Q | I | 1 | 2 | 3 | | s |
| 20 | 5 | R19 A7 S4 L2 Q | R | s | s | s | | 5 |
| 21 | 4 | Y18 F13 W I | Y | | 2 | s | s | s |
| 22 | 6 | F14 Y14 H2 A N S | F | | s | 3 | 4 | |
| 23 | 2 | Y32 F | Y | | | s | s | |
| 24 | 4 | N26 K3 D3 S | N | | s | 3 | | |
| 25 | 10 | A12 S5 Q3 P3 W3 L2 T2 K G R | A | | | s | s | |
| 26 | 9 | K16 A6 T2 E2 S2 R2 G H V | K | | s | 3 | 4 | |
| 27 | 5 | A18 S8 K3 L2 T2 | A | | 2 | 3 | 4 | |
| 28 | 7 | G13 K10 N5 Q2 R H M | G | | 2 | s | s | |
| 29 | 10 | L9 Q7 K7 A2 F2 R2 M G T N | L | | 2 | 3 | | |
| 30 | 1 | C33 | C | | x | x | x | |
| 31 | 7 | Q12 E11 L4 K2 V2 Y N | Q | | 2 | 3 | 4 | |
| 32 | 11 | T12 P5 K4 Q3 E2 L2 G V S R A | T | | 2 | 3 | s | |
| 33 | 1 | F33 | F | x | x | x | x | |
| 34 | 11 | V11 I8 T3 D2 N2 Q2 F H P R K | V | 1 | 2 | 3 | s | |
| 35 | 2 | Y31 W2 | Y | s | s | s | | 5 |
| 36 | 3 | G27 S5 R | G | 1 | | | | |
| 37 | 1 | G33 | G | x | | | | x |
| 38 | 3 | C31 T A | C | 1 | | | s | 5 |
| 39 | 7 | R13 G9 K4 Q3 D2 P M | R | 1 | | | 4 | s |
| 40 | 2 | G22 A11 | A | s | | | s | 5 |
| 41 | 3 | N20 K11 D2 | K | | | | 4 | s |
| 42 | 9 | A11 R9 S4 G3 H2 D Q K N | R | | | | s | 5 |
| 43 | 2 | N31 G2 | N | | | | | s |
| 44 | 3 | N21 R11 K | N | | | | | s |
| 45 | 2 | F32 Y | F | | | | | s |
| 46 | 8 | K24 E2 S2 D H V Y R | K | | | | | 5 |
| 47 | 2 | T19 S14 | S | | s | | | 5 |
| 48 | 9 | A11 I9 E4 T2 W2 L2 R K D | A | | 2 | s | | s |
| 49 | 7 | E19 D6 A2 Q2 K2 T H | E | | 2 | | | s |
| 50 | 6 | E16 D12 L2 M Q K | D | | s | | | 5 |
| 51 | 1 | C33 | C | | x | | | x |
| 52 | 7 | R13 M10 L3 E3 Q2 H V | M | | 2 | | | s |
| 53 | 8 | R21 Q3 E2 H2 C2 G K D | R | | s | | | 5 |
| 54 | 7 | T23 A3 V2 E2 I Y K | T | | | | | 5 |
| 55 | 1 | C33 | C | | | | | x |
| 56 | 8 | G15 VS I3 E2 R2 A L S | G | | | | | |
| 57 | 8 | G19 V4 A3 P2 −2 R L N | G | | | | | |
| 58 | 8 | A11 −10 P3 K3 S2 Y2 R F | A | | | | | |
| 59 | 9 | −24 G2 Q E A Y S P R | — | | | | | |
| 60 | 6 | −28 Q R I G D | — | | | | | |
| 61 | 3 | −31 T P | — | | | | | |
| 62 | 2 | −32 D | — | | | | | |
| 63 | 2 | −32 K | — | | | | | |
| 64 | 2 | −32 S | — | | | | | | s indicates secondary set
x indicates in or close to surface but buried and/or highly conserved.

TABLE 35

Distances from $C_\beta$ to Tip of Side Group in Å

| Amino Acid type | Distance |
| --- | --- |
| A | 0.0 |
| C (reduced) | 1.8 |
| D | 2.4 |
| E | 3.5 |
| F | 4.3 |
| G | — |
| H | 4.0 |
| I | 2.5 |
| K | 5.1 |
| L | 2.6 |
| M | 3.8 |
| N | 2.4 |
| P | 2.4 |
| Q | 3.5 |
| R | 6.0 |
| S | 1.5 |
| T | 1.5 |
| V | 1.5 |
| W | 5.3 |
| Y | 5.7 |

Notes: These distances were calculated for standard model parts with all side groups fully extended.

TABLE 36

Distances, BPTI residue set #2
Distances in Å between $C_\beta$
Hypothetical $C_\beta$ was added to each Glycine.

|  | R17 | I19 | Y21 | A27 | G28 | L29 | Q31 | T32 | V34 | A48 |
| --- | --- | --- | --- | --- | --- | --- | --- | --- | --- | --- |
| I19 | 7.7 | | | | | | | | | |
| Y21 | 15.1 | 8.4 | | | | | | | | |
| A27 | 22.6 | 17.1 | 12.2 | | | | | | | |
| G28 | 26.6 | 20.4 | 13.8 | 5.3 | | | | | | |
| L29 | 22.5 | 15.8 | 9.6 | 5.1 | 5.2 | | | | | |
| Q31 | 16.1 | 10.4 | 6.8 | 6.8 | 10.6 | 6.8 | | | | |
| T32 | 11.7 | 5.2 | 6.1 | 12.0 | 15.5 | 10.9 | 5.4 | | | |
| V34 | 5.6 | 6.5 | 11.6 | 17.6 | 21.7 | 18.0 | 11.4 | 8.2 | | |
| A48 | 18.5 | 11.0 | 5.4 | 12.6 | 13.3 | 8.4 | 8.8 | 8.3 | 15.7 | |
| E49 | 22.0 | 14.7 | 8.9 | 16.9 | 16.1 | 12.2 | 13.9 | 13.3 | 19.8 | 5.5 |
| M52 | 23.6 | 16.3 | 8.6 | 12.2 | 10.3 | 7.6 | 11.3 | 13.2 | 20.0 | 6.2 |
| P9 | 14.0 | 11.3 | 9.0 | 12.2 | 15.4 | 13.3 | 7.9 | 9.2 | 8.7 | 13.9 |
| T11 | 9.5 | 11.2 | 13.5 | 18.8 | 22.5 | 19.8 | 13.5 | 12.1 | 5.7 | 18.5 |
| K15 | 7.9 | 14.6 | 20.1 | 27.4 | 31.3 | 27.9 | 21.4 | 18.1 | 10.3 | 24.6 |
| A16 | 5.5 | 10.1 | 15.9 | 25.2 | 28.5 | 24.6 | 18.6 | 14.5 | 8.6 | 19.8 |
| I18 | 6.1 | 6.0 | 11.2 | 21.3 | 24.4 | 20.2 | 14.7 | 10.4 | 7.0 | 15.0 |
| R20 | 10.6 | 5.9 | 5.4 | 16.0 | 18.5 | 14.6 | 9.8 | 6.9 | 7.8 | 10.2 |
| F22 | 15.6 | 10.9 | 5.6 | 10.5 | 12.8 | 10.3 | 6.2 | 8.1 | 10.8 | 10.3 |
| N24 | 19.9 | 14.7 | 9.4 | 4.1 | 7.3 | 6.1 | 4.8 | 10.0 | 14.7 | 11.4 |
| K26 | 24.4 | 20.1 | 15.2 | 5.4 | 7.7 | 9.8 | 10.1 | 15.3 | 19.0 | 17.0 |
| C30 | 18.9 | 12.1 | 4.6 | 8.8 | 9.5 | 5.3 | 5.9 | 8.2 | 14.9 | 4.9 |
| F33 | 10.8 | 7.4 | 7.7 | 12.6 | 16.4 | 13.0 | 6.6 | 5.6 | 5.5 | 12.2 |
| Y35 | 8.4 | 7.4 | 9.4 | 18.4 | 21.4 | 17.9 | 12.2 | 9.5 | 5.8 | 14.4 |
| S47 | 17.6 | 10.6 | 6.6 | 17.3 | 17.9 | 13.4 | 12.6 | 10.4 | 15.9 | 5.3 |
| D50 | 20.0 | 13.6 | 7.2 | 17.2 | 16.8 | 13.5 | 13.5 | 12.9 | 17.6 | 7.6 |
| C51 | 18.9 | 12.2 | 4.0 | 12.1 | 12.2 | 8.8 | 8.8 | 9.7 | 15.3 | 5.4 |
| R53 | 25.4 | 18.6 | 11.0 | 17.2 | 15.0 | 13.0 | 15.7 | 16.7 | 22.3 | 9.7 |
| R39 | 15.4 | 16.9 | 17.1 | 24.9 | 27.2 | 24.9 | 20.1 | 18.7 | 13.8 | 22.3 |

|  | E49 | M52 | P9 | T11 | K15 | A16 | I18 | R20 | F22 | N24 |
| --- | --- | --- | --- | --- | --- | --- | --- | --- | --- | --- |
| M52 | 6.1 | | | | | | | | | |
| P9 | 17.7 | 15.5 | | | | | | | | |
| T11 | 22.1 | 21.5 | 7.2 | | | | | | | |
| K15 | 27.5 | 28.7 | 16.4 | 9.5 | | | | | | |
| A16 | 22.2 | 24.2 | 14.9 | 9.8 | 6.2 | | | | | |
| I18 | 17.4 | 19.5 | 12.2 | 9.5 | 10.4 | 4.9 | | | | |
| R20 | 13.0 | 13.8 | 8.0 | 9.4 | 14.9 | 10.6 | 6.2 | | | |
| F22 | 13.8 | 11.4 | 4.1 | 10.6 | 19.1 | 16.3 | 12.7 | 6.9 | | |
| N24 | 15.6 | 11.2 | 8.4 | 15.3 | 24.1 | 21.9 | 18.2 | 12.7 | 6.6 | |
| K26 | 20.9 | 15.7 | 12.1 | 18.6 | 27.9 | 26.6 | 23.3 | 18.1 | 11.6 | 5.9 |
| C30 | 8.7 | 5.6 | 10.6 | 16.6 | 24.1 | 20.2 | 15.7 | 9.8 | 6.8 | 6.9 |
| F33 | 16.5 | 15.4 | 4.2 | 7.1 | 15.0 | 12.8 | 9.6 | 6.1 | 5.6 | 9.3 |
| Y35 | 17.2 | 17.8 | 7.8 | 5.8 | 11.0 | 7.6 | 4.9 | 4.3 | 8.8 | 14.8 |
| S47 | 4.7 | 9.1 | 15.3 | 18.5 | 23.1 | 17.6 | 12.8 | 9.1 | 12.0 | 15.3 |
| D50 | 5.5 | 7.7 | 14.7 | 18.6 | 24.2 | 19.2 | 14.7 | 9.9 | 11.0 | 14.7 |
| C51 | 7.1 | 5.4 | 11.0 | 16.4 | 23.5 | 19.2 | 14.6 | 8.7 | 6.9 | 9.6 |
| R53 | 6.3 | 5.6 | 17.9 | 23.1 | 29.6 | 24.8 | 20.3 | 15.0 | 13.8 | 15.5 |
| R39 | 23.9 | 24.0 | 13.0 | 9.5 | 12.0 | 11.8 | 12.5 | 12.8 | 14.7 | 20.8 |

TABLE 36-continued

Distances, BPTI residue set #2
Distances in Å between $C_\beta$
Hypothetical $C_\beta$ was added to each Glycine.

|     | K26  | C30  | F33  | Y35  | S47  | D50  | C51 | R53  |
|-----|------|------|------|------|------|------|-----|------|
| C30 | 12.4 |      |      |      |      |      |     |      |
| F33 | 13.9 | 10.1 |      |      |      |      |     |      |
| Y35 | 19.5 | 13.5 | 6.4  |      |      |      |     |      |
| S47 | 21.0 | 8.8  | 13.5 | 13.2 |      |      |     |      |
| D50 | 20.1 | 8.6  | 14.3 | 13.7 | 5.0  |      |     |      |
| C51 | 15.0 | 3.7  | 10.9 | 12.5 | 6.9  | 5.2  |     |      |
| R53 | 19.9 | 9.9  | 18.2 | 18.8 | 9.4  | 5.8  | 7.4 |      |
| R39 | 24.3 | 20.6 | 14.4 | 9.6  | 20.4 | 19.0 | 18.8| 23.4 |

TABLE 37 vgDNA to vary BPTI set #2.1

```
                                                        +
              | g   | p   | c   | k   | a   | X   |
              | 35  | 36  | 37  | 38  | 39  | 40  |
 5'-| CAC | CCT| GGG | CCC | TGC | AAA | GCG | qfk |         208
     spacer  | Apa I    |

+
  | i   | X   | r   | y   | f   | y   | n   | a   | k   |
  | 41  | 42  | 43  | 44  | 45  | 46  | 47  | 48  | 49  |
  | ATC | qfk | CGT | TAT | TTC | TAC | AAC | GCT | AAA |     235

| 3' = olig#27        72 nts
    +   !   +                                  +
  | X | g | X | c   | q   | t   | f   | X   | y   | g   | g   |
  | 50| 51| 52| 53  | 54  | 55  | 56  | 57  | 58  | 59  | 60  |
  |gfk|GGt|gfk| TGC | CAG | ACC | TTc | qfk | TAC | GGT | GGT |   268
 olig#28 = 3'-       ac g  gt c  t gg  aag  **m  at g  c c a  c c a
 78 nts
 Overlap = 12 (7 CG, 5 AT)

| c   | r   | a   | k   | r   | n   | n   | f   | k   |
  | 61  | 62  | 63  | 64  | 65  | 66  | 67  | 68  | 69  |
  | TGC | CGT | GCT | AAG | CGT | AAC | AAC | TTT | AAA |         295
    ac g  gc a  c ga  t t c  g c a  t t g  t t g  aaa   t t t
              | Esp I            |

+
  | s   | X   | e   | d   | c   | m   |
  | 70  | 71  | 72  | 73  | 74  | 75  |
  | TCT | qfk | GAG | GAT | TGC | ATG | C                        322
    agc   **m   ctc   cta   acg  tac  gca  ccc  acc  -5'
                            | Sph I   | spacer         |
``` k = equal parts of T and G;
m = equal parts of C and A;
q = (.26 T, .18 C, .26 A, and .30 G);
f = (.22 T, .16 C, .40 A, and .22 G);
* = complement of symbol above Residue         40   42   50   52   57   71
Possibilities   $21 \times 21 \times 21 \times 21 \times 21 \times 21 = 8.6 \times 10^7$
Abundance × 10:
of PPBD         .768 .271 .459 .671 .600 .459
Produce = $1.77 \times 10^{-8}$ Parent = $1/(5.5 \times 10^7)$     least favored = $1/(4.2 \times 10^9)$
Least favored one-amino-acid substitution from PPBD present at 1 in $1.6 \times 10^7$

TABLE 38

Result of varying set#2 of BPTI 2.1

| | | | | | | | | l 29 CTC Ava Xho | e 30 GAG I I | 178 |

| p 31 CCG | p 32 CCA PflM I | y 33 TAT | t 34 ACT | g 35 GGG | p 36 CCC Apa I Dra II Pss I | c 37 TGC | k 38 AAA | a 39 GCG | D 40 GAT | 208 |

| i 41 ATC | Q 42 CAG | r 43 CGT | y 44 TAT | f 45 TTC | y 46 TAC | n 47 AAC | a 48 GCT | k 49 AAA | | 235 |

| E 50 GAG | g 51 GGC | L 52 CTG | c 53 TGC | q 54 CAG | t 55 ACC | f 56 TTT | S 57 TCG | y 58 TAC | g 59 GGT | g 60 GGT | 268 |

| c 61 TGC | r 62 CGT Esp I | a 63 GCT | k 64 AAG | r 65 CGT | n 66 AAC | n 67 AAC | f 68 TTT | k 69 AAA | 295 |

| s 70 TCG | W 71 TGG | e 72 GAA | d 73 GAT | c 74 TGC | m 75 ATG Sph I | r 76 CGT | t 77 ACC | c 78 TGC | g 79 GGT | 325 |

| g 80 GGC Bbe I Nar I | a 81 GCC |

TABLE 39 vgDNA to vary set#2 BPTI 2.2

```
                                                                      +
                                      | g   | p   | c   | X   | a   | D   |
                                      | 35  | 36  | 37  | 38  | 39  | 40  |
5'-        cg   gca   cgc             | GGG | CCC | TGC | mrA | GCG | GAT |    208
              spacer                        Apa I
```

```
 +               +     +
| X  | Q  | X  | X  | f  | y  | n  | a  | k  |
| 41 | 42 | 43 | 44 | 45 | 46 | 47 | 48 | 49 |
|rwA |CAG |rvk |TwT |TTC |TAC |AAC |GCT |AAA |                          235
```

```
           +                +     +
| E  | X  | L  | c  | X  | X  | f  | S  | y  | g  | g  |
| 50 | 51 | 52 | 53 | 54 | 55 | 56 | 57 | 58 | 59 | 60 |
|GAG |qfk |CTG |TGC |qfk |qfk |TTT |TCG |TAC |GGT |GGT |                268
                              91 nts olig#30 3'-  g  cca  cca
```

Overlap = 15 (11 CG, 4 AT)

```
              /-3'  olig#29  94 nts
| c  | r  | a  | k  | r  | n  | n  | f  | k  |
| 61 | 62 | 63 | 64 | 65 | 66 | 67 | 68 | 69 |
|TGC |CGT |GCT |AAG |CGT |AAC |AAC |TTT |AAA |                          295
 acg  gca  cga  ttc  gca  ttg  ttg  aaa  ttt
            Esp I
```

```
|  s  |  W  |  X  |  d  |  c  |  m  |
| 70  | 71  | 72  | 73  | 74  | 75  |
| TCG | TGG | qfk | GAT | TGC | ATG | C
  agc   acc  **m   cta   acg   tac   gcg   acc   tgc -5'
                         Sph I            spacer
```

TABLE 39-continued vgDNA to vary set#2 BPTI 2.2 k = equal parts of T and G; v = equal parts of C, A, and G;
m = equal parts of C and A; r = equal parts of A and G;
w = equal parts of A and T;
q = (.26 T, .18 C, .26 A, and .30 G);
f = (.22 T, .16 C, .40 A, and .22 G);
* = complement of symbol above Residue       38   41   43   44   51   54   55   72
Possibilities 4× × 4× × 9× × 2× × 21× × 21× × 21× × 21 = 6.2 × 10$^7$ Abundance × 10  2.5  2.5  .833  5.  .663  .397  .437  .602
Product = 2.3 × 10$^{-8}$ Parent = 1/(4.4 × 10$^7$)    least favored = 1/(1.25 × 10$^9$)
Least favored one-amino-acid substitution from PPBD present at 1 in 1.2 × 10$^7$

TABLE 40

Result of varying set#2 of BPTI 2.2

| | | | | | | | | l<br>29<br>CTC | e<br>30<br>GAG<br>Xho I | 178 |
|---|---|---|---|---|---|---|---|---|---|---|

| p<br>31<br>CCG | p<br>32<br>CCA | y<br>33<br>TAT<br>PflM I | t<br>34<br>ACT | g<br>35<br>GGG | p<br>36<br>CCC<br>Apa I | c<br>37<br>TGC | E<br>38<br>GAG | a<br>39<br>GCG | D<br>40<br>GAT | 208 |
|---|---|---|---|---|---|---|---|---|---|---|

| V<br>41<br>GTT | Q<br>42<br>CAG | N<br>43<br>AAT | F<br>44<br>TTT | f<br>45<br>TTC | y<br>46<br>TAC | n<br>47<br>AAC | a<br>48<br>GCT | k<br>49<br>AAA | 235 |
|---|---|---|---|---|---|---|---|---|---|

| E<br>50<br>GAG | F<br>51<br>TTT | L<br>52<br>CTG | c<br>53<br>TGC | S<br>54<br>TCT | A<br>55<br>GCT | f<br>56<br>TTT | S<br>57<br>TCG | y<br>58<br>TAC | g<br>59<br>GGT | g<br>60<br>GGT | 268 |
|---|---|---|---|---|---|---|---|---|---|---|---|

| c<br>61<br>TGC | r<br>62<br>CGT | a<br>63<br>GCT<br>Esp I | k<br>64<br>AAG | r<br>65<br>CGT | n<br>66<br>AAC | n<br>67<br>AAC | f<
68<br>TTT | k<br>69<br>AAA | 295 |
|---|---|---|---|---|---|---|---|---|---|

| s<br>70<br>TCG | W<br>71<br>TGG | Q<br>72<br>CAG | d<br>73<br>GAT | c<br>74<br>TGC | m<br>75<br>ATG<br>Sph I | r<br>76<br>CGT | t<br>77<br>ACC | c<br>78<br>TGC | g<br>79<br>GGT | 325 |
|---|---|---|---|---|---|---|---|---|---|---|

| g<br>80<br>GGC<br>Bbe I<br>Nar I | a<br>81<br>GCC |
|---|---|

TABLE 41 vg DNA set#2 of BPTI 2.3

| | | | | | | | 5'- c g  a g c  c t g<br>spacer | l<br>29<br>CTC<br>Xho I | e<br>30<br>GAG | 178 |
|---|---|---|---|---|---|---|---|---|---|---|

| p<br>31<br>CCG | +<br>X<br>32<br>v mg | y<br>33<br>TAT | +<br>X<br>34<br>v mg | g<br>35<br>GGG | p<br>36<br>CCC | c<br>37<br>TGC | E<br>38<br>GAG | a<br>39<br>GCG | +<br>X<br>40<br>q f k | 208 |
|---|---|---|---|---|---|---|---|---|---|---|

TABLE 41-continued vg DNA set#2 of BPTI 2.3

| V | Q | N | X̄ | f | y | n | a | k | | | | |
|---|---|---|---|---|---|---|---|---|---|---|---|---|
| 41 | 42 | 43 | 44 | 45 | 46 | 47 | 48 | 49 | | | | |
| GTT | CAG | AAT | Tdk | TTC | TAC | AAC | GCc | AAg | -3' | olig#33 | 71 | nts |
| 67 nts olig#34 | | | 3'- g | at g | t t g | c g g | t t c | | | | | |

Overlap = 13 (7 CG, 6 AT)

| X̄ | F | X̄ | c | S | X̄ | f | X̄ | y | g | g | |
|---|---|---|---|---|---|---|---|---|---|---|---|
| 50 | 51 | 52 | 53 | 54 | 55 | 56 | 57 | 58 | 59 | 60 | |
| vAG | TTT | nTk | TGC | TCT | qfk | TTT | qfk | TAC | GGT | GGT | 268 |
| btc | aaa | nam | acg | aga | **m | aaa | **m | at g | cca | cca | |

| c | r | a | k | | | | |
|---|---|---|---|---|---|---|---|
| 61 | 62 | 63 | 64 | | | | |
| TGC | CGT | GCT | AAG | C | | | |
| acg | gca | cga | ttc | gcg | acc | ggc | |
| | | Esp I | | spacer | | | | k = equal parts of T and G; m = equal parts of C and A;
w = equal parts of A and T; n = equal parts of A,C,G,T;
d = equal parts A,G,T; v = equal parts A,C,G;
q = (.26 T, .18 C, .26 A, and .30 G);
f = (.22 T, .16 C, .40 A, and .22 G);
* = complement of symbol above Residue       32  34  40  44  50  52  55  57
Possibilities  6× 6×21× 6× 3× 5×21×21 = 3 × 10⁷

Abundance × 10
of PPBD       10/6  10/6  .545  10/6  10/3  30/8  .459  .701
product = 1.01 × 10⁻⁷ parent = 1/(1 × 10⁷)    least favored = 1/(4 × 10⁸)
Least favored one-amino-acid substitution from PPBD present at 1 in 3 × 10⁷

TABLE 42

Result of varying set#2 of BPTI 2.3

| | | | | | | | | l | e | |
|---|---|---|---|---|---|---|---|---|---|---|
| | | | | | | | | 29 | 30 | |
| | | | | | | | | CTC | GAG | 178 |
| | | | | | | | | Ava I | | |
| | | | | | | | | Xho I | | |

| p | E | y | Q | g | p | c | E | a | A | |
|---|---|---|---|---|---|---|---|---|---|---|
| 31 | 32 | 33 | 34 | 35 | 36 | 37 | 38 | 39 | 40 | |
| CCG | GAG | TAT | CAG | GGG | CCC | TGC | GAG | GCG | GCT | 208 |
| | | | | Apa I | | | | | | |

| V | Q | N | W | f | y | n | a | k | |
|---|---|---|---|---|---|---|---|---|---|
| 41 | 42 | 43 | 44 | 45 | 46 | 47 | 48 | 49 | |
| GTT | CAG | AAT | TGG | TTC | TAC | AAC | GCT | AAA | 235 |

| Q | F | M | c | S | L | f | H | y | g | g | |
|---|---|---|---|---|---|---|---|---|---|---|---|
| 50 | 51 | 52 | 53 | 54 | 55 | 56 | 57 | 58 | 59 | 60 | |
| CAG | TTT | ATG | TGC | TCT | CTT | TTT | CAT | TAC | GGT | GGT | 268 |

| c | r | a | k | r | n | n | f | k | |
|---|---|---|---|---|---|---|---|---|---|
| 61 | 62 | 63 | 64 | 65 | 66 | 67 | 68 | 69 | |
| TGC | CGT | GCT | AAG | CGT | AAC | AAC | TTT | AAA | 295 |
| | | Esp I | | | | | | | |

| s | W | Q | d | c | m | r | t | c | g | |
|---|---|---|---|---|---|---|---|---|---|---|
| 70 | 71 | 72 | 73 | 74 | 75 | 76 | 77 | 78 | 79 | |
| TCG | TGG | CAG | GAT | TGC | ATG | CGT | ACC | TGC | GGT | 325 |
| | | | | Sph I | | | | | | |

TABLE 42-continued

Result of varying set#2 of BPTI 2.3

| g 80 GGC Bbc I Nar I | a 81 GCC |
|---|---|

TABLE 50

| IPBD | Number Amino Acids | Structure | Cross Links | Secreted | Source Organism | AfM |
|---|---|---|---|---|---|---|
| | | | Preferred IPBDs | | | |
| Aprotinin | 58 | X-ray, NMR | 3 SS 5–55, 14–38 30–51 (1:6, 2:4, 3:5) | yes | *Bos taurus* | trypsin |
| Crambin | 46 | X-ray, NMR | 3 SS | yes | rape seed | ?, Mab |
| CMTI-III | 26 | NMR | 3 SS | yes | cucumber | trypsin |
| ST-$I_A$ | 13 | NMR | 3 SS | yes | *E. coli* | MAbs & guanylate cyclase |
| Third domain, ovomucoid | 56 | X-ray, NMR | 3 SS | yes | *Coturnix coturnix japonica* | trypsin |
| Ribonuclease A | 124 | X-ray, NMR | | yes | *Bos taurus* | RNA, DNA |
| Ribonuclease | 104 | X-ray, NMR? | | yes | *A. oruzae* | RNA, DNA |
| Lysozyme | 129 | X-ray, NMR? | 4 SS | yes | *Gallus gallus* | NAG-NAM-NAG |
| Azurin | 128 | X-ray | Cu:CYS, $HIS^2$, MET | | *P. aerugenosa* | Mab |
| | | | Characteristics of Known IPBDs | | | |
| α-Conotoxins | 13–15 | NMR | 2 SS | yes | Conus snails | Receptor |
| μ-Conotoxins | 20–25 | NMR | 3 SS | yes | Conus snails | Receptor |
| Ω-Conotoxins | 25–30 | — | 3 SS | yes | Conus snails | Receptor |
| King-kong peptides | 25–30 | — | 3 SS | yes | Conus snails | Mabs |
| Nuclease (staphylococcal) | 141 | X-ray | none | yes | *S aurius* | RNA, DNA |
| Charybdotoxin (scorpion toxin) | 37 | NMR | 3 SS 7–28, 13–33 17–35 (1:4, 2:5, 3:6) | Yes | *Leiurus guinguestriatus hebraeus* | $Ca^{+2}$ -dependent $K^+$ channel |
| Apamin (bee venom) | 12 | NMR | 2 SS (1:3, 2:4) | yes | Bees | Mabs, Receptor (?) |
| | | | Other suitable IPBDs | | | |

Ferredoxin
Secretory trypsin inhibitor
Soybean trypsin inhibitor
SLPI (Secretory Leukocyte Protease Inhibitor) (THOM86) and SPAI (ARAK90)
Cystatin and homologues (MACH89, STUB90)
Eglin (MCPH85)
Barley inhibitor (CLOR87a, CLOR87b, SVEN82)

TABLE 101a

VIIIsignal::bpti::VIII-coat gene
pbd mod14: 9 V 89 : Sequence cloned into pGEM-MB1
pGEM-3Zf(–) [HincII]::lacUV5 SacI/gene/
TrpA attenuator/(SalI)::pGEM-3Zf(–)[HincII]!

```
5'-(GAATTC GAGCTCGGTACCCGG GGATCC TCTAGAGTC)- ! polylinker
GGC tttaca CTTTATGCTTCCGGCTCG tataat GTG ! lacUV5
TGG aATTGTGAGCGcTcACAATT         ! lacO-symm operator
gagctc AG(G)AGG CttaCT  ! Sac I; Shine-Dalgarno seq.ᵃ
atg aag aaa tct ctg gtt ctt aag gct agc ! 10, M13 leader
gtt gct gtc gcg acc ctg gta cct atg ttg ! 20 <- codon #
tcc ttc gct cgt ccg gat ttc tgt ctc gag ! 30
cca cca tac act ggg ccc tgc aaa gcg cgc ! 40
atc atc cgC tat ttc tac aat gct aaa gca ! 50
ggc ctg tgc cag acc ttt gta tac ggt ggt ! 60
tgc cgt gct aag cgt aac aac ttt aaa tcg ! 70
gcc gaa gat tgc atg cgt acc tgc ggt ggc ! 80
gcc gct gaa ggt gat gat ccg gcc aaG gcg ! 90
```

TABLE 101a-continued

VIIIsignal::bpti::VIII-coat gene
pbd mod14: 9 V 89 : Sequence cloned into pGEM-MB1
pGEM-3Zf(−) [HincII]::lacUV5 SacI/gene/
TrpA attenuator/(SalI)::pGEM-3Zf(−)[HincII]!

gcc ttc aat tct ctG caa gct tct gct acc ! 100
gag tat att ggt tac gcg tgg gcc atg gtg ! 110
gtg gtt atc gtt ggt gct acc atc ggg atc ! 120
aaa ctg ttc aag aag ttt act tcg aag gcg ! 130
tct taa tga tag GGTTACC !   BstEII
AGTCTA AGCCCGC CTAATGA GCGGGCT TTTTTTTT ! terminator
aTCGA- ! (SalI ghost)
(GACCTGCAGGCATGCAAGCTT . . . . -3') ! pGEM polylinker Notes: a Designed sequence contained AGGAGG, but sequencing indicates that actual DNA contains AGAGG.

TABLE 101b

VIII-signal::bpti::VIII-coat gene
BamHI-SalI cassette, after insertion of SalI linker in PstI
site of pGEM-MB1.

pGEM-3Zf(−)[HincII]::lacUV5 SacI/gene/
TrpA attenuator/(SalI)::pGEM-3Zf(−)[HincII]!
5'-GAATTC GAGCTC GGTACCCGG GGATCC TCTAGA GTC- !  BamHI
GGC tttaca CTTTATGCTTCCGGCTCG tataat GTG  ! lacUV5
TGG aATTGTGAGCGcTcACAATT           ! lacO-symm operator
gagctc AGAGG CttaCT      ! Sac I; Shine-Dalgarno seq.

| atg | aag | aaa | tct | ctg | gtt | ctt | aag | gct | agc | ! 10, | M13 leader |
|-----|-----|-----|-----|-----|-----|-----|-----|-----|-----|-------|------------|
| gtt | gct | gtc | gcg | acc | ctg | gta | cct | atg | ttg | ! 20  | ← codon # |
| tcc | ttc | gct | cgt | ccg | gat | ttc | tgt | ctc | gag | ! 30  |            |
| cca | cca | tac | act | ggg | ccc | tgc | aaa | gcg | cgc | ! 40  |            |
| atc | atc | cgC | tat | ttc | tac | aat | gct | aaa | gca | ! 50  |            |
| ggc | ctg | tgc | cag | acc | ttt | gta | tac | ggt | ggt | ! 60  |            |
| tgc | cgt | gct | aag | cgt | aac | aac | ttt | aaa | tcg | ! 70  |            |
| gcc | gaa | gat | tgc | atg | cgt | acc | tgc | ggt | ggc | ! 80  |            |
| gcc | gct | gaa | ggt | gat | gat | ccg | gcc | aaG | gcg | ! 90  |            |
| gcc | ttc | aat | tct | ctG | caa | gct | tct | gct | acc | ! 100 |            |
| gag | tat | att | ggt | tac | gcg | tgg | gcc | atg | gtg | ! 110 |            |
| gtg | gtt | atc | gtt | ggt | gct | acc | atc | ggg | atc | ! 120 |            |
| aaa | ctg | ttc | aag | aag | ttt | act | tcg | aag | gcg | ! 130 |            |
| tct | taa | tga | tag | GGTTACC | ! | BstEII | | | | | |

AGTCTA AGCCCGC CTAATGA GCGGGCT TTTTTTTT                ! terminator aTCGA GACctgca GGTCGACC ggcatgc-3'
      |   SalI   |

TABLE 102a

Annotated Sequence of gene found in pGEM-MB1

| | nucleotide number |
|---|---|
| 5'-(G GATCC TCTAGA GTC) GGC-<br>from pGEM polylinker | 3 |
| tttaca CTTTATGCTTCCGGCTCG tataat GTGTGG-<br>−35       lacUV5        −10 | 39 |
| aATTGTGAGCGcTcACAATT-<br>lacO-symm operator | 59 |

TABLE 102a-continued

Annotated Sequence of gene found in pGEM-MB1

| gagctc | AG(G)/AGG | CttaCT- | | | | | | | | | 77 |
| SacI | Shine-Dalgarno seq.[a] | | | | | | | | | | |

| fM | K | K | S | L | V | L | K | A | S | | |
| 1 | 2 | 3 | 4 | 5 | 6 | 7 | 8 | 9 | 10 | | |
| ATG | AAG | AAA | TCT | CTG | GTT | CTT | AAG | GCT | AGC | - | 107 |
|  |  |  |  |  |  | Afl II | Nhe I |  |  | | |

| V | A | V | A | T | L | V | P | M | L | | |
| 11 | 12 | 13 | 14 | 15 | 16 | 17 | 18 | 19 | 20 | | |
| GTT | GCT | GTC | GCG | ACC | CTG | GTA | CCT | ATG | TTG | - | 137 |
|  |  | Nru I |  |  | Kpn I |  |  |  |  | | |

| S | F | A | R | P | D | F | C | L | E | | |
| 21 | 22 | 23 | 24 | 25 | 26 | 27 | 28 | 29 | 30 | | |
| TCC | TTC | GCT | CGT | CCG | GAT | TTC | TGT | CTC | GAG | - | 167 |
|  |  |  | AccIII |  |  |  |  | Ava I | | | |
|  |  |  |  |  |  |  |  | Xho I | | | |

M13/BPTI Jnct

| P | P | Y | T | G | P | C | K | A | R | | |
| 31 | 32 | 33 | 34 | 35 | 36 | 37 | 38 | 39 | 40 | | |
| CCA | CCA | TAC | ACT | GGG | CCC | TGC | AAA | GCG | CGC | - | 197 |
|  | PflM I |  |  |  |  |  |  | BssH II | | | |
|  |  |  |  | Apa I |  |  |  |  | | | |
|  |  |  |  | Dra II |  |  |  |  | | | |
|  |  |  |  | Pss I |  |  |  |  | | | |

| I | I | R | Y | F | Y | N | A | K | A | | |
| 41 | 42 | 43 | 44 | 45 | 46 | 47 | 48 | 49 | 50 | | |
| ATC | ATC | CGC | TAT | TTC | TAC | AAT | GCT | AAA | GC | - | 226 |

| G | L | C | Q | T | F | V | Y | G | G | | |
| 51 | 52 | 53 | 54 | 55 | 56 | 57 | 58 | 59 | 60 | | |
| A GGC | CTG | TGC | CAG | ACC | TTT | GTA | TAC | GGT | GGT | - | 257 |
| Stu I |  |  |  |  |  | Acc I |  |  | | | |
|  |  |  |  |  |  | Xca I |  |  | | | |

| C | R | A | K | R | N | N | F | K | | | |
| 61 | 62 | 63 | 64 | 65 | 66 | 67 | 68 | 69 | | | |
| TGC | CGT | GCT | AAG | CGT | AAC | AAC | TTT | AAA | - | | 284 |
|  |  | Esp I |  |  |  |  |  |  | | | |

| S | A | E | D | C | M | R | T | C | G | | |
| 70 | 71 | 72 | 73 | 74 | 75 | 76 | 77 | 78 | 79 | | |
| TCG | GCC | GAA | GAT | TGC | ATG | CGT | ACC | TGC | GGT | - | 314 |
| Xma III |  |  |  | Sph I |  |  |  |  | | | |

BPTI/M13 boundary

| G | A | A | E | G | D | D | P | A | K | A | A | |
| 80 | 81 | 82 | 83 | 84 | 85 | 86 | 87 | 88 | 89 | 90 | 91 | |
| GGC | GCC | GCT | GAA | GGT | GAT | GAT | CCG | GCC | AAG | GCG | GCC | -350 |
| Bbe I |  |  |  |  |  |  |  | Sfi I |  |  |  | |
| Nar I |  |  |  |  |  |  |  |  |  |  |  | |

| F | N | S | L | Q | A | S | A | T | | | |
| 92 | 93 | 94 | 95 | 96 | 97 | 98 | 99 | 100 | | | |
| TTC | AAT | TCT | CTG | CAA | GCT | TCT | GCT | ACC | - | | 377 |
|  |  |  |  | Hind 3 |  |  |  |  | | | |

| E | Y | I | G | Y | A | W | | | |
| 101 | 102 | 103 | 104 | 105 | 106 | 107 | | | |
| GAG | TAT | ATT | GGT | TAC | GCG | TGG | - | | 398 |

| A | M | V | V | V | I | V | G | A | | |
| 108 | 109 | 110 | 111 | 112 | 113 | 114 | 115 | 116 | | |
| GCC | ATG | GTG | GTG | GTT | ATC | GTT | GGT | GCT | - | 425 |
|  | BstX I |  |  |  |  |  |  |  | | |
|  | Nco I |  |  |  |  |  |  |  | | |

TABLE 102a-continued

Annotated Sequence of gene found in pGEM-MB1

| T 117 ACC | I 118 ATC | G 119 GGG | I 120 ATC |- 437

| K 121 AAA | L 122 CTG | F 123 TTC | K 124 AAG | K 125 AAG | F 126 TTT | T 127 ACT | S 128 TCG | K 129 AAG | A 130 GCG |- 467
                                                            |_ Asu II _|

| S 131 TCT | . 132 TAA | . 133 TGA | . 134 TAG |  GGTTACC-   486
                                                  BstE II

AGTCTA AGCCCGC CTAATGA GCGGGCT TTTTTTTT-   521
       terminator aTCGA   (GACctgcaggcatgc)-3'
(SalI)  from pGEM polylinker Notes:
<sup>a</sup>Designed called for shine-Dalgarno sequence, AGGAGG, but sequencing shows that actual constructed gene contains AGAGG.
Note the following enzyme equivalences, Xma III = Eag I          Acc III = BspM II
Dra II = EcoO109 I       Asu II = BstB I TABLE 102b Annotated Sequence of gene after insertion of SalI linker nucleotide number 5'-(G GATCC TCTAGA GTC) GGC-                                    3
    from pGEM polylinker tttaca CTTTATGCTTCCGGCTCG tataat GTGTGG-                        39
 -35      lacUV5           -10 aATTGTGAGCGcTcACAATT-                                    59
       lacO-symm operator gagctc       AGAGG           CttaCT-                            77
 SacI    Shine-Dalgarno seq.

| fM 1 ATG | K 2 AAG | K 3 AAA | S 4 TCT | L 5 CTG | V 6 GTT | L 7 CTT | K 8 AAG | A 9 GCT | S 10 AGC |- 107
                                                   |_ Afl II _|         |_ Nhe I _|

| V 11 GTT | A 12 GCT | V 13 GTC | A 14 GCG | T 15 ACC | L 16 CTG | V 17 GTA | P 18 CCT | M 19 ATG | L 20 TTG |- 137
                      |_ Nru I _|                      |_ Kpn I _|

| S 21 TCC | F 22 TTC | A 23 GCT | R 24 CGT | P 25 CCG | D 26 GAT | F 27 TTC | C 28 TGT | L 29 CTC | E 30 GAG |- 167
                               ↑          |_ AccIII _|                                 |_ Ava I _|
                        M13/BPTI Jnct                                                  |_ Xho I _|

| P 31 CCA | P 32 CCA | Y 33 TAC | T 34 ACT | G 35 GGG | P 36 CCC | C 37 TGC | K 38 AAA | A 39 GCG | R 40 CGC |- 197
                      |_ PflM I _|                                           |_ BssH II _|
                                  |_ Apa I _|
                                  |_ Dra II _|
                                  |_ Pss I _|

TABLE 102b-continued

Annotated Sequence of gene after insertion of SalI linker

| | I 41 ATC | I 42 ATC | R 43 CGC | Y 44 TAT | F 45 TTC | Y 46 TAC | N 47 AAT | A 48 GCT | K 49 AAA | A 50 GC | - | 226 |

| A | G 51 GGC | L 52 CTG | C 53 TGC | Q 54 CAG | T 55 ACC | F 56 TTT | V 57 GTA | Y 58 TAC | G 59 GGT | G 60 GGT | - | 257 |

Stu I                                                   Acc I / Xca I

| | C 61 TGC | R 62 CGT | A 63 GCT | K 64 AAG | R 65 CGT | N 66 AAC | N 67 AAC | F 68 TTT | K 69 AAA | - | 284 |

Esp I

| S 70 TCG | A 71 GCC | E 72 GAA | D 73 GAT | C 74 TGC | M 75 ATG | R 76 CGT | T 77 ACC | C 78 TGC | G 79 GGT | - | 314 |

Xma III                      Sph I

BPTI/M13 boundary ↓

| G 80 GGC | A 81 GCC | A 82 GCT | E 83 GAA | G 84 GGT | D 85 GAT | D 86 GAT | P 87 CCG | A 88 GCC | K 89 AAG | A 90 GCG | A 91 GCC | -350 |

Bbe I / Nar I                                               Sfi I

| | F 92 TTC | N 93 AAT | S 94 TCT | L 95 CTG | Q 96 CAA | A 97 GCT | S 98 TCT | A 99 GCT | T 100 ACC | - | 377 |

Hind 3

| | E 101 GAG | Y 102 TAT | I 103 ATT | G 104 GGT | Y 105 TAC | A 106 GCG | W 107 TGG | - | 398 |

| | | A 108 GCC | M 109 ATG | V 110 GTG | V 111 GTG | V 112 GTT | I 113 ATC | V 114 GTT | G 115 GGT | A 116 GCT | - | 425 |

BstX I / Nco I

| | | | T 117 ACC | I 118 ATC | G 119 GGG | I 120 ATC | - | 437 |

| | | K 121 AAA | L 122 CTG | F 123 TTC | K 124 AAG | K 125 AAG | F 126 TTT | T 127 ACT | S 128 TCG | K 129 AAG | A 130 GCG | - | 467 |

Asu II

| | | | S 131 TCT | . 132 TAA | . 133 TGA | . 134 TAG | GGTTACC- | 486 |

BstE II

AGTCTA AGCCCGC CTAATGA GCGGGCT TTTTTTTT-    521
    terminator aTCGA     GACctgca GGTCGAAC ggcatgc-3'
                                SalI Note the following enzyme equivalences,

| | |
|---|---|
| Xma III = Eag I | Acc III = BspM II |
| Dra II = EcoO109 I | Asu II = BstB I |

TABLE 102c

Annotated Sequence of osp-ipbd gene
Calculated properties of Peptide

For the apoprotein

| | | |
|---|---|---|
| Molecular weight of peptide | = | 16192 |
| Charge on peptide | = | 9 |
| [A+G+P] | = | 36 |
| [C+F+H+I+L+M+V+W+Y] | = | 48 |
| [D+E+K+R+N+Q+S+T+.] | = | 48 |

For the mature protein

| | | |
|---|---|---|
| Molecular weight of peptide | = | 13339 |
| Charge on peptide | = | 6 |
| [A+G+P] | = | 31 |
| [C+F+H+I+L+M+V+W+Y] | = | 37 |
| [D+E+K+R+N+Q+S+T+.] | = | 41 |

TABLE 102d

Codon Usage

| First Base | Second Base t | c | a | g | Third base |
|---|---|---|---|---|---|
| t | 3 | 4 | 2 | 1 | t |
|   | 5 | 1 | 4 | 5 | c |
|   | 0 | 0 | 0 | 0 | a |
|   | 1 | 2 | 0 | 1 | g |
| c | 1 | 1 | 0 | 4 | t |
|   | 1 | 1 | 0 | 2 | c |
|   | 0 | 2 | 1 | 0 | a |
|   | 5 | 2 | 1 | 0 | g |
| a | 1 | 2 | 2 | 0 | t |
|   | 5 | 5 | 2 | 1 | c |
|   | 0 | 0 | 5 | 0 | a |
|   | 4 | 0 | 7 | 0 | g |
| g | 4 | 9 | 4 | 6 | t |
|   | 1 | 5 | 0 | 2 | c |
|   | 2 | 1 | 2 | 0 | a |
|   | 2 | 5 | 2 | 2 | g |

TABLE 102e

Amino-acid frequency

Encoded polypeptide

| AA | # | AA | # | AA | # | AA | # |
|---|---|---|---|---|---|---|---|
| A | 20 | C | 6 | D | 4 | E | 4 |
| F | 8 | G | 10 | H | 0 | I | 6 |
| K | 12 | L | 8 | M | 4 | N | 4 |
| P | 6 | Q | 2 | R | 6 | S | 8 |
| T | 7 | V | 9 | W | 1 | Y | 6 |
| . | 1 | | | | | | |

Mature protein

| AA | # | AA | # | AA | # | AA | # |
|---|---|---|---|---|---|---|---|
| A | 16 | C | 6 | D | 4 | E | 4 |
| F | 7 | G | 10 | H | 0 | I | 6 |
| K | 9 | L | 4 | M | 2 | N | 4 |
| P | 5 | Q | 2 | R | 6 | S | 5 |
| T | 6 | V | 5 | W | 1 | Y | 6 |

TABLE 102f

Enzymes used to manipulate BPTI-gp8 fusion

| | |
|---|---|
| SacI | GAGCT\|C |
| AflII | C\|TTAAG |
| NheI | G\|CTAGC |
| NruI | TCG\|CGA |
| KpnI | GGTAC\|C |
| AccIII = BspMII | T\|CCGGA |
| AvaI | C\|yCGrG |
| XhoI | C\|TCGAG |
| PflMI | CCAnnnn\|nTGG |
| BssHII | G\|CGCGC |
| ApaI | GGGCC\|C |
| DraII = Eco109I | rGGnC\|Cy (Same as PssI) |
| StuI | AGG\|CCT |
| AccI | GT\|mkAC |
| XcaI | GTA\|TAC |
| EspI | GC\|TnAGC |
| XmaIII | C\|GGCCG (Supplier ?) |
| SphI | GCATG\|C |
| BbeI | GGCGC\|C (Supplier ?) |
| NarI | GG\|CG\|CC |
| SfiI | GGCCnnnn\|nGGCC |
| HindIII | A\|AGCTT |
| BstXI | CCAnnnnn\|nTGG |
| NcoI | C\|CATGG |
| AsuII = BstBI | TT\|CGAA |
| BstEII | G\|GTnACC |
| SalI | G\|TCGAC |

TABLE 103

Annotated Sequence of osp-ipbd gene
Underscored bases indicate sites of overlap between annealed synthetic duplexes.

5'-
/GGC tttaca C<u>TTTAT</u>, GCTTCCGGCTCG tataat GTGTGG-
      lacUV5 a<u>ATTGTGAGCG</u>cTcACAATT-
    lacO-symm operator gagctc      AG(G)/AGG       CttaCT-
      Sac I      Shine-Dalgarno seq.

| fM | K | K | S | L | V | L | K | A | S |
|---|---|---|---|---|---|---|---|---|---|
| 1 | 2 | 3 | 4 | 5 | 6 | 7 | 8 | 9 | 10 |
| ATG | AAG, | AAA | TCT | CTG | GTT | CTT | AAG | GCT | AGC |
| | | | | | | | Afl II | | Nhe I |

-

TABLE 103-continued

Annotated Sequence of osp-ipbd gene
Underscored bases indicate sites of overlap between annealed synthetic duplexes.

```
 V   | A   | V   | A   | T   | L   | V   | P   | M   | L
 11  | 12  | 13  | 14  | 15  | 16  | 17  | 18  | 19  | 20
 GTT | GCT | GTC | GCG | ACC | CTG | GTA | CCT | ATG | T/TG  -
           |  Nru I  |       |  Kpn I  |

C   | F   | A   | R   | P   | D   | F   | C   | L   | E
 21  | 22  | 23  | 24  | 25  | 26  | 27  | 28  | 29  | 30
 TCC | TTC | GCT | CG,T| CCG | GAT | TTC | TGT | CTC | GAG  -
                 |  AccIII  |                 |  Ava I  |
                 ↑                             |  Xho I  |
         M13/BPTI Jnct P   | P   | Y   | T   | G   | P   | C   | K   | A   | R
 31  | 32  | 33  | 34  | 35  | 36  | 37  | 38  | 39  | 40
 CCA | CCA | TAC | ACT | GGG | CCC | TGC | AAA | GCG | CGC  -
       |  PflM I  |             |              |  BssH II |
                       |  Apa I  |
                       |  Dra II |
                       |  Pss I  |

I   | I   | R   | Y   | F   | Y   | N   | A   | K   | A
 41  | 42  | 43  | 44  | 45  | 46  | 47  | 48  | 49  | 50
 ATC | ATC | CG/C| TAT | TTC | TAC | AAT | GC,T| AAA | GC   -

G   | L   | C   | Q   | T   | F   | V   | Y   | G   | G
     51  | 52  | 53  | 54  | 55  | 56  | 57  | 58  | 59  | 60
 A | GGC | CTG | TGC | CAG | ACC | TTT | GTA | TAC | GGT | GGT -
   |  Stu I  |                         |  Acc I  |
                                       |  Xca I  |

C   | R   | A   | K   | R   | N   | N   | F   | K
 61  | 62  | 63  | 64  | 65  | 66  | 67  | 68  | 69
 TGC | CGT | GCT | AAG | CGT | /AAC| AAC | TTT | AAA  -
             |  Esp I  |

S   | A   | E   | D   | C   | M   | R   | T   | C   | G
 70  | 71  | 72  | 73  | 74  | 75  | 76  | 77  | 78  | 79
 TCG,| GCC | GAA | GAT | TGC | ATG | CGT | ACC | TGC | GGT  -
 |  Xma III  |             |  Sph I  |

BPTI/M13 boundary
                 ↓
 G   | A   | A   | E   | G   | D   | D   | P   | A   | K   | A   | A
 80  | 81  | 82  | 83  | 84  | 85  | 86  | 87  | 88  | 89  | 90  | 91
 GGC | GCC | GCT | GAA | GGT | GAT | GAT | CCG | GCC | AAG | GCG | G/CC -
 | Bbe 1 |                                   |          Sfi I         |
 | Nar I |

F   | N   | S   | L   | Q   | A   | S   | A   | T
 92  | 93  | 94  | 95  | 96  | 97  | 98  | 99  | 100
 TTC | AAT | TCT | CTG | C,AA| GCT | TCT | GCT | ACC  -
                         |  Hind 3  |

E   | Y   | I   | G   | Y   | A   | W
 101 | 102 | 103 | 104 | 105 | 106 | 107
 GAG | TAT | ATT | GGT | TAC | GCG | TGG  -

A   | M   | V   | V   | V   | I   | V   | G   | A
 108 | 109 | 110 | 111 | 112 | 113 | 114 | 115 | 116
 GCC | ATG | GTG | GTG | GTT | AT/C| GTT | GGT | GCT  -
       |  BstX I  |
       | Nco I |

T   | I   | G   | I
         117 | 118 | 119 | 120
         ACC,| ATC | GGG | ATC  -

K   | L   | F   | K   | K   | F   | T   | S   | K   | A
 121 | 122 | 123 | 124 | 125 | 126 | 127 | 128 | 129 | 130
 AAA | CTG | TTC | AAG | AAG | TTT | ACT | TCG | AAG | GCG  -
                                         |  Asu II  |
```

TABLE 103-continued

Annotated Sequence of osp-ipbd gene
Underscored bases indicate sites of overlap between annealed synthetic duplexes.

```
| S   |     |     |     |
|131  |132  |133  |134  |
|TCT  |TAA  |TGA  |TAG  |   GGTTA/CC-
                             BstE II

AGTCTA AGCCC,GC CTAATGA GCGGGCT TTTTTTTT-
                                 terminator a/(TCGA),-3'
(Sal I)
```

TABLE 104

Definition and alignment of oligonucleotides

Lines ending with "–" are continued on a following line. Blocks of ten bases are delimited by "–" within a line.
When a break in one strand does not correspond to a ten-base mark in the other strand, "–" is inserted in the other strand.

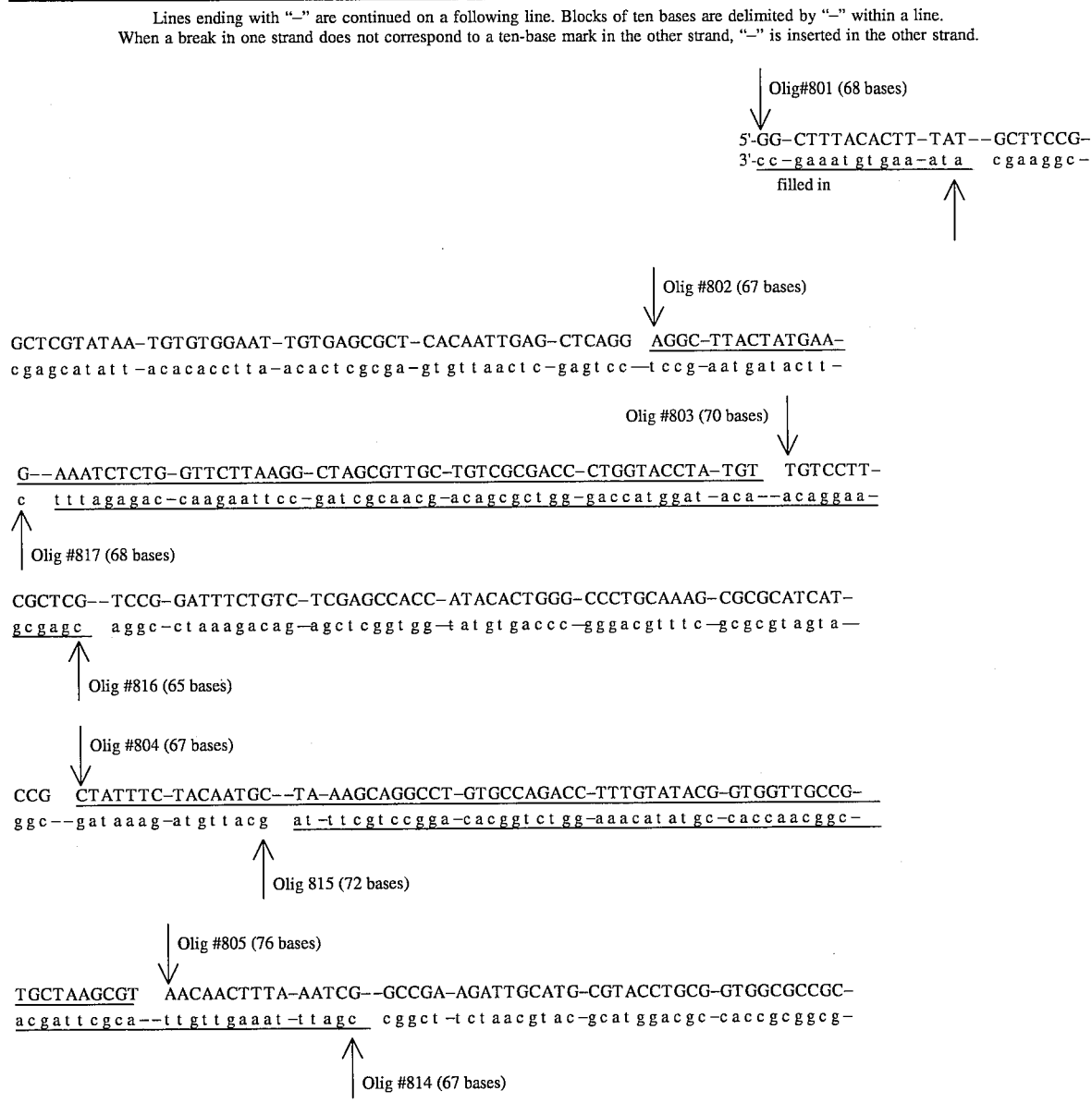

TABLE 104-continued

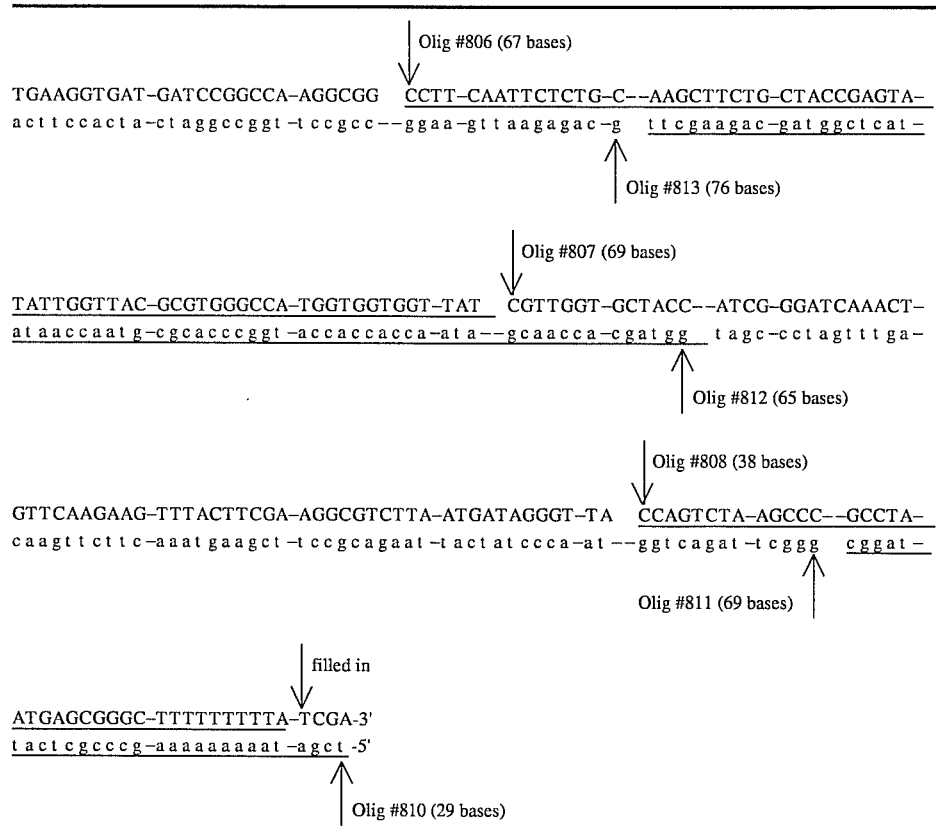

```
                        | Olig #806 (67 bases)
                        ↓
TGAAGGTGAT-GATCCGGCCA-AGGCGG   CCTT-CAATTCTCTG-C--AAGCTTCTG-CTACCGAGTA-
a c t t c c a c t a -c t a g g c c g g t -t c c g c c --g g a a -g t t a a g a g a c -g   t t c g a a g a c -g a t g g c t c a t -
                                                                          ↑
                                                                          | Olig #813 (76 bases)

| Olig #807 (69 bases)
                    ↓
TATTGGTTAC-GCGTGGGCCA-TGGTGGTGGT-TAT   CGTTGGT-GCTACC--ATCG-GGATCAAACT-
a t a a c c a a t g -c g c a c c c g g t -a c c a c c a c c a -a t a --g c a a c c a -c g a t g g   t a g c -c c t a g t t t g a-
                                                                      ↑
                                                                      | Olig #812 (65 bases)

| Olig #808 (38 bases)
                                ↓
GTTCAAGAAG-TTTACTTCGA-AGGCGTCTTA-ATGATAGGGT-TA   CCAGTCTA-AGCCC--GCCTA-
c a a g t t c t t c -a a a t g a a g c t -t c c g c a g a a t -t a c t a t c c c a -a t --g g t c a g a t -t c g g g   c g g a t -
                                                                              ↑
                                                            Olig #811 (69 bases) |

| filled in
        ↓
ATGAGCGGGC-TTTTTTTTTA-TCGA-3'
t a c t c g c c c g -a a a a a a a a a t -a g c t -5'
                ↑
                | Olig #810 (29 bases)
```

| Overlap Sequences | Junction | Tm |
|---|---|---|
| AGGCTTACTATGAAG | 802:817 | 42. |
| TGTCCTTCGCTCG | 803:816 | 42. |
| CTATTTCTACAATGC | 804:815 | 40. |
| AACAACTTTAAATCG | 805:814 | 38. |
| CCTTCAATTCTCTGC | 806:813 | 44. |
| CGTTGGTGCTACC | 807:812 | 42. |
| CCAGTCTAAGCCC | 808:811 | 42. |

All these ends, as well as the SalI end, was tested for self annealing, hair-pin loop formation, and cross hybridization. No unwanted hybridization is likely. Ideally, all fragments would be the same length, but placement of overlaps to avoid restriction sites (which are usually palindromic) and to avoid cross hybridization lead to fragments varying from 65 to 76 bases, plus two fragments of 29 to 38 bases.

TABLE 105

Individual sequences of Oligonucleotides 801–817.

Olig #801 (68 bases)
5'-ggcTTTAcAc TTTATgcTTc cggcTcgTAT AATgTgTggA ATTgTgAgcg cTcAcAATTg AgcTcAgg-3
Olig #802 (67 bases)
5'-AggcTTAcTA TgAAgAAATc TcTggTTcTT AAggcTAgcg TTgcTgTcgc gAcccTggTA ccTATgT-3'
Olig #803 (70 bases)
5'-TgTccTTcgc TcgTccggAT TTcTgTcTcg AgccAccATA cAcTgggccc TgcAAAgcgc gcATcATccg-3'
Olig #804 (67 bases)
5'-cTATTTcTAc AATgcTAAAg cAggccTgTg ccAgAccTTT gTATAcggTg gTTgccgTgc TAAgcgT-3'
Olig #805 (76 bases)
5'-AAcAAcTTTA AATcggccgA AgATTgcATg cgTAccTgcg gTggcgccgc TgAAggTgAT gATccggccA
Aggcgg-3'
Olig #806 (67 bases)
5'-ccTTcAATTc TcTgcAAgcT TcTgcTAccg AgTATATTgg TTAcgcgTgg gccATggTgg TggTTAT-3'
Olig #807 (69 bases)
5'-cgTTggTgcT AccATcgggA TcAAAcTgTT cAAgAAgTTT AcTTcgAAgg cgTcTTAATg ATAgggTTA-3'
Olig #808 (38 bases)
5'-ccAgTcTAAg cccgccTAAT gAgcgggcTT TTTTTTTA-3'
Olig #810 (29 bases)
5'-TcgATAAAAA AAAAgcccgc TcATTAggc-3'
Olig #811 (69 bases)
5'-gggcTTAgAc TggTAAcccT ATcATTAAgA cgccTTcgAA gTAAAcTTcT TgAAcAgTTT gATcccgAT-3'
Olig #812 (65 bases)

TABLE 105-continued

Individual sequences of Oligonucleotides 801–817.

5'-ggTAgcAccA AcgATAAccA ccAccATggc ccAcgcgTAA ccAATATAcT cggTAgcAgA AgcTT-3'
Olig #813 (76 bases)
5'-gcAgAgAATT gAAggccgcc TTggccggAT cATcAcaTTc AgcggcgccA ccgcAggTAc gcATgcAATc
TTcggc-3'
Olig #814 (67 bases)
5'-cgATTTAAAg TTgTTAcgcT TAgcAcggcA AccAccgTAT AcAAAggTcT ggcAcAggcc TgcTTTA-3'
Olig #815 (72 bases)
5'-gcATTgTAgA AATAgcggAT gATgcgcgcT TTgcAgggcc cAgTgTATgg TggcTcgAgA cAgAAATccg gA-3'
Olig #816 (65 bases)
5'-cgAgcgAAgg AcAAcATAgg TAccAgggTc gcgAcAgcAA cgcTAgccTT AAgAAccAgA gATTT-3'
Olig #817 (68 bases)
5'-cTTcATAgTA AgccTccTgA gcTcAATTgT gAgcgcTcAc AATTccAcAc ATTATAcgAg ccggAAgc-3'

TABLE 106

Signal Peptides

| | | |
|---|---|---|
| PhOA | M K q s t i a l l p l l f t p v t K a /R T ... | (17) |
| MalE | M K I K T G a R i l a l s a l t t m m f s a s a l a /K I ... | (18) |
| OmpF | M M K R n i l a v i v p a l l v a g t a n a /a E ... | (19) |
| Bla | M S I Q H F R v a l i p f f a a f c l p v f a /h p ... | (<18) |
| LamB | M M I T L R K l p l a v a v a a g v m s a q a m a /v D ... | (19) |
| Lpp | M K A T A K l v l g a v i l g s t l l a g /c s ... | (<17) |
| gpIII | M K K l l f a i p l v v p f y s h s /a E T V E ... | (16) |
| gpIII-BPTI | M K K l l f a i p l v v p f y s g a /R P D ... | (15) |
| gpVIII | M K K S L V L K a s v a v a t l v p m l s f a /a E G D D ... | (16) |
| gpVIII-BPTI | M K K S L V L K a s v a v a t l v p m l s f a /R P D ... | (15) |
| gpVIII' | M K K s l v l l a s v a v a t l v p m l s f a /a E G D D ... | (21) |

TABLE 107

In vitro transcription/translation analysis of vector-encoded signal::BPTI::mature VIII protein species

| | 31 kd species[a] | 14.5 kd species[b] |
|---|---|---|
| No DNA (control) | —[c] | — |
| pGEN-3Zf(−) | + | − |
| pGEM-MB16 | + | − |
| pGEM-MB20 | + | + |
| pGEM-MB26 | + | + |
| pGEM-MB42 | + | + |
| pGEM-MB46 | ND | ND |

Notes:
a.) pre-beta-lactamase, encoded by the amp (bla) gene.
b.) pre-BPTI/VIII peptides encoded by the synthetic gene and derived constructs.
c.) − for absence of product; + for presence of product; ND for Not Determined.

TABLE 108

Western analysis[a] of in vivo expressed signal::BPTI::mature VIII protein species

| | signal | 14.5 kd species[b] | 12 kd species[c] |
|---|---|---|---|
| A) expression in strain XL1-Blue | | | |
| pGEM-3Zf(−) | — | —[d] | — |
| pGEM-MB16 | VIII | − | − |
| pGEM-MB20 | VIII | ++ | − |
| pGEM-MB26 | VIII | +++ | +/− |
| pGEM-MB42 | phoA | ++ | + |
| B) expression in strain SEF' | | | |
| pGEM-MB42 | phoA | +/− | +++ |

Notes:
a) Analysis using rabbit anti-BPTI polyclonal antibodies and horse-radish-peroxidase-conjugated goat anti-rabbit IgG antibody.
b) pro-BPTI/VIII peptides encoded by the synthetic gene and derived constructs.
c) processed BPTI/VIII peptide encoded by the synthetic gene.
d) not present −
weakly present +/−
present +
strong presence ++
very strong presence +++

TABLE 109

M13 gene III

| | | | | |
|---|---|---|---|---|
| 1579 | 5'-GT | GAAAAAATTA | TTATTCGCAA | TTCCTTTAGT |
| 1611 | TGTTCCTTTC | TATTCTCACT | CCGCTGAAAC | TGTTGAAAGT |
| 1651 | TGTTTAGCAA | AACCCCATAC | AGAAAATTCA | TTTACTAACG |
| 1691 | TCTGGAAAGA | CGACAAAACT | TTAGATCGTT | ACGCTAACTA |
| 1731 | TGAGGGTTGT | CTGTGGAATG | CTACAGGCGT | TGTAGTTTGT |
| 1771 | ACTGGTGACG | AAACTCAGTG | TTACGGTACA | TGGGTTCCTA |

TABLE 109-continued

M13 gene III

| | | | | |
|---|---|---|---|---|
| 1811 | TTGGGCTTGC | TATCCCTGAA | AATGAGGGTG | GTGGCTCTGA |
| 1851 | GGGTGGCGGT | TCTGAGGGTG | GCGGTTCTGA | GGGTGGCGGT |
| 1891 | ACTAAACCTC | CTGAGTACGG | TGATACACCT | ATTCCGGGCT |
| 1931 | ATACTTATAT | CAACCCTCTC | GACGGCACTT | ATCCGCCTGG |
| 1971 | TACTGAGCAA | AACCCCGCTA | ATCCTAATCC | TTCTCTTGAG |
| 2011 | GAGTCTCAGC | CTCTTAATAC | TTTCATGTTT | CAGAATAATA |
| 2051 | GGTTCCGAAA | TAGGCAGGGG | GCATTAACTG | TTTATACGGG |
| 2091 | CACTGTTACT | CAAGGCACTG | ACCCCGTTAA | AACTTATTAC |
| 2131 | CAGTACACTC | CTGTATCATC | AAAAGCCATG | TATGACGCTT |
| 2171 | ACTGGAACGG | TAAATTCAGA | GACTGCGCTT | TCCATTCTGG |
| 2211 | CTTTAATGAG | GATCCATTCG | TTTGTGAATA | TCAAGGCCAA |
| 2251 | TCGTCTGACC | TGCCTCAACC | TCCTGTCAAT | GCTGGCGGCG |
| 2291 | GCTCTGGTGG | TGGTTCTGGT | GGCGGCTCTG | AGGGTGGTGG |
| 2331 | CTCTGAGGGT | GGCGGTTCTG | AGGGTGGCGG | CTCTGAGGGA |
| 2371 | GGCGGTTCCG | GTGGTGGCTC | TGGTTCCGGT | GATTTTGATT |
| 2411 | ATGAAAAGAT | GGCAAACGCT | AATAAGGGGG | CTATGACCGA |
| 2451 | AAATGCCGAT | GAAAACGCGC | TACAGTCTGA | CGCTAAAGGC |
| 2491 | AAACTTGATT | CTGTCGCTAC | TGATTACGGT | GCTGCTATCG |
| 2531 | ATGGTTTCAT | TGGTGACGTT | TCCGGCCTTG | CTAATGGTAA |
| 2571 | TGGTGCTACT | GGTGATTTTG | CTGGCTCTAA | TTCCCAAATG |
| 2611 | GCTCAAGTCG | GTGACGGTGA | TAATTCACCT | TTAATGAATA |
| 2651 | ATTTCCGTCA | ATATTTACCT | TCCCTCCCTC | AATCGGTTGA |
| 2691 | ATGTCGCCCT | TTTGTCTTTA | GCGCTGGTAA | ACCATATGAA |
| 2731 | TTTTCTATTG | ATTGTGACAA | AATAAACTTA | TTCCGTGGTG |
| 2771 | TCTTTGCGTT | TCTTTTATAT | GTTGCCACCT | TTATGTATGT |
| 2811 | ATTTTCTACG | TTTGCTAACA | TACTGCGTAA | TAAGGAGTCT |
| 2851 | TAATCATGCC | AGTTCTTTTG | GGTATTCCGT | |

TABLE 110

Introduction of NarI into gene III

A) Wild-type, III, portion encoding the signal peptide

```
           M   K   K   L   L   F   A   I   P   L
           1   2   3   4   5   6   7   8   9   10
1579     5'-GTG AAA AAA TTA TTA TTC GCA ATT CCT TTA
```
                                   / Cleavage site
                                   ↓

```
        V   V   P   F   Y   S   H   S   A   E   T   V
        11  12  13  14  15  16  17  18  19  20  21  22
1609    GTT GTT CCT TTC TAT TCT CAC TCC GCT GAA ACT GTT-3'
```

B) III, portion encoding the signal peptide with NarI site

```
           m   k   l   l   f   a   I   p   l
           1   2   3   4   5   6   7   8   9   10
1579     5'-gtg aaa aaa tta tta ttc gca att cct tta
```
                                   / Cleavage site
                                   ↓

```
        v   v   p   f   y   s   G   A   a   e   t   v
        11  12  13  14  15  16  17  18  19  20  21  22
1609    gtt gtt cct ttc tat tct GGc Gcc gct gaa act gtt-3'
```

TABLE 111

IIIsp::bpti::matureIII fusion gene.

```
        m   k   k   l   l   f   a   I   p   l
        1   2   3   4   5   6   7   8   9   10
      5'-gtg aaa aaa tta tta ttc gca att cct tta
       |◄─────── gene III signal peptide ───────
```
                          / cleavage site
                          ↓

```
    v   v   p   f   y   s   G   A
    11  12  13  14  15  16  17  18
    gtt gtt cct ttc tat tct GGc Gcc
   ─────────────────────►|
```

TABLE 111-continued

IIIsp::bpti::matureIII fusion gene.

```
                    | R  | P  | D  | F  | C  | L  | E  |
                    | 19 | 20 | 21 | 22 | 23 | 24 | 25 |
                    |CGT |CCG |GAT |TTC |TGT |CTC |GAG | -
                          |  AccIII |         |  Ava I  |
                                              |  Xho I  |
M13/BPTI Junct
```

```
| P  | P  | Y  | T  | G  | P  | C  | K  | A  | R  |
| 26 | 27 | 28 | 29 | 30 | 31 | 32 | 33 | 34 | 35 |
|CCA |CCA |TAC |ACT |GGG |CCC |TGC |AAA |GCG |CGC | -
        |  PflM I  |                        |  BssH II |
                |   Apa II  |
                |   Dra II  |
                |   Pss I  |
```

```
| I  | I  | R  | Y  | F  | Y  | N  | A  | K  | A  |
| 36 | 37 | 38 | 39 | 40 | 41 | 42 | 43 | 44 | 45 |
|ATC |ATC |CGC |TAT |TTC |TAC |AAT |GCT |AAA |GC  | -
```

```
  | G  | L  | C  | Q  | T  | F  | V  | Y  | G  | G  |
  | 46 | 47 | 48 | 49 | 50 | 51 | 52 | 53 | 54 | 55 |
A |GGC |CTG |TGC |CAG |ACC |TTT |GTA |TAC |GGT |GGT | -
  |  Stu I  |                        |  Acc I  |
                                     |  Xca I  |
```

```
| C  | R  | A  | K  | R  | N  | N  | F  | K  |
| 56 | 57 | 58 | 59 | 60 | 61 | 62 | 63 | 64 |
|TGC |CGT |GCT |AAG |CGT |AAC |AAC |TTT |AAA | -
           |   Esp I   |
```

```
| S  | A  | E  | D  | C  | M  | R  | T  | C  | G  |
| 65 | 66 | 67 | 68 | 69 | 70 | 71 | 72 | 73 | 74 |
|TCG |GCC |GAA |GAT |TGC |ATG |CGT |ACC |TGC |GGT | -
   |  XmaIII  |         |  Sph I  |
```

BPTI/M13 boundary
↓

```
| G  | A  |
| 75 | 76 |
|GGC |GCC | -
|  Bbe I  |
|  Nar I  |
```

```
        G   A   a   e   t   v   e   s
        77  78  79  80  81  82  83  84
        GGc Gcc gct gaa act gtt GAA AGT
```

```
1651 TGTTTAGCAA AACCCCATAC AGAAAATTCA TTTACTAACG
1691 TCTGGAAAGA CGACAAAACT TTAGATCGTT ACGCTAACTA
1731 TGAGGGTTGT CTGTGGAATG CTACAGGCGT TGTAGTTTGT
1771 ACTGGTGACG AAACTCAGTG TTACGGTACA TGGGTTCCTA
1811 TTGGGCTTGC TATCCCTGAA AATGAGGGTG GTGGCTCTGA
1851 GGGTGGCGGT TCTGAGGGTG GCGGTTCTGA GGGTGGCGGT
1891 ACTAAACCTC CTGAGTACGG TGATACACCT ATTCCGGGCT
1931 ATACTTATAT CAACCCTCTC GACGGCACTT ATCCGCCTGG
1971 TACTGAGCAA AACCCCGCTA ATCCTAATCC TTCTCTTGAG
2011 GAGTCTCAGC CTCTTAATAC TTTCATGTTT CAGAATAATA
2051 GGTTCCGAAA TAGGCAGGGG GCATTAACTG TTTATACGGG
2091 CACTGTTACT CAAGGCACTG ACCCCGTTAA AACTTATTAC
2131 CAGTACACTC CTGTATCATC AAAAGCCATG TATGACGCTT
2171 ACTGGAACGG TAAATTCAGA GACTGCGCTT TCCATTCTGG
2211 CTTTAATGAG GATCCATTCG TTTGTGAATA TCAAGGCCAA
2251 TCGTCTGACC TGCCTCAACC TCCTGTCAAT GCTGGCGGCG
2291 GCTCTGGTGG TGGTTCTGGT GGCGGCTCTG AGGGTGGTGG
2331 CTCTGAGGGT GGCGGTTCTG AGGGTGGCGG CTCTGAGGGA
2371 GGCGGTTCCG GTGGTGGCTC TGGTTCCGGT GATTTTGATT
2411 ATGAAAAGAT GGCAAACGCT AATAAGGGGG CTATGACCGA
2451 AAATGCCGAT GAAAACGCGC TACAGTCTGA CGCTAAAGGC
2491 AAACTTGATT CTGTCGCTAC TGATTACGGT GCTGCTATCG
2531 ATGGTTTCAT TGGTGACGTT TCCGGCCTTG CTAATGGTAA
2571 TGGTGCTACT GGTGATTTTG CTGGCTCTAA TTCCCAAATG
2611 GCTCAAGTCG GTGACGGTGA TAATTCACCT TTAATGAATA
2651 ATTTCCGTCA ATATTTACCT TCCCTCCCTC AATCGGTTGA
2691 ATGTCGCCCT TTTGTCTTTA GCGCTGGTAA ACCATATGAA
```

TABLE 111-continued

IIIsp::bpti::matureIII fusion gene.

```
2731  TTTTCTATTG ATTGTGACAA AATAAACTTA TTCCGTGGTG
2771  TCTTTGCGTT TCTTTTATAT GTTGCCACCT TTATGTATGT
2811  ATTTTCTACG TTTGCTAACA TACTGCGTAA TAAGGAGTCT
2851  TAATCATGCC AGTTCTTTTG GGTATTCCGT
```

TABLE 112

Annotated Sequence of Ptac::RBS(GGAGGAAATAAA)::VIII-signal::mature-bpti::mature-VIII-coat-protein gene 5'-GGATCC actccccatcccc
   |____|
   BamHI ctg TTGACA attaatcatcgGCTCG tataat GTGTGG-
    ‾‾‾‾‾‾            ‾‾‾‾‾‾
    −35        tac       −10 aATTGTGAGCGcTcACAATT-
lacO-symm operator

GAGCTC    T         ggagga         AATAAA-
‾‾‾‾‾‾         Shine-Dalgarno seq.
SacI

| fM  | K   | K   | S   | L   | V   | L   | K   | A   | S   |
|-----|-----|-----|-----|-----|-----|-----|-----|-----|-----|
| 1   | 2   | 3   | 4   | 5   | 6   | 7   | 8   | 9   | 10  |
| ATG | AAG | AAA | TCT | CTG | GTT | CTT | AAG | GCT | AGC |
|     |     |     |     |     |     |   Afl II  |   Nhe I   |

| V   | A   | V   | A   | T   | L   | V   | P   | M   | L   |
|-----|-----|-----|-----|-----|-----|-----|-----|-----|-----|
| 11  | 12  | 13  | 14  | 15  | 16  | 17  | 18  | 19  | 20  |
| GTT | GCT | GTC | GCG | ACC | CTG | GTA | CCT | ATG | TTG |
|     |     |   Nru I   |     |   Kpn I   |     |     |

| S   | F   | A   | R   | P   | D   | F   | C   | L   | E   |
|-----|-----|-----|-----|-----|-----|-----|-----|-----|-----|
| 21  | 22  | 23  | 24  | 25  | 26  | 27  | 28  | 29  | 30  |
| TCC | TTC | GCT | CGT | CCG | GAT | TTC | TGT | CTC | GAG |
|     |     |     |     |   AccIII  |     |     |   Ava I   |
|     |     |     |     |           |     |     |   Xho I   |

↑
M13/BPTI Jnct

| P   | P   | Y   | T   | G   | P   | C   | K   | A   | R   |
|-----|-----|-----|-----|-----|-----|-----|-----|-----|-----|
| 31  | 32  | 33  | 34  | 35  | 36  | 37  | 38  | 39  | 40  |
| CCA | CCA | TAC | ACT | GGG | CCC | TGC | AAA | GCG | CGC |
|     |   PflM I  |     |   Apa I   |     |     |   BssH II |
|     |           |     |   Dra II  |     |     |           |
|     |           |     |   Pss I   |     |     |           |

| I   | I   | R   | Y   | F   | Y   | N   | A   | K   | A   |
|-----|-----|-----|-----|-----|-----|-----|-----|-----|-----|
| 41  | 42  | 43  | 44  | 45  | 46  | 47  | 48  | 49  | 50  |
| ATC | ATC | CGC | TAT | TTC | TAC | AAT | GCT | AAA | GC  |

|   | G   | L   | C   | Q   | T   | F   | V   | Y   | G   | G   |
|---|-----|-----|-----|-----|-----|-----|-----|-----|-----|-----|
|   | 51  | 52  | 53  | 54  | 55  | 56  | 57  | 58  | 59  | 60  |
| A | GGC | CTG | TGC | CAG | ACC | TTT | GTA | TAC | GGT | GGT |
|   |  Stu I    |     |     |     |     |   Acc I   |     |     |
|   |           |     |     |     |     |   Xca I   |     |     |

| C   | R   | A   | K   | R   | N   | N   | F   | K   |
|-----|-----|-----|-----|-----|-----|-----|-----|-----|
| 61  | 62  | 63  | 64  | 65  | 66  | 67  | 68  | 69  |
| TGC | CGT | GCT | AAG | CGT | AAC | AAC | TTT | AAA |
|     |     |   Esp I   |     |     |     |     |

| S   | A   | E   | D   | C   | M   | R   | T   | C   | G   |
|-----|-----|-----|-----|-----|-----|-----|-----|-----|-----|
| 70  | 71  | 72  | 73  | 74  | 75  | 76  | 77  | 78  | 79  |
| TCG | GCC | GAA | GAT | TGC | ATG | CGT | ACC | TGC | GGT |
|   Xma III |     |     |   Sph I   |     |     |     |

TABLE 112-continued

Annotated Sequence of Ptac::RBS(GGAGGAAATAAA)::
VIII-signal::mature-bpti::mature-VIII-coat-protein gene BPTI/M13 boundary ↓

| G | A | A | E | G | D | D | P | A | K | A | A |
|---|---|---|---|---|---|---|---|---|---|---|---|
| 80 | 81 | 82 | 83 | 84 | 85 | 86 | 87 | 88 | 89 | 90 | 91 |
| GGC | GCC | GCT | GAA | GGT | GAT | GAT | CCG | GCC | AAG | GCG | GCC |

Bbe I / Nar I ... Sfi I

| F | N | S | L | Q | A | S | A | T |
|---|---|---|---|---|---|---|---|---|
| 92 | 93 | 94 | 95 | 96 | 97 | 98 | 99 | 100 |
| TTC | AAT | TCT | CTG | CAA | GCT | TCT | GCT | ACC |

Hind 3

| E | Y | I | G | Y | A | W |
|---|---|---|---|---|---|---|
| 101 | 102 | 103 | 104 | 105 | 106 | 107 |
| GAG | TAT | ATT | GGT | TAC | GCG | TGG |

| A | M | V | V | V | I | V | G | A |
|---|---|---|---|---|---|---|---|---|
| 108 | 109 | 110 | 111 | 112 | 113 | 114 | 115 | 116 |
| GCC | ATG | GTG | GTG | GTT | ATC | GTT | GGT | GCT |

BstX I / Nco I

| T | I | G | I |
|---|---|---|---|
| 117 | 118 | 119 | 120 |
| ACC | ATC | GGG | ATC |

| K | L | F | K | K | F | T | S | K | A |
|---|---|---|---|---|---|---|---|---|---|
| 121 | 122 | 123 | 124 | 125 | 126 | 127 | 128 | 129 | 130 |
| AAA | CTG | TTC | AAG | AAG | TTT | ACT | TCG | AAG | GCG |

Asu II

| S | . | . | . |
|---|---|---|---|
| 131 | 132 | 133 | 134 |
| TCT | TAA | TGA | TAG |

GGTTACC-
BstE II

AGTCTA AGCCCGC CTAATGA GCGGGCT TTTTTTTT-
terminator aTCGA GACctgca GGTCGACC ggcatgc-3'
Sal I

TABLE 113

Annotated Sequence of
pGEM-MB42 comprising Ptac::RBS(GGAGGAAATAAA)::
phoA-signal::mature-bpti::mature-VIII-coat-protein 5'-GGATCC actccccatcccc
BamHI ctg TTGACA attaatcatcgGCTCG tataat GTGTGG-
−35          tac         −10 aATTGTGAGCGcTcACAATT-
lacO-symm operator

| | M | K | Q | S | T |
|---|---|---|---|---|---|
| | 1 | 2 | 3 | 4 | 5 |
| GAGCTCCATGGGAGAAAATAAA | ATG | AAA | CAA | AGC | ACG |
| SacI | ←-------- phoA signal peptide | | | | |

| I | A | L | L | P | L | L | F | T | P | V | T |
|---|---|---|---|---|---|---|---|---|---|---|---|
| 6 | 7 | 8 | 9 | 10 | 11 | 12 | 13 | 14 | 15 | 16 | 17 |
| ATC | GCA | CTC | TTA | CCG | TTA | CTG | TTT | ACC | CCT | GTG | ACA |

-------------------- phoA signal continues --------------------

TABLE 113-continued

Annotated Sequence of
pGEM-MB42 comprising Ptac::RBS(GGAGGAAATAAA)::
phoA-signal::mature-bpti::mature-VIII-coat-protein (There are no residues 20–23.)

| | K 18 AAA | A 19 GCC | R 24 CGT | P 25 CCG | D 26 GAT | F 27 TTC | C 28 TGT | L 29 CTC | E 30 GAG | - | phoA signal ⟶
phoA/BPTI Jnct
AccIII
Ava I
Xho I
⟵ --------- BPTI insert ---------

| | P 31 CCA | P 32 CCA | Y 33 TAC | T 34 ACT | G 35 GGG | P 36 CCC | C 37 TGC | K 38 AAA | A 39 GCG | R 40 CGC | - |

PflM I
Apa I
Dra II
Pss I
BssH II

| | I 41 ATC | I 42 ATC | R 43 CGC | Y 44 TAT | F 45 TTC | Y 46 TAC | N 47 AAT | A 48 GCT | K 49 AAA | A 50 GC | - |

| A | G 51 GGC | L 52 CTG | C 53 TGC | Q 54 CAG | T 55 ACC | F 56 TTT | V 57 GTA | Y 58 TAC | G 59 GGT | G 60 GGT | - |

Stu I
Acc I
Xca I

| | C 61 TGC | R 62 CGT | A 63 GCT | K 64 AAG | R 65 CGT | N 66 AAC | N 67 AAC | F 68 TTT | K 69 AAA | - |

Esp I

| | S 70 TCG | A 71 GCC | E 72 GAA | D 73 GAT | C 74 TGC | M 75 ATG | R 76 CGT | T 77 ACC | C 78 TGC | G 79 GGT | - |

Xma III
Sph I
-------------------- BPTI insert ---------------------

BPTI/M13 boundary
↓

| | G 80 GGC | A 81 GCC | A 82 GCT | E 83 GAA | G 84 GGT | D 85 GAT | D 86 GAT | P 87 CCG | A 88 GCC | K 89 AAG | A 90 GCG | A 91 GCC | - |

Bbe I
Nar I
Sfi I
--- BPTI ----⟶ ⟵-------- mature gene VIII coat protein --------

| | F 92 TTC | N 93 AAT | S 94 TCT | L 95 CTG | Q 96 CAA | A 97 GCT | S 98 TCT | A 99 GCT | T 100 ACC | - |

Hind 3

| | E 101 GAG | Y 102 TAT | I 103 ATT | G 104 GGT | Y 105 TAC | A 106 GCG | W 107 TGG | - |

| | A 108 GCC | M 109 ATG | V 110 GTG | V 111 GTG | V 112 GTT | I 113 ATC | V 114 GTT | G 115 GGT | A 116 GCT | - |

BstX I
Nco I

| | T 117 ACC | I 118 ATC | G 119 GGG | I 120 ATC | - |

| | K 121 AAA | L 122 CTG | F 123 TTC | K 124 AAG | K 125 AAG | F 126 TTT | T 127 ACT | S 128 TCG | K 129 AAG | A 130 GCG | - |

Asu II

TABLE 113-continued

Annotated Sequence of
pGEM-MB42 comprising Ptac::RBS(GGAGGAAATAAA)::
phoA-signal::mature-bpti::mature-VIII-coat-protein

```
  S    .    .    .
 131  132  133  134
 TCT  TAA  TGA  TAG      GGTTACC-
                         BstE II
```

AGTCTA AGCCCGC CTAATGA GCGGGCT TTTTTTTT-
_____terminator aTCGA   GACctgca GGTCGAC-3'
               | SalI |

TABLE 114

Neutralization of Phage Titer Using
Agarose-immobilized Anhydro-Trypsin

| Phage Type | Addition | Percent Residual Titer As a Function of Time (hours) | | |
|---|---|---|---|---|
| | | 1 | 2 | 4 |
| MK-BPTI | 5 μl IS | 99 | 104 | 105 |
| | 2 μl IAT | 82 | 71 | 51 |
| | 5 μl IAT | 57 | 40 | 27 |
| | 10 μl IAT | 40 | 30 | 24 |
| MK | 5 μl IS | 106 | 96 | 98 |
| | 2 μl IAT | 97 | 103 | 95 |
| | 5 μl IAT | 110 | 111 | 96 |
| | 10 μl IAT | 99 | 93 | 106 |

Legend:
IS = Immobilized streptavidin
IAT = Immobilized anhydro-trypsin

TABLE 115

Affinity Selection of MK-BPTI Phage
on Immobilized Anhydro-Trypsin

| Phage Type | Addition | Percent of Total Phage Recovered in Elution Buffer |
|---|---|---|
| MK-BPTI | 5 μl IS | <<1[a] |
| | 2 μl IAT | 5 |
| | 5 μl IAT | 20 |
| | 10 μl IAT | 50 |
| MK | 5 μl IS | <<1[a] |
| | 2 μl IAT | <<1 |
| | 5 μl IAT | <<1 |
| | 10 μl IAT | <<1 |

Legend:
IS = Immobilized streptavidin
IAT = Immobilized anhydro-trypsin
[a] not detectable.

TABLE 116 translation of Signal-III::bpti::mature-III

| 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|
| fM | K | K | L | L | F | A | I | P | L | V | V | P | F | Y |
| GTG | AAA | AAA | TTA | TTA | TTC | GCA | ATT | CCT | TTA | GTT | GTT | CCT | TTC | TAT |

|<---------- gene III signal peptide ----------

| 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|
| S | G | A | R | P | D | F | C | L | E | P | P | Y | T | G |
| TCT | GGC | GCC | cgt | ccg | gat | ttc | tgt | ctc | gag | cca | cca | tac | act | ggg |

---------->|<-------- BPTI insertion -------------

| 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|
| P | C | K | A | R | I | I | R | Y | F | Y | N | A | K | A |
| ccc | tgc | aaa | gcg | cgc | atc | atc | cgc | tat | ttc | tac | aat | gct | aaa | gca |

| 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|
| G | L | C | Q | T | F | V | Y | G | G | C | R | A | K | R |

TABLE 116-continued translation of Signal-III::bpti::mature-III

| | | | | | | | | | | | | | | |
|---|---|---|---|---|---|---|---|---|---|---|---|---|---|---|
| ggc | ctg | tgc | cag | acc | ttt | gta | tac | ggt | ggt | tgc | cgt | gct | aag | cgt |
| 61 | 62 | 63 | 64 | 65 | 66 | 67 | 68 | 69 | 70 | 71 | 72 | 73 | 74 | 75 |
| N | N | F | K | S | A | E | D | C | M | R | T | C | G | G |
| aac | aac | ttt | aaa | tcg | gcc | gaa | gat | tgc | atg | cgt | acc | tgc | ggt | ggc |
| 76 | 77 | 78 | 79 | 80 | 81 | 82 | 83 | 84 | 85 | 86 | 87 | 88 | 89 | 90 |
| A | G | A | A | E | T | V | E | S | C | L | A | K | P | H |
| gcc | GGC | GCC | GCT | GAA | ACT | GTT | GAA | AGT | TGT | TTA | GCA | AAA | CCC | CAT |

|<------------ mature gene III protein --------------------------------------

| 91 | 92 | 93 | 94 | 95 | 96 | 97 | 98 | 99 | 100 | 101 | 102 | 103 | 104 | 105 |
|---|---|---|---|---|---|---|---|---|---|---|---|---|---|---|
| T | E | N | S | F | T | N | V | W | K | D | D | K | T | L |
| ACA | GAA | AAT | TCA | TTT | ACT | AAC | GTC | TGG | AAA | GAC | GAC | AAA | ACT | TTA |
| 106 | 107 | 108 | 109 | 110 | 111 | 112 | 113 | 114 | 115 | 116 | 117 | 118 | 119 | 120 |
| D | R | Y | A | N | Y | E | G | C | L | W | N | A | T | G |
| GAT | CGT | TAC | GCT | AAC | TAT | GAG | GGT | TGT | CTG | TGG | AAT | GCT | ACA | GGC |
| 121 | 122 | 123 | 124 | 125 | 126 | 127 | 128 | 129 | 130 | 131 | 132 | 133 | 134 | 135 |
| V | V | V | C | T | G | D | E | T | Q | C | Y | G | T | W |
| GTT | GTA | GTT | TGT | ACT | GGT | GAC | GAA | ACT | CAG | TGT | TAC | GGT | ACA | TGG |
| 136 | 137 | 138 | 139 | 140 | 141 | 142 | 143 | 144 | 145 | 146 | 147 | 148 | 149 | 150 |
| V | P | I | G | L | A | I | P | E | N | E | G | G | G | S |
| GTT | CCT | ATT | GGG | CTT | GCT | ATC | CCT | GAA | AAT | GAG | GGT | GGT | GGC | TCT |
| 151 | 152 | 153 | 154 | 155 | 156 | 157 | 158 | 159 | 160 | 161 | 162 | 163 | 164 | 165 |
| E | G | G | G | S | E | G | G | G | S | E | G | G | G | T |
| GAG | GGT | GGC | GGT | TCT | GAG | GGT | GGC | GGT | TCT | GAG | GGT | GGC | GGT | ACT |
| 166 | 167 | 168 | 169 | 170 | 171 | 172 | 173 | 174 | 175 | 176 | 177 | 178 | 179 | 180 |
| K | P | P | E | Y | G | D | T | P | I | P | G | Y | T | Y |
| AAA | CCT | CCT | GAG | TAC | GGT | GAT | ACA | CCT | ATT | CCG | GGC | TAT | ACT | TAT |
| 181 | 182 | 183 | 184 | 185 | 186 | 187 | 188 | 189 | 190 | 191 | 192 | 193 | 194 | 195 |
| I | N | P | L | D | G | T | Y | P | P | G | T | E | Q | N |
| ATC | AAC | CCT | CTC | GAC | GGC | ACT | TAT | CCG | CCT | GGT | ACT | GAG | CAA | AAC |
| 196 | 197 | 198 | 199 | 200 | 201 | 202 | 203 | 204 | 205 | 206 | 207 | 208 | 209 | 210 |
| P | A | N | P | N | P | S | L | E | E | S | Q | P | L | N |
| CCC | GCT | AAT | CCT | AAT | CCT | TCT | CTT | GAG | GAG | TCT | CAG | CCT | CTT | AAT |
| 211 | 212 | 213 | 214 | 215 | 216 | 217 | 218 | 219 | 220 | 221 | 222 | 223 | 224 | 225 |
| T | F | M | F | Q | N | N | R | F | R | N | R | Q | G | A |
| ACT | TTC | ATG | TTT | CAG | AAT | AAT | AGG | TTC | CGA | AAT | AGG | CAG | GGG | GCA |
| 226 | 227 | 228 | 229 | 230 | 231 | 232 | 233 | 234 | 235 | 236 | 237 | 238 | 239 | 240 |
| L | T | V | Y | T | G | T | V | T | Q | G | T | D | P | V |
| TTA | ACT | GTT | TAT | ACG | GGC | ACT | GTT | ACT | CAA | GGC | ACT | GAC | CCC | GTT |
| 241 | 242 | 243 | 244 | 245 | 246 | 247 | 248 | 249 | 250 | 251 | 252 | 253 | 254 | 255 |
| K | T | Y | Y | Q | Y | T | P | V | S | S | K | A | M | Y |
| AAA | ACT | TAT | TAC | CAG | TAC | ACT | CCT | GTA | TCA | TCA | AAA | GCC | ATG | TAT |
| 256 | 257 | 258 | 259 | 260 | 261 | 262 | 263 | 264 | 265 | 266 | 267 | 268 | 269 | 270 |
| D | A | Y | W | N | G | K | F | R | D | C | A | F | H | S |
| GAC | GCT | TAC | TGG | AAC | GGT | AAA | TTC | AGA | GAC | TGC | GCT | TTC | CAT | TCT |
| 271 | 272 | 273 | 274 | 275 | 276 | 277 | 278 | 279 | 280 | 281 | 282 | 283 | 284 | 285 |
| G | F | N | E | D | P | F | V | C | E | Y | Q | G | Q | S |
| GGC | TTT | AAT | GAG | GAT | CCA | TTC | GTT | TCT | GAA | TAT | CAA | GGC | CAA | TCG |
| 286 | 287 | 288 | 289 | 290 | 291 | 292 | 293 | 294 | 295 | 296 | 297 | 298 | 299 | 300 |
| S | D | L | P | Q | P | P | V | N | A | G | G | G | S | G |
| TCT | GAC | CTG | CCT | CAA | CCT | CCT | GTC | AAT | GCT | GGC | GGC | GGC | TCT | GGT |
| 301 | 302 | 303 | 304 | 305 | 306 | 307 | 308 | 309 | 310 | 311 | 312 | 313 | 314 | 315 |
| G | G | S | G | G | G | S | E | G | G | G | S | E | G | G |
| GGT | GGT | TCT | GGT | GGC | GGC | TCT | GAG | GGT | GGT | GGC | TCT | GAG | GGT | GGC |
| 316 | 317 | 318 | 319 | 320 | 321 | 322 | 323 | 324 | 325 | 326 | 327 | 328 | 329 | 330 |
| G | S | E | G | G | G | S | E | G | G | G | S | G | G | G |

TABLE 116-continued translation of Signal-III::bpti::mature-III

| | | | | | | | | | | | | | | |
|---|---|---|---|---|---|---|---|---|---|---|---|---|---|---|
| GGT | TCT | GAG | GGT | GGC | GGC | TCT | GAG | GGA | GGC | GGT | TCC | GGT | GGT | GGC |
| 331 | 332 | 333 | 334 | 335 | 336 | 337 | 338 | 339 | 340 | 341 | 342 | 343 | 344 | 345 |
| S | G | S | G | D | F | D | Y | E | K | M | A | N | A | N |
| TCT | GGT | TCC | GGT | GAT | TTT | GAT | TAT | GAA | AAG | ATG | GCA | AAC | GCT | AAT |
| 346 | 347 | 348 | 349 | 350 | 351 | 352 | 353 | 354 | 355 | 356 | 357 | 358 | 359 | 360 |
| K | G | A | M | T | E | N | A | D | E | N | A | L | Q | S |
| AAG | GGG | GCT | ATG | ACC | GAA | AAT | GCC | GAT | GAA | AAC | GCG | CTA | CAG | TCT |
| 361 | 362 | 363 | 364 | 365 | 366 | 367 | 368 | 369 | 370 | 371 | 372 | 373 | 374 | 375 |
| D | A | K | G | K | L | D | S | V | A | T | D | Y | G | A |
| GAC | GCT | AAA | GGC | AAA | CTT | GAT | TCT | GTC | GCT | ACT | GAT | TAC | GGT | GCT |
| 376 | 377 | 378 | 379 | 380 | 381 | 382 | 383 | 384 | 385 | 386 | 387 | 388 | 389 | 390 |
| A | I | D | G | F | I | G | D | V | S | G | L | A | N | G |
| GCT | ATC | GAT | GGT | TTC | ATT | GGT | GAC | GTT | TCC | GGC | CTT | GCT | AAT | GGT |
| 391 | 392 | 393 | 394 | 395 | 396 | 397 | 398 | 399 | 400 | 401 | 402 | 403 | 404 | 405 |
| N | G | A | T | G | D | F | A | G | S | N | S | Q | M | A |
| AAT | GGT | GCT | ACT | GGT | GAT | TTT | GCT | GGC | TCT | AAT | TCC | CAA | ATG | GCT |
| 406 | 407 | 408 | 409 | 410 | 411 | 412 | 413 | 414 | 415 | 416 | 417 | 418 | 419 | 420 |
| Q | V | G | D | G | D | N | S | P | L | M | N | N | F | R |
| CAA | GTC | GGT | GAC | GGT | GAT | AAT | TCA | CCT | TTA | ATG | AAT | AAT | TTC | CGT |
| 421 | 422 | 423 | 424 | 425 | 426 | 427 | 428 | 429 | 430 | 431 | 432 | 433 | 434 | 435 |
| Q | Y | L | P | S | L | P | Q | S | V | E | C | R | P | F |
| CAA | TAT | TTA | CCT | TCC | CTC | CCT | CAA | TCG | GTT | GAA | TGT | CGC | CCT | TTT |
| 436 | 437 | 438 | 439 | 440 | 441 | 442 | 443 | 444 | 445 | 446 | 447 | 448 | 449 | 450 |
| V | F | S | A | G | K | P | Y | E | F | S | I | D | C | D |
| GTC | TTT | AGC | GCT | GGT | AAA | CCA | TAT | GAA | TTT | TCT | ATT | GAT | TGT | GAC |
| 451 | 452 | 453 | 454 | 455 | 456 | 457 | 458 | 459 | 460 | 461 | 462 | 463 | 464 | 465 |
| K | I | N | L | F | R | G | V | F | A | F | L | L | Y | V |
| AAA | ATA | AAC | TTA | TTC | CGT | GGT | GTC | TTT | GCG | TTT | CTT | TTA | TAT | GTT |

|<------------ uncharged anchor region -------------

| | | | | | | | | | | | | | |
|---|---|---|---|---|---|---|---|---|---|---|---|---|---|
| 460 | 467 | 468 | 469470 | 471 | 472 | 473 | 474 | 475 | 476 | 477 | 478 | 479 | 480 |
| A | T | F | M Y | V | F | S | T | F | A | N | I | L | R |
| GCC | ACC | TTT | ATG TAT | GTA | TTT | TCT | ACG | TTT | GCT | AAC | ATA | CTG | CGT |

-------------------- uncharged anchor region continues ---------------------->|

| 481 | 482 | 483 | 484 | 485 |
|---|---|---|---|---|
| N | K | E | S | . |
| AAT | AAG | GAG | TCT | TAA |

Molecular weight of peptide = 58884
Charge on peptide = −20
[A + G + P] = 143
[C + F + H + I + L + M + V + W + Y] = 140
[D + E + K + R + N + Q + S + T + .] = 202

Second Base

| | | t | c | a | g | |
|---|---|---|---|---|---|---|
| | t | 15 | 21 | 15 | 8 | t |
| | | 12 | 5 | 10 | 6 | c |
| | | 10 | 4 | 0 | 0 | a |
| | | 0 | 3 | 0 | 4 | g |
| | c | 6 | 20 | 2 | 8 | t |
| | | 3 | 4 | 0 | 3 | c |
| | | 1 | 4 | 9 | 1 | a |
| | | 4 | 3 | 7 | 0 | g |
| | a | 5 | 19 | 21 | 1 | t |
| | | 5 | 4 | 11 | 1 | c |
| | | 2 | 4 | 16 | 1 | a |
| | | 8 | 2 | 4 | 2 | g |
| | g | 13 | 22 | 14 | 41 | t |
| | | 6 | 7 | 12 | 29 | c |

TABLE 116-continued translation of Signal-III::bpti::mature-III

| | 4 1 | | 5 3 | | 12 16 | | 1 4 | | a g |
|---|---|---|---|---|---|---|---|---|---|
| AA | # | AA | # | AA | # | AA | # | | |
| A | 37 | G | 14 | D | 26 | E | 28 | | |
| F | 27 | C | 75 | H | 2  | I | 12 | | |
| K | 20 | L | 24 | M | 9  | N | 32 | | |
| P | 31 | Q | 16 | R | 15 | S | 35 | | |
| T | 29 | V | 23 | W | 4  | Y | 25 | | |
| .  | 1  |   |    |   |    |   |    | | |

15

TABLE 130

Sampling of a Library encoded by (NNK)$^6$

A. Numbers of hexapeptides in each class total = 64,000,000 stop-free sequences.
α can be one of [WMFYCIKDENHQ]
Φ can be one of [PTAVG]
Ω can be one of [SIR]

| | | | | |
|---|---|---|---|---|
| αααααα | = | 2985984. | Φααααα | = 7464960. |
| Ωααααα | = | 4478976. | ΦΦαααα | = 7776000. |
| ΦΩαααα | = | 9331200. | ΩΩαααα | = 2799360. |
| ΦΦΦααα | = | 4320000. | ΦΦΩααα | = 7776000. |
| ΦΩΩααα | = | 4665600. | ΩΩΩααα | = 933120. |
| ΦΦΦΦαα | = | 1350000. | ΦΦΦΩαα | = 3240000. |
| ΦΦΩΩαα | = | 2916000. | ΦΩΩΩαα | = 1166400. |
| ΩΩΩΩαα | = | 174960.  | ΦΦΦΦΦα | = 225000. |
| ΦΦΦΦΩα | = | 675000.  | ΦΦΦΩΩα | = 810000. |
| ΦΦΩΩΩα | = | 486000.  | ΦΩΩΩΩα | = 145800. |
| ΩΩΩΩΩα | = | 17496.   | ΦΦΦΦΦΦ | = 15625. |
| ΦΦΦΦΦΩ | = | 56250.   | ΦΦΦΦΩΩ | = 84375. |
| ΦΦΦΩΩΩ | = | 67500.   | ΦΦΩΩΩΩ | = 30375. |
| ΦΩΩΩΩΩ | = | 7290.    | ΩΩΩΩΩΩ | = 729. |

ΦΦΩΩαα, for example, stands for the set of peptides having two amino acids from the α class, two from Φ, and two from Ω arranged in any order. There are, for example, 729 = 3$^6$ sequences composed entirely of S, L, and R.

B. Probability that any given stop-free DNA sequence will encode a hexapeptide from a stated class.

| | P | % of class |
|---|---|---|
| αααααα ... | 3.364E-03 | (1.13E-07) |
| Φααααα ... | 1.682E-02 | (2.25E-07) |
| Ωααααα ... | 1.514E-02 | (3.38E-07) |
| ΦΦαααα ... | 3.505E-02 | (4.51E-07) |
| ΦΩαααα ... | 6.305E-02 | (6.76E-07) |
| ΩΩαααα ... | 2.839E-02 | (1.01E-06) |
| ΦΦΦααα ... | 3.894E-02 | (9.01E-07) |
| ΦΦΩααα ... | 1.051E-01 | (1.35E-06) |
| ΦΩΩααα ... | 9.463E-02 | (2.03E-06) |
| ΩΩΩααα ... | 2.839E-02 | (3.04E-06) |
| ΦΦΦΦαα ... | 2.434E-02 | (1.80E-06) |
| ΦΦΦΩαα ... | 8.762E-02 | (2.70E-06) |
| ΦΦΩΩαα ... | 1.183E-01 | (4.06E-06) |
| ΦΩΩΩαα ... | 7.097E-02 | (6.08E-06) |
| ΩΩΩΩαα ... | 1.597E-02 | (9.13E-06) |
| ΦΦΦΦΦα ... | 8.113E-03 | (3.61E-06) |
| ΦΦΦΦΩα ... | 3.651E-02 | (5.41E-06) |
| ΦΦΦΩΩα ... | 6.571E-02 | (8.11E-06) |
| ΦΦΩΩΩα ... | 5.914E-02 | (1.22E-05) |
| ΦΩΩΩΩα ... | 2.661E-02 | (1.83E-05) |
| ΩΩΩΩΩα ... | 4.790E-03 | (2.74E-05) |
| ΦΦΦΦΦΦ ... | 1.127E-03 | (7.21E-06) |
| ΦΦΦΦΦΩ ... | 6.084E-03 | (1.08E-05) |
| ΦΦΦΦΩΩ ... | 1.369E-02 | (1.62E-05) |
| ΦΦΦΩΩΩ ... | 1.643E-02 | (2.43E-05) |
| ΦΦΩΩΩΩ ... | 1.109E-02 | (3.65E-05) |
| ΦΩΩΩΩΩ ... | 3.992E-03 | (5.48E-05) |
| ΩΩΩΩΩΩ ... | 5.988E-04 | (8.21E-05) |

TABLE 130-continued

Sampling of a Library encoded by (NNK)⁶

C. Number of different stop-free amino-acid sequences in
each class expected for various library sizes

| Class | Number | % | Class | Number | % |
|---|---|---|---|---|---|
| \multicolumn{6}{c}{Library size = 1.0000E+06} |
| \multicolumn{3}{c}{total = 9.7446E+05} | \multicolumn{3}{c}{% sampled = 1.52} |
| ααααααα... | 3362.6 | (.1) | Φααααα... | 16803.4 | (.2) |
| Ωααααα... | 15114.6 | (.3) | ΦΦαααα... | 34967.8 | (.4) |
| ΦΩαααα... | 62871.1 | (.7) | ΩΩαααα... | 28244.3 | (1.0) |
| ΦΦΦααα... | 38765.7 | (.9) | ΦΦΩααα... | 104432.2 | (1.3) |
| ΦΩΩααα... | 93672.7 | (2.0) | ΩΩΩααα... | 27960.3 | (3.0) |
| ΦΦΦΦαα... | 24119.9 | (1.8) | ΦΦΦΩαα... | 86442.5 | (2.7) |
| ΦΦΩΩαα... | 115915.5 | (4.0) | ΦΩΩΩαα... | 68853.5 | (5.9) |
| ΩΩΩΩαα... | 15261.1 | (8.7) | ΦΦΦΦα... | 7968.1 | (3.5) |
| ΦΦΦΦΩα... | 35537.2 | (5.3) | ΦΦΦΩΩα... | 63117.5 | (7.8) |
| ΦΦΩΩΩα... | 55684.4 | (11.5) | ΦΩΩΩΩα... | 24325.9 | (16.7) |
| ΩΩΩΩΩα... | 4190.6 | (24.0) | ΦΦΦΦΦΦ... | 1087.1 | (7.0) |
| ΦΦΦΦΦα... | 5767.0 | (10.3) | ΦΦΦΦΩΩ... | 12637.2 | (15.0) |
| ΦΦΦΩΩΩ... | 14581.7 | (21.6) | ΦΦΩΩΩΩ... | 9290.2 | (30.6) |
| ΦΩΩΩΩΩ... | 3073.9 | (42.2) | ΩΩΩΩΩΩ... | 408.4 | (56.0) |
| \multicolumn{6}{c}{Library size = 3.0000E+06} |
| \multicolumn{3}{c}{total = 2.7885E+06} | \multicolumn{3}{c}{% sampled = 4.36} |
| ααααααα... | 10076.4 | (.3) | Φααααα... | 50296.9 | (.7) |
| Ωααααα... | 45190.9 | (1.0) | ΦΦαααα... | 104432.2 | (1.3) |
| ΦΩαααα... | 187345.5 | (2.0) | ΩΩαααα... | 83880.9 | (3.0) |
| ΦΦΦααα... | 115256.6 | (2.7) | ΦΦΩααα... | 309107.9 | (4.0) |
| ΦΩΩααα... | 275413.9 | (5.9) | ΩΩΩααα... | 81392.5 | (8.7) |
| ΦΦΦΦαα... | 71074.5 | (5.3) | ΦΦΦΩαα... | 252470.2 | (7.8) |
| ΦΦΩΩαα... | 334106.2 | (11.5) | ΦΩΩΩαα... | 194606.9 | (16.7) |
| ΩΩΩΩαα... | 41905.9 | (24.0) | ΦΦΦΦα... | 23067.8 | (10.3) |
| ΦΦΦΦΩα... | 101097.3 | (15.0) | ΦΦΦΩΩα... | 174981.0 | (21.6) |
| ΦΦΩΩΩα... | 148643.7 | (30.6) | ΦΩΩΩΩα... | 61478.9 | (42.2) |
| ΩΩΩΩΩα... | 9801.0 | (56.0) | ΦΦΦΦΦΦ... | 3039.6 | (19.5) |
| ΦΦΦΦΦα... | 15587.7 | (27.7) | ΦΦΦΦΩΩ... | 32516.8 | (38.5) |
| ΦΦΦΩΩΩ... | 34975.6 | (51.8) | ΦΦΩΩΩΩ... | 20215.5 | (66.6) |
| ΦΩΩΩΩΩ... | 5879.9 | (80.7) | ΩΩΩΩΩΩ... | 667.0 | (91.5) |
| \multicolumn{6}{c}{Library size = 1.0000E+07} |
| \multicolumn{3}{c}{total = 8.1204E+06} | \multicolumn{3}{c}{% sampled = 12.69} |
| ααααααα... | 33455.9 | (1.1) | Φααααα... | 166342.4 | (2.2) |
| Ωααααα... | 148871.1 | (3.3) | ΦΦαααα... | 342685.7 | (4.4) |
| ΦΩαααα... | 609987.6 | (6.5) | ΩΩαααα... | 269958.3 | (9.6) |
| ΦΦΦααα... | 372371.8 | (8.6) | ΦΦΩααα... | 983416.4 | (12.6) |
| ΦΩΩααα... | 856471.6 | (18.4) | ΩΩΩααα... | 244761.5 | (26.2) |
| ΦΦΦΦαα... | 222702.0 | (16.5) | ΦΦΦΩαα... | 767692.5 | (23.7) |
| ΦΦΩΩαα... | 972324.6 | (33.3) | ΦΩΩΩαα... | 531651.3 | (45.6) |
| ΩΩΩΩαα... | 104722.3 | (59.9) | ΦΦΦΦα... | 68111.0 | (30.3) |
| ΦΦΦΦΩα... | 281976.3 | (41.8) | ΦΦΦΩΩα... | 450120.2 | (55.6) |
| ΦΦΩΩΩα... | 342072.1 | (70.4) | ΦΩΩΩΩα... | 122302.6 | (83.9) |
| ΩΩΩΩΩα... | 16364.0 | (93.5) | ΦΦΦΦΦΦ... | 8028.0 | (51.4) |
| ΦΦΦΦΦα... | 37179.9 | (66.1) | ΦΦΦΦΩΩ... | 67719.5 | (80.3) |
| ΦΦΦΩΩΩ... | 61580.0 | (91.2) | ΦΦΩΩΩΩ... | 29586.1 | (97.4) |
| ΦΩΩΩΩΩ... | 7259.5 | (99.6) | ΩΩΩΩΩΩ... | 728.8 | (100.0) |
| \multicolumn{6}{c}{Library size = 3.0000E+07} |
| \multicolumn{3}{c}{total = 1.8633E+07} | \multicolumn{3}{c}{% sampled = 29.11} |
| ααααααα... | 99247.4 | (3.3) | Φααααα... | 487990.0 | (6.5) |
| Ωααααα... | 431933.3 | (9.6) | ΦΦαααα... | 983416.5 | (12.6) |
| ΦΩαααα... | 1712943.0 | (18.4) | ΩΩαααα... | 734284.6 | (26.2) |
| ΦΦΦααα... | 1023590.0 | (23.7) | ΦΦΩααα... | 2592866.0 | (33.3) |
| ΦΩΩααα... | 2126605.0 | (45.6) | ΩΩΩααα... | 558519.0 | (59.9) |
| ΦΦΦΦαα... | 563952.6 | (41.8) | ΦΦΦΩαα... | 1800481.0 | (55.6) |
| ΦΦΩΩαα... | 2052433.0 | (70.4) | ΦΩΩΩαα... | 978420.5 | (83.9) |
| ΩΩΩΩαα... | 163640.3 | (93.5) | ΦΦΦΦα... | 148719.7 | (66.1) |
| ΦΦΦΦΩα... | 541755.7 | (80.3) | ΦΦΦΩΩα... | 738960.1 | (91.2) |
| ΦΦΩΩΩα... | 473377.0 | (97.4) | ΦΩΩΩΩα... | 145189.7 | (99.6) |
| ΩΩΩΩΩα... | 17491.3 | (100.0) | ΦΦΦΦΦΦ... | 13829.1 | (88.5) |
| ΦΦΦΦΦα... | 54058.1 | (96.1) | ΦΦΦΦΩΩ... | 83726.0 | (99.2) |
| ΦΦΦΩΩΩ... | 67454.5 | (99.9) | ΦΦΩΩΩΩ... | 30374.5 | (100.0) |
| ΦΩΩΩΩΩ... | 7290.0 | (100.0) | ΩΩΩΩΩΩ... | 729.0 | (100.0) |
| \multicolumn{6}{c}{Library size 7.6000E+07} |
| \multicolumn{3}{c}{total = 3.2125E+07} | \multicolumn{3}{c}{% sampled = 50.19} |
| ααααααα... | 245057.8 | (8.2) | Φααααα... | 1175010.0 | (15.7) |
| Ωααααα... | 1014733.0 | (22.7) | ΦΦαααα... | 2255280.0 | (29.0) |
| ΦΩαααα... | 3749112.0 | (40.2) | ΩΩαααα... | 1504128.0 | (53.7) |
| ΦΦΦααα... | 2142478.0 | (49.6) | ΦΦΩααα... | 4993247.0 | (64.2) |
| ΦΩΩααα... | 3666785.0 | (78.6) | ΩΩΩααα... | 840691.9 | (90.1) |
| ΦΦΦΦαα... | 1007002.0 | (74.6) | ΦΦΦΩαα... | 2825063.0 | (87.2) |

TABLE 130-continued

Sampling of a Library encoded by (NNK)[6]

| | | | | | |
|---|---|---|---|---|---|
| ΦΦΩΩαα... | 2782358.0 | (95.4) | ΦΩΩΩαα... | 1154956.0 | (99.0) |
| ΩΩΩΩαα... | 174790.0 | (99.9) | ΦΦΦΦα... | 210475.6 | (93.5) |
| ΦΦΦΦΩα... | 663929.3 | (98.4) | ΦΦΩΩΩα... | 808298.6 | (99.8) |
| ΦΦΩΩΩα... | 485953.2 | (100.0) | ΦΩΩΩΩα... | 145799.9 | (100.0) |
| ΩΩΩΩΩα... | 17496.0 | (100.0) | ΦΦΦΦΦ... | 15559.9 | (99.6) |
| ΦΦΦΦα... | 56234.9 | (100.0) | ΦΦΦΩΩ... | 84374.6 | (100.0) |
| ΦΦΦΩΩΩ... | 67500.0 | (100.0) | ΦΦΩΩΩΩ... | 30375.0 | (100.0) |
| ΦΩΩΩΩΩ... | 7290.0 | (100.0) | ΩΩΩΩΩΩ... | 729.0 | (100.0) |

Library size = 1.0000E+08 total = 3.6537E+07     % sampled = 57.09

| | | | | | |
|---|---|---|---|---|---|
| αααααα... | 318185.1 | (10.7) | Φαααα... | 1506161.0 | (20.2) |
| Ωααααα... | 1284677.0 | (28.7) | ΦΦααα... | 2821285.0 | (36.3) |
| ΦΩααα... | 4585163.0 | (49.1) | ΩΩαααα... | 1783932.0 | (63.7) |
| ΦΦΦααα... | 2566085.0 | (59.4) | ΦΦΩααα... | 5764391.0 | (74.1) |
| ΦΩΩααα... | 4051713.0 | (86.8) | ΩΩΩααα... | 888584.3 | (95.2) |
| ΦΦΦΦαα... | 1127473.0 | (83.5) | ΦΦΦΩαα... | 3023170.0 | (93.3) |
| ΦΦΩΩαα... | 2865517.0 | (98.3) | ΦΩΩΩαα... | 1163743.0 | (99.8) |
| ΩΩΩΩαα... | 174941.0 | (100.0) | ΦΦΦΦα... | 218886.6 | (97.3) |
| ΦΦΦΦΩα... | 671976.9 | (99.6) | ΦΦΦΩΩα... | 809757.3 | (100.0) |
| ΦΦΩΩΩα... | 485997.5 | (100.0) | ΦΩΩΩΩα... | 145800.0 | (100.0) |
| ΩΩΩΩΩα... | 17496.0 | (100.0) | ΦΦΦΦΦ... | 15613.5 | (99.9) |
| ΦΦΦΦα... | 56248.9 | (100.0) | ΦΦΦΩΩ... | 84375.0 | (100.0) |
| ΦΦΦΩΩΩ... | 67500.0 | (100.0) | ΦΦΩΩΩΩ... | 30375.0 | (100.0) |
| ΦΩΩΩΩΩ... | 7290.0 | (100.0) | ΩΩΩΩΩΩ... | 729.0 | (100.0) |

Library size = 3.0000E+08 total = 5.2634E+07     % sampled = 82.24

| | | | | | |
|---|---|---|---|---|---|
| αααααα... | 856451.3 | (28.7) | Φααααα... | 3668130.0 | (49.1) |
| Ωααααα... | 2854291.0 | (63.7) | ΦΦαααα... | 5764391.0 | (74.1) |
| ΦΩαααα... | 8103426.0 | (86.8) | ΩΩαααα... | 2665753.0 | (95.2) |
| ΦΦΦααα... | 4030893.0 | (93.3) | ΦΦΩααα... | 7641378.0 | (98.3) |
| ΦΩΩααα... | 4654972.0 | (99.8) | ΩΩΩααα... | 933018.6 | (100.0) |
| ΦΦΦΦαα... | 1343954.0 | (99.6) | ΦΦΦΩαα... | 3239029.0 | (100.0) |
| ΦΦΩΩαα... | 2915985.0 | (100.0) | ΦΩΩΩαα... | 1166400.0 | (100.0) |
| ΩΩΩΩαα... | 174960.0 | (100.0) | ΦΦΦΦα... | 224995.5 | (100.0) |
| ΦΦΦΦΩα... | 674999.9 | (100.0) | ΦΦΦΩΩα... | 810000.0 | (100.0) |
| ΦΦΩΩΩα... | 486000.0 | (100.0) | ΦΩΩΩΩα... | 145800.0 | (100.0) |
| ΩΩΩΩΩα... | 17496.0 | (100.0) | ΦΦΦΦΦ... | 15625.0 | (100.0) |
| ΦΦΦΦα... | 56250.0 | (100.0) | ΦΦΦΩΩ... | 84375.0 | (100.0) |
| ΦΦΦΩΩΩ... | 67500.0 | (100.0) | ΦΦΩΩΩΩ... | 30375.0 | (100.0) |
| ΦΩΩΩΩΩ... | 7290.0 | (100.0) | ΩΩΩΩΩΩ... | 729.0 | (100.0) |

Library size = 1.0000E+09 total = 6.1999E+07     % sampled = 96.87

| | | | | | |
|---|---|---|---|---|---|
| αααααα... | 2018278.0 | (67.6) | Φααααα... | 6680917.0 | (89.5) |
| Ωααααα... | 4326519.0 | (96.6) | ΦΦααααα... | 7690221.0 | (98.9) |
| ΦΩαααα... | 9320389.0 | (99.9) | ΩΩαααα... | 2799250.0 | (100.0) |
| ΦΦΦααα... | 4319475.0 | (100.0) | ΦΦΩααα... | 7775990.0 | (100.0) |
| ΦΩΩααα... | 4665600.0 | (100.0) | ΩΩΩααα... | 933120.0 | (100.0) |
| ΦΦΦΦαα... | 1350000.0 | (100.0) | ΦΦΦΩαα... | 3240000.0 | (100.0) |
| ΦΦΩΩαα... | 2916000.0 | (100.0) | ΦΩΩΩαα... | 1166400.0 | (100.0) |
| ΩΩΩΩαα... | 174960.0 | (100.0) | ΦΦΦΦα... | 225000.0 | (100.0) |
| ΦΦΦΦΩα... | 675000.0 | (100.0) | ΦΦΦΩΩα... | 810000.0 | (100.0) |
| ΦΦΩΩΩα... | 486000.0 | (100.0) | ΦΩΩΩΩα... | 145800.0 | (100.0) |
| ΩΩΩΩΩα... | 17496.0 | (100.0) | ΦΦΦΦΦ... | 15625.0 | (100.0) |
| ΦΦΦΦα... | 56250.0 | (100.0) | ΦΦΦΩΩ... | 84375.0 | (100.0) |
| ΦΦΦΩΩΩ... | 67500.0 | (100.0) | ΦΦΩΩΩΩ... | 30375.0 | (100.0) |
| ΦΩΩΩΩΩ... | 7290.0 | (100.0) | ΩΩΩΩΩΩ... | 729.0 | (100.0) |

Library size = 3.0000E+09 total = 6.3890E+07     % sampled = 99.83

| | | | | | |
|---|---|---|---|---|---|
| αααααα... | 2884346.0 | (96.6) | Φααααα... | 7456311.0 | (99.9) |
| Ωααααα... | 4478800.0 | (100.0) | ΦΦαααα... | 7775990.0 | (100.0) |
| ΦΩαααα... | 9331200.0 | (100.0) | ΩΩαααα... | 2799360.0 | (100.0) |
| ΦΦΦααα... | 4320000.0 | (100.0) | ΦΦΩααα... | 7776000.0 | (100.0) |
| ΦΩΩααα... | 4665600.0 | (100.0) | ΩΩΩααα... | 933120.0 | (100.0) |
| ΦΦΦΦαα... | 1350000.0 | (100.0) | ΦΦΦΩαα... | 3240000.0 | (100.0) |
| ΦΦΩΩαα... | 2916000.0 | (100.0) | ΦΩΩΩαα... | 1166400.0 | (100.0) |
| ΩΩΩΩαα... | 174960.0 | (100.0) | ΦΦΦΦα... | 225000.0 | (100.0) |
| ΦΦΦΦΩα... | 675000.0 | (100.0) | ΦΦΦΩΩα... | 810000.0 | (100.0) |
| ΦΦΩΩΩα... | 486000.0 | (100.0) | ΦΩΩΩΩα... | 145800.0 | (100.0) |
| ΩΩΩΩΩα... | 17496.0 | (100.0) | ΦΦΦΦΦ... | 15625.0 | (100.0) |
| ΦΦΦΦα... | 56250.0 | (100.0) | ΦΦΦΩΩ... | 84375.0 | (100.0) |
| ΦΦΦΩΩΩ... | 67500.0 | (100.0) | ΦΦΩΩΩΩ... | 30375.0 | (100.0) |
| ΦΩΩΩΩΩ... | 7290.0 | (100.0) | ΩΩΩΩΩΩ... | 729.0 | (100.0) |

D. Formulae for tabulated quantities.

Lsize is the nonber of independent transformants.
31**6 is 31 to sixth power; 6*3 means 6 times 3.
A = Lsize/(31**6)

TABLE 130-continued

Sampling of a Library encoded by (NNK)$^6$

α can be one of [WMFYCIKDENHQ.]
Φ can be one of [PTAVG]
Ω can be one of [SLR]

| | | |
|---|---|---|
| F0 = (12)6 | F1 = (12)5 | F2 = (12)**4 |
| F3 = (12)3 | F4 = (12)2 | F5 = (12) |
| F6 = 1 | | |

| | | |
|---|---|---|
| αααααα | = | F0 * (1-exp(−A)) |
| Φααααα | = | 6 * 5 * F1 * (1-exp(−2*A)) |
| Ωααααα | = | 6 * 3 * F1 * (1-exp(−3*A)) |
| ΦΦαααα | = | (15) * 5**2 * F2 * (1-exp(−4*A)) |
| ΦΩαααα | = | (6*5)*5*3 *F2 * (1-exp(−6*A)) |
| ΩΩαααα | = | (15) * 3**2 * F2 * (1-exp(−9*A)) |
| ΦΦΦααα | = | (20)*(5**3) * F3 * (1-exp(−8*A)) |
| ΦΦΩααα | = | (60)*(5*5*3)*F3* (1-exp(−12*A)) |
| ΦΩΩααα | = | (60)*(5*3*3)*F3*(1-exp(−18*A)) |
| ΩΩΩααα | = | (20)*(3)**3*F3*(1-exp(−27*A)) |
| ΦΦΦΦαα | = | (15)*(5)**4*F4*(1-exp(−16*A)) |
| ΦΦΦΩαα | = | (60)*(5)**3*3*F4*(1-exp(−24*A)) |
| ΦΦΩΩαα | = | (90)*(5*5*3*3)*F4*(1-exp(−36*A)) |
| ΦΩΩΩαα | = | (60)*(5*3*3*3)*F4*(1-exp(−54*A)) |
| ΩΩΩΩαα | = | (15)*(3)**4 * F4 *(1-exp(−81*A)) |
| ΦΦΦΦΦα | = | (6)*(5)**5 * F5 * (1-exp(−32*A)) |
| ΦΦΦΦΩα | = | 30*5*5*5*3*F5*(1-exp(−48*A)) |
| ΦΦΦΩΩα | = | 60*5*5*5*3*3*F5*(1-exp(−72*A)) |
| ΦΦΩΩΩα | = | 60*5*5*3*3*3*F5*(1-exp(−108*A)) |
| ΦΩΩΩΩα | = | 30*5*3*3*3*3*F5*(1-exp(−162*A)) |
| ΩΩΩΩΩα | = | 6*3*3*3*3*3*F5*(1-exp(−243*A)) |
| ΦΦΦΦΦΦ | = | 5**6 * (1-exp(−64*A)) |
| ΦΦΦΦΦΩ | = | 6*3*5**5*(1-exp(−96*A)) |
| ΦΦΦΦΩΩ | = | 15*3*3*5**4*(1-exp(−144*A)) |
| ΦΦΦΩΩΩ | = | 20*3**3*5**3*(1-exp(−216*A)) |
| ΦΦΩΩΩΩ | = | 15*3**4*5**2*(1-exp(−324*A)) |
| ΦΩΩΩΩΩ | = | 6*3**5*5*(1-exp(−486*A)) |
| ΩΩΩΩΩΩ | = | 3**6*(1-exp(−729*A)) |
| total | = | αααααα + Φααααα + Ωααααα + ΦΦαααα + ΦΩαααα + ΩΩαααα + ΦΦΦααα + ΦΦΩααα + ΦΩΩααα + ΩΩΩααα + ΦΦΦΦαα + ΦΦΦΩαα + ΦΦΩΩαα + ΦΩΩΩαα + ΩΩΩΩαα + ΦΦΦΦΦα + ΦΦΦΦΩα + ΦΦΦΩΩα + ΦΦΩΩΩα + ΦΩΩΩΩα + ΩΩΩΩΩα + ΦΦΦΦΦΦ + ΦΦΦΦΦΩ + ΦΦΦΦΩΩ + ΦΦΦΩΩΩ + ΦΦΩΩΩΩ + ΦΩΩΩΩΩ + ΩΩΩΩΩΩ |

TABLE 131

Sampling of a Library
Encoded by (NNT)$^4$(NNG)$^2$

X can be F, S, Y, C, L, P, H, R, I, T, N, V, A, D, G
Γ can be L$^1$, R$^2$, S, W, P, Q, M, T, K, V, A, E, G
Library comprises 8.55 · 10$^6$ amino-acid sequences; 1.47 · 10$^7$
DNA sequences.
Total number of possible aa sequences = 8,555,625

| | |
|---|---|
| X | LVPTARGFYCHIND |
| S | S |
| Θ | VPTAGWQMKES |
| Ω | LR |

The first, second, fifth, and sixth positions can hold x or S; the third and
fourth position can hold Θ or Ω. I have lumped sequences by the
number of xs, Ss, Θs, and Ωs.
For example xxΘΩSS stands for:
 [xxΘΩSS, xSΘΩxS, xSΘΩSx, SSΘΩxx, SxΘΩxS, SxΘΩSx,
 xxΩΘSS, xSΩΘxS, xSΩΘSx, SSΩΘxx, SxΩΘxS, SxΩΘSx]
The following table shows the likelihood that any
particular DNA sequence will fall into one of the defined
classes.

| | Library size = 1.0 | | Sampling = .00001% |
|---|---|---|---|
| total . . . | 1.0000E+00 | % sampled . . . | 1.1685E-07 |
| xxΘΘxx . . . | 3.1524E-01 | xxΘΩxx . . . | 2.2926E-01 |
| xxΩΩxx . . . | 4.1684E-02 | xxΘΩxS . . . | 1.8013E-01 |
| xxΘΘxS . . . | 1.3101E-01 | xxΩΩxS . . . | 2.3819E-02 |
| xxΘΘSS . . . | 3.8600E-02 | xxΘΩSS . . . | 2.8073E-02 |
| xxΩΩSS . . . | 5.1042E-03 | xSΘΘSS . . . | 3.6762E-03 |
| xSΘΩSS . . . | 2.6736E-03 | xSΩΩSS . . . | 4.8611E-04 |

TABLE 131-continued

Sampling of a Library Encoded by $(NNT)^4(NNG)^2$

| | | | | | |
|---|---|---|---|---|---|
| SSΘΘSS... | 1.3129E-04 | | SSΘΩSS... | 9.5486E-05 | |
| SSΩΩSS... | 1.7361E-05 | | | | |

The following sections show how many sequences of each class are expected for libraries of different sizes.

| Type | Number | % | Type | Number | % |
|---|---|---|---|---|---|
| \multicolumn{6}{c}{Library size = 1.0000E+05} |
| total... | 9.9137E+04 | | fraction sampled = 1.1587E-02 | | |
| xxΘΘxx... | 31416.9 | (.7) | xxΘΩxx... | 22771.4 | (1.3) |
| xxΩΩxx... | 4112.4 | (2.7) | xxΘΘxS... | 17891.8 | (1.3) |
| xxΘΨxS... | 12924.6 | (2.7) | xxΩΩxS... | 2318.5 | (5.3) |
| xxΘΘSS... | 3808.1 | (2.7) | xxΘΩSS... | 2732.5 | (5.3) |
| xxΩΩSS... | 483.7 | (10.3) | xSΘΘSS... | 357.8 | (5.3) |
| xSΘΩSS... | 253.4 | (10.3) | xSΩΩSS... | 43.7 | (19.5) |
| SSΘΘSS... | 12.4 | (10.3) | SSΘΩSS... | 8.6 | (19.5) |
| SSΩΩSS... | 1.4 | (35.2) | | | |
| \multicolumn{6}{c}{Library size = 1.0000E+06} |
| total... | 9.2064E+05 | | fraction sampled = 1.0761E-01 | | |
| xxΘΘxx... | 304783.9 | (6.6) | xxΘΩxx... | 214394.0 | (12.7) |
| xxΩΩxx... | 36508.6 | (23.8) | xxΘΘxS... | 168452.5 | (12.7) |
| xxΘΨxS... | 114741.4 | (23.8) | xxΩΩxS... | 18383.8 | (41.9) |
| xxΘΘSS... | 33807.7 | (23.8) | xxΘΩSS... | 21666.6 | (41.9) |
| xxΩΩSS... | 3114.6 | (66.2) | xSΘΘSS... | 2837.3 | (41.9) |
| xSΘΩSS... | 1631.5 | (66.2) | xSΩΩSS... | 198.4 | (88.6) |
| SSΘΘSS... | 80.1 | (66.2) | SSΘΩSS... | 39.0 | (88.6) |
| SSΩΩSS... | 3.9 | (98.7) | | | |
| \multicolumn{6}{c}{Library size = 3.0000E+06} |
| total... | 2.3880E+06 | | fraction sampled = 2.7912E-01 | | |
| xxΘΘxx... | 855709.5 | (18.4) | xxΘΩxx... | 565051.6 | (33.4) |
| xxΩΩxx... | 85564.7 | (55.7) | xxΘΘxS... | 443969.1 | (33.4) |
| xxΘΨxS... | 268917.8 | (55.7) | xxΩΩxS... | 35281.3 | (80.4) |
| xxΘΘSS... | 79234.7 | (55.7) | xxΘΩSS... | 41581.5 | (80.4) |
| xxΩΩSS... | 4522.6 | (96.1) | xSΘΘSS... | 5445.2 | (80.4) |
| xSΘΩSS... | 2369.0 | (96.1) | xSΩΩSS... | 223.7 | (99.9) |
| SSΘΘSS... | 116.3 | (96.1) | SSΘΩSS... | 43.9 | (99.9) |
| SSΩΩSS... | 4.0 | (100.0) | | | |
| \multicolumn{6}{c}{Library size = 8.5556E+06} |
| total... | 4.9303E+06 | | fraction sampled = 5.7626E-01 | | |
| xxΘΘxx... | 2046301.0 | (44.0) | xxΘΩxx... | 1160645.0 | (68.7) |
| xxΩΩxx... | 138575.9 | (90.2) | xxΘΘxS... | 911935.6 | (68.7) |
| xxΘΨxS... | 435524.3 | (90.2) | xxΩΩxS... | 43480.7 | (99.0) |
| xxΘΘSS... | 128324.1 | (90.2) | xxΘΩSS... | 51245.1 | (99.0) |
| xxΩΩSS... | 4703.6 | (100.0) | xSΘΘSS... | 6710.7 | (99.0) |
| xSΘΩSS... | 2463.8 | (100.0) | xSΩΩSS... | 224.0 | (100.0) |
| SSΘΘSS... | 121.0 | (100.0) | SSΘΩSS... | 44.0 | (100.0) |
| SSΩΩSS... | 4.0 | (100.0) | | | |
| \multicolumn{6}{c}{Library size = 1.0000E+07} |
| total... | 5.3667E+06 | | fraction sampled = 6.2727E-01 | | |
| xxΘΘxx... | 2289093.0 | (49.2) | xxΘΩxx... | 1254877.0 | (74.2) |
| xxΩΩxx... | 143467.0 | (93.4) | xxΘΘxS... | 985974.9 | (74.2) |
| xxΘΨxS... | 450896.3 | (93.4) | xxΩΩxS... | 43710.7 | (99.6) |
| xxΘΘSS... | 132853.4 | (93.4) | xxΘΩSS... | 51516.1 | (99.6) |
| xxΩΩSS... | 4703.9 | (100.0) | xSΘΘSS... | 6746.2 | (99.6) |
| xSΘΩSS... | 2464.0 | (100.0) | xSΩΩSS... | 224.0 | (100.0) |
| SSΘΘSS... | 121.0 | (100.0) | SSΘΩSS... | 44.0 | (100.0) |
| SSΩΩSS... | 4.0 | (100.0) | | | |
| \multicolumn{6}{c}{Library size = 3.0000E+07} |
| total... | 7.8961E+06 | | fraction sampled = 9.2291E-01 | | |
| xxΘΘxx... | 4040589.0 | (86.9) | xxΘΩxx... | 1661409.0 | (98.3) |
| xxΩΩxx... | 153619.1 | (100.0) | xxΘΘxS... | 1305393.0 | (98.3) |
| xxΘΨxS... | 482802.9 | (100.0) | xxΩΩxS... | 43904.0 | (100.0) |
| xxΘΘSS... | 142254.4 | (100.0) | xxΘΩSS... | 51744.0 | (100.0) |
| xxΩΩSS... | 4704.0 | (100.0) | xSΘΘSS... | 6776.0 | (100.0) |
| xSΘΩSS... | 2464.0 | (100.0) | xSΩΩSS... | 224.0 | (100.0) |
| SSΘΘSS... | 121.0 | (100.0) | SSΘΩSS... | 44.0 | (100.0) |
| SSΩΩSS... | 4.0 | (100.0) | | | |
| \multicolumn{6}{c}{Library size = 5.0000E+07} |
| total... | 8.3956E+06 | | fraction sampled = 9.8130E-01 | | |
| xxΘΘxx... | 4491779.0 | (96.6) | xxΘΩxx... | 1688387.0 | (99.9) |
| xxΩΩxx... | 153663.8 | (100.0) | xxΘΘxS... | 1326590.0 | (99.9) |
| xxΘΨxS... | 482943.4 | (100.0) | xxΩΩxS... | 43904.0 | (100.0) |
| xxΘΘSS... | 142295.8 | (100.0) | xxΘΩSS... | 51744.0 | (100.0) |
| xxΩΩSS... | 4704.0 | (100.0) | xSΘΘSS... | 6776.0 | (100.0) |
| xSΘΩSS... | 2464.0 | (100.0) | xSΩΩSS... | 224.0 | (100.0) |
| SSΘΘSS... | 121.0 | (100.0) | SSΘΩSS... | 44.0 | (100.0) |
| SSΩΩSS... | 4.0 | (100.0) | | | |

TABLE 131-continued

Sampling of a Library
Encoded by $(NNT)^4(NNG)^2$

Library size = 1.0000E+08
total ... 8.5503E+06   fraction sampled = 9.9938E-01

| | | | | |
|---|---|---|---|---|
| xxΘΘxx ... | 4643063.0 | (99.9) | xxΘΩxx ... | 1690302.0 | (100.0) |
| xxΩΩxx ... | 153664.0 | (100.0) | xxΘΘxS ... | 1328094.0 | (100.0) |
| xxΘΩxS ... | 482944.0 | (100.0) | xxΩΩxS ... | 43904.0 | (100.0) |
| xxΘΘSS ... | 142296.0 | (100.0) | xxΘΩSS ... | 51744.0 | (100.0) |
| xxΩΩSS ... | 4704.0 | (100.0) | xSΘΘSS ... | 6776.0 | (100.0) |
| xSΘΩSS ... | 2464.0 | (100.0) | xSΩΩSS ... | 224.0 | (100.0) |
| SSΘΘSS ... | 121.0 | (100.0) | SSΘΩSS ... | 44.0 | (100.0) |
| SSΩΩSS ... | 4.0 | (100.0) | | | |

TABLE 132

Relative efficiencies of various simple variegation codons

| | Number of codons | | |
|---|---|---|---|
| | 5 | 6 | 7 |
| vgCodon | #DNA/#AA [#DNA] (#AA) | #DNA/#AA [#DNA] (#AA) | #DNA/#AA [#DNA] (#AA) |
| NNK assuming stops vanish | 8.95 [2.86 · 10^7] (3.2 · 10^6) | 13.86 [8.87 · 10^8] (6.4 · 10^7) | 21.49 [2.75 · 10^10] (1.28 · 10^9) |
| NNT | 1.38 [1.05 · 10^6] (7.59 · 10^5) | 1.47 [1.68 · 10^7] (1.14 · 10^7) | 1.57 [2.68 · 10^8] (1.71 · 10^8) |
| NNG assuming stops vanish | 2.04 [7.59 · 10^5] (3.7 · 10^5) | 2.36 [1.14 · 10^6] (4.83 · 10^6) | 2.72 [1.71 · 10^8] (6.27 · 10^7) |

TABLE 140

Affect of anti BPTI IgG on phage titer.

| Phage Strain | Input | +Anti-BPTI | +Anti-BPTI +Protein A(a) | Eluted Phage |
|---|---|---|---|---|
| M13MP18 | 100 (b) | 98 | 92 | 7 · 10^-4 |
| BPTI.3 | 100 | 26 | 21 | 6 |
| M13MB48 (c) | 100 | 90 | 36 | 0.8 |
| M13MB48 (d) | 100 | 60 | 40 | 2.6 |

(a) Protein A-agarose beads.
(b) Percentage of input phage measured as plaque forming units
(c) Batch number 3
(d) Batch number 4

TABLE 141

Affect of anti-BPTI or protein A on phage titer.

| Strain | Input | No Addition | +Anti-BPTI | +Protein A (a) | +Anti-BPTI +Protein A |
|---|---|---|---|---|---|
| M13MP18 | 100 (b) | 107 | 105 | 72 | 65 |
| M13MB48 (b) | 100 | 92 | 7 · 10^-3 | 58 | <10^-4 |

(a) Protein A-agarose beads
(b) Percentage of input phage measured as plaque forming units
(c) Batch number 5

TABLE 142

Affect of anti-BPTI and non-immune serum on phage titer

| Strain | Input | +Anti-BPTI | +NRS (a) | +Anti-BPTI +Protein A (b) | +NRS +Protein A |
|---|---|---|---|---|---|
| M13MP18 | 100 (c) | 65 | 104 | 71 | 88 |
| M13MB48 (d) | 100 | 30 | 125 | 13 | 121 |
| M13MB48 (e) | 100 | 2 | 105 | 0.7 | 110 |

(a) Purified IgG from normal rabbit serum.
(b) Protein A-agarose beads.
(c) Percentage of input phage measured as plaque forming units
(d) Batch number 4
(e) Batch number 5

TABLE 143

Loss in titer of display phage with anhydrotrypsin.

| | Strain | | | |
|---|---|---|---|---|
| | Anhydrotrypsin Beads | | Streptavidin Beads | |
| | Start | Post Incubation | Start | Post Incubation |
| M13MP18 | 100 (a) | 121 | ND | ND |
| M13MB48 | 100 | 58 | 100 | 98 |
| 5AA Pool | 100 | 44 | 100 | 93 |

(a) Plaque forming units expressed as a percentage of input.

TABLE 144

Binding of Display Phage to Anhydrotrypsin.

Experiment 1.

| Strain | Eluted Phage (a) | Relative to M13MP18 |
|---|---|---|
| M13MP18 | 0.2 (a) | 1.0 |
| BPTI-IIIMK | 7.9 | 39.5 |
| M13MB48 | 11.2 | 56.0 |

Experiment 2.

| Strain | Eluted Phage (a) | Relative to M13mp18 |
|---|---|---|
| M13mp18 | 0.3 | 1.0 |
| BPTI-IIIMK | 12.0 | 40.0 |

TABLE 144-continued

Binding of Display Phage to Anhydrotrypsin.

| | | |
|---|---|---|
| M13MB56 | 17.0 | 56.7 |

(a) Plaque forming units acid eluted from beads, expressed as a percentage of the input.

TABLE 145

Binding of Display Phage to Anhydrotrypsin or Trypsin.

| | Strain | | | |
|---|---|---|---|---|
| | Anhydrotrypsin Beads | | Trypsin Beads | |
| | Eluted Phage (a) | Relative Binding (b) | Eluted Phage | Relative Binding |
| M13MP18 | 0.1 | 1 | $2.3 \times 10^{-4}$ | 1.0 |
| BPTI-IIIMK | 9.1 | 91 | 1.17 | $5 \times 10^3$ |
| M13.3X7 | 25.0 | 250 | 1.4 | $6 \times 10^3$ |
| M13.3X11 | 9.2 | 92 | 0.27 | $1.2 \times 10^3$ |

(a) Plaque forming units eluted from beads, expressed as a percentage of the input.
(b) Relative to the non-display phage, M13MP18.

TABLE 146

Binding of Display Phage to Trypsin or Human Neutrophil Elastase.

| | Strain | | | |
|---|---|---|---|---|
| | Trypsin Beads | | HNE Beads | |
| | Eluted Phage (a) | Relative Binding (b) | Eluted Phage | Relative Binding |
| M13MP18 | $5 \times 10^{-4}$ | 1 | $3 \times 10^{-4}$ | 1.0 |
| BPTI-IIIMK | 1.0 | 2000 | $5 \times 10^{-3}$ | 16.7 |
| M13MB48 | 0.13 | 260 | $9 \times 10^{-3}$ | 30.0 |
| M13.3X7 | 1.15 | 2300 | $1 \times 10^{-3}$ | 3.3 |
| M13.3X11 | 0.8 | 1600 | $2 \times 10^{-3}$ | 6.7 |
| BPTI3.CL (c) | $1 \times 10^{-3}$ | 2 | 4.1 | $1.4 \times 10^4$ |

(a) Plaque forming units acid eluted from the beads, expressed as a percentage of input.
(b) Relative to the non-display phage, M13MP18.
(c) BPTI-IIIMK (K15L MGNG)

TABLE 155

Distance in Å between alpha carbons in octapeptides:

| | 1 | 2 | 3 | 4 | 5 | 6 | 7 | 8 |
|---|---|---|---|---|---|---|---|---|
| Extended Strand: angle of $C_\alpha 1 - C_\alpha 2 - C_\alpha 3 = 138°$ | | | | | | | | |
| 1 | — | | | | | | | |
| 2 | 3.8 | — | | | | | | |
| 3 | 7.1 | 3.8 | — | | | | | |
| 4 | 10.7 | 7.1 | 3.8 | — | | | | |
| 5 | 14.2 | 10.7 | 7.1 | 3.8 | — | | | |
| 6 | 17.7 | 14.1 | 10.7 | 7.1 | 3.8 | — | | |
| 7 | 21.2 | 17.7 | 14.1 | 10.6 | 7.0 | 3.8 | — | |
| 8 | 24.6 | 20.9 | 17.5 | 13.9 | 10.6 | 7.0 | 3.8 | — |
| Reverse turn between residues 4 and 5. | | | | | | | | |
| 1 | — | | | | | | | |
| 2 | 3.8 | — | | | | | | |
| 3 | 7.1 | 3.8 | — | | | | | |
| 4 | 10.6 | 7.0 | 3.8 | — | | | | |
| 5 | 11.6 | 8.0 | 6.1 | 3.8 | — | | | |
| 6 | 9.0 | 5.8 | 5.5 | 5.6 | 3.8 | — | | |
| 7 | 6.2 | 4.1 | 6.3 | 8.0 | 7.0 | 3.8 | — | |
| 8 | 5.8 | 6.0 | 9.1 | 11.6 | 10.7 | 7.2 | 3.8 | — |
| Alpha helix: angle of $C_\alpha 1 - C_\alpha 2 - C_\alpha 3 = 93°$ | | | | | | | | |
| 1 | — | | | | | | | |
| 2 | 3.8 | — | | | | | | |
| 3 | 5.5 | 3.8 | — | | | | | |
| 4 | 5.1 | 5.4 | 3.8 | — | | | | |
| 5 | 6.6 | 5.3 | 5.5 | 3.8 | — | | | |
| 6 | 9.3 | 7.0 | 5.6 | 5.5 | 3.8 | — | | |
| 7 | 10.4 | 9.3 | 6.9 | 5.4 | 5.5 | 3.8 | — | |
| 8 | 11.3 | 10.7 | 9.5 | 6.8 | 5.6 | 5.6 | 3.8 | — |

TABLE 156

Distances between alpha carbons in closed mini-proteins of the form disulfide cyclo (CXXXXC)

| | 1 | 2 | 3 | 4 | 5 | 6 |
|---|---|---|---|---|---|---|
| Minimum distance | | | | | | |
| 1 | — | | | | | |
| 2 | 3.8 | — | | | | |
| 3 | 5.9 | 3.8 | — | | | |
| 4 | 5.6 | 6.0 | 3.8 | — | | |
| 5 | 4.7 | 5.9 | 6.0 | 3.8 | — | |
| 6 | 4.8 | 5.3 | 5.1 | 5.2 | 3.8 | — |
| Average distance | | | | | | |
| 1 | — | | | | | |
| 2 | 3.8 | — | | | | |
| 3 | 6.3 | 3.8 | — | | | |
| 4 | 7.5 | 6.4 | 3.8 | — | | |
| 5 | 7.1 | 7.5 | 6.3 | 3.8 | — | |
| 6 | 5.6 | 7.5 | 7.7 | 6.4 | 3.8 | — |
| Maximum distance | | | | | | |
| 1 | — | | | | | |
| 2 | 3.8 | — | | | | |
| 3 | 6.7 | 3.8 | — | | | |
| 4 | 9.0 | 6.9 | 3.8 | — | | |
| 5 | 8.7 | 8.8 | 6.8 | 3.8 | — | |
| 6 | 6.6 | 9.2 | 9.1 | 6.8 | 3.8 | — |

TABLE 160 pH Profile of BPTI-III MK phage and Shad 1 phage binding to Cat G beads.

| BPTI-IIIMK | Total pfu in Fraction | Percentage of Input |
|---|---|---|
| pH | | |
| 7 | $3.7 \times 10^5$ | $3.7 \times 10^{-2}$ |
| 6 | $3.1 \times 10^5$ | $3.1 \times 10^{-2}$ |
| 5 | $1.4 \times 10^5$ | $1.4 \times 10^{-2}$ |
| 4.5 | $3.1 \times 10^4$ | $3.1 \times 10^{-3}$ |
| 4 | $7.1 \times 10^3$ | $7.1 \times 10^{-4}$ |
| 3.5 | $2.6 \times 10^3$ | $2.6 \times 10^{-4}$ |
| 3 | $2.5 \times 10^3$ | $2.5 \times 10^{-4}$ |
| 2.5 | $8.8 \times 10^2$ | $8.8 \times 10^{-5}$ |
| 2 | $7.6 \times 10^2$ | $7.6 \times 10^{-5}$ |
| (total input $1 \times 10^9$ phage) | | |
| Shad 1 | | |
| 7 | $2.5 \times 10^5$ | $1.1 \times 10^{-2}$ |
| 6 | $6.3 \times 10^4$ | $2.7 \times 10^{-3}$ |
| 5 | $7.4 \times 10^4$ | $3.1 \times 10^{-3}$ |
| 4.5 | $7.1 \times 10^4$ | $3.0 \times 10^{-3}$ |

TABLE 160-continued pH Profile of BPTI-III MK phage and Shad 1 phage binding to Cat G beads.

| BPTI-IIIMK | Total pfu in Fraction | Percentage of Input |
|---|---|---|
| 4 | $4.1 \times 10^4$ | $1.7 \times 10^{-3}$ |
| 3.5 | $3.3 \times 10^4$ | $1.4 \times 10^{-3}$ |
| 3 | $2.5 \times 10^3$ | $1.1 \times 10^{-4}$ |
| 2.5 | $1.4 \times 10^4$ | $5.7 \times 10^{-4}$ |
| 2 | $5.2 \times 10^3$ | $2.2 \times 10^{-4}$ |

(total input $2.35 \times 10^8$ phage).

TABLE 201

Elution of Bound Fusion Phage from Immobilized Active Trypsin

| Type of Phage | Buffer | Total Plaque-Forming Units Recovered in Elution Buffer | Percent of Input Phage Recovered | Ratio |
|---|---|---|---|---|
| BPTI-III MK | CBS | $8.80 \cdot 10^7$ | $4.7 \cdot 10^{-1}$ | 1675 |
| MK | CBS | $1.35 \cdot 10^6$ | $2.8 \cdot 10^{-4}$ | |
| BPTI-III MK | TBS | $1.32 \cdot 10^8$ | $7.2 \cdot 10^{-1}$ | 2103 |
| MK | TBS | $1.48 \cdot 10^6$ | $3.4 \cdot 10^{-4}$ | |

The total input for BPTI-III MK phage was $1.85 \cdot 10^{10}$ plaque-forming units while the input for MK phage was $4.65 \cdot 10^{11}$ plaque-forming units.

TABLE 202

Elution of BPTI-III MK and BPTI(K15L)-III MA Phage from Immobilized Trypsin and HNE

| Type of Phage | Immobilized Protease | Total Plaque-Forming Units in Elution Fraction | Percentage of Input Phage Recovered |
|---|---|---|---|
| BPTI-III MK | Trypsin | $2.1 \cdot 10^7$ | $4.1 \cdot 10^{-1}$ |
| BPTI-III MK | HNE | $2.6 \cdot 10^5$ | $5 \cdot 10^{-3}$ |
| BPTI(K15L)-III MA | Trypsin | $5.2 \cdot 10^4$ | $5 \cdot 10^{-3}$ |
| BPTI(K15L)-III MA | HNE | $1.0 \cdot 10^6$ | $1.0 \cdot 10^{-1}$ |

The total input of BPTI-III MK phage was $5.1 \cdot 10^9$ pfu and the input of BPTI(K15L)-III MA phage was $9.6 \cdot 10^8$ pfu.

TABLE 203

Effect of pH on the Disociation of Bound BPTI-III MK and BPTI(K15L)-III MA Phage from Immobilized HNE

| | BPTI-III MK | | BPTI(K15L)-III MA | |
|---|---|---|---|---|
| pH | Total Plaque-Forming Units in Fraction | % of Input Phage | Total Plaque-Forming Units in Fraction | % of Input Phage |
| 7.0 | $5.0 \cdot 10^4$ | $2 \cdot 10^{-3}$ | $1.7 \cdot 10^5$ | $3.2 \cdot 10^{-2}$ |
| 6.0 | $3.8 \cdot 10^4$ | $2 \cdot 10^{-3}$ | $4.5 \cdot 10^5$ | $8.6 \cdot 10^{-2}$ |
| 5.0 | $3.5 \cdot 10^4$ | $1 \cdot 10^{-3}$ | $2.1 \cdot 10^6$ | $4.0 \cdot 10^{-1}$ |
| 4.0 | $3.0 \cdot 10^4$ | $1 \cdot 10^{-3}$ | $4.3 \cdot 10^6$ | $8.2 \cdot 10^{-1}$ |
| 3.0 | $1.4 \cdot 10^4$ | $1 \cdot 10^{-3}$ | $1.1 \cdot 10^6$ | $2.1 \cdot 10^{-1}$ |
| 2.2 | $2.9 \cdot 10^4$ | $1 \cdot 10^{-3}$ | $5.9 \cdot 10^4$ | $1.1 \cdot 10^{-2}$ |
| | Percentage of Input Phage = $8.0 \cdot 10^{-3}$ | | Percentage of Input Phage = 1.56 | |

TABLE 203-continued

Effect of pH on the Disociation of Bound BPTI-III MK and BPTI(K15L)-III MA Phage from Immobilized HNE

| | BPTI-III MK | | BPTI(K15L)-III MA | |
|---|---|---|---|---|
| pH | Total Plaque-Forming Units in Fraction | % of Input Phage | Total Plaque-Forming Units in Fraction | % of Input Phage |
| | Recovered | | Recovered | |

The total input of BPTI-III MK phage was $0.030 \text{ ml} \times (8.6 \cdot 10^{10} \text{ pfu/ml}) = 2.6 \cdot 10^9$.
The total input of BPTI(K15L)-III MA phage was $0.030 \text{ ml} \times (1.7 \cdot 10^{10} \text{ pfu/ml}) = 5.2 \cdot 10^8$.
Given that the infectivity of BPTI(K15L)-III MA phage is 5 fold lower than that of BPTI-III MK phage, the phage inputs utilized above ensure that an equivalent number of phage particles are added to the immobilized HNE.

TABLE 204

Effect of Mutation of Residues 39 to 42 of BPTI on the ability of BPTI(K15L)-III MA to Bind to Immobilized HNE

| | BPTI(K15L)-III MA | | BPTI (K15L,MGNG)-III MA | |
|---|---|---|---|---|
| pH | Total Plaque-Forming Units | % Input | Total Plaque-Forming Units | % Input |
| 7.0 | $3.0 \cdot 10^5$ | $8.2 \cdot 10^{-2}$ | $4.5 \cdot 10^5$ | $1.63 \cdot 10^{-1}$ |
| 6.0 | $3.6 \cdot 10^5$ | $1.00 \cdot 10^{-1}$ | $6.3 \cdot 10^5$ | $2.27 \cdot 10^{-1}$ |
| 5.5 | $5.3 \cdot 10^5$ | $1.46 \cdot 10^{-1}$ | $7.3 \cdot 10^5$ | $2.64 \cdot 10^{-1}$ |
| 5.0 | $5.6 \cdot 10^5$ | $1.52 \cdot 10^{-1}$ | $8.7 \cdot 10^5$ | $3.16 \cdot 10^{-1}$ |
| 4.75 | $9.9 \cdot 10^5$ | $2.76 \cdot 10^{-1}$ | $1.3 \cdot 10^6$ | $4.60 \cdot 10^{-1}$ |
| 4.5 | $3.1 \cdot 10^5$ | $8.5 \cdot 10^{-2}$ | $3.6 \cdot 10^5$ | $1.30 \cdot 10^{-1}$ |
| 4.25 | $5.2 \cdot 10^5$ | $1.42 \cdot 10^{-1}$ | $5.0 \cdot 10^5$ | $1.80 \cdot 10^{-1}$ |
| 4.0 | $5.1 \cdot 10^4$ | $1.4 \cdot 10^{-2}$ | $1.3 \cdot 10^5$ | $4.8 \cdot 10^{-2}$ |
| 3.5 | $1.3 \cdot 10^4$ | $4 \cdot 10^{-3}$ | $3.8 \cdot 10^4$ | $1.4 \cdot 10^{-2}$ |
| | Total Percentage = 1.00 Recovered | | Total Percentage = 1.80 Recovered | |

The total input of BPTI(K15L)-III MA phage was $0.030 \text{ ml} \times (1.2 \cdot 10^{10} \text{ pfu/ml}) = 3.6 \cdot 10^8$ pfu.
The total input of BPTI(K15L,MGNG)-III MA phage was $0.030 \text{ ml} \times (9.2 \cdot 10^9 \text{ pfu/ml}) = 2.8 \cdot 10^8$ pfu.

TABLE 205

Fractionation of a Mixture of BPTI-III MK and BPTI(K15L,MGNG)-III MA Phage on Immobilized HNE

| | BPTI-III MK | | BPTI(K15L,MGNG)-III MA | |
|---|---|---|---|---|
| pH | Total Kanamycin Transducing Units | % of Input | Total Ampicillin Transducing Units | % of Input |
| 7.0 | $4.01 \cdot 10^3$ | $4.5 \cdot 10^{-3}$ | $1.39 \cdot 10^5$ | $3.13 \cdot 10^{-1}$ |
| 6.0 | $7.06 \cdot 10^2$ | $8 \cdot 10^{-4}$ | $7.18 \cdot 10^4$ | $1.62 \cdot 10^{-1}$ |
| 5.0 | $1.81 \cdot 10^3$ | $2.0 \cdot 10^{-3}$ | $1.35 \cdot 10^5$ | $3.04 \cdot 10^{-1}$ |
| 4.0 | $1.49 \cdot 10^3$ | $1.7 \cdot 10^{-3}$ | $7.43 \cdot 10^5$ | 1.673 |

The total input of BPTI-III MK phage was $0.015 \text{ ml} \times (5.94 \cdot 10^9 \text{ kanamycin transducing units/ml}) = 8.91 \cdot 10^7$ kanamycin transducing units.
The total input of BPTI(K15L,MGNG)-III MA phage was $0.015 \text{ ml} \times (2.96 \cdot 10^9 \text{ ampicillin transducing units/ml}) = 4.44 \cdot 10^7$ ampicillin transducing units.

TABLE 206

Characterization of the Affinity of
BPTI(K15V,R17L)-III MA Phage for Immobilized HNE

| pH | BPTI(K15V,R17L)-III MA | | BPTI (K15L,MGNG)-III MA | |
|---|---|---|---|---|
| | Total Plaque-Forming Units Recovered | Percentage of Input Phage | Total Plaque-Forming Units Recovered | Percentage of Input Phage |
| 7.0 | $3.19 \cdot 10^6$ | $8.1 \cdot 10^{-2}$ | $9.42 \cdot 10^4$ | $4.6 \cdot 10^{-2}$ |
| 6.0 | $5.42 \cdot 10^6$ | $1.38 \cdot 10^{-1}$ | $1.61 \cdot 10^5$ | $7.9 \cdot 10^{-2}$ |
| 5.0 | $9.45 \cdot 10^6$ | $2.41 \cdot 10^{-1}$ | $2.85 \cdot 10^5$ | $1.39 \cdot 10^{-1}$ |
| 4.5 | $1.39 \cdot 10^7$ | $3.55 \cdot 10^{-1}$ | $4.32 \cdot 10^5$ | $2.11 \cdot 10^{-1}$ |
| 4.0 | $2.02 \cdot 10^7$ | $5.15 \cdot 10^{-1}$ | $1.42 \cdot 10^5$ | $6.9 \cdot 10^{-2}$ |
| 3.75 | $9.20 \cdot 10^6$ | $2.35 \cdot 10^{-1}$ | — | — |
| 3.5 | $4.16 \cdot 10^6$ | $1.06 \cdot 10^{-1}$ | $5.29 \cdot 10^4$ | $2.6 \cdot 10^{-2}$ |
| 3.0 | $2.65 \cdot 10^6$ | $6.8 \cdot 10^{-2}$ | — | — |
| | Total Input = 1.73 Recovered | | Total Input = 0.57 Recovered | |

Total input of BPTI(K15V,R17L)-III MA phage was 0.040 ml × (9.80 · $10^{10}$ pfu/ml) = 3.92 · $10^9$ pfu.
Total input of BPTI(K15L,MGNG)-III MA phage was 0.040 ml × (5.13 · $10^9$ pfu/ml) = 2.05 · $10^8$ pfu.

TABLE 207

Sequence of the EpiNEα Clone Selected From the Mini-Library

```
 1  1  1  1  1  1  1  2  2
 3  4  5  6  7  8  9  0  1
 P  C  V  A  M  F  Q  R  Y
CCT.TGC.GTG.GCT.ATG.TTC.CAA.CGC.TAT
```

TABLE 208

SEQUENCES OF THE EpiNE CLONES IN THE P1 REGION

| CLONE IDENTIFIERS | SEQUENCE | |
|---|---|---|
| 3, 9, 16, 17, 18, 19 | `1  1  1  1  1  1  1  2  2`<br>`3  4  5  6  7  8  9  0  1`<br>`P  C  V  G  F  F  S  R  Y`<br>`CCT.TGC.GTC.GGT.TTC.TTC.TCA.CGC.TAT` | EpiNE3 |
| 6 | `1  1  1  1  1  1  1  2  2`<br>`3  4  5  6  7  8  9  0  1`<br>`P  C  V  G  F  F  Q  R  Y`<br>`CCT.TGC.GTC.GGT.TTC.TTC.CAA.CGC.TAT` | EpiNE6 |
| 7, 13, 14 15, 20 | `1  1  1  1  1  1  1  2  2`<br>`3  4  5  6  7  8  9  0  1`<br>`P  C  V  A  M  F  P  R  Y`<br>`CCT.TGC.GTC.GCT.ATG.TTC.CCA.CGC.TAT` | EpiNE7 |
| 4 | `1  1  1  1  1  1  1  2  2`<br>`3  4  5  6  7  8  9  0  1`<br>`P  C  V  A  I  F  P  R  Y`<br>`CCT.TGC.GTC.GCT.ATC.TTC.CCA.CGC.TAT` | EpiNE4 |
| 8 | `1  1  1  1  1  1  1  2  2`<br>`3  4  5  6  7  8  9  0  1`<br>`P  C  V  A  I  F  K  R  S`<br>`CCT.TGC.GTC.GCT.ATC.TTC.AAA.CGC.TCT` | EpiNE8 |
| 1, 10 11, 12 | `1  1  1  1  1  1  1  2  2`<br>`3  4  5  6  7  8  9  0  1`<br>`P  C  I  A  F  F  P  R  Y`<br>`CCT.TGC.ATC.GCT.TTC.TTC.CCA.CGC.TAT` | EpiNE1 |
| 5 | `1  1  1  1  1  1  1  2  2`<br>`3  4  5  6  7  8  9  0  1`<br>`P  C  I  A  F  F  Q  R  Y`<br>`CCT.TGC.ATC.GCT.TTC.TTC.CAA.CGC.TAT` | EpiNE5 |
| 2 | `1  1  1  1  1  1  1  2  2`<br>`3  4  5  6  7  8  9  0  1`<br>`P  C  I  A  L  F  K  R  Y`<br>`CCT.TGC.ATC.GCT.TTG.TTC.AAA.CGC.TAT` | EpiNE2 |

TABLE 209

DNA sequences and predicted amino acid sequences around the P1 region of BPTI analogues selected for binding to Cathepsin G.

| Clone | P1 15 | 16 | 17 | 18 | 19 |
|---|---|---|---|---|---|
| BPTI | AAA . LYS | GCG . ALA | CGC . ARG | ATC . ILE | ATC ILE |
| EpiC 1 (a) | ATG . MET | GGT . GLY | TTC . PHE | TCC . SER | AAA LYS |
| EpiC 7 | ATG . MET | GCT . ALA | TTG . LEU | TTC . PHE | AAA LYS |
| EpiC 8 (b) | TTC . PHE | GCT . ALA | ATC . ILE | ACC . THR | CCA PRO |
| EpiC 10 | ATG . MET | GCT . ALA | TTG . LEU | TTC . PHE | CAA GLN |
| EpiC 20 | ATG . MET | GCT . ALA | ATC . ILE | TCC . SER | CCA PRO |

(a) Clones 11 and 31 also had the identical sequence.
(b) Clone 8 also contained the mutation Tyr 10 to ASN.

TABLE 210

Derivatives of EpiNE7 Obtained by Variegation at positions 34, 36, 39, 40 and 41

```
EpiNE7
               ♦♦ ♦ ♦♦                     ****
RPDFCLEPPYTGPCvAmfpRYFYNAKAGLCQTFVYGGCmgng NNFKSAEDCMRTCGGA
         1          2         3         4         5
1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8
```

EpiNE7.6       ↓↓↓↓                    ♦  ♦  ♦♦♦↓
RPDFCLEPPYTGPCvAmfpRYFYNAKAGLCQTFl Yg GCk gkGNNFKSAEDCMRTCGGA EpiNE7.8, EpiNE7.9, and EpiNE7.31
RPDFCLEPPYTGPCvAmfpRYFYNAKAGLCQTFe Yg GCwakGNNFKSAEDCMRTCGGA EpiNE7.11
RPDFCLEPPYTGPCvAmfpRYFYNAKAGLCQTFg Ya GCr akGNNFKSAEDCMRTCGGA EpiNE7.7
RPDFCLEPPYTGPCvAmfpRYFYNAKAGLCQTFe Yg GCh aeGNNFKSAEDCMRTCGGA EpiNE7.4 and EpiNE7.14
RPDFCLEPPYTGPCvAmfpRYFYNAKAGLCQTFl Yg GCwaqGNNFKSAEDCMRTCGGA EpiNE7.5
RPDFCLEPPYTGPCvAmfpRYFYNAKAGLCQTFr Yg GCl aeGNNFKSAEDCMRTCGGA EpiNE7.10 and EpiNE7.20
RPDFCLEPPYTGPCvAmfpRYFYNAKAGLCQTFd Yg GCh adGNNFKSAEDCMRTCGGA EpiNE7.1
RPDFCLEPPYTGPCvAmfpRYFYNAKAGLCQTFk Yg GCl ahGNNFKSAEDCMRTCGGA EpiNE7.16
RPDFCLEPPYTGPCvAmfpRYFYNAKAGLCQTFt Yg GCwanGNNFKSAEDCMRTCGGA EpiNE7.19
RPDFCLEPPYTGPCvAmfpRYFYNAKAGLCQTFn Yg GCe gkGNNFKSAEDCMRTCGGA EpiNE7.12
RPDFCLEPPYTGPCvAmfpRYFYNAKAGLCQTFq Yg GCe gyGNNFKSAEDCMRTCGGA EpiNE7.17
RPDFCLEPPYTGPCvAmfpRYFYNAKAGLCQTFq Yg GCl geGNNFKSAEDCMRTCGGA EpiNE7.21
RPDFCLEPPYTGPCvAmfpRYFYNAKAGLCQTFh Yg GCwgqGNNFKSAEDCMRTCGGA

TABLE 210-continued

Derivatives of EpiNE7 Obtained
by Variegation at positions 34, 36, 39, 40 and 41

EpiNE7
```
                ♦♦ ♦ ♦♦                           * * * *
RPDFCLEPPYTGPCvAmfpRYFYNAKAGLCQTFVYGGCmgng NNFKSAEDCMRTCGGA
          1         2         3         4         5
1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8
```

EpiNE7.22  ↓↓↓↓                              ♦ ♦  ♦♦♦↓
RPDFCLEPPYTGPCvAmfpRYFYNAKAGLCQTFh Yg GCwgeGNNFKSAEDCMRTCGGA EpiNE7.23
RPDFCLEPPYTGPCvAmfpRYFYNAKAGLCQTFk Yg GCwgkGNNFKSAEDCMRTCGGA EpiNE7.24
RPDFCLEPPYTGPCvAmfpRYFYNAKAGLCQTFk Yg GCh gnNNFKSAEDCMRTCGGA EpiNE7.25
RPDFCLEPPYTGPCvAmfpRYFYNAKAGLCQTFp Yg GCwakGNNFKSAEDCMRTCGGA EpiNE7.26
RPDFCLEPPYTGPCvAmfpRYFYNAKAGLCQTFk Yg GCwghGNNFKSAEDCMRTCGGA EpiNE7.27
RPDFCLEPPYTGPCvAmfpRYFYNAKAGLCQTFn Yg GCwgkGNNFKSAEDCMRTCGGA EpiNE7.28
RPDFCLEPPYTGPCvAmfpRYFYNAKAGLCQTFt Yg GCl ghGNNFKSAEDCMRTCGGA EpiNE7.29
RPDFCLEPPYTGPCvAmfpRYFYNAKAGLCQTFt Yg GCl gyGNNFKSAEDCMRTCGGA EpNE7.30, EpiNE7.34, and EpiNE7.35
RPDFCLEPPYTGPCvAmfpRYFYNAKAGLCQTFk Yg GCwaeGNNFKSAEDCMRTCGGA EpiNE7.32
RPDFCLEPPYTGPCvAmfpRYFYNAKAGLCQTFg Yg GCwgeGNNFKSAEDCMRTCGGA EpiNE7.33
RPDFCLEPPYTGPCvAmfpRYFYNAKAGLCQTFe Yg GCwanGNNFKSAEDCMRTCGGA EpiNE7.36
RPDFCLEPPYTGPCvAmfpRYFYNAKAGLCQTFv Yg GCh gdNNFKSAEDCMRTCGGA EpiNE7.37
RPDFCLEPPYTGPCvAmfpRYFYNAKAGLCQTFmYg GCq gkNNFKSAEDCMRTCGGA EpiNE7.38
RPDFCLEPPYTGPCvAmfpRYFYNAKAGLCQTFy Yg GCwakGNNFKSAEDCMRTCGGA EpiNE7.39  ↓↓↓↓                              ♦ ♦  ♦♦♦↓
RPDFCLEPPYTGPCvAmfpRYFYNAKAGLCQTFmYg GCwgdGNNFKSAEDCMRTCGGA EpiNE7.40
RPDFCLEPPYTGPCvAmfpRYFYNAKAGLCQTFt Yg GCh gnNNFKSAEDCMRTCGGA Notes:
a) δ indicates variegation residue. * indicates imposed change. ↓ indicates carry over from EpiNE7.
b) The sequence $M_{39}GNG$ in EpiNE7 (indicated by *) was imposed to increase similarity to ITI-D1.
b) Lower case letters in EpiNE7.6 to 7.38 indicate changes from BPTI that were selected in the first round (residues 15 –19) or positions where the PBD was variegated in the second round (residues 34, 36, 39, 40, and 41).
c) All EpiNE7 derivatives have $G_{42}$.

TABLE 211

Effects of antisera on phage infectifity

| Phage (dilution of stock) | Incubation Conditions | pfu/ml | Relative Titer |
|---|---|---|---|
| MA-ITI ($10^{-1}$) | PBS | $1.2 \cdot 10^{11}$ | 1.00 |
|  | NRS | $6.8 \cdot 10^{10}$ | 0.57 |
|  | anti-ITI | $1.1 \cdot 10^{10}$ | 0.09 |
| MA-ITI | PBS | $7.7 \cdot 10^{8}$ | 1.00 |
| ($10^{-3}$) | NRS | $6.7 \cdot 10^{8}$ | 0.87 |
|  | anti-ITI | $8.0 \cdot 10^{6}$ | 0.01 |
| MA ($10^{-1}$) | PBS | $1.3 \cdot 10^{12}$ | 1.00 |
|  | NRS | $1.4 \cdot 10^{12}$ | 1.10 |

TABLE 211-continued

Effects of antisera on phage infectifity

| Phage (dilution of stock) | Incubation Conditions | pfu/ml | Relative Titer |
|---|---|---|---|
| | anti-ITI | $1.6 \cdot 10^{12}$ | 1.20 |
| MA | PBS | $1.3 \cdot 10^{10}$ | 1.00 |
| ($10^{-3}$) | NRS | $1.2 \cdot 10^{10}$ | 0.92 |
| | anti-ITI | $1.5 \cdot 10^{10}$ | 1.20 |

TABLE 212

Fractionation of EpiNE-7 and MA-ITI phage on HNE beads

| | EpiNE-7 | | MA-ITI | |
|---|---|---|---|---|
| Sample | Total pfu in sample | Fraltion of input | Total pfu in sample | Fraltion of input |
| INPUT | $3.3 \cdot 10^9$ | 1.00 | $3.4 \cdot 10^{11}$ | 1.00 |
| Final TBS-TWEEN Wash | $3.8 \cdot 10^5$ | $1.2 \cdot 10^{-4}$ | $1.8 \cdot 10^6$ | $5.3 \cdot 10^{-6}$ |
| pH 7.0 | $6.2 \cdot 10^5$ | $1.8 \cdot 10^{-4}$ | $1.6 \cdot 10^6$ | $4.7 \cdot 10^{-6}$ |
| pH 6.0 | $1.4 \cdot 10^6$ | $4.1 \cdot 10^{-4}$ | $1.0 \cdot 10^6$ | $2.9 \cdot 10^{-6}$ |
| pH 5.5 | $9.4 \cdot 10^5$ | $2.8 \cdot 10^{-4}$ | $1.6 \cdot 10^6$ | $4.7 \cdot 10^{-6}$ |
| pH 5.0 | $9.5 \cdot 10^5$ | $2.9 \cdot 10^{-4}$ | $3.1 \cdot 10^5$ | $9.1 \cdot 10^{-7}$ |
| pH 4.5 | $1.2 \cdot 10^6$ | $3.5 \cdot 10^{-4}$ | $1.2 \cdot 10^5$ | $3.5 \cdot 10^{-7}$ |
| pH 4.0 | $1.6 \cdot 10^6$ | $4.8 \cdot 10^{-4}$ | $7.2 \cdot 10^4$ | $2.1 \cdot 10^{-7}$ |
| pH 3.5 | $9.5 \cdot 10^5$ | $2.9 \cdot 10^{-4}$ | $4.9 \cdot 10^4$ | $1.4 \cdot 10^{-7}$ |
| pH 3.0 | $6.6 \cdot 10^5$ | $2.0 \cdot 10^{-4}$ | $2.9 \cdot 10^4$ | $8.5 \cdot 10^{-8}$ |
| pH 2.5 | $1.6 \cdot 10^5$ | $4.8 \cdot 10^{-5}$ | $1.4 \cdot 10^4$ | $4.1 \cdot 10^{-8}$ |
| pH 2.0 | $3.0 \cdot 10^5$ | $9.1 \cdot 10^{-5}$ | $1.7 \cdot 10^4$ | $5.0 \cdot 10^{-8}$ |
| SUM* | $6.4 \cdot 10^6$ | $3 \cdot 10^{-3}$ | $5.7 \cdot 10^6$ | $2 \cdot 10^{-5}$ |

*SUM is the total pfu (or fraction of input) obtained from all pH elution fractions

TABLE 213

Fractionation of EpiC-10 and MA-ITI phage on Cat-G beads

| | EpiC-10 | | MA-ITI | |
|---|---|---|---|---|
| Sample | Total pfu in sample | Fraltion of input | Total pfu in sample | Fraltion of input |
| INPUT | $5.0 \cdot 10^{11}$ | 1.00 | $4.6 \cdot 10^{11}$ | 1.00 |
| Final TBS-TWEEN Wash | $1.8 \cdot 10^7$ | $3.6 \cdot 10^{-5}$ | $7.1 \cdot 10^6$ | $1.5 \cdot 10^{-5}$ |
| pH 7.0 | $1.5 \cdot 10^7$ | $3.0 \cdot 10^{-5}$ | $6.1 \cdot 10^6$ | $1.3 \cdot 10^{-5}$ |
| pH 6.0 | $2.3 \cdot 10^7$ | $4.6 \cdot 10^{-5}$ | $2.3 \cdot 10^6$ | $5.0 \cdot 10^{-6}$ |
| pH 5.5 | $2.5 \cdot 10^7$ | $5.0 \cdot 10^{-5}$ | $1.2 \cdot 10^6$ | $2.6 \cdot 10^{-6}$ |
| pH 5.0 | $2.1 \cdot 10^7$ | $4.2 \cdot 10^{-5}$ | $1.1 \cdot 10^6$ | $2.4 \cdot 10^{-6}$ |
| pH 4.5 | $1.1 \cdot 10^7$ | $2.2 \cdot 10^{-5}$ | $6.7 \cdot 10^5$ | $1.5 \cdot 10^{-6}$ |
| pH 4.0 | $1.9 \cdot 10^6$ | $3.8 \cdot 10^{-6}$ | $4.4 \cdot 10^5$ | $9.6 \cdot 10^{-7}$ |
| pH 3.5 | $1.1 \cdot 10^6$ | $2.2 \cdot 10^{-6}$ | $4.4 \cdot 10^5$ | $9.6 \cdot 10^{-7}$ |
| pH 3.0 | $4.8 \cdot 10^5$ | $9.6 \cdot 10^{-7}$ | $3.6 \cdot 10^5$ | $7.8 \cdot 10^{-7}$ |
| pH 2.5 | $2.0 \cdot 10^5$ | $4.0 \cdot 10^{-7}$ | $2.7 \cdot 10^5$ | $5.9 \cdot 10^{-7}$ |
| pH 2.0 | $2.4 \cdot 10^5$ | $4.8 \cdot 10^{-7}$ | $3.2 \cdot 10^5$ | $7.0 \cdot 10^{-7}$ |
| SUM* | $9.9 \cdot 10^7$ | $2 \cdot 10^{-4}$ | $1.4 \cdot 10^7$ | $3 \cdot 10^{-5}$ |

*SUM is the total pfu (or fraction of input) obtained from all pH elution fractions

TABLE 214

Abbreviated fractionation of display phage on HNE beads

| | DISPLAY PHAGE | | | |
|---|---|---|---|---|
| | EpiNE-7 | MA-ITI 2 | MA-ITI-E7 1 | MA-ITI-E7 2 |
| INPUT (pfu) | 1.00 ($1.8 \cdot 10^9$) | 1.00 ($1.2 \cdot 10^{10}$) | 1.00 ($3.3 \cdot 10^9$) | 1.00 ($1.1 \cdot 10^9$) |
| WASH | $6 \cdot 10^{-5}$ | $1 \cdot 10^{-5}$ | $2 \cdot 10^{-5}$ | $2 \cdot 10^{-5}$ |
| pH 7.0 | $3 \cdot 10^{-4}$ | $1 \cdot 10^{-5}$ | $2 \cdot 10^{-5}$ | $4 \cdot 10^{-5}$ |
| pH 3.5 | $3 \cdot 10^{-3}$ | $3 \cdot 10^{-6}$ | $8 \cdot 10^{-5}$ | $8 \cdot 10^{-5}$ |
| pH 2.0 | $1 \cdot 10^{-3}$ | $1 \cdot 10^{-6}$ | $6 \cdot 10^{-6}$ | $2 \cdot 10^{-5}$ |
| SUM* | $4.3 \cdot 10^{-3}$ | $1.4 \cdot 10^{-5}$ | $1.1 \cdot 10^{-4}$ | $1.4 \cdot 10^{-4}$ |

*SUM is the total fraction of input pfu obtained from all pH elution fractions

TABLE 215

Fractionation of EpiNE-7 and MA-ITI-E7 phage on HNE beads

| | EpiNE-7 | | MA-ITI-E7 | |
|---|---|---|---|---|
| Sample | Total pfu in sample | Fraction of input | Total pfu in sample | Fraction of input |
| INPUT | $1.8 \cdot 10^9$ | 1.00 | $3.0 \cdot 10^9$ | 1.00 |
| pH 7.0 | $5.2 \cdot 10^5$ | $2.9 \cdot 10^{-4}$ | $6.4 \cdot 10^4$ | $2.1 \cdot 10^{-5}$ |
| pH 6.0 | $6.4 \cdot 10^5$ | $3.6 \cdot 10^{-4}$ | $4.5 \cdot 10^4$ | $1.5 \cdot 10^{-5}$ |
| pH 5.5 | $7.8 \cdot 10^5$ | $4.3 \cdot 10^{-4}$ | $5.0 \cdot 10^4$ | $1.7 \cdot 10^{-5}$ |
| pH 5.0 | $8.4 \cdot 10^5$ | $4.7 \cdot 10^{-4}$ | $5.2 \cdot 10^4$ | $1.7 \cdot 10^{-5}$ |
| pH 4.5 | $1.1 \cdot 10^6$ | $6.1 \cdot 10^{-4}$ | $4.4 \cdot 10^4$ | $1.5 \cdot 10^{-5}$ |
| pH 4.0 | $1.7 \cdot 10^6$ | $9.4 \cdot 10^{-4}$ | $2.6 \cdot 10^4$ | $8.7 \cdot 10^{-6}$ |
| pH 3.5 | $1.1 \cdot 10^6$ | $6.1 \cdot 10^{-4}$ | $1.3 \cdot 10^4$ | $4.3 \cdot 10^{-6}$ |
| pH 3.0 | $3.8 \cdot 10^5$ | $2.1 \cdot 10^{-4}$ | $5.6 \cdot 10^3$ | $1.9 \cdot 10^{-6}$ |
| pH 2.5 | $2.8 \cdot 10^5$ | $1.6 \cdot 10^{-4}$ | $4.9 \cdot 10^3$ | $1.6 \cdot 10^{-6}$ |
| pH 2.0 | $2.9 \cdot 10^5$ | $1.6 \cdot 10^{-4}$ | $2.2 \cdot 10^3$ | $7.3 \cdot 10^{-7}$ |
| SUM* | $7.6 \cdot 10^6$ | $4.1 \cdot 10^{-3}$ | $3.1 \cdot 10^5$ | $1.1 \cdot 10^{-4}$ |

*SUM is the total pfu (or fraction of input) obtained from all pH elution fractions

CITATIONS

AKOH72: Ako, H, R J Foster, and C A Ryan, "The preparation of anhydro-trypsin and its reactivity with naturally occurring proteinase inhibitors", Biochem Biophys Res Commun (USA) (1972), 47 (6) 1402–7.

ALBR83a: Albrecht, G, K Hochstrasser, and O L Schonberger, "Kunitz-type proteinase inhibitors derived by limited proteolysis of the inter-α-trypsin inhibitor, IX: isolation and characterization of the inhibitory parts of inter-α-trypsin inhibitors from several mammalian sera", Hoppe-Seyler's Z Physiol Chem (1983), 364:1697–1702.

ALBR83b: Albrecht, G J, K Hochstrasser, and J-P Salier, "Elastase inhibition by the inter-α-trypsin inhibitor and derived inhibitors of man and cattle", Hoppe-Seyler's Z Physiol chem (1983), 364:1703–1708.

ALMA83a: Almassy, R C, J C Fontecilla-Camps, F L Suddath, and C E Bugg, "Structure of scorpion neurotoxin at 18 Å resolution", Entry 1SN3 in Brookhaven Protein Data Bank, (1983).

ALMA83b: Almassy, RC, JC Fontecilla-Camps, F L Suddath, and C E Bugg, "Structure of variant-3 scorpion neurotoxin from Centruroides Sculpturatus ewing refined at 1.8 Å resolution", J Mol Biol (1983), 170:497ff.

ALMQ89: Almquist, R G, S R Kadambi, D M Yasuda, F L Weitl, W E Polgar, and L R Toll, "Paralytic activity of (des-Glu1)conotoxin GI analogs in the mouse diaphragm", Int J Pept Protein Res, (Dec. 1989), 34(6)455–62.

ANFI73: Anfinsen, C B, "Principles that govern the folding of protein chains", Science (1973), 181(96)223–30.

ARGO87: Argos, P, "Analysis of Sequence-similar Pentapeptides in Unrelated Protein Tertiary Structures", J Mol Biol (1987), 197:331–348.

ARAK90: Araki, K, M Kuwada, O Ito, J Kuroki, and S Tachibana, "Four disulfide bonds allocation of Na+, K+-ATPase inhibitor (SPAI)", Biochem Biophys Res Comm (1990), 172(1)42–46.

ARMS81: Armstrong, J, R N Perham, and J E Walker, "Domain structure of Bacteriophage fd Adsorption Protein", FEBS Lett (1981), 135(1) 167–172.

ARMS83: Armstrong, J, J A Hewitt, and R N Perham, "Chemical modification of the coat protein in bacteriophage fd and orientation of the virion during assembly and disassembly", EMBO J (1983), 2 (10)1641–6.

ARNA90: Arnaout, M A, "Leukocyte Adhesion Molecules Deficiency: Its STructural Basis, Pathophysiologyand Implications for Modulating the Inflammatory Response", Immunological Reviews (1990), 114:145–180.

AUER87: Auerswald, E-A, W Schroeder, and M Kotick, "Synthesis, Cloning and Expression of Recombinant Aprotin-in", Biol Chem Hoppe-Seyler (1987), 368:1413–1425.

AUER88: Auerswald, E-A, D Hoerlein, G Reinhardt, W Schroder, and E Schnabel, "Expression, Isolation, and Characterization of Recombinant [Arg$^{15}$, Glu$^{52}$]Aprotinin", Bio Chem Hoppe-Seyler (1988), 369(Supplement):27–35.

AUER89: Auerswald, E-A, W Bruns, D Hoerlein, G Reinhardt, E Schnabel, and W Schroder, "Variants of bovine pancreatic trypsin inhibitor produced by recombinant DNA technology", UK Patent Application GB 2,208,511 A.

AUER90: Auerswald, E-A,W Schroeder, E Schnabel, W Bruns, G Reinhard, and M Kotick, "Homologs of Aprotinin produced from a recombinant host, process ecpression vector and recombinant host therefor and pharmaceutical use thereof", U.S. Pat. No. 4,894,436 (16 Jan 1990).

AUSU87: Ausubel, F M, R Brent, R E Kingston, D D Moore, J G Seidman, J A Smith, and K Struhl, Editors Current Protocols in Molecular Biology, Greene Publishing Associates and Wiley-Interscience, Publishers: John Wiley & Sons, New York, 1987.

BAKE87: Baker, K, N Mackman, and I B Holland, "Genetics and Biochemistry of the Assembly of Proteins into the Outer Membrane of E. coli", Prog Biophys molec Biol (1987), 49:89–115.

BALD85: Balduyck, M, M Davril, C Mizon, M Smyrlaki, A Hayem, and J Mizon, "Human urinary proteinase inhibitor: inhibitory properties and interaction with bovine trypsin", Biol Chem Hoppe-Seyler (1985), 366:9–14.

BANN81: Banner, D W, C Nave, and D A Marvin, "Structure of the protein and DNA in fd filamentous bacterial virus", Nature (1981), 289:814–816.

BARB85: Barbe, J, J A Vericat, M Llagostera, and R Guerrero, "Expression of the SOS genes of Escherichia coli in Salmonella typhimurium", Microbiologia (1985), 1 (1–2)77–87.

BECK80: Beck, E, "Nucleotide sequence of the gene ompA coding the outer membrane protein II* of Escherichia coli K-12", Nucl Acid Res (1980), 8(13)3011–3024.

BECK83: Beckwith, J, and T J Silhavy, "Genetic Analysis of Protein Export in Escherichia coli", Methods in Enzymology (1983), 97:3–11.

BECK88b: Beckmann, J, A Mehlich, W Schroeder, H R Wenzel, and H Tschesche, "Preparation of chemically 'mutated' aprotinin homologues by semisynthesis: P1 substitutions change inhibitory specificity", Eur J Biochem (1988), 176:675–82.

BECK89a: Beckmann, J, A Mehlich, W Schroeder, H R Wenzel, and H Tschesche, "Semisynthesis of Arg15, Glu$^{15}$, Met$^{15}$, and Nle$^{15}$-Aprotinin Involving Enzymatic Peptide Bond Resynthesis", J Protein Chem (1989), 8(1)101–113.

BECK89b: Becker, S, E Atherton, H Michel, and R D Gordon, "Synthesis and characterization of conotoxin IIIa", J Protein Chem, (Jun 1989 ), 8(3)393–4.

BECK89c: Becker, S, E Atherton, and R D Gordon, "Synthesis and characterization of mu-conotoxin IIIa", Eur J Biochem, (Oct. 20 1989), 185(1)79–84.

BENS84: Benson, S A, E Bremer, and T J Silhavy, "Intragenic regions required for LamB export", Proc Natl Acad Sci USA (1984), 81:3830–34.

BENS 87b: Benson, S A, and E Bremer, "In vivo selection and characterization of internal deletions in the lamB::lacZ gene fusion", Gene (1987), 52 (2–3) 165–73.

BENS87c: Benson, S A, M N Hall, and B A Rasmussen, "Signal Sequence Mutations That Alter Coupling of Secretion and Translation of an Escherichia coli Outer Membrane Protein", J Bacteriol (1987), 169(10)4686–91.

BENS 88: Benson, S A, J L Occi, B A Sampson, "Mutations that alter the pore function of the OmpF porin of Escherichia coli K12", J Mol Biol (1988) 203(4)961–70.

BENZ88a: Benz, R, and K Bauer, "Permeation of hydrophilic molceules through the outer membrane of gram-negative bacteria", Eur J Biochem (1988), 176:1–19.

BENZ88b: Benz, R, "Structure and Fucntion of Porins from Gram-Negative Bacteria", Ann Rev Microbiol (1988), 42:359–93.

BERG88: Berg, J M, "Proposed structure for the zinc-binding domains from transcription factor IIIA and related proteins", Proc Natl Acad Sci USA (1988), 85:99–102.

BETT88: Better, M, C P Chang, R R Robinson, and A H Horwitz, "Escherichai coli Secretion of an Active Chimeric Antibody Fragment", Science (1988), 240:1041–1043.

BHAT86: Bhatnagar, PK, and J C Frantz, "Synthesis and Antigenic activity of E. coli ST and its analogues", Develop biol Standard (1986), 63:79–87.

BIRD67: Birdsell, D C, and E H Cota-Robles, "Production and Ultrastructure of lysozyme and ethylenediamine-tetraacetate-lysozyme spheroplasts of E. coli", J Bacteriol (1967), 93:427–437.

BIET86: Bieth, J G, "Elastase: Catalytic and Biological Properties", pp. 217–320 in Regulation of Matrix Accumulation, Editor: R P Mecham, Academic Press, Orlando, 1986.

BLOW72: Blow &al., J Mol Biol (1972), 69:137ff.

BODE89: Bode, W, H J Greyling, R Huber, J Otlewski, and T Wilusz, "The refined 2.0 A X-ray crystal structure of the complex formed between bovine beta-trypsin and CMTI-I, a trypsin inhibitor from squash seeds (Cucurbita maxima). Topological similarity of the squash seed inhibitors with the carboxypeptidase A inhibitor from potatoes", FEBS Lett (Jan. 2, 1989), 242(2)285–92.

BOEK80: Boeke, J D, M Russel, and P Model, "Processing of Filamentous Phage Pre-coat Protein: Effect of Sequence Variations near the Signal Peptidase Cleavage Site", J Mol Biol (1980), 144:103–116.

BOEK82: Boeke, J D, P Model, and N D Zinder, "Effects fo Bacteriophage f1 Gene III Protein on the Host Cell Membrane", Molec and Gen Genet, (1982), 186:185–192.

BOQU87: Boquet, P L, C Manoil, and J Beckwith, "Use of TnphoA to Detect Genes for Exported Proteins in Escherichia coli: Identification of the Plasmid-Encoded Gene for a Periplasmic Acid Phosphatase", J Bacteriol (1987), 169:1663–1669.

BOTS85: Botstein, D, and D Shortle, "Strategies and applications of in vitro mutagenesis", Science, (1985), 229(4719)1193–201.

BOUG84: Bouges-Bocquet, B, H Villarroya, and M Hofnung, "Linker Mutagenesis in the Gene of an Outer Membrane Protein of *Escherichia coli*, LamB", J Cellular Biochem (1984), 24:217–28.

BOUL86a: Boulain, J C, A Charbita and M Hofnung, "Mutagenesis by random linker insertion into the lamB gene of *Escherichia coli* K12", Mol Gen Genet, (1986), 205 (2) 339–48.

BRAW87: Brawerman, G, "Determinants of messenger RNA stability", Cell (1987), 48 (1) 5–6.

CALA90: Calamia, J, and C Manoil, "lac permease of *Escherichia coli:* topology and sequence elements promoting membrane insertion", Proc Natl Acad Sci USA, (Jul. 1990), 87(13)4937–41.

CAMP90: Campanelli, D, M Melchior, Yiping Fu, M Nakata, H Shuman, C Nathan, and J E Gabay, "Cloning of cDNA for Proteinase 3: A Serine Protease, Antibiotic, and Autoantigen from Human Neutrophils", J Exp Med (Dec. 1990), 172:1709–15.

CARM90: Carmel, G, D Hellstern, D Henning, and J W Coulton, "Insertion mutagenesis of the gene encoding the ferri-chrome-iron receptor of *Escherichia coli* K-12", J Bacteriol, (Apr. 1990), 172(4)1861–9.

CARU85: Caruthers, M H, "Gene Synthesis Machines: DNA Chemistry and Its Uses", Science (1985), 230:281–285.

CARU87: Caruthers, M H, P Gottlieb, L P Bracco, and L Cummings, "The Thymine 5-Methyl Group: A Protein-DNA Contact Site Useful for Redesigning Cro Repressor to Recognize a New Operator", in Protein Structure, Folding, and Design 2, 1987, Ed. D Oxender (New York, AR Liss Inc) p.9ff.

CAST79: Castillo, M J, K Nakajima, M Zimmerman, and J C Powers, "Sensitive substrates for human leukocyte and porcine pancreatic elastase: a study of the merits of various chromophoric and fluorogenic leaving groups in assays for serine proteases", Anal Biochem (1979), 99(1)53–64.

CATR87: Catron, K M, and C A Schnaitman, "Export of Protein in *Escherichia coli:* a Novel Mutation in ompC Affects Expression of Other Major Outer Membrane Proteins", J Bacteriol (1987), 169:4327–34.

CHAM82: Chambers, R W, I Kucan, and Z Kucan, "Isolation and characterization of phi-X174 mutants carrying lethal missense mutations in gene G", Nucleic Acids Res (1982), 10(20)6465–73.

CHAN79: Chang, C N, P Model, and G Blobel, "Membrane biogenesis: Cotranslational integration of the bacteriophage f1 coat protein into an *Escherichia coli* membrane fraction", Proc Natl Acad Sci USA (1979), 76:1251–1255.

CHAP90: Chapot, M P, Y Eshdat, S Marullo, J G Guillet, A Charbit, A D Strosberg, and C Delavier-Klutchko, "Localization and characterization of three different beta-adrenergic receptors expressed in *Escherichia coli*", Eur J Biochem ( 1990 ), 187(1) 137–44.

CHAR84: Charbit, A, J-M Clement, and M Hofnung, "Further Sequence Analysis of the Phage Lambda Receptor Site", J Mol Biol (1984), 175: 395–401.

CHAR86a: Charbit, A, J C Boulain, A Ryter, and M Hofnung, "Probing the topology of a bacterial membrane protein by genetic insertion of a foreign epitope; expression at the cell surface", EMBO J, (1986), 5(11)3029–37.

CHAR86b: Charbit, A, J-C Boulain, and M Hofnung, "Une methode genetique pur exposer un epitope choisi a la surface de la bacteria *Escherichia coli*. Perspectives [A genetic method to expose a chosen epitope on the surface of the bacteria *E. coli*]", Comptes Rendu Acad Sci, Paris, (1986), 302:617–24.

CHAR87: Charbit, A, E Sobczak, M L Michel, A Molla, P Tiollais, and M Hofnung, "Presentation of two epitomes of the preS2 region of hepatitis B virus on live recombinant bacteria", J Immunol (1987), 139:1658–64.

CHAR88a: Charbit, A, K Gehring, H Nikaido, T Ferenci, and M Hofnung, "Maltose transport and starch binding in phage-resistant point mutants of maltoporin. Functional and topological implications", J Mol Biol (1988), 201(3)487–96.

CHAR88b: Charbit, A, A Molla, W Saurin, and M Hofnung, "Versatility of a vector for expressing foreign polypeptides at the surface of gram-negative bacteria", Gene (1988), 70(1) 181–9.

CHAR88c: Charbit, A, S Van der Werf, V Mimic, JC Boulain, M Girard, and M Hofnung, "Expression of a poliovirus neutralization epitope at the surface of recombinant bacteria: first immunization results", Ann Inst Pasteur Microbiol (1988), 139(1)45–58.

CHAR90: Charbit, A, A Molla, J Ronco, J M Clement, V Favier, E M Bahraoui, L Montagnier, A Leguern, and M Hofnung, "Immunogenicity and antigenicity of conserved peptides from the envelope of HIV-1 expressed at the surface of recombinant bacteria", AIDS (1990), 4(6)545–51.

CHAV88: Chavrier, P; P Lemaire, O Revelant, R Bravo, and P Charnay, "Characterization of a Mouse Multigene Family That Encodes Zinc Finger Structures", Molec Cell Biol (1988), 8(3)1319–26.

CHAZ85: Chazin, W J, D P Goldenberg, T E Creighton, and K Wuthrich, "Comparative studies of conformation and internal mobility in native and circular basic pancreatic trypsin inhibitor by $^1$H nuclear magnetic resonance in solution", Eur J Biochem (1985), 152:(2)429–37.

CHOT75: Chothia, C, and J Janin, "Principles of protein-protein recognition", Nature (1975), 256:705–708.

CHOT76: Chothia, C, S Wodak, and J Janin, "Role of subunit interfaces in the allosteric mechanism of hemoglobin", Proc Natl Acad Sci USA (1976), 73:3793–7.

CHOU74: Chou, P Y, and G D Fasman, "Prediction of protein conformation" Biochemistry (1974), 13: (2)222–45.

CHOU78 a: Chou, P Y, and G D Fasman, "Prediction of the secondary structure of proteins from their amino acid sequence", Adv Enzymol (1978), 47:45–148.

CHOU 78 b: Chou, P Y, and G D Fasman, "Empirical predictions of protein conformation" Annu Rev Biochem (1978), 47: 251–76.

CHOW87: Chowdhuury, K, U Deutsch, and P Gruss, "A Multigene Family Encoding Several 'Finger' Structures Is Present and Differentially Active in Mammalian Genomes", Cell (1987), 48:771–778.

CLEM81: Clement, J M, and M Hofnung, "The sequence of the lambda receptor, an outer membrane protein of *E. coli* K12", Cell (1981), 27:507–514.

CLEM83: Clement J M, E Lepouce, C Marchal, and M Hofnung, "Genetic Study of a membrane protein: DNA sequence alterations due to 17 LamB point mutations affecting adsorption of phage lambda", EMBO J (1983), 2:77–80.

CLIC88: Click, E M, G A McDonald, and C A Schnaitman, "Translational Control of Exported Proteins That Results from OmpC Porin Overexpression", J Bacteriol (1988), 170.:2005–2011.

CLOR86: Clore, GM, AT Brunger, M Karplus, AM Gronenborn, "Application of Molecular Dynamics with Interproton Distance Restraints to Three-dimensional Protein Structure Determination: A model study of Crambin", J Mol Biol (1986), 191:523–551.

CLOR87a: Clore, G M, A M Gronenborn, M Kjaer, and F M Poulsen, "The determination of the three-dimensional structure of barley serine proteinase inhibitor 2 by nuclear magnetic resonance distance geometry and restrained molecular dynamics", Protein Engineering (1987), 1(4)305–311.

CLOR87b: Clore, G M, A M Gronenborn, M N G James, M Kjaer, C A McPhalen, and F M Poulsen, "Comparison of the solution and X-ray structures of barley serine proteinase inhibitor 2", Protein Engineering (1987), 1(4)313–318.

CLUN84: Clune, A, K-S Lee, and T Ferenci, "Affinity Engineering Of Maltoporin: Variants with Enhanced Affinity for Particular Ligands", Biochem and Biophys Res Comm (1984), 121:34–40.

CREI74: Creighton, T E, "Intermediates in the Refolding Of Reduced Pancreatic Trypsin Inhibitor", J Mol Biol (1974), 87: 579–602.

CREI77a: Creighton, T E, "Conformational Restrictions on the Pathway of Folding and Unfolding of the Pancreatic Trypsin Inhibitor", J Mol Biol (1977), 113:275–293.

CREI77b: Creighton, T E, "Energetics of Folding and Unfolding of Pancreatic Trypsin Inhibitor", J Mol Biol (1977), 113:295–312.

CREI80: Creighton, T E, "Role of the Environment in the Refolding of Reduced Pancreatic Trypsin Inhibitor", J Mol Biol (1980), 144:521–550.

CREI84: Creighton, T E, Proteins: Structures and Molecular Principles, W H Freeman & Co, New York, 1984.

CREI87: Creighton, T E, and I G Charles, "Biosynthesis, Processing, and Evolution of Bovine Pancreatic Trypsin Inhibitor", Cold Spring Harb Symp Quant Biol (1987), 52:511–519.

CREI88: Creighton, T E, "Disulphide Bonds and Protein Stability", BioEssays (1988), 8(2) 57–63.

CRIS84: Crissman, J W, and G P Smith, "Gene-III Protein of Filamentous Phages: Evidence for a Carboxyl-Terminal Domain with a Role in Morphogenesis", Virology (1984), 132:445–55.

CRUZ85: Cruz, L J, W R Gray, B M Olivera, R D Zeikus, L Kerr, D Yoshikami, and E Moczydlowski, "Conus geographus toxins that discriminate between neuronal and muscle sodium channels", J Biol Chem, (1985), 260(16)9280–8.

CRUZ89: Cruz, L J, G Kupryszewski, G W LeCheminant, W R Grey, B M Oliveria, and J Rivier, "mu-Conotoxin GIIIA, a Peptide Ligand for Muscle Scodium Channels: Chemical Synthesis, Radiolabeling, and Receptor Characterization", Biochem (1989), 28:3437–3442.

CWIR90: Cwirla, S E, E A Peters, R W Barrett, and W J Dower, "Peptides on Phage: A vast library of peptides for identifying ligands", Proc Natl Acad Sci USA, (August 1990), 87:6378–6382.

DAIL90: Dailey, D, G L Schieven, M Y Lim, H Marquardt, T Gilmore, J Thorner, and G S Martin, "Novel yeast protein kinase (YPK1 gene product) is a 40-kilodalton phosphotyrosyl protein associated with protein-tyrosine kinase activity", Mol Cell Biol (Dec. 1990), 10(12)6244–56.

DALL90: Dallas, W S, "The Heat-Stable Toxin I Gene from *Escherichia coli* 18D", J Bacteriol (1990) 172 (9)5490–93.

DARG88: Dargent, B, A Charbit, M Hofnung, and F Pattus, "Effect of point mutations on the in-vitro pore properties of maltoporin, a protein of *Escherichia coli* outer membrane", J Mol Biol (1988), 201 (3)497–506.

DAWK86: Dawkins, R, The Blind Watchmaker, W W Norton & Co, New York, 1986.

DAYL88: Day, L A, C J Marzec, S A Reisberg, and A Casadevall, "DNA Packing in Filamentous Bacteriophage", Ann Rev Biophys Biophys Chem (1988), 17:509–39.

DAYR86: Dayringer, H, A Tramantano, and R Fletterick, "Proteus Software for Molecular Modeling" p.5–8 in Computer Graphics and Molecular Modeling, Cold Spring Harbor Laboratory, Cold Spring Harbor, N.Y., 1986.

DEBR86: Debro, L, P C Fitz-James, and A Aronson, "Two different parasporal inclusions are produced by *Bacillus thuringiensis* subsp finitimus.", J Bacteriol (1986), 165:258–68.

DEGE84: de Geus, P, H M Verheij, N H Reigman, W P M Hoekstra, and G H de Haas, "The pro- and mature forms of the *E. coli* K-12 outer memberane phospholipase A are identical", EMBO J (1984), 3(8) 1799–1802.

DEGR87: DeGrado, W F, L Regan, and S P Ho, "The Design of a Four-helix Bundle Protein", Cold Spring Harbor Symp Quant Biol, (1987), 52:521–6.

DELA88: de la Cruz, V F, A A Lal and T F McCutchan, "Immunogenicity and epitope mapping of foreign sequences via genetically engineered filamentous phage", J Biol Chem, (1988), 263(9)4318–22.

DENH78: Denhardt, D T, D Dressler, and D S Ray editors, The Single-Stranded DNA Phages, Cold Spring Harbor Laboratory, 1978.

DEVL90: Devlin, J J, L C Panganiban, and P E Devlin, "Random Peptide Libraries: A Source of Specific Protein Binding Molecules", Science, (27 Jul. 1990), 249:404–406.

DEVO78: DeVore, D P, and R J Gruebel, "Dityrosine in adhesive formed by the sea mussel, *Mytilus edulis*", Biochem Biophys Res Commun (1978), 80(4)993–9.

DEVR84: de Vries, G, C K raymond, and R A Ludwig, "Extension of bacteriophage λ host range: Selection, cloning, and characterization of a constitutive λ receptor gene", Proc Natl Acad Sci USA (1984), 81:6080–4.

DIAR90: Diarra-Mehrpour, M, J Bourguignon, R Sesboue, J-P Salier, T Leveillard and J-P Martin, "Structural analysis of the human inter-α-trypsin inhibitor light-chain gene", Eur J Biochem (1990), 191:131–139.

DICK83: Dickerson, R E, and I Geis, Hemoglobin: Structure, Function, Evolution, and Pathology, The Bejamin/Cummings Publishing Co, Menlo Park, Calif.,, 1983.

DILL87: Dill, K A, "Protein Surgery", Protein Engineering (1987), 1:369–371.

DOUG84: Dougan, G, and P Morrissey, "Molecular analysis of the virulence determinants of enterotoxigenic *Escherichia coli* isolated from domestic animals: applications for vaccine development", Vet Microbiol (1984/5), 10:241–57.

DONO 87 Donovan, W, Z Liangbiao, K Sandman, and R Losick, "Genes Encoding Spore Coat Polypeptides from *Bacillus subtilis*", J Mol Biol (1987), 196:1–10.

DUCH88: Duchene, M, A Schweized, F Lottspeich, G Krauss, M Marget, K Vogel, B-U von Specht, and H Domdey, "Sequence and Transcriptional Start Site of the *Pseudomonas aeruginosa* Outer Membrane Porin Protein F Gene", J Bacteriol (1987),170:155–162.

DUFT85: Dufton, M J, "Proteinase inhibitors and dendrotoxins", Eur J Biochem (1985), 153:647–654.

DULB86: Dulbecco, R, "Viruses with Recombinant Surface Proteins", U.S. Pat. No. 4,593,002, Jun. 3, 1986.

DUPL88: Duplay, P, and M Hofnung, "Two Regions of Mature Periplasmic Maltose-Binding Protein of *Escherichia coli* Involved in Secretion", J Bacteriol (1988), 170(10)4445–50.

DWAR89: Dwarakanath, P, S S Viswiswariah, Y V B K Subrahmanyam, G Shanthi, H M Jagannatha, and T S Balganesh, "Cloning and hyperexpression of a gene encoding the heat-stable toxin of *Escherichia coli*", Gene (1989), 81:219–226.

EHRM90: Ehrmann, M, D Boyd, and J Beckwith, "Genetic analysis of membrane protein topology by a sandwich gene fusion approach", Proc Natl Acad Sci USA, (Oct. 1990), 87(19)7574–8.

EIGE90: Eigenbrot, C, M Randal, and A A Kossiakoff, "Structural effects induced by removal of a disulfide-bridge: the X-ray structure of the C30A/C51A mutant of basic pancreatic trypsin inhibitor at 16 Å", Protein Engineering (1990), 3(7)591–598.

EISE85: Eisenbeis, S J, M S Nasoff, S A Noble, L P Bracco, D R Dodds, M H Caruthers, "Altered Cro Repressors from engineered mutagenesis of a synthetic cro gene", Proc Natl Acad Sci USA (1985), 82:1084–1088.

ELLE88: Elleman, T C, "Pilins of *Bacteroides nodosus*: molecular basis of serotypic variation and relationships to other bacterial pilins", Microbiol Rev (1988), 52(2)233–47.

EMPI82: Empie, M W, and M Laskowski, Jr, "Thermodynamics and Kinetics fo Single Residue Replacements in Avian Ovomucoid Third Domains: Effect on Inhibitor Interactions with Serine Proteinases", Biochemistry (1982), 21:2274–84.

ENGH89: Enghild, J J, I B Thogersen, S V Pizzo, and G Salvesen, "Anallysis of inter-α-trypsin inhibitor and a novel inhibitor, pre-α-trypsin inhibitor, from human plasma: polypeptide chain stoichiometry and assembly by glycan", J Biol Biochem (1989), 264:15975–15981.

EPST63: Epstein, C J, R F Goldberger, and C B Anfinsen, Cold Spr Harb Symp Quant Biol (1963), 28:439ff.

ERIC86: Erickson, B W, S B Daniels, P A Reddy, C G Unson, J S Richardson, and D C Richardson, "Betabellin: An Engineered Protein", Current Communications in Molecular Biology: Computer Graphics and Molecular Modeling, Cold Spring Harbor Laboratoary, Cold Spring Harbor, N.Y., 1986, Fletterick, R and M Zoller, Editors.

EVAN88: Evans, R M, and S M Hollenberg, "Zinc Fingers: Gilt by Association", Cell ( 1988 ), 52: 1–3.

FAVE89: Favel, A, D Le-Nguyen, M A Coletti-Previero, and C Castro, "Active site chemical mutagenesis of *Ecbalium elaterium* Trypsin Inhibitor II: New microproteins inhibiting elastase and chymotrypsin", Biochem Biophys Res Comm (1989), 162:79–82.

FERE80c: Ferenci, T, "The recognition of maltodextrins by *Escherichia coli*", Eur J Biochem (1980), 108:631–6.

FERE82a: Ferenci, T, "Affinity-chromatographic Studies based on the Binding-specificity of the Lambda Receptor of *Escherichia coli*", Ann Microbiol (Inst Pasteur) (1982), 133A:167–169.

FERE82b: Ferenci, T, and K-S Lee, "Directed Evolution of the Lambda Receptor of *Escherichia coli* through Affinity Chromatographic Selection", J Mol Biol (1982), 160.:431–444.

FERE83: Ferenci, T, and K S Lee, "Isolation by affinity chromatography, of mutant *Escherichia coli* cells with novel regulation of lamB expression", J Bacteriol (1983), 1.54:984–987.

FERE84: Ferenci, T, "Genetic manipulation of bacterial surfaces through affinity-chromatographic selection", Trends in Biological Science (1984) Vol. 9:44–48.

FERE86a: Ferenci, T, and K-S Lee, "Temperature-Sensitive Binding of α-Glucans by *Bacillus stearothermophilus*", J Bacteriol (1986), 166:95–99.

FERE86b: Ferenci, T, M Muir, K-S Lee, and D Maris, "Substrate specificity of the *Escherichia coli* maltodextrin transport system and its component proteins.", Biochimica et Biophysica Acta (1986), 860:44–50.

FERE89a: Ferenci, T, and K S Lee, "Channel architecture in maltoporin: dominance studies with lamb mutations influencing maltodextrin binding provide evidence for independent selectivity filters in each subunit", J Bacteriol (1989) 171(2)855–61.

FERE89b: Ferenci, T, and S Stretton, "Cysteine-22 and cysteine-38 are not essential for the function of maltoporin (LamB protein)", FEMS Microbiol Lett (1989), 52(3)335–9.

FERR90: Ferrer-Lopez, P, P Renesto, M Schattner, S Bassot, P Laurent, and M Chignard, "Activation of human platelets by C5a-stimulated neutrophils: a role for cathepsin G", American J Physiology (1990) 258:C1100–C1107.

FIOR85: Fioretti, E, G Iacopino, M Angeletti, D Barra, F Bossa, and F Ascoli, "Primary Structure and Antiproteolytic Activity of a Kunitz-type Inhibitor from Bovine Spleen", J Biol Chem (1985), 260:11451–11455.

FIOR88: Fioretti, E, M Angeletti, L Fiorucci, D Barra, F Bossa, and F Ascoli, "Aprotinin-Like Isoinhibitors in Bovine Organs", Biol Chem Hoppe-Seyler (1988), 369(Suppl) 37–42.

FRAN87: Frankel, A D, J M Berg, and C O Pabo, "Metal-dependent folding of a single zinc finger from transcription factor IIIA", Proc Natl Acad Sci USA (1987), 84:4841–45.

FRAN88: Frankel, A, and CO Pabo, "Fingering Too Many Proteins", Cell (1988), 53: 675.

FRAN89: Franconi, G M, P D Graf, S C Lazarus, J A Nadel, G H Caughey, "Mast Cell Tryptase and Chymase Reverse Airway Smooth Muscle Relaxation Induced by Vasoactive Intestinal Peptide in the Ferret", J Pharmacol and Exp Therap (1989), 248(3)947–51.

FREI90: Freimuth, P I, J W Taylor, and ET Kaiser, "Introduction of Guest Peptides into *Escherichia coli* Alkaline Phosphatase", J Biol Chemistry, (15 Jan. 1990), 265(2)896–901.

FREU89: Freudl, R, H Schwarz, M Degen, and U Henning, "A lower size limit exists for export of fragments of an outer membrane protein (OmpA) of Escherichia coli K-12", J Mol Biol (1989), 205(4)771–5.

FRIT85: Fritz, H-J, "The Oligonucleotide-directed Construction of Mutations in Recombinant Filamentous Phage", DNA Cloning, Editor: D M Glover, IRL Press, Oxford, UK, 1985.

GARI84: Gariepy, J, P O'Hanley, S A Waldman, F Murad, and G K Schoolnik, "A common antigenic determinant found in two functionally unrelated toxins", J Exp Med, (1984), 160(4)1253–8.

GARI86: Gariepy, J, A Lane, F Frayman, D Wilbur, W Robien, G Schoolnik, and O Jardetzky, "Structure of the Toxic Domain of the *Eshcerichia coli* Heat-Stable Enterotoxin ST I", Biochem (1986), 25:7854–7866.

GARI87: Gariepy, J, A K Judd, and G K Schoolnik, "Importance of disulfide bridges in the structure and activity of *Escherichia coli* enterotoxin ST1b", Proc Natl Acad Sci USA (1987), 84:8907–11.

GAUSS7: Gauss, P, K B Krassa, D S McPheeters, M A Nelson, and L Gold "Zinc(II) and the single-stranded DNA binding protein of bacteriophage T4", Proc Natl Acad Sci USA (1987), 84:8515–19.

GEBH86: Gebhard, W, and K Hochstrasser, "Inter-α-trypsin inhibitor and its close relatives", in Barret and Salvesen (eds.) *Protease Inhibitors* (1986) Elsevier Science Publishers BV (Biomedical Division) pp.389–401.

GEBH90: Gebhard, W, K Hochstrasser, H Fritz, J J Enghild, S V Pizzo, and G Salvesen, "Structure of the inter-α-inhibitor (inter-α-trypsin inhibitor) and pre-α-inhibitor: current state and proposition of a new terminology", Biol Chem Hoppe-Seyler (1990), 371,suppl 13–22.

GEHR87: Gehring, K, A Charbit, E Brissaud, and M Hofnung, "Bacteriophage lambda receptor site on the *Escherichia coli* K-12 LamB protein", J Bacteriol (1987), 169 (5) 2103–6.

GERD84: Gerday, C, M Herman, J Olivy, N Gerardin-Otthiers, D Art, E Jacquemin, A Kaeckenbeeck, and J van Beeumen, "Isolation and characterization of the Heat Stable enterotoxin for a pathogenic bovine strain of *Escherichia coli*", Vet Microbiol (1984), 9:399–414.

GETZ88: Getzoff, E D, H E Parge, D E McRee, and J A Tainer, "Understanding the Structure and Antigenicity of Gonococcal Pili", Rev Infect Dis (1988), 10(Suppl 2)S296–299.

GIBS88: Gibson, T J, J P M Postma, R S Brown, and P Argos, "A model for the tertiary structure of the 28 residue DNA-binding motif ('Zinc finger') common to many eukaryotic transcriptional regulatory proteins", Protein Engineering (1988), 2(3)209–218.

GIRA89: Girard, T J, L A Warren, W F Novotny, K M Likert, S G Brown, J P Miletich, and G J Broze Jr, "Functional significance of the Kunitz-type inhibitory domains of lipoprotein-associated coagulation inhibitor", Nature (1989), 338:518–20.

GOLD83: Goldenberg, D P, and T E Creighton, "Circular and circularly permuted forms of bovine pancreatic trypsin inhibitor.", J Mol Biol (1983), 165 (2) 407–13.

GOLD84: Goldenberg, D P, and T E Creighton, "Folding Pathway of a circular Form of Bovine Pancreatic Trypsin Inhibitor", J Mol Biol (1984), 179: 527–45.

GOLD85: Goldenberg, D P, "Dissecting the Roles of Individual Interactions in Protein Stability: Lessons From a Circularized Protein", J Cellular Biochem (1985), 59:321–335.

GOLD87: Gold, L, and G Stormo, "Translation Initiation", Volume 2, Chapter 78, p 1302–1307, *Escherichia coli* and *Salmonella typhimurium:* Cellular and Molecular Biology, Neidhardt, F C, Editor-in-Chief, Amer Soc for Microbiology, Washington, DC, 1987.

GOLD88: Goldenberg, D P, "Kinetic Analysis of the Folding and Unfolding of a Mutant Form of Bovine Pancreatic Trypsin Inhibitor Lacking the Cysteine-14 and -38 Thiols", Biochem (1988), 27:2481–89.

GOTT87: Gottesman, S, "Regulation by Proteolysis", Volume 2, chapter 79, p 1308–1312. *Escherichia coli* and *Salmonella typhimurium:* Cellular and Molecular Biology, Neidhardt, F C, Editor-in-Chief, Amer Soc for Microbiology, Washington, DC, 1987.

GRAY81a: Gray, W R, A Luque, B M Olivera, J Barrett, and L J Cruz, "Peptide Toxins from *Conus geographicus* Venom", J Biol Chem (1981), 256:4734–40.

GRAY81 b: Gray, C W, R S Brown, and D A Marvin, "Adsorption Complex of Filamentous Virus", J Mol Biol (1981), 146:621–627.

GRAY83: Gray, W R, J E Rivier, R Galyean, L J Cruz, and B M Olivera, "Conotoxin MI. Disulfide bonding and conformational states", J Biol Chem, (1983), 258(20) 12247–51.

GRAY84: Gray, W R, F A Luque, R Galyean, E Atherton, and RC Sheppard, B L Stone, A Reyes, J Alford, M Mcintosh, B M Olivera et al. "Conotoxin GI: disulfide bridges, synthesis, and preparation of iodinated derivatives", Biochemistry, (1984), 23 (12) 2796–802.

GRAY88: Gray, W R, and B M Olivera, "Peptide Toxins from Venomous Conus Snails", Ann Rev Biochem (1988), 27:665–700.

GREC79: Greco, W R, and M T Hakala, "Evaluation of Methods for Estimating the Dissociation Constant of Tight Binding Enzyme Inhibitors", J Biol Chem ( 1979 ), 254: 12104–109.

GREE53: Green, N M, and E Work, "Pancreatic Trypsin Inhibitor: 2 Reactions with Trypsin", Biochem J (1953), 54:347–52.

GUAR89: Cuarino, A, R Giannella, and M R Thompson, "*Citrobacter freundii* Produces an 18-Amino-Acid Heat-Stable Enterotoxin Identical to the 18-amino-acid *Escherichia coli* Heat-Stable Enterotoxin (ST Ia)", Infection And Immunity (1989), 27(2)649–52.

GUDM89: Gudmundsdottir, A, P E Bell, M D Lundrigan, and C Bradbeer, and R J Kadner, "Point mutations in a conserved region (TonB box) of *Escherichia coli* outer membrane protein BtuB affect vitamin B12 transport", J Bacteriol, (Dec. 1989), 171(12)6526–33.

GUPT90: Gupta, S K, J L Niles, R T McCluskey, M A Arnaout, "Identity of Wegener's autoantigen (p29) with proteinase 3 and myeloblastin", Blood (Nov. 15 1990), 76(10)2162.

GUSS88: Guss, J M, E A Merritt, R P Phizackerley, R Hedman, M Murata, K O Hodgson, H C Freeman, "Phase Determination by Multiple-Wavelength X-ray Diffraction: Crystal Structure of a Basic "Blue" Copper Protein from Cucumbers", Science (1988), 241:806–11.

GUZM87: Guzman-Verduzco, L-M, and Y M Kupersztoch, "Fusion of *Escherichia coli* Heat-Stable Enterotoxin and Heat-Labile Enterotoxin B Subunit", J Bacteriol (1987), 169:5201–8.

GUZM89: Guzman-Verduzco, L-M, and Y M Kupersztoch, "Rectification of Two *Escherichia coli* Heat-Stable Enterotoxin Allel Sequences and Lack of Biological Effect of Changing the Carboxy-Terminal Tyrosine to Histidine", Infection and Immunity (1989), 57(2)645–48.

GUZM90: Guzman-Verduzco, L-M, and Y M Kupersztoch, "Export and processing analysis of a fusion between the extracellular heat-stable enterotoxin and the periplasmic B subunti of the heat-labile enterotoxin in *Escherichia coli*", Molec Microbiol (1990), 4:253–64.

HALL82: Hall, M N, M Schwartz, and T J Silhavy, "Sequence Information within the lamB Gene is Required for Proper Routing of the Bacteriophage λ Receptor Protein to the Outer Membrane of *Escherichia coli* K-12", J Mol Biol (1982), 156:93–112.

HANC87: Hancock, R E W, "Role of Porins in Outer Membrane Permeability", J Bacteriol (1987), 169:929–33.

HARD90: Hard, T, E Kellenbach, R Boelens, B A Maler, K Dahlman, L P Freedman, J Carlstedt-Duke, K R Yamamoto, J-A Gustafsson, and R Kaptein, "Solution Sturcture of the Glucocorticoid Receptor DNA-Binding Domain", Science (13 Jul. 1990), 249:157–60.

HARK86: Harkki, A, T R Hirst, J Holmgren, and E T Palva, "Expression of the *Escherichia coli* lamB gene in *Vibrio cholerae*", Microb Pathog (1986), 1(3)283–8.

HARK87: Harkki, A, H Karkku, and ET Palva, "Use of lambda vehicles to isolate ompC-lacZ gene fusions in *Salmonella typhimurium* LT2", Mol Gen Genet (1987), 209(3)607–11.

HASH85: Hashimoto, K, S Uchida, H Yoshida, Y Nishiuchi, S Sakakibara, and K Yukari, "Structure-activity relations of conotoxins at the neuromuscular junction", Eur J Pharmacol (1985), 118(3)351–4.

HATA90: Hatanaka, Y, E Yoshida, H Nakayama, and Y Kanaoka, "Synthesis of mu-conotoxin GIIIA: a chemical probe for sodium channels", Chem Pharm Bull (Tokyo), (Jan 1990), 38: 236–8.

HECH90: Hecht, M H, J S Richardson, D C Richardson, and R C Ogden, "De Novo Design, Expression, and Characterization of Felix: A Four-Helix Bundle Protein of Native-Like Sequence", Science, (24 Aug. 1990), 249:884–91.

HEDE89: Hedegaard, L, and P Klemm, "Type 1 fimbriae of *Escherichia coli* as carriers of heterologous antigenic sequences", Gene, (Dec. 21 1989), 85(1) 115–24.

HEIJ90: Heijne, G yon, and C Manoil, "Review: Membrane proteins: from sequence to structure", Protein Engineering (1990), 4(2)109–112.

HEIN87: Heine, H G, J Kyngdon, and T Ferenci, "Sequence determinants in the lamb gene of *Escherichia coli* influencing the binding and pore selectivity of maltoporin", Gene (1987), 53:287–92.

HEIN88: Heine, H G, G Francis, K S Lee, and T Ferenci, "Genetic analysis of sequences in maltoporin that contribute to binding domains and pore structure.", J Bacteriol (April 1988), 170:1730–8.

HEIT89: Heitz, A, L Chiche, D Le-Nguyen, and B Castro, "$^1$H 2D NMR and Distance Geometry Study of the Folding of *Ecballium elaterium* Trypsin Inhibitor, a Member of the Squash Inhibitor Family", Biochem (1989), 28:2392–98.

HENR87: Henriksen, A Z, and J A Maeland, "The Porin Protein of the Outer Membrane of *Escherichia coli*: Reactivity in Immunoblotting, Antibody-binding by the Native Protein, and Cross-Reactivity with other Enteric Bacteria", Acta path microbiol immunol scand, Sect B (1987), 95:315–321.

HIDA90: Hidaka, Y, K Sato, H Nakamura, J Kobayashi, Y Ohizumi, and Y SHimonishi, "Disulfide Pairings in geographutoxin I, a peptide neurotoxin from *Conus geographus*", FEBS Lett (1990), 264(1)29–32.

HILL89: Hillyard, D R, B M Olivera, S Woodward, G P Corpuz, W R Gray, C A Ramilo, L J Cruz, "A Molluscivorus Conus Toxin: Conserved Framework in Conotoxins", Biochem (1989), 28:358–61.

HINE80: Hines, J C, and D S Ray, "Construction and characterization of new coliphage M13 cloning vectors.", Gene (1980), 11:(3–4)207–18.

HOCH84: Hoschstrasser, K, and E Wachter, "Elastase inhibitors, a process for their preparation and medicaments containing these inhibitors", U.S. Pat. No. 4,485,100 (27 Nov. 1984).

HOCJ85: Ho, C, M Jasin, and P Schimmel, "Amino acid replacements that compensate for a large polypeptide deletion in an enzyme", Science (1985), 229:389–93.

HOJI82: Hojima, Y, J V Pierce, and J J Pisano, "Pumpkin Seed Inhibitor of Human Factor $XII_a$ (activated Hageman Factor) and Bovine Trypsin", Biochem (1982), 21:3741–46.

HOLA89a: Holak, T A, D Gondol, J Otlewski, and T Wilusz, "Determination of the Complete Three-Dimensional Structure of the Trypsin Inhibitor from Squash Seeds in Aqueous Solution by Nuclear Magnetic Resonance and a Combination of Distance Geometry and Dynamic Simulated Annealing", J Mol Biol (1989), 210:635–648.

HOLA89b: Holak, T A, W Bode, R Huber, J Otlewski, and T Wilusz, "Nuclear magnetic resonance solution and X-ray structures of squash trypsin inhibitor exhibit the same conformation of the proteinase binding loop", J Mol Biol (Dec. 5 1989), 210(3)649–54.

HORV89: Horvat, S, B Grgas, N Raos, and V I Simeon, "Synthesis and acid ionization constants of cyclic cystine peptides

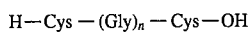

(n=0–4)", Int J Peptide Protein Res (1989), 34:346–51.

HOOP87: Hoopes, B C, and W R McClure, "Strategies in Regulation of Transcription Initiation", Volume 2, Chapter 75, p 1231–1240, *Escherichia coli* and *Salmonella typhimurium*: Cellular and Molecular Biology, Neidhardt, F C, Editor-in-Chief, Amer Soc for Microbiology, Washington, DC, 1987.

HOUG84: Houghten, R A, J M Ostresh, and F A Klipstein, "Chemical synthesis of an octadecapeptide with the biological and immunological properties of human heat-stable *Escherichia coli* enterotoxin", Eur J Biochem (1984), 145:157–162.

HUBB86: Hubbard, R C, and R G Crystal, "Antiproteases and Antioxidants: Strategies for the Pharmacologic Prevention of Lung Destruction", Respiration (1986), 50(Suppl 1)56–73.

HUBB89: Hubbard, R C, M A Casolaro, M Mitchell, S E Sellers, F Arabia, M A Matthay, and R G Crystal, "Fate of aerosolized recombinant DNA-produced $\alpha$-1-antitrypsin: Use of the epithelial surface of the lower respiratory tract to administer proteins of therapeutic importance", Proc Natl Acad Sci USA (1989), 86:680–4.

HUBE74: Huber, R, D Kukla, W Bode, P Schwager, K Bartels, J Deisenhofer, and W Steigemann, "Structure of the Complex formed by Bovine Trypsin and Bovine Pancreatic Tryspin Inhibitor", J Mol Biol (1974), 89:73–101.

HUBE75: Huber, R, W Bode, D Kukla, and U Kohl, "The Structure of the Complex Formed by Bovine Trypsin and Bovine Pancreatic Trypsin Inhibitor: III. Structure of the Anhydrotrypsin-Inhibitor Complex", Biophys Struct Mechan (1975), 1:189–201.

HUBE77: Huber, R, W Bode, D Kukla, U Kohl, CA Ryan, "The structure of the complex formed by bovine trypsin and bovine pancreatic trypsin inhibitor III. Structure of the anhydro-trypsin-inhibitor complex.", Biophys Struct Mech (1975), 1(3)189–201.

HUTC87: Hutchinson, DCS, "The role of proteases and antiproteases in bronchial secretions", Eur J Respir Dis (1987), 71(Suppl.153)78–85.

HYNE90: Hynes, T R, M Randal, L A Kenedy, C Eigenbrot, and A A Kossiakoff, "X-ray crystal structure of the protease inhibitor domain of Alzheimer's amyloid beta-protein precursor", Biochemistry (1990), 29:10018–10022.

ILIC89: Il'ichev, A A, O O Minenkova, S I Tat'kov, N N Karpyshev, A M Eroshkin, V A Petrenko, and L S Sandakhchiev, "[Production of a viable variant of the M13 phage with a foreign peptide inserted into the basic coat protein] <Original> Poluchenie zhiznesposobnogo varianta faga M13 so vstroennym chuzherodnym peptidom v osnovnoi belok obolochki", Dokl Akad Nauk SSSR, (1989), 307(2)481–3.

INOU82: Inouye, H, W Barnes, and J Beckwith, "Signal Sequence of Alkaline Phosphatase of *Escherichia coli*", J Bacteriol (1982), 149(2)434–439.

INOU86: Inouye, M, and R Sarma, Editors, Protein Engineering: Applications in Science, Medicine, and Industry., Academic Press, New York, 1986.

ITOK79: Ito, K, G Mandel, and W Wickner, "Soluble precursor of an integral membrane protein: Synthesis of procoat protein in *Escherichia coli* infected with bacteriophage M13.", Proc Natl Acad Sci USA (1979), 76:1199–1203.

JANA89: Janatova, J, K B M Reid, and A C Willis, "Disulfide Bonds Are Localized within the Short Consensus Repeat Units of Complement Regulatory Proteins: C4b-Binding Protein", Biochem (1989), 28:4754–61.

JANI85: Janin, J, and C Chothia, "Domains in Proteins: Definitions, Location, and Structural Principles", Methods in Enzymology (1985), 115(28)420–430.

JENN89: Jennings, P A, M M Bills, D O Irving, and J S Mattick, "Fimbriae of Bacteroides nodosus: protein engineering of the structural subunit for the production of an exogenous peptide", Protein Eng, (Jan 1989), 2(5)365–9.

JERI74a: Jering, H, and H Tschesche, "Replacement of Lysine by Arginine, Phenylalanine, and Tryptophan in the Reactive Site of the Trypsin-Kallikrein Inhibitor (Kunitz)", Angew Chem internat Edit (1974), 13:662–3.

JERI76b: Jering, H, and H Tschesche, "Replacement of Lysine by Arginine, Phenylalanine, and Tryptophan in the Reactive Site of the Bovine Trypsin-Kallekrein Inhibitor (Kunitz) and Change of the Inhibitory Properties", Eur J Biochem (1976), 61:453–63.

JOUB84: Joubert, F J, "Trypsin Isoinhibitors from Momordica Repens Seeds", Phytochemistry (1984), 23:1401–6.

JUDD85: Judd, R C, "Structure and surface exposure of protein IIs of *Neisseria gonorrhoeae* JS3", Infect Immun (1985), 48(2)452–7.

JUDD86: Judd, R C, "Evidence for N-terminal exposure of the protein IA subclass of *Neisseria gonorrhoeae* protein I", Infect Immun (1986), 54(2)408–14.

KABS84: Kabsch, W, and C Sander, "On the use of sequence homologies to predict protein structure: identical pentapeptides can have completely different conformations", Proc Natl Acad Sci USA (1984), 81(4)1075–8.

KAIS87a: Kaiser, C A, D Preuss, P Grisafi, and D Botstein, "Many Random Sequences Functionally Replace the Secretion Signal Sequence of Yeast Invertase", Science (1987), 235:312–7.

KAOR88: Kao, R C, N G Wehner, K M Skubitz, B H Gray, and J R Hoidal, "Proteinase 3, A Distinct Human Polymorphonuclear Leukocyte Proteinase that Produces Emphysema in Hamsters", J Clin Invest (1988), 82:1963–73.

KAPL78: Kaplan, D A, L Greenfield, and G Wilcox, "Molecular Cloning of Segments of the M13 Genome", in The Single-Stranded DNA Phages, Denhardt, D T, D Dressier, and D S Ray editors, Cold Spring Harbor Laboratory, 1978., p461–467.

KATZ86: Katz, B A, and A Kossiakoff, "The Crystallographically Determined Structures of Atypical Stained Disulfides Engineered into Subtilisin", J Biol Chem (1986), 216(33)15480–85.

KATZ90: Katz, B, and A A Kossiakoff, "Crystal Structures of Subtilisin BPN' Variants Containing Disulfide Bonds and Cavities: Concerted Structural Rearrangements Induced by Mutagenesis", Proteins, Struct, Funct, and Genet (1990), 7:343–57.

KAUM86: Kaumerer, J F, J O Polazzi, and M P Kotick, "The mRNA for a proteinase inhibitor related to the HI-30 domain of inter-$\alpha$-trypsin inhibitor also encodes $\alpha_1$-microglobulin (protein HC)", Nucleic Acids Res (1986), 14:7839–7850.

KIDO88: Kido, H, Y Yokogoshi, and N Katunuma, "Kunitz-type Protease Inhibitor Found in Rat Mast Cells", J Biol Chem (1988), 263:18104–7.

KIDO90: Kido, H, A Fukutomi, J Schelling, Y Wang, B Cordell, and N Katunuma, "Protease-Specificity of Kunitz Inhibitor Domain of Alzheimer's Disease Amyloid Protein Precursor", Biochem & Biophys Res Comm (16 Mar. 1990), 167(2)716–21.

KING86: King, T C, R Sirdeskmukh, and D Schlessinger, "Nucleolytic processing of ribonucleic acid transcripts in procaryotes", Microbiol Rev (1986), 50(4)428–51.

KISH85: Kishore, R, and P Balaram, "Stablization of gamma-Turn Conformations in Peptides by Disulfide Bridges", Biopolymers (1985), 24:2041–43.

KOBA89: Kobayashi, Y, T Ohkubo, Y Kyogoku, Y Nishiuchi, S Sakakibara, W Braun, nad N Go, "Solution Conformation of Conotoxin GI Determined by $^1$H Nuclear Magnetic Resonance Spectroscopy and Distance Geometry Calculations", Biochemistry (1989), 28:4853–60.

KUBO89: Kubota, H, Y Hidaka, H Ozaki, H Ito, T Hirayama, Y Takeda, and Y Shimonishi, "A Long-acting Heat-Stable Enterotoxin Analog of Enterotoxigenic *Esherichia coli* with a Single D-Amino Acid.", Biochem Biophys Res Comm (1989), 161:229–235.

KUHN85a: Kuhn, A, and W Wickner, "Conserved Residues Of the Leader Peptide Are Essential for Cleavage by Leader Peptidase", J Biol Chem (1985), 260:15914–15918.

KUHN85b: Kuhn, A, and W Wickner, "Isolation of Mutants in M13 Coat Protein That Affect Its Synthesis, Processing, and Assembly into Phage", J Biol Chem (1985), 260:15907–15913.

KUHN87: Kuhn, A, "Bacteriophage M13 Procoat Protein Inserts into the Plasma Membrane as a Loop Structure", Science (1987), 238:1413–1415.

KUHN88: Kuhn, A, "Alterations-in the extracellular domain of M13 procoat protein make its membrane insertion dependent on secA and secY", Eur J Biochem (1988), 177(2)267–71.

KUKS89: Kuks, P F M, C Creminon, A-M Leseney, J Bourdais, A Morel, and P Cohen, "*Xenopus laevis* Skin Arg-Xaa-Val-Arg-Gly-endoprotease", J Biol Chem (1989), 264 (25) 14609–12.

KUOM90: Kuo, M D, S S Huang, and J S Huang, "Acidic fibroblast growth factor receptor purified from bovine liver is a novel protein tyrosine kinase." J Biol Chem (1990), 265(27)16455–63.

KUPE 90: Kupersztoch, Y M, K Tachias, C R Moomaw, L A Dreyfus, R Urban, C Slaughter, and S Whipp, "Secretion of Methanol-Insoluble Heat-Stable Enterotoxin ($ST_B$): Energy- and secA-Dependent Conversion of Pre-$ST_B$ to an Intermediate Indistingurisable from the Extracellular Toxin", J Bacteriol (1990), 172(5)2427–32.

LAMB90: Lambert, P, H Kuroda, N Chino, T X Watanabe, T Kimura, and S Sakakibara, "Solution Synthesis of Charybdotoxin (ChTX), A $K^+$ Channel Blocker", Biochem Biophys Res Comm (1990), 170(2)684–690.

LAND87: Landick, R, and C Yanofsky, "Transcription Attenuation", Volume 2, Chapter 77, p. 1276–1301, *Escherichia Coli* and *Salmonella typhimurium*: Cellular and Molecular Biology, Neidhardt, F C, Editor-in-Chief, Amer Soc for Microbiology, Washington, DC, 1987.

LASK80: Laskowski, M, Jr, and I Kato,. "Protein Inhibitors of Proteases", Ann Rev Biochem (1980), 49:593–626.

LAZU83: Lazure, C, N G Seidah, M Chretien, R Lallier, and S St-Pierre, "Primary structure determination of *Escherichia coli* heat-stable enterotoxin of porcine origin", Canadian J Biochem Cell Biol (1983), 61:287–92.

LECO87: Lecomte, J T J, D Kaplan, M Llinas, E Thunberg, and G Samuelsson, "Proton Magnetic Resonance Characterization of Phoratoxins and Homologous Proteins Related to Crambin", Biochemistry (1987), 26:1187–94.

LEEB71: Lee, B, and F M Richards, "The interpretation of protein structures: estimation of static accessibility.", J Mol Biol (1971), 55: (3)379–400.

LEEC83: Lee, C H, S L Moseley, H W Moon, S C Whipp, C L Gyles, and M So, "Characterization of the Gene Encoding Heat-Stable Toxin II and Preliminary Molecular Epidemiological Studies of Enterotoxigenic *Escherichia coli* Heat-Stable Toxin II Producers", Infection and Immunity (1983), 42:264–268.

LEEC86: Lee, C, and J Beckwith, "Cotranssational and Posttranslational Protein Translocation in Prokaryotic systems", Ann Rev Cell Biol (1986), 2:315–336.

LENG89b: Le-Nguyen, D, D Nalis, and B Castro, "Solid phase synthesis of a trypsin inhibitor isolated from the Cucurbitaceae *Ecballium elaterium*", Int J Peptide Protein Res (1989), 34:492–97.

LISS85: Liss, L R, B L Johnson, and D B Oliver, "Export defect adjacent to the processing site of staphylococcal nuclease is suppressed by a prlA mutation", J Bacteriol (1985), 164(2)925–8.

LOPE85a: Lopez, J, and R E Webster, "Assembly site of bacteriophage f1 corresponds to adhesion zones between the inner and outer membranes of the host cell", J Bacteriol (1985), 163(3) 1270–4.

LOPE85b: Lopez, J, and R E Webster, "fiPB and fipC: two bacterial loci required for morphogenesis of the filamentous bacteriophage f1", J Bacteriol (1985), 163 (3)900–5.

LOSI86: Losick, R, P Youngman, and P J Piggot, "Genetics of Endospore formation in *Bacillus subtilis*", Ann Rev Genet (1986), 20:625–669.

LUGT83: Lugtenberg, B, and L van Alphen, "Molecular Architecture and Function of-the-Outer Membrane of *Escherichia coli* and other Gram-Negative Bacteria", Biochim Biophys Acta (1983), 737:51–115.

LUIT83: Luiten, R G M, J G G Schoenmakers, and R N H Konings, "The major coat protein gene of the filamentous *Pseudomonas aeruginosa* phage Pf3: absence of an N-terminal leader signal sequence", Nucleic Acids Research (1983), 11(22)8073–85.

LUIT85: Luiten, R G M, D G Putterman, J G G Schoenmakers, R N H Konings, and L A Day, "Nucleotide Sequence of the Genome of Pf3, an IncP-1 Plasmid-Specific Filamentous Bacteriophage of *Pseudomonas aeruginosa*", J Virology, (1985), 56(1) 268–276.

LUIT87: Luiten, R G M, R I L Eggen, J G G Schoenmakers, and R N H Konings, "Spontaneous Deletion Mutants of Bacteriophage Pf3: Mapping of Signals Involved in Replication and Assembly", DNA (1987), 6(2)129–37.

LUND86: Lundeen, M, "Preferences of the Side Chains in Proteins for Helix, Beta Strand, Turn, and Other Conformations. Secondary Structures of Copper Proteins", J Inorgan Biochem (1986), 27: 151–62.

MACH89: Machleidt, W, U Thiele, B Laber, I Assfalg-Machleidt, A Esterl, G Wiegand, J Kos, V Turk, and W Bode, "Mechanism of inhibition of papain by chicken egg white cystatin", FEBS Lett (1989), 243(2)234–8.

MACI88: MacIntyre, S, R Freudl, M L Eschbach, and U Henning, "An artificial hydrophobic sequence functions as either an anchor or a signal sequence at only one of two positions within the *Escherichia coli* outer membrane protein OmpA", J Biol Chem (1988), 263(35)19053–9.

MAKO80: Makowski, L, D L D Caspar, and D A Marvin, "Filamentous Bacteriophage Pf1 Structure Determined at 7 A Resolution by Refinement of Models for the alpha-Helical Subunit.", J Mol Biol (1980), 140:149–181.

MALA64: Malamay, M H, and B L Horecker, "Release of alkaline phosphotase from cells of *E. coli* upon lysozyme spheroplast formation", Biochem (1964), 3:1889–1893.

MANI82: Maniatis, T, E F Fritsch, and J Sambrook, *Molecular Cloning*, Cold Spring Harbor Laboratory, 1982.

MANO86: Manoil, C, and J Beckwith, "A Genetic Approach to Analyzing Membrane Protein Topology", Science (1986), 233:1403–1408.

MANO88: Manoil, C, D Boyd, and J Beckwith, "Molecular genetic analysis of membrane protein topology", Topics in Genetics (1988), 4(8)223–6.

MARK86: Marks, C B, M Vasser, P Ng, W Henzel, and S Anderson, "Production of native, correctly folded bovine pancreatic trypsin inhibitor in *Escherichia coli*", J Biol Chem (1986), 261:7115–7118.

MARK87: Marks, C B, H Naderi, P A Kosen, I D Kuntz, and S Anderson, "Mutants of Bovine Pancreatic Trypsin Inhibitor Lacking Cysteines 14 and 38 Can Fold Properly", Science (1987), 235:1370–1373.

MARQ83: Marquart, M, J Walter, J Deisinhoffer, W Bode, and R Huber, "The geometry of the reactive site and of the peptide groups in trypsin, trypsinogen, and its complexes with inhibitors", Acta Cryst, B (1983), 39:480ff.

MARV75: Marvin, D A and E J Wachtel, "Structure and assembly of filamentous bacterial viruses", Nature (1975), 253: 19–23.

MARV78: Marvin, DA, "Structure of the Filamentous Phage Virion", in *The Single-Stranded DNA Phages*, Denhardt, D T, D Dressier, and D S Ray editors, Cold Spring Harbor Laboratory, 1978., p583–603.

MARV80: Marvin, D, and L Makowski, "Helical Viruses", Progr Clin Biol Res (1980), 40:347–48.

MASS90: Massefski, W, Jr, A G Redfield, D R Hare, and C Miller, "Molecular Structure of Charybdotoxin, a Pore-Directed Inhibitor of Potassium Ion Channels", Science (3 Aug. 1990), 249:521–524.

MATS89: Matsumura, M, W J Becktel, M Levitt, and B W Matthews, "Stabilization of phage T4 lysozyme by engineered disulfide bonds", Proc Natl Acad Sci USA (1989), 86:6562–6.

MCCA90: McCafferty, J, A D Griffiths, G Winter, and D J Chiswell, "Phage antibodies: filamintous phage displaying antibody variable domains", Nature, (6 Dec. 1990), 348:552–4.

MCKE85: McKern, N M, I J O'Donnell, D J Stewart, and B L Clark, "Primary structure of pilin protein from Bacteroides nodosus strain 216: comparison with the corresponding protein from strain 198", J Gen Microbiol (1985), 131(Pt 1)1–6.

MCPH85: McPhalen, C A, H P Schnebli, and M N G James, "Crystal and molecular structure of the inhibitor eglin from leeches in complex with subtilisin Carlsberg", FEBS Lett (1985), 188(1)55–8.

MCWH89: McWherter, C A, W F Walkenhorst, E J Campbell, and G I Glover, "Novel Inhibitors of Human Leukocyte Elastase and Cathepsin G. Sequence Variants of Squash Seed Protease Inhibitor with Altered Protease Selectivity", Biochemistry (1989), 28:5708–14.

MEDV89: Medved, L V, T F Busby, and K C Ingham, "Calorimetric Investigation of the Domain Structure of Human Complement C1s: Reversible Unfolding of the Short Consensus Repeat Units", Biochem (1989), 28:5408–14.

MESS77: Messing, J, B Gronenborn, B Muller-Hill, and P H Hofschneider, "Filamentous coliphage M13 as a cloning vehicle: insertion of a HindII fragment of the lac regulatory region in M13 replicative form in vitro.", Proc Natl Acad Sci USA (1977), 74:3642–6.

MESS78: Messing, J, and B Gronenborn, "The Filamentous Phage M13 as a Carrier DNA for Operon Fusions In Vitro.", in *The Single-Stranded DNA Phages*, Denhardt, D T, D Dressier, and D S Ray editors, Cold Spring Harbor Laboratory, 1978.,p449–453.

MILL87a: Miller, S, J Janin, A M Lesk, and C Chothia, "Interior and Surface Monomeric Proteins", J Mol Biol (1987), 196:641–656.

MILL87b: Miller, E S, J Karam, M Dawson, M Trojanowska, P Gauss, and L Gold, "Translational repression: biological activity of plasmid-encoded bacteriophage T4 RegA protein.", J Mol Biol (1987), 194:397–410.

MISR88a: Misra, R, and S A Benson, "Genetic identification of the pore domain of the OmpC porin of *Escherichia coli* K-12", J Bacteriol (1988), 170(8)3611–7.

MISR88b: Misra, R, and S A Benson, "Isolation and Characterization of OmpC Porin Mutants with Altered Pore Properties", J Bacteriol (1988), 170:528–33.

MOLL89: Molla, A, A Charbit, A Le Guern, A Ryter, and M Hofnung, "Antibodies against synthetic peptides and the topology of LamB, an outer membrane protein from *Escherichia coli* K12", Biochem (1989), 28(20)8234–41.

MORS87: Morse, S A, T A Mietzner, G Bolen, A Le Faou, and G Schoolnik, "Characterization of the major iron-regulated protein of *Neisseria gonorrhoeae* and *Neisseria meningitidis*", Antonie Van Leeuwenhoek (1987), 53(6)465–9.

MORS 88: Morse, S A, C-Y Chen, A LeFaou, and T A Meitzner, "A Potential Role for the Major Iron-Regulated Protein Expressed by Pathogenic Neisseria Species", Rev Infect Dis (1988), 10(Suppl 2)S306–10.

MOSE82: Moses, P B, and K Horiuchi, "Effects of Transposition and Delection upon Coat Protein Gene Expression in Bacteriophage f1", Virology (1982), 119:231–244.

MOSE83: Moser, R, R M Thomas, and B Gutte, "An Artificial Crystalline DDT-binding polypeptide", FEBS Letters (1983), 157:247–251.

MOSE85: Moser, R, S Klauser, T Leist, H Langen, T Epprecht, and B Gutte, "Applications of Synthetic Peptides", Angew Chemie, Int Edition English (1985), 24(9)719–27.

MOSE87: Moser, R, S Frey, K Muenger, T Hehlgans, S Klauser, H Langen, E-L Winnacker, R Mertz, and B Gutte, "Expression of the synthetic gene of an artificial DDT-binding polypeptide in *Escherichia coli*", Protein Engineering (1987), 1:339–343.

NADE87: Nadel, J A, and B Borson, "Secretion and ion transport in airways during inflammation", Biorheology (1987), 24:541–549.

NADE90: Nadel, J A, "Neutrophil Proteases and Mucus Secretion", 1990 Cystic Fibrosis Meeting, Arlington, Va., p156.

NAKA81: Nakashima, Y, B Frangione, R L Wiseman, W H Konigsberg, "Primary Structure of the Major Coat Protein of the Filamentous Bacterial Viruses, If1 and Ike", J Biol Chem (1981), 256(11)5792–7.

NAKA86a: Nakae, T, J Ishii, and T Ferenci, "The Role of the Maltodextrin-binding Site in Determining the Transport Properties of the Lamb Protein", J Biol Chem (1986), 261:622–26.

NAKA86b: Nakae, T, "Outer-Membrane Permeability of Bacteria", CRC Crit Rev Microbiol (1986), 13:1–62.

NAKA87: Nakamura, T, T Hirai, F Tokunaga, S Kawabata, and S Iwanaga, "Purification and Amino Acid Sequence of Kunitz-type Protease Inhibitor Found in the Hemocytes of Horseshoe Crab (*Tachypleus tridentatus*)", J Biochem (1987), 101:1297–1306.

NICH88: Nicholson, H, W J Becktel, and B W MAtthews, "Enhanced protein thermostability from desgined mutations that interact with α-helix dipoles", Nature (1988), 336:651–56.

NIKA84: Nikaido, H, and H C P Wu, "Amino acid sequence homology among the major outer membrane proteins of *Escherichia coli*", Proc Natl Acad Sci USA (1984), 81:1048–52.

NILE89: Niles, J L, R T McCluskey, M F Ahmad, and M A Arnaout, "Wgener's Granulomatosis Autoantigen Is a Novel Neutrophil Serine Proteinase", Blood (1989), 74(6)1888–93.

NISH82: Nishiuchi, Y, and S Sakakibara, "Primary and secondary structure of conotoxin GI, a neurotoxic tridecapeptide from a marine snail", FEBS Lett (1982), 148:260–2.

NISH86: Nishiuchi, Y, K Kumagaye, Y Noda, T X Watanabe, and S Sakakibara, "Synthesis and secondary-structure determination of omega-conotoxin GVIA: a 27-peptide with three intramolecular disulfide bonds", Biopolymers, (1986), 25:S61–8.

NORR89a: Norris, K, and L C Petersen, "Aprotinin analogues and process for the production thereof", European Patent Application 0 339 942 A2.

NORR89b: Norris, K, F Norris, S BJorn, "Aprotinin Homologues and Process for the Production of Aprotinin and aprotinin homologues in Yeast", PCT patent application WO89/01968.

OAST88: Oas, T G, and P S Kim, "A peptide model of a protein folding intermediate", Nature (1988), 336:42–48.

ODOM90: Odom, L, "Inter-α-trypsin inhibitor: a plasma proteinase inhibitor with a unique chemical structure", Int J Biochem (1990), 22: 925–930.

OHKA81: Ohkawa, I, and R E Webster, "The Orientation of the Major Coat Protein of Bacteriophage f1 in the Cytoplasmic Membrane of *Esherichia coli.*", J Biol Chem (1981), 256:9951–9958.

OKAM87: Okamoto, K, K Okamoto, J Yukitake, Y Kawamoto, and A Miyama, "Substitutions of Cysteine Residues of *Escherichia coli* Heat-Stable Enterotoxin by Oligonucleotide-Directed Mutagenesis", Infection and Immunity (1987), 55:2121–2125.

OKAM88: Okamoto, K, K Okamoto, J Yukitake, and A Miyama, "Reduction of Enterotoxic Activity of *Escherichia coli* Heat-Stable Enterotoxin by Substitution for an Aspartate Residue", Infection and Immunity (1988), 56:2144–8.

OKAM90: Okamoto, K, and M Takahara, "Synthesis of *Escherichia coli* Heat-Stable Enterotoxin STp as a Pre-Pro Form and Role of the Pro Sequence in Secretion", J Bacteriol (1990), 172(9)5260–65.

OLIP86: Oliphant, A R, A L Nussbaum, and K Struhl, "Cloning of random-sequence oligodeoxynucleotides", Gene (1986), 44:177–183.

OLIP87: Oliphant, AR, and K Struhl "The Use of Random-Sequence Oligonucleotides for Determining Consensus Sequences", in *Methods in Enzymology* 155 (1987)568–582. Editor Wu, R; Academic Press, New York.

OLIV85a: Oliver, D, "Protein Secretion in *Escherichia coli.*", Ann Rev Microbiol (1985), 39: 615–648.

OLIV85b: Olivera, B M, W R Gray, R Zeikus, J M McIntosh, J Varga, J Rivier, V de Santos, and L J Cruz, "Peptide Neurotoxins from Fish Hunting Cone Snails", Science (1985), 230:1338–43.

OLIV87b: Olivera, B M, L J Cruz, V de Santos, G W LeCheminant, D Griffin, R Zeikus, J M McIntosh, R Galyean, J Varga, W R Gray, et al. "Neuronal calcium channel antagonists. Discrimination between calcium channel subtypes using omega-conotoxin from Conus magus venom", Biochemistry, (1987), 26(8)2086–90.

OLIV90a: Olivera, B M, J Rivier, C Clark, C A Ramilo, G P Corpuz, F C Abogadie, E E Mena, S R Woodward, D R Hillyard, L J Cruz, "Diversity of Conus Neuropeptides", Science, (20 Jul. 1990), 249:257–263.

OLIV90b: Olivera, B M, D R Hillyard, J Rivier, S Woodward, W R Gray, G Corpuz, L J Cruz, "Conotoxins: Targeted Peptide Ligands from Snail Venoms", Chapter 20 in Marine Topxins, American Chemical Society, 1990.

OLTE89: Oltersdorf, T, L C Fritz, D B Schenk, I Lieberburg, K L Johnson-Wood, E C Beattie, P J Ward, R W Blacher, H F Dovey, and S Sinha, "The Secreted form of the Alzheimer's amyloid precursor protein with the Kunitz domain is protease nexin-II", Nature (1989), 341:144–7.

ORND85: Orndorff, P E, and S Falkow, "Nucleotide Sequence of pilA, the Gene Encoding the Structural Component of Type 1 Pili in *Escherichia coli*", J Bacteriol (1985), 162:454–7.

OTLE85: Otlewski, J, and T Wilusz, "The Serine Proteinase Inhibitor from Summer Squash (*Cucurbita pepo*): Some Structural Features, Stability and Proteolytic Degradation", Acta Biochim Polonica (1985), 32(4)285–93.

OTLE87: Otlewski, J, H Whatley, A Polanowski, and T Wilusz, "Amino-Acid Sequences of Trypsin Inhibitors from Watermelon (*Citrullus vulgaris*) and Red Bryony (*Bryonia dioica*) Seeds", Biol Chem Hoppe-Seyler (1987), 368:1505–7.

PABO79: Pabo, C O, R T Sauer, J M Sturtevant, and M Ptashne, "The Lambda Repressor Contains Two Domains", Proc Natl Acad Sci USA (1979), 76:1608–1612.

PABO86: Pabo, C O, and E G Suchanek, "Computer-Aided Model Building Strategies for Protein Design", Biochem (1986), 25:5987–91.

PAGE88: Pages, J M, and J M Bolla, "Assembly of the OmpF porin of *Escherichia coli* B. Immunological and kinetic studies of the integration pathway", Eur J Biochem (1988), 176(3)655–60.

PAGE90: Pages, J M, J M Bolla, A Bernadac, and D Fourel, "Immunological approach of assembly and topology of OmpF, an outer membrane protein of *Escherichia coli*", Biochimie (1990), 72:169–76.

PAKU86: Pakula, A A, V B Young, and R T Sauer, "Bacteriophage λ cro mutations: Effects on activity and intracellular degradation.", Proc Natl Acad Sci USA (1986), 83:8829–8833.

PANT87: Pantoliano, M W, R C Ladner, P N Bryan, M L Rollence, J F Wood, and T L Poulos, "Protein Engineering of Subtilisin BPN': Enhanced Stabilization through the Introduction of Two Cysteines To Form a Disulfide Bond", Biochem (1987), 26:2077–82.

PANT90: Pantoliano, MW, and RC Ladner, "Computer Designed Stabilized Proteins and Method for Producing Same", U.S. Pat. No. 4,908,773, 13 Mar. 1990.

PAOL86: Paoletti, E, and D Panicali, "Modified Vaccinia Virus", U.S. Pat. No. 4,603,112, Jul. 29, 1986.

PAPA82: Papamokos, E, E Weber, W Bode, R Huber, M Empie, I Kato, and M Laskowski Jr, "Crystallographic Refinement of Japanese Quail Ovomucoid, a Kazal-type Inhibitor, and Model Building Studies of Complexes with Serine Proteases", J Mol Biol (1982), 158:515–537.

PARD89: Pardi, A, A Galdes, J Florance, and D Maniconte, "Solution Structres of α-Conotoxin G1 Determined by Two-Dimensional NMR Spectroscopy", Biochemistry (1989), 28:5494–5501.

PARG87: Parge, H E, D E McRee, M A Capozza, S L Bernstein, E D Getzoff, and J A Tainer, "Three dimensional structure of bacterial pili", Antonie Van Leeuwenhoek (1987), 53 (6) 447–53.

PARM88: Parmley, S F, and G P Smith, "Antibody-selectable filamentous fd phage vectors: affinity purification of target genes", Gene (1988), 73:305–318.

PARR88: Parraga, G, S J Horvath, A Eisen, W E Taylor, L Hood, E T Young, R E Klevit, "Zinc-Dependent Structures of a Single-Finger Domain of Yeast ADR1", Science (1988), 241:1489–92.

PEAS88: Pease, J H B, and D E Wemmer, Biochem (1988), 27:8491–99.

PEAS 90: Pease, J H B, R W Storrs, and D E Wemmer, "Folding and activity of hybrid sequence, disuylfide-stabilized peptides", Proc Natl Acad Sci USA (1990), 87:5643–47.

PEET85: Peeters, B P H, R M Peters, J G G Schoenmakers, and R N H Konings, "Nucleotide Sequence and Genetic Organization of the Genome of the N-Specific Filamentous Bacteriophage Ike: Comparison with the Genome of the F-Specific Filamentous Phages M13, fd, and f1", J Mol Biol (1985), 181:27–39.

PEET87: Peeters, B P H, J G G Schoenmakers, and R N H Konings, "Comparison of the DNA Sequences Involved in Replication and Packaging of the Filamentous Phages IKe, and Ff (M13, fd, and f1)", DNA (1987), 6(2)139–147.

PERR84: Perry, L J, and R Wetzel, "Disulfide Bond Engineered into T4 Lysozyme: Stablilation of the Protein Toward Thermal Inactivation", Science (1984), 226:555–7.

PERR86: Perry, L J, and R Wetzel, "Unpaired Cysteine-54 Interferes with the Ability of an Engineered Disulfide To Stabilize T4 Lysozyme", Biochem (1986), 25:733–39.

PETE89: Peterson, M W, "Neutrophil cathepsin G increases transendothelial albumin flux", J Lab Clin Med (1989), 113(3)297–308.

PONT88: Ponte, P, P Gonzalez-DeWhitt, J Schilling, J Miller, D Hsu, B Greenberg, K Davis, W Wallace, I Liederburg, F Fuller, and B Cordell, "A new A4 amyloid mRNA contains a domain homologous to serine proteinase inhibitors", Nature (1988), 331:525–7.

POTE83: Poteete AR, "Domain Structure and Quaternary Organization of the Bacteriophage P22 Erf Protein.", J Mol Biol (1983), 171.:401–418.

QUIO87: Quiocho, F A, N K Vyas, J S Sack and M A Storey, "Periplasmic Binding Proteins: Structure and New Understanding of Protein-Ligand Interactions", in Crystallography in Molecular Biology, Moras, D. et al., editors, Plenum Press, 1987.

RAND87: Randall, L L, S J S Hardy, and J R Thom, "Export of Protein: A Biochemical View", Ann Rev Microbiol (1987), 41:507–41.

RASC86: Rasched, I, and E Oberer, "Ff Coliphages: Structural and Functional Relationships", Microbiol Rev (1986) 50:401–427.

RASH84: Rashin, A, "Prediction of Stabilities of Thermolysin Fragments", Biochemistry (1984), 23:5518.

RAYC87: Ray, C, K M Tatti, C H Jones, and C P Moran Jr, "Genetic Analysis of RNA Polymerase-Promoter Interaction during Sporulation in *Bacillus subtilis*", J Bacteriol (1987), 169(5)1807–1811.

REID88a: Reidhaar-Olson, J F, and R T Sauer, "Combinatorial Cassette Mutagenesis as a Probe of the Information Content of Protein Sequences", Science (1988), 241:53–57.

REID88b: Reid, J, H Fung, K Gehring, P E Klebba, and H Nikaido, "Targeting of porin to the outer membrane of *Escherichia coli*. Rate of trimer assembly and identification of a dimer intermediate", J Biol Chem (1988), 263(16)7753–9.

REST88: Rest, R F, "Human Neutrophil and Mast Cell Proteases Implicated in Inflammation", Meth Enzymol (1988), 163:309–27.

RICH81: Richardson, JS, "The Anatomy and Taxonomy of Protein Structure", Adv Protein Chemistry (1981), 34:167–339.

RICH86: Richards, J H, "Cassette mutagenesis shows its strength.", Nature (1986), 323:187.

RITO83: Ritonja, A, B Meloun, and F Gubensek, "The Primary Structure of *Vipera ammodytes* venom chymotrypsin inhibitor", Biochim Biophys Acta (1983), 746:138–145.

RIVI87b: Rivier, J, R Galyean, WR Gray, A Azimi-Zonooz, J M McIntosh, L J Cruz, and B M Olivera, "Neuronal calcium channel inhibitors. Synthesis of omega-conotoxin GVIA and effects on 45Ca uptake by synaptosomes", J Biol Chem, (1987), 262(3)1194–8.

ROBE86: Roberts, S, and A R Rees "The cloning and expression of an anti-peptide antibody: a system for rapid analysis of the binding properties of engineered antibodies.", Protein Engineering (1986), 1:59–65.

RONC90: Ronco, J, A Charbit, and M Hofnung, "Creation of targets for proteolytic cleavage in the LamB protein of *E coli* K12 by genetic insertion of foreign sequences: implications for topological studies", Biochimie (1990), 72(2–3)183–9.

ROSE85: Rose, G D, "Automatic Recognition of Domains in Globular Proteins", Methods in Enzymololgy (1985), 115(29)430–440.

ROSS81: Rossman, M, and P Argos, "Protein Folding.", Ann Rev Biochem (1981), 50:497–532.

RUEH73: Ruehlmann, A, D Kukla, P Schwager, K Bartels, and R Huber, "Structure of the Complex formed by Bovine Trypsin and Bovine Pancreatic Trypsin Inhibitor: Crystal Structure Determination and Stereochemistry of the Contact Region", J Mol Biol (1973), 77:417–436.

RUSS81: Russel, M, and P Model, "A mutation dowanstream from the signal peptidase cleavage site affects cleavage but not membrane insertion of phage coat protein.", Proc Natl Acad Sci USA (1981), 78:1717–1721.

SALI64: Salivar, WO, H Tzagoloff, and D Pratt, "Some physical, chemical, and biological properties of the rod-shaped coliphage M13", Virology (1964), 24: 359–71.

SALI87: Salier, J P, M Diarra-Mehrpour, R Sesboue, J Bourguignon, R Benarous, I Ohkubo, S Kurachi, K Kurachi, and J P Martin, "Isolation and characterization of cDNAs encoding the heavy chain of human inter-alphy-trypsin inhibitor (IaTI): Unambiguous evidence for multipolypeptide chain sturcture of IaTI", Proc Nat Acad Sci USA (1987), 84:8271–8276.

SALI88: Sali, D, M Bycroft, and A R Fersht, "Stabilization of protein structure by interaction of α-helix dipole with a charged side chain", Nature (1988), 335:740–3.

SALI 90: Salier, J-P, "Inter-α-trypsin inhibitor: emergence of a family within the Kunitz-type protease inhibitor superfamily", TIBS (1990), 15:435–439.

SALV87: Salvesen, G, D Farley, J Shuman, A Przybyla, C Reilly, and J Travis, "Molecular Cloning of Human Cathepsin G: Structural Similarity to Mast Cell and Cytotoxic T Lymphocyte Proteinases", Biochem (1987),26:2289–93.

SAMB89: Sambrook, J, E F Fritsch, and T Maniatis, Molecular Cloning, A Laboratory Manual, Second Edition, Cold Spring Harbor Laboratory, 1989.

SASA84: Sasaki, T, "Amino Acid Sequence of a Novel Kunitz-type chymotrypsin inhibitor from hemolymph of silkworm larvae, *Bombyx mori*", FEBS Lett (1984), 168:227–230.

SAUE86: Sauer, R T, K Hehir, R S Stearman, M A Weiss, A Jeitler-Nilsson, E G Suchanek, and C O Pabo, "An Engineered Intersubunit Disulfide Enhances the Stability and DNA Binding of the N-Terminal Domain of λ Repressor", Biochem (1986), 25:5992–98.

SCHA78: Schaller, H, E Beck, and M Takanami, "Sequence and Regulatory Signals of the Filamentous Phage Genome.", in *The Single-Stranded DNA Phages*, Denhardt, D. T., D. Dressier, and D. S. Ray editors, Cold Spring Harbor Laboratory, 1978., p139–163.

SCHN86: Schnabel E, W Schroeder, and G Reinhardt, "[Ala$_2^{14,38}$]Aprotinin: Preparation by Partial Desulphurization of Aprotinin by Means of Raney Nickel and Comparison with other Aprotinin Derivatives", Biol Chem Hoppe-Seyler (1986), 367:1167–76.

SCHN88a: Schnabel, E, G Reinhardt, W Schroeder, H Tschesche, H R Wenzel, and A Mehlich, "Enzymatic Resynthesis of the 'Reactive Site' Bond in the Modified Aprotinin Derivatives [Seco-15/16]Aprotinin and [Di-seco-15/16,39/40]Aprotinin", Biol Chem Hoppe-Seyler (1988), 369:461–8.

SCHU79: Schulz, G E, and R H Schirmer, *Principles of Protein Structure*, Springer-Verlag, New York, 1979.

SCHW87: Schwarz, H, H J Hinz, A Mehlich, H Tschesche, and H R Wenzel, "Stability studies on derivatives of the bovine pancreatic trypsin inhibitor.", Biochemistry (1987), 26: (12)p3544–51.

SCOT87a: Scott, M J, C S Huckaby, I Kato, W J Kohr, M Laskowski Jr., M-J Tsai and B W O'Malley, "Ovoinhibitor Introns Specify Functional Domains as in the Related and Linked Ovomucoid Gene", J Biol Chem (1987), 262(12)5899–5907.

SCOT87b: Scott, C F, H R Wenzel, H R Tschesche, and R W Colman, "Kinetics of Inhibition of Human Plasma Kallikrein by a Site-Specific Modified Inhibitor Arg$^{15}$-Aprotinin: Evaluation Using a Microplate System and Comparison With Other Proteases", Blood (1987), 69:1431–6.

SCOT90: Scott, J K, and G P Smith, "Searching for Peptide Ligands with an Epitope Library", Science, (27 July 1990), 249:386–390.

SEKI85: Sekizaki, T, H Akaski, and N Terakado, "Nucleotide sequences Of the genes for *Escherichia coli* heat-stable enterotoxin I of bovine, avian, and porcine origins", Am J Vet Res (1985), 46:909–12.

SELL87: Selloum, L, M Davril, C Mizon, M Balduyck, and J Mizon, "The effect of the glycosaminoglycan chain removal on some properties of the human urinary trypsin inhibitor", Biol Chem Hoppe-Seyler (1987), 368:47–55.

SERW87: Serwer, P, "Review: Agarose Gel Electrophoresis of Bacteriophages and Related Particles", J Chromatography (1987), 418:345–357.

SHIM87: Shimonishi, Y, Y Hidaka, M Koizumi, M Hane, S Aimoto, T Takeda, T Miwatani, and Y. Takeda, "Mode of disulfide bond formation of a heat-stable enterotoxin ($ST_h$) produced by a human strain of enterotoxigenic *Escherichia coli*", FEBS Lett (1987), 215:165–170.

SHOR81: Shortle, D, D Koshland, G M Weinstock, and D Botstein, "Segment-directed mutagenesis: Construction in vitro of point mutations limited to a small predetermined region of a circular DNA molecule", Proc Natl Acad Sci USA (1980), 77:5375–79.

SHOR85: Shortle, D, and B Lin, "Genetic Analysis of Staphylococcal Nuclease: Identification of Three Intragenic 'Global' Suppressors of Nuclease-Minus Mutations.", Genetics (1985), 110:539–555.

SIEK87: Siekmann, J, H R Wenzel, W Schroeder, H Schutt, E Truscheit, A Arens, E Rauenbusch, W H CHazin, K Wutrich, and H Tschesche, "Pyroglutamul-aprotinin, a new aprotinin homologue from bovine lungs-isolation, properties, sequence analysis nad characterization using $^1$H nuclear magnetic resonance in solution", Biol Chem Hoppe-Seyler (1987), 368:1589–96.

SIEK88: Siekmann, J, H R Wenzel, W Schroeder, and H Tschesche, "Characterization and Sequence Determination of Six Aprotinin homologues from bovine lungs", Biol Chem Hoppe-Seyler (1988), 369: 157–163.

SIEK89: Siekmann, J, J Beckmann, A Mehlich, H R Wenzel, H Tschesche, E Schnabel, W Mueller-Esterl, "Immunological Characterization of Natural and Semisynthetic Aprotinin Variants", Biol Chem Hoppe-Seyler (1989), 370:677–81.

SILH77: Silhavy, T J, H A Shuman, J Beckwith, and M Schwartz, "Use of gene fusions to study outer membrane protein localization in *Escherichia coli*", Proc Natl Acad Sci USA (1977), 74(12)5411–5415.

SILH85: Silhavy, T J, and J R Beckwith, "Uses of lac Fusions for the Study of Biological Problems", Microbiol Rev (1985), 49(4)398–418.

SINH90: Sinha, S, H F Dovey, P Seubert, P J Ward, R W Blacher, M Blaber, R A Bradshaw, M Arici, W C Mobley, and I Lieberburg, "The Protease Inhibitory Properties of the Alzheimer's beta-amyloid Precursor Protein", J Biol Chem (1990), 265(16)8983–5.

SMIT85: Smith G P, "Filamentous Fusion Phage: Novel Expression Vectors That Display Cloned Antigens on the Virion Surface", Science (1985), 228:1315–1317.

SMIT88a: Smith, G P, "Filamentous Phage Assembly: Morphogenetically Defective Mutants That Do Not Kill the Host", Virology (1988), 167:156–165.

SMIT88b: Smith, G P, "Filamentous Phages as Cloning Vectors", Chapter 3 in Vectors: A Survey of Molecular Cloning Vectors and Their Uses, Editors: R L Rodriguez and D T Denhardt, Butterworth, Boston, 1988.

SODE85: Sodergren, E J, J Davidson, R K Taylor, and T J Silhavy, "Selection for Mutants Altered in the Expression or Export of Outer Membrane Porin OmpF", J Bacteriol (1985), 162(3)1047–1053.

SOME85: So, M, E Billyard, C Deal, E Getzoff, P Hagblom, T F Meyer, E Segal, and J Tainer, "Gonococcal Pilus: Genetics and Structure", Curr Top in Microbiol & Immunol (1985), 118:13–28.

SOMM89: Sommerhoff, C P, G A Caughey, W E Finkbeiner, S C Lazarus, C B Basbaum, and J A Nadel, "A Potent Secretagogue for Airway Gland Serous Cells", J Immunol (1989), 142:2450–56.

SOMM90: Sommerhoff, C P, J A Nadel, C B Basbaum, and G H Caughey, "Neutrophil Elastase and Cathepsin G Stimulate Secretion from Cultured Bovine Airway Gland Serous Cells", J Clin Invest (March 1990), 85:682–689.

STAD86: Stader, J, S A Benson, and T J Silhavy, "Kinetic analysis of lamb mutants suggests the signal sequence plays multiple roles in protein export", J Biol Chem (1986), 261(32)15075–80.

STAD89: Stader, J, L J Gansheroff, and T J Silhavy, "New suppressors of signal-sequence mutations, prlG, are linked tightly to the secE gene of *Escherichia coli*", Genes & Develop (1989), 3:1045–1052.

STAT87: States, DJ, T E Creighton, C M Dobson, and M Karplus, "Conformations of intermediates in the folding of the pancreatic trypsin inhibitor.", J Mol Biol (1987), 195(3)731–9.

STEI85: Steiner, BioScience Repts. (1985), 5:973ff.

STUB90: Stubbs, M T, B Laber, W Bode, R Huber, R Jerala, B Lenarcic, and V Turk, "The refined 2.4 521 X-ray crystal structure of recombinant human stefin B in complex with the cysteine proteinase papain: a novel type of proteinase inhibitor interaction", EMBO J (1990), 9(6) 1939–47.

SUNX87: Sun, X P, H Takeuchi, Y Okano, and Y Nozawa, "Effects of synthetic omega-conotoxin GVIA (omega-CgTX GVIA) on the membrane calcium current of an identifiable giant neurone, d-RPLN, of an African giant snail (*Achatina fulica* Ferussac), measured under the voltage clamp condition", Comp Biochem Physiol [C], (1987), 87(2)363–6.

SUTC87a: Sutcliffe, M J, I Haneef, D Carney, and T L Blundell, "Knowledge based modelling of homologous proteins, part I: three-dimensional frameworks derived from the simultaneous superposition of multiple structures", Protein Engineering (1987), 1:377–384.

SUTC87b: Sutcliffe, M J, F R F Hayes, and T L Blundell, "Knowledge based modelling of homologous proteins, part II: rules for the conformations of substituted sidechains", Protein Engineering (1987), 1:385–392.

SVEN82: Svendsen, I B, "Amino Acid Sequence of Serine Protease Inhibitor CI-1 from Barley. Homology with Barley Inhibitor CI-2, Potato Inhibitor I, and Leech Elgin", Carlsberg Res Comm (1982), 47:45–53.

SWAI88: Swaim, M W, and S V Pizzo, "Modification of the tandem reactive centres-of human inter-α-trypsin inhibitor with butanedione and cis-dichlorodiammineplatinum(II)", Biochem J (1988), 254:171–178.

TAKA74: Takahashi, H, S Iwanage, T Kitagawa, Y Hokama, and T Suzuki, "Snake venom proteinase inhibitors. II. Chemical structure of inhibitor II isolated from the venom of Russell's viper (*Vipera russelli*).", J Biochem (1974), 76:721–733.

TAKA85: Takao, T, N Tominaga, S Yoshimura, Y Shimonishi, S Hara, T Inoue, and A Miyama, "Isolation, primary structure and synthesis of heat-stable enterotoxin produced by *Yersinia enterocolitica*", Eur J Biochem (1985), 152:199–206.

TAKE90: Takeda, T, G B Nair, K Suzuki, and Y Shimonishi, "Production of a Monoclonal Antibody to *Vibrio cholerae* Non-01 Heat-Stable Enterotoxin (ST) Which is Cross-Reactive with *Yersinia enterocolitica* ST", Infection and Immunity (1990), 58(9)2755–9.

TANK77: Tan, N H, and E T Kaiser, "Synthesis and Characterization of a Pancreatic Trypsin Inhibitor Homologue and a Model Inhibitor", Biochemistry, (1977), 16:1531–41.

THER88; Theriault, N Y, J B Carter, and S P Pulaski, "Optimization of Ligation Reaction Conditions in Gene Synthesis", BioTechniques (1988), 6(5) 470–473.

THOM83: Thomas, G J, B Prescott, and L A Day, "Structure Similarity, Difference and Variability in the Filamentous Viruses fd, If1, Ike, Pf1, and Xf", J Mol Biol (1983), 165:321–56.

THOM85a: Thompson, M R, M Luttrell, G Overmann, R A Giannella, "Biological and Immunological Characteristics of $^{125}$I-4Tyr and -18Tyr *Escherichia coli* Heat-Stable Enterotoxin Species Purified by High-Performance Liquid Chromatography", Analytical Biochem (1985), 148:26–36.

THOM85b: Thompson, M R, and R A Giannella, "Revised Amino Acid Sequence for a Heat-Stable Enterotoxin Produced by an *Escherichia coli* Strain (18D) that is Pathogenic for Humans", Infection & Immunity (1985), 47:834–36.

THOM86: Thompson, RC, and K Ohlsson, "Isolation, properties, and complete amino acid sequence of human secretory leukocyte protease inhibitor, a potent inhibitor or leukocyte elastase", Proc Natl Acad Sci USA (1986), 83:6692–96.

THOM88a: Thomas, G J, Jr, B Prescott, S J Opella, and L A Day, "Sugar Pucker and Phosphodiester Conformations in Viral Genomes of Filamentous Bacteriophages: fd, If1, IKe, Pf1, Xf, and Pf3", Biochem (1988), 27:4350–57.

THOR88: Thornton, J M, B L Sibinda, M S Edwards, and D J Barlow, "Analysis, Design, and Modification of Loop Regions in Proteins.", BioEssays (1988), 8(2):63–69.

TOMM82: Tommassen, J, P van der Ley, A van der Ende, H Bergmans, and B Lugtenberg, "Cloning of ompF, the Structural Gene for an Outer Membrane Pore Protein of *E. coli* K12: Physical Localization and Homology with the phoE Gene", Mol gen Genet ( 1982 ), 185: 105–110.

TOMM85: Tommassen, J, P van der Ley, M van Zeijl, and M Agterberg, "Localization of functional domains in *E. coli* K-12 outer membrane porins", EMBO J (1985), 4(6) 1583–7.

TRAB86: Traboni, C, R Cortese, "Sequence of a full length cDNA coding for human protein HC ($\alpha_1$ microglobulin)", Nucleic Acids Res (1986) , 14 (15) 6340.

TRIA88: Trias, J, E Y Rosenberg, and H Nikaido, "Specificity of the glucose channel formed by protein D1 of *Pseudomonas aeruginosa*", Biochim Biophys Acta (1988), 938:493–496.

TSCH86: Tschesche, H, H Wenzel, R Schmuck, and E Schnabel, "Homologues of Aprotinin with, in place of lysine, other amino acids in position 15, process for their preparation and their use as medicaments", U.S. Pat. No. 4,595,674 (17 Jun. 1986).

TSCH87: Tschesch, H, J Beckmann, A Mehlich, E Schnabel, E Truscheit, and H R Wenzel, "Semisynthetic engineering of proteinase inhibitor homologues", Biochimica et Biophysica Acta (1987), 913:97–101.

VAND86: van der Ley, P, M Struyve, and J Tommassen, "Topology of outer membrane pore protein PhoE of *Escherichia coli*. Identification of cell surface-exposed amino acids with the aid of monoclonal antibodies", J Biol Chem (1986), 261(26) 12222–5.

VAND89: Vanderslcie, P, C S Craik, J A Nadel, G H Caughey, "Molecular Cloning of Dog Mast Cell Tryptase and a Related Protease: Structural Evidence of a Unique Mode of Serine Protease Activation", Biochem (1989), 28:4148–55.

VAND90: van der Werf, S, A Charbit, C Leclerc, V Mimic, J Ronco, M Girard, and M Hofnung, "Critical role of neighbouring sequences on the immunogenicity of the C3 poliovirus neutralization epitope expressed at the surface of recombinant bacteria", Vaccine (1990), 8(3)269–77.

VERS86a: Vershon, A K, K Blacker, and R T Sauer, "Mutagenesis of the Arc Repressor Using Synthetic Primers with Random Nucleotide Substitutions", pp243–256 in *Protein Engineering. Applications in Science, Medicine, and Industry,* Academic Press, 1986.

VERS86b: Vershon, A K, J U Bowie, T M Karplus, and R T Sauer, "Isolation and Analysis of Arc Repressor Mutants: Evidence for an Unusual Mechanism of DNA Binding", pp302–311 in *Proteins: Structure, Function, and Genetics,* Alan R. Liss, Inc., 1986.

VINC72: Vincent &al, Biochem (1972), 11:2967ff.

VINC74: Vincent &al., Biochem (1974), 13:4205.

VITA84: Vita, C, D Dalzoppo, and A Fontana, "Independent Folding of the Carboxyl-Terminal Fragment 228–316 of Thermolysin", Biochemistry (1984), 23:5512–5519.

VOGE86: Vogel, H, and F Jahnig, "Models for the structure of outer membrane proteins of *E. coli* derived from Raman spectroscopy and prediction methods", J Mol Biol (1986), 190:191–99.

VOND86: Vonderviszt, F, G Y Matrai, and I Simon, "Characteristic sequential residue environment of amino acids in proteins", Int J Peptide Protein Res (1986), 27:483–92.

WACH79: Wachter, E, K Hochstrasser, G Bretzel, and S Heindl, "Kunitz-Type Proteinase Inhibitors Derived by Limited Proteolysis of the Inter-$\alpha$-trypsin Inhibitor, II. Characterization of a Second Inhibitory Inactive Domain by Amino Acid Sequence Determination", Hoppe-Seyler Z Physiol Chem (1979), 360:1297–1303.

WACH80: Wachter, E, K Deppner, and K Hochstrasser, "A New Kunitz-type Inhibitor from Bovine Serum, Amino Acid Sequence Determination.", FEBS Letters (1980), 119:58–62.

WAGN78: Wagner, G, K Wuthrich, and H Tschesche, "A H Nuclear-Magnetic-Resonance Study of the Solution Conformation of the Isoinhibitor K from *Helix pomatia.*", Eur J Biochem (1978), 89:367–377.

WAGN79: Wanger, G, H Tschesche, and K Wuthrich, "The Influence of Localized Chemical Modifications of the Basic Pancreatic Trypsin Inhibitor on Static and Dynamic Aspects of the Molecular Conformation in Solution", Eur J Biochem (1979), 95:239–248.

WANG87: Wagner, G, D Bruhwiler, and K Wuthrich, "Reinvestigation of the aromatic side-chains in the basic pancreatic trypsin inhibitor by heteronuclear two-dimensional nuclear magnetic resonance.", J Mol Biol (1987), 196(1)227–31.

WAIT83: Waite, J H, "Evidence for a repeating 3,4-dihydroxyphenylalanine- and hydroxyproline-containing decapeptide in the adhesive protein of the mussel, *Mytilus edulis* L.", J Biol Chem (1983), 258(5)2911–5.

WAIT85: Waite, J H, T J Housley, and M L Tanzer, "Peptide repeats in a mussel glue protein: theme and variations.", Biochemistry (1985), 24(19)5010–4.

WAIT86: Waite, J H, "Mussel glue from Mytilus californianus Conrad: a comparative study.", J Comp Physiol [B] (1986), 156(4)491–6.

WATS87: *Molecular Biology of the Gene, Fourth Edition,* Watson, J D, N H Hopkins, J W Roberts, J A Steitz, and A M Weiner, Benjamin/Cummings Publishing Company, Inc., Menlo Park, Calif., 1987.

WEBS78: Webster, R E, and J S Cashman, "Morphogenesis of the Filamentous Single-stranded DNA Phages.", in *The Single-Stranded DNA Phages,* Denhardt, D T, D Dressier, and D S Ray editors, Cold Spring Harbor Laboratory, 1978., p557–569.

WEHM89: Wehmeier, U, G A Sprenger, and J W Lengeler, "The use of lambda plac-Mu hybrid phages in Klebsiella pneumoniae and the isolation of stable Hfr strains", Mol Gen Genet (1989), 215(3)529–36.

WEIN83: Weinstock, G M, Cap Rhys, M L Berman, B Hampar, D Jackson., T J Silhavy, J Weisemann, and M Zweig, "Open reading frame expression vectors: A general method for antigen production in *Escherichia coli* using protein fusions to beta-galactosidase", Proc Natl Acad Sci USA (1983), 80:4432–4436.

WELL86: Wells, J A, and D B Powers, "In vivo Formation and Stability of Engineered Disulfide Bonds in Subtilisin", J Biol Chem (1986), 261:6564–70.

WELL87a: Wells, J A, B C Cunningham, T P Graycar, and D A Estell, "Recruitment of substrate-specificity properties from one enzyme into a related one by protein engineering", Proc Natl Acad Sci USA (1987), 84:5167–71.

WELL87b: Wells, J A, D B Powers, R R Bott, T P Graycar, and DA Estell, "Designing substrate specificity by protein engineering of electrostatic interactions", Proc Natl Acad Sci USA (1987), 84:1219–23.

WEMM83: Wemmer, D, and N R Kallenbach, Biochem (1983), 22:1901–6.

WENZ80: Wenzel, H R, and H Tschesche, Hoppe-Seyler Z Physiol Chem (1980), 361:345.

WENZ81: Wenzel, H R, and H Tschesche, "'Chemical Mutation' by Amino Acid Exchange in the Reactive Site of a Proteinase Inhibitor and Alteration of Its Inhibitor Specificity", Angew Chem Int Ed Engl (1981), 20(3)295–6.

WETZ88: Wetzel, R, et al., Proc Natl Acad Sci USA (1988), 85:401–5.

WEWE87: Wewers, M D, M A Casolaro, S E Sellers, S C Swayze, K M McPhaul, J T Wittes, and R G Crystal, "Replacement therapy for α-1-antitrypsin deficiency associated with emphysema", New Engl J Med (1987), 316(17)1055–62.

WHAR86: Wharton, R P, *The Binding Specificity Determinants of 434 Repressor.*, Harvard U. PhD Thesis, 1986, University Microfilms, Ann Arbor, Michigan.

WIEC85: Wieczorek, M, J Otlewski, J Cook, K Parks, J Leluk, A Wilimowska-Pelc, A Polanowski, T Wilusz, and L Laskowski, Jr, "The Squash Family of Serine Protease Inhibitors. Amino Acid Sequences and association equilibrium constants of inhibitors from squash, summer squash, zucchini, and cucumber seeds", Biochem Biophys Res Comm (1985), 126(2)646–652.

WILK84: Wilkinson, A J, A R Fersht, D M Blow, P Carter, and G Winter, "A large increase in enzyme-substrate affinity by protein engineering.", Nature (1984), 307:187–188.

WINT87b: Winter, A J, "Outer membrane proteins of Brucella", Ann Inst Pasteur Microbiol (1987), 138 (1) 87–9.

WLOD84: Wlodawer, A, J Walter, R Huber, and L Sjolin, "Structure of bovine pancreatic trypsin inhibitor. Results of joint neutron and X-ray refinement of crystal form II.", J Mol Biol (1984), 180 (2) 301–29.

WLOD87a: Wlodawer, A, J Nachman, G L Gilliland, W Gallagher, and C Woodward, "Structure of form III crystals of bovine pancreatic trypsin inhibitor.", J Mol Biol (1987), 198(3)469–80.

WLOD87b: Wlodawer, A, J Deisenhofer, and R Huber, "Comparison of two highly refined structures of bovine pancreatic trypsin inhibitor.", J Mol Biol (1987), 193(1)145–56.

WOOD90: Woodward, S R, L J Cruz, B M Olivera, and D R Hillyard, "Constant and hypervariable regions in conotoxin propeptides", EMBO J (1990), 9:1015–1020.

WUNT88: Wun, T-C, K K Kretzmer, T J Girard, J P Miletich, and G J Broze, Jr, "Cloning and Characterization of a cDNA Coding for the Lipoprotein-associated Coagulation Inhibitor Shows That It Consists of Three Tandem Kunitz-type Inhibitory Domains", J Biol Chem (1988), 263.:6001–4.

YAGE87: Yager, T D, and P H yon Hippel, "Transcription Elongation and Termination in *E. coli*", Volume 2, Chapter 76, p 1241–1275, *Escherichia coli* and *Salmonella typhimurium:* Cellular and Molecular Biology, Neidhardt, F C, Editor-in-Chief, Amer Soc for Microbiology, Washington, DC, 1987.

YANI85: Yanisch-Perron, C, J Vieira, and J Messing, "Improved M13 phage cloning vectors and host strains: nucleotide sequeices of the M13mp18 and pUC19 vectors", Gene, (1985), 33:103–119.

YOKO77: Yokosawa, H, and S-I Ishii, "Anhydrotrypsin: New Features in Ligand Interactions Revealed by Affinity Chromatography and Thionine Replacement", J Biochem (1977), 81:647–56.

YOSH85: Yoshimura, S, H Ikemura, H Watanabe, S Aimoto, Y Shimonishi, S Hara, T Takeda, T Miwatani, and Y Takeda, "Essential structure for full enterotoxigenic activity of heat-stable enterotoxin produced by enterotoxigenic *Escherichia coli*", FEBS Lett (1985), 181:138–42.

ZAFA88: Zafaralla, G C, C Ramilo, W R Gray, R Karlstrom, B M Olivera, and L J Cruz, "Phylogenetic specificity of cholinergic ligands: α-conotoxin SI", Biochemistry, (1988), 27(18)7102–5.

ZIMM82: Zimmermann, R, C Watts, and W Wickner, "The Biosynthesis of Membrane-bound M13 Coat Protein: Energetics and Assembly Intermediatesy" J Biol Chem (1982), 257:6529–6536.

ZOLL84: Zoller, M J, and M Smith, "Oligonucleotide-Directed Mutagenesis: A Simple Method Using Two Oligonucleotide Primers and a Single-Stranded DNA Template.", DNA (1984), 3(6)479–488.

We claim:

1. A method of obtaining a nucleic acid encoding a binding protein having a proteinaceous binding domain that binds a predetermined target material comprising:

a) preparing a variegated population of amplifiable genetic packages, said genetic packages being selected from the group consisting of cells, spores and viruses, each said genetic package being genetically alterable and having an outer surface including a genetically determined outer surface protein, each package including a first nucleic acid construct coding for a chimeric potential binding protein, each said chimeric protein comprising and each said construct comprising nucleic acid encoding (i) a potential binding domain which is a mutant of a predetermined domain of a predetermined parental protein other than a single chain antibody, and (ii) an outer surface transport signal for obtaining the display of the potential binding domain on the outer surface of the genetic package, the expression of which construct results in the display of said chimeric potential binding protein and its potential binding domain on the outer surface of said genetic package; and wherein said variegated population of genetic packages collectively display a plurality of different potential binding domains, the differentiation among said plurality of different potential binding domains occurring through the at least partially random variation of one or more predetermined amino acid positions of said parental binding domain to randomly obtain at each said position an amino acid belonging to a predetermined set of two or more amino acids; the amino acids of said set occurring at said position in statistically predetermined expected proportions, said genetic packages being amplifiable in cell culture and separable on the basis of the potential binding domain displayed thereon, b) causing the expression of said chimeric potential binding proteins and the display of said potential binding domains on the outer surface of said packages;

c) contacting said packages with the predetermined target material such that said potential binding domains and the target material may interact;

d) separating packages displaying a potential binding domain that binds the target material from packages that do not so bind, and e) recovering at least one package displaying on its outer surface a chimeric binding protein comprising a successful binding domain (SBD) which bound said target, said package comprising nucleic acid encoding said successful binding domain, and amplifying said SBD-encoding nucleic acid in vivo or in vitro, with the proviso that when the target is an antibody, the predetermined parental protein is not an antigen specifically bound by that antibody.

2. The method of claim 1 wherein the parental protein is not an antibody and the mutated domain is not an antibody domain.

3. The method of claim 2 wherein, in said step (a), the differentiation among said potential binding domains of said variegated population is limited to no more than about 20 predetermined amino acid residues of said sequence and where the permissible variation at said alterable residue positions is also predetermined.

4. The method of claim 3, further comprising the steps of: (f) determining the amino acid sequence of a successful binding domain and (g) preparing a new variegated population of replicable genetic packages according to said step (a), the parental binding domain for the potential binding domains of said new packages being a successful binding domain whose sequence was determined in step (f), and repeating steps (b)–(e) with said new population.

5. The method of claim 4 wherein a potential binding domain is considered successful only if it has at least a certain predetermined degree of affinity for target material, the required degree of affinity being increased for each new variegated population, and wherein each new variegated population dislays its parental binding domain in detectable amounts.

6. The method of claim 3 wherein the initially chosen parental binding domain has a melting point of at least 50° C.

7. The method of claim 3 wherein the initially chosen parental potential binding domain is selected from the group consisting of (a) binding domains of bovine pancreatic trypsin inhibitor, crambin, Cucurbita maxima trypsin inhibitor III, heat-stable enterotoxin of *Exchericia coli*, α Conotoxin GI, μConotoxin GIII, ω Conotoxin GIV, apamin, charybdotoxin, secretory leukocyte protease inhibitor, cystatin, eglin, barley protease inhibitor, ovomucoid, T4 lysozyme, hen egg white lysozyme, ribonuclease, azurin, tumor necrosis factor, and CD4, and (b) domains at least substantially homologous with any of the foregoing domains which have a melting point of at least 50° C.

8. The method of claim 3, further comprising determining which amino acid residues of said parental binding domain are likely to lie on the surface of said domain and limiting the variegation to codons encoding such amino acids.

9. The method of claim 3, said target material comprising one or more discrete molecules, said parental potential binding domain being characterized as a sequence of amino acids, further comprising identifying an interaction set of amino acids which are on the surface of the parental potential binding domain and which can all simultaneously touch a single molecule of the target material, and obtaining a variegated population wherein for each amino acid residue in said interaction set there is at least one potential binding domain wherein a different amino acid is substituted therefor, said interaction set comprising from about eight to about sixteen residues.

10. The method of claim 3 wherein the initially chosen parental binding domain is not a binding domain of a binding protein for the predetermined target.

11. The method of claim 3 wherein the initially chosen parental binding domain contains no more than 30 residues and at least 2 disulfides.

12. The method of claim 3 wherein the initially chosen parental binding domain contains no more than 60 residues and at least 3 disulfides.

13. The method of claim 3 wherein the initially chosen parental binding domain contains no more than 80 residues and at least 4 disulfides.

14. The method of claim 2 wherein the genetic package is a single-stranded DNA bacteriophage other than bacteriophage lambda and the package is replicated in a bacterial host cell.

15. The method of claim 14 wherein said construct further comprises a cytoplasmic secretion signal sequence which codes for a signal peptide which directs the immediate expression product to the inner membrane of the bacterial host cell infected by said phage where it is processed to remove said signal peptide, yielding a mature chimeric protein comprising the potential binding domain and at least a portion of a coat protein of the phage, said chimeric protein being assembled with wild-type coat protein into the phage coat so that said phage displays the potential binding domain on the surface of its coat.

16. The method of claim 15 wherein the secretion signal sequence is derived from a first gene, and the nucleic acid sequence encoding the outer surface transport signal is derived from a second gene, the first and second genes being different.

17. The method of claim 15 wherein the secretion signal is encoded by a signal sequence selected from the group consisting of the signal sequences of the phoA, bla and geneIII genes.

18. The method of claims 14 wherein the replicable genetic package is a filamentous phage.

19. The method of claim 18 wherein the outer surface. transport signal is provided by the major coat protein of a filamentous phage or a assemblable fragment thereof.

20. The method of claim 18 wherein the outer surface transport signal is provided by the gene III protein of a filamentous phage or an assemblable fragment thereof.

21. The method of claim 2 wherein the replicable genetic package is a bacterial cell and said DNA construct further comprises a periplasmic secretion signal sequence.

22. The method of claim 21 wherein the bacterial cell is selected from the group consisting of strains of *Escherichia coli, Salmonella typhimurium, Pseudomonas aeruginosa, Klebsiella pneumonia, Neisseria gonorrhoeae,* and *Bacillus subtilis*.

23. The method of claim 22 wherein the outer surface transport signal is derived from a bacterial outer surface protein selected from the group consisting of the lamB protein, OmpA, OmpC, OmpF, Phospholipase A, and pilin, or an assemblable segment thereof.

24. The method of claim 23 wherein the chimeric surface protein substantially corresponds to LamB with the foreign potential binding domain inserted at 153.

25. The method of claim 23 wherein the chimeric potential binding protein substantially corresponds to the first 153 amino acids of Lamb fused in frame to the potential binding domain.

26. The method of claim 2 wherein the replicable genetic package is a bacterial spore.

27. The method of claim 26 wherein the bacterial spore is a Bacillus endospore.

28. The method of claim 27 wherein the replicable genetic package is an endospore of a strain of *B. subtilis*.

29. The method of claim 28 wherein the outer surface transport signal is the cotA, cotB, cotC or cotD protein or an assemblable segment thereof.

30. The method of claim 2 wherein the potential binding proteins are intergeneric chimeric proteins.

31. The method of claim 2 wherein said population is characterized by the display of at least $10^5$ different potential binding domains.

32. The method of claim 2 wherein, for any potentially encoded potential binding domain, the probability that it will be displayed by at least one package in said population is at least 50%.

33. The method of claim 32 wherein, for any potentially encoded potential binding domain, the probability that it will be displayed by at least one package in said population is at least 90%.

34. The method of claim 1, said potential binding domain being a mini-protein sequence of less than about sixty amino acids and having at least one intrachain covalent crosslink between a first amino acid position and a second amino acid position thereof, the amino acids at said first and second positions being invariant in all of the chimeric proteins displayed by said population.

35. The method of claim 34 wherein the crosslink is a disulfide bond and the the amino acids at the first and second, amino acid positions are cysteines.

36. The method of claim 35 in which the mini-protein domain has a single disulfide bond and the span of the bond is not more than nine amino acid residues.

37. The method of claim 35 wherein the mini-protein domain has a disulfide bond which bridges a sequence of amino acids which under affinity separation conditions collectively assume a hairpin supersecondary structure.

38. The method of claim 37 wherein the hairpin secondary structure is selected from the group consisting of (a) an α helix, a turn, and a β strand; (b) an α helix, a turn, and an α helix; and (c) a β strand, a turn, and a β strand.

39. The method of claim 35 wherein the mini-protein domain comprises a plurality of intrachain disulfide bonds.

40. The method of claim 39 wherein the mini-protein domain has two disulfide bonds having a connectivity pattern of 1–3 , 2–4.

41. The method of claim 40 wherein the mini-protein domain substantially corresponds in sequence to an α-conotoxin.

42. The method of claim 39 wherein the mini-protein domain has three disulfide bonds having a connectivity pattern of 1–4, 2–5, 3–6.

43. The method of claim 42 wherein the mini-protein domain substantially corresponds in sequence to a mu- or omega-conotoxin.

44. The method of claim 39 wherein the mini-protein domain substantially corresponds in sequence to a mini-protein selected from the group consisting of *Escherichia coli* heat stable toxin I ($ST_A$), the bee venom apamin, or a squash-seed trypsin inhibitor, the scorpion toxin, charybdotoxin and secretory leukocyte protease inhibitor.

45. The method of claim 2 wherein the population of replicable genetic packages of step (a) is obtained by:
  i) preparing a variegated population of DNA inserts, said inserts comprising a plurality of variegated codons, which collectively encode a plurality of different potential binding domains, and
  ii) incorporating the resulting population of DNA inserts into the chosen replicable genetic packages to produce a variegated population of replicable genetic packages.

46. The method of claim 45 in which at least one variegated codon is a simply variegated codon selected from the group consisting of NNT, NNG, RNG, RMG, VNT, RRS, and SNT.

47. The method of claim 45 wherein none of the variegated codons is a simply variegated codon selected from the group consisting of NNN, NNK and NNS.

48. The method of claim 45 in which at least one variegated codon is a complexly variegated codon.

49. The method of claim 48 in which the complexly variegated codon is prepared so as to yield a ratio of most favored amino acid to least favored amino acid which is less than 2.6.

50. The method of claim 48 wherein the distribution of nucleotides incorporated at said complexly variegated codon is further chosen to yield the largest value for the quantity {(1.-abundance(stop codons)) times (abundance of the least abundant amino acid)/(abundance of the most abundant amino acid)}.

51. The method of claim 50 wherein the distribution of nucleotides incorporated at said variegated codon is chosen to yield substantially equal abundances of acidic and basic amino acids.

52. The method of claim 50 wherein at least one variegated codon provides at least ten different amino acids at not less than 5% abundance.

53. The method of claim 45 wherein for at least one variegated codon the ratio of amino acids encoded to possible. trinucleotide sequences is at least 2:3.

54. The method of claim 45 wherein for at least one. variegated codon there are at least four equally most-favored amino acids.

55. The method of claim 45 wherein the ratio of amino acid sequences encoded to possible polynucleotide sequences is at least 1:3.

56. The method of claim 1, wherein the method further comprises (i) isolating from the first nucleic acid construct of a package bearing a successful binding domain, a nucleic acid fragment consisting essentially of nucleic acid encoding said successful binding domain, or (ii) determining enough of the sequence of the first nucleic acid construct of (i) above to deduce the amino acid sequence of the successful binding domain and then preparing a second nucleic acid construct comprising nucleic acid encoding the successful binding domain, said first and second nucleic acid constructs encoding different proteins.

57. The method of claim 56 wherein the second nucleic acid construct encodes a second binding protein consisting essentially of said successful binding domain.

58. The method of claim 1 wherein the parental protein is a single domain protein.

59. A method of producing a binding protein which binds a predetermined target material which comprises:
  (i) obtaining, by the method of claim 1, a first nucleic acid construct encoding a chimeric binding protein having a binding domain which binds the predetermined target material, and
  (ii) producing either said chimeric binding protein, or a second binding protein having essentially the same binding domain.

60. The method of claim 59 wherein the sequence of the binding domain is determined by sequencing at least a portion of either said first nucleic acid construct or said chimeric binding protein, and the determined sequence is then used to guide production of said second binding protein.

61. The method of claim 59 wherein said second binding protein is produced by expressing a second nucleic acid construct derived at least in part from the first nucleic acid construct.

62. The method of claim 59 wherein the second binding protein is produced by recombinant DNA techniques.

63. The method of claim 59 wherein the second binding protein is produced by nonbiological peptide synthesis techniques.

64. The method of claim 59 wherein the second binding protein consists essentially of said successful binding domain.

65. In a process for developing novel binding proteins, other than single chain antibodies, with a desired binding activity against a particular target material, by mutagenesis of a gene encoding a known protein other than a single chain antibody, the improvement comprising displaying a proteinaceous potential binding domain on the outer surface of an amplifiable genetic package selected from the group consisting of cells, spores and viruses, each said genetic package being genetically alterable, said potential binding domain not being natively associated with the outer surface of said package, said package containing the gene encoding said binding domain and means for directing said domain to the outer surface of said package, contacting the package with the target material, and determining whether the package displaying the potential binding domain binds to said target material, with the proviso that when the target is an antibody, the predetermined parental protein is not an antigen specifically bound by that antibody.

66. The process of claim 65 wherein the known protein is not an antibody and the mutated domain is not an antibody domain.

67. A variegated population of replicable genetic packages, each package including a nucleic acid construct coding for a chimeric potential binding protein, each said construct comprising DNA encoding (i) a potential binding domain which is a mutant of a predetermined parental binding domain, and (ii) an outer surface transport signal for obtaining the display of the potential binding domain on the outer surface of the genetic package, wherein said initial binding domain is not a single chain antibody and is not identical to or substantially homologous with a binding domain natively associated with said transport signal, and wherein said variegated population of genetic packages collectively display a plurality of different potential binding domains, the differentiation among said plurality of different potential binding domains occurring through the at least partially random variation of one or more predetermined amino acid positions of said parental binding domain to randomly obtain at each said position an amino acid belonging to a predetermined set of two or more amino acids, the amino acids of said set occurring at said position in predetermined expected proportions.

68. A variegated population of DNA molecules encoding chimeric binding proteins, each said chimeric binding protein comprising (i) a binding domain, and (ii) at least a segment of an outer surface protein of a cell or virus, said segment acting to cause the display of the chimeric binding protein or a processed form thereof on the outer surface of the cell or virus, said binding domain being capable of binding to a target material to which said outer surface protein is not capable of preferentially binding, wherein said variegated population of DNA molecules encode chimeric binding proteins which collectively include a plurality of different binding domains, the differentiation among said plurality of different potential binding domains occurring through the at least partially random variation of one or more predetermined amino acid positions thereof to randomly obtain at each said position an amino acid belonging to a predetermined set of two or more amino acids, the amino acids of said set occurring at said position in predetermined expected proportions.

69. A process for developing novel binding proteins with a desired binding activity against a particular target material which comprises providing a library of phage which each displays on its surface, as a result of expression of a first phage gene, one or more copies of a particular chimeric coat protein, each chimeric coat protein comprising (a) a potential binding domain which is a mutant of a known protein domain foreign to said phage, as well as (b) at least a functional portion of a coat protein native to said phage, said library collectively displaying a plurality of potential binding domains, wherein the differentiation among said plurality of different potential binding domains occurs through the controlled random variation of one or more predetermined amino acid positions of said known domain to randomly obtain at each said position an amino acid belonging to a predetermined set of two or more amino acids, the amino acids of said set occurring at said position in predetermined expected proportions, contacting said library of phage with the target material, and separating the phage on the basis of their affinity for the target materials characterized in that said chimeric coat protein further comprises a linker peptide which is specifically cleavable by a site-specific proteases said linker peptide being positioned in between (a) said epitope or potential binding domain, and (b) said native coat protein sequence, whereby (a) may be freed from (b).

70. The method of claim 69 wherein the site. specific protease is Factor Xa, Factor XIa, kallikrein, thrombin, Factor XIIa, collagenase or enterokinase.

71. The method of claim 69 wherein, after said library of phage is contacted with said target material, (1) low affinity phage are removed, (2) high affinity phage still bound to said target material are released by cleavage of said chimeric coat protein at said linker by means of a site-specific protease, and the released high affinity phage are recovered.

72. The method of claims 69 wherein the phage further comprises a second phage gene encoding the cognate wild-type coat protein of the phage.

73. A process for developing novel binding proteins with a desired binding activity against a particular target material which comprises providing a library of phage which each displays on its surface, as a result of expression of a first phage gene, one or more copies of a particular chimeric coat protein, each chimeric coat protein comprising a mutant of a known protein domain foreign to said phage, said library collectively displaying a plurality of potential binding domains, wherein the differentiation among said plurality of different potential binding domains occurs through the controlled random variation of one or more predetermined amino acid positions of said known domain to randomly obtain at each said position an amino acid belonging to a predetermined set of two or more amino acids, the amino acids of said set occurring at said position in predetermined expected proportions, contacting said library of phage with the target material, and separating the phage on the basis of their affinity for the target material, characterized in that said potential binding domain has at least one intrachain covalent crosslink between a first amino acid position and a second amino acid position thereof, the amino acids at said first and second positions being invariant in all of the chimeric proteins displayed by said library, and where low affinity phage are removed from said target material first, and then high affinity phage are released or rendered more readily eluted from the target material by treating the phage with a reagent which cleaves the crosslink.

74. The method of claim 73 in which the cleaving reagent does not kill the phage.

75. The method of claim 73 wherein the crosslink is a disulfide bond and the amino acids at said first and second positions are cysteines.

76. The method of claim 75 wherein the reagent is dithiothreitol.

77. The method of claim 73 wherein the phage further comprises a second phage gene encoding the cognate wild-type coat protein of the phage.

78. A process for developing binding proteins with a desired binding activity against a particular target material which comprises providing a library of phage which each displays on its surface, as a result of expression of a first phage gene, one or more copies of a particular chimeric coat protein, each chimeric coat protein comprising a potential epitope, or a potential binding domain which is a mutant of a known protein domain foreign to said phage, said library collectively displaying a plurality of potential epitomes or binding domains, wherein the differentiation among said plurality of different potential binding domains occurs through the controlled random variation of one or more predetermined amino acid positions of said known domain to randomly obtain at each said position an amino acid belonging to a predetermined set of two or more amino acids, the amino acids of said set occurring at said position in predetermined expected proportions, contacting said library of phage with the target material, and separating the phage on the basis of their affinity for the target material, characterized in that the chimeric coat protein includes only an assemblable fragment of a coat protein of said phage, and not that portion of the coat protein which is responsible for pilus binding, and the phage also comprises a second phage gene encoding the cognate native coat protein of the phage.

79. The process of claim 78 wherein the initiation codon of the second phage gene is a CTG codon.

80. A process for developing binding proteins with a desired binding activity against a particular target material which comprises providing a library of phage which each displays on its surface, as a result of expression of a first phage gene, one or more copies of a particular chimeric coat, protein, each chimeric coat protein comprising a potential binding domain which is a mutant of a known protein domain foreign to said phage, said library collectively displaying a plurality of potential binding domains, wherein the differentiation among said plurality of different potential binding domains occurs through the controlled random variation of one or more predetermined amino acid positions of said known domain to randomly obtain at each said position an amino acid belonging to a predetermined set of two or more amino acids, the amino acids of said set occurring at said position in predetermined expected proportions, contacting said library of phage with the target material, and separating the phage on the basis of their affinity for the target material, characterized in that the phage also comprises a second phage gene encoding the cognate native coat protein of the phage, and the initiation codon of the second phage gene is a Leucine codon.

81. A library of display phage which each displays on its surface, as a result of expression of a first phage gene, one or more copies of a particular chimeric coat protein, each chimeric coat protein comprising a potential binding domain which is a mutant of a known protein domain foreign to said phage, said library collectively displaying a plurality of potential binding domains, wherein the differentiation among said plurality of different potential binding domains occurs through the controlled random variation of one or more predetermined amino acid positions of said known domain to randomly obtain at each said position an amino acid belonging to a predetermined set of two or more amino acids, the amino acids of said set occurring at said position in predetermined expected proportions, contacting said library of phage with the target material, and separating the phage on the basis of their affinity for the binding protein target material, wherein the differentiation among said plurality of different potential binding domains occurs through the at least partially random variation of one or more predetermined amino acid positions of said known domain to randomly obtain at each said position an amino acid belonging to a predetermined set of two or more amino acids, the amino acids of said set occurring at said position in predetermined expected proportions, and in substantially all sets the ratio of the frequency of occurrence of the most favored amino acid to that for the least favored amino acid is less than 2.6, characterized in that, at at least one such position, the predetermined set consists of less than all twenty different genetically encodable amino acids, but includes three or more of the classes of genetically encodable amino acids.

82. A library of display phage which each displays on its surface, as a result of expression of a first phage gene, one or more copies of a particular chimeric coat protein, each chimeric coat protein comprising (a) a potential binding domain which is a mutant of a known protein domain foreign to said phage, as well as (b) at least a functional portion of a coat protein native to said phage, said library collectively displaying a plurality of potential binding domains, wherein said chimeric coat protein further comprises a linker peptide which is specifically cleavable by said site-specific protease, said linker peptide being positioned inbetween (a) said potential binding domain, and (b) said native coat protein sequence, whereby (a) may be freed from (b).

83. A process for developing novel binding proteins with a desired binding activity against a particular target material which comprises providing a library of phage which each displays on its surface, as a result of expression of a first phage gene, one or more copies of a particular chimeric coat protein, each chimeric coat protein comprising (a) a potential binding domain which is a mutant of a known protein domain foreign to said phage, as well as (b) at least a functional portion of a coat protein native to said phage, said library collectively displaying a plurality of potential binding domains, wherein the differentiation among said plurality of different potential binding domains occurs through the controlled random variation of one or more predetermined amino acid positions of said known domain to randomly obtain at each said position an amino acid belonging to a predetermined set of two or more amino acids, the amino acids of said set occurring at said position in predetermined expected proportions, contacting said library of phage with the target materials and separating the phage on the basis of their affinity for the target material, wherein the phage gene encoding said chimeric coat protein further comprises a cytoplasmic secretion signal sequence which codes for a signal peptide which directs the immediate expression product to the inner membrane of the bacterial host cell infected by said phage, where it is processed to remove said signal peptide, yielding a mature chimeric coat protein comprising the potential binding domain and at least a portion of a geneVIII like protein of the phage, said chimeric protein being assembled with wild-type coat protein into the phage coat, wherein the secretion signal is encoded by a signal sequence selected from the group consisting of the signal sequences of the phoA, bla and geneIII genes.

* * * * *

UNITED STATES PATENT AND TRADEMARK OFFICE
CERTIFICATE OF CORRECTION

PATENT NO. : 5,571,698
DATED : November 5, 1996
INVENTOR(S) : Ladner, et al.

It is certified that error appears in the above-indentified patent and that said Letters Patent is hereby corrected as shown below:

Column 311, lines 30-50, cancel claim 67 in its entirety.

Column 311, line 53, after "binding domain", insert --not a single chain antibody--.

Signed and Sealed this

Eighteenth Day of March, 1997

Attest:

BRUCE LEHMAN

Attesting Officer

Commissioner of Patents and Trademarks